US008455187B2

(12) United States Patent
Cole et al.

(10) Patent No.: US 8,455,187 B2

(45) Date of Patent: Jun. 4, 2013

(54) METHOD FOR ISOLATING A POLYNUCLEOTIDE OF INTEREST FROM THE GENOME OF A MYCOBACTERIUM USING A BAC-BASED DNA LIBRARY: APPLICATION TO THE DETECTION OF MYCOBACTERIA

(75) Inventors: Stewart Cole, Clamat (FR); Roland Buchrieser-Brosch, Paris (FR); Stephen Gordon, Paris (FR); Alain Billault, Roissy-en-Brie (FR)

(73) Assignee: Institut Pasteur, Paris (FR)

( * ) Notice: Subject to any disclaimer, the term of this patent is extended or adjusted under 35 U.S.C. 154(b) by 531 days.

(21) Appl. No.: 11/341,914

(22) Filed: Jan. 30, 2006

(65) Prior Publication Data

US 2007/0092884 A1 Apr. 26, 2007

Related U.S. Application Data

(60) Division of application No. 10/259,678, filed on Sep. 30, 2002, now Pat. No. 6,991,904, which is a continuation of application No. 09/670,314, filed on Sep. 26, 2000, now Pat. No. 6,492,506, which is a division of application No. 09/060,756, filed on Apr. 16, 1998, now Pat. No. 6,183,957.

(51) Int. Cl.

| | |
|---|---|
| ***C12Q 1/68*** | (2006.01) |
| ***C07H 19/00*** | (2006.01) |
| ***C07H 21/00*** | (2006.01) |

(52) U.S. Cl.
USPC .......................... 435/6.1; 435/6.15; 536/22.1

(58) Field of Classification Search
USPC ................................ 435/6.1, 6.15; 536/22.1
See application file for complete search history.

(56) References Cited

U.S. PATENT DOCUMENTS 6,641,814 B1 * 11/2003 Andersen et al. .......... 424/190.1

FOREIGN PATENT DOCUMENTS

| | | |
|---|---|---|
| WO | WO93/03187 | 2/1993 |
| WO | WO93/18166 | 9/1993 |
| WO | WO 97/9429 * | 3/1997 |
| WO | WO97/23624 | 7/1997 |
| WO | WO99/54487 | 10/1999 |
| WO | WO99/54487 A2 * | 10/1999 |

OTHER PUBLICATIONS

Greenspan et al. (Nature Biotechnology 7: 936-937, 1999).*
Colman et al. (Research in Immunology 145: 33-36, 1994, p. 33 col. 2, p. 35 col. 1).*
GenBank Z79701[gi:1524225] (submitted Sep. 2, 1996; posted Sep. 6, 1996; replaced Jun. 27, 1998) (23 pages).
GenBank Z79701 Revision history (1 page), (submitted Sep. 2, 1996, posted Sep. 6, 1996; replaced Jun. 27, 1998)).
"On the Preparation and Utilization of Isolated and Purified Oligonucleotides," including attached disk of polynucleotides, Mar. 9, 2002.
Brosch et al., "Use of a *Mycobacterium tuberculosis* H37Rv Bacterial Aritificial Chromosome Library for Genome Mapping Sequencing, and Comparative Genomics," *Infection and Immunity*, vol. 66, No. 5, pp. 2221-2229 (May 1998).
Cole et al., "Deciphering the Biology of *Mycobacterium tuberculosis* from the Complete Genome Sequence," *Nature*, vol. 393, pp. 537-545 (Jun. 11, 1998).
Cole et al., Novartis Foundation Symposium, pp. 160-177 (1998).
Kim et al., "Construction and Characterization of a Human Bacterial Artificial Chromosome Library," *Genomics*, vol. 34, pp. 213-218 (Jun. 1, 1996).
International Search Report of PCT/IB99/00740, Oct. 28, 1999.
Philipp et al., "Physical Mapping of *Mycobacterium bovis* BCG Pasteur Reveals Differences from the Genome Map of *Mycobacterium tuberculosis* H37Rv and from *M. bovis," Microbiology*, vol. 142:3135-3145 (1996).
Philipp et al., "An Integrated Map of the Genome of the Tubercle Bacillus, *Mycobacterium tuberculosis* H37Rv, and Comparison with *Mycobacterium leprae,", P.N.A.S.*, vol. 93:3132-3137 (1996).
Zimmer et al., "Construction and Characterization of Large-Fragmented Chicken Bacterial Artificial Chromosome Library", *Genomics*, vol. 42:217-226 (1997).
GenEmbl AD00001 Dec. 3, 1996.
GenEmbl AD000017 Dec. 10, 1996.
GenEmbl 400013 Mar. 1, 1994.
GenEmbl X63508 Nov. 20, 1996.

* cited by examiner

*Primary Examiner* — Gary Nickol
*Assistant Examiner* — Nina Archie
(74) *Attorney, Agent, or Firm* — Finnegan, Henderson, Farabow, Garrett & Dunner L.L.P.

(57) ABSTRACT

A method for detecting *Mycobacterium tuberculosis* involves contacting a biological sample with the product of expression of at least one ORF contained in a polynucleotide present in *Mycobacterium tuberculosis* and absent in *Mycabacterium bovis* BCG; and detecting whether an immunological complex is formed between the product thereof and antibodies contained in the biological sample, wherein the presence of a complex indicates an infection with *Mycobacterium tuberculosis*.

3 Claims, 12 Drawing Sheets

Figure 1A:
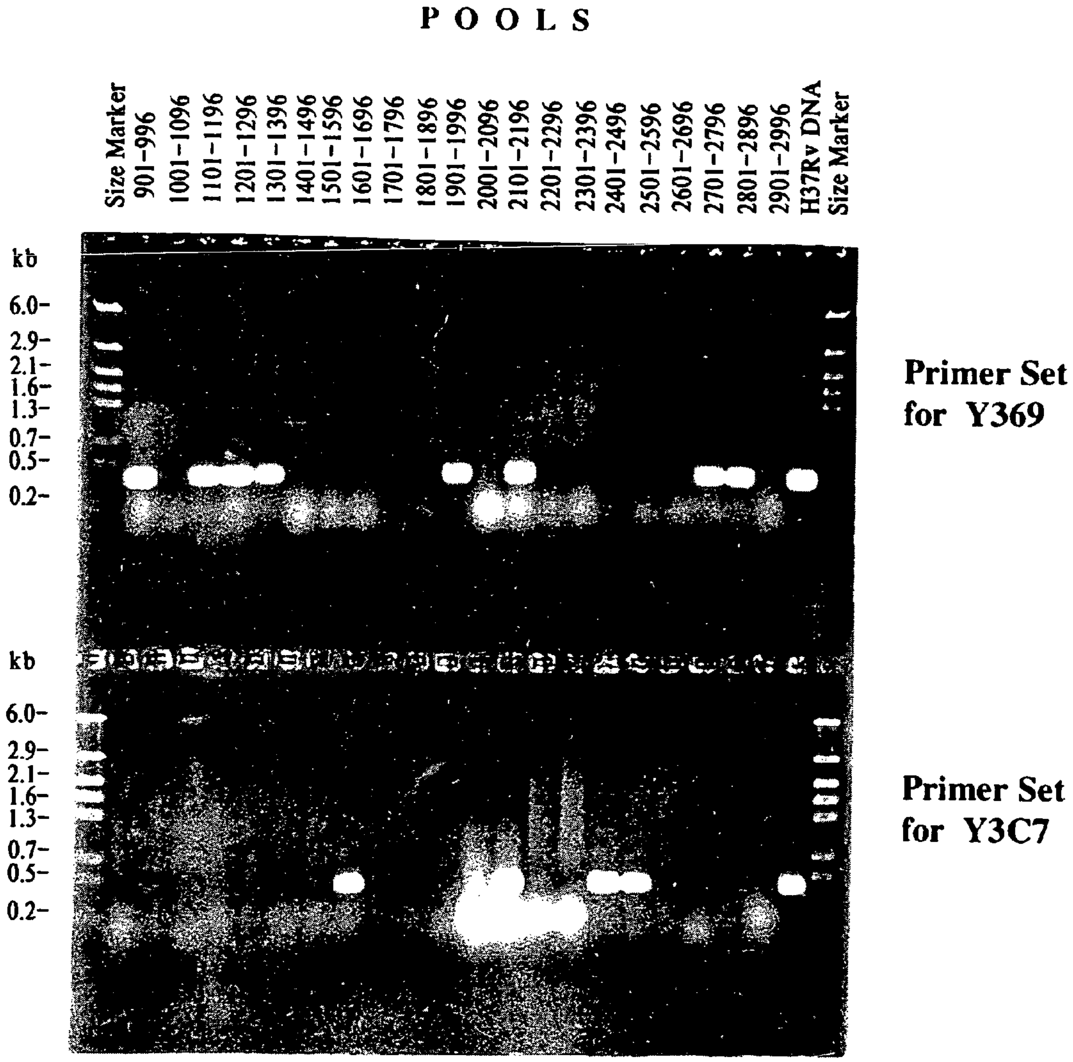

```
(SEQ ID NO. 727) H37Rv ·····PTQTLTGRPLIGNGTPGAVGSGATGAPGGWLLGDGGAGGSGAAGSGAPGGAGGAAGLWGT    837273
(SEQ ID NO. 728) BCG ·······PTQTLTGRPLIGNGTPGAVGSGATGAPGGWLLGDGGAGGSGAAGSGAPGGAGGAAGLWGT

H37Rv ···GGAGGAGGSSAGGGGAGGAGGAGGWLLGDGGAGGIGGASTVLGGTGGGGGVGGLWGAGGA    837453
BCG ·····------------------------------GGAGGIGGASTVLGGTGGGGGVGGLWGAGGA

H37Rv ···GGAGGTGLVGGDGGAGGAGGTGGLLAGLIGAGGGHGGTGGLSTNGDGGVGGAGGNAGMLA    837633
BCG ·····GGAGGTGLVGGDGGAGGAGGTGGLLAGLIGAGGGHGGTGGLSTNGDGGVGGAGGNAGMLA

H37Rv ···GPGGAGGAGGDGENLDTGGDGGAGGSAGLLFGSGGAGGAGGFGFLGGDGGAGGNAGLLLS    837813
BCG ·····GPGGAGGAGGDGENLDTGGDGGAGGSAGLLFGSGGAGGAGGFGFLGGDGGAGGNAGLLLS

                                          837897
H37Rv ···SGGAGGFGGFGTAGGVGGAGGNAGWLGF--------------------------------
BCG ·····SGGAGGFGGFGTAGGVGGAGGNAGWLGFGAGGIGGIGGNANGGAGGNGGTGGQLWGSGGA

H37Rv ···--------------GGAGGVGGSAGLIGTGGNGGNGGTGANAGSPGTGGAGGLLLGQNGLNGLP    838047
BCG ·····GVEGGAALSVGDTGGAGGVGGSAGLIGTGGNGGNGGTGANAGSPGTGGAGGLLLGQNGLNGLP
```

FIG. 6 pBeloBAC11

(SEQ ID NO. 728) GCGGCCGCAA GGGGTTCGCG TCAGCGGGTG TTGGCGGGTG TCGGGGCTGG
*NotI* restriction site

CTTAACTATG CGGCATCAGA GCAGATTGTA CTGAGAGTGC ACCATATGCG

GTGTGAAATA CCGCACAGAT GCGTAAGGAG AAAATACCGC ATCAGGCGCC

ATTCGCCATT CAGGCTGCGC AACTGTTGGG AAGGGCGATC GGTGCGGGCC

TCTTCGCTAT TACGCCAGCT GGCGAAAGGG GGATGTGCTG CAAGGCGATT
primer T7-BAC1

AAGTTGGGTA ACGCCAGGGT TTTCCCAGTC ACGACGTTGT AAAACGACGG

CCAGTGAATT GTAATACGAC TCACTATAGG GCGAATTCGA GCTCGGTACC
T7-promoter sequence

CGGGGATCCT CTAGAGTCGA CCTGCAGGCA TGCAAGCTTG AGTATTCTAT
primer T7-Belo2 *Hind*III cloning site SP6-promoter AGTGTCACCT AAATAGCTTG GCGTAATCAT GGTCATAGCT GTTTCCTGTG
sequence (complementary strand) primer SP6-Mid (complementary strand)

TGAAATTGTT ATCCGCTCAC AATTCCACAC AACATACGAG CCGGAAGCAT

AAAGTGTAAA GCCTGGGGTG CCTAATGAGT GAGCTAACTC ACATTAATTG
primer SP6-BAC1 (complementary strand)

CGTTGCGCTC ACTGCCCGCT TTCCAGTCGG GAAACCTGTC GTGCCAGCTG

CATTAATGAA TCGGCCAACG CGAACCCCTT GCGGCCGCCC GGGCCGTCGA
*NotI* restriction site

FIG. 7

SEQUENCE LISTING

<160> NUMBER OF SEQ ID NOS: 743

<210> SEQ ID NO 1
<211> LENGTH: 12732
<212> TYPE: DNA
<213> ORGANISM: Mycobacterium tuberculosis

<400> SEQUENCE: 1
acctgcgctt gcagagatca aatagggcgc atgggtcagc atagtacagg tcgtcgcgca 60
tctttgatgc atcggaataa gatgtcaggc aattaaaaga gaagccacgg cgactcgcgg 120
cattcagcat gtcgagcgtc gcttcgatgt gagcgcacca ttccgtgtcc aacgatttca 180
gacgaacatt gaatattcca ctcgcgacgc tatagtccgc ctcccgatct atgcgcgccg 240
cgcagatgaa gtctgcgttc gcccgacctt cgaaacgtag tgcggccgcg cgcaccattt 300
cgggggagac gtcgatgccg gtgtaatcag ttttgaagcc acgcgcatct aggtagtcca 360
gtagagcccc atagccacag cctagatcgt tgatcgaaaa tgggtccgcc gcattgacaa 420
tgcgcaccag ctggtcaaag cgcaacgcct gcccggcttc gccgttccaa tcgacgccgc 480
gcgggtgccg tgtgcttcga gtttcgatgc gtagtaacgg gccacgtcag cgagcatggt 540
cgttgcgtct tccgccatga agctgcctca cgatttgtgt gtgtgggcgt cggtgcgtgg 600
gtccgagact ataccttcaa cagttgcatg ccgaggctgc ggcgggcaat gacccaaaaa 660

-continued

```
cccgccggca cggttcgccg agcaaggaag cgtggagacg atagataatt tcactggcga    720
cagtacctca aatagtccgg agcctcggct ccgacgttaa agagcagatc cagaatcgac    780
acggcgggct cgaaccctcc ccacaattgc ttataatcgc ggtagccgtc ataatcgaac    840
caagttaccc ggatgctaag ttcgtcgaac acgcgctcat cgacatacga acgggctgag    900
gggccagaga catattcggt cgctgcggcc tgttggcaga ggttggccag tctctcggtc    960
ttgccgtcgg ctaattcgta gtcccacgaa tttgccagtc gcgtgctgat accgagataa   1020
ctgcaaatcg cattcaatag acgcctgttg agtaaggaaa gattcgtgtg ctgttcttcg   1080
aggtaaatcg gcgcgagcca gtcagcgatc tccgcaaaat gagcggccgc gctgtagttg   1140
aattctagtg cccgccagtg cgctttcgcc caatcggtgc cgtcgatcag cgtctcacgt   1200
atcttttgat ggaaacgtcc cttcacctgg acgggaacag ttatccactg taacccctgg   1260
ctcgttttga tccgatttct gtttcgccaa tcacgcttgg tatattgcat gtcatcatag   1320
atgatgaatt catcgacgaa tgcaatcagg tcaaaatatc ctcgccaagg tatgtaattt   1380
gattgaacaa tcgcgacttt cttcaacgcg gtgtctccaa tttagaataa caaatacgtc   1440
gcgcccgcga cagctccgct ggagcgagtt caagcgattc tgcgacatat tcaatatggt   1500
gctcgggaag gccaggatgg gccgcgaccc ggggcgtccg gtgcgcgatg aacgtcgcat   1560
cgtctcctgt gagataattg catccgatca tatagggctg gctgcggcta ggttgctggc   1620
aaaaagatat cgcggccgat ccgtttctgg ttttgtcttg atgatcaaat ccgcttccgt   1680
tcacgagatc gattcctggt cttcccccag cgtcgcgatg tcgataggtg tcgcgctttg   1740
ttcgtacccg cactacgcgg cggcgagaac ctcgccaccg aatcgggatt ggggggagga   1800
taccactcgg tcgaggcccg tcaccggcct tctagcgggt tgaccatcag tgtttgcagg   1860
gccctatccc ggtatggcgc accacgggat cggcagcgtt ccggttgctg gcgtggtacc   1920
tcgttgtggc gccgtggtcc atgtcgattg agtgcgtgga tcagtgtaaa ccgttgcgcg   1980
ccatgttctg taggcactgg ttcgggttgt ggttaggctg cacggttggc aggttaccaa   2040
ccactgagcc cctgggcgga tgtgagctcg gactccgcct atggggtgta attttggcag   2100
attgggccgg gtccccgtgg tgaggactcc tcaaccggat tgggtaagca tgaggtggtg   2160
ctggcagcgg tgtcctggtc gctctcccga gtaggcccgt tgtgactgtc atgtgggcga   2220
gcgggtttgc gcgcgtagga gacgatgatt actacgcacg tgaccaacca caagaacggt   2280
gcccatgtca ccgtggtgaa aacgagtggc gtggtaccga ctaccccttt ggctcccagc   2340
tgtccataga gcggcacgta gaacggctgg cccgggaccg cgacgttgac gatgctcagc   2400
gccacggcca aactcacgca gacgccgacc gcgcggcggc ggtctccatg ggctgcgagt   2460
tggtcgaata tcccagcacc aggaggcccg ttggggtctc gggctaccag tgcagcgatt   2520
ggcaagacga aaacgagata gtagaaggcg acgtccgcgg gggagaaggt ggcggtggcg   2580
agcaacacaa tccccaccat gacaggcggg atacggcgtc cgagcgccag cacggcgacc   2640
acgactatga ctaggacagc aaacccgatc tgcgttcgcg gaccagtgag gaaaccctct   2700
gggatcttgc ccgattgata gttcttgatg ctatcgggga tcagcaggag tgccttgcca   2760
aaggacacgt tccgcgggtc tcgaagccct ccgaacgaac tattgaactt gatgatgccg   2820
tggatcgact gtgcgatcgt ccccgggaag cctcgtggcc acaacagaaa ggctgcgata   2880
ttggacacca ccacgccggt gatcccgata ccagcccacc gccattgtcg agccgccaac   2940
aacaccacgc cgagaacgac gaactgcggc tttaccagga cggccaagat caccgtgatg   3000
gtggcgaggc cccaccgctg tcgggacaac gccacgaagt aagccagcgc gatcggtacc   3060
```

-continued acgaaccctg tcgagttgcc tcgatcgatg accccccacg ccgggatggc cgcggcgccc 3120
agtgtcacga agatgaccac tcgctccaga ccacgtgccc cccgggccgc ccagatggcg 3180
ggagatatga ccgccatcgt tagggcgacc aggtaacaga tcagccccaa gcgcggcgca 3240
cccagccaat ggctgggtag tccgaaaatc gcatacggta tgcgggcggg ggcccatgca 3300
gcaaccgcgg tcggctggta atcggcgggt agcgagatca ggtagtccgc gggattgggt 3360
tgaatcccgg cggcggcgac catggcgtag tcgctgaagc agtgccgacc gatattcatg 3420
ccccaatcaa gccaacagtc cccagggact accaaaagag tggaaaagac gtcgaccgcg 3480
taccactgac tgagggcgta cgccgtcgcc gccgaaatca ccgacgccag caggatggtg 3540
ccgagcatga gggtgcgctc ggattgggag ccgatcgccc agagccgctc ccggctcgcg 3600
gtcacggcac cgcgcaacac ctccgggggt cgcttcatct ggattctcct cggttctgcg 3660
cgaaacggta gcagagcgcc atggttgcca acgcggtcgc cgggcagtct agaccggatc 3720
ttcctcgtgg caaccgacaa caggacgtcg ttgccgaaag ggcgctgggc accgacatct 3780
aggatgaacc cacagccacg ccccgacgtt atgccatggc gaagagcgac cggcaggagc 3840
gggaacccag tgaagcgagc gctcatcacc ggaatcacag gaccggacgg ctcgtatctc 3900
gctaagctcc cgctgaaggg atatgtggcc gctggtagcc cggccgaggt ctatttctgc 3960
tgggcgacac ggaattatcg cgaattgtat gggttgctcg cggtcaacag catctggttc 4020
aatcacgaat caccgcgtca cggcgagaca ttcatgactc gtaatcctgc accatatcgc 4080
ggtcggcaac gaggcgctga tcgatgcgca gacgctgatg cgccggccca cccggatagg 4140
tatcagtatt ggggcgttcc ggccagcgta cgaggcgtga tcgaccgcgc aatgggtgtt 4200
tgcgttgagt aataatctga accgtgtgaa cgcatgcatg gatggattcc ttgcccgtat 4260
ccgctcacat gttgatgcgc acgcgccaga attgcgttca ctgttcgata cgatggcggc 4320
cgaggcccga tttgcacgcg actggctgtc cgaggacctc gcgcggttgc ctgtcggtgc 4380
agcattgctg gaagtgggcg ggggggtact tctgctcagc tgtcaactgg cggcggaggg 4440
atttgacatc accgccatcg agccgacggg tgaaggtttt ggcaagttca gacagcttgg 4500
cgacatcgtg ctggaattgg ctgcagcacg acccaccatc gcgccatgca aggcggaaga 4560
ctttatttcc gagaagcggt tcgacttcgc cttctcgctg aatgtgatgg agcacatcga 4620
ccttccggat gaggcagtca ggcgggtatc ggaagtgctg aaaccggggg ccagttacca 4680
cttcctgtgc ccgaattacg tattcccgta cgaaccgcat ttcaatatcc caacattctt 4740
caccaaagag ctgacatgcc gggtgatgcg acatcgcatc gagggcaata cgggcatgga 4800
tgacccgaag ggagtctggc gttcgctcaa ctggattacg gttcccaagg tgaaacgctt 4860
tgcggcgaag gatgcgacgc tgaccttgcg cttccaccgt gcaatgttgg tatggatgct 4920
ggaacgcgcg ctgacggata aggaattcgc tggtcgccgg gcacaatgga tggtcgctgc 4980
tattcgctcg gcggtgaaat tgcgtgtgca tcatctggca ggctatgttc ccgctacgct 5040
gcagcccatc atggatgtgc ggctaacgaa gaggtaatga catggcgcaa gcgacatcgg 5100
gcattcgcgc ggcactttcg caacctgctg tgtatgaggc gtatcagcgg attgcgggcg 5160
ctaaaagcgg gcttgcgtgg atcacaaccg accccatcca gtcgttgcca ggcatgcgta 5220
ctctcgacct cggttgctgg ccagcggtga tacacagctc cccgccagtg gacgtgacat 5280
gtacgagaga cggcatgagc gcggaatgtg cgaccgtgcc gtcgagatga ccgacgtcgg 5340
cgctacggca gcccccaccg gacctatcgc gcggggcagc gtcgctcggg tcggcgcggc 5400
gaccgcgttg gccgttgcct gcgtctacac ggtcatctat ctggcggccc gcgacctacc 5460

-continued

```
cccggcttgt ttttcgatat tcgcggtgtt ttggggggcg ctcggcattg ccaccggcgc   5520
cacccacggc ctcctgcaag aaacgacccg cgaggtccgc tgggtgcgct ccacccaaat   5580
agttgcgggc catcgtaccc atccgctgcg ggtggccggg atgattggca ccgtcgcggc   5640
cgtcgtaatt gcgggtagct caccgctgtg gagccgacag ctattcgtcg aggggcgctg   5700
gctgtccgtg gggctactca gcgttggggt ggccgggttc tgcgcgcagg cgaccctgct   5760
gggcgcgctg gccggcgtcg accggtggac acagtacggg tcactgatgg tgaccgacgc   5820
ggtcatccgg ttggcggtcg ccgcggcagc ggttgtgatc ggatggggtc tggccgggta   5880
cttgtgggcc gccaccgcgg gagcggtggc gtggctgctc atgctgatgg cctcgcccac   5940
cgcgcgcagc gcggccagcc tgctgacgcc cgggggaatc gccacgttcg tgcgcggtgc   6000
cgctcattcg ataaccgccg cgggtgccag cgcgattctg gtaatgggtt tcccagtgtt   6060
gctcaaagtg acctccgacc agttaggggc aaagggcgga gcggtcatcc tggctgtgac   6120
cttgacgcgt gcgccgcttc tggtcccact gagcgcgatg caaggcaacc tgatcgcgca   6180
tttcgtcgac cggcgcaccc aacggcttcg ggcgctgatc gcaccggcgc tggtcgtcgg   6240
cggcatcggt gcggtcggga tgttggccgc agggcttacc ggtccctggt tgctgcgtgt   6300
tggattcggc cccgactacc aaactggcgg ggcgttgctg gcctggttga cggcagcggc   6360
ggtagctatc gccatgctga cgctgaccgg cgccgccgcg gtcgcggccg cactgcaccg   6420
ggcgtatttg ctgggctggg tcagcgcgac ggtggcgtcg acgctgttgc tgctgctgcc   6480
gatgccgctg gagacgcgca ccgtgatcgc gctgttgttc ggtccaacgg tgggaatcgc   6540
catccatgtg gccgcgttgg cgcggcgacc cgactgattt gtgccccagg tcgacaaatc   6600
acgccgtctc gtcagtgagc actccgtcct cgggtccgat ccttccagga gacgttgcaa   6660
cctgatttgg ctcaaattgg tgcgcaccga gggtcgggca catcgtaggg tcgcaacagt   6720
cacatgtgtc actgcaccgg gcgacacccg atgtcccggc tctcagcgac agctgtctga   6780
cctgtggttt tgttcccaag ttggtcgtgg ctgtgcggga ttggaggtgg cgtgggggtc   6840
gcgtcgtatg gattctcctc ctcggttccg cgcgaaacgg ccgcaggcgc aatggtcacc   6900
aacttggccg cggtggagtc tagcctcaca ttttcctggt cgccccccgac aaccaggagg   6960
tcgctgcaga acgggcgttc cctacccaca tctactatga agcgacagcg gcgccccgct   7020
gtgatggctg agcatgaccg acagaggcgg gaagacagtg aagcgagcgc tcatcaccgg   7080
aatcaccggc caggacggct cgtatctcgc cgaactgctg ctggccaagg ggtatgaggt   7140
tcacgggctc atccggcgcg cttcgacgtt caacacctcg cggatcgatc acctctacgt   7200
cgacccgcac caaccgggcg cgcggctgtt tctgcactat ggtgacctga tcgacggaac   7260
ccggttggtg accctgctga gcaccatcga acccgacgag gtgtacaacc tggcggcgca   7320
gtcacacgtg cgggtgagct tcgacgaacc cgtgcacacc ggtgacacca ccggcatggg   7380
atccatgcga ctgctggaag ccgttcggct ctctcgggtg cactgccgct tctatcaggc   7440
gtcctcgtcg gagatgttcg gcgcctcgcc gccaccgcag aacgagctga cgccgttcta   7500
cccgcggtca ccgtatggcg ccgccaaggt ctattcgtac tgggcgaccc gcaattatcg   7560
cgaagcgtac ggattgttcg ccgttaacgg catcttgttc aatcacgaat caccgcggcg   7620
cggtgagacg ttcgtgaccc gaaagatcac cagggccgtg gcacgcatca aggccggtat   7680
ccagtccgag gtctatatgg gcaatctgga tgcggtccgc gactgggggt acgcgcccga   7740
atacgtcgaa ggcatgtggc ggatgctgca gaccgacgag cccgacgact tcgttttggc   7800
gaccgggcgc ggtttcaccg tgcgtgagtt cgcgcgggcc gcgttcgagc atgccggttt   7860
```

-continued

```
ggactggcag cagtacgtga aattcgacca acgctatctg cggcccaccg aggtggattc   7920
gctgatcggc gacgcgacca aggctgccga attgctgggc tggagggctt cggtgcacac   7980
tgacgagttg gctcggatca tggtcgacgc ggacatggcg gcgctggagt gcgaaggcaa   8040
gccgtggatc gacaagccga tgatcgccgg ccggacatga acgcgcacac ctcggtcggc   8100
ccgcttgacc gcgcggcccg ggtctacatc gccgggcatc gcggcctggt cgggtccgcg   8160
ctgctacgca cgtttgcggg cgcggggttc accaacctgc tggtgcggtc acgcgccgag   8220
cttgatctga cggatcgggc cgcgacgttc gacttcgttc tcgagtcgag gccgcaggtc   8280
gtcatcgacg cggcggcccg ggtcggcggc atcctggcca acgacaccta cccggccgat   8340
ttcctgtcgg aaaacctcca gatccaggtc aacctgctgg atgccgccgt ggcggcgcgg   8400
gtgccgcggc tgctgttcct gggctcgtcg tgcatctacc cgaaactcgc cccgcagccg   8460
atcccggaga gcgcgctgct caccggtccg ttggagccga ccaacgacgc gtacgcgatc   8520
gccaaaatcg ccggcatcct tgcggtccag gcggtgcgcc gccaacatgg cctgccgtgg   8580
atctcggcga tgcccaccaa cctgtacggg ccaggcgaca acttttcgcc gtccggctcg   8640
catctgctgc cggcactcat ccgccgctat gacgaggcca aagccagtgg cgcgcccaac   8700
gtgaccaact ggggcaccgg cacgccccga cgggagttgc tgcacgtcga cgacctggcg   8760
agcgcatgcc tgtatctgct ggaacatttc gacgggccga cccatgtcaa cgtgggaacc   8820
ggcatcgacc acaccatcgg cgagatcgcc gagatggtcg cctcggcggt aggctatagc   8880
ggcgaaaccc gctgggatcc aagcaaaccg gacggaacac cacgcaaact gctggatgtt   8940
tcggtgctac gggaggcggg atggcggcct tcgatcgcgc tgcgcgacgg catcgaggcg   9000
acggtggcgt ggtatcgcga gcacgcggga acggttcggc aatgaggctg gcccgtcgcg   9060
ctcggaacat cttgcgtcgc aacggcatcg aggtgtcgcg ctactttgcc gaactggact   9120
gggaacgcaa tttcttgcgc caactgcaat cgcatcgggt cagtgccgtg ctcgatgtcg   9180
gggccaattc ggggcagtac gccaggggtc tgcgcggcgc gggcttcgcg ggccgcatcg   9240
tctcgttcga gccgctgccc gggccctttg ccgtcttgca gcgcagcgcc tccacggacc   9300
cgttgtggga atgccggcgc tgtgcgctgg gcgatgtcga tggaaccatc tcgatcaacg   9360
tcgccggcaa cgagggcgcc agcagttccg tcttgccgat gttgaaacga catcaggacg   9420
cctttccacc agccaactac gtgggcgccc aacgggtgcc gatacatcga ctcgattccg   9480
tggctgcaga cgttctgcgg cccaacgata ttgcgttctt gaagatcgac gttcaaggat   9540
tcgagaagca ggtgatcgcg ggtggcgatt caacggtgca cgaccgatgc gtcggcatgc   9600
agctcgagct gtctttccag ccgttgtacg agggtggcat gctcatccgc gaggcgctcg   9660
atctcgtgga ttcgttgggc tttacgctct cgggattgca acccggtttc accgaccccc   9720
gcaacggtcg aatgctgcag gccgatggca tcttcttccg gggcagcgat tgacgcgccg   9780
gcgcgtcaat ctatttcgac attcgcgtga agacgttttc ccagaatcga ctgttgtagg   9840
cgtagaactc ccggccgcgt aggtaggcat gtgatattcg ccttcccccg aacgggtagc   9900
ggcgatgaag gtcgcccatg cggcgcagat caccgaagac cgcgcttggt tcccggtgcg   9960
agccgacgcc cgtggtgtcg aactcgcaca gcacacaccg aatcgtgacc ggctcgcata  10020
ccagcgcggc ccgcaatatg aattcctggt cggcggcgat cccgaaatca aggtcgtagc  10080
caccgatctt ggccaccagc gatgatccga agaacgatgc ttgatgcgga acaacctgct  10140
tgccggccag gaatttgcgc aggctgaaag gtatcgggcc gcgcacccga tcgagcccga  10200
cgagacgatc catcccgaag ccccacaatt cggacaccgg tcccttgccg gatagcgcct  10260
```

-continued ccacggcctg ggctaccacg tcgggcccgg aaaaacgatc ggcggagtgc aagaaccaca 10320
acagatcacc cgatgcgtgc gcgatgccct ggttcatcgc gtcgtaccgc ccgccgtcgg 10380
gctcggactg ccaatacgcg aagcctggtt cacacccgga caggtatgcc accacgtcgt 10440
cgccgctgcc accgtcgatt acgatgtgct cgatgcgtcc ccggtagcgt tgcgcccgca 10500
cacttttcac cgtgcgctgc aacccgtcga ggtcgttgaa cgagatcgtt atcaccgaga 10560
cggtcggagc agacgtcacc gagttcccct aggttgctgg cggcgattgt ggatcaccgg 10620
gtcttgatac cgatgaaggt gcctcgaaga ttcgccgcat aggaacctcc gagcaacgac 10680
tcggcgatgc ttggttccaa gttgtcgtac tcctccatca ccaggtcgac gccgacgtct 10740
ttgatggcct gaagtaggtg ctcgcgttga atccagaatg accggcgatt gtcccaggac 10800
gcccattttg cggtgtcgcg ctggccaaac gagcggtcgt cggaaaactc ggtaaaccac 10860
ctaccgggaa gtccctcatg ttcggtgggc gccgagagca tgaacttcac cggcgccggc 10920
cgccgcagca accgatcggt caattgtcgt gccgtcgtgg gcaaccggag ccatttatcg 10980
ctccggttga tgatcgagaa gtgcgtctgg agaatcagca gcttgttcgt taccgacgag 11040
agggtttcca ggtattgctt cggattctcc aggtggtaga agaggccgca gcagaagacg 11100
gtatcgaaga gcccgtggtt ggcgatgttg agggcgttgt cgtggacgaa ccggagattc 11160
ggcaggttgg tcttcgattt gatgtagttg caggccgcca tgttcagctc gcgaacctcg 11220
atcccgagga cctgaaatcc catgcgcgcg aacccgaccg cgtacccgcc ttccaagcag 11280
ccgacatcgg ccaggcgtag gtggctcttg tccccgggaa agacggtttc cagaatcccg 11340
cgcgccgaga tgaaccagga cgattcgtct aacgtgcgcg aggactccgg tatcgtcaag 11400
gttccgtcgt cgaggcgaac gttgtgggcg gtgaattgta ccgcgccggc cgaatgttcc 11460
tgtgccatca cttggttagc cccttcggct ggtcctgggt ttgtcgacat ggtcaggctc 11520
gacagccgcg tcggagccgg gagggccaca catccacgag ccccctgcgg ctcggcgtcg 11580
cggcggcgag cttgcgccac tgggtcttga gccgccgcgc gggtgtcgcc ccgcggtgct 11640
gcagcgccag catggcgatc cggggatggc gcgcgatggt ttcctgcagc gcggcgcgcc 11700
cctccgggcc tggaacgttg gcgatctggc gaaggatcca gtcggccatg acggcgatga 11760
gctcctcgcg cgcggggtct cccgggaaca ggtcgagcat cgcgtcaaac gtcgccgcat 11820
gccccggacc ctgcgtcaac cagaactttg gcgggtccac cacctggttg tgccacatgc 11880
cttgggcgtg gcggcgatac acggccatgg tgtcgggcaa catggcgatg tcgccatgca 11940
ccgcgtgccg gacgtgcaga taccagtcca ggggcatgac gtcggcagga atgtcgtcgt 12000
agcgctcgag gcgacggtac acggccgagt tggtctggat gaagttcatc aagatcaacg 12060
catccaggct caagttgccc cgcacccgaa ccggggggaa cttcgagtcc ttggcatggc 12120
cgtcctccca tatcactcgg acgggatgga agcacaccgt cgtcttgggg tgccggtcga 12180
ggaatgcgac ctgtttgctt agcttcagcg gatcgatcca gtagtcgtcc gcctcgcaca 12240
acgcgacgta ctcgccgcga gcggccgaca gggcgccggt caggttccca ttgaggccga 12300
ggttttcggt cctgaagatc ggccggaaca cgtgcgggta ccgctcggcg tactcacgga 12360
tgatcgccgg ggtggcatcg gtcgacgcgt cgtcggcgac gatgatctcc accgggaagt 12420
cggtttgctg gtcgagaaag ctgtcgaagg cctgacgggc gtagcccgcc tggttgtgag 12480
tggtcgagac gatgctcacc ttggggcaaa gctggggact caccgtcggc ccttttcctg 12540
cgcggccgca agggtattgc gatggcgaac gtgaatcgcc tgtgcccgcc ggccgtcggc 12600
cgtcgtggcc tggtggtcgg cggacgtacg gcacacgctg gcgaagtata gcgagggtgc 12660
actgacgttg ggctcgaacc gcgtggcgcg cggtgtgggc gcaccgtctc gagtcggtgc 12720
tggttggctc gc 12732

<210> SEQ ID NO 2
<211> LENGTH: 289
<212> TYPE: DNA
<213> ORGANISM: Mycobacterium tuberculosis

<400> SEQUENCE: 2
atactcaagc ttgccgcaat cgaaaccaac ctgtttgtgc cgcaagaaat tacgccgtgg 60
cccggcgccg atcaagaaac gccccggcgc gcggcggtgt cgtcgtatgg catgacgggc 120
accaatgtgc acgccattgt cgagcaggca ccggtgccag cccccgaatc cggtgcacca 180
ggcgacaccc cggccacacc cggtatcgac ggcgcgctgc tgttcgcgct gtcggccagc 240
tcgcaggacg cgctgcggca aaccgccgcg cggctggccg attgggtct 289

<210> SEQ ID NO 3
<211> LENGTH: 278
<212> TYPE: DNA
<213> ORGANISM: Mycobacterium tuberculosis

<400> SEQUENCE: 3
ttggcgggtt ggccacacac ccgccggtga cggcgacgat gctgggctgg ttgcggccct 60
gcgccaccgc ggcttgcatg ctggttggct gtcttgggac gatcccgaaa tagtccacgc 120
ggatctggtg attttgcggg ctacccgcga ttaccccgcg cggctcgacg agtttttggc 180
ctggactacc cgcgtggcca atctgctgaa ctcgcggccg gtggtggcct ggaatgtcca 240
cgccgttcac ctacgtgacc ttgatgggat ccgggggt 278

<210> SEQ ID NO 4
<211> LENGTH: 1280
<212> TYPE: DNA
<213> ORGANISM: Mycobacterium tuberculosis

<400> SEQUENCE: 4
ccgacccaga cactgaccgg gcgaccgctg atcggcaacg gcacccccgg ggcggtcggc 60
agcggggcca ccggggcccc cggtgggtgg ctgctcggcg acggcggggc cggcgggtcc 120
ggcgcggcgg gctcgggcgc gcccggcggg gcgggcgggg ctgccgggct gtggggtacc 180
ggcggggccg gcgggatcgg cggagccagc accgtactcg gcggcaccgg cgggggaggc 240
ggggtcggtg ggctgtgggg cgccggtggg gccggcgggg ccggtggaac cggccttgtt 300
ggtggcgacg gcggggccgg tggggccggc gggaccggcg gactgctggc cgggctgatc 360
ggtgccggcg gaggtcacgg cgggaccggc gggctcagca ctaatggcga cggcggggtt 420
ggcggggccg gcgggaatgc cggaatgctc gccgggccgg gcggcgccgg cggagccggc 480
ggtgacggcg aaaacctgga caccggtggg gacggcgggg ccggcggtag cgcagggctg 540
ctgttcggca gcggcggcgc cggcggcgcc ggcggatttg gtttcctcgg tggggacggc 600
ggggccggtg gcaacgccgg gctgctgttg tccagcggcg gggccggcgg gttcggcggg 660
ttcggcaccg ccggtggggt cggtggggcc ggcggcaatg ccggctggct gggcttcggc 720
ggggccgggg gcatcggcgg aatcggcggt aacgctaacg gggcgccgg tgggaacggc 780 ggcaccggcg gtcagttatg ggtagcggc ggcgccggcg tcgaaggcgg cgcagcctta 840
agcgtcggcg acaccggcgg ggccggtggc gtcggcggca gcgccgggct gatcggcacc 900
ggcggcaacg gcggcaacgg cggcaccggc gccaacgccg gcagccccgg aaccggcggc 960
gccggcgggt tgctgctggg ccaaaacggg ctcaacgggt tgccgtagcc gggcggcacg 1020
gcatggcttc cgggcgtcaa ccactcgccg gtgatgcaga tcggctgcgg agcgggccgc 1080
caaaatgggg gccgccgcgc caggtatctc ggcgaagatc cccggcgctc gagcgctttg 1140
tcagaggccc gtcgcgggtc gtcgtgacga cggctatccg ggcggtgcgg gtttcgcggc 1200
gcgccctgtg cccggcaccg ccgcccgttt gtcggcaacg ccgccgcgac ccgtgagccg 1260
tccagcagct ggcgcctgcg 1280

<210> SEQ ID NO 5
<211> LENGTH: 127
<212> TYPE: DNA
<213> ORGANISM: Mycobacterium tuberculosis

<400> SEQUENCE: 5
gggcatcggc ggaatcggcg gtaacgctaa cgggggcgcc ggtgggaacg gcggcaccgg 60
cggtcagtta tggggtagcg gcggcgccgg cgtcgaaggc ggcgcagcct taagcgtcgg 120
cgacacc 127

<210> SEQ ID NO 6
<211> LENGTH: 434
<212> TYPE: DNA
<213> ORGANISM: Mycobacterium tuberculosis

<400> SEQUENCE: 6
aatactcaag cttgcccagc cgtcgatgac aagaaatatg tccgcaaaag actcagcggc 60
cgactttgct cgcagctggc ggtaccgcgc caccgattct atgccgtggt cgcggaaaaa 120
tgcctcccga aatcgcacgg ccgactccag ttcggcgagc atccgcgatg ccagctgcgg 180
ctgcgccctg ccggccacgg cacccacatg cggcagttcg tccacctggg ccagcgcccc 240
gccgccgaat tccaaacaat agaactgcac ccggcccgca tcgtgggtaa cagccaacgc 300
catgatcagc gtccgcagcg cggttgactt gcccgtttgc ggtgcaccta cgaacgcgac 360
attgcctgcg gccccggaca agtcgatcgt gcgcggcacc cgtgactgct ctaacgggcg 420
attgaaattc cgat 434

<210> SEQ ID NO 7
<211> LENGTH: 332
<212> TYPE: DNA
<213> ORGANISM: Mycobacterium tuberculosis

<400> SEQUENCE: 7
ccacccgtgt aatttgggat gggcaaaaag gcgaagcacc gcgtggccac gaacgccggg 60
agggacaatc tcgggcggtt agggcttctc gcgggaaggc ccgaacgtac ggcgtttcaa 120
cacctcgcgt cgccctccga ccgcgaacat tcggggatgg cagcaacctg ctggcaccct 180
ggccgggcga tgatctgcag cgtcgccgcg ggtagtcgcc gcccgggcgg ctacactctg 240
aaacgcgatg accatcgatg tgtggatgca gcatcccgac gcaacggttc ctacaccgcg 300
atatgttcgc ctcgctgccc cggtggaccg gt 332

<210> SEQ ID NO 8
<211> LENGTH: 354
<212> TYPE: DNA
<213> ORGANISM: Mycobacterium tuberculosis

<400> SEQUENCE: 8
aatactcaag ctttccgccg atacccgcca tgtcgcgcac atccaggact tctgggggga 60
tccgctgaca gcggcgggat cccaaagtgc ggatgatcgg gccgcctacg tcgtggtgta 120
cctcgtcggt aacaacgaaa ccgaagcgta tgactcggtc cacgcggtgc ggcacatggt 180
ggacaccaca ccgccaccgc acggggtgaa ggcctatgtc accggtccgg cagcactcaa 240
tgccgaccag gccgagggcg gagacaaaag tatcgctaag gtcaccgcga tcaccaacat 300
ggtgatcgca gcaatgttgc tagtgatcta tcgctccgta attaccgcgg ttct 354

<210> SEQ ID NO 9
<211> LENGTH: 353
<212> TYPE: DNA
<213> ORGANISM: Mycobacterium tuberculosis

<400> SEQUENCE: 9
gtgccgttcc aacccgaatt ggctttcggc gccatcggtg aggacggcgt gcgggtgctc 60
aacgacgacg tcgtccgcgg gacacacctc gatgctgccg ccatggacgc ggtcgaacgc 120
aagcagctga tcgagctaca acgccgcgcg gaacgcttcc gccgcgggcg tgaccgcatc 180
ccgttgaccg ggcggatcgc ggtgatcgtc gatgacggca tcgccaccgg agcgacggcc 240
aaggcggcgt gccaggtcgc ccgggcgcac ggtgcggaca aggtggtgct ggcggtcccg 300
atcggcccag acgacatcgt ggcgagattc gccgggtacg ccgatgaggt ggt 353

<210> SEQ ID NO 10
<211> LENGTH: 279
<212> TYPE: DNA
<213> ORGANISM: Mycobacterium tuberculosis

<400> SEQUENCE: 10
aatactcaag ctttcggcgg aaacggacac attgcgaata ttgatgacaa aataaaaatc 60
attgatggtt tgagtcacca ggccgatcaa gccttcgccg agccaaattc caatcaagag 120
gcccaagccc gtaccaatca gcccggcaac gagggattcc gtcattatca gccaaaataa 180
ctgctctcgg gttacaccca aacagcgcaa tatggcgaaa aacggtcgcc gttgcacgac 240
attaaatgtc acggtattgt agattaaaaa gatacccac 279

<210> SEQ ID NO 11
<211> LENGTH: 376
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 11
tgctcccgaa acctgggggt gtgcctgctc tgtatgcacg gcatacggac atccttcccc 60
tgagacccgc ggtcgaacca gccacgtgtc catcatagng ggtcaacccc ggccaagggc 120
gacggcacgc caagttcgcc gaccgttaac ctagtgctgt tagcttcatt tgctgcgatc 180
aaaacagctg gtcggccgtt aggaactgaa ttgaaactca accgatttgg tgccgccgta 240
ggtgtcctgg ctgcgggtgc gctggtgttg tccgcgtgtg gtaacgacga caatgtgacc 300
gggggaggtg caaccactgg ccaggcgtcg gcaaaggtcg attgcggggg gaagaagaca 360
ctcaaagcca gtgggt 376

<210> SEQ ID NO 12
<211> LENGTH: 393
<212> TYPE: DNA
<213> ORGANISM: Mycobacterium tuberculosis

<400> SEQUENCE: 12
atactcaagc tttgccgacg agcgggcgat gttgatgacg ggaaacccca gcgcacaacc 60
gacgattttg gcgtagccgg cggacgtctg ctcgattccg atcacgtcgg cgctcgcatc 120
gagcatggcg ccggcgacgg ctagcagcga tccgccgtcg tcgaggagca cgacacgagc 180
cgtacgcccg gccgtaagcc gcgcccagga ttcggcgaaa aaccgttcta cgtggcgggt 240
gtactgggtg tcgaatgatt cgtggggtgc gtaggcgtcg ctgcaatcgt cgacatagat 300
gccgtcgggc cgcatcgcgt cgacaactcc gggtgagtgg aatagcactt gccgatcacc 360
gcgacgttgc gcggatgagg ccgaacccga ata 393

<210> SEQ ID NO 13
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 13
tcctatgtcc ctgccgagca ngtgatcgaa cgcggtgaca gatttgtcta tcctggacct 60
gacggtgagg tcgaagtttt ccaggaattc ggcaaaatcg gtaagagcct gaagaattcg 120
gtatcgccgg acgaaatctg cgacgcatac gggggcatat acgcttcggg tttacgagat 180
gtcgatgggg ccgctggagg cttcacgtcc atgggccaca aaggatgttg tcggcgcgta 240
ccgttttctg cagcgggtgt ggcgcttggt cg 272

<210> SEQ ID NO 14
<211> LENGTH: 286
<212> TYPE: DNA
<213> ORGANISM: Mycobacterium tuberculosis

<400> SEQUENCE: 14
atactcaagc ttgattccgc cgaaaccgac cgtgagcacc ccgccagcca ccacgctcgg 60
gtcgggcgcc gggcccgggc cgccaggctg ctccgctcgg tgatggcacg ccaccgcgac 120
accacccggc tgcgctacgt ctaaccattc caggcggagc tacatcagct cggccgccca 180
gtgttcgggc cctctttcca ggtcgaagtc tataccgata tgcgcatccg cagccgccac 240
cctggagaac agaacgatgc cctactaatg cttgtctggc ggggcc 286

<210> SEQ ID NO 15
<211> LENGTH: 357
<212> TYPE: DNA
<213> ORGANISM: Mycobacterium tuberculosis

<400> SEQUENCE: 15
ggtacgcttc ggtcgcagtc tgcgagtgat gcatgacgac cgggacctcg tcggcatctt 60
ccatagcccg ccacaccttc agttgctcac cggaatccaa ccggtagaag gtcggcgagc 120
gctcggcatt ggtcatcggg atatgccgct cgggacggtc agagccctcg ggtccggcca 180
gcactccgca ggcttcgtcg gggtggtcgc gacgcgcatg ggccaccatc gcattcacca 240
ggtctgcgcg aatcaccagc acgtagacgg ttcctttcct aagcaacacc gaagtttcag 300
gacccgaatg ctccgggaaa catgtcacgg taggtcggta ttccggctac cggctga 357

<210> SEQ ID NO 16

-continued

<211> LENGTH: 83
<212> TYPE: DNA
<213> ORGANISM: Mycobacterium tuberculosis

<400> SEQUENCE: 16
ggcgtcaacg gtgtcggaac ccgcgtcaag caattggtag gcctgcagtc tgtgaatcag 60
gccgacgctg tggccgccgc ggc 83

<210> SEQ ID NO 17
<211> LENGTH: 383
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 17
ggctngcgta cccggtaccg gccgcgggcc taccacgtgc cggaactgga agcgcagtaa 60
gccctcaacg cgccaccgct ttggcccgcg cgcccggcgt aggcgcatcg gcggtggccg 120
tggggcggcg cactgcgacc tcaccagcgg ctttcgagct ttgttcgatc aaccggccag 180
catggtcgan gatgcattcg agaccatatt cgaaattggt ttcatcgggg gccccgatcc 240
gatgccccct cccagttgcg tgagcaanca gcggagtcnt cgcgggatcg atggccacgg 300
ggtgttcaat ggcggatggt ccgctgcccg ccgactggct cttgcgggag aaccgatcta 360
gcaccaccga tccgcgcacg tng 383

<210> SEQ ID NO 18
<211> LENGTH: 603
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 18
cgtaatntcg cgcacancca ngacttctgg ggggatcngc tgacagtggt nggatcccaa 60
attgcggatg atcgggccgc cnacgtcgtt gtgtacctcn tcngtcacaa cnaanccgaa 120
ncgtatgact cggtccacgc ggtgcggcac atggtggaca ccacaccgcc accgcncggg 180
gtgaaggcct atgtcaccgg tccggcaaca ctcaatgccg accaggccga ngccggacac 240
nanagtatcn ctaacgtcac cgcgatcacg agcatggtga tcgnncaatg ttnctantga 300
tctatcgctc cgtaattacc gcggttctcg tcttgatcat ggtcgcancg aactccggcg 360
caatccgcgg attcatcgnc ttgctcgccg atcacatatt ttcagccttt cacattgcaa 420
cnaacctgct cgtctcatgg ngatgcggcg acacggacta ccgatatcat gctcgccgtt 480
acacaatcnc gccacgccgc gaagacngga aacgcttcta cacaatnttc ncgggacgcc 540
actnaacttg gttcnggttt gacattgccg cgcatgtntg cccagctttg ccggctcccc 600
tta 603

<210> SEQ ID NO 19
<211> LENGTH: 190
<212> TYPE: DNA
<213> ORGANISM: Mycobacterium tuberculosis
<220> FEATURE:
<221> NAME/KEY: unsure
<222> LOCATION: (various positions within the sequence)

<223> OTHER INFORMATION: applicants are uncertain of bases designated as “n”

<400> SEQUENCE: 19
tgaatttccc gatcccacaa tctcggttca gatacaggtc gccatacccc ttacttcggc 60
aacgctgggc ggattggccc tgcngctgca gcanaccatc gacgccatcg aattgccggc 120
aatctcgttc agccaatcca tacccatcga cattccgccg atcgacatcc cggccttcnc 180
cctttaacgg 190

<210> SEQ ID NO 20
<211> LENGTH: 506
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 20
aacagctatg accatgntta cgccaagcta tttaggtaac actatanaat actcaagctt 60
ttacggtgat cgcgcatcac ctggttcatg aactggaagc agcgcancgc ttccttttcg 120
gccgcaacat gagccagcct ctcgtccgcg gtcnggtgca ggtgctcggg cagctcggcc 180
gcgacagccg cctgaccctg aaaccagctt ccatatcccg cgacnaacna cnccagtccg 240
ctacgtaacc cctccgcgac tgtccatgga caacagcgcg ttctccaccg accgggcccg 300
ggtgtggggt gtttcggcga ccggcagcca ggtggtccac actgccgacg ggcgccgcga 360
gccgttcacc gaccaagccg ccgaacaagt ccgccccgatc gcatactcca accggttgcg 420
gtactgcagg tcagctggcg tacctcctcn tcncgctcgg cgaagtcttg ctccancacg 480
tcgcagaacg gcaaggaaca cgttca 506

<210> SEQ ID NO 21
<211> LENGTH: 388
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 21
gaccgnncca tgtttccaca atgtggtgcc agtncggngg ctacgtgcca tcnanacact 60
ggcgcaggct atcgcacccg ttatcngcta cgaacaaatc ncggtatgcg ttctttanca 120
tgagtcggcg accgncgatc atggtcgaca cccacgacng aaatacgcag atcgccntcn 180
agcntgtgtg ccgcggatta tcangactga cctcctggct gaccggnntg tntggtcgcg 240
atgcctggcg cccggccggc gtgntcgtgg tcggctcgga tagcgaagtc agctaattct 300
cgtggcagct cgaaagggtc ctgccggtgc cggtctttgc gcaaaccatg cncatgttac 360
ggtccctcgg gtgcggcctg gcggcggc 388

<210> SEQ ID NO 22
<211> LENGTH: 138
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 22
gggatgggcg ggcccgctaa actcttcgtg ttccactaac tccgggaggg ncaatctcgg 60
gccgttatgg ctcacgtcgc gtcgccctcc gaccgcgaac attcggagtt ggcagcaacc 120
tggtagcacc ctggccgg 138

<210> SEQ ID NO 23
<211> LENGTH: 142
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 23
nccgtcgttg acaagtaaat atgtccgcaa aagtctcagc ggccgacttt gctcgcaggt 60
ggcggtaccg cgccaccgag tcgatgccgt ggtcgcggaa gaatgcctcc cgaaatcgca 120
cggccttccc nntttaaacg ga 142

<210> SEQ ID NO 24
<211> LENGTH: 441
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 24
tttaggtgac actatagaat actcaagctt ttggtctagc cggccgagca cgatacgggt 60
gtcattggcc accggcggcg gctgtccggg aaatggcggg tccccggtgg ttttgctgat 120
gagtgctgaa ccgtantcga agtgggcggc gtcagactcc acccanccag caggcagcgc 180
gaagctgaat cctccaaccg ggttgtcnat ccggacaagt tggggtgcgt ttggggcaat 240
gacaggtggc ngcggtgcgt tcgggtccgc cggcggaagt gctgcgttgg gatcncccgc 300
tgggcattcg gcntttttgc ggcggccggt ggtngggggg caacaggtnt cccngtgcgg 360
gtggcgctca acggtcnacg gcgcaagccg ccgttgttgg taccnggggc gctggctccg 420
gatcgcgttg gcggtcnccg g 441

<210> SEQ ID NO 25
<211> LENGTH: 453
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 25
ctacaccatc gaatacgacg gcgtcgccna ctttccgcgg tacccgctca actttgtgtc 60
gaccctcaac gccattgccg gcacctacta cgtgcactcc aactacttca tcctgacgcc 120
ggaacaaatt gacgcagcgg ttccgctgac caatacggtc ggtcccacga tgacccagta 180
ctacatcatt cgcacggana acctgccgct gctagagcca ctgcgatcgg tgccgatcgt 240
ggggaaccca ctggcgaacc tggttcaacc aaacttgaan gtgattgtta acctgggcta 300
cngcgacccg gcctatggtt attcnacctc nccgcccaat gttgcgactc cgttcgggtt 360
gttcccanaa gtcnncccgg tcgtcatcgc cgaanctctc ntcccgggac ccacagggaa 420
tcngcnattt cncctacaaa tcanccacct cca 453

<210> SEQ ID NO 26
<211> LENGTH: 228
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 26
gcatgatcgg ccacctttcg ggccgcccgg catacggcgg cgtaccgatc tccgcgtcat 60
acacccgcgg gtaatcgccg acggtgccgg ttcgcgagcc gaaggtgacg actctgattg 120
aatcgagttc caggtccagc gggtggcgca ccaacggcgc gagctcaacg acgtcaatcn 180
cgttgtcgct ttctacggtc accgaccctg gtgaccgtag ttcncccg 228

<210> SEQ ID NO 27
<211> LENGTH: 357
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 27
gacactatag aatactcaag cttgccaacc gccagcctgc atccggcggc gancactgct 60
ccgccgacca gtacgaacca acctgcggtg cccaggccat tgacgatgtg ctggtcggcg 120
cccgcgagtc cgcgcaccat caacgccgcg ggcaccacca nggcggcccc accctgcacg 180
gcgacgatca ttccggcgcc gctcacggcg ggcggggctc gaacangcac agcatcaacg 240
tngtcacccg gccgtgaccg gcccgcatcg tcacaccacc caagcccatt gccgtcctcc 300
tcaacngggc gacccggccc gcatcgtcac acggnctaag gccattgccg tcctcct 357

<210> SEQ ID NO 28
<211> LENGTH: 384
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 28
tcggcgccat cggcaccttc gaggacctgt atttcgacgc cgtggccnac ctgaggttgg 60
cggtggacna agtgtgcacc cggttgattc gctcggcctt gccggatgcc acccngcgcc 120
tggtggtcga tccgcnaana gacaanttgt ggtggangct tctgctgcct gcgacaccca 180
cnacgtggtg gcaccgggca gctttagctg gcatgtcctg accgcgctgg ccgacnactc 240
cagacnttcc acnaanggtc gccnncccaa tgtnccgnan tgtctccggn tcccttttacc 300 ncccaatggg cngnttccac nggttacggg ccccntnccg gcgggtctnc ctcccaanct 360
accaaatacg cccgacnttc cgga 384

<210> SEQ ID NO 29
<211> LENGTH: 266
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 29
atactcaagc ttttatggtg atcgcgcatc acctggttca tgaactggaa gcagcgcagc 60
gcttcctttt cggccgcaac atgagccagc ctctcgtcgg cggtcgggtg caggtgctcg 120
ggcagctcgg ccgcgaacag cccggcttga accctgaaaa ccngctttcc atatcccgcg 180
acgaaagaac gccagttccg ctacttaacc cctccgcgaa ccgtccatgg acaacagcgc 240
gttctccacc aaccgggccc gggtgt 266

<210> SEQ ID NO 30
<211> LENGTH: 423
<212> TYPE: DNA
<213> ORGANISM: Mycobacterium tuberculosis

<400> SEQUENCE: 30
tcggctcagg ccgcgctgct ggtagagtcg ctgaccggtg caggtttcga caatgtggtg 60
ccggttcggc ggctacgtgc catcgagaca ctggcgcagg ctatcgcacc cgttatcggc 120
tacgaagcaa atcgcggtat gcgttcttga gcatgagtcg gcgaccgtcg tcatggtcga 180
cacccacgac ggaaagacgc agatcgccgt caagcatgtg tgccgcggat tatcaggact 240
gacctcctgg ctgaccggca tgtttggtcg cgatgcctgg cgcccggccg gcgtggtcgt 300
ggtcggctcg gatagcgagg tcagcgaatt ctcgtggcag ctcgaaaggg tcctgccggt 360
gccggtcttt gcgcaaacaa tagcgcaggt tacggtcgcg cggggtgcgg cctggcggcg 420
gcc 423

<210> SEQ ID NO 31
<211> LENGTH: 455
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 31
caagctattt aggtgacact atagaatact caagcttcgc gtctacgccg gcccggagca 60
tccgcacagc gctcagcagc cggttccgta cganctcaag caggtggcgc aatgaccgaa 120
accaccccag ccccgcaaac cccggcggcc ccggccgggc ccgcacaatc gttcgtgttg 180
gagcggccca tccanaccgt tgggcgccgt aaggangccg tggtacgaat gcggctggtg 240
cccggcaccg gcaagttcga cctcaacggc cgcagcttgg angactactt cccaaacaag 300
gtgcaccagc agttgatcaa ggcacccctg gtcaccgtgg atcgggtgga aagtttcgac 360
atctttgccc acctgggcgg cggcggccgt ccggtcaggc cgggcctgcc ctgggtatcg 420
cccgggcatt gattctggta tccccngaag aaccg 455

<210> SEQ ID NO 32
<211> LENGTH: 371
<212> TYPE: DNA

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 32
cggttggcca ccgcttctgc ggtgccgccg ccgtcgacaa tgaccgtgtc gtccttgctg 60
accaccacgc gtcgggccga gcccagcacc tccaagccca cctcgcgcag caccatgccg 120
gcgtcggggt tgaccacctg gccacccgtc accaccgcca ggtcctcaag gaaacgcctt 180
acggcggtca ccgaagtacg gccccttgac cgcgaccgct ttcaacgtct tgcgaatcgc 240
gttgacgacc agcgtcgcca acgcttcgcc ctccacgtct tcagccacga tcagtagtgg 300
cttacccgtt cctgcaacct tttccagcaa tggcaacaga tcgggaagcg anctgatctt 360
gtcttggtgc n 371

<210> SEQ ID NO 33
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 33
ccaagctatt taggtgacac tatagaatac tcaagctttt ggctgggtcg ccttcgaatt 60
cngcgtgcac cgctatgggt tgcancagcg gctggcgccg cacaccccac tggcccgggt 120
gttttcgccc cgaacccgga tcatggtgag cgaaaaggan attcncctgt tcgatgctgg 180
gattcgccac gccaaggcat ctancgatta ctctccncgg ggtgggaaaa gtgcccaatc 240
cccctccctc caactttccn aacaatcatt ccggttccnc cntccggttg gnggtaaccn 300
nccaataaaa cccctgcccg 320

<210> SEQ ID NO 34
<211> LENGTH: 383
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 34
gcccgcncat ggccaatccc cgaagacatc attggccagt ggccgggcgc taacaggttc 60 cagccccccca ccantgccgc tcgaacatgc ggtgcaaccc attcgcaggc cggcagggaa 120
agcaccgcgg aagccgcaaa gggctgcagt tccgcgccca ataatgtcgt ccgcaaccag 180
atgcgctcna aaaccncncc ggcagtcagc gcacccgacg cgangtcgaa agacgtcntc 240
agcgcgccca catggggtgc caatcggcac ggcaggtatg ccgcgcgcaa cccgagcgcg 300
tggtgcatgc ccacggtccg cangangcgc ancacccgcc aatgccgaan cccacgaaac 360
atcgggcgca tccaccttca acc 383

<210> SEQ ID NO 35
<211> LENGTH: 275
<212> TYPE: DNA
<213> ORGANISM: Mycobacterium tuberculosis

<400> SEQUENCE: 35
atactcaagc ttgcccagcc gtcgatgaca agaaatatgt ccgcaaaaga ctcagcggcc 60
gactttgctc gcagctggcg gtaccgcgcc accgagtcga tgccgtggtc gcggaagaat 120
gcctcccgaa ttcgcacggc caattccatt ccgggaagca tccgcaatgc cagctgcggt 180
tgccccctgc cggccacggc acccacttgc ggcattgcgt ccacctgggc cagcgccccg 240
ccgccaaatt ccaaacaata aaaattgcac ccggc 275

<210> SEQ ID NO 36
<211> LENGTH: 322
<212> TYPE: DNA
<213> ORGANISM: Mycobacterium tuberculosis

<400> SEQUENCE: 36
ccacccgtgt attttgggat gggcaaaaag gcgaagcacc gcgtggccac gaacgccggg 60
agggacaatc tcgggcggct agggcttctc gcgggaaggc ccgaacgtac ggcgtttcaa 120
cacgtcgcgt cgccctccga ccgcgaacat tcggggatgg cagcaacctg gtagcaccct 180
ggccgggcga tgatctgcag cgtcgccgcg ggtagtcgcc gcccgggcgg ctacagtctg 240
aaacgcgatg accatcgatg tgtggatgca gcatccgacg caacggttcc tacacggcga 300
tatgttcgcc tccctgcccc gt 322

<210> SEQ ID NO 37
<211> LENGTH: 167
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 37
ctgcccatgt ttggggacgc ccgaccagcc gatgctggag gcctacacgg cccttggtgc 60
gctggccacg gcgaccgagc ggctgcaact gggcgcgttg gtgaccggca atacctaccg 120
cagccngacc cctntcncaa naggatnttg ttcgccggac cccnctc 167

<210> SEQ ID NO 38
<211> LENGTH: 287
<212> TYPE: DNA
<213> ORGANISM: Mycobacterium tuberculosis

<400> SEQUENCE: 38
ccgactttcc gcggtacccg ctcaactttg tgtcgaccct caacgccatt gccggcacct 60
actacgtgca ctccaactac ttcatcctga cgccggaaca aattgacgca gcggttccgc 120
tgaccaatac ggtcggtccc acgatgaccc agtactacat cattcgcacg gagaacctgc 180
cgctgctaga gccactgcga tcggtgccga tcgtggggaa cccactggcg aacctggttc 240
aaccaaactt gaaggtgatt gttaacctgg gctacgcgac cgcccttt 287

<210> SEQ ID NO 39
<211> LENGTH: 322
<212> TYPE: DNA
<213> ORGANISM: Mycobacterium tuberculosis

<400> SEQUENCE: 39
atactcaagc tttgtcacac caagtgtttc gaccaggcgc tccatccggc gagtggatac 60
tcccagcagg tagcaggtcg ccaccacgct ggtcagtgcg cgttcagctc gcttgcggcg 120
ctgcagcagc cattcgggga aatacctgcc ctggcgcagc tgggggatcc caacttcaat 180
ggttgcggca cgggtgtcaa attcacggtg gcggtagccg ttgccctaat tggaccgctc 240
atcgctgctt tcgcggtacc ccgccccgca cagggcttcg gcttcagccc ccatcagggc 300
ggcaataaac ttcaagagca cc 322

<210> SEQ ID NO 40
<211> LENGTH: 471
<212> TYPE: DNA
<213> ORGANISM: Mycobacterium tuberculosis

<400> SEQUENCE: 40
gaggcagctt cgccggcaat tctactagcg agaagtctgg cccgatacgg atctgaccga 60
agtcgctgcg gtgcagccca ccctcattgg cgatggcgcc gacgatggcg cctggaccga 120
tcttgtgccg cttgccgacg gcgacgcggt aggtggtcaa gtccggtcta cgcttgggcc 180
tttgcggacg gtcccgacgc tggtcgcggt tgcgccgcga aagcggcggg tcgggtgcca 240
tcaggaatgc ctcaccgccg cggcactgca cggccagtgc cgcggcgatg tcagccatcg 300
ggacatcatg ctcgcgttca tactcctcga ccagtcggcg gaacagctcg attcccggac 360
cgcccagcgc attggtgatg gaatcggcga acttggccac ccgctgggtg ttgacatcct 420
cgacggtggg caattgcgcc tcggtaagct ttgccgcgta gccttttcat c 471

<210> SEQ ID NO 41
<211> LENGTH: 247
<212> TYPE: DNA
<213> ORGANISM: Mycobacterium tuberculosis

<400> SEQUENCE: 41
atactcaagc ttcactgaca agggacgaat tcgtcggccg cctgttcgac tgggtggtgg 60
ccgagctggt cgccaccact caggccgcgg tcacggcggt accggcgcgg gagcaaactc 120
gcgcgggcat ggccaacttc ttgcggacca tcaccgcaga cgcccgcttc ggacccctgc 180
tgtccaccac acagttggcc aacgcattaa tcacccgcaa gcttgcggaa tccaccgccc 240
tgttcgc 247

<210> SEQ ID NO 42
<211> LENGTH: 325
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 42
tccatcaccc gatgtggcng gagcactgcc atgtcgatct caactaccac ctccggccgt 60
ggcggttgcg cgccccgggg ggtccgcgcg aactcgacga ggcggtcgga gaaatcgcca 120
ncaccccgct gaaccgcgac cacccgctgt gggagatgta cttcgttgag gggcttgcca 180
accaccggat cgcggtggtt gccaaaattc accatgcgtt ggctgacggt gttgcctcgg 240
caaacatgat ggcacggggg atggatctgc cgccgggacc ggaggtcggc cgctatgtgc 300
ctgaccccgc tcctaccaag cggca 325

<210> SEQ ID NO 43
<211> LENGTH: 221

-continued

<212> TYPE: DNA
<213> ORGANISM: Mycobacterium tuberculosis

<400> SEQUENCE: 43
agctttgcag ttgctgagta atgtcggcca acgtcaccac aaccgcgatg aattcaatca 60
tgccgcccag ggcggccaac ccaatggtgg ccgcgagcgg cagctcgatc gcagcgcgga 120
ggttgccggc cgccagttga ttcacgaaca gggtgaggtc ataggcgggc aggatagtga 180
cgaaggcaag acctccatct gccgtcggaa gaagtatcga g 221

<210> SEQ ID NO 44
<211> LENGTH: 285
<212> TYPE: DNA
<213> ORGANISM: Mycobacterium tuberculosis

<400> SEQUENCE: 44
agcttcagaa caggcctgtt gtgggcgcac ccggctcgcc gagttctgca cgcaccgcct 60
caagtgcggc ccgcaccgcc ggcatctccc ggtcacgcag ggccgcggcc cgcgccgcag 120
cgacggcgtg ttcgcgcagt tcgccgtcaa tgatgctgac ctgatcggcc acccgggcgt 180
tctcggcgtc gtcgcgttca ctaatcgcgg tgctcagcag cgtctcgaca gccaccaccc 240
gagtggcgac cagctgctcc accacggacc gcagcgatgc ccgtc 285

<210> SEQ ID NO 45
<211> LENGTH: 179
<212> TYPE: DNA
<213> ORGANISM: Mycobacterium tuberculosis

<400> SEQUENCE: 45
atactcaagc ttcagttcct ccacgacgcg ttcccaaatg aatttcccga tcccacaatc 60
tcggttcaga tacaggtcgc catacccctt acttcggcaa cgctgggcgg attggccctg 120
ccgctgcacc aaaccatcaa cgccttcaaa ttgccggcaa tctcgttcag ccaatccat 179

<210> SEQ ID NO 46
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 46
gctctacgcc gcctacgggt cgaacatgca tcccgagcag atgctcgagc gcgcacccca 60
ctcgccgatg gccggaaccg gctggttacc cgggtggcgg ctgacgttcg gcggcgagga 120
catcngctgg gaaggggcgc ttgccaccgt cgtcnaagac ccaaattcga aggtgttcgt 180
cgtgctctac gacatgaccc cggcggacga gaagaacctt gaccggtggg aaggctccga 240
gttcggtatc caccagaaga tccgatgccg cgtggagcgc atttcctcgg acaccacaac 300
gggatcccgt cctcg 315

<210> SEQ ID NO 47
<211> LENGTH: 285
<212> TYPE: DNA
<213> ORGANISM: Mycobacterium tuberculosis

<400> SEQUENCE: 47
atactcaagc ttgccaaaga gacctcgtcc accaagcagg acgcgaccgt cgaggtggcg 60

-continued

```
atccggcttg gcgtcgaccc gcgtaaggca aaccagatgg ttcgcggcac ggtcaacctg    120

cccacaccgg cactggttaa gaactgcccg cgtcgcggtt ttcgcggttg gtgaaaaggc    180

caatgcctgc gtttgccgtg gggcggatg  ttgtcgggag tgacaatctg atcaaaagga    240

ttcagggcgg ttggctggaa ttcaatgccg caatcgcgac accgg                    285
```

<210> SEQ ID NO 48
<211> LENGTH: 369
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 48

```
ccacggcgtg gatcaaggta ccggccggga tgttgcgcaa tggcaggttg ttgcccggct     60

tgatgtcggc gttagcgccg gattccacca catccccttg cgaaagtccg ttgggtgcaa    120

tgatgtagcg cttctcccca tcgagatagt ggagcaacgc aatccgtgcg gtacggttcg    180

ggtcgtactc gatgtgcgcg accttggcgt tgacaccatc tttgtcattg cggcgaaagt    240

cgatcatccg gtaagcgcgc ttatgaccgc cgcctttgtg ccgggtggta atccggccat    300

gcgcgttgcg tccaccgcga cgtgcagcgg gcgcaccagc gacttctccg gggttgaccg    360

ggtnatctc                                                            369
```

<210> SEQ ID NO 49
<211> LENGTH: 461
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 49

```
gcagcatgac ggcggtagcg aacaccgccg gatgcagcgc aagtagcgtc gatgtgctca     60

cggaatcgcc ccggcaccgc gatctcgang atcaccagtg ccaccccctg cagcgcnaca    120

ccgacgattc cgtacaccgc cacgccgatc aggccctggg ccatctgatt ggagctggcg    180

tanatggcgg cgatggtgac gatggccagc gccacataca ttgtggcggc cagaaccacg    240

gcgttggggc ggcggtcgat gaacactagg cgacgcagat cgcccggggt caacaggttg    300

accatcagaa agcctgcgac tagcacggcg gcgccactag gaagtacaag aangtggcca    360

ccaccccatg caggatcggg gtaaggctga tggtcccgaa atcgactccg gcctaataca    420

tgactctctc ctttgcgtca tcgccttact tgtgcgcgga a                        461
```

<210> SEQ ID NO 50
<211> LENGTH: 127
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 50

```
gggacacacc tcgatgctgc cgcnatggac gcggtcgaac gcaagcagct gatcgagcta     60

caacgccgcg cggaacgctt ccgccgcggg cgtgacgcat cccgttgacc ggccgggancn    120
```

ctctcta 127

<210> SEQ ID NO 51
<211> LENGTH: 305
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 51
tgggcgcctc tttcggcctt cccnntttaa acgnagcang acattctggg tatcgagttg 60
tactggatgg tgttggcgat gtcggtgatc ctgctcctgg cggtgggatc cgactacaat 120
ctgctgctga tttcccggtt gaaagaggaa attggggccg gattgaacac cggaattatc 180
cgtgccatgg ctggtaccgg gggagtggtg acggctgccg gcatggtgtt cgccgttacc 240
atgtcgttgt ttgtgttcag cgatttgcga attattggtc agatcggtac caccatcgcc 300
ttccc 305

<210> SEQ ID NO 52
<211> LENGTH: 449
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 52
ccgatcggcg ccgcanctgg ttggtgttnc ggatgaatcc gcagcgaaaa tgtagctgcg 60
gtggcgtgtc gtgactcgtn ggcgtcgacg ctcgtggcag ccaccgancg gttggtccag 120
gatctggatg ggcaaagttg tgcggcccgg ccggtgacgg ccgatgagct gaccgaggtc 180
gacagcgccg tgttggctga cttggaaccg acatggagtc gccccggttg gcgtcacctc 240
aagcatttca atggttatgc gaccagtttt tgggttacgc cgtcagacat cacgtcggag 300
acttggatga gctgtgtctg ccagatagcc ccgaatcggg acgaccgtgg tcacggtgcg 360
tctgaccact cgggtcgggt cgcccgcgct atcggcatgg gtgcgtnatc acagcgacac 420
gcgcctgccc aaggangtnc ggncggacc 449

<210> SEQ ID NO 53
<211> LENGTH: 160
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 53
cgggttgcgg atccacgcgt gcgggttgtc agcagctacg gcactgaacc gcgcccacag 60
ctcgccgatc cgctttcggt ggttctcgat cgactcgccg taggcgatgc gcagcgcctg 120
ctcgaatatc gggtacacgt aggccggcct tcccncttta 160

<210> SEQ ID NO 54
<211> LENGTH: 308
<212> TYPE: DNA

<213> ORGANISM: Mycobacterium tuberculosis

<400> SEQUENCE: 54
cttgattttg atcatcatga cgatcatcac cctaattttg ctacccgcac tggttatcgt 60
gggtaccgtc gtgctttcca tgggcgcctc tttcgggctt tccgtattgg tctggcagga 120
cattctgggt atcgatttgt actggatggt gttggcgatg tcggtgatcc tgctcctggc 180
ggtgggatcc gactacaatc tgctgctgat ttcccggttg aaaaaggaaa ttggggccgg 240
attgaacacc ggaattatcc gtgccatggc tggtaccggg ggagtggtga cggctgccgg 300
catggtgt 308

<210> SEQ ID NO 55
<211> LENGTH: 460
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 55
ggggatccct agatcgacct gcaggcatgc aagcttggcg tgtcgttcca acccgaattg 60
gctttcggcg ccatcggtga ggcgggacac acctcgatgc tgccgccatg gacgcggtcg 120
aacgcaagca gctgatcgag ctacaacgcc gcgcggaacg cttccgccgc gggcgtgacc 180
gcatcccgtt gaccgggcgg atcgcggtga tcgtcgatga cggcatcgcc accggagcna 240
ctgtcaaggc ggcgtgccag gtcgcccggg cgcacggtgc ggacaaggtg gtgctggcgg 300
tcccgatcgg cccagacgac atcgtggcga gattcgncgg gtacgccgat gaggtggtgt 360
gtttggcgac gccggcgtng ttcttcgccg ncgggcangg ttaccgcaac ttcacccaga 420
cctccgacga cgaggtggtg gcgtctcctg gatcgtgctc 460

<210> SEQ ID NO 56
<211> LENGTH: 299
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 56
aaggctgcag gtcgaagcgg ntggttacga ctccctgtgt gtgatggacc agttctacta 60
tctgcgtcta cacggccctt ggtgcgctgg ccacggcgac cgagcggctg caactgggcg 120
cgttggtgac cggcaatacc taccgcagcc ccgaccctgc tggcaaagat natcaccacg 180
ctcgacgtgg ttagcgccgg tcgagcgatc ctcggcattg gagccggcgg gtttgaactg 240
gaacaccgcc agctcggctt cgagtccggc acttccagtg accggttcaa ccggctcga 299

<210> SEQ ID NO 57
<211> LENGTH: 373
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 57

```
ctttccgcgg tacccgctca actttgtgtc gaccctcaac gccattgccg gcacctacta     60

cgtgcactcc aactacttca tcctgacgcc ggaacaaatt gacgcngcgg ttccgctgac    120

caatacggtc ggtcccacga tgacccagta ctacatcatt cgcacggaga acctgccgct    180

gctacagcca ctgcgatcgg tgccgatcgt ggggaaccca ctggcgaacc tggttcaacc    240

aaacttgaag gtgattgtta acctgggcta cggcgacccg gcctatggtt attcgacctc    300

gccgnccaat gttgcgactc cgttcgggtt gttccagang tcagcccggt cgtcatcgcc    360

gacgctctcg tcn                                                       373
```

```
<210> SEQ ID NO 58
<211> LENGTH: 338
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 58

cggtcatagc cctcgggtcc ggccagcact ccgcaggctt cgtcggggtg gtcgcgacgc     60

gcatgggcca ccatcgcatt caccaggtct gcgcgaatca ccagcacgta gacggttcct    120

ttcctaagca acaccgaagt ttcacgaccc gaatgctccg ggaaacatgt cacggtaggt    180

cggtattccg gctaccggct gagcattgag cacgccggcc agcaccgcac gagccaggca    240

atcagccgcc gccgcaccga tcgcggtgac cagctgagtc tccggagaca atgcggccgg    300

cacgccggnc tccggcggca ccgctacngc gcccgtgg                            338
```

```
<210> SEQ ID NO 59
<211> LENGTH: 374
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 59

gtgatggcac gccaccgcga caccacccgg ctgcgctacn tcgagccata ccgggcggag     60

ctacatcggc tcggccgccc agtgttcggg ccctctttcg aggtcgaggt cgataccgat    120

ttgcgcatcc gcanccgcnc cctggacgac agaaccgtgc cctacgagtg cttgtcgggc    180

ggggccaaag aacagcttgg catcctggcg cgattggccg gcgcggcgct ggtcgccaag    240

gacgacgccg ttccggtgct gatcgacgac gcgctggggt tcaccgatcc ggagcgacta    300

tcaagatggg ggaggtctct gacaccatcg gccccnacgg acatgtgatc gtgccgacgt    360

gcagtcccac cccg                                                      374
```

```
<210> SEQ ID NO 60
<211> LENGTH: 448
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 60
```

-continued

```
gcgaaagtcc gttgggtgca atgatgtagc gcttctcccc atcgagatag tggagcaacg     60

caatccgtgc ggtacggttc gggtcgtact cgatgtgcgc gaccttggcg ttgacaccat    120

ctttgtcatt gcggcgaaag tcgatcatcc ggtnngcgcg cttatgaccg ccgcctttgt    180

gccgggtggt aatccggcca tgcgcgttgc gtccaccgcg accgtgcagc gggcgcacca    240

gcgacttctc cggggttgac cgggtgatct cggcgaaatc agatacgctg gcgccgcgac    300

gaccaggcgt cgtgggcttg tncttgcgaa ttgncatgtc taatcangtc tttctctcac    360

gctctcgtcg ccgggctagg ccgcattgcc ctgctcctcc tcatcgcttc gctctgcatc    420

gtccccgggc taagcccgtg ccccgaaa                                        448
```

<210> SEQ ID NO 61
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 61

```
gatggttcgc ggcacggtca acctgccaca cggcactggt aagactgccc gcgtcgcggt     60

attcgcggtt ggtgaaaagg ccgatgctgc cgttgccgcg ggggcggatg ttgtcgggag    120

tgacgatctg atcgagagga ttcagggcgg ctggctggaa ttcgatgccg cgatcgcgaa    180

caccggatca gaatggccaa agtcggtcgc atcgctcggg tgctgggtcc gcgcggcctg    240

atgcccaacc cgaaaaccgg caccgtcacc gccgactccc catggcgtcc cggatatcaa    300

gggccggcaa atcaacttcc cggttgatca gcaaggcaac ctgcctccnc ctccgg         356
```

<210> SEQ ID NO 62
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 62

```
atactcaagc ttcgtcataa gaccatggtg cgctttcttt cacccgtcca gagtcggggg     60

catccgcacc ggctcgcatc gcatcatcct cccacgacgg gccgctcatc agcttgggcc    120

atttcaatgt acttgatacc ccgcgctgcg ggtaggccac tgcgacaatt caaacacggt    180

gtcacacggt gaatagtgtc gagatgggct ctgatcaacc gtcgcaaacc cggtttcgca    240

tcaatagcgg aatcccaccg ggttgcatgg aggctgctga ccttggaaaa caaaattttt    300

tcattacaac aaaacaaccg ccncggaaac tttgca                               336
```

<210> SEQ ID NO 63
<211> LENGTH: 489
<212> TYPE: DNA
<213> ORGANISM: Mycobacterium tuberculosis

<400> SEQUENCE: 63

```
cgaattcggc gtgcaccgct atgggttgca gcagcggctg gcgccgcaca ccccactggc     60

ccgggtgttt tcgccccgaa cccggatcat ggtgagcgaa aaggagattc gcctgttcga    120

tgctgggatt cgccaccgcg aggccatcga ccgattactc gccaccgggg tgcgagaggt    180
```

gccgcagtcc cgctccgtcg acgtctccga cgatccatcc ggcttccgcc gtcgggtggc 240
ggtagccgtc gatgaaatcg ctgccggccg ctacctgcaa ggtgattctg tcccgttgtg 300
tcgaagtgcc tttcgcgatc gactttccgt tgacctaccg gctggggcgt cggcacaaca 360
ccccggtgag gtcgtttttg ttgcagttgg gcggaatccg tgctctgggt tacagccccg 420
aactcgtcac ggcggtgcgc gccgacggag ttgttatcac cgatccgttg gccgtaccgc 480
gccttgggc 489

<210> SEQ ID NO 64
<211> LENGTH: 448
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 64
tcagactcca cccagccagc aggcagcgcg aagctgaatc ctccaaccgg gttgtcgatc 60
cggacaggtt ggggtgcgtt tggggcaatg acaggtggcg gcggtgcgtt cgggtcggcc 120
ggcggaggtg ctgcgttggg atcgcccggc tgggcattcn gcgtgttggc ggcggccggt 180
ggtggggggg caacaggtgt cgccggtgcg ggtggcgctg cagcggtcga cggcggcgaa 240
gcggccgttg tgggtaccgg gggcgctggc tccggatcgg cgttggcggt cgcgggcacc 300
gcaacggtca ccaagctggc gctggccatc gccgcgatag ccagtgccgc caatcgtccc 360
ttgcgacgtg tcaagtnggg gtccacctga tgcatggcca aagaacctac cgtgttaacg 420
gcncaacnca aggaccgcgc cggtcgcn 448

<210> SEQ ID NO 65
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 65
tttccgcggt acccgctcaa ctttgtgtcn accctcaacg ccattgccgg cacctactac 60
gtncactcca actacttcat cctgacgccg gaacaaattg acgcagcggg tccgctgaac 120
aattcggtcc gtcccacgaa agaaccagtt ttncntcttt cncacggaga acctgccgct 180
gctagagcca ctgcgatcgg tgccgatcgt ggggaaccca ctggcgaacc tgtgtttcaa 240
ccaacactta gagtgtaatt gtaaacctgg gctaggggaa accggctcta gtttttccac 300
cntctccgcc ccntgtttcg aatactccgt tcgggttgtc cccaaa 346

<210> SEQ ID NO 66
<211> LENGTH: 277
<212> TYPE: DNA
<213> ORGANISM: Mycobacterium tuberculosis

<400> SEQUENCE: 66
gcttccggct cgtatgttgt gtggaattgt gaccggatac caatttcaca caggaaacag 60
ctatgaccat gattacgcca agctagttag gtgacactat acaatactca agcttgccgg 120
ctggtgggcc gaccacttcg atggcacgac ccgtgaactg ctgcccggcc aattcttctt 180
ggtcgcccgg accgatggac cgcggctggg attccagaag gtgcccgatc ccgcccctgg 240
gaaaaaccgc gtgcacctct acttcacgac caacgac 277

<210> SEQ ID NO 67
<211> LENGTH: 434
<212> TYPE: DNA
<213> ORGANISM: Mycobacterium tuberculosis

<400> SEQUENCE: 67
ccgatcgact gatgcgccga caaccacgcc ccaacaactg gaatgaaccg tcgtgaccat 60
catcagcacg cggttgtagg cgacttgcga catgttcaac ccgccgtact cggacggaat 120
cttcaaaccg aaacagccca gctcggccag gcctttcacg tactcgtcgg ggatctgggc 180
accacgctcg aggacgctgc cgtccacggt gtctaggaat tcccgcagtt tgaccagaaa 240
cgcctcggtt cgggcctcct cggcgtccga cggcttggga aatgggtgta tgagccctac 300
gggaaaccgg cccacaaaga gttctttggc gaaggacggt ttatcccaac cactttcgcg 360
agattcctcg gcaagggccc gcgcttgctc ctcggtgacc tgagtttgct gtgccatcgc 420
cgcctcctcc ctga 434

<210> SEQ ID NO 68
<211> LENGTH: 465
<212> TYPE: DNA
<213> ORGANISM: Mycobacterium tuberculosis

<400> SEQUENCE: 68
tgcatccggc tcgtatgttg tgtggaattg tgagcggata acaatttcac acaggaaaca 60
gctatgacca tgattacgcc aagctattta ggtgacacta tagaatactc aagcttttac 120
ggtgatcgcg catcacctgg ttcatgaact ggaagcagcg cagcgcttcc ttttcggccg 180
caacatgagc cagcctctcg tcggcggtcg ggtgcaggtg ctcgggcagc tcggccgcga 240
cagccgcctg accctgaaac cagcttccat atcccgcgac gaacgacgcc agtccgctac 300
gtaacccctc cgcgactgtc catggacaac agcgcgttct ccaccgaccg ggcccgggtg 360
tggggtgttt cggcgaccgg cagccaggtg gtccacactg ccgacgggcg ccgcgagccg 420
ttcaccgacc aggccgccga gcaagtccgc ccgatcgcat actcc 465

<210> SEQ ID NO 69
<211> LENGTH: 463
<212> TYPE: DNA
<213> ORGANISM: Mycobacterium tuberculosis

<400> SEQUENCE: 69
gggggcgctg ctggtatagt cgctgaccgg tgcaggtttc gacaatgtgg tgccggttcg 60
gcggctacgt gccatcgaga cactggcgca ggctatcgca cccgttatcg gctacgagca 120
aatcgcggta tgcgttcttg agcatgagtc ggcgaccgtc gtcatggtcg acacccacga 180
cggaaagacg cagatcgccg tcaagcatgt gtgccgcgga ttatcaggac tgacctcctg 240
gctgaccggc atgtttggtc gcgatgcctg gcgcccggcc ggcgtggtcg tggtcggctc 300
ggatagcgag gtcagcgaat tctcgtggca gctcgaaagg gtcctgccgg tgccggtctt 360
tgcgcaaacg atggcgcagg ttacggtcgc gcggggtgcg gcctggcggc ggccagagca 420
cgagttcacc gatgcgcagc tagtggcgac agcgtcagcc aac 463

<210> SEQ ID NO 70
<211> LENGTH: 447
<212> TYPE: DNA

<213> ORGANISM: Mycobacterium tuberculosis

<400> SEQUENCE: 70
tgcttccggc tcgtatgttg tgtggaattg tgagcggata acaatttcac acaggaaaca 60
gctatgacca tgattacgcc aagctattta ggtgacacta tagaatactc aagcttccgt 120
acaggtcgcc tccaacacgg cggggaagcg acaccagcct accgagcttg gagtccagga 180
cgccagcggc ggcgtcggtc tgcgtcgtgg tgccgccggg gtggcgttgg ctggcaacga 240
tctccaccca gccggtcggg ttacccacga tctcggcata gacgcgggcc gaggccggtg 300
cgataccgta ttgcgtcaat tgggacgcgg ttgtgcattc ggctagctcg gttgccacac 360
ccgtcagggg ttcgacgttg gcgggttcgg cgggccccag caccgctgtc accatgcccg 420
ccaagccgac ctgcggcgcc accaact 447

<210> SEQ ID NO 71
<211> LENGTH: 460
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 71
cggcatgacc accgacaggc ccgactggtc gtaccactcg aacgccgggg tgttgatgtc 60
ccagccgctg aagtcgtcct gcgcgcgcag gccgtcgagc aggtacaggg cgggcgagtt 120
ggcaccacca ctttggaatt ggaccttgat gtcacggccc atcgacggcg acggcacctg 180
caggtactcc accggcaagc ccggccggga aaatgccccc gcggtcgccg tgccaccgac 240
ggcgccgacc agacccgaca ctagggccgc gccgacggcc ccgaccacga gtcgacgcga 300
catacccgtg acggcgccac gaaccctgtc aacaagctgc attcttgctt ccctcatcct 360
catctcaacg catccatgca tgtttgggcg catcctgaat tangtcagac tgcaggcgct 420
gggccggcag tgctcgtgta tcaaccacaa cttcgggcgt 460

<210> SEQ ID NO 72
<211> LENGTH: 404
<212> TYPE: DNA
<213> ORGANISM: Mycobacterium tuberculosis

<400> SEQUENCE: 72
ttccaaccct aattggcttt cggccccatc cgtgaggacg gggtgcgggt gctcaacaac 60
aacgtcgtcc gcgggacaca cctctatgct gccgccatgg acgcggtcca acgcaagcag 120
ctgatcgagc tacaaccccg cgcggaacgc ttccgccgcg ggcgtgaccg catcccgttg 180
accgggcgga tcgcggtgat cgtcgatgac ggcatcgcca ccggagcgac ggccaaggcg 240
gcgtgccacg tcgcccgggc gcacggtgcg gacaaggtgg tgctggcggt cccgatcggc 300
ccaaacgaca tcgtggcgag attcgccggg tacgccgatg aggtggtgtg tctggcgacg 360
ccggcgttgt tcttcgccct cgggcagggt taccgcaact tcac 404

<210> SEQ ID NO 73
<211> LENGTH: 465
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 73
caggcatgca agctttccgc cgatacccgc catgtcgcgc acatccagga cttctggggg 60
gatccgctga cagcggcggg atcccaaagt gcggatgatc gggccgccta cgtcgtggtg 120
tacctcgtcg gtaacaacga aaccgaagcg tatgactcgg tccacgcggt gcggcacatg 180
gtggacacca caccgccacc gcacggggtg aaggcctatg tcaccggtcc ggcagcactc 240
aatgccgacc aggccgaggc cggagacaaa agtatcgcta aggtcaccgc cgatcacnag 300
catggtgatc gcagcaatgt tgctagtgat ctatcgctcc gtaattaccg cggttctcgt 360
cttgatcatg gtcggcatcg actcggccaa tccgcggatt catcgccttg ctcgccgaac 420
acaacatttt cacctttcac atttgcacca acctgctctt ctcat 465

<210> SEQ ID NO 74
<211> LENGTH: 387
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 74
cactactcaa gctctctcnt cattaccacc cctgtaattt gggatgggca aaaaggcgaa 60
gcaccgcttg gccacnaacg ccgggaggga caatctcggg cggctatggc ttctcccggg 120
aaggccccaa cgtacggcgt ttcaacacgt cgcgtcgccc tccgaccgcg aacattcggg 180
gattggcacc aacctgntac caccctggcc gggcgatgat ctgcagcgtc gccgcgggta 240
gtccccgccc gggcggctac agtctgaaac cccgatgacc atcgatgtgt ggatgcagca 300
tccgacgcaa cggttcctac acggcggata tgttctcctc gctgcgccgg tggaccggtg 360
ggtctatccc ctgaaaccga catcccn 387

<210> SEQ ID NO 75
<211> LENGTH: 445
<212> TYPE: DNA
<213> ORGANISM: Mycobacterium tuberculosis

<400> SEQUENCE: 75
caggcatgca agctttcgtc agttcattgc gccagcagac caacaagagc atcgggacat 60
acggagtcaa ctacccggcc aacggtgatt tcttggccgc cgctgacggc gcgaacgacg 120
ccagcgacca cattcagcag atggccagcg cgtgccgggc cacgaggttg gtgctcggcg 180
gctactccca gggtgcggcc gtgatcgaca tcgtcaccgc cgcaccactg cccggcctcg 240
ggttcacgca gccgttgccg cccgcagcgg acgatcacat cgccgcgatc gccctgttcg 300
ggaatccctc gggccgcgct ggcgggctga tgagcgccct gacccctcaa ttcgggtcca 360
agaacatcaa cctctgcaac aacggcgacc catttgttcg gacggcaacc ggtggcaacg 420
cacctaagct acttgcccgg gatga 445

<210> SEQ ID NO 76
<211> LENGTH: 345
<212> TYPE: DNA
<213> ORGANISM: Mycobacterium tuberculosis

<400> SEQUENCE: 76
gtttatgcac tggttaggtg tttccatgag tttcattctg aacatccttt aatcattgct 60
ttgcgttttt ttattaaatc ttgcaattta ctgcaaagca acaacaaaat cgcaaagtca 120
tcaaaaaacc gcaaagttgt ttaaaataag agcaacacgt acacaaggag ataagaagag 180
cacatacctc agtcacttat tatcactagc gcccgccgca gccgtgtaac cgagcatagc 240
gagcgaactg gcgaggaagc aaagaagaac tgttctgtca gatagctctt acgctcagcg 300
caagaagaaa tatccaccgt ggggaaaaac tccaggtaga ggtac 345

<210> SEQ ID NO 77
<211> LENGTH: 139
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 77
atactcaagc ttgggtgtag ccgatcaccg gaagtcncat gatcagccac gttccgcgcc 60
gcccggcata cggtggtgta ccgatctccg cgtcatacac ccgcgggtaa tcgccgacgg 120
tgccggttcg cgagccgaa 139

<210> SEQ ID NO 78
<211> LENGTH: 298
<212> TYPE: DNA
<213> ORGANISM: Mycobacterium tuberculosis

<400> SEQUENCE: 78
agctttatcg aaagcgcgaa cagctcgcgg cggcccacga cgtgctgcgt cggattgccg 60
gcggcgagat caattccagg cagctcccgg acaatgcggc tctgctggcc cgcaacgaag 120
gactcgaggt caccccggtg cccggggtcg tggtgcacct gccgatcgca caggttggcc 180
cacaaccggc cgcttgatgc ccggtcggca agcccggcag ttgccaaacc catcgtgatc 240
aggctcggct cgcgagttcg gcgaagaaat ggttcgcctg atcacctacc atcggcca 298

<210> SEQ ID NO 79
<211> LENGTH: 300
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 79
tcaacacgcc gccagccacc acgcgcgggt cgggcgccgg gcccgggcct ccaggctnct 60
ccgctcggtg atggcacgcc accgcgacac cacccggctg cgctacgtcg agccataccg 120
ggcggagcta catcggcccg gccgcccagt gttcgggccc tctcgcccag gtcgaggtcg 180
acaccgattt gcgcatccgc agccgcaccc tgcgacgaca gaaccgcggc cctacccact 240
gcttgtcggg cgggggccaa agaaccagct tgncatcctg ccacaattgg ccggcgcccg 300

<210> SEQ ID NO 80
<211> LENGTH: 321
<212> TYPE: DNA
<213> ORGANISM: Mycobacterium tuberculosis

<400> SEQUENCE: 80
caggcatgca agcttcacgt ccgtacggct cgggtacgct tcggtcgcag tgtgcgagtg 60
atagatgacg accgggacct cgtcggcatc ttccatagcc cgccacacct tcagttgctc 120
accggaatcc aaccggtaga aggtcggcca gcgctcggca ttggtcatcg ggatatgccg 180
ctcgggacgg tcagagccct cgggtccggc cagcactccg caggcttcgt cggggtggtc 240
gcgacgcgca tgggccacca tcgcattcac caggtctgcg cgaatcacca gcacgtagac 300
ggttcctttc ctaagcaaca c 321

<210> SEQ ID NO 81
<211> LENGTH: 340
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 81
aatattcaag ctttcggcgg aaacggacnc cttgcgaaca ttgataacaa aatagaaatc 60
attgatggtt tgagtcacca ggccgatcaa gccttcgccg agccaaattc caatcaagag 120
gcccaagccc gtaccaatca gcccggcaac gagggattcc gtcnttatca gccnaaataa 180
ctgctctcgg gtaccaccca aacagcgcaa tatggcgaaa aacggtcgcc gttgcacaac 240
attaaatgtc tcggtattgt tgattaaaaa gatacccacc accagggcaa tccaactgag 300
agcggttaaa ttgaccgtaa aaacctcccg tcatctgttt 340

<210> SEQ ID NO 82
<211> LENGTH: 394
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 82
caggcatgca agcttgctgc atcttcctgt gactgctccc gaaacctggg ggtgtgcctg 60
ctgtgtatgc acggcatacg gacatccttc ccctgatacc cgcggtcgaa ccagccacgt 120
gtccatcatc aggggtcaac cccggccaag ggcgacggca cgccaagttc gccgaccgtt 180
aacctagtgc tgttagcttc atttgctgcg agcaaaacag ctggtcggcc gttaggaact 240
gaattgaaac tcaaccgatt tggtgccgcc gtaagtgtcc tgtctgcggg tgcgctggtg 300
ttgtccgcgt gtggtaacga cgacaatgtg accgggggag gtgcaaccac tggccaggcg 360
tccgcgaaag tccattgcng ggggaagaag acac 394

<210> SEQ ID NO 83
<211> LENGTH: 487
<212> TYPE: DNA
<213> ORGANISM: Mycobacterium tuberculosis

<400> SEQUENCE: 83
gaaagtgccc caaggtgttg gtgaaactcg ctggacggtc cccaggatgt tggcagcaca 60
ttcaccggac atgaccggag caagaccgga catcctccca taccgtcgtc gccgtgtaca 120
tccgtagccc gtcctggcag gtgctgggtt gaacaaaatc agcccaacac ctgccacgac 180
gaagaagcgg gttgcgctgg catgtcttgt cggctcggcg atcgaattct acgaattcct 240
tatctacggg accgctgcgg cgctggtgtt tcccaccgtg ttcttcccac acctggatcc 300
cacggtggcc gccgtggcct ccaaggggac atttgctgtg gcgttcctat cccggccgtt 360
cggcgcggcc gtctttggat actttggaga ccgcctcggc cgccagaaga ccctggtcgc 420
cacactgttg atcatgggcc tggcaaccgt gactgttggg ctggttccac gacagtggcc 480
atcgcgc 487

<210> SEQ ID NO 84
<211> LENGTH: 418
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 84
atattcaagc tttgtcacac caagtgttcc gaccaancgc tccatccggc gagtggatac 60
tcccagcagg tagcaggtcg ccaccacgct ggtcagtgcg cgttcatctc gcttgcggcg 120
ctgcagcagc cagtccggga aatagctgcc ctggcgcagc ttggggatcg cgacgtcgat 180
ggttgcggca cgggtgtcga aatcacggtg gcggtagccg ttgcgctgat tggaccgctc 240
atcgctgcgt tcgcggtagc ccnccccgca cagggcgtcg gcttcagccc ccatccaagg 300
cggcgatgaa cgtcgagagc agcccgcgca gcaaatccgg gctcgcctgt gcgagttggt 360
cagccagaag ctgctcggtg tcataagatg agaagaggtc agtgcgtcct ttccttcg 418

<210> SEQ ID NO 85
<211> LENGTH: 399
<212> TYPE: DNA
<213> ORGANISM: Mycobacterium tuberculosis

<400> SEQUENCE: 85
caggcatgca agctttttga gcgtctcgcg gggcagcttc gccggcaatt ctactagcga 60
gaagtctggc ccgatacgga tctgaccgaa gtcgctgcgg tgcagcccac cctcattggc 120
gatggcgccg acgatggcgc ctggaccgat cttgtgccgc ttgccgacgg cgacgcggta 180
ggtggtcaag tccggtctac gcttgggcct ttgcggacgg tcccgacgct ggtcgcggtt 240
gcgccgccaa agcggcgggt cgggtgccat catgaatgcc tcaccgccgc cgcactgcac 300
ggccagtgcc ccggcgatgt cagccatcgg gacatcatgc tcgcgttcat actcctcgac 360
cagtccgcgg aacagctcca ttcccggacc gcccaacgc 399

<210> SEQ ID NO 86
<211> LENGTH: 474
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 86
atactcaagc ttttggctgg gtcgccttcc aattcagcgt gcaccgctat gggttgcagc 60
agcggctggc nccgcacacc ccactggccc gggtgttttc gccccgaacc cggatcatgg 120
tgagcgaaaa ggagattcnc ctgttcgatg ctgggattcg ccaccgcgag gccatcgacc 180
gattactcgc caccggggtg cgagaggtgc cgcagtcccg ctccgtcgac gtctccgacg 240
atccatccgg cttccgccgt cgggtggcgg tagccgtcga tgaaatcgct gccggccgct 300
accacaaggt gattctgtcc cgttgtgtcc aagtgccttt cgcgatcgac tttccgttga 360
cctaccggct ggggcgtcgg cacaacaccc cggtgaggtc gtttttgttg cagttgggcg 420
gaatccgtgc tctgggttac agccccgaac tcgtcacggc ggtgcgccgc cgac 474

<210> SEQ ID NO 87
<211> LENGTH: 383
<212> TYPE: DNA
<213> ORGANISM: Mycobacterium tuberculosis

<400> SEQUENCE: 87
caggcatgca agcttcaacc tattgacgca ttgtgcgaac tgacggcgcc cgcgcatggc 60
caatccggaa gaccatcatt ggccagtggc cgggcgctaa caggttccag ccccccacca 120
gtgccgctcg aacatgcggt gcaacccatt cgcaggccgg cagggaaagc accgcggaag 180
ccgcaaaggg ctgcagttcc gcgcccaata gtgtcgtccg caaccagatg cgctcgaaaa 240
ccgccgccgg cagtcagcgc acccgacgcg aggtcgagag acgtcgtcag cgcgcccaca 300
tggggtgcca atcggcacgg caggtaggcc gcgcgcaacc ccaacgcgtg gtgcatgcca 360
cggtccgcag gaggccacca ccc 383

<210> SEQ ID NO 88
<211> LENGTH: 455
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 88
atactcaagc ttcccggccg caggtgacgg cgcggcctag cgccacttga tgccgcaccc 60
gatcgacggn cgttggtcgg ggttgactgg ccgcccggcg agcagggcgt caaccgcggc 120
ccggacgtcg gcggccgtca ccggtcggcc attgcccggg cgggagtcgt cgagctgacc 180
acggtagaca agtcggcgct ggccgtcgaa gacaaacgtg tcgggtgtgc aggccgcgga 240
gaaggcgcng gcgacgtctc gggtttcgtc gtagagatac gggaacgtcc agccgtggcg 300
gcgggcctcg gcgaccatct gatcgggccc gtcctgcggg taggtgacca cgtccttact 360
ggagataccg accatcggga ccctttgatc ggcgaggtcc cggccgaccg tggccaatcc 420
ggcggcgacg tgtcgcccgt accggccagt ggttc 455

<210> SEQ ID NO 89
<211> LENGTH: 429
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 89
caggcatgca agctttanca ncatcaaccc cgccccgcac cagcaccgac acgatgtcga 60
tgccatcgag gtgaatgtcg aactggcnca aaccatctgg cgaccgcgac caccggcaac 120
atgggtaccg gcgatttccg gtgccaatgc cgacccgacg ggccgctctc accgcaggtg 180
acctcgatca ccgagaccag ccggccgtta tactcacgca cccctaccgt gtcacgccca 240
aaacggcgct ggtggtcgat tgccggagtg caccccgcac ccagtgtcgt gcccggatcc 300
gccgaccaat cccgcaccca cgtcgccaaa cccgaaatca ccgtgatgcc gtggtaactg 360
accaccgaca gtaacgtcac tacggccgcc acgccgacgc cgaaccacca cgcacatgat 420
gatcggctg 429

<210> SEQ ID NO 90
<211> LENGTH: 321
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 90
atattcaacc ttgcacacat tgacgatacc ttggtcacga gaccccaaaa gctggcctcc 60
accgcgcgcc ggggaccacg gtcatacctt ganncngctt tcgatcgttg atgctgcgtc 120
ttggtccgcg gaaaccgcag gctggcatat gcacgtgggc gcactggcga tctgcgatcc 180
ccaccgattc gcccgaatac agctttcagc ggctccccaa gttgatcatc gaccggctgc 240
cggatatccc gcacttgcgg tggcgggtca ccggcgcccc gctcggactg gaccggccgt 300
ggttcgtcga ggaccacgaa c 321

<210> SEQ ID NO 91
<211> LENGTH: 134
<212> TYPE: DNA
<213> ORGANISM: Mycobacterium tuberculosis

<400> SEQUENCE: 91
caggcatgca agcttcatgc ccgcggcatg atagccacat gcacgcaatc gaactcagcg 60
aaaccggcgg gccaggcgtc ttacgccacc tcaccagcgc gcaacctcaa cccggccacg 120
gagacctcct gatc 134

<210> SEQ ID NO 92
<211> LENGTH: 513
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 92
atactcaagc ttgattttga tcatcatgat gatcatcacc cgaattgtgg tagccgcagt 60
ggttatcgtg ggtaccgtcg tgctttccat gggcgcctct ttcgggcttt ccgtattggt 120
ctggcaggac attctgggta tcgagttgta ctggatggtg ttggcgatgt cggtgatcct 180
gctcntggcg gtgggatccg actacaatct gctgctgatt tcccggttga aagaggaaat 240
tggggccgga ttgaacaccg gaattatccg tgccatggct ggtaccgggg gagtggtgac 300
ggctgccggc atggtgttcg ccgttaccat gtcgttgttt gtgttcagcg atttgcgaat 360
tattggtcag atcggtacca ccatcggcct gggcttgctg ttcgacaccc tcgtcgtgcc 420
tcgttcatga aaccgtccat tgctgccctg ctgggacctg gttctggtgg ccgctacggg 480
tgcgcccgcg cccggcagtc aaatcttccg ccg 513

<210> SEQ ID NO 93
<211> LENGTH: 345

<212> TYPE: DNA
<213> ORGANISM: Mycobacterium tuberculosis

<400> SEQUENCE: 93
caggcatgca agcttggcgt gccgttccaa cccgaattgg ctttcggcgc catcggtgag 60
gacggcgtgc gggtgctcaa cgacgacgtc gtccgcggga cacacctcga tgctgccgcc 120
atggacgcgg tcgaacgcaa gcagctgatc gagctacaac gccgcgcgga acgcttccgc 180
cgcgggcgtg accgcatccc gttgaccggg cggatcgcgg tgatcgtcga tgacggcatc 240
gccaccggag cgacggccaa ggcggcgtgc caggtcgccc gggcgcacgg tgcggacaac 300
gtggtgctgg cggtccccat cggcccagac gacatcgtgg cgaga 345

<210> SEQ ID NO 94
<211> LENGTH: 302
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 94
atactcaagc ttttacggtg atcgcgcatc acctggttca tgaactggaa gcagcgcagc 60
gcttcctttt cggccgcaac atgagccagc ctctcgtcgg cggtcgggtg caggtgctcg 120
ggcagctcgg ccgcgacagc cgcctgaccc tgaaaccagc ttccatatcc cgcgacgaac 180
gacgccagtc cgctacgtaa cccctccgcg actgtccatg gacaacagcg cgttctccac 240
cgaccgggcc cgggtgtggg gtgtttcggc gaccggcagc cangtggtcc acactgccga 300
ag 302

<210> SEQ ID NO 95
<211> LENGTH: 286
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 95
tagtcgctga ccggtgcagg tttcgacnat gtggtgccgg ttcggcggct acgtgccatc 60
gagacactgg cgcaggctat cgcacccgtt atcggctacg agcaaatcgc ggtatgcgtt 120
cttgagcatg agtcggcgac cgtcgtcatg gtcgacaccc acgacggaaa gacgcagatc 180
gccgtctanc ntgtgtgccg cggattatca ggactgacct cctggctgac cggcatgttt 240
ggtcgcgatg cctggcgccc ggccggcgtg gtcgtggtcg gctcgg 286

<210> SEQ ID NO 96
<211> LENGTH: 482
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 96
atactcaagc tttccgccga tacccgccat gtcgcgcaca tccagaactt ctggggggat 60

```
ccgctgacag cggcgggatc ccaaagtgcg gatgatcggg ccgcctacgt cgtggtgtac      120

ctcgtcggta acaacgaaac cgaagcgtat gactcggtcc acgcggtgcg gcacatggtg      180

gacaccacac cgccaccgca cggggtgaag gcctatgtca ccggtccggc agcactcaat      240

gccgaccagg ccgaggccgg agacaaaagt atcgctaagg tcaccgcgat cacgagcatg      300

gtgatcgcag caatgttgct agtgatctat cgccccgtaa ttaccgcggt tctcgtcttg      360

atcatggtcg gcatcgacct cggcgcaatc cgcggattcn tcgccttgct cgccgaccac      420

aacattttca gcctttcaac atttgcgaca acctgctcgt tctcatggcg attgcngcga      480

ac                                                                     482
```

<210> SEQ ID NO 97
<211> LENGTH: 395
<212> TYPE: DNA
<213> ORGANISM: Mycobacterium tuberculosis

<400> SEQUENCE: 97

```
caggcatgca agcttggcgt gccgttccaa cccgaattgg ctttcggcgc catcggtgag      60

gacggcgtgc gggtgctcaa cgacgacgtc gtccgctgga cacacctcga tgctgccgcc      120

atggacgcgg tcgaacgcaa gcagctgatc gagctacaac gccgcgcgga acgcttccgc      180

cgcgggcgtg accgcatccc gttgaccggg cggatcgcgg tgatcgtcga tgacggcatc      240

gccaccggag cgacggccaa ggcggcgtgc caggtcgccc gggcgcacgg tgcggacaag      300

gtggtgctgg cggtcccgat cggcccagac gacatcgtgg cgagattcgc cgggtacgcc      360

gatgaagtgg tgttgtttgg cgacccggcg ttgtt                                 395
```

<210> SEQ ID NO 98
<211> LENGTH: 439
<212> TYPE: DNA
<213> ORGANISM: Mycobacterium tuberculosis

<400> SEQUENCE: 98

```
atactcaagc tttggcattg tgcacatttt ccacccgtgc tctattaatg ctgagccgct      60

aattgtgacc ccagtcggga aacacgcgga gcaccaaatt caccgcagcg gccggggcgg      120

ttcaactcac catggatcgc tctcgtcgtc tggtgctgga caatcgtcgc tgtagcgcgt      180

cgcgaacacc tcagcttctg ctgccgcggc ttcttccggc gatggtaacc cccaggtttc      240

gcccacggtc ttacgtagca gtgcgacgcg gtgttcatct gcatcgacct gttgactcat      300

cctgtcaagg atgaaggcgt actgggccga ctgcgccttc tgccgcgcca ggtcggcaat      360

caccaggatc tcagaaacga gctgcgactc actcttccag gccaccctgg ccgaaagctc      420

gacatggtca atccggccg                                                   439
```

<210> SEQ ID NO 99
<211> LENGTH: 348
<212> TYPE: DNA
<213> ORGANISM: Mycobacterium tuberculosis

<400> SEQUENCE: 99

```
caggcatgca agcttgcggg ccggagtggt ttcgacggcc gctcgcttct cggcatcggt      60

ttgggctgtc accagcagtt ggtagttctt cacgtactgt tgttcgagcg tcgagccgcc      120

gcgcgtgtcg aggtcgccgg acgcgtatcc cgccaggccg gtcagggtgc ccttccagtc      180

cacgccgctg tggtcggcga accgcttatc ttcaatcgag acgatcgcca gcttcatcgt      240

gttggcgatc ttgtccgagg gcacctcgaa ccggcgctgc gagtacagcc acgcgatcgt      300
```

-continued gttgcccttc gcgtcgacca tcgtcgatac cgcaggcact tgcccctc 348

<210> SEQ ID NO 100
<211> LENGTH: 436
<212> TYPE: DNA
<213> ORGANISM: Mycobacterium tuberculosis

<400> SEQUENCE: 100
atactcaagc ttcccggcgg ccagtaccga aagcgcgaac agctcgcggc agcccacgac 60
gtgctgcgtc ggattgccgg cggcgaaatc aattccaggc agctcccgga caatgcggct 120
ctgctggccc gcaacgaagg actcgaggtc accccggtgc ccggggtcgt ggtgcacctg 180
ccgatcgcac aggttggccc acaaccggcc gcttgatgcc cggtcggcaa gcccggcagt 240
tgccaaaccc agcgtgatca ggctcggctc gcgagttcgg cgaagaagtg gctcgcctga 300
tcacctacca tcggccagga tctgcgtgtc atcacaacgc tcgccaagga ggttgttgtg 360
gtgctatcga cggcctttag ccagatgttc ggaatcgact atccgatagt gtccgcgcca 420
atggacttga tcgccg 436

<210> SEQ ID NO 101
<211> LENGTH: 445
<212> TYPE: DNA
<213> ORGANISM: Mycobacterium tuberculosis

<400> SEQUENCE: 101
agcttcggtg tagccgatca ccggaagccg catgatcagc cacgtttcgc gccgcccggc 60
atacggcggc gtaccgatct ccgcgtcata cacccgcggg taatcgccga cggtgccggt 120
tcgcgagccg aaggtgacga cgctgattga atcgagttcc aggtccagcg ggtggcgcag 180
caacggcgcg agctcaacga cgtcaatcac gttgtcgctt tctacggtca ccgacccggt 240
gaccgtagtc gcccggtgcg ctcggccgag aagttgcacc gccaccaccg cgacaccgtc 300
ttgcacgcgg acgccacccc cggatcggtt gttggccaag gtaattgggt cattccattt 360
gacgggacgc cgaccccgca gccccagtac cgcccacgac cacgccggct gacccaccac 420
tgtacgaaca ccaaggcgac gccga 445

<210> SEQ ID NO 102
<211> LENGTH: 261
<212> TYPE: DNA
<213> ORGANISM: Mycobacterium tuberculosis

<400> SEQUENCE: 102
atactcaagc ttcggtggct tcgcccgccc tgccgggtgg acttcatgac aacgcggggg 60
cgattacccc cgctaccgcc agcagcatga cggcggtacc taacaccgcc cggatgcctc 120
gcacgtgcct cgatgtgctc acggaatcgc cccggcaccg cgatctcgag gatcaccagc 180
gttacccccg gcagcgcgac accgacaatt ccgtacaccg ccacgccgat ccggccctgg 240
gccagctgat tggagctggc g 261

<210> SEQ ID NO 103
<211> LENGTH: 244
<212> TYPE: DNA
<213> ORGANISM: Mycobacterium tuberculosis

<400> SEQUENCE: 103
caggcatgca agcttccaca tgtacggatc cacgaacatc ccgttgaact gacaggtgcg 60
gcccggctcg atcaggccgg ccacttgttc tacgcggtta ccgaagatct cttcggtgac 120
ctgcccgccg ccggccagct cggcccagtg cccggcgttg gccgccgcgg cgacgatctt 180
ggcgtccacg gtggtccggg tcttgcccgc tagcacgatc cgcgagtcgg ccggtcaccc 240
gggt 244

<210> SEQ ID NO 104
<211> LENGTH: 376
<212> TYPE: DNA
<213> ORGANISM: Mycobacterium tuberculosis

<400> SEQUENCE: 104
atactcaagc tttccaagtc ccaagtgtcg atcatggcca aagagctcga caaagccgta 60
gaggcgtttc ggacccgccc gctcgatgcc ggcccgtata ccttcctcgc cgccgacgcc 120
ctggtgctca aggtgcgcga ggcaggccgc gtcgtcgggg tgcacacctt gatcgccacc 180
ggcgtcaacg ccgagggcta ccgaaagatc ctgggcatcc aggtcacctc cgccgaagac 240
ggggccggct ggctggcgtt cttccgcgac ctggtcgccc gcggcctgtc cggggtcgcg 300
ctggtcacca gcgacgccca cgccggcctg gtggccgcga tcggggccac cctgcccgca 360
gcggcctggc agcgct 376

<210> SEQ ID NO 105
<211> LENGTH: 284
<212> TYPE: DNA
<213> ORGANISM: Mycobacterium tuberculosis

<400> SEQUENCE: 105
caggcatgca agcttcacac gtaggcgccg tcgataaatg actccgccgc gcttcgcaca 60
tcctcgtagc gatccttggc gagcaggtca accgggcgct gcccgtcgag gagccggttt 120
ttggcgtgca gccactggcc gacacctcgg ggggtaagcg aatccgagag caggaggacg 180
aggtcacgaa gctgcgccag ccggtcgtac cgctcagggc ggatgtcgcc ggtccgccac 240
ccgcgtaccg cccgatcgga cacctgtatg accgcggcga cgtc 284

<210> SEQ ID NO 106
<211> LENGTH: 140
<212> TYPE: DNA
<213> ORGANISM: Mycobacterium tuberculosis

<400> SEQUENCE: 106
cgcggcggcg cattaccccc gctaccgtca gcagcttgac ggcggtagcg aacaccgccg 60
gatgcagcgc aggtgcgtct atgtgcacac ggaatcgccc cggcaccgcg atctcgagga 120
tcaccagtgc ccgccccctg 140

<210> SEQ ID NO 107
<211> LENGTH: 491
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 107
gggatcgagg aacagcgcgt tgaactgata ggtgcggccc ggctcgagca ggccggccat 60
ttgttcgatg cggttaccga agatctcttc ggtgacctgc ccgccgccgg ccagctcggc 120
ccagtgcccg gcgttggccg ccgcggcgac gatcttggcg tccacggtgg tcggggtcat 180
gcccgcgagc aggatcggcg agcggccggt cagccgggtg aacttcgtcg agagcttgac 240
cctgccgtcg gggaggcgaa ccacggtcgg tgcgtatctc gaccaggccc gggcaacctc 300
gggggtggcg ccgacggtga acaggttgcg ctggccaccg cgggtagccg ccggcactat 360
gccgatgccc aggccgcgga tcaccggtgc ggtcagtcgg gtcaggatgt cgcccggccc 420
caggtcgaag atccagcggg cgccggccgc gtggacacng gtgatctcgt ccaccatcga 480
ctttctgatc a 491

<210> SEQ ID NO 108
<211> LENGTH: 364
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 108
taactcaagg cttgcgttga ggccccaggc ccatcgacgg tttggcggcc ttaaatgcac 60
tgaggtcgtc aattgacccc acagcggaaa tgccgactat tcgcaggcct ccttcgcctt 120
ggctgccgga gaggggctcc gcgggaaccg catgcaggta tatgacctcg gtttctcggg 180
tgctaccgcg tgccttgtcg aggatgaact cggcgttgga attgtccagc cggcccaatt 240
catcgagcgc agattcgtac acatggccgg cggcgacata cgcttcaccg tggatctgct 300
ccacacggac cgccctgtcg ggatcctgct cacgggtaaa ggaacttacn tggcnctcgg 360
tgcc 364

<210> SEQ ID NO 109
<211> LENGTH: 453
<212> TYPE: DNA
<213> ORGANISM: Mycobacterium tuberculosis

<400> SEQUENCE: 109
ccttctgcgc cacccacacc gtcaacgccc gcgaagtcga cgtcgtccag gccatcggcg 60
gcctcacgga tggattcggc gcggacgtgg tgatcgacgc cgtcggccga ccggaaacct 120
accagcaggc cttctacgcc cgcgatctcg ccggaaccgt tgtgctggtg ggtgtgccga 180
cgcccgacat gcgcctggac atgccgctgg tcgacttctt ctctcacggc ggtgcgctga 240
agtcgtcgtg gtacggcgat tgcctgcccg aaagcgactt ccccacgctg atcgaccttg 300
acctgcatgg ccggctgccg ctgcagcggt tcgtttccga acgcatcggg ctcgaagacg 360
tcgaggaggc gttccacaag atgcatggcg gcaaggtatt gcgttcggtg gtgatgttgt 420
gatggccgcc atcgagcgcg tcatcaccca cgg 453

<210> SEQ ID NO 110
<211> LENGTH: 329
<212> TYPE: DNA
<213> ORGANISM: Mycobacterium tuberculosis

<400> SEQUENCE: 110
atactcaagc ttgattttga tcatcatgat gatcatcacc cgaagtgtgg tagccgcagt 60
ggttatcgtg ggtaccgtcg tgctttccat gggcgcctct ttcgggcttt ccgtattggt 120
ctggcaggac attctgggta tcgagttgta ctggatggtg ttggcgatgt cggtgatcct 180
gctcctggcg gtgggatccg actacaatct gctgctgatt tcccggttga aaaaagaaat 240
tggggccgga ttgaacaccg gaattatccg tgccatggct ggtaccgggg gagtggttac 300
cgctgccggc atggtgttcg ccgttacca 329

<210> SEQ ID NO 111
<211> LENGTH: 438
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 111
attgnctttc ggcgccatcg gtgaggacgg cgtgcgggtg ctcaacgacg acgtcgtccg 60
cgggacacac ctcgatgctg ccgccatgga cgcggtcgaa cgcaagcagc tgatcgagct 120
acaacgccgc gcggaacgct tccgccgcgg gcgtgaccgc atcccgttga ccgggcggat 180
cgcggtgatc gtcgatgacg gcatcgccac cggagcgacg gccaaggcgg cgtgccaggt 240
cgcccgggcg cacggtgcgg acaaggtggt gctggcggtc ccgatcggcc cagacgacat 300
cgtggcgaga ttcgccgggt acgccgatga ggtggtgtgt ttggcgacgc cggcgttgtt 360
cttcgccgtc gggcagggtt accgcaactt cacccagacc tccgacgaag aagtggtggc 420
gttttctgga tcgtgctc 438

<210> SEQ ID NO 112
<211> LENGTH: 438
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 112
atactcaagc ttttcccgtc cgtcatcgcc caagcgcgtg aggccgaagc ggctggttac 60
gactccctgt ttgtgatgga ccacttctac caactgccca tgttggggac gcccgaccag 120
ccgatgctgg aggcctacac ggcccttggt gcgctggcca cggcgaccga gcggctgcaa 180
ctgggcgcgt tggtgaccgg caatacctac cgcagcccga ccctgctggc aaagatcatc 240
accacgctcg acgtggttag cgccggtcga gcgatcctcg gcattggagc cggttggttt 300
gagctggaac accgccagct cggcttcgag ttcggcactt tcagtgaccg gttcaaccgg 360
ctcgaanagg cgctacagat cctcgagcca atggtcaagg gtgagcgcca acgtttttcg 420
gcgattggta cccaccga 438

<210> SEQ ID NO 113
<211> LENGTH: 482
<212> TYPE: DNA
<213> ORGANISM: Mycobacterium tuberculosis

<400> SEQUENCE: 113
cggccaccgg ggccactccg cacaatctgt acccgaccaa gatctacacc atcgaatacg 60
acggcgtcgc cgactttccg cggtacccgc tcaactttgt gtcgaccctc aacgccattg 120
ccggcaccta ctacgtgcac tccaactact tcatcctgac gccggaacaa attgacgcag 180
cggttccgct gaccaatacg gtcggtccca cgatgaccca gtactacatc attcgcacgg 240
agaacctgcc gctgctagag ccactgcgat cggtgccgat cgtggggaac ccactggcga 300
acctggttca accaaacttg aaggtgattg ttaacctggg ctacggcgac ccggcctatg 360
gttattcgac ctcgccgccc aatgttgcga ctccgttcgg gttgttccca gaggtcagcc 420
cggtcgtcat cgccgacgct ctcgtcgccg ggaccagcag ggaatcggcg atttcgccta 480
ca 482

<210> SEQ ID NO 114
<211> LENGTH: 388
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 114
atactcaagc ttggggtggc gctgtcggtc ggtgtgcttg gcggcgtcgg tatcaacacc 60
gcccacgaaa tggggcacaa gaaggattcg ctggagcggt ggctgtccaa aatcaccctc 120
gcccagacct gctacgggca cttctacatc gagcacaacc gtggccatca cntccgggtg 180
tccacaccgg aggacccggc gtcggcgcgg ttcggcgaaa cgttgtggga gttcctgccc 240
cgcagtgtta tcggcggctt gcgctcggcc gttcatttgg aggcccaacg gctgcgtcgg 300
ctcggcgtca gcccctggaa tcccatgacg tatctgcgca acgacgtgcn caacncgtgg 360
ctgatgtcng tggtgttgtg gggtgggc 388

<210> SEQ ID NO 115
<211> LENGTH: 455
<212> TYPE: DNA
<213> ORGANISM: Mycobacterium tuberculosis

<400> SEQUENCE: 115
tcgccaccgc accgcggcga acgctcaaag gcacctactg gcaccaaggc cccacacgtc 60
accctgtgac ctcctgcgcc gaccccgccc gaggtcctgg ccgttaccac cgaacgggcg 120
agccgggagt ctggtacgca tcgaacaaag agcaaggtgc atgggcggag ttgttccgcc 180
acttcgtcga tgacggggtc gatccattcg aggtccgtcg ccgcgtcggt cgagtggcgg 240
tcacactcca ggtactcgac ctcacagacg agaggactcg atcccatcta ggtgtggacg 300
aaacagatct tctgtccgac gactacacca ccacccaggc catcgccgcc gcccgcgatg 360
ccaacttcga cgccgtactg gccccggcgg cggcgctccc cggttgtcaa acactttgcc 420
gtgttcgttc acgcactgcc caacatcgag cccga 455

<210> SEQ ID NO 116
<211> LENGTH: 328
<212> TYPE: DNA
<213> ORGANISM: Mycobacterium tuberculosis

<400> SEQUENCE: 116
atgaaataag aagagcacat ccctcagtcg gttatcatca ctagcgctcg ccgcacccgt 60
gtaaccgatc atagcgagcg aactggcgag gaagcaaaga atatctgttc tgtcagatag 120
ctcttacgct cagcgcaaga agaaatatcc cccgcgggaa caactccagg tagaggtaca 180
cacgcggata gccaattcag agtaataaac tgtgacactc acaccctcat caatgatgac 240
gaactacacc ccgatatccg gtcacatgac gaagggaaag agaaggatat catctgtgac 300
aaactgccct caaatttggc ttccttaa 328

<210> SEQ ID NO 117
<211> LENGTH: 318

<212> TYPE: DNA
<213> ORGANISM: Mycobacterium tuberculosis

<400> SEQUENCE: 117
atactcaagc ttgtcgaact ccttcttgaa taccggccgg ccatccacag atgcccggaa 60
gaacttccag gtacccatgg cggctggatc agggggcggc acagttggtc ttgtcctgcc 120
tcgagtggcg tcgttgtccg gcttggacgg ggctccgacg gtaccggagg gcagcgacaa 180
aacacttatg cacttgggcg acccgccgag acggtgcgac acccatcccg acggcacaag 240
ctcagccgcg gccgctcttg ttcttcgtcg gatcgacatt cacccacttc tgaccgggct 300
tgggcgaagg aagcagaa 318

<210> SEQ ID NO 118
<211> LENGTH: 405
<212> TYPE: DNA
<213> ORGANISM: Mycobacterium tuberculosis

<400> SEQUENCE: 118
ggtatagtcg ctgaccggtg caggtttcga caatgtggtg ccggttcggc ggctacgtgc 60
catcgagaca ctggcgcagg ctatcgcacc cgttatcggc tacgagcaaa tcgcggtatg 120
cgttcttgag catgagtcgg cgaccgtcgt catggtcgac acccacgacg gaaagacgca 180
gatcgccgtc aagcatgtgt gccgcggatt atcaggactg acctcctggc tgaccggcat 240
gtttggtcgc gatgcctggc gcccggccgg cgtggtcgtg gtcggctcgg atagcgaggt 300
cagcgaattc tcgtggcagc tcgaaagggt cctgccggtg ccggtctttg cgcaaacgat 360
ggcgcaggtt acggtcgcgc ggggtgcggc cctggcggcg gccca 405

<210> SEQ ID NO 119
<211> LENGTH: 89
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 119
gacactatat natactcaag cttcaggtca atgtgcgcca agccctgacg ctggccgacc 60
aggccaccgc cgccggancc ctntctaga 89

<210> SEQ ID NO 120
<211> LENGTH: 354
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 120
ctgtagccac ctgttgccat ccccgtcatg cccgactctg gtcatctcgg atccgctgac 60
accccgctaa ggctgctcct ctcggtgcat tacctcaccg acggcgaacn cccccagctt 120
tacgactatc cggatgacgg cacctggttg ccggctaact tcaccgtcag cttggacggc 180
ggcgctaccg tcgatggcgc cagcggggcg atggccgggc ccggcgaccg attcgtcntc 240
ancctgtcgc gtgaacttgc cgacgtcatc gtggtcggtg tgggcaccgt gcgcattgag 300
ggctactccg gcgtccggat gggtgtcgtc aagcgcccgc accggcaggc ccga 354

<210> SEQ ID NO 121
<211> LENGTH: 379
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 121
atactcaagc ttcgcacgct cggcgcgcgc ggtaccgccc aggtcgccca acagatcgtc 60
gatgttcgcg tcgtccgcct cgcgcacgtg gtctgtcacc agtcaacgtt aacgccgccg 120
cacatgtcct gcggccgggc aaaaacgtga aaaacgagcg ggcgactgcn atgtcatgac 180
accgacggcc gccgatgggc ccagggtctg gcaaattcga tctgtgcggc cagtgccagc 240
agcgtcgcct cgtcatacgg ccggccgacg agttgaaccg acatgggcag gccgtcgccg 300
tcgaagtccc acggcaccac gggcgcgggc tggccggtca gattccaaaa ttgaaagtac 360
ggaaccgctg caccaccaa 379

<210> SEQ ID NO 122
<211> LENGTH: 393
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 122
atcgtttcga ccaggcgctc catccggcga gtggatactc ccagcaggta gcaggtcgcc 60
accacgctgg tcagtgcgcg ttcagctcgc ttgcggcgct gcagcagcca gtccgggaaa 120
tagctgccct ggcgcagctt ggggatcgcg acgtcgatgg ttgcggcacg ggtgtcgaaa 180
tcacggtggc ggtagccgtt gcgctgattg gaccgctcat cgctgcgttc gcggtagccc 240
gccccgcaca gggcgtcggc ttcagccccc atcaaggcgg cgatgaacgt cgagagcagc 300
ccgcgcagca gatccgggct cgcctgtgcg agttggtcag ccagaagctg ctcggtgtcg 360
ataagatgan aagaagtcat tgcgttattt cct 393

<210> SEQ ID NO 123
<211> LENGTH: 333
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 123
atactcaagc ttgggtgttg ccgatcaccg gaagccgcat gatcagccac gtttcgcgcc 60
gcccggcata cggcggcgta ccgatctccg cgtcatacac ccgcgggtaa tcgccgacgg 120
tgccggttcg cgagccgaag gtgacgacgc tgattgaatc gagttccagg tccagcgggt 180
ggcgcagcaa cggcgcgagc tcaacnacgt caatcacgtt gtcgctttct acggtcaccg 240
acccggtgac cgtagtcgcc cggtgcgctc ggccgagaag ttgcaccgcc accaccgcga 300
caacgtcttg cacgcggacg ccaccccccg gat 333

<210> SEQ ID NO 124
<211> LENGTH: 426
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 124
gcgcnaacag ctcgcggcag cccacgacgt gctgcgtcgg attgccggcg gcgagatcaa 60
ttccaggcag ctcccggaca atgcggctct gctggcccgc aacgaaggac tcgaggtcac 120
cccggtgccc ggggtcgtgg tgcacctgcc gatcgcacag gttggcccac aaccggccgc 180
ttgatgcccg gtcggcaagc ccggcagttg ccaaacccag cgtgatcagg ctcggctcgc 240
gagttcggcg aaaaagtggc tcgcctgatc acctaccatc ggccaggatc tgcgtgtcat 300
cacgacgctc gccaaggagg ttgttgtggt gctatcgacg gcctttagcc agatgttcgg 360
aatcgactat ccgatagtgt ccgcgccaat ggacttgatc gccggcggtg agctggctgc 420 cgcngt 426

<210> SEQ ID NO 125
<211> LENGTH: 336
<212> TYPE: DNA
<213> ORGANISM: Mycobacterium tuberculosis

<400> SEQUENCE: 125
atactcaagc tttctccgat acccgccatg tcgcgcacat ccaggacttc tggggggatc 60
cgctgacagc ggcgggatcc caaagtgcgg atgatcgggc cgcctacgtc gtggtgtacc 120
tcgtcggtaa caacgaaacc gaagcgtatg actcggtcca cgcggtgcgg cacatggtgg 180
acaccacacc gccaccgcac ggggtgaagg cctatgtcac cggtccggca gcactcaatg 240
ccgaccaggc cgaggccgga aacaaaagta tcgctaaggt caccgcgatc acgaacatgg 300
tgatcgcagc aatgttgcta gtgatctatc gctccg 336

<210> SEQ ID NO 126
<211> LENGTH: 347
<212> TYPE: DNA
<213> ORGANISM: Mycobacterium tuberculosis

<400> SEQUENCE: 126
ccatgagcac cgccagccga gcacgaggcc aaactccgcc gacgcaggcc ggttggactt 60
gtcgtgctgg acaaggggtt tagccgccga agcagtgacg tacatcggcg aagagcagtt 120
cgcctgtcga ccgacggcgc aaaccgtgag gctagggaag cgaggagcac atggccgccg 180
acccgcaatg tacacgctgc aagcaaacca tcgaacccgg atggctatac atcaccgccc 240
atcgccgcgg tcaagccggg atcgtcgatg acggcgcagt actgattcac gtgcccggtg 300
aatgccgcac cccggggagc actttccgcc aaaactaacc cggttgg 347

<210> SEQ ID NO 127
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 127

```
cgggtgtcat tggccaccgg cggcggctgt ccgggaaatg gcgggtcccc ggtggttttg     60

ctgaggagtg ctgaaccgta gtcgaagtgg gcggcgtcag actccaccca gccagcaggc    120

agcgcgaanc tgaatcctcc aaccgggttg tcnatccgga caggttgggg tgcgtttggg    180

gcaatnacag gtggcggcgg tgcgttcggg tcggccggcg gaggtgctgc nttgggatcc    240

ccggctgggc attcggcntg ttggcggcgg ccggtggtgg ggggggcaac acgtgtcncc    300

ggtgcgggtg gccct                                                     315
```

<210> SEQ ID NO 128
<211> LENGTH: 354
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 128

```
ccaagatcta caccatcgaa tacgacggcg tcgccgactt tccgcggtac ccgctcaact     60

ttgtgtcgac cctcaacgcc attgccggca cctactacgt gcactccaac tacttcatcc    120

tgacgccgga acaanttgac gcagcggttc cgctgaccaa tacggtcggt cccacgatga    180

cccagtacta catcattcgc acggagaacc tgccgctgct agagccactg cgatcggtgc    240

cgatcgtggg ganacccact ggcgaacctg ggttcaacca aacttgaagg tgattgttaa    300

cctgggctac ggcgacccgg cctatggtta ttcgacctcg ccgcccaaat gttg          354
```

<210> SEQ ID NO 129
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 129

```
agcttcccga gttcggcttt ggatcaagac cccagtccgc gggcgcgatc cggcngctcg     60

gtgactacat caagccacaa atcgacggct ttcggggtgc cgataccgat gacgtggcgg    120

atgtcgagtg ttgagttctc ggcggggcgg atgctcacct ggcgatcacc tgcctctcgt    180

tgacgatcga tcgtctatgc cgccgtctct gcgggaacag gccnccagta catcgccaca    240

gacgggatcc acccgcattt cggctacggt tgctcgtttc ggtgttcgga ctagtcggtc    300

ctggtgacgt gccggtgatg cggaccggtc ctagcactga ccaatggcca aaatgcgggc    360
```

<210> SEQ ID NO 130
<211> LENGTH: 483
<212> TYPE: DNA
<213> ORGANISM: Mycobacterium tuberculosis

<400> SEQUENCE: 130

```
cggggggcct cttaatagtg taggaaagaa gctctacata ttcaggagga ttcaccatgg     60

ctcgtgcggt cgggatcgac ctcgggacca ccaactccgt cgtctcggtt ctggaaggtg    120

gcgacccggt cgtcgtcgcc aactccgagg gctccaggac caccccgtca attgtcgcgt    180

tcgcccgcaa cggtgaggtg ctggtctgcc agcccgccaa gaaccaggca gtgaccaacg    240
```

tcgatcgcac cgtgcgctcg gtcaagcgac acatgggcag cgactggtcc atagagattg 300
acggcaagaa atacaccgcg ccggagatca gcgcccgcat tctgatgaag ctgaagcgcg 360
acgccgaggc ctacctcggt gaggacatta ccgacgcggt tatcacgacg cccgcctact 420
tcaatgacgc ccagcgtcag gccaccaagg acccggccag atcgccggtc tcacgtgctg 480
cgg 483

<210> SEQ ID NO 131
<211> LENGTH: 423
<212> TYPE: DNA
<213> ORGANISM: Mycobacterium tuberculosis

<400> SEQUENCE: 131
atactcaagc ttcataacag gcctgttgtg ggcgcacccg gctcgccgag ttctgcacgc 60
accgcctcaa gtgcggcccg caccgccggc atctcccggt cacgcagggc cgcggcccgc 120
gccgcagcga cggcgtgttc gcgcagttcg ccgtcaatga tgctgacctg atcggccacc 180
cgggcgttct cggcgtcttc gcgttcacta atcgcggtgc tcagcagcgt ctcgacagcc 240
accacccgag tggcgaccag ctgctccacc acggaccgca gcgatgccgt cacctcaccc 300
gtccagcggt ccaccacgac acggtcgtgc accagcgcgc gggcattcac cacccaggcg 360
gtcaccgcca ggccgatcgc cacacccgcc accatccccg atgcagccag gccgggagta 420
aga 423

<210> SEQ ID NO 132
<211> LENGTH: 338
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 132
ctggtgctgg acggagccta gtacaacttc ctctccaatg ctcttgcccc gatcgcggcg 60
accaggatga cccaggacat cctgccgccc gaagtactgg aaaagctcac acccgagttc 120
gtcgcaccgg tggtggccta cctgtgcacc gaggagtgtg ccgacaaccc atcggtgtac 180
gtcgtcagtg gtggttaggt gcagcgagtt gcgctgtttg gcaacgacgg cgccaacttc 240
gacaaaccgc cgtcngtaca agatgttgcg gcgcggtggg ccgagatcnc cgatctgtcc 300
ggtgcgaaaa ttgctggatt caagttgtag aactaaat 338

<210> SEQ ID NO 133
<211> LENGTH: 173
<212> TYPE: DNA
<213> ORGANISM: Mycobacterium tuberculosis

<400> SEQUENCE: 133
atactcaagc ttttccggcg tcgtccacct gacccaaaaa gcgcaggtgc gccgccaaac 60
ggcccgcctg gccgcgcaac tggtcggcgt cgccgtggcc gacaatcagt agctggacat 120
ccggaaaccg ctgcaccacc ttcggcagcg cgtcaagcaa aaacggccat tcc 173

<210> SEQ ID NO 134
<211> LENGTH: 255
<212> TYPE: DNA
<213> ORGANISM: Mycobacterium tuberculosis

<400> SEQUENCE: 134
tttcagatct catttttatg acatgactgg agatctgtct agattgcagc tcctgtgagc 60
gtgggtaccg gattcaagcc ggtcggtcac gccgcggtgg taccggcttt gcggcagtgc 120
tcggcctcga gttcggcgat cgcgcgcgaa gtgcgtttcg cgcaccaaga tcgcggccta 180
atggccggcg atgaccgcga tgaccagcgc gatccaggaa aaaccgttcc aaccagtgct 240
gggcggccat ccccg 255

<210> SEQ ID NO 135
<211> LENGTH: 285
<212> TYPE: DNA
<213> ORGANISM: Mycobacterium tuberculosis

<400> SEQUENCE: 135
atactcaagc ttcccgacca caagttgaac agcaccgatt tcggcgagca cttcgtcaac 60
ttccagggtg cccgcaccaa gtatttcgac aagtatttcc gtcgggccgc cgccgccggc 120
gcgcggcagg tggtcatcct ggcggcgggg ctggactccc gcgcgtaccg gctgccttgg 180
cccgacggga ccacggtttt tgagctggac cgcccgcagg tccttgattt caagcgcgag 240
gtgctcgcca gccacggtgc ccaaccgcgc gccctgcgcc cgcga 285

<210> SEQ ID NO 136
<211> LENGTH: 494
<212> TYPE: DNA
<213> ORGANISM: Mycobacterium tuberculosis

<400> SEQUENCE: 136
gtgtgctgtc aattcagagc tgagcctgat gcactcaact tactgagcat gctaacgctg 60
gtcgtgcggg tcttgttccc gcgtgtcggc agggcacacg ctcggggcgt agctgggaga 120
ggccccggtc aagcccggag agcagtgctc agtccgccag cttgaccgac tttcgatgag 180
aacgcgcttc tcgccgtatt gaactggcgt gctgacggtc gctgagcagc gctcgccgag 240
tgcggccgct gattctttca tcgagccagg aggcgcattc gtgttcggcc gcctgcgggt 300
cggccccatc gtcgacgcga tccgtcaccc actcctcgat caggtctgcc tcatcgaacg 360
ggccaacggt gctgtcggag tatgtgtgcg tgggcacggc gagccgggtg ctgtggtaca 420
cccaccgttg catgaccaag ttgacgcctg actggctgag caccgcgatc cgctcacagg 480
tcggaacgtt ggtg 494

<210> SEQ ID NO 137
<211> LENGTH: 357
<212> TYPE: DNA
<213> ORGANISM: Mycobacterium tuberculosis

<400> SEQUENCE: 137
atactcaagc ttttggtcta gccggccgag cccgatacag gtgtcattgg ccaccggcgg 60
cggctgtccg ggaaatggcg ggtccccggt ggttttgctg aggagtgctg aaccgtatgc 120
gaagtgggcg gcgtcagact ccacccagcc agcaggcagc gcgaaactga atcctccaac 180
cgggttgtcg atccggacag gttggggtgc gtttggggca atgacaggtg gcggcggtgc 240
gtccgggtcg gccggcggaa gtgctgcgtt gggatcgccc ggctgggcat tctgcgtgtt 300
ggcggcggcc ggtggtgggg gggcaacagg tgtctccggt gcgggtggcg ctgcacc 357

<210> SEQ ID NO 138
<211> LENGTH: 458
<212> TYPE: DNA
<213> ORGANISM: Mycobacterium tuberculosis

<400> SEQUENCE: 138
ggggccactc cgcacaatct gtacccgacc aagatctaca ccatcgaata cgacggcgtc 60
gccgactttc cgcggtaccc gctcaacttt gtgtcgaccc tcaacgccat tgccggcacc 120
tactacgtgc actccaacta cttcatcctg acgccggaac aaattgacgc agcggttccg 180
ctgaccaata cggtcggtcc cacgatgacc cagtactaca tcattcgcac ggagaacctg 240
ccgctgctag agccactgcg atcggtgccg atcgtgggga acccactggc gaacctggtt 300
caaccaaact tgaaggtgat tgttaacctg ggctacggcg acccggccta tggttattcg 360
acctcgccgc ccaatgttgc gactccgttc gggttgttcc cagaggtcag cccggtcgtc 420
atcgccgacg ctctcgtcgc cgggacccag cacggaat 458

<210> SEQ ID NO 139
<211> LENGTH: 595
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 139
ttctntcttc ccnnattcgt nnntctcnta ctaccngggc cncaaaacac cttggcnaac 60
gctcaaaggc gntacnggca ccaaggcccc acacgtcacc ctgtgacctc ctgcgccgac 120
cccgcccgag gtcctggccg ttaccactga acgggcgagc cgggagtctg gtacgcatcg 180
aacaaagagc aaggtgcatg ggcggagttg ttccgccnct ttttttatga cggggtcgat 240
ccattcgagg tccgtcgccg cgtcggtcga gtggcggtca cactccaggt actcgacctc 300
ncagacgaga ggactcgatc ccatctangt gtggacnaaa cagatcttct gtccgacgac 360
tacacaccac ccaggccatc gccgccgccc gcgatgccaa cttcnacncc gtnctggccc 420
cggcggcggc gctccccggt tgtcaaacac ctgccgtgtt cgttcacnca ctgcccaaca 480
tcnagcccga ncnatccnag gtccgtccaa cgcctccgcg gctcnccaac ctnctcccnc 540
tgatcntccg caccaaacac atgcccgact ccntgcnccn attgcttgna tccct 595

<210> SEQ ID NO 140
<211> LENGTH: 434
<212> TYPE: DNA
<213> ORGANISM: Mycobacterium tuberculosis

<400> SEQUENCE: 140
ccgctatcgg tcggtgtgct tggcggcgtc ggtatcaaca ccgcccacga aatggggcac 60
aagaaggatt cgctggagcg gtggctgtcc aagatcaccc tcgcccagac ctgctacggg 120
cacttctaca tcgagcacaa ccgtggccat cacgtccggg tgtccacacc ggaggacccg 180
gcgtcggcgc ggttcggcga gacgttgtgg gagttcctgc cccgcagtgt tatcggcggc 240
ttgcgctcgg ccgttcattt ggaggcccaa cggctgcgtc ggctcggcgt cagcccctgg 300
aatcccatga cgtatctgcg caacgacgtg ctcaacgcgt ggctgatgtc ggtggtgttg 360
tggggtgggc tgatcgcggt cttcggcccg gcgctgatcc cgttcgtcat catccaggca 420
gtcttcggct tcag 434

<210> SEQ ID NO 141
<211> LENGTH: 321
<212> TYPE: DNA

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 141
atactcatgc ttgccgaagt tccgatgggt cgcgccggcg ancccagcga agtcgctagc 60
gtggccgtgt tcttggcttc ggatctatcc tcgtacatga ccggcaccgt gttggacgtg 120
actggcggcc ggttcatatg acaccgagat cattgccacg gtacggcaat tcgtcaagaa 180
ggaaatcttt cccaatgcac cggccctcga acgtggcaac agctacccgc aagaaatcgt 240
cgatcggctg ggtgttattg gcttgctcgg tcgccggctg caagggtatc gacaccaccg 300
agttcattct ccgggcgtgc c 321

<210> SEQ ID NO 142
<211> LENGTH: 348
<212> TYPE: DNA
<213> ORGANISM: Mycobacterium tuberculosis

<400> SEQUENCE: 142
ggcgtcaacg gtgtcggcac cggcgtcctg cagttggtag gcctgcagtt tgtgcatcag 60
gccgatgccg cggccctcgt ggccacgcat gtacagcacc acgccgcgcc cctcacgggc 120
gaccatcgcc agcgcggcgt ccagctgagg cccgcaatcg cagcggcgtg acccaaacac 180
atcgccggtc aagcactccg aatgcacccg gaccagcacg tcgtcaccgt cggcgttggg 240
cccggcgatc tcgccgcgga ccagcgcgac atgttccacg tcctcgtaga tgctggtgta 300
gccgatggcg cgaatctccc atgacgagtc ggaatccgcg cctcggcg 348

<210> SEQ ID NO 143
<211> LENGTH: 339
<212> TYPE: DNA
<213> ORGANISM: Mycobacterium tuberculosis

<400> SEQUENCE: 143
atactcaagc ttcggcctcg ctgcaggagt gggagccgca gggctggaaa tccgaaaaac 60
gagccggtga tcgcactgtc gccgatcggg gccgcacctg gttggtgtta ccgatgaatc 120
cgcacccaaa atgtggctgc ggtggcgttt cttgactcct tggcgtcgac tcttgtggca 180
gccaccgagc ggttggtcca ggatctggat gggcaaagtt gtgcggcccg gccggtgacg 240
gccgatgagc tgaccgaggt cgacagcgcc gtgttggctg acttggaacc gacatggatt 300
cgccccggtt ggcgtcacct caagcatttc aatggttat 339

<210> SEQ ID NO 144
<211> LENGTH: 269
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 144
atgcgtcacc ccgatgcgcc cagatcgggg cttcgcaaat aaagcacgaa caggcgggca 60
aaacgtctat ctcggagccg gaagggcaat cagccgaccg tcgacgaacg acaccggcga 120
taaccactta ggcgttgaac ggccggccca aacattacgc ctccgttgat aaggctttcg 180
gtctcttccc cggtcatccc aagcaccttg cggcaaattt gaacgctttc ctgtccgggc 240
accggccccg ggctttgggg tccntccga 269

<210> SEQ ID NO 145
<211> LENGTH: 285
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 145
atactcaagc ttcaatcgcg ccgccacaat ccaaatatgc gtctagcgtc tcgatgagcg 60
tcggtccggc atcggctagg ggccgcatca cgtcggtatg cagggccacg atcgcccaag 120
gcgtcgccca tcaagggcgc gttcgggcaa aaattcccct atccagcacg ggccgcggcg 180
ctccgcncca gccggcgacg gcgttcatcc cggagatcgc ctcgctagcg ctgcggtgcg 240
ccgcggtcag catgggcgcc gtggggccga tgaccaccgg ggcgt 285

<210> SEQ ID NO 146
<211> LENGTH: 75
<212> TYPE: DNA
<213> ORGANISM: Mycobacterium tuberculosis

<400> SEQUENCE: 146
ttcggcgggt ctgtagattg cggtcggcca ccccacaggc actcatgaac cgcagcccac 60
gatcgatctc ggtgg 75

<210> SEQ ID NO 147
<211> LENGTH: 164
<212> TYPE: DNA
<213> ORGANISM: Mycobacterium tuberculosis

<400> SEQUENCE: 147
gcgcaccatc gccagtaggt gcccgtggtc gggcgcgtcg agccacccga gcggaaacgc 60
gagtccgaac agcaacagca ggacgggcgc aaccagggcg gtgaccatgc ccccggcgct 120
gaacatcaac cacaggaagg gctccgccga gcgtccgcgc gacc 164

<210> SEQ ID NO 148
<211> LENGTH: 228
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 148
catcgtcgaa cttcggtccg ggttgntagn accgcagcac caaacgcacc caccgacccc 60
cacgcttcac gccaaccctt tagttcattg gcgtgaacag cagcgtagcc ggttgccccg 120
atatatgtgg aaaaatcgtt cggacgtaca aaaaaagttc ctgacgctgg cgtcaactcg 180
aaactgcctc ggaagtcaat gatgatccat cagtcaatat taaagtcg 228

<210> SEQ ID NO 149
<211> LENGTH: 238
<212> TYPE: DNA
<213> ORGANISM: Mycobacterium tuberculosis
<220> FEATURE:

```
<221> NAME/KEY: unsure
<222> LOCATION: (various positions within the sequence)
<223> OTHER INFORMATION: applicants are uncertain of bases designated
      as "n"

<400> SEQUENCE: 149

atactcaagc ttgtctgctg cctcagcgta tgcatccaac agcgcatcgc gatcaacgat     60

caggcgcgcc gatttcgggc cgcgggcagt ggcactggcc agatggccgt ttttttcgag    120

aaacttcaac gcctgagcgc tgcttcccat cgagagaccg gtggcctcta caaccgatgc    180

gacagttgga ccggcgatgt tcgccagcag cgcttcacat acggcaagtn tggcgcgg      238


<210> SEQ ID NO 150
<211> LENGTH: 162
<212> TYPE: DNA
<213> ORGANISM: Mycobacterium tuberculosis

<400> SEQUENCE: 150

ttgtccaggc ggggaatcgg gcagggagac gacaccttcg ttcggttcga tcgtcgcgaa     60

cgggtagttg gccgcgacca cgttgtttcg ggtcagcgcg ttgaaaagtg tcgacttgcc    120

gacgttgggc aggcccacga tccccaggct caagctcaca ga                       162


<210> SEQ ID NO 151
<211> LENGTH: 377
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 151

atactcatgc ttggcgcctg ggtggcagcc cacctgccca ccacacggac cgcggtgcgg     60

acgcggctga cgcgcctggt ggtcagcatc gtggccggtc tgctgttgta tgccaacttc    120

ccgccgcgca actgctggtg ggcggcggtg gttgcgctcg cattgctggc ctgggtgctg    180

acccnccgcn cnacaacacc ggtgggtggg ctgggctacg gcctgctatt cggcctggtg    240

ttctacgtct cgttgttgcc gtggatcggc gagctggtgg gccccgggcc ctggttggca    300

ctggcgacga cgtncgcgct gttccccggc atcttcggtc tgttcgccgt cgtggtaccc    360

tgttgccggg ttggccc                                                   377


<210> SEQ ID NO 152
<211> LENGTH: 308
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 152

cgccaattca cgatatcgtt aaccgatatc ccgagccgat agctggcggg ctcgggtggt     60

ggccagcggc gctgcgacga aaggtgtgac cgtcatgaaa cagacaccac cggcggccgt    120

cggccgtcgt cacctgctcg agatctcagc atccgcagcc ggtgtgatcg cgctttcggc    180

gtgtagtggg tcgccgcccg accccggcaa aggccggccc gacacaaccc cggaacagga    240

agtcccggtc accgcgcccg aagnacttga tgcgcgaacn cggagtgctc caaacgcatc    300

ctgctgat                                                             308
```

<210> SEQ ID NO 153
<211> LENGTH: 377
<212> TYPE: DNA
<213> ORGANISM: Mycobacterium tuberculosis

<400> SEQUENCE: 153
atactcaagc ttgggcactg acttcggtac cccctccgcc tttggccagc agcagccaca 60
gcgcggttcg cggaccgaac gtggacatca atagcccgga atcggtgtgt gcaagttggt 120
aaacggtgtt gatcccaagc tttgccagcc ttttcgtagt cttgggcccc acacccccaca 180 gtgcttcgac ggtacggtca cccatgatgg ccatccagtt ggcatcggtg agctgataaa 240
tgccagctgg tttcgccaac ccggtagcga tcttggcgcg ctgcttgttg tcactgatac 300
ctatcgagca agacagcccg gtttgcgaca aaatgacttt tcggatctct tcggcgactt 360
cgatggggtc gtcggga 377

<210> SEQ ID NO 154
<211> LENGTH: 259
<212> TYPE: DNA
<213> ORGANISM: Mycobacterium tuberculosis

<400> SEQUENCE: 154
aaagtcctgt gccggttcgc taaacacccg gcggacactc agacggtgct ggtggtgcgg 60
catggcaccg cgggcagcaa agcgcacttc tccgggggac gacagcaagc gaccgctaga 120
caagaggggt cgtgcgcagg cagaaacgtt ggtacacagc tgctggcgtt cggcgccacc 180
gatgtttatg ccgccgaccg ggtgcgctgc caccagacga tggagccact cgccgcggaa 240
ctgaacgtga ccatacaca 259

<210> SEQ ID NO 155
<211> LENGTH: 372
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 155
atactcaagc ttgggttcca cgcccgcgca gccacgccgt cacctttcca cgagacctca 60
cctgccgatc cgaaatggaa tcggccgtga cggaattggc gcaccgaaca cccaacgagg 120
tggtggcttc gtcgcgaacc gtcacccgag tcgcggccac cgtgcgcacg gcgacgttct 180
acacccgcac caagatccga aagctgcaag ctcccagcac cgatcccgac gtcatcaccg 240
ctgccgcccg gcacgtcctt gacctattcg agctggatcg gcccgtccgg ttgctgggag 300
tgcggttaga actggcctag aaccggcggg cacaccgcnc ctgggcgggg cgaattcttg 360
accgcnccgg cc 372

<210> SEQ ID NO 156
<211> LENGTH: 290
<212> TYPE: DNA
<213> ORGANISM: Mycobacterium tuberculosis

<400> SEQUENCE: 156
cgcggttggc gtagttggac gggtcgccct ccgaggccaa tgatgacgat gaccacgccg 60
atcacgatgg ccaccgagag ggacaacaac agaaagctga cgaatccctc cttggcggcc 120
ggggctttgt ggtcgccggt cgcgatgggc gcgaatttac ggcccgctcc cccaggccgc 180
cgcgaagcag ggtccccagc cagttggcgt aggcggaatt aacgatcagc gccaccgcga 240
taacctgcca tgcctcgggc atatcgatgt gcggccagaa caggccgaac 290

<210> SEQ ID NO 157
<211> LENGTH: 470
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 157
ccaacaagag catcgggaca tacggagtca actacccggc caacggtgat ttcttggccg 60
ccgctgacgg cgcgaacgac gccagcgacc acattcagca gatggccagc gcgtgccggg 120
ccacgaggtt ggtgctcggc ggctactccc agggtgcggc cgtgatcgac atcgtcaccg 180
ccgcaccact gcccggcctc gggttcacgc agccgttgcc gcccgcagcg gacgatcaca 240
tcgccgcgat cgccctgttc gggaatccct cgggccgcgc tggcgggctg atgagcgccc 300
tgacccctca attcgggtcc aagaccatca ncctctgcaa caacggcgac ccgatttgtt 360
cngacggcaa ccggtggcga gcgcacctag gctacgtgcc cgggatgacc aaccaggcgg 420
cgcgtttcgt cgcgagcagg atctaaccgc gagccgccca tagattcccg 470

<210> SEQ ID NO 158
<211> LENGTH: 434
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 158
taanacccgt gtaatttggg atgggcaaaa aggccaagca ccgcgtggcc acgaacgccg 60
ggagggacaa tctcgggcgg ctagggcttc tcgcgggaag gcccgaacgt acggcgtttc 120
aacacgtcgc gtcnccctcc gaccgcgaac attcggggat ggcagcaacc tggtagcncc 180
ctggccgggc gatgatctgc agcgtcgccg cgggtagtcg ccgcccgggc ggctacagtc 240
tgaaacgcga tgaccatcga tgtgtggatg cagcatccga cgcaacggtt cctacacggc 300
gatatgttcg cctcgctgcg ccggtggacc ggtgggtcta tcccggagac cgacntcccg 360
atcgaagcga ccgtctcctc gatggacgcc ggcggcgtca ccctgggttt gctcaccgcc 420
tggcgtggcc ccaa 434

<210> SEQ ID NO 159
<211> LENGTH: 363
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 159
gtccgcaaaa gactcagcgg ccgactttgc tcgcagctgg cggtaccgcg ccaccgattc 60
gatgccgtgg tcgcggaaga atgcctcccg aaatcgcacg gccgactcca gttcggcgag 120

-continued

```
catccgcgat gccagctgcg gctgcgccct gccggccacg gcacccacat gcggcagttc    180

gtccacctgg gccagcgccc cgccgccgaa gtccaaacaa tagaactgca cccggcccgc    240

atcgtgggta gcagccaacg ccatgatcag cgtccgcagc gcggttgact tgcccgtttg    300

cggtgcacct acgaccgcga cattgcctgc ggccccggac aagtcgatcg tcagcggcac    360

ccn                                                                  363
```

<210> SEQ ID NO 160
<211> LENGTH: 301
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 160

```
cgtggccacg aacgccggga gggacantct cgggcggcta gggcttctcg cgggaaggcc     60

cgaacgtacg gcgtttcaac acgtcgcgtc gccctccgac cgcgaacatt cggggatggc    120

agcaacctgg cagctacctg gccgggcgat gatctgcagc gtcgccgcgg gtagtcgccg    180

cccgggcggc tacagtctga aacgcgatga ccatcgatgt gtggatgcat catccgacgc    240

aacggttcct acacggcgat atgttcncct cgctgcgccg gtggaccggt gggtctatcc    300

c                                                                    301
```

<210> SEQ ID NO 161
<211> LENGTH: 436
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 161

```
atactcaagc tttgcggcgg gcgccgaaat gtgaacgcac caaacccgcc cgctgcgggt     60

cggcgggcca ctcgacctcg aatttcgccg ccgtgaccat ccagcccgac ggcagttggg    120

cacccggccc cccggtcgcg gcataactgt tggcgtcgcc gtcataaagc tcgaacagca    180

ccgaaaccga ctccaccacc ggccggtgcg cctcaaaatc cacgccgatc tccacatacc    240

gggaaaacgt cggtgtccca tcgggtttcg gcttgcccgc cagctgcaca ccaccggtgg    300

cctcggccac cttcgcggcc tgagcgcagc tacncatcct gacgatcatc accccgcccc    360

cggctcacgc ttggcctccg tgaccgcacg catcgcccgg ttgcgcgcac cgcgacgccc    420

gtacagccgc gcgcac                                                    436
```

<210> SEQ ID NO 162
<211> LENGTH: 390
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 162

```
agcttgccgg gactgcggaa cagaagcggc ggttcctacc gcggtgtgcg gccggcgcga     60
```

tatcggcctt tttactaacc gaacccgatg tgggctccga tccggcgcgc atggcatcga 120
cggcgacgcc gatcgatgac ggccaggctt acgagcttga gggtgtgaag ttgtggacca 180
ccaacggtgt ggtagcggac ctgctagtgg ttatggcgcg ggtaccgcgc agtgaagggc 240
accgaggggg aatcagcgcc tttgtcgtcg aggctgattc gcccgggatc accgtggagc 300
ggcgcaacaa gttcatggga ctgcgtggca tcnaaaacgg cgtgacccgg cttcatcgcg 360
tcngggtgcc caaagacaac ttgatcggca 390

<210> SEQ ID NO 163
<211> LENGTH: 75
<212> TYPE: DNA
<213> ORGANISM: Mycobacterium tuberculosis

<400> SEQUENCE: 163
ctcaagcttg gcgatgcggg ctggccaaaa ctggccgggc gggggttggc ttgttcaatc 60
aagggtgggt tgccg 75

<210> SEQ ID NO 164
<211> LENGTH: 110
<212> TYPE: DNA
<213> ORGANISM: Mycobacterium tuberculosis

<400> SEQUENCE: 164
ccgaaggccc gttcccgggc gttcagcaag cgatcgtcgg ttggcccact gcgggtcgaa 60
tcttgcggcc gcgccggtcg tggaacgccc aggtcacccg gcggcgtacc 110

<210> SEQ ID NO 165
<211> LENGTH: 455
<212> TYPE: DNA
<213> ORGANISM: Mycobacterium tuberculosis

<400> SEQUENCE: 165
atactcaagc ttttttctgc tcatgaaggt tagatgcctg ctgcttaagt aattcctctt 60
tatctgtaaa ggctttttga agtgcatcac ctgaccgggc aaatagttca ccggggtgag 120
aaaaaagagc aacaactgat ttaggcaatt tggcggtgtt gatacagcgg gtaataatct 180
tacgtgaaat attttccgca tcagccagcg cagaaatatt tccagcaaat tcattctgca 240
atcggcttgc ataacgctga ccacgttcat aagcacttgt tgggcgataa tcgttaccca 300
atctggataa tgcagccatc tgctcatcat ccagctcgcc aaccagaaca cgataatcac 360
tttcggtaag tgcagcagct ttacgacggc gactcccatc ggcaatttct atgacaccag 420
atactcttcg accgaacgcc ggtgtctgtt gacca 455

<210> SEQ ID NO 166
<211> LENGTH: 309
<212> TYPE: DNA
<213> ORGANISM: Mycobacterium tuberculosis

<400> SEQUENCE: 166
ctcaagcttg gtgccgacat ggccgggctg gagcccgcgt atggcaaggt tccgctcaat 60
gtggttgtga tgcagcagga ctacgttcgc ctcaatcagc tcaaacgtca cccccgtggc 120
gtgctgcgca gcatgaaggt cggcgcccgc acgatgtggg cgaaggcaac aggtaaaaac 180
ctggtcggca tgggtcgagc cctcattggg ccgttgcgga tcgggttgca ccgcgccgga 240
gtgccggtcg aactcaacac cgccttcacc gatcttttcg tcaaaaatgg cgtcgtgtcc 300
ggggtatac 309

<210> SEQ ID NO 167
<211> LENGTH: 232
<212> TYPE: DNA
<213> ORGANISM: Mycobacterium tuberculosis

<400> SEQUENCE: 167
ccgaagcgtg ggaaatcctg accgaatacc gcgacgtgct ggacactttg gccggcgagc 60
tgctggaaaa ggagaccctg caccgacccg agctggaaag catcttcgct gacgtctaaa 120
agcggccgcg gctcaccatg ttcgacgact tcggtggccg gatcccgtcg gacaaaccgc 180
ccatcaagac acccggggga gatcgcgatc gaaacgcggc gaaacttggg cc 232

<210> SEQ ID NO 168
<211> LENGTH: 455
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 168
cgactcgaca agcattcttg acagttgttt tggctcggca tggttagcca aggttctgcg 60
gtcccaccag atcatcttgg tccggtagcg ctcgtccggg tatgctgccg ccgggattct 120
cgctgctatt actcccccg aaaaacgcca ccggtccagc gcgtgggccg ccgcggtccc 180
catcacaaac tgaaccccca acaggggaca tgcttagcgg tagggcgcgc gccaaggcgg 240
cagcaatcgc atcactgcgc tgcgcgtcac tattaaccca cccggacttc acttccacga 300
ccccgaatgg cgcccggtca ttgatcatct tgcgcaccgc ggataatccg ggattgccag 360
cccattcgac taccgcatgc gagtcatcgg ctgaccgcag cggtccgatt acccgagcgc 420
cccgantaca tctcctccaa tatcaatggg cgcaa 455

<210> SEQ ID NO 169
<211> LENGTH: 428
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 169
gcggtntagc ttcccgtcgt accggcgacc gccagccgag aagctcgttt tcccagtgtt 60
gctggggatt ctcacgctgc tgctgagtgc gtgccagacc gcttccgctt cgggttacaa 120
cgagccgcgg ggctacgatc gtgcgacgct gaagttggtg ttctccatgg acttggggat 180
gtgcctgaac cggttcacct acgactccaa gctggcgccg tctcgtccgc aggtcgttgc 240
ttgcgatagc cgggaggccc ggatccgcaa tgacggattc catgccaacg ctccgagttg 300
catgcggatc gactacgaat tgatcaccca gaaccatcgg gcgtattact gcctgaagta 360
cctggtgcgg gtcggatact gctatccggc ggtgacgacc cccggcaagc cgccatccgt 420
gctgctgt 428

<210> SEQ ID NO 170
<211> LENGTH: 385
<212> TYPE: DNA
<213> ORGANISM: Mycobacterium tuberculosis

<400> SEQUENCE: 170
ctcaagcttg ggcgtgacgg ccaccggggc cactccgcac aatctgtacc cgaccaagat 60
ctacaccatc gaatacgacg gcgtcgccga ctttccgcgg tacccgctca actttgtgtc 120
gaccctcaac gccattgccg gcacctacta cgtgcactcc aactacttca tcctgacgcc 180
ggaacaaatt gacgcagcgg ttccgctgac caatacggtc ggtcccacga tgacccagta 240
ctacatcatt cgcacggaga acctgccgct gctaaagcca ctgcgatcgg tgccgatcgt 300
ggggaaccca ctggcgaacc tggttcaacc aaacttgaag gtgattgtta acctgggcta 360
cggcgacccg gcctatggtt attcc 385

<210> SEQ ID NO 171
<211> LENGTH: 318
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 171
cgggtgtcat tggccaccgg cggcggctgt ccgggaaatg gcgggtcccc ggtggttttg 60
ctgaggagtg ctgaaccgta gtcgaagtgg gcggcgtcag actccaccca gccagcaggc 120
agcgcgaagc tgaatcctcc aaccgggttg tcgatccgga caggttgggg tgcgtttggg 180
gcaatgacag gtggcggcgg tgcgttcggg tcggccggcg gaggtgctgc gttgggatcg 240
cccggctggg cattcggcgt gttggcggcg gccggtggtg ggggggcaac angtgtcgcc 300
ggtgcgggtg gcgctgca 318

<210> SEQ ID NO 172
<211> LENGTH: 443
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 172
ncttgatatt ggcgtcaacg gtgtcggcac cggcgtcctg cagttggtag gcctgcagtt 60
tgtgcatcag gccgatgccg cggccctcgt ggccacgcat gtacagcacc acgccgcgcc 120
cctcacgggc gaccatcgcc agcgcggcgt ccagctgagg cccgcaatcg cagcggcgtg 180
acccaaacac atcgccggtc aagcactccg aatgcacccg gaccagcacg tcgtcaccgt 240
cggcgttggg cccggcgatc tcgccgcgga ccagcgcgac atgttccacg tcctcgtaga 300
tgctggtgta gccgatggcg cgaaactccc catgacgagt cggaatccgc gcctcggcga 360
cccgctcaat gtgcttctcg tgcttgcgcc gccattcgat caagtcagca atggtgatca 420
gcgccagacc gtgctcntcg gcg 443

<210> SEQ ID NO 173
<211> LENGTH: 420
<212> TYPE: DNA
<213> ORGANISM: Mycobacterium tuberculosis

<400> SEQUENCE: 173
cataagggcc ggcgtacccg gtaccggccg cgggcctacc acgtgccgga actggaagcg 60

-continued

```
cagtaagccc tcaacgcgcc accgctttgg cccgcgcgcc cggcgtaggc gcatcggcgg    120

tggccgtggg gcggcgcact gcgacctcac cagcggcttt cgagctttgt tcgatcaacc    180

ggccagcatg gtcgaggatg cattcgagac catattcgaa attggtttca tcgggggccc    240

cgatccgatg ccccctccca gttgcgtgag caagcagcgg agtcgtcgcg ggatcgatgg    300

ccacggggtg ttcaatggcg gatggtccgc tgcccgccga ctggctcttg cgggagagcc    360

gatctagcac caccgatccg cgcacgtgga ccgaaaccgc cgagtagatg tcgaaagcgt    420


<210> SEQ ID NO 174
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 174

cgtccttttc cccaagatag aaaggcagga gagtgtcttc tgcatgaata tgaagatctg     60

gtacccatcc gtgatacatt gaggctgttc cctgggggtc gttaccttcc acnagcaaaa    120

cacgtagccc cttcagagcc nnatcctgag caanatgaac agaaactgag gttttgtaaa    180

cgccaccttt atgggcagca accccgatca ccggtggaaa tacgtcttca gcacgtcgca    240

atcgcgtacc aaacacatca cgcatatgat taatttgttc aattgtataa ccaacacgtt    300

gctcaacccg tcctcgaatt tccatatccg ggtgcg                              336


<210> SEQ ID NO 175
<211> LENGTH: 264
<212> TYPE: DNA
<213> ORGANISM: Mycobacterium tuberculosis

<400> SEQUENCE: 175

ctcaagcttc atgtccgtac ggctcgggta cgcttccgtc gcagtgtgcg agtgataaat     60

gacgaccggg acctcgtcgg catcttccat agcccgccac accttcagtt gctcaccgga    120

atccaaccgg tagaaggtcg gcgagcgctc ggcattggtc atcgggatat gccgctcggg    180

acggtcagag ccctcgggtc cggccagcac tccgcaggct tcgtcggggt ggtcgcgaca    240

cgcatgggcc accatcgcat tcac                                           264


<210> SEQ ID NO 176
<211> LENGTH: 325
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 176

ncgccgccag ccaccacgcg cgggtcgggc gccgggcccg ggccgccagg ctgctccgct     60

cggtgatggc acgccaccgc gacaccaccc ggctgcgcta cgtcgagcca taccgggcgg    120

agctacatcg gctcggccgc ccagtgttcg ggccctcttt cgaggtcgag gtcgataccg    180

atttgcgcat ccgcagccgc accctggacg acagaaccgt gccctacgan tgcttgtcgg    240

gcggggccaa agaacagctt ggcatcctgg cgcgattggc cggcgcggcg ctggtctcca    300

aagaagacgc ccttccggtg ctgat                                          325
```

<210> SEQ ID NO 177
<211> LENGTH: 243
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 177

```
cgccacgttc atgggcaaca accccgatca ccggtggaaa tacgtcttca gcacgtcgca     60

atcgcgtacc aaacacatca cgcatatgat taattcgtcc aattgtataa ccaacacgtt    120

gctcaacccg tcctcgaatt tccatatccg ggtgcggtag tcgccctgct ttctcggcat    180

ctctgatagc ctgagaagaa accccaacta aatccgctgc ttcncctatt ctccagcgcc    240

ggg                                                                  243
```

<210> SEQ ID NO 178
<211> LENGTH: 430
<212> TYPE: DNA
<213> ORGANISM: Mycobacterium tuberculosis

<400> SEQUENCE: 178

```
atactcaagc ttcaaccgat tgacgcattg tgcgaactga cggcgcccgc gcatggccaa     60

tccggaagac catcattggc cagtggccgg gcgctaacag gttccagccc cccaccagtg    120

ccgctcgaac atgcggtgca acccattcgc aggccggcag ggaaagcacc gcggaagccg    180

caaagggctg cagttccgcg cccaatagtg tcgtccgcaa ccagatgcgc tcgaaaaccg    240

cgccggcagt cagcgcaccc gacgcgaggt cgagagacgt cgtcagcgcg cccacatggg    300

gtgccaatcg gcacggcagg taggccgcgc gcaacccgaa cgcgtggtgc atgcccacgg    360

tccgcaggag gcgcagcacc cgccaatgcc gaagcccacg aaacatcggg cgcatccacg    420

cttcaacctc                                                           430
```

<210> SEQ ID NO 179
<211> LENGTH: 448
<212> TYPE: DNA
<213> ORGANISM: Mycobacterium tuberculosis

<400> SEQUENCE: 179

```
agcttttggc agggtctcct tcgaattcgg cgtgcaccgc tatgggttgc agcagcggct     60

ggcgccgcac accccactgg cccgggtgtt ttcgccccga acccggatca tggtgagcga    120

aaaggagatt cgcctgttcg atgctgggat tcgccaccgc gaggccatcg accgattact    180

cgccaccggg gtgcgagagg tgccgcagtc ccgctccgtc gacgtctccg acgatccatc    240

cggcttccgc cgtcgggtgg cggtagccgt cgatgaaatc gctgccggcc gctaccacaa    300

ggtgattctg tcccgttgtg tcgaagtgcc tttcgcgatc gactttccgt tgacctaccg    360

gctggggcgt cggcacaaca ccccggtgag gtcgtttttg ttgcagttgg gcggaatccg    420

tgctctgggt tacagcccga atcgtcac                                       448
```

<210> SEQ ID NO 180
<211> LENGTH: 380
<212> TYPE: DNA
<213> ORGANISM: Mycobacterium tuberculosis

<400> SEQUENCE: 180

```
atactcaagc tttgtcacac caactgtttc caccaggcgc tccatccggc gagtggatac     60
```

tcccagcagg tagcaggtcg ccaccacgct ggtcagtgcg cgttcagctc gcttgcggcg 120
ctgcagcagc cagtccggga aatagctgcc ctggcgcagc ttggggatcg cgacttctat 180
ggttgcggca cgggtgtcga aatcacggtg gcggtagccg ttgcgctgat tggaccgctc 240
atcgctgcgt tcgcggtagc ccgccccgca cagggcgtcg gcttcagccc ccatcaaggc 300
ggcgatgaac gtcgagagca gcccgcgcag cagatccggg ctcgcctgtg cgagttggtc 360
agccagaacc tgctcggtgt 380

<210> SEQ ID NO 181
<211> LENGTH: 532
<212> TYPE: DNA
<213> ORGANISM: Mycobacterium tuberculosis

<400> SEQUENCE: 181
ccttaagccc cgcagggccc ggcacgcgcg gtaccgccca ggtcgcccaa cagatcgtcg 60
atgttcgcgt cgtccgcctc gcgcacgtgg tctgtcacca gtcaacgtta acgccgccgc 120
acatgtcctg cggccgggca aaaacgtgaa aaacgagcgg gcgactgcaa tgtcatgaca 180
ccgacggccg ccgatgggcc cagggtctgg cagattcgat ctgtgcggcc agtgccagca 240
gcgtcgcctc gtcatacggc cggccgacga gttgaaccga catgggcagg ccgtcgccgt 300
cgaagtccca cggcaccacg gccgcgggct ggccggtcag attccagact tgaaagtacg 360
gaacccgctg caccaccagc agcaacgtcg aaactgcacc ccggcgttgg taggcgccga 420
tgcgggacgg gccggtcgcg gcgcctggcg tcacaactac gtcgacatcg tcgaagatcg 480
actggatcgg ctgctcacac cactcggcgg ccgcaggccg ccatccgccg tc 532

<210> SEQ ID NO 182
<211> LENGTH: 477
<212> TYPE: DNA
<213> ORGANISM: Mycobacterium tuberculosis

<400> SEQUENCE: 182
agctttttga gcgtcgcgcg gggcagcttc gccggcaatt ctactagcga gaagtctggc 60
ccgatacgga tctgaccgaa gtcgctgcgg tgcagcccac cctcattggc gatggcgccg 120
acgatggcgc ctggaccgat cttgtgccgc ttgccgacgg cgacgcggtg ggtggtcaag 180
tccggtctac gcttgggcct ttgcggacgg tcccgacgct ggtcgcggtt gcgccgcgaa 240
agcggcgggt cgggtgccat caggaatgcc tcaccgccgc ggcactgcac ggccagtgcc 300
gcggcgatgt cagccatcgg gacatcatgc tcgcgttcat actcctcgac cagtcggcgg 360
aacagctcga ttcccggacc gcccagcgca ttggtgatgg aatcggcgaa cttggccacc 420
cgctgggtgt tgacatcctc gacggtgggc aattgccccc ggtaacgttt gccgcct 477

<210> SEQ ID NO 183
<211> LENGTH: 461
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 183
cggtccgacc ctgttcgacg gctacctgaa tcaacccgat gccaccgccg cggcgttcga 60
cgccgacagc tggtaccgca ccggcgacgt cgcggtggtc gacggcagtg ggatgcaccg 120
catcgtggga cgcgagtcgg tcgacttgat caagtcgggt ggataccggg tcggcgccgg 180
tgaaattgaa acggtgctgc tcgggcatcc ggacgtggcg gaggcggcag tcgtcggggt 240
gcccgacgat gatctaggcc agcggatcgt tgcctacgta gtcggctcag cgaatgtcga 300
tgcggacggg cttatcaact ttgttgccca acaactttcg gtgcacaagc gcccgcgcga 360
ggtgcgtatc gtanatgcgc tgccgcgcaa cgccttgggg aaagtgctcc agaacattgc 420
tgtcagaagc tganctacgc gaattatcgt gttacgctgg a 461

<210> SEQ ID NO 184
<211> LENGTH: 440
<212> TYPE: DNA
<213> ORGANISM: Mycobacterium tuberculosis

<400> SEQUENCE: 184
atactcaagc ttgccgaagt tccgatgggt cgcgccggcg agcccagcga agtcgctacc 60
gtggccgtgt tcttggcttc ggatctatcc tcgttcatga ccggcaccgt gttggacgtg 120
actggcggcc ggtccatatg acaccgagat cattgccacg gtacggcaat tcgtcaagaa 180
ggaaatcttt cccaatgcac cggccctcga acgtggcaac agctacccgc aagaaatcgt 240
cgatcggctg ggtgttattg gcttgctcgg tcgccggctg caagggtatc gacaccaccg 300
agttcattct cgggcgtgcc ggcgcattcg agctggcggt gcgcgctgcc cagcaccgtc 360
ataggtactt gacgatggtc cacgtcggac gagcgcctcc acgtcgctgc cgaacggtat 420
gcatggcggc tacgattctc 440

<210> SEQ ID NO 185
<211> LENGTH: 515
<212> TYPE: DNA
<213> ORGANISM: Mycobacterium tuberculosis

<400> SEQUENCE: 185
cggtgtcggc accggcgtcc tgcagttggt aggcctgcag tttgtgcatc aggccgatgc 60
cgcggccctc gtggccacgc atgtacagca ccacgccgcg cccctcacgg gcgaccatcg 120
ccagcgcggc gtccagctga ggcccgcaat cgcagcggcg tgacccaaac acatcgccgg 180
tcaagcactc cgaatgcacc cggaccagca cgtcgtcacc gtcggcgttg ggcccggcga 240
tctcgccgcg gaccagcgcg acatgttcca cgtcctcgta gatgctggtg tagccgatgg 300
cgcgaaactc cccatgacga gtcggaatcc gcgcctcggc gacccgctca atgtgcttct 360
cgtgcttgcg ccgccattcg atcaagtcag caatggtgat cagcgccaga ccgtgctcat 420
cggcgaacac cgcaattcat cggtgttgcg ccatcgagcc ctcatctttt tggctgacga 480
tctcgcaaat cgcccccgcg ggttgcagcc ggcat 515

<210> SEQ ID NO 186
<211> LENGTH: 345
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 186
atactcaagc tttgggtgaa agccgatcac cggaagccgc atgatcagcc acgtttcgcg 60
ccgcccggca tacggcggcg taccgatctc cgcgtcatac acccgcgggt aatcgccgac 120
ggtgccggtt cgcgagccga aggtgacgac gctgattgaa tcgagttcca ggtccagcgg 180
gtggcgcagc aacggcgcga gctcaacgac gtcaatcacg ttgtcgcttt ctacggtcac 240
cgacccggtg accgtnctcg cccggtgcgc tcggccgata agttgcaccg ccaccaccgc 300
gacaccgtct tgcacgcgga cccacccccg gatccgttgt tggcc 345

<210> SEQ ID NO 187
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 187
agcttgctgg catccgctcc agtagcgccc cgcgcgtggc ttccagcgcc cgcagatgct 60
ccatgagccg gccggtcgag tcggcgccgg cgttcaccgc cacccgccag gagctggcgg 120
ccagcatctc cgccttcacg cattgcgcga tcacagagag aatatacgtc tcatattcgt 180
tggaggtcgt cgcaggcaat cggtcgatga cggatttgat ggcatcgagc tgtgcttcgg 240
cgtagccctc cagcacgtcg gtatcgctgt ggcggtccac gacgaccgca ccggcgcggc 300
ggacagccgt cgggttggac gntgtgcggc gatcagtccg gccagctccg cctcgggatc 360
agcggc 366

<210> SEQ ID NO 188
<211> LENGTH: 423
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 188
atactcaagc ttgctgcagc ttcctatgac tgctcccgaa acctgggggt gtgcctgctg 60
tgtatgcacg gcatacggac atccttcccc tgagacccgc ggtcgaacca gccacgtgtc 120
catcatcagg ggtcaacccc ggccaagggc gacggcacgc caagttcgcc gaccgttaac 180
ctagtgctgt tagcttcatt tgctgcgagc aaaacagctg gtcggccgtt aggaactgaa 240
ttgaaactca accgatttgg tgccgccgta ggtgtcctgg ctgcgggtgc gctggtgttg 300
tccgcgtgtg gtaacnacna caatgtgacc gggggaggtg caaccactgg ccaggcgtcg 360
gcgaaggtcg attgcggggg gaagaagaac tcaaagccag tgggtcgacg cgcaggccaa 420
cgc 423

<210> SEQ ID NO 189
<211> LENGTH: 453
<212> TYPE: DNA
<213> ORGANISM: Mycobacterium tuberculosis

<400> SEQUENCE: 189
agcttgacgc ggagacggac acattgcgaa cattgatgac aaaatagaaa tcattgatgg 60
tttgagtcac caggccgatc aagccttcgc cgagccaaat tccaatcaag aggcccaagc 120
ccgtaccaat cagcccggca acgagggatt ccgtcattat cagccaaaat aactgctctc 180
gggttacacc caaacagcgc aatatggcga aaaacggtcg ccgttgcacg acattaaatg 240
tcacggtatt gtagattaaa aagataccca ccaacaaggc aatcaaactg agagcggtta 300
aattgaccgt aaaagcgtcc gtcatctgtt tgacggtgtc ccgttgggta tccgacgttt 360
ccatacgcac accggccggc agtctttgtt ggatgcgtgt tgcagtggcc tcatctttga 420
tgatcaaatc gatgtggctc agtcttccgg gca 453

<210> SEQ ID NO 190
<211> LENGTH: 402
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 190
atactcaagc ttcggctcag gcggcgctgc tggtaaagtc gctgaccggt gcaggtttcg 60
acaatgtggt gccggttcgg cggctacgtg ccatcgagac actggcgcag gctatcgcac 120
ccgttatcgg ctacgagcaa atcgcggtat gcgttcttga gcatgagtcg gcgaccgtcg 180
tcatggtcga cacccacgac ggaaagacgc agatcgccgt caagcatgtg tgccgcggat 240
tatcaggact gacctcctgg ctgaccggca tgtttggtcg cgatgcctgg cgcccggccg 300
gcgtggtcgt ggtccgctcg gatagcgagg tcagcgaatt cncntggcag ctccaaaggg 360
tcctgccggt gccggtcttt gcgcaaacna aggcncaggt ta 402

<210> SEQ ID NO 191
<211> LENGTH: 427
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 191
tgatcgcgca tcacctgctt cataaactgg aagcagcgca gcgcttcctt ttcggccgca 60
acatgagcca gcctctcgtc ggcggtcggg tgcaggtgct cgggcagctc ggccgcgaca 120
gccgcctgac cctgaaacca gcttccatat cccgcgacga acgacgccag tccgctacgt 180
aacccctccg cgactgtcca tggacaacag cgcgttctcc accgaccggg cccgggtgtg 240
gggtgtttcg gcgaccggca gccaggtggt ccacactgcc gacgggcgcc gcgagccgtt 300
caccgaccag gccgccgagc aagtccgccc gatcgcatac tccaaccggt tgcggtactg 360
caggttcagc tggcgtactc ctcgtcgcgc tcggcgaggt cttgctccag cacgtcgcan 420
acggcag 427

<210> SEQ ID NO 192
<211> LENGTH: 347
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 192
caaagcgcga actgctcgcg gcagcccacg acgtgctgcg tcggattgcc ggcggcgaaa 60
tcaattccag gcagctcccg gacaatgcgg ctctgctggc ccgcaacgaa ggactcgagg 120

```
tcaccccggt gcccggggtc gtggtgcacc tgccgatcgc acaggttggc ccacaaccgg    180

ccgcttgatg cccggtcggc aagcccggca gttgccaaac ccagcgtgat caggctcggc    240

tcgcgagttc cgggaagaag tggctccgcc tgatcaccta ccatccgcca ggatctgcgt    300

gtcttcacca cgcccgccaa ggaggttgtt gtggtgctat cgaccgn                  347


<210> SEQ ID NO 193
<211> LENGTH: 330
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 193

ccggaagccg catgatcagc caagtttcgc gccgcccggc atacggcggc gtaccgatct     60

ccgcgtcata cacccgcggg taatcgccga cggtgccggt tcgcgagccg aaggtgacga    120

cgctgattga atcgagttcc aggtccagcg ggtggcgcag caacggcgcg agctcaacga    180

cgtcaatcac gttgtcgctt tctacggtca ccgacccggt gaccgtngtc gcccggtgcg    240

ctcggccgaa aanttgcacc gccaccaccg cgaaaccgtc ttgcacnccg gaagccaccc    300

ccgatccgtt gttgggccag gttattgggt                                      330


<210> SEQ ID NO 194
<211> LENGTH: 215
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 194

ccggaaccgc cgacggcacg gtataacgcc tccgcatatg ggtcgacaac cagcgggtcg     60

gacttctggg cttctagcgt tcgcgcngtc gcgacaaaca gcgcggtcga accgacactc    120

gttgtgatgt cctagctatc acgttcggta cgcacccaat cgagtctagc gcgggtagnt    180

cagccccgat ctccangctc cgccgagcca ggcgc                                215


<210> SEQ ID NO 195
<211> LENGTH: 225
<212> TYPE: DNA
<213> ORGANISM: Mycobacterium tuberculosis

<400> SEQUENCE: 195

ctggtttatg tcccgttgaa gttccatcac ccgatgtggc gggagcactg ccaggtcgat     60

ctcaactacc acatccggcc gtggcggttg cgcgccccgg ggggtcggcg cgaactcgac    120

gaggcggtcg gagaaatcgc cagcaccccg ctgaaccgcg accacccgct gtgggagatg    180

tacttcgttg aggggcttgc caaccaccgg atcgcggtgg ttgcc                    225


<210> SEQ ID NO 196
<211> LENGTH: 161
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"
```

<400> SEQUENCE: 196
ccgagcagtt gggaatcgct ctgcancaaa ccaatattct gcgcgacgtc gcgcgacgag 60
ctggaccgat taggcgtacg cctccgnctg gacgacaccg gggcactcga tgaccccgac 120
gcctacgctc gcaggatatt gttcgccgga cccctctcta g 161

<210> SEQ ID NO 197
<211> LENGTH: 240
<212> TYPE: DNA
<213> ORGANISM: Mycobacterium tuberculosis

<400> SEQUENCE: 197
tatataatac tcaagcttgc cgacgccaac gctcgcgcga tgttgttagc ccgacccggc 60
tcttacatgg caccggtgcc ccacacgtca gcctgtgacg tcctgcaccg cgactcttta 120
catagaatgt ggattgccgg attggggatg tccggcatcg ctcaatctgt agtccgcgtt 180
gtcccgcgag ggccatgtgg atggggggaa ggatccgtgg cgtccgggat caccatgggg 240

<210> SEQ ID NO 198
<211> LENGTH: 348
<212> TYPE: DNA
<213> ORGANISM: Mycobacterium tuberculosis

<400> SEQUENCE: 198
atactcaagc ttgccgaagt tccgatgggt cgcgccggcg agcccaacga aatcgctagc 60
gtggccgtgt tcttggcttc ggatctatcc tcgtacatga ccggcaccgt gttggacgtg 120
actggcggcc ggttcatatg acaccgagat cattgccacg gtacggaaat tcgtccagaa 180
ggaaatcttt cccaatgcac cggccctcga acgtggcaac agctacccgc aagaaatcgt 240
caatcggctg ggtgttattg gcttgctcgg tcgccggctg cgagggtttc tacaccaccg 300
agttcattct cgggcgtgcc ggcgcattcg aactggcggt gcgcgctg 348

<210> SEQ ID NO 199
<211> LENGTH: 371
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 199
gcaccggcgt cctgcagttg gtaggcctgc agtttgtgca tcaggccgat gccgcggccc 60
tcgtggccac gcatgtacag caccacgccg cgcccctcac gggcgaccat cgccagcgcg 120
gcgtccagct gaggcccgca atcgcagcgg cgtgacccaa acacatcgcc ggtcaagcac 180
tccgaatgca cccggaccag cacgtcttca ccgtcggcgt tgggcccggc gatctcgccg 240
cggaccaacg cgacatgttc cacgtcctcg tagatgctgg tgtagccgat ggcgcgaaac 300
tccccangac aagtcggaat ccgcgcctcg gcgaaccgct caatgtgcct ctcgtgcttg 360
cgccgccatt c 371

<210> SEQ ID NO 200
<211> LENGTH: 165
<212> TYPE: DNA
<213> ORGANISM: Mycobacterium tuberculosis

<400> SEQUENCE: 200

```
tggtccgtgt gcgcatacca atacaacgcg ccgggcacct gacgcggcgg ccgcaaccaa     60

tcggtggcca tcgccatctt ctgctacccg gtcaacggac gcaccttctc ctggccgacg    120

tagtgcgccc acccgccgcc gttgcgtccc atcgatccgg tcaac                    165


<210> SEQ ID NO 201
<211> LENGTH: 390
<212> TYPE: DNA
<213> ORGANISM: Mycobacterium tuberculosis

<400> SEQUENCE: 201

ggcgtgttgg ccaccggggc cactccgcac aatctgtacc cgaccaagat ctacaccatc     60

gaatacgacg gcgtcgccga ctttccgcgg tacccgctca actttgtgtc gaccctcaac    120

gccattgccg gcacctacta cgtgcactcc aactacttca tcctgacgcc ggaacaaatt    180

gacgcagcgg ttccgctgac caatacggtc ggtcccacga tgacccagta ctacatcatt    240

cgcacggaga acctgccgct gctaaagcca ctggcgatcg gtgccgatcg tggggaaccc    300

actggcgaac ctggttcaac caaacttgaa ggtgattgtt tacctgggct acggcgaccc    360

ggcctatggt tattcgacct ccccgcccaa                                     390


<210> SEQ ID NO 202
<211> LENGTH: 427
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 202

cgtccgtgnc ccctcaancg cgtgnngccg aagcggctgg ttacgactcc ctgtttgtga     60

tggacacttc taccaactgc ccatgttggg gacgcccgac cagccgatgc tggaggccta    120

cacggccctt ggtgcgctgg ccacggcgac cgancggctg caactgggcg cgttggtgac    180

cggcaatacc taccgcagcc cgaccctgct ggcaaagatc atcaccacgc tcgacgtggt    240

tagcgccggt cgagcgatcc tcggcattgg agccggttgg tttgagctgg aaacaccgcc    300

agctcggctt cgagttcggc actttcagtg accggttcaa ccggctcgaa gaggcgctac    360

agatcctcca gccaatggtc aagggtgagc gcccaacgtt tttcggcgat tggtacacca    420

ccgaatc                                                              427


<210> SEQ ID NO 203
<211> LENGTH: 498
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 203

ccgcttccgt gtaaccgagc anngcgagcg anctggcgag gaagcaaaga agaactgttc     60

tgtcagatag ctcttacgct cagcgcaaga agaaatatcc accgtgggaa aaactccagg    120

tagaggtaca cacgcggata gccaattcag agtaataaac tgtgataatc aaccctcatc    180

aatgatgacg aactatcccc cgatatcagg tcacatgacg aagggaaaga gaaggaaatc    240

aactgtgaca aactgccctc aaatttggct tccttaaaaa ttacagttca aaaagtatga    300
```

gaaaatccat gcaggctgaa ggaaacagca aaactgtgac aaattaccct cagtaggtca 360
gaacaaatgt gacgaaccnc cctcaaatct gtgacagata accctcagac tatcctgtcg 420
tcatggaagt gatatcgcgg aaggaaaata cgatntgagt cgtctggcgg cctttctttt 480
tctcaatgta tgagagcg 498

<210> SEQ ID NO 204
<211> LENGTH: 265
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 204
tgacacccaa cagagggcac ttaagatggc aatgcggccg cctacctgca cgttttcgcg 60
atgtcagagg atgccgaggg agaacaatgc gagcacggcc gctgacnttg ctcaccgctt 120
tggcggcggt gacattggtg gtggttgcgg gctgcnaggc ccgantcnag gccgaagcat 180
atagcgcggc cgaccgcatt tcgtctcgac cgcaagcgcg acctcagccg cagccggtgg 240
agctactgct gcgcgccatc acgcc 265

<210> SEQ ID NO 205
<211> LENGTH: 369
<212> TYPE: DNA
<213> ORGANISM: Mycobacterium tuberculosis

<400> SEQUENCE: 205
acgggcgacg ctgaggtggg cccgcggcta ttcatgctgt cgtccacgtc cagcgacgca 60
ctgcgccaga cggcccgcca actagccacc tgggtggaag aacaccagga ctgcgtggcg 120
gcctcggatc tggcctacac gctggcgcgt ggccgcgcgc accggccggt gcgcaccgcg 180
gtggttgccg ccaacctgcc ggagctcgtc gagggtttgc gcgaggtggc cgacggtgac 240
ccctctatga cgcggcggtg ggacactgtg atctaagacc ggtctgggtc ttctccgggc 300
aagggtctca gtgggcggcg atgggcaccc aattgctcgc cagcgaacca gtgttcgcgg 360
ccaccatcg 369

<210> SEQ ID NO 206
<211> LENGTH: 428
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 206
atactcaagc ttcgcgagat ccggatggca ctcacgctgg acaagacctt cacaaaatct 60
gaaatcctga cccgatactt gaacctggtc tcgttcggca ataactcgtt cggcgtgcag 120
gacgcggcgc aaacgtactt cggcatcaac gcgtccgacc tgaattggca gcaagcggcg 180
ctgctggccg gcatggtgca atcgaccagc acgctcaacc cgtacaccaa ccccgacggc 240
gcgctggccc ggcggaacgt ggtcctcgac accatgatcn aaaacttccc ggggaggcgg 300
aggcgttgcg tgccgcccag ggcgaaccgc tgggggttct gccgcagccc aatgattgcc 360
gcgcggctgc atcgcgggcg gcgaccgcca ttcttctgcg aatacgtcca ggagtactgt 420
ctcggggc 428

<210> SEQ ID NO 207
<211> LENGTH: 378
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 207
agcttatgtg gccgcccacc taccttatct agcctagcta actaaatcca gtgccgacag 60
tgcgcggctg gccacccagc atgaggttat gaccacggca tatgccagcg cgctggcggc 120
gatgccgacg ctgaccgagt tggccgctaa tcacaccagc catgcggtgt tgctgggaac 180
gaatttcttt ggaatcaata cgatcccgat cgcgctcaat gaggccgact atgcgcggat 240
gtggattcag gcggccacca cgatgagtat ctatgagggc acctccgatg cggcgctggc 300
gtcngcaccg caaaccacac cggctccggt actgttcaac ggcggtgctg gcgtttgcca 360
gcgcctgccg gcgatctc 378

<210> SEQ ID NO 208
<211> LENGTH: 284
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 208
atactcaagc ttgccaccca tgccgagcaa ggtcgactca gcgatgacga attgttcttc 60
ttcgcggtgt tgctgctggt tgcgggctat gagagcactg ctcatatgat tagcacnttg 120
tttctgacgc tggccgacta tccagatcag ctgacactcc ttgcgcagca accagacctg 180
atcccgtcgg cgatcgagga gcacctccgc tttatatcgc aatccaaaac atctgccgca 240
caacgcgcgt cgactattcg gtcggtcaag cggtcatccc ggga 284

<210> SEQ ID NO 209
<211> LENGTH: 236
<212> TYPE: DNA
<213> ORGANISM: Mycobacterium tuberculosis

<400> SEQUENCE: 209
ccggggtaga acgatgcgat ctgggccatg tcgacatcgg tggtacaggt aaaccgcgcc 60
gtgtgcgcgg tctcggagat cagaacgtgg tcgcagttga caccgcgggc tttcagccag 120
tcgcgataat cggcgaagtc ggcgcctgcc gccccaacta gcgcgacctc gccacctagc 180
acaccgatgg cgaaggccat gtttccggcc acgccgccgc ggtgcatcat caactc 236

<210> SEQ ID NO 210
<211> LENGTH: 278
<212> TYPE: DNA
<213> ORGANISM: Mycobacterium tuberculosis

<400> SEQUENCE: 210
atactcaagc ttggcggcaa cgccactacc gggctcacca ggtcctgtgc cgccaccgcc 60
ggcgccgaaa gcaccatcag gtcgtagttg tctggacgtt cgacaccgta agcgaacaca 120
atgccgccgc ccatgctgtg cccgagcacg atgcgcttgc acccgggata ttcccgggtg 180
gcgatcccaa cgagggtgtc gaagtcagcg gtgtatctga gatgtctctc actatcatcc 240
gtttggcacc cgagcgggca tgcccgcggg gggtcaac 278

<210> SEQ ID NO 211
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 211
gtcgacggca tcaaggtccg cagtgatggt gttcatctca cccaggaagg cgtgaagtgg 60
ctgataccgt ggcttgagga ttcggtgcgg gtcgccagtt aatccgccgt gtgctccgga 120
tgagcgcgac ggtaaccctg gaattgtgct gtgtgctggc tgtgtcgttg tgatgagcct 180
gtctaagtgg tgcgtaaccg tttgacgagc cgcggcctcg ctgcaaacat tgaagcccgc 240
acgtctgggt ttgtatttac acaacgaggg cgctccccga tctggcgcgc gcaacgaggt 300
gcncactatc cattcgaggt gaactggact ccttgatgct catgccggtg cggttttgtc 360

<210> SEQ ID NO 212
<211> LENGTH: 256
<212> TYPE: DNA
<213> ORGANISM: Mycobacterium tuberculosis

<400> SEQUENCE: 212
atactcaagc ttgcgttcga tgaagtagtc gtcggtcagc gccgcctctt cgagctcctt 60
ggcgatgccc agcaaggagt catcgccgcc gagcttggcc aggatcttgt cggcctgttc 120
cttgacgatg cgggcccgcg gatcgtagtt cttgtagaca cgatgaccga aacccatcaa 180
tttgaccccg gcctcgcggt tcttgacctt gcgttacaaa ctcgctgacg tcgtcgccgc 240
tgtcgcgaat gccctc 256

<210> SEQ ID NO 213
<211> LENGTH: 262
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 213
ngtcaagccg agcatgcgcg aggnaacgac gaacccaaca agccatggtg gttggcgccg 60
tcgagaggtc ggcggtcgcc acaacgggaa gatcgccttg agcgtcgctc gaccgccgcc 120
tcgagttggg tcataacgaa gtagctgatg ccgatcatgt cgacgtttcc gtcgcatcag 180
cgtgcagcgg cgacccactc gacgaggtct cggtgccgcc gcggccaggg caccagcagt 240
gacgattcca ggcgccgtcg gg 262

<210> SEQ ID NO 214
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)

<223> OTHER INFORMATION: applicants are uncertain of bases designated as "n"

<400> SEQUENCE: 214
cgataatcgc ttccggtaag tgcagcagct ttacgacggc gactcccatc ggcaatttct 60
atgacaccag atactcttcg accgaacgcc ggtgtctgtt gaccagtcag tagaaaagaa 120
gggatgagat ctccccgtgc gtcctcagta agcagctcct ggtcgcgttc attacctgac 180
catacccgag aggtcttctc aacactatca ccccggagca cttctagagt aaacttccca 240
tcccgaccac atataggcta aggtaatggg cattaccgcg agccattact cctacgcgcg 300
caattaacga atccaccatc ggggccgctg gtgtcn 336

<210> SEQ ID NO 215
<211> LENGTH: 259
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 215
naatactcaa gctttctcgt gattaccacc cgtgtaattt gggatgggca aaaaggcgaa 60
tcaccgcgtg gccacaaacg ccgggaggga caatctcggg cggctagggc ttctcgcggg 120
aaggcccgaa cgtacggcgt ttcaacacgt cgcgtcgccc tccgaccgcg aacattcggg 180
gatggcagca acctggtatc accctggccg ggcaatgatc tgcagcgtcg ccgcgggtag 240
tgnccgcccg ggcggctac 259

<210> SEQ ID NO 216
<211> LENGTH: 325
<212> TYPE: DNA
<213> ORGANISM: Mycobacterium tuberculosis

<400> SEQUENCE: 216
ccaactagag catcgggaca tacggagtca actacccggc caacggtgat ttcttggccg 60
ccgctgacgg cgcgaacgac gccagcgacc acattcagca gatggccagc gcgtgccggg 120
ccacgatgtt ggtgctcggc ggctactccc agggtgcggc cgtgatcgac atcgtcaccg 180
ccgcaccact gcccggtctc gggttcacgc agccgttgcc gcccgcagcg gacgatcaca 240
tcgccgcgat cgccctgttc gggaatccct cggggccgcg ctggcgggct gatgatcgcc 300
ctgacccctc aattcgggtc caaga 325

<210> SEQ ID NO 217
<211> LENGTH: 300
<212> TYPE: DNA
<213> ORGANISM: Mycobacterium tuberculosis

<400> SEQUENCE: 217
atactcaagc ttgctgcagc ttcctgtgac tgctcccgaa acctgggggt gtgcctgctg 60
tgtatgcacg gcatacggac atccttcccc tgagacccgc ggtcgaacca gccacgtgtc 120
catcatcagg ggtcaacccc ggccaagggc gacggcacgc caagttcgcc gaccgttaac 180
ctagtgctgt tagcttcatt tgctgcgagc aaaacagctg gtcggccgtt aggaactgaa 240
ttgaaactca accgatttgg tgccgcccgt aagtgtcctg gctgccggtg cgctggtgtt 300

<210> SEQ ID NO 218

<211> LENGTH: 265
<212> TYPE: DNA
<213> ORGANISM: Mycobacterium tuberculosis

<400> SEQUENCE: 218
agcttgcgcg gcgtggcgat cgcggttcaa ggcgcgctct tcgagcacaa cgagcgaaga 60
cagctcggcg acggagcctt tatcgacatc cgttcgggct ggctgaccgg cggcgaagaa 120
ctgctggacg cgttgttgtc gacggtgccg tggcgagccg agcgccgtca gatgtacgac 180
cgggtggtcg atgtgccgcg gctggtgagt tttcacgacc tgaccatcga agatccgccg 240
catccgcagc tggcgcggat gcgcc 265

<210> SEQ ID NO 219
<211> LENGTH: 362
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 219
aatactcaag cttgcgcacg accaggacgt cgagtggcgc ttgcagtgac ttggcgacct 60
caaaggccac cggtaccccg ccgcgcggca agccaaggac nacnacggcc ttgccggata 120
gctgcgccag gcgttgcgcc aactggcgtc cagcgtcgcc acgatcgtca aagagcttca 180
tctgccgagt gtgtcgccat ctcatggctc caaatatgga attaggtccc tgggccgact 240
gacgacagtc cctcagcgac cggattgcgc atcccgcctt gtacgctgct ccgcaaatcc 300
cgggcttgcg tccgcggaag cgaactcggc ggcgctacgg tggtggctca cttcggccgt 360
gc 362

<210> SEQ ID NO 220
<211> LENGTH: 486
<212> TYPE: DNA
<213> ORGANISM: Mycobacterium tuberculosis

<400> SEQUENCE: 220
ggttggtgcg gtccaccttc gcggcggcgg cgcgatatgc cttgctggtc ttgctcattt 60
gatatccaat ctatgggtcg tggttactca gcgggccgaa gctggccctc ccacgggtag 120
ggccctattc gacggtgatg cccatcgacc gagcggtacc ggcgatgatc ttggccgcag 180
cgtcgacgtc gttggcgttg aggtccgtct tcttggtctc ggcgatttcg cggacttgat 240
cccaggtgac tttggcgacc ttggtcttgt gcggctccgc cgaacccttc gccacaccag 300
cggccttaag cagcagcttg gcggcgggcg gcgtcttcag cgtgaaagtg aagctacggt 360
cttcataaac ggtgatctcc accgggatga cgttgccgcg ctggttctcc gtcgcggcgt 420
tgtacgcctt gcagaactcc atgatgttga cccgtgctga ccgaacgcgg ggcccactgg 480
cggggc 486

<210> SEQ ID NO 221
<211> LENGTH: 373
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 221
atactcaagc ttttcgaccc gcaagccggc ggtgcccctc ctcgttccgc tgcccggtct 60
gctcgatcgg ttcggggtcg ccgcgctagg cccaattgcc cggctcctcc tcgggccgtt 120
ccacaacccg catcgtcgcc gggctaggtt caagccatgc cggtaaaccc caggacgcca 180
gtgctgatcg gctatggaca ggtcaaccac cgaggcgaca tcgacgccna aaatcagtcc 240
atcgaacccg tcgacctgat ggccnccgcg gcccggaaag ccgccgagtc caccgtgctc 300
gaagcggtgg attccatccg tgtggtgcac atgctgtcgg cgcattaccg gaattcccgg 360
gcgtctcctc ggc 373

<210> SEQ ID NO 222
<211> LENGTH: 331
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 222
ncctggttca tgaactggaa gcagcgcagc gcttcctttt cggccgcaac atgagccagc 60
ctctcgtcgg cggtcgggtg caggtgctcg ggcagctcgg ccgcgacagc cgcctgaccc 120
tgaaaccagc ttccatatcc cgcgacgaac gacgccagtc cgctacgtaa cccctccgcg 180
actgtccatg gacaacagcg cgttctccac cgaccggggc cgggtgttgg ggtgttcggc 240
aacggcaacc aagttggtcc acactgccga cgggcgccgc aaatccgttc accgaaccag 300
gccgccnaaa caattccgcc cgatcccata t 331

<210> SEQ ID NO 223
<211> LENGTH: 377
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 223
atactcaagc ttgtcgggat caatctcgag ggcatccacg cacgaaaagt aaactctatc 60 aagcttttttg acgacaccca cggacgcccc atatatgttc gggtgggcaa gaacggtccc 120
tacctggaac gtttggtggc cggcgacacc ggtgagccca cgccgcagcg ggccaacctc 180
agcgactcga ttaccccgga cgaactgact ctacaggtgg ccgaagagct ctttgccaca 240
ccgcaacagg gacggacttt gggcttggac ccagaaaccg gccacgaaat ctttgccagg 300
ggaaggccgg tttgggcctt atgttaccta tatcctgccg gaacctgcgg ctgatgcggc 360
cgcggccgct cagggan 377

<210> SEQ ID NO 224
<211> LENGTH: 436
<212> TYPE: DNA
<213> ORGANISM: Mycobacterium tuberculosis

<400> SEQUENCE: 224
agcagctagc cgcgctcgcc gcgctggtcg gtgcgtgcat gctcgcagcc ggatgcacca 60
acgtggtcga cgggaccgcc gtggctgccg acaaatccgg accactgcat caggatccga 120
taccggtttc agcgcttgaa gggctgcttc tcgacttgag ccagatcaat gccgcgctgg 180
gtgcgacatc gatgaaggtg tggttcaacg ccaaggcaat gtgggactgg agcaagagcg 240
tggccgacaa gaattgcctg ggctatcgac ggtccagcac aggaaaaggt ctatgccggc 300
accgggtgga ccgctatgcg cggccaacgg ctggatgaca gcatcgatga ctccaagaaa 360
cgcgaccact acgccattca agcggtcgtc ggcttcccga ccgcacatga tgccgaagaa 420
ttctacagct cctccg 436

<210> SEQ ID NO 225
<211> LENGTH: 539
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 225
cgcgactggc tccccggncg gctgctcggg tccgccgata gagaccggga tgtcgcccga 60
cgacgggcag ccgggttgcg tgggacgggg cgggggtcgg gcagcccaag caacgggcta 120
gtccccgaat cctacggagc cgtcacctac gcctacgtaa tagtagctat caataacagt 180
tgacatacgc aacgatctgt gagatcaata ttgcctgacg catgtcaaga caggcgtcaa 240
gacaggtgtc aataattcgc tccgctggtg acggtaaccg gtcgtgcggg tgtgtgacgc 300
ctaaggaagg agtgtgggtg gtgacgctga gagtggttcc tgagggtttg gcggccgcca 360
gtgcggcggt ggaggcgttg accgcacggc tggccgccgc acacgctggc gcggcgccgg 420
cgattacggc ggtggtggcg cccgcggcgg atccggtgtc gttgcagaat gcggtggggt 480
ttagcgcctt aagtagccag catgccgcga tcgccggcga aagggtccaa gaactgggt 539

<210> SEQ ID NO 226
<211> LENGTH: 517
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 226
atactcaagc ttattgaacc gcgggtcgca ggcaaagtgg acctcataac gactcgggtc 60
cagcgaccgc gccaacacga acggccggac gacgtgggcc agggtcgcgg cctcccctac 120
aaacaggatc cgttgcctgc gaacgacagg ctccggtgcg gcgttgggcg ccgtgctcgt 180
cccagcgtcc ggtcccgggt cgccggcgac gcttgtttcc tccatactcg ccccctaatc 240
tcgaggcagc ccgtacccgc aggcaacctc ccaaaaatgc aatcccgcaa aatgcaatgc 300
gtcnagctat ttctcacacc gaccgctagt tgcggatcag aaatccgttg ggcgcggaag 360
tccagccgaa tttgttctcc cgctccgcat catgcttgta atcgtttgga aattcatcct 420
catatgcctc gatcgcttca tagggtccag gcccaaaccc gggcaggact gggtggccgt 480
tgatgttgga atcctccact actaggtatt caccggc 517

<210> SEQ ID NO 227
<211> LENGTH: 488
<212> TYPE: DNA
<213> ORGANISM: Mycobacterium tuberculosis

<400> SEQUENCE: 227
gtctcgatca tggccaaaga gctcgacgaa gccgtagagg cgtttcggac ccgcccgctc 60
gatgccggcc cgtatacctt cctcgccgcc gacgccctgg tgctcaaggt gcgcgaggca 120
ggccgcgtcg tcggggtgca caccttgatc gccaccggcg tcaacgccga gggctaccga 180
gagatcctgg gcatccaggt cacctccgcc gaggacgggg ccggctggct ggcgttcttc 240
cgcgacctgg tcgcccgcgg cctgtccggg gtcgcgctgg tcaccggcga cgcccacgcc 300
ggcctggtgg ccgcgatcgg cgccaccctg cccgcagcgg cctggcagcg ctgcagaacc 360
cactacgcag ccaatctgat ggcagccacc ccgaagccct cctggccgtg ggtgcgcacc 420
ctgctgcact ccatctacga ccagcccgac gccgaatcag ttgttgccaa tatgatcggg 480
ttctcgac 488

<210> SEQ ID NO 228
<211> LENGTH: 264
<212> TYPE: DNA
<213> ORGANISM: Mycobacterium tuberculosis

<400> SEQUENCE: 228
atactcaagc tttcgtcagt tcatggcgcc agcagaccaa caagagcatc gggacatacg 60
gagtcaacta cccggccaac ggtgatttct tggccgccgc tgacggcgcg aacgacgcca 120
gcgaccacat tcagcaaatg gccagcgcgt gccgggccac gaggttggtg ctcggcggct 180
actcccaggg tgcggccgtg atcaagatct tcaccgccgc accactgccc ggcctcgggt 240
tcacgcatcc gtttggccgc cgcc 264

<210> SEQ ID NO 229
<211> LENGTH: 229
<212> TYPE: DNA
<213> ORGANISM: Mycobacterium tuberculosis

<400> SEQUENCE: 229
gccccgtgta atttgggatg ggcaaaaagc gaagcaccgc gtggccacga acgccgggag 60
ggacaatctc gggcggctag ggcttctcgc gggaaggccc gaacgtacgg cgtttcaaca 120
cgtcgcgtcg ccctccgacc gcgaacattc ggggatggca gcaacctggt agcaccctgg 180
ccgggcgatg atctgcagcg tcgccgcggg tagtctccgc ccgggccgc 229

<210> SEQ ID NO 230
<211> LENGTH: 266
<212> TYPE: DNA
<213> ORGANISM: Mycobacterium tuberculosis

<400> SEQUENCE: 230
atactcaagc ttcctttgac cgaacgcgtc caccgcaccg tgagattggt ggcgccattc 60
gtcgtggtgt agctgctgtt ggcggcgtcg ccgtattgtg cgggccagcc ttgtgcgggg 120
gccgcttcta cccacaagtc ggcacttccg caaccgccca gctcgaccgc gaattacggc 180
ggccgcaacg gccgccggaa ggcgtcacgc aatcgcttat cctttccagg ttcccaaatc 240
ctccgcttac ttgggtcctt catcgg 266

<210> SEQ ID NO 231
<211> LENGTH: 258
<212> TYPE: DNA
<213> ORGANISM: Mycobacterium tuberculosis
<220> FEATURE:
<221> NAME/KEY: unsure
<222> LOCATION: (various positions within the sequence)

<223> OTHER INFORMATION: applicants are uncertain of bases designated as "n"

<400> SEQUENCE: 231
ggcagcggcg acaaccggaa cgtccgcacg gtgctcaatc acgggtgcac ggtgtgcatc 60
agaatggcgg gggttcgttg tcgcggtgag gcgttcggcg aggaggtagt gtctacccct 120
tgcccgcggg ttcgtgcgga ctgaaaggga tttcattggg aacccacggc tgcgtatcgc 180
agggcctcgg tgacgtctgc ttcctcnagc tcaggaagtt cggcgagaat ctcggtggat 240
gttatttggt ccgcctac 258

<210> SEQ ID NO 232
<211> LENGTH: 224
<212> TYPE: DNA
<213> ORGANISM: Mycobacterium tuberculosis

<400> SEQUENCE: 232
atactcaagc tttctcggct tctctgatag cctgagaaga aaccccaagt taatccgctg 60
cttcacctat tctccagcgc cgggttattt tcctcgcttc cgggctgtca tcattaaact 120
gtgcaatggc gatagccttc gtcatttcat gaccagcgtt tatgcactgg ttaagtgttt 180
ccatgagttt cattctgaac atcctttatt cattgttttg cgtt 224

<210> SEQ ID NO 233
<211> LENGTH: 333
<212> TYPE: DNA
<213> ORGANISM: Mycobacterium tuberculosis

<400> SEQUENCE: 233
atactcaagc ttggtgaccg gcaccgcgat acgttgcggc aggcatctgg gctggcggtg 60
gttcgccgct ccgaagccgt cgaacaccat cgccagcgcg gcttccacat caacgaccat 120
ttcggccagc ttgcggcgca tcagcggctt gtcgatgagc gccccaccga atgcccgccg 180
ctgcccggcg tatcacatcg attcgaccat cgcgcggcgc gcgttgccga gggcgaacga 240
ggcggtgccc aaccgcaatc tgtttggtca gctccctcat gcgggttgat tccttgccgt 300
ccggacgggc ccgcgtcatg cgctcggttc gcc 333

<210> SEQ ID NO 234
<211> LENGTH: 407
<212> TYPE: DNA
<213> ORGANISM: Mycobacterium tuberculosis

<400> SEQUENCE: 234
ccgttgcgca gcgtgagccg atagttgaca tccggctcgg tgaaggtgaa atcgatggcc 60
aggtcgaggt cccatgcgcg tgggccattg atgctgatcg ccaggacgtc aaagatttgg 120
tccggcgtca gctgggcgaa aaacgtgggc gccgggactt gcccggagct gcccgggttc 180
ccgtcgcgca gctcggcggc cccggtcaga aagaaattgc gccaggtcgc acactccgcg 240
ccgtaggcca gctgctccag ggtgtcggca tagagcccgc gggccgcagc gtgctcgctg 300
tcggcgaaca ccgcatggtc gagaagcgtt gccgcccaac gggaaatcac ctgcgtcgaa 360
agcttcgcgg gccagctcca gcactcggtc gatgccaccc aacgcgt 407

<210> SEQ ID NO 235
<211> LENGTH: 389
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 235
atactcaagc ttgcggatgt taccccctgac agcgtgaact atgtcnaaac acacggcacc 60
ggaacggtgt tgggggaccc catcgagttc gagtcgctgg cggccactta tggcctgggt 120
aaaggccagg gcgagagccc gtgcgcattg gggtcggtca aaaccaacat cggccacctg 180
gaggcggccg ccggtgtggc tggattcatc aaggcggtgc tggcggtgca acgtgggcac 240
attccccgca acttgcactt cacccggtgg aacccggcca tcaacacgtc ggcgacgcgg 300
ctgttcgtgc cgaccgaaag cgccccgtgg ccggcggctg ccggtccacg cagggctgcg 360
gtgtcatcgt tcggcctcag cgggaccaa 389

<210> SEQ ID NO 236
<211> LENGTH: 432
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 236
ccggtaacca gatcagctcg tcgacctcac tgccgggggt gaattcccca ccggtgctgc 60
gcgctgccca gtagtgcacc ttcttgacgc ctcgaaaagg ggagtcggtc gggtaggtca 120
ccgtcaggag ccgcctaccc aggttggcgc ggtgaccggt ctcctcgagt atctcccgca 180
ccgcccccac cggtgcggtc tcgcccggat ccactttgcc cttgggcagc gaccagtcgt 240
cgtaacgggg gcggtgaatg acagcgatct cgaccggccc ttccgaatcg gcactgccgg 300
gtcgccagaa caccgcaccg gcggcgtaca caatccggcc cgccgagcgc cggcgggcgg 360
acganttctg gatcgacacc tcaactcctg caggtcaatt cggccaagct gctcgcggtc 420
gtggatgtgg tc 432

<210> SEQ ID NO 237
<211> LENGTH: 287
<212> TYPE: DNA
<213> ORGANISM: Mycobacterium tuberculosis

<400> SEQUENCE: 237
atactcaagc ttgatgccgc cgaaaccgag cgtgagcacg ccgccaccca ccacgcgcgg 60
gtcgggcgcc gggcccgggc cgccaggctg ctccgctcgg tgatggcacg ccaccgcgac 120
accacccggc tgcgctacgt cgagccatac cgggcggagc tacatcggct cggccgccca 180
gtgttcgggc cctctttcga ggtcgaggtc tataccgatt tgcgcatccg cagccgcacc 240
ctggtcgtct cgtaccgtgc cctacctctg cttgtcgggc ggggcca 287

<210> SEQ ID NO 238
<211> LENGTH: 272
<212> TYPE: DNA
<213> ORGANISM: Mycobacterium tuberculosis

<400> SEQUENCE: 238
tccgtacggc ccgggtacgc ttcggtcgca gtgtgcgagt gatagatgac gaccgggacc 60
tcgtcggcat cttccatagc ccgccacacc ttcagttgct caccggaatc caaccggtag 120
aaggtcggcg agcgctcggc attggtcatc gggatatgcc gctcgggacg gtcagagccc 180
tcgggtccgg ccagcactcc gcaggcttcg tcggggtggt cgcgacgcgc atgggccacc 240
atccatccac caggtctgcg cgaatcaccc gc 272

<210> SEQ ID NO 239
<211> LENGTH: 410
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 239
ggacacattg cgaacattga tgacaaaata gaaatcattg atggtttgag tcaccaggcc 60
gatcaagcct tcgccgagcc aaattccaat caagaggccc aagcccgtac caatcagccc 120
ggcaacgagg gattccgtca ttatcagcca aaataactgc tctcgggtta cacccaaaca 180
gcgcaatatg gcgaaaaacg gtcgccgttg cacgacatta aatgtcacgg tattgtaaat 240
taaaaagata cccaccaaca aggcaatcaa actgagagcg gttaaattga ccgtaaaagc 300
gtccgtcatc tgtttgacgg tgtcccgttg ggtntccgac gtttccatac gcacaccggc 360
cggcagtctt tgttggatgc gtgttgcagt ggcctcatct ttgatgatca 410

<210> SEQ ID NO 240
<211> LENGTH: 439
<212> TYPE: DNA
<213> ORGANISM: Mycobacterium tuberculosis

<400> SEQUENCE: 240
gcctggccca ggtgaaggcc gacctcgacg ccaaagccgc tgatccggca catgagtcgg 60
tggactggga cttgaagtcg ctgcgatggg cgtggaaccg agccaaagat gacgtggcgc 120
cgtggtgggc cgagaattcc aaggagtgct actcgtcggg gttggccgat ctggcccagg 180
gcctggctaa ttggaaagct ggcaagaacg ggacccgcaa aggccggcgg gtgggcttcc 240
cgcgattcaa atccgggcgg cgtgatcctg gcagggtgcg gttcaccacc ggcaccatgc 300
gcatagagga tgaccggcgc acgatcacgg tcccggtgat cgggccgctg cgggccaagg 360
agaacacccg ccgggtgcaa cgccacctcg tgagcgggcg cgcgcagatc ctgaacatga 420
ccttgtcgca gcggtgggg 439

<210> SEQ ID NO 241
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 241
taactcaagc ttcaagtccg cngtccgacc ctgttcgacg gctacctgaa tcaacccgat 60
gccccgccgc ggcgttcgac ccgacagctg gtaccgcacc ggcgacgtcg cggtggtcga 120
cggcagtggg atgcaccgca tcgtgggacg cgagtcggtc gacttgatca agtcgggtgg 180
ataccgggtc ggcgccggtg aaattgaaac ggtgctgctc gggcatccgg acgtggcgga 240
ngcggcagtc gtcggggtgc tcgactatta tctaggccag cggatcgttg cctacgtagt 300
cggctcagcg aatgtcgatg cggacgggct tatcaacttt gttgcccaac aacttt 356

<210> SEQ ID NO 242
<211> LENGTH: 341
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 242
ccatgtcgcc caacatatcg tcgatgttcg cgtcgtccgc ctcgcgcacg tggtctgtca 60
ccagtcaacg ttaacgccgc cgcacatgtc ctgcggccgg gcaaaaacgt gaaaaacgag 120
cgggcgactg caatgtcatg acaccgacgc cgccgatggg cccagggtct ggcagattcg 180
atctgtgcgg ccagtgccag cagcgtcgcc tcgtcatacg gccggccgac gagttgaacc 240
gacatgggca tgccgtcgcc gtcgaagtcc cacggcacca cggccgcggg ctggccggtc 300
agattccana cttgaaagta ctgaagccgc tgcaccacca g 341

<210> SEQ ID NO 243
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 243
cgaaagcgtg aaacagctcg cggcagcccc cgacgtgctg cgtcggatag ccggcgggcg 60
aagatcaatt ccaggcagct cccggacaat gcggctctgc tggcccgcaa cgaaggactc 120
gaggtcaccc cggtgcccgg ggtcgtggtg cacctgccga tcgcacaggt tggcccacaa 180
ccggccgctt gatgcccggt cggcaagccc ggcagttgcc aaacccagcg tgatcntgct 240
cngctctnta nttcggcgaa gaagtggctc gcctgatcac ctaccatcgg ccaggatctg 300
cgtgtcatca caacgctcgc caaggaggtt gttgtg 336

<210> SEQ ID NO 244
<211> LENGTH: 337
<212> TYPE: DNA
<213> ORGANISM: Mycobacterium tuberculosis

<400> SEQUENCE: 244
tccgccacgc ttcgcgccgc ccggcatacg gcgcgtaccg atctccgcgt catacaccgc 60
gggtaatcgc cgacggtgcc ggttcgcgag ccgaaggtga cgacgctgat tgaatcgagt 120
tccaggtcca gcgggtggcg cagcaacggc gcgagctcaa cgacgtcaat cacgttgtcg 180
ctttctacgg tcaccgaccc ggtgaccgta gtcgcccggt gcgctcggcc gagaagctgc 240
accgccacca ccgcgacacc gtcttgcacg cggacccacc ccggatcggt tgttggccaa 300
ggtaattggg tcattccatt tgacgggacg ccgaccc 337

<210> SEQ ID NO 245
<211> LENGTH: 337
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 245
cattctttaa cagttgtttt gggctcggca tggttagcca acgttctgcg gtccaccata 60
tcatcttggt ccggtagcgc tcgtccgggg tatgctgccg ccgggattct cgctgctatt 120
actccccccg aagaaccgcc accggtccag cgcgtgggcc gncgcggtcc catcacaaac 180
tgaaccccca acagggacat gcttatcggt agggcgcgcg ccaaggcggc agcaatcgca 240
tcactgcgct ctgcgcgtca ctattaaccc acccggactt cacttccacc accccgaatg 300
gcgcccggtc attgatcatc tggcgcaccg cggataa 337

<210> SEQ ID NO 246
<211> LENGTH: 343
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 246
cggtgtcctg cagttggtag gcctgcagtt tgtgcatcat gccgatgccg cggcctcgtg 60
gccacgcatg tacagcacca cgccgcgccc ctcacgggcg aacatcgcca gcgcggcgtc 120
cagctgaagc ccgcaatcgc agcggcgtga ccaaacacat cgccggtcaa gcactccgaa 180
tgcaccggac cagcacgtcg tcaccgtcgg cgttgggccc ggcgatctcg ccgcggacca 240
tgcgcgacat gttccacgtc ctcgtanatg ctggtgtagc cgatggcgcg aaactcccca 300
tgacgagtcg gaatccgcgc ctcggcgacc cgctcaatgt gct 343

<210> SEQ ID NO 247
<211> LENGTH: 340
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 247
cggcatctgg cggctgaacc tgttcttggg caacatgccg aggatcgcct cttccaccac 60
gcggtcgggg tggcgttgca ttacctcacc gatggtgcgc ttgtgcaggc cgccgggata 120
ccccgagtgc cggtaaacca tcttgtgctg cagtttgtcg ccgctgatgg cgaccttgtc 180
ggcgttgatc acgatnacna atcaccgcca ncgacattgg gggcgaacgt cggctcgtgc 240
ttgccgcgca gcaggctggc cgccgcgacg caaggcgcca accaccacgt ccgtggcgtc 300
gatgacgtac caccatcgcg tggtgtcacc cgccttgggc 340

<210> SEQ ID NO 248
<211> LENGTH: 322
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 248
gcggcaaaaa ttgaagcact cntggccact nccgccggga gggacaatct cgggcggcta 60

```
gggcttctcg cgggaaggcc cgaacgtact gcgtttcaac acgtcgcgtc gccctccgac    120

cgcgaacatt ctgggatggc agcaacctgt tagcaccctg gccgggcgat gatctgcagc    180

gtcgccgcgg gtagtcgccc ccgggcggct acagtctgaa acgcgatgac catcgatgtg    240

tggacgccgc atccgacnca acggttccta cactgtgata tgttcgcctc gctgcgccgg    300

tggacggtgg gtctatcccg ga                                             322

<210> SEQ ID NO 249
<211> LENGTH: 278
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 249

cgcgttgaac tgaaggggtg ccgcccggct cgagcaggca agccatttgt tcgatgcggt     60

taccgaagat ctcttcggtg actgcccgcc gccggccagc tcggctcagt gtccggcgtt    120

ggtcgccgcg gcgacaatct tggcgtccac ggtggtcggg gtcatgcccg cgagcaggat    180

tggcgagcgg ncggtcagcc gggtgaactt cgtcaagagc tgacgctgcg gttggggagg    240

cgaatcatgg tcggtgcgta gcctcgacta ggcccggg                            278

<210> SEQ ID NO 250
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 250

tgacaacgcg gcggcgatta ccccgctacc gcagcagcat gacgcggtag cgaacaccgc     60

cggatgcagc gcaggtgcgt cgatgtgctc acggaatcgc cccggcaccg cgatctcgag    120

gatcaccagt gccaccccct gcagcgcgac accgacgatt ccgtacaccg ccacgccgat    180

caggccctgg gccagctgat tggagctggc gtatatggcg gcgatggtga cgatggtcat    240

cgcctcttac attgtggcgg ccagaaccac ggcgttgggg cggcggtcga tgaacactag    300

gcgaccanat ccccggggtc aacaggttga ccatcc                              336

<210> SEQ ID NO 251
<211> LENGTH: 95
<212> TYPE: DNA
<213> ORGANISM: Mycobacterium tuberculosis

<400> SEQUENCE: 251

cgcggacatc ccgaacgagg acacgcgacc gcttcggtgt gtgatctatc agggctcgca     60

ccacgcgcaa ccgcttccgg ctacctagac gcggt                                95

<210> SEQ ID NO 252
<211> LENGTH: 94
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
```

as "n"

<400> SEQUENCE: 252
gcatgcgggt gatgccgttc tcagtgcgca acagcgttcg acgcggcata cccagccgca 60
catgccgtgc acgccggngc cggggcggga atct 94

<210> SEQ ID NO 253
<211> LENGTH: 302
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 253
ctcaagcttc agnccntcta agcggtctgc gcggcgatcg caaagatcgc cctttgccgg 60
cgttgggggc ttctgctcgg gggtgttgta caccttctcg aacacctcgg caccgacacc 120
accaccgtcg gcttgaacac cgccaacatc ggcagcanat cttgatgtcc tggtgaatcc 180
acggtgactt tggagtggaa ggcggccata ctgatcgcgc gcgccaccac atgagctagc 240
ggcaggaaaa ccagcagccg ctcacccttg cgcagcagcg tcgggtgata tgcctggcgc 300
cc 302

<210> SEQ ID NO 254
<211> LENGTH: 291
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 254
agtcgaangt cagtccggtc tcctctccga ctacggccaa gaactggggc gacggtgtca 60
gtgcagaaca gcggaaactg gtggcgccct aggcgagcga acgctcacaa acggcggtga 120
ccgcttctgg tcgtgcacca tcgagccgtg cccagcccgg ccgcgtgccg tcagccgcat 180
ccactggatg cccttctcgg cggtttcaat cangtacagg cgacgttcgc caccatcgtg 240
ccggggcacg gttagcgaga aacgccgact tcaccgattg cctcggtgat g 291

<210> SEQ ID NO 255
<211> LENGTH: 454
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 255
agcttcgcgg cgtggcgatc gcggttcaag gcgcgctctt cgagcacaac gagcgaagac 60
agctcggcga cggagccttt atcgacatcc gttcgggctg gctgaccggc ggcgaagaac 120
tgctggacgc gttgttgtcg acggtgccgt ggcgagccga gcgccgtcag atgtncgacc 180
gggtggtcga tgtgccgcgg ctggtgagtt ttcacgacct gaccatcgaa gatccgccgc 240
atccgcagct ggcgcggatg cgccggcggc tcaacgacat ctacggcggc gaactgggtg 300
agcccttcac caccgccggg ctgtgctact accgcgacgg ctctgacagc gtcgcctggc 360
atggcgacac cattggtcgc ggcagcactg aggacactat ggtggcgatc gtcagcctcg 420
gcgccacccg cgtcttcgcg ctgcggccgc gtgg 454

<210> SEQ ID NO 256
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 256
agcttcagct gatactcgac cagccccact cgggccaata cgtgaatgtc tagcatcttc 60
acccgttcac gggctantcg agtagtagac attgattagc ctgaacgtac ctccgacgcc 120
agctgacgaa cgggtatgac ggatggattt cgtggtgtcg cgcccgaggt caattcgtta 180
cggatgtatc tcggggccgg atcggggccg atgttggcgg ccgcggcggc ctgggacgga 240
ctatccgacg aactggcggt ggcggcgtcg tggtttgggt cggtgacctc gggcctggcg 300
gatgcggcgt ggcgcggccc gcggcggttg cgatggcncg cgcggt 346

<210> SEQ ID NO 257
<211> LENGTH: 339
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 257
ctggtcatgg acgttgctcc ggtagtggct cactgccgat cctcctcgtt gagagtgcca 60
cctcagggtt gggtagggtt gggtactcga aaccaagtta cccaccagta acaccgtcaa 120
aatatatccg ttgcataggt caatgcaagt tgatgtgagc tacattgcac caactaacta 180
accaaccggt tgggttagcg gtgatcctgg ccgtgtcggt cctctcacct gcggtgatag 240
cgatcaaatg aagaatatgc ggagtctagg gcggcagcgc ctggcancgt agatcatcgg 300
ctcacgcgga tgcggcctct tggtacggac atgcgcgcg 339

<210> SEQ ID NO 258
<211> LENGTH: 182
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 258
ctcgtgagta gcacccctgt aatttgggat cggcaaaaag gcgaatcacc gcgtggccac 60
gacacgccgg gagggacnat ctcgggcggc tagggcttct cgcgggaagg cccgaacgta 120
cggcgtttca acacgtcgcg tcgccctccg accgcgaaca ttcggggatg gcagcaacct 180
gg 182

<210> SEQ ID NO 259
<211> LENGTH: 213
<212> TYPE: DNA

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 259
ggatcaacta ccggccaacg gtgattcttg ggcgccgctg acgcgcgaac gacccagcga 60
cacattcagc agatggccag cgcgtgccgg gccacgatgt tggtgctcgg cggctactcc 120
catggtgcgg cncgtgatcg acatcgtcac cgccgcacca ctgccggcct cgggttcacg 180
cagccgttgc cgcccgcagc ggacgatcac atc 213

<210> SEQ ID NO 260
<211> LENGTH: 321
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 260
aggaccgtca gcacggcgac gtgctactcg ccgagcagtg ggaatcgctc tgcagcaaac 60
cattactctg cgcgacgttc gagatgacct tctgaatgga cggatctacc tgccgcgcga 120
cgacctggac cgcgtatgcg tccgcctccg cctggacgac accggggcac tctatgaccc 180
cgacggacgg ctcgcggtac tgctgcggtt caccgccgac gcccgcacgg tacgcgtcgg 240
gactgcgctg agtccancct cgacgccgta gcgctgctgc tgtgcggcca tgtctggcat 300
ctaccgccgt cgctcccttg a 321

<210> SEQ ID NO 261
<211> LENGTH: 334
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 261
cgactctgtt ggccactgcg ggtcgatctt gcggccgccc cggtcgtgga acgcccaggt 60
cacccggcgg cgcaccgcgg tcagcgcgtc gttggccagc gtggtcacat ggaagtggtc 120
gacgacgagc ttggcgttgg gcagcagccc gggcgtgcgg atcgccgagg cgtatgcagc 180
ggcggggtcg atggccaccg tactggatgc tctcccggaa ctgcggtgtg cgcgcttgca 240
gccatgccag caccgccgcg ccgccgcggc cttcatgctg cccataaacc ctgataccgg 300
ccaggtcgac naaccngtat cccacggtca accc 334

<210> SEQ ID NO 262
<211> LENGTH: 208
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 262
cacacggacg gcggtgcgga cgcagctgac gcgcatggtg gtcagcatcg cggccggtct 60
gctgttgtat gcctacttcg cgccgcgcaa atgctggtgg gcggcggtgg tggcgctcgc 120
atggctgggc tgggtgctga cccaactctc gaaccacacc ggtgggtggg ctgggctatg 180
gcctgccata tcggcctggt gttctacn 208

<210> SEQ ID NO 263
<211> LENGTH: 233
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 263
ccgatatccg agccgatagc tggcgggctc gggtggtngc cagcggcgct gcgacgaaag 60
tgtgaccgtc atgaaacaga caccaccggc ggccgtcggc cgtcgtcacc tgctcgagat 120
ctcagcatcc gcagccggtg tgatcgcgct ttcggcgtgt agtgggtcgc cgcccgagcc 180
cggcaaacgc cggcccgaca caaccccgga acaggaagtc cggtcaccgc gcc 233

<210> SEQ ID NO 264
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 264
gcttcaggac aaattgnatc cctatgcacc cgttgtcacg ccgatgagtg aagactgcac 60
gcaatcgccg gaatccggca aaaccctgca caagcgaaat caaccggagg ctgacaaggc 120
aacgtcggtg atccgtaccg cctggttgga caaacggcag aaggcgcctc gtccggtcca 180
tctacgccga gcacactggt gatagcgcca tcggcatcgg tgcggccacg gtggagacga 240
acgtccgcng gcgtctgggt cagtaacccg ccgaccagtt ctcgggcaag ctggtcaaca 300
tcgggcgcca cgtctccaac 320

<210> SEQ ID NO 265
<211> LENGTH: 304
<212> TYPE: DNA
<213> ORGANISM: Mycobacterium tuberculosis

<400> SEQUENCE: 265
gtttggcggc cttattgcac tgaggtcgtc aattgaccca cagcggaaat gccgactatt 60
cgcaggcctc cttcgccttg gctgccggag atgggctccg cgggaaccgc atgcaggtat 120
atgacctcgg tttctcgggt gctaccgcgt gccttgtcga ggatgaactc ggcgttggaa 180
ttgtccagcc ggcccaattc atcgagcgca gattcgtaca catggccggc ggcgacatac 240
cttcaccgtg gatctgctcc acacggaccg ccctgtcggg atctgctcac gggtaaagga 300
atta 304

<210> SEQ ID NO 266
<211> LENGTH: 217
<212> TYPE: DNA
<213> ORGANISM: Mycobacterium tuberculosis
<220> FEATURE:

<221> NAME/KEY: unsure
<222> LOCATION: (various positions within the sequence)
<223> OTHER INFORMATION: applicants are uncertain of bases designated
as "n"

<400> SEQUENCE: 266
gcgcactcct ccttatcgct ccgctctgca tcgtcgcggc gcggtcaggt gcaaacgcct 60
tcgggggtgg gggtcctgcg gagcacaccg gatacggagc gcaacgcgtc gcgttgtgcg 120
ggcaaacaag tgtgcaggnn ccaatgccat gtccagcagc ttatcagtgt cgaacgtgcg 180
aacgtcgcgc cttcgccggt gcctgaatct ctacaag 217

<210> SEQ ID NO 267
<211> LENGTH: 174
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 267
cgctgaaagc caccattcgc gggtcgggcg ccgggctcgg gccgccaggc tgctccgctc 60
ggtgatggca cgccaccgcg acaccacccg gctgcgctac gtcgagccat accgggcgga 120
gctacatcgg ctcggccgcc tagtgttcgg gncctctttc gaggtcgagg tcga 174

<210> SEQ ID NO 268
<211> LENGTH: 144
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 268
tgtaatttgg gatgggcaaa aagcaaanca ccgcgtggcc acaaacgcgg ggagggacaa 60
tctcgggcgg ctagggcttc tcgcgggaag cccgaaacgt acggcgtttc aacacgtcgc 120
gtcgcctccg acgcgaaatt cggg 144

<210> SEQ ID NO 269
<211> LENGTH: 216
<212> TYPE: DNA
<213> ORGANISM: Mycobacterium tuberculosis

<400> SEQUENCE: 269
cttgggcaac atgctgagga tcgccttttc accacgcggt cggggtggcg ttgcattagc 60
tcaccgatgg tgcgcttgtt gcaggccgcc gggatacccg agtgccggta aaccatcttg 120
tgctgcagtt tgtcccgctg atggcgacct tgtcgcgttg atcacgatga cgaagtcacc 180
gccatcgaca ttgggggcga actcggcttg tgcttg 216

<210> SEQ ID NO 270
<211> LENGTH: 199
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 270
gcatgcttca ttatctaatc tccagccgtg gtttaatcag acgatcgaaa attcatgcag 60
acggtcccaa atagaaagac attctccagg caccagttga agaggttgat caatggtctg 120
ttcaaaaaca agttctcatc cggattgaac tttaccaact tcatccgttt catgtacaac 180
atttttagaa ncatgcttc 199

<210> SEQ ID NO 271
<211> LENGTH: 230
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 271
atactcaagc ttgatgccgc cgaaaccgag cgtgagcacg ccgccagcca ccacgcgcgg 60
gtcgggcgcc gggcccgggc cgccaggctg ctccgctcgg tgatggcacg ccaccgcgac 120
accacccggc tgcgctacgt ctatccatac cgggcggagc tacatcggct cggccgccca 180
ttgttcnggc cctctttcga ggtcgaggtc tataccgatt tgcgcatccg 230

<210> SEQ ID NO 272
<211> LENGTH: 188
<212> TYPE: DNA
<213> ORGANISM: Mycobacterium tuberculosis

<400> SEQUENCE: 272
tccgtactgg tcgggtacgc ttcggtcgca gtgtgcgagt gatagatgac gaccgggacc 60
tcgtcggcat cttccatagc ccgccacacc ttcagttgct caccggaatc caaccggtag 120
aaggtcggcg agcgctcggc attggtcatc gggatatgcc gctcgggacg gtcagaacct 180
cgggtccg 188

<210> SEQ ID NO 273
<211> LENGTH: 158
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 273
gttctcgcac gatttcggat tagcgggatg gtctcaattg ggtatgcggg gaaggcgctg 60
acattcgccg cgattagctg tttgatggac cgggggtgat ttttgatcac ggaaatgggt 120
gtttatncag gtcgcacgct ttcatccggg gcggaacg 158

<210> SEQ ID NO 274
<211> LENGTH: 237
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 274
gggtgtgcct gctgtgtatg cacggcatac ggacatcctt cccctgaaga cccgcggtcg 60
aacagccacg tgtccatcat canggggtca accccggcca agggcgacgg cacgccaagt 120
tcgccgaccg ttaacctagt gctgttagct tcatttgctg cgagcaaaac agctggtcgg 180
ncgttaggaa tgaattgaaa ctcaaccgat ttggtgccgc cgtaggtgtc ctggctg 237

<210> SEQ ID NO 275
<211> LENGTH: 262
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 275
actacccggc caacggtgat ntcttggccg ccgctgacng cgcgaacgac gccagcgacc 60
acattcagca gatggccagc gcgtgccggg ccacgangtt ggtgctcggc ggctactccc 120
anggtgcggn cgtgatcgac atcntcaccg ccgcaccact gcccggcctc gggttcacca 180
gccgttgccg cccgcagcgg acgatcacat cgcttttatt tnntnttcng gaatccctcg 240
ggccgcgctg gcgggctgat ga 262

<210> SEQ ID NO 276
<211> LENGTH: 222
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 276
acgtcgggan actgttcgcg ttcatcctcg tctcggcgga ttggtctgct gcgccggacc 60
gaccgatctt cagcgggggg tcacgctccg tggggtgccg ttacttccga tcgcccagtg 120
tgcgcgtgct gtggctgatg ctgaacctca ccgcgttgan ttggatcggt tcgggatctg 180
gctggtggcc ggaacgcnat ttatgtcgct acgggcgccg gc 222

<210> SEQ ID NO 277
<211> LENGTH: 166
<212> TYPE: DNA
<213> ORGANISM: Mycobacterium tuberculosis

<400> SEQUENCE: 277
gctcaaaggc actactggca ccaaggccca cacgtcacct gtgactcctg cgccgacccg 60
cccgaggtct ggccgttaca ccgaacgggc gagccgggag ttggtaccat cgaacaagac 120
aaggtgcatg ggcggagttg ttccgccact tcgtcgatga cgggtc 166

<210> SEQ ID NO 278
<211> LENGTH: 330
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 278
cgataccggc tgcttaccga gacatccacc atgccacccg aatcaccgca cgcgccgaaa 60

```
tcgcacaaca gcttgacgcc ttgcaggttc cgcgattgga attgccgacg gtctctgacg    120

gcgtcgacct tggcagcctc tacgagctct cggaatcact tgcccagcag ggggttcgat    180

gagtgtcaca ccgaagacct cgatatgggc gcaatcctgg ccgacacatc caaccgggtg    240

gttgtgtgct gcggcgccgg tggggtcngc aanacactac cgcggccgcg ctggcgttgc    300

gcgcggccga atatggccgc actgtggtcg                                     330
```

<210> SEQ ID NO 279
<211> LENGTH: 332
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 279

```
cgtcgtcgtc gtggtatgcg atagccatcc cgtcgggcta ctcgccatca ccgatcagct     60

tcgccccgaa gccgccgcgg cgatttccgc tgcgaccaaa ctgaccgggg ccaaaccggt    120

attgcttacc ggcgacaacc gggccaccgc cgatcggctc ggtgtacang ttggcatcga    180

cgacgtacgg gccgggctac tgccgacgac aangtcgcag ccgtgcngcn gctgcaagct    240

ggaggtgcca gattgaccgt ggtcggtgac ggtatcaacg acctccggcc ttagcggccg    300

cgcatgtcgc atcgccatgg gcagcgcccg ac                                  332
```

<210> SEQ ID NO 280
<211> LENGTH: 222
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 280

```
gcacgcaatc gaagtcaccc aaaccgggcg ggccaggcgt ctnacgccac gtcnaccagc     60

cgcaacctca acccggccac ggcgagctcc tgatcaaggc cgaggccatc ggtgtctact    120

tcatcgacac ctacttccgc tccgggcaat atccgcgcga actcccgttc gtcatctgct    180

ccgaagtatg cggcacggtg gangccgtcg gccaggggtt ac                       222
```

<210> SEQ ID NO 281
<211> LENGTH: 184
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 281

```
tcgactgtgt ggccacagat cacgccccgc atgccgagca cgagaaatgc gtcgaattcg     60

ccgcgggccg gccggcatgc tcgggttgca gacggcattg tcggtggtgg tgcatacaat    120

ggtggcgccg gcttgttgan ttnggcgcga tatcgcgcgg gtgatgagtg anaaccggcg    180

tgca                                                                 184
```

<210> SEQ ID NO 282
<211> LENGTH: 409

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 282
gaacctgaca ccctggtcac gggtgagcac ggacttgatt tcttcnctat tggtcggcgc 60
tgttgagcac accacgccgc tgacggccgt cgcgtcctcg ctgtgctcgg tctggtggag 120
cgcgctgccc gcggccnaac atcntaaatc aagcgtattc gtcaacagat atcatcaatg 180
tcggcgctgg actattcaaa tcatcgatat actggtgacc tggtccttcg ccatcgatca 240
atggcgatag tcacgcaaat cgtcacggac atcgtcggcg tcccagctgg cccgtgccaa 300
cagatgctgc aacccatcgg ggtggtatca ccgcggtgct cggcgatggt ccacaattct 360
tgcggtccaa gcccnaaaca tcccgggcat gaattcaccg gcatgcgcn 409

<210> SEQ ID NO 283
<211> LENGTH: 413
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 283
ctatcgtacc cgcgccggtc accttctgga tatcgccggc ctggtcaagg gggcgtccga 60
gggagccggg ctgggtnaca agttcctggc tcatatccgc gaatgcgacg ccatttgtca 120
ggtggtgcgg gtgttcgtcg acgacgacgt gactcatgtc accggacggg tcgatcccca 180
gtccgacatt gaggtcgtcg agaccgagct gatcctggca gatctgcaaa ccctggagcg 240
ggccacgggc cggctggaga atgaagcgcg caccaacaag gcgcgcaagc cggtctacga 300
agcggcactg cgtgcccagc angtgctcga cgccgggcaa gacgctgttc gccgcggggg 360
tggatgccgc cgcgttgcgc gactgaaact gctgaccacc aagcccttcc tgt 413

<210> SEQ ID NO 284
<211> LENGTH: 283
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 284
tactcaagct tcaggccgcc acgtccgccg tccgtcggcg acgtgacctc gagcgccgag 60
ttcgactcga catcgccgcc ggcgcatgcc gacatgaacg cggcactcac cgcaagcccg 120
tcggacgtca ggtcgatcga ctccgcttca agcaccggat cgtccgggca actcgcggcc 180
tcggcctgtg cgaacggcac acccgtcgtg gcggcncccc gcgcggaact gggctcatca 240
cggtcgttgc gagccggtcg cgtcaccgcg taccgacgcc gtc 283

<210> SEQ ID NO 285
<211> LENGTH: 397
<212> TYPE: DNA
<213> ORGANISM: Mycobacterium tuberculosis

<400> SEQUENCE: 285
ccgacatcga gtgggctcgc agtgacttgg cgacctccaa gccaccggta cccgccgcgc 60
ggcaagccaa ggacgacgac ggccttgccg gatagctgcg ccaggcgttg cgccaactgg 120
cgtccagcgt cgccacgatc gtcaaagagc ttcatctgcc gagtgtgtcg ccatctcatg 180
gctccaaata tggaattagg tccctgggcc gactgacgac agtccctcag cgaccggatt 240
gcgcatcccg ccttgtacgc tactccgcaa atcccgggct tgcgtccgcg gaagcgaact 300
cggcggcgct acgtggtggt tcacttcggc cgtgcgcact cggatcgacg ggccgatggt 360
ggccgggccc gcgcgcttct tggtcatccg attgagt 397

<210> SEQ ID NO 286
<211> LENGTH: 342
<212> TYPE: DNA
<213> ORGANISM: Mycobacterium tuberculosis

<400> SEQUENCE: 286
atactcaagc ttgtcgcggt aaaccgcacg cagggcggtg ggtgcggtgt caaagacacc 60
cacacttctt tgcggttcgg tgatctcgac accggccgcg agccgaccac catgcgcgcg 120
tagatcggcg atcagcgcgt cggctatcgc ctgggtgccg cccaccggaa tcggccagcc 180
gaccgaatgg gccagcgttg ccagcatcag tccggcgccg gccgacacca gtgacggcaa 240
cggtgaaatc gcgtgggcgg caacgccggt gaacaacgcg cgggcatcct cgcccgccaa 300
cgaccgccag gcagggtgcc tgggccatca tccgcagccc ga 342

<210> SEQ ID NO 287
<211> LENGTH: 430
<212> TYPE: DNA
<213> ORGANISM: Mycobacterium tuberculosis

<400> SEQUENCE: 287
tggactcata acgatcgggt cagcgacgcg ccaacacgaa cggccggacg agtgggccag 60
ggtcgcgcct cccctacaaa caggatccgt tgcctgcgag cgacaggctc cggtgcggcg 120
ttgggcgccg tgctcgtccc agcgtccggt cccgggtcgc cggcgacgct tgtttcctcc 180
atactcgccc cctaatctcg aggcagcccg tacccgcagg caacctccca aaaatgcaat 240
cccccaaaat gcaatgcgtc gagctatttc tcacaccgac cgctagttgc ggatcagaaa 300
tccgttgggc gcggaagtcc agccgaattt gttctcccgc tccgcatcat gcttgtaatc 360
gtttggaaat catcctcata tgcctcgatc gcttcatagg tcaagcccaa acccggcagg 420
atgggtggcc 430

<210> SEQ ID NO 288
<211> LENGTH: 473
<212> TYPE: DNA
<213> ORGANISM: Mycobacterium tuberculosis

<400> SEQUENCE: 288
ctttacactt tatgcttccg gctcgtatgt tgtgtggaat tgtgagcgga taacaatttc 60
acacaggaaa cagctatgac catgattacg ccaagctatt taggtgacac tatagaatac 120
tcaagcttag tggttgcgca cgtaaattcg tcaggtgacc gatcccctgc tgtctcactc 180
gcctcacagc gaccaccacg gctggcgctc aaggcgggca cgtgcggagc agatgaggaa 240
tgtgcgacgt cttgatgcag cctgtcagaa caccgagacc ctcgacgaac ttacgatcga 300
aaccgcttag gccaaccggt gacgggggtg tctttccgcg gctagggcgc cttatcgtcc 360
gaaggccgtg ggtggtgatc gccttctggg tcgcgcttgc gggtctgctt gcgccgacgg 420
tgccgtccct ggaccgatct cccagcggca tccagtggcg attctgccat cgg 473

<210> SEQ ID NO 289
<211> LENGTH: 418
<212> TYPE: DNA
<213> ORGANISM: Mycobacterium tuberculosis

<400> SEQUENCE: 289
caggcatgca agcttgcgat gtatcaacac gccgttgcgc agcgtgagcc gatagttgac 60
atccggctcg gtgaaggtga aatcgatggc caggtcgagg tcccatgcgc gtgggccatt 120
gatgctgatc gccaggacgt caaagatttg gtccggcgtc agctgggcga aaaacgtggg 180
cgccgggact tgcccggagc tgcccgggtt cccgtcgcgc agctcggcgg ccccggtcag 240
aaagaaattg cgccaggtcg cacactccgc gccgtaggcc agctgctcca cggtgtcggc 300
atatagcccg cgggccgcag cgtgctcgct gtcggcgaac accgcatggt cgagaagcgt 360
tgccgcccaa cggaaatcac tgcgtcaaag cttcgccggg ccactccagc actccgtc 418

<210> SEQ ID NO 290
<211> LENGTH: 194
<212> TYPE: DNA
<213> ORGANISM: Mycobacterium tuberculosis

<400> SEQUENCE: 290
atactcaagc ttgaccgacg ctgatcgcac cgcacgcggg aacctcaagg gcactactgg 60
cacaagggcc cacacgtcaa cctgttaact cctgcgccga ccccggccga agtccttggc 120
gttaacaccg aacgggccaa cccgggaatt tgggttccat caaaacaaat agcaggtgcc 180
tgggcggagt gttc 194

<210> SEQ ID NO 291
<211> LENGTH: 166
<212> TYPE: DNA
<213> ORGANISM: Mycobacterium tuberculosis

<400> SEQUENCE: 291
gtcgtcgtgt gctggggcgt ccgtatcagc acgcccacga aatggggcac aagaaggatt 60
cctggaacgg tggctgtcca agatcaccct cgcccaaaac tgctacgggc acttctacat 120
cgagcacaac cgtggccatc acgtccgcgg tgtccacacc gggagg 166

<210> SEQ ID NO 292
<211> LENGTH: 291
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 292
atatgccttg ctgagctttt cggatcgcag cgagtcgtac ccgcgccggt caccttcgtg 60
gatatcgccg gcctggtcaa gggggcgtcc gagggagccg ggctgggtaa caagttcctg 120
gctcatatcc gcgaatgcga cgccatttgt caggtggtgc gggtgttcgt cgacaacgac 180
gtgactcatg tcaccggacg ggtcgatccc cagtccgaca ttgaggtcgt cgagaccgag 240
ctgatcctgg cagatctgca agccctggag cgggccacgg ggcggctnga a 291

<210> SEQ ID NO 293
<211> LENGTH: 442
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 293
gacaccctgg tcacgggtga gcaggactcg atttcttcgc tattggtcgg cgctgttgag 60
gcacagcacg ccgctgaggc cgtcgcgtcc tcgctgtgct cggtctggtg gagcgcgctg 120
cccgcggccg aacatcgtaa atcaagcgta ttcgtcaaca gatatcatca atgtcggcgc 180
tggactattc aaatcatcga tatactggtg acctggtcct tcgccatcga tcaatggcga 240
tagtcacgca gatcgtcacg gacatcgtct gcgtcccagc tggcccgtgc caacagatgc 300
tgcaacccat cggggtggta tcnccgcggt gctcggcgat ggtccaacaa ttcttgcggt 360
ccaagcccga aaccatccgg ccatgagttc accggcatgg cgcaacggct ggtgccgggc 420
aaaacgcggc gcgatcgaat tc 442

<210> SEQ ID NO 294
<211> LENGTH: 150
<212> TYPE: DNA
<213> ORGANISM: Mycobacterium tuberculosis

<400> SEQUENCE: 294
tgtagaaggt gggtcccgtc caacttcgcg gcggcggcgc gatatgcctt gctggtcttg 60
ctcatttgat atccaatcta tgggtcgtgg ttactcaacg ggccgaagct ggccctccca 120
cgggtagggt cctattcgac ggtgatgtcc 150

<210> SEQ ID NO 295
<211> LENGTH: 321
<212> TYPE: DNA
<213> ORGANISM: Mycobacterium tuberculosis

<400> SEQUENCE: 295
cccgaatccg gtggccggca gggggcctgg cgacgtggac accttctaac ttgtctttac 60
cggtcactgt tgcaccccaa cacctttaac gacgtggacg gacgttacat cggattcgac 120
ggtgtcatcc acagcgttgc cattgggcac acccactacg ccaatttctc cgactgggac 180
acctaccgca gcctcgcccc actgcaggga ctgttgttcc cgcaacgggc catcgacatg 240
atccagtcgt tggtgaccga cgcggagcag actggtgcgt atccgcgttg ggcgctggcg 300
aaattccgcc accggcatga t 321

<210> SEQ ID NO 296
<211> LENGTH: 184
<212> TYPE: DNA
<213> ORGANISM: Mycobacterium tuberculosis

<400> SEQUENCE: 296
ttgagatgct ggtcgggatg ccgatggttg gaacatggtc ccctggcgtc gaatacgcgc 60
gagcgcatga gctcaccggt tcggaacaac gtatcgaaga actcgcactg ctggcagatg 120
gtatctccga tgtggttgta atttgtatcc caactctaac tgtgctatcg gatctgcgtg 180
aata 184

<210> SEQ ID NO 297

<211> LENGTH: 259
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 297
cgtaatcacg atcccgctga gacacttgac cttacggccg aagtgacttc gctgctgcta 60
tgccgacacc cgatttccat acgctgctgt acacgacggc cgggccggtg gcctccatca 120
cgctcaaccg cccggaacag ctcaacacca tcgtcccgcc catgcccgac gagatcgagg 180
ccgctatcgg gttggtcgaa cgcgaccagg acatcaaggt catcntnctg cgcggtggcg 240
ggcgcgcctt ctccggcgg 259

<210> SEQ ID NO 298
<211> LENGTH: 369
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 298
caagcttaag ctggttccgg ccactccatg agccgtagtg caatggttcg tgcacggcga 60
ggccgaactt gccataaaca tccctgacga aagtctccgg caagccgatt gcttcttcgg 120
gccgcttctt gtggattgtc cgataacccg gtccctcatg ctggaagttg tgcgcactct 180
ttccttccgc gatgtgggct aacgactcgt cattgagcaa gaagtacgtg cacaggcatc 240
gtccgccggg cttcagcacg cgggagatct cgtccagata gtgctccacg tccggnggga 300
aacatgtggg tgaacaccga ggtnagaaac accncatcca acgacgcatc cgggatatgg 360
aaagcgaaa 369

<210> SEQ ID NO 299
<211> LENGTH: 387
<212> TYPE: DNA
<213> ORGANISM: Mycobacterium tuberculosis

<400> SEQUENCE: 299
tatggtcttc gtcgaccagt acgtcgtagg cgccatgagc cagcgactga agccgcgcca 60
tgcctgcacg gcccgctcat ccagcgaggc ggccatctcc cgcagatagc ctgccgcctc 120
ggcgcgcacg ctgtccggat cgcgtccgag ctcgtcggcc agcgcacgca gccgctcgtc 180
ataccatcgg gcatccagca gttgggtaac ctcaacgggg tcggtcgcta gcggcgtcat 240
tgattcagca acaataccga tgcgctgcag caactttcgc agtccgatgc ggcccacctc 300
ccgtgcagtc actggctagc ccccgtcatg ccggttgtgt cgatggcacg gcagcgggct 360
cgtaaacctg cggtctcagc tcgctgg 387

<210> SEQ ID NO 300
<211> LENGTH: 73
<212> TYPE: DNA
<213> ORGANISM: Mycobacterium tuberculosis

<400> SEQUENCE: 300
gcttagcggt cttgctcgaa ccgacattgc gtgccactca tgagcgggtg gcggtcgcgg 60
tgcttacaca tct 73

<210> SEQ ID NO 301
<211> LENGTH: 156
<212> TYPE: DNA
<213> ORGANISM: Mycobacterium tuberculosis

<400> SEQUENCE: 301
gtatctggcg cctctcgaat atccttgaac gtcccgcggt gccacccaga tagatcgcag 60
cgccctgcaa tggagttccc tttatggcct ctctagcctc ccgcttgatc ggctcgaccc 120
gagagatgcc ctcgggcgtt gcgggatctc cctcca 156

<210> SEQ ID NO 302
<211> LENGTH: 394
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 302
cttcacgccg atccgcgacc gcgaacgcga cggtgacggt gggcgacaag gttcggttgg 60
tcgccgcggc gctgggcgat atcagctcac ccggtttcga ggtgttcggc gaccggacgg 120
tgctgcagac attcttgagc gtcctcgacc ggcccgattc ggccttcaac atcgtgacgc 180
cgtatttcgg cggtaccgct cggcgccgag tcgaaggcgg cctgagctaa agccgggcat 240
tgcgcgagtg gtaaacaagt tcggtgactt cggttgaccg actcgacggg ctcgatctgg 300
gcgcgctgga ccggtatctg cgttcgctgg ggatcgggcc naccgcnant tgcgttgcga 360
nctgattccg gtggagctcc aatctgactt ccgg 394

<210> SEQ ID NO 303
<211> LENGTH: 404
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 303
gcagctaccg accctagcga cgagtgtgtt cgcagcgtcg aatgtgaacg ttcggcgtga 60
ttcggcgcgc gggttcccgc tctcagcgca cgttcggcgc cgaggnggct agtccctggt 120
taagcaatgt ctcggtcgcc gccagcagcg cgcatgtcgc caacccgtcn accgcgttgc 180
gcatgtccgg taccgacgga aacgacggcg cgatccggat gttcttgtcg tccggatcct 240
ttcgatacgg gaacgacccc ccgcctcggt caccgcgata ccaacgtcct tagccaangc 300
tacngtccgg cgcgcggtcc cgggcaacac gtcgaagctg atgaantaac cacccttggg 360
ctcggtccaa gangcgatct tggactcctt aaccgctgat ncaa 404

<210> SEQ ID NO 304
<211> LENGTH: 479
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 304
tccccatcgg cgccggaccg tttgaaagtc caagcacggg tgggatggaa tcgacgacag 60
ttgagcgccg tcggtggccg tggtcagcag ctgttcgcga acgcaccagg tcacatccct 120
tcgacatctc accgacgtgg cacgggcgac atcaacagga agattgacga atccctcgca 180
ggcgcggcac gtccgcaggc caacgccaac tacggggcca ccagcgatcc tccgctcacg 240
caccagccca agccaggctc anccacccaa gtcggcccgc gctctccctc gccccctggt 300
ctccggggcc ttgttaaaca actaccggaa gtccaccaat cctcgctgca tctcgacacc 360
gtccgcctca ctcccttcct cccgcccctc tccacacnac acacctcttg cattaaggtc 420
acggagcggt cacttttcgt cggacgaaat tcgcaatccg gccgctcgcc gccagagat 479

<210> SEQ ID NO 305
<211> LENGTH: 260
<212> TYPE: DNA
<213> ORGANISM: Mycobacterium tuberculosis

<400> SEQUENCE: 305
cggaaagtgg atactcccag caggtagcag gtcgccacca cgctggtcag tgcgcgttca 60
gctcgcttgc ggcgctgcag cagccagtcc gggaaatagc tgccctggcg cagcttgggg 120
atcgcgacgt cgatggttgc ggcacgggtg tcgcaaatca cggtggcggt agccgttgcg 180
ctgattggac cgctcatcgc tgcgttcgcg gtagcccgcc ccgcacaggg cgtcggcttc 240
agcccccatc aaggcggcga 260

<210> SEQ ID NO 306
<211> LENGTH: 464
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 306
ggccgagtcc agcacttcgc actatgtgca gaccaaanac ccggtggtcg ccgcgctgcg 60
gcagcggctg gcaacggcgc cggtgatcac cgagtggtgc gnagttgccg accggcagtt 120
cgccgcgggc ttactacgag aagggcctgc gcgacgtcat caggtatcac gtgtcgatga 180
cgtcgagcgt taacttcccc gaccagacgg cgacctcgcc gatggacccc gcgttgtacc 240
tggtgtgggc gcaagctaac gccgccgcan gctatcggta ctcggtcgaa gcgcagccgg 300
ggtcgcaagc gctagcgggc aaggtcgcga cgatctcggt cacctggacc aactacggcg 360
ctgctgccgc caccgaatag tgngtgcccg gctaccggct ggtggattcc acgggacatg 420
tggttcggac ctgccggcag cggtggaact gaagangctg gtct 464

<210> SEQ ID NO 307
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 307
agcttcaagg acatcgtcat cgcgaccaaa accgcgagct aggtcggcat ccgggaagca 60
tcgcgacacc gtggcgccga gcgccgctgc cggcaggccg attaggcggg cagattagcc 120
cgccgcggct cccggctccg attacggcgc cccgaatggc gtcaccggct ggtaaccacg 180
cttgcgcgcc tgggcggcgg cctgccggat caggtggtat atgccgacaa agcctgcgtg 240
atcggtcatc accaacggtg acagcagccg gttgtgcacc atcgcnaacg ccaccccggt 300
ctccgggtct gtcan 315

<210> SEQ ID NO 308
<211> LENGTH: 331
<212> TYPE: DNA
<213> ORGANISM: Mycobacterium tuberculosis

<400> SEQUENCE: 308
gctcgcggtc cagcagcaga cgtgtctgac cccgacgccc ggccgccggt accgaaaccg 60
gatcggcccg ccgatggccg cggccacggc gtctgcctta cccggcccgg ataccagcag 120
ccacacctcg cgggaacgct gaatcgccgg cagggtcaag gtgattcggc gtggcggcgg 180
tttcgcgaat cgtccaccgc caccaccatg cgggtgctct cgaagacgcg gggctgtgcg 240
ggaacagcga gttaatgtgg ccctcgggcc ccatgcccag caggtggacg tcgaaattcg 300
gcccgggtca cctggtgcgg cactggcggc c 331

<210> SEQ ID NO 309
<211> LENGTH: 286
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 309
agcttgtcga tcgtccggca gcgtccggcg agtcaagtcg aagccagtcc ggtctcctct 60
ccgactacgg ccaagaactg ggcgacggtg tcagtgcata ccagcggana ctggtggcgc 120
cctaggcgag cgaccgcctc acaaacggcg gtgaccgcgt tctggtcgtg caccatcgag 180
ccgtgcccat cccggccgcg tgccgtcagc cgcatccact ggatgccctt ctcggcggtt 240
tcaatcaggt acaggcgacg ttcgccanca tcgtgccggg gcangg 286

<210> SEQ ID NO 310
<211> LENGTH: 331
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 310
ttggtgatca tcgncccaac gaccccgagg cgatgttctt gcacaccgag gagtgtcgca 60
agctggggct ggccttcgcc gccgatccgt ctcagcagct ggcgaagctg tcggggtgag 120
gaaattcgca ggctcgtcaa cggtgctgct tacttgttca ccaacgacta ctaatgggat 180
ctgctgctgt ccaagaccgg ctggtcagan gccgatgtga tggcgcagat cgacctgcgg 240
gtgaccacat tgggtcctaa gggtgtcgat ttggtagaac ctgacgcacc accatccacg 300
tcggcgttgg tccccgaaac agccagaccg a 331

<210> SEQ ID NO 311
<211> LENGTH: 458
<212> TYPE: DNA
<213> ORGANISM: Mycobacterium tuberculosis

<400> SEQUENCE: 311
ggctcgtatg ttgtgtggaa ttgtgagcgg ataacaattt cacacaggaa acagctatga 60
ccatgattac gccaagctat ttaggtgaca ctatagaata ctcaagcttg attttgatca 120
tcatgatgat catcacccga agtgtggtag ccgcagtggt tatcgtgggt accgtcgtgc 180
tttccatggg cgcctctttc gggctttccg tattggtctg gcaggacatt ctgggtatcg 240
agttgtactg gatggtgttg gcgatgtcgg tgatcctgct cctggcggtg ggatccgact 300
acaatctgct gctgatttcc cggttgaaag aggaaattgg ggccggattg aacaccggaa 360
ttatccgtgc catggctggt accgggggag tggtgacggc tgccggcatg gtgttcgccg 420
ttaccatgtc gttgtttgtg ttcagcgatt tgcgaatt 458

<210> SEQ ID NO 312
<211> LENGTH: 289
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 312
caggcatgca agcttggcgt gccgttccaa cccgaattgg ctttcggcgc catcggtgag 60
gacggcgtgc gggtgctcaa cgacgacgtc gtccgcggga cacacctcga tgctgccgcc 120
atggacgcgg tcgaacgcaa gcagctgatc gagctacaac gccgcgcgga acgcttccgc 180
cgcgggcgtg accgcatccc gttgaccggg cggatcgcgg tgatcgtcga tgacggcatc 240
gccaccggag cgacggccaa ggcggcgtgc caggtcnccc gggcgcacg 289

<210> SEQ ID NO 313
<211> LENGTH: 154
<212> TYPE: DNA
<213> ORGANISM: Mycobacterium tuberculosis

<400> SEQUENCE: 313
ggcatcttgg ccgccatgtt agccacactg ccaccggcta tagaagcgat gcgcaccgtc 60
ctgccagcac attgcggcgc tcctccctgg aaagcaagat aaccaagctc atgccgtggt 120
tgtgggtggc gtggtttggt ttgggtaact ttgg 154

<210> SEQ ID NO 314
<211> LENGTH: 324
<212> TYPE: DNA
<213> ORGANISM: Mycobacterium tuberculosis

<400> SEQUENCE: 314
tcggctaata atcgtcgacg ccggcctcct ctgcaatcgc cttggcggtc gccgggttgt 60
caccggtgat catcacggtg cggatgctca ttcggcgcat ttcgtcgaat cgttcccgta 120
tgcccacctt gacgatgtcc ttcagatgga cgacgccgat ggcccgcgcg ctgctgttat 180
cggtccattc cgcaacgact aggggtgtcc cccgccggag ctgatgccgt cgacaatggc 240
acccacctcc tcggtggggt gggcaccgtg atcgcgaacc cacttcatca ccgcagccgc 300
ggcaccttgc ggattcgacg gatg 324

<210> SEQ ID NO 315
<211> LENGTH: 322
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 315
ctcaagcttg gaggcgtggc gatcgcggtc caaggcgcgc tctccgagca caacgagcga 60
agacngctcg gcgacggagc ctttatcgac ntccgttcgg gctggctgac ggcggcnaaa 120
taatgctgga ctcgttgttg tcgacggtgc cgtggcgagc cgagcgccgt cagatgtacg 180
accgggtggt ctatgtgccg cggttggtga gtttccacga cctgaccatc gaagatccgc 240
cgcatccgct gctggcgcgg atgcgccggt ggctcaacta attctacggc ggcgaactgg 300
gtnatccctt cnccaccgtc gg 322

<210> SEQ ID NO 316
<211> LENGTH: 404
<212> TYPE: DNA
<213> ORGANISM: Mycobacterium tuberculosis

<400> SEQUENCE: 316
cctaggtcaa ccgtaccgtc atcggatcgg ggtcgaccgc acagatggac tggagcttcg 60
gcgaggtcat cgcctatgcc tcgcgggggg tgacgctgac cccgggtgac gtgttcggct 120
cgggcacggt gcccacctgc acgctcgtcg aagcacctca ggccaccgga aatcattccc 180
gggctggctg cacgactgcg acgtggtcac cctccaggtc gaagggctgg gcgagacgat 240
gcagaccgtc cggacgagcg gcactccttt tccgttggct cttcggccga atccggacgc 300
cgaacccgac cggcgcgggg tcaacccggc accgacgcgg gtgccgttta cccgcgggct 360
gcacaaatcc cgacgggtat gggctttgac ctgccgacgg ggga 404

<210> SEQ ID NO 317
<211> LENGTH: 346
<212> TYPE: DNA
<213> ORGANISM: Mycobacterium tuberculosis

<400> SEQUENCE: 317
agcttggcgt gacaccaaca cagggcactt aagatggcaa tgcgccgcct acctgcacgt 60
tttcgcgatg tcagaggatg ccgaggggag aacaatgcga gcacggccgc tgacgttgct 120
caccgctttg gcggcggtga cattggtggt ggttgcgggc tgcgaggccc gagtctaggc 180
cgaagcatat agcgcggccg accgcatttc gtctcgaccg caagcgcgac ctcagccgca 240
gccggtggag ctactgctgc gcgccatcac gccgcctagg gctccggcgg cgtcgccgaa 300
cgtcgggttt ggcgaactgc ctacccgggt ccggcaggca accgat 346

<210> SEQ ID NO 318
<211> LENGTH: 333
<212> TYPE: DNA
<213> ORGANISM: Mycobacterium tuberculosis

<400> SEQUENCE: 318
tcatgccgtt ggaccgacca tcggagttag ttgccgaacc gcgggaccac cgcaagcacc 60
cggtcctggt cgcgcaccgc gtcggccaac cgcttgagca ccaccacgcc gcagccctcg 120
ccgcgcacga atccatccgc gttggcgtcg aagctgttgc atcggccggt cggtgacagc 180
gccgaccact tggacagcgc gatggcggtg aacggtgaca aggtgagctg caccccgccc 240
gccaatgcca cgtcggtttc acgcaggcga agctctgaca cgccaagtga attgccacca 300
gcgacgacga acaagcggta tctacggcga tgg 333

<210> SEQ ID NO 319
<211> LENGTH: 207
<212> TYPE: DNA
<213> ORGANISM: Mycobacterium tuberculosis

<400> SEQUENCE: 319
gggtcgactt tctgcaaggc gaggctacac cgtcgtcgtc gtggtatgcg atagccatcc 60
cgtcgggcta ctcgccatca ccgatcagct tcgccccgaa gccgccgtgg tgatttccgc 120
tgcgaccaaa ctgaacgggg ccaaaccggt attgcttacc ggcgacaacc gggccaccgc 180
cgatcggctc ggtgttcagg ttggcat 207

<210> SEQ ID NO 320
<211> LENGTH: 250
<212> TYPE: DNA
<213> ORGANISM: Mycobacterium tuberculosis

<400> SEQUENCE: 320
aatccgaaat cctgaccgat acttgaacct ggtctcgttc ggcaataact cgtcggcgtg 60
caggacgcgg cgcaaacgta cttcggcatc aacgcgtccg acctgaattg gcagcaagcg 120
gcgctgctgg ccggcatggt gcaatctaac agcacgctct tcccgtacac caaccccgac 180
ggcgcgctgg cccgggcgga acgtggtcct cgacaccatg atcgaaaaac cttcccgggg 240
aggcggatgc 250

<210> SEQ ID NO 321
<211> LENGTH: 365
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 321
ttccgaattt cgggtccngg tcatatgacc ctcatggaag aagaagcggc cgccccgcgc 60
ccgtgcgacg gcgaatgaaa accctcaccc aggccgcatt gaacgccgac aagacggtgg 120
agcaggtcga agacgtcctg gacggtctgg gtaagaccat ggccgagctg aacagctcgc 180
tgtcacagct gaacagcacc gtggagcgct tggaggacgg tctggaccat ctcgaaggta 240
ccctgcacag cctggacgat ctcgcgaaac ggctcatcgt gttggtcgag ccggtggaag 300
ccatcgtcga tcggatcgac tacatcgtga gcctcggcga aacggtgatg tcaccgctgt 360
cggtc 365

<210> SEQ ID NO 322
<211> LENGTH: 413
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 322
nctcgatctt ggggtacgtt cgatgaggct gctgaccaac aacccggcca agcgggtggg 60
actggatgga tacggattgc acatcatcga gcgcgtgccg ctgccggtgc gggccaacgc 120
ggaagaacat ccgttacctg atgaccaagc gtgacaaatt ggggcacgac ttggctgggt 180
tggacgattt tcacgaatcc gtgcatctgc ccggagaatt cggcggtgcc ttgtgaaggt 240
ggcgccgggg tgccggatct gccgtcgctg gatcgtctgg tgtgcggctg gcgattgtcg 300
ccagcagctg gcacggaaag atctgcgacg cgctgttgga cggcgcccgc aagtggccgc 360
cgggtgtggc ctcgatgacc gactgtggtt cgggtgctcc gcgcgatcga tat 413

<210> SEQ ID NO 323
<211> LENGTH: 364
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 323
tcatcccgac caaaacgcga gctaggtcgg catccgggaa gcatcgcgac accgtggcgc 60
cgagcgcgct gccggcaggc cgattaggcg ggcatattat cccgccgcgg ctcccggctc 120
cgagtacggc gccccgaatg gcgtcaccgg ctggtaaccg ctcttgcgcg cctgggcggc 180
ggcctgccgg atcaggtggt agatgccnac aaagcctgcg tgatcggtca tcaccaacgg 240
tgacagcagc cggttgtgca ccaagcgcga acgccacccc ggtctccggg tctgtccaac 300
cgatcgaccg cccaagccca catgaacaaa ccccggcatc acgttgccga tcggcatacc 360
gtga 364

<210> SEQ ID NO 324
<211> LENGTH: 488
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 324
ttggcgggtt ggcccagcag cccgccggtg acggcgacga tgctgggctg gttgcggccc 60
tgcgccaccg cggcttgcat gctggttggc tgtcttggga cgatcccgaa atagtccacg 120
cggatctggt gattttgcgg gctacccgcg attaccccgc gcggctcgac gagtttttgg 180
cctggactac ccgcgtggcc aatctgctga actcgcggcc ggtggtggcc tggaatgtcg 240
agcgccgtta cctacgtgac ctgatggatc ggggggtgcc gaccgtgccc ggcgatgtgt 300
atgtgccggg anagccggtc cggttgccac gcaaaggcca tgtcttcgtc ggtccgacca 360
tcggtaccgg gacacggcgc tgtattgccc ggttcgctgc cgagttcgtc gcgcaactgc 420
acgcnggcgg gccagcggtg ctcgttcanc ccggaggttc cggtgacgat gatcgtgttg 480
gtctccct 488

<210> SEQ ID NO 325
<211> LENGTH: 396
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 325
gtaggagaga acaaagaccg tcgataggac acgtgttacg ccggtagctg tcattggtat 60
ggggtgccgc tgccgggggg catctactca cccgatcggt tgtgggaggc gttgctgcgg 120
ggcgacaatc tggtcaccga gatccccgcc gaccgctggg acatctacga gtactacgac 180
cccgaacccg gcgtgcccgg acgcaccgac tgcaaatggg gcgcgtacct cgataacgtc 240
ggcgactttg atcccgagtt cttcgggatc ggggagaaag aaacgatagc gatcgatccg 300
cagcaccgct tgttgctgga aacctcctgg gaagccatgg aacacggcgg gctaacaccg 360
aaccatatgc ctcccgacan gggttttcgt ggggtt 396

<210> SEQ ID NO 326
<211> LENGTH: 394
<212> TYPE: DNA
<213> ORGANISM: Mycobacterium tuberculosis

<400> SEQUENCE: 326
cgaactgagc ccatagaaag gcagcgacta attcgctggg caaataggaa gaccctttgt 60
cctgccacgt atatttgtcg acctcgttgc gaaggaagcg gctgcgattg gtgccctttt 120
ccctggagaa tctctgcccg gagcaggaag tcttatgagt tgacaagcag gggcgccgcc 180
ttcgccggaa atcacattct tggtctcgtg aaatgagagc gctcccaggt cgccgatgct 240
gccgagcgcc cgcccacgat acgacgccat cgcgccttgg gccgcgtctt cgaccaccgc 300
caggttgtgg tgcgtggcga tcttcatgat cgcgtccatc tcgcaggcca cccggcatag 360
tgaacgggga ccatggcctc ggttcgcggg tgaa 394

<210> SEQ ID NO 327
<211> LENGTH: 140
<212> TYPE: DNA
<213> ORGANISM: Mycobacterium tuberculosis

<400> SEQUENCE: 327
cttagacgcc acctccgggc cgagctccac ggggtggata agtacggccg gatgtggccg 60
caatgggaag ttgttgcccg cttgactgtc cgggttaacg ccggattcca ccacatcccc 120
ttgcgaaagg ccgttgggtt 140

<210> SEQ ID NO 328
<211> LENGTH: 242
<212> TYPE: DNA
<213> ORGANISM: Mycobacterium tuberculosis

<400> SEQUENCE: 328
gatcgcgatc gtcgatgtgg ccatccggct tggcgtcgac ccgcgtaagg cagaccagat 60
ggttcgcggc acggtcaacc tgccacacgc actggtaaga ctgcccgcgt cgcggtattc 120
gcggttggtg aaaaggccga tgctgccgtt gccgcggggg ctgatgctgt cggatcgacg 180
atctgatcga gaggatcagg gcggctggct ggaattcgat gccgcgatcg cgataccgga 240
tt 242

<210> SEQ ID NO 329
<211> LENGTH: 220
<212> TYPE: DNA
<213> ORGANISM: Mycobacterium tuberculosis
<220> FEATURE:

<221> NAME/KEY: unsure
<222> LOCATION: (various positions within the sequence)
<223> OTHER INFORMATION: applicants are uncertain of bases designated
as "n"

<400> SEQUENCE: 329
agcttacgcc gctttcgctt cngatttggg acgccgcatc gaaagcgcag ttggaagcgc 60
ggcgcccggc tggtcgagct gctcaagcag ccgcaatccc agcccatgcc cgttgaggag 120
caagtggttt cgatcttcct gggcaccggc ggtcacctgg actcggtgcc cgtcaaggat 180
gtcggcggtt cgaaaccgaa ttactggacc acatgcgggc 220

<210> SEQ ID NO 330
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 330
cgacgggacc tcgtcgcatc ttccatagcc cgccacacct tcagttgctc accggaatcc 60
aaccggtata aggtcggcga agcgctcggc attggtcatc gggatatgcc gctcgggacg 120
gtcagatgcc ctcgggtccn gccagcactc ctcaggcttc gtcggggtgg tcgcgaccgc 180
atgggccaca tcgcattcac caggtctgcg cgaatcacca gcacgtanac ggttcctttc 240
ctaagcaaca ccgaaatttc aggacccgaa tgctccggga aaacatgtca cggtaagtcc 300
ggtattccgg gtaccggttg agcattga 328

<210> SEQ ID NO 331
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 331
cggcatcggt ttgggctgtc accagcagtt ggtagttctt cactactgtt gttcgagcgt 60
cgagccgccg cgcgtgtcga ggtcgccgga cgcgtacccg ccaggccggt cagggtgccc 120
ttccagtcca cgcngctgtg gtcggctaac cgcttatctt caatcgagac natcgccagc 180
ttcatcgtgt tggcgatctt gtccgagggc acctcgaacc ggcgctgcga ntacagccac 240
gcgatcgtgt tgcccttcgc gtcgaccatc gtcgataccg caggcacttg cccctcgagc 300
agctgggccg atccgttggc aacgacctca gaggcacgat tggacatcag ccctagcccg 360
cctgcg 366

<210> SEQ ID NO 332
<211> LENGTH: 407
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 332
ccgtcgangc cgccgacttg gcttgaccga caccaacatg gcctgagggt gttcaacaag 60
accgtggccg acgggctgaa catcaccatg agcggcatga gccacgccac cgagttcatc 120
atgttgatcg ccgaaaacca ttggcgggta gcggaagaac ggtcgaggtg ctctacaccg 180
agtattcgaa gtcgaaaggc caaccgctgc tcaacggcgt caacatcatt ttcgacgggt 240
ttctgcgagg gaggatgcca cgatgaactg gatccaggtg ctgttgatcg cgtcgatcat 300
cgggttgctg ttctacctgt tgcggtcgcg ccgaagcgcg cggtccgtgc ctgggtcaag 360
gtgggctatg tcttgttcgt gctcccggca tctatgccgt gctgaga 407

<210> SEQ ID NO 333
<211> LENGTH: 473
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 333
ttacacgncc tgcttccggc tcgtatgttg tgtggaattg tgagcggata acaatttcac 60
acaggaaaca gctatgacca tgattacgcc aagctattta ggtgacacta tagaatactc 120 aagcttttg agcgtcgcgc ggggcagctt cgccggcaat tctactagcg agaagtctgg 180
cccgatncgg atctgaccga agtcgctgcg gtgcagccca ccctcattgg cgatggcgcc 240
gacnatggcg cctggaccga tcttgtgccg cttgccgacg gngacgcggt angtggtcaa 300
gtccggtcta cncttgggcc tttgcggacg gtcccgacgc tggtcgcggt tgcgccgcgg 360
aaagcggcgg gtcgggtgcc atcaggaatg cctcaccgcc gcggcactgn acggccagtg 420
ccgcggcgat gtcngccatc gggacatcat gctcgcgttc atactcctcg acc 473

<210> SEQ ID NO 334
<211> LENGTH: 305
<212> TYPE: DNA
<213> ORGANISM: Mycobacterium tuberculosis

<400> SEQUENCE: 334
caggcatgca agctttgtca caccaagtgt ttcgaccagg cgctccatcc ggcgagtgga 60
tactcccagc aggtagcagg tcgccaccac gctggtcagt gcgcgttcag ctcgcttgcg 120
gcgctgcagc agccagtccg ggaaatagct gccctggcgc agcttgggga tcgcgacgtc 180
gatggttgcg gcacgggtgt cgaaatcacg gtggcggtag ccgttgcgct gattggaccg 240
ctcatcgctg cgttcgcggt agcccgcccc gcacagggcg tcggcttcag cccccatcaa 300
ggcgg 305

<210> SEQ ID NO 335
<211> LENGTH: 432
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 335
agcttagcca gtttttctac tcttgggccc acacccacag tgcttcgacg gtacggtcac 60
ccatgatggc catccagttg gcatcggtga gctgataaat gccagctggt ttcgccaacc 120
cggtagcgat cttggcgcgc tgcttgttgt cactgatacc tatcgagcaa gacagcccgg 180
tttgcgacaa gatgactttt cggatctctt cggcgacttc gatggggtcg tcgggagtcc 240
cgggcgccac cgcgaggtaa gcctcgtccc agccccatac ctcgaccggg tatcccaggt 300
cgcgcaataa cgccaccacc tcctcggacg ccgcgttgta ggcggctggg ttcgacggca 360
agaagtggcc tcagggcatc gtcggcgcgg tcccaacggc ntgccggcgc gcacaccgta 420
ggcgcggggc tc 432

<210> SEQ ID NO 336
<211> LENGTH: 429
<212> TYPE: DNA
<213> ORGANISM: Mycobacterium tuberculosis

<400> SEQUENCE: 336
ccggcggaac tcagacgtgc tggtggtgcg gcatggcacc gcgggcagca aagcgcactt 60
ctccggggac gacagcaagc gaccgctaga caagaggggt cgtgcgcagg cagaagcgtt 120
ggtaccacag ctgctggcgt tcggcgccac cgatgtttat gccgccgacc gggtgcgctg 180
ccaccagacg atggagccac tcgccgcgga actgaacgtg accatacaca acgagcccac 240
cctgaccgaa gagtcctacg ccaacaaccc caaacgcggc cgacaccgag tgctgcagat 300
cgtcgagcaa gtaggcacac ccgtgatctg cacgcagggc aaggtcattc ccgatctgat 360
cacgtggtgg tgcgagcgcg accgtgtgcc cccgacagtc ccgcaatcgc aaaggcagca 420
cgttggtgt 429

<210> SEQ ID NO 337
<211> LENGTH: 94
<212> TYPE: DNA
<213> ORGANISM: Mycobacterium tuberculosis

<400> SEQUENCE: 337
gtatggtcag ctgtccatcc ggcgctgtcg gccgagctgc cagatctcgt cagccgtaac 60
cgggttgcgg gatccacgcg tgcgggttgt ctac 94

<210> SEQ ID NO 338
<211> LENGTH: 351
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 338
ccgactttcc gcgggtaccc gctcaacttt gtgtcnacct caacgccatt gccggcacct 60
actacgtgca ctccaactac ttcatcctga cgccggaaca aattgacgca gcggttccgc 120
tgaccaatac ggtcggtccc acgatgaccc agtactacat cattcgcacg gagaacctgc 180
cgctgctaga gccactgcga tcggtgccga tcgtggggaa cccactggcg aacctggttc 240
aaccaaactt gaaggtgatt gttaacctgg gctacgcgac ccggcctatg gttattcgac 300
ctcgccgccc aatgttgcga ctccgttcgg ttgttccaga angtcagccc g 351

<210> SEQ ID NO 339
<211> LENGTH: 152
<212> TYPE: DNA
<213> ORGANISM: Mycobacterium tuberculosis

<400> SEQUENCE: 339
gcaccgatgt cggcgagcac ttcgtcaact tccaggggtg cccgcaccaa gtatttcgac 60
gagtatttcc gtcgggccgc cgccgccggt gcgcggcagg tggtcatcct ggcggcgggg 120
ctgggactcg cgcgcgtacc ggctgcctcg gc 152

<210> SEQ ID NO 340
<211> LENGTH: 263
<212> TYPE: DNA
<213> ORGANISM: Mycobacterium tuberculosis

<400> SEQUENCE: 340
tgcacccaac ttactgagca tgctaacgct ggtcgtgcgg gtcttgttcc cgcgtgtcgg 60
cagggcacac gctcggggcg tagctgggag aggccccggt caagcccgga gagcagtgct 120
cagtccgcca gcttgaccga ctttcgatga gaacgcgctt ctcgccgtat tgaactggcg 180
tgctgacggt cgctgagcag cgctcgccga gtgcggccgc tgattctttc atcgagccag 240
gacgcgcatt cgtgttcggc cgc 263

<210> SEQ ID NO 341
<211> LENGTH: 249
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 341
agcttacggc cggtcgacgc gacgagtggt tcatgacacc acaaaccgtc aacgcctact 60
acaacccggg gatgaacgaa atcgtcttcc cgcagcgatt ttacagccac catttttcga 120
tccgcaggcc gacgaggccg ccaactacgg cgggatcggg gcgcgtgatc gggcacgatg 180
atcgggcacg gtttcgacga tagggcgcca aatacgangg cgacgcaatc tggtcnattg 240
gtggatcga 249

<210> SEQ ID NO 342
<211> LENGTH: 269
<212> TYPE: DNA
<213> ORGANISM: Mycobacterium tuberculosis

<400> SEQUENCE: 342
atgtcgtcac gtcaccacaa tcgcgaggac ccaatcatgc cgcccagggc ggccaaccca 60
atggtggccg cgaagcggca gctcgatcgc agcgcggagg tgccggccgc cagttgattc 120
acgaacaggg tgaggtcata ggcgggcagg atagtgacga acgcaagacc tatatctgcc 180
gtcggagtaa gaatcgagta gccggtcgac caacggaagc gaaagtgtcc gcgatgttga 240
tgagcgtcgc cggttgtggc ggcggtggc 269

<210> SEQ ID NO 343
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 343
agcttcacca gcgtgccgat gctgttcgcn acacctccct actatgcgca attcgccgac 60
acgggtggca tcaacacggg cgataaggtg gacatcgctg gggtgaacgt cgggctggtg 120
cgctcgctgg caatccgcgg caaccgcgtg ttgatcggat tctcgttgcc cggcaagaca 180
atcgggatgc aaagccgggc agcaattcgc accgacacca ttcttggccg taagaacctg 240
gaaatcgaac cccgcggttc ggagccgttg aaacccaacg gtttcctgcc gttggcgcag 300
aacactacgc cataccaaat ctatgacgcg ttcgtc 336

<210> SEQ ID NO 344
<211> LENGTH: 417
<212> TYPE: DNA
<213> ORGANISM: Mycobacterium tuberculosis

<400> SEQUENCE: 344
ctgccgcggt ggcggtcagc gcctggcaag tcaccgcacc gccgtccggt tcatcggcag 60
gctcccccga aaagggccct ggcaacagaa ggtgatcaat gagctcccgc agaccttcgc 120
cgatctggga ccgacatacg tgaagttcgg ccagatcatc gcgtccagcc cgggagcatt 180
cggtgagtcg ctgtcgcggg gaattccgcg gcctgctcga ccgggtgccg cccgcaaaaa 240
ccgacgaggt gcacaagctc ttcgtcgagg aactcggcga cgagccggcc cggctgttcg 300
cctccttcga ggaagaaccg ttcgcgtctg cgtccatcgc ccaagtgcac tacgcgacct 360
gcgcagcggc gaagaagtgt ggtcaagatc cacggccggg catccgccgc cgcgttt 417

<210> SEQ ID NO 345
<211> LENGTH: 405
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 345
gatcgtgccg gccccccggc ggcagtagca gatcagctcg tcgaaatcgc ggcaaccagt 60
ccagtcgatt tccatacggg cgccgtcaat caactctgcg aacatcgcga tcggcaccgg 120
aaaccggcga gccgcgtcag ccagcgcaac cagcaccggg atcggatgaa tcatcaatat 180
tatcaagtga tttcctgatg gcatcgagct cggtgatctt ggtctcgggg gccagctcgc 240
cgtcggcgac gtcgtcgatc cggcggccga gcgcatagac cgcaaatagt gccgctcgct 300
tttcgcgcgg caagagtcgg atgccgtaat atangtttct ggcggccgtg cgcgtgatcn 360
actcggtgat tcgatacgcc tgttcatctc ggtcatgccg tcctc 405

<210> SEQ ID NO 346
<211> LENGTH: 414
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 346
ggtggcgcaa tgaccgaaac caccccagcc ccgcaaaccc cggcggcccc ggccgggccc 60
gcacaatcgt tcgtgttgga gcggcccatc cagaccgttg ggcgccgtaa ggaggccgtg 120
gtacgagtgc ggctggtgcc cggcaccggc aagttcgacc tcaacggccg cagcttggag 180
gactacttcc caaacaaggt gcaccagcag ttgatcaagg cacccctggt caccgtggat 240
cgggtggaaa gtttcgacat ctttgcccac ctgggcggcg gcggcccgtc gggtcatggc 300
cggcgcgctg cgcctgggta tcgcccgggc attgattctn gtatcgccgg atgaccggcc 360
cgcgctgaat aangccggct tcttgaccgt gatccacgcg ccaccgaacg caaa 414

<210> SEQ ID NO 347
<211> LENGTH: 331
<212> TYPE: DNA
<213> ORGANISM: Mycobacterium tuberculosis

<400> SEQUENCE: 347
cacaatagat tactcaagct tcgaaccagc ggccttatca cgtatccccg ctgagacctt 60
gacccttagg gccgaagtga cttcgctgct gctatgccga cacccgattt ccagacgctg 120
ctgttacacg acggccgggc cggtggccac catcacgctc aaccgcccgg aacagctcaa 180
caccatcgtc ccgcccatgc ccgacgagat cgaggccgct atcgggttgg ccgagcgcga 240
ccaggacatc aaggtcatcg tgctgcgcgg tgccggccgc gccttctccg gcggttacaa 300
cttcggcggc gggttccaac attgggggca t 331

<210> SEQ ID NO 348
<211> LENGTH: 386
<212> TYPE: DNA
<213> ORGANISM: Mycobacterium tuberculosis

<400> SEQUENCE: 348
tcaggacgct tatggttggc agatggtcgc cctggcgtcg aatacgcgcg agcgcatgag 60
ctcaccggtt cggaacaacg tatcgaagaa cgtcgcactg ctggcagatg gtatctccga 120
tgtggttgta atttgtatcc caactctaac tgtgctatcg gatcagcgtg aatatcgaga 180
tattgcgaat gcgatgacag gccgccattc ggtttattcg cttacgcttc ccgggttcga 240
ttcgtctgat gcactgccgc aaaacgcgga tatgattgtt gaaaccgtat ctaacgcaat 300
tattgatgtg gtaggcggca gctgccgttt tgtgctgtcg ggctattcat cgggtggggg 360
tgtttggcta tgccctctgc tcccat 386

<210> SEQ ID NO 349
<211> LENGTH: 187
<212> TYPE: DNA
<213> ORGANISM: Mycobacterium tuberculosis

<400> SEQUENCE: 349
cgcagctgtc gccgatctgg tccggaatac ctagctccag gttctgagtg gagatgagtg 60
cggccatcga agtgttgtca atgtactcca ggatgtcagg tgccaggccg ctggcgagga 120
tcttgggcac cgccgccatg acttggtcga agtcggcgaa cggggcgagc acgctggcgt 180
cgtggtc 187

<210> SEQ ID NO 350
<211> LENGTH: 241
<212> TYPE: DNA
<213> ORGANISM: Mycobacterium tuberculosis

<400> SEQUENCE: 350
gtagttcgtt catccaaaca cagtgcggta ccggctcaag cggatcaccg acttcaccgg 60
gcgcgatccc acccagccac gcgatgccta tgtccttcgg gtggcggcca ccgtgggtca 120
actcaactat ccgacgccgc actgaagcat cgacagcaat gccgtgtcat agattccctc 180
gccggtcaga gggggtccag caggggcccc ggaaaagata ccaggggcgc cgtcggaccg 240
a 241

<210> SEQ ID NO 351
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 351
tccgctcgct tctccgagag gttgagtgcc aacgctctgc cgatgcccga agccggcccc 60
ggtgatgacg gcgaccttgc cttcgaatga gctcatttga ctactccccg tggttgtccc 120
tgcgattggt ggaggtggcc gcgcagcctt gccccgaggt cggcgatcgc gtctcgggct 180
tcggggagca gactgacctg cagatggaag tcgtgccaca tgcccgcgaa ccggcgatgc 240
tcgatgcttg ttttcgaagc ggcgcaggcg gtttcgatct tgtccgcgtc aacacngatc 300
ggatcgtcgc ccgcggtctg catgacgaat gggcg 335

<210> SEQ ID NO 352
<211> LENGTH: 441
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 352
atgggaggcc accgattacc atcttgcaca caccgattcc gggctattga tgtccacgtt 60
cggtccgcga accgcgctgt ggctgctgct ggccaaaggc ggaggcgata ccgaagtcag 120
tgcccaagct tgggttccac gctcgcgcag ccacgccgtc acctttccac gagacctcac 180
ctgccgatcc gaaatggaat cggccgtgac ggaattggcg cagcgaacac tcaacgaggt 240
ggtggcttcg tcgcgaaccg tcacccgagt cgcggtcacc gtgcgcacgg cgacgttcta 300
cacccgcacc aagatccgaa agctgcaagc tcccagcacc gatcccgacg tcatcaccgc 360
tgccgcccgg cacgttcttg aacctattcg agctggaatc ggccgtccgg ttgctgggaa 420
ttgcngttaa gaactgggcc t 441

<210> SEQ ID NO 353
<211> LENGTH: 332
<212> TYPE: DNA
<213> ORGANISM: Mycobacterium tuberculosis

<400> SEQUENCE: 353
gctttgcgcg cttctccgag aggttggagt gccaacgctc tgccgatgcc cgagccggcc 60
ccggtgatga cggcgacctt gccttcgaat gagctcattt gactactccc cgtggttgtc 120
cctgcgattg gtggaggtgg ccgcgcagcc ttgccccgag gtcggcgatc gcgtcgcggg 180
cttcggggag caaactgacc tgcagatgga agtcgtgcca catgcccgcg aaccggcgat 240
gctcgatgct tgttttcgaa gcggcgcagg cggttcgatc ttgtccgcgt caacgcagat 300
cggatcgtcg cccgcgggtc tgcatgaaga at 332

<210> SEQ ID NO 354
<211> LENGTH: 334

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 354
ctcacgcagc cacgccgtca cctttccacg aagacctcac ctgccgatcc gaaatggaat 60
cggccgtgac ggaaattggc gcagcgaaac actcaacgag gtggtggctt cgtcgcgaac 120
cgtcacccga gtcgcggtca ccgtgcgcac ggcgacgttc tacacccgca ccaacatccg 180
aaagctgcaa gctcccagca ccgatcccga cgtcatcacc gctgccgccc ggcacgttct 240
tgacctattc gagctggatc ggcccgtccg gttgctggga gtgcggttag aaactggcct 300
agaaaccggc gggcacaccg cacctgggcg gggn 334

<210> SEQ ID NO 355
<211> LENGTH: 341
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 355
tgcttccggc tcgtatgttg tgtggaattg tgagcggata acaatttcac acaggaaaca 60
gctatgacca tgattacgcc aagctattta ggtgacacta tagaatactc aagcttgatg 120
ccgccgaaac cgagcgtgag cacgccgcca gccaccacnc gcgggtcggg cgccgggccc 180
gggtcgccan gctgctccgc tcggtgatgg cacgccaccg cgacaccacc cggctgcgct 240
acgtcgagcc ataccgggcg gagctacatc ggctcggccg cccagtgttc gggccctctt 300
tcgaagtcga agtcgatacc gattgcgcat ccgcngccgc a 341

<210> SEQ ID NO 356
<211> LENGTH: 259
<212> TYPE: DNA
<213> ORGANISM: Mycobacterium tuberculosis

<400> SEQUENCE: 356
caggcatgca agcttcacgt ccgtacggct cgggtacgct tcggtcgcag tgtgcgagtg 60
atagatgacg accgggacct cgtctgcatc ttccatagcc cgccacacct tcagttgctc 120
accggaatcc aaccggtaga aggtcggcga gcgctcggca ttggtcatcg ggatatgccg 180
ctcgggacgg tcagaaccct cgggtccggc cagcactccg caggcttcgt cggggtggtc 240
gcgacgcgca tgggccacc 259

<210> SEQ ID NO 357
<211> LENGTH: 349
<212> TYPE: DNA
<213> ORGANISM: Mycobacterium tuberculosis

<400> SEQUENCE: 357
gcttgtctat cgtcccggcc aggtccggcc agtcaaggtc gaaggccagt ccggtctcct 60
ctccgactac ggccaagaac tgggcgacgg tgtcagtgca gaccagcgga aactggtggc 120
gccctaggcg agcgaccgcc tcacaaacgg cggtgaccgc gttctggtcg tgcaccatcg 180
agccgtgccc agcccggccg cgtgccgtca gccgcatcca ctggatgccc ttctcggcgg 240
tttcaatcag gtacaggcga cgttcgccac catcgtgccg gggcacggtt agcgagaaac 300
cgccgacttc acgattgcct cggtgatgcc gtcgaaacag atcgggcct 349

<210> SEQ ID NO 358
<211> LENGTH: 325
<212> TYPE: DNA
<213> ORGANISM: Mycobacterium tuberculosis

<400> SEQUENCE: 358
gcgcgccatg ttgaggttgt ccgacggtga cgacggtgaa ccacaactgt ttgacctgtc 60
cgcacacacc gtgtggatcg gcgagcggac ccgacaaatc gatggcgcgc acatcgcgtt 120
tgcccaggtg attgctaatc cggtcggggt caagttgggc cccaacatga ccccggaact 180
ggccgtggag tacgtcgagc ggctcgaccc gcacaataag ccgggccggc tgacttggtg 240
agcaggatgg gcaaccacaa ggtccgcgat ctgttgccac cgatcgtgga gaacgtccat 300
gccaccgggc atcaggtcat ctggc 325

<210> SEQ ID NO 359
<211> LENGTH: 191
<212> TYPE: DNA
<213> ORGANISM: Mycobacterium tuberculosis

<400> SEQUENCE: 359
ttgccttcca tgccgagcaa ggtcgactca gcgatgacga attgttcttc ttcgcgggtg 60
ttgctgctgg ttgcgggcta tgagagcact gctcatatga ttagcacatt gtttctgacg 120
ctggccgact atccagatca gctgacactc cttgcgcagc aaccagacct gatcccgccg 180
gcgatcgagg a 191

<210> SEQ ID NO 360
<211> LENGTH: 74
<212> TYPE: DNA
<213> ORGANISM: Mycobacterium tuberculosis

<400> SEQUENCE: 360
cgacgctggg cccaactgcg accaccaggt cctggtatgg caggacatgg ccgggttcag 60
cggcgccaat accg 74

<210> SEQ ID NO 361
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 361
taacgactcg ggtccagcga ccgcgccaac acnaacggcc ggacnacgtg ggccagggtc 60
gcggcctccc ctacaaacag gatccgttgc ctgcgaacga caggctccgg tgcggcgttg 120
ggcgccgtgc tcgtcccagc gtccggtccc gggtcgccgg cgacgcttgt ttcctccata 180
ctcgccccct aatctcgagg cagcccgtac ccgcaggcaa cctcccaaaa atgcaatccc 240
ccaaaatgca atgcgtcnag ctatttctca caccgaccgc tagttgcgga tcanaaatcc 300
gttgggcgcg ga 312

<210> SEQ ID NO 362

<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 362
cntggcggtg ggtgcggtgt cgaacacgac cacacttctt tgcggttcgg tgatctcgac 60
accggccgcg agccgaccac catgcgcgcg tagatcggcg atcagcgcgt cggctatcgc 120
ctgggtgccg cccaccggaa tcggccagcc gaccgaatgg gccagcgttg ccatcatcag 180
tccggcgccg gccgacacca gtgacggcaa cggtgaaatc ncgtgggcgg caacgccggt 240
gaacaacgcg cgggcatcct cgcccgccag cgaccgccag gcaggggtgc cctgggccag 300
catccgcagc ccgagacnca ggaccgancc cagtg 335

<210> SEQ ID NO 363
<211> LENGTH: 386
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 363
gcttttcnga tcgcagcgag tcgtacccgc gccggtcacc ttcgtggata tcgccggcct 60
ggtcaagggg gcgtccgagg gagccgggct gggtaacaag ttcctggctc atatccgcga 120
atgcnacgcc atttgtcagg tggtgcgggt gttcgtcaac aacnacttga ctcatgtcac 180
cggacgggtc gatccccant ccgacattga ggtcgtcgan accgagctga tcctggcana 240
tctgcaaacc ctggagcggg ccacgggccg gctggagaag gaancgcgca ccaacaaggc 300
gcgcaagccg gtctacgacg cggcactgcg tgcccagcag gtgctcgacg ccggcaanac 360
gctgttcgcc gcgggggtgg atgccg 386

<210> SEQ ID NO 364
<211> LENGTH: 386
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 364
gtcgtacgcc attngtcggt gtgcgcatac cagtacgacg cgccgggcac ctgacgcggc 60
ggccgcgacc agtcggtggc catcgccatc gtctgccacc cggtcaacgg acgcaccttc 120
tcctggccga cgtagtgcgc ccacccgccg ccgttgcgtc ccatcnatcc ggtcaacatg 180
agcagcgcca acaccgagcg gtacatgaca tcgctgtgga accagtgaca gattccgccg 240
cccatgatga tcatcgaccg tcctccggat tcggtcgcgt tgcgggcgaa attccttggc 300
aaaccggatt gcctgcgcgg ccggcacacc ggtgatcgac tcctgccagg ccggggtgtt 360
ctgctgggtt cggtcgtggt accggt 386

<210> SEQ ID NO 365
<211> LENGTH: 335

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 365
gcgaggcggt atcgcttccc gtcgtaccgg cgaccgccag ccgagaagct cgttttccca 60
gtgttgctgg ggattctcac gctgctgctg antgcgtgcc anaccgcttc cgcttcgggt 120
tacaacgagc cgcggggcta cgatcgtgcg acgctgaant tggtgttctc catggacttg 180
gggatgtgcc tgaaccggtt cacctacnac tccaagctgg cgccgtctcg tccgcaggtc 240
gttgcttgcg atagccggga ggcccggatc cgcaatgacg gattccatgc caacgctccg 300
agttgcatgc ggatcgaata cnaattgatc accca 335

<210> SEQ ID NO 366
<211> LENGTH: 396
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 366
tgggtcttgc cggcgagccc agcgaagtcg ctagcgtggc cgtgtttctt ggcttcggat 60
ctatcctcgt tacatgaccg gcaccgtgtt ggacgtgact ggcggccggt tcatatgaca 120
ccgagatcat tgccacggta cggcaattcg tcaagaagga aatctttccc natgcaccgg 180
ccctcgaacg tggcaacagc tacccgcaag aaatcgtcga tcggctgggt gttattggct 240
tgctcggtcg ccggctgcaa gggtatcgac accaccgagt tcattctcgg gcgtgccggc 300
gcattcgagc tggcggtgcg cgctgcccag caccgtcata agtacttgan gatggtcaaa 360
cgtcggacga accgccacca cgtcgctgcc gaacgg 396

<210> SEQ ID NO 367
<211> LENGTH: 262
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 367
tagatgccca agcttgccnt tanagacctc gtcgaccaag cacggacgcg accgtcgaag 60
gtggcgaatc cgggcttggc gtcnacccgc gtaaggcaga ccagatggtt cgcggcacgg 120
tcaacctgcc acacggcact ggtaagactg cccgcgtcgc ggtattcgcg gttggtgaaa 180
aggccgatgc tgccgttgcc gcgggggcgg atgttgtcgg gagtgacgat ctgatcgaga 240
ggattcaggg cggctggctg ga 262

<210> SEQ ID NO 368
<211> LENGTH: 303
<212> TYPE: DNA
<213> ORGANISM: Mycobacterium tuberculosis
<220> FEATURE:
<221> NAME/KEY: unsure
<222> LOCATION: (various positions within the sequence)

<223> OTHER INFORMATION: applicants are uncertain of bases designated
as "n"

<400> SEQUENCE: 368
tctccacggc gtggatcaag gtaccggccg ggatgttgcg caatggcagg ttgttgcccg 60
gcttgatgtc tgcgttagcg ccggattcca ccacatcccc ttgcgaaaag tccgttgggt 120
gcaatgatgt agcgcttctc cccatcgaga tagtggagca acgcaatccg tgcggtacgg 180
ttcgggtcgt actcgatgtg cgcgaccttg gcgttgacac catctttgtc attgcggcga 240
aagtcgatca tccggtaagc gcgcttatga ccgccgcctt tgtgccgggt nggtaatccg 300
gcc 303

<210> SEQ ID NO 369
<211> LENGTH: 367
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 369
gcccggttcg atcgggcatg tccgcagtcg tcgttaccgg aggcggtcgt ggccgcgcta 60
atcggcgtcg gcgccgacaa gatgtgggat atccgcaatc ggggcgtcat ccctgcgggc 120
gcgctccccc gcgtccgagc cttcgtcgac gcaatcgagg caagtcacga cgcggatgag 180
gggcagcagt gaattacagc gaggtcgagc tgttgagtcg cgctcatcaa ctgttcgccg 240
gaaacagtcg gcgaccgggg ttggatgcgg gcaccacacc ctacggggga tctgctgtct 300
cgggctgccg acctgaatgt nggtgcgggc ancgccggta tcnactcccg tggaacacag 360
ccggggc 367

<210> SEQ ID NO 370
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 370
ctcggcgtgg atatcggtgt agccggcgcc ggtgaangtc ggctccttac gtccactcga 60
caacagctca tagcgatcca accagtangc aaccgccttc agcagtacaa ccgcgccggc 120
gaacactgcg agttgaacgc gagctgcctg ggtcagcatg cctctgccgg ttgtcagccg 180
aaggccgccg aacaggtaat gcgtcaacag gctcgctaga aacgccagaa ccacggccac 240
gaacagccag ttcagcaccg accggtagaa cggcagatcg aagacgaaaa aacccaatgt 300
catagccgaa ttcggggtcc acgatgccaa aggtgccccc gtgtacaaca actgaacctt 360
caccca 366

<210> SEQ ID NO 371
<211> LENGTH: 455
<212> TYPE: DNA
<213> ORGANISM: Mycobacterium tuberculosis

<400> SEQUENCE: 371
tccggctcgt atgttgtgtg gaattgtgag cggataacaa tttcacacag gaaacagcta 60
tgaccatgat tacgccaagc tatttaggtg acactataga atactcaagc ttcacgtccg 120
tacggctcgg gtacgcttcg gtcgcagtgt gcgagtgata gatgacgacc gggacctcgt 180
cggcatcttc catagcccgc cacaccttca gttgctcacc ggaatccaac cggtagaagg 240
tcggcgagcg ctcggcattg gtcatcggga tatgccgctc gggacggtca gagccctcgg 300
gtccggccag cactccgcag gcttcgtcgg ggtggtcgcg acgcgcatgg gccaccatcg 360
cattcaccag gtctgcgcga atcaccagca cgtagacggt tcctttccta agcaacaccg 420
aagtttcagg accgaatgct ccgggaaaca tgtca 455

<210> SEQ ID NO 372
<211> LENGTH: 196
<212> TYPE: DNA
<213> ORGANISM: Mycobacterium tuberculosis

<400> SEQUENCE: 372
caggcatgca agcttgatgc cgccgaaacc gagcgtgagc acgccgccag ccaccacgcc 60
cgggtcgggc gccgggcccg ggccgccagg ctgctccgct cggtgatggc acgccaccgc 120
gacaccaccc ggctgcgcta cgtcgagcca taccgggcgg agctccatcc gctcggccgc 180
cagtgtccgg gccctc 196

<210> SEQ ID NO 373
<211> LENGTH: 443
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 373
cctgcatccg gctcgtatgt tgtgtggaat tgtgancgga taacaatttc acacaggaaa 60
cagctatgac catgattacg ccaagctatt taggtgacac tatagaatac tcaagcttcc 120
aatccccctg ccctgatacg cgtcggcaac cgtgaacgcg atctcggcga ccgtcggatc 180
ggtttcatcc cgcacaaaac gcgcgtcggc tacggggtcg cttccgtcgg tcaccaccca 240
gacgaagtgg tcgacgtagt cgacttccga caggtagtgc atcaacgccg gactgggaac 300
acnagccgac atgaaccgtc gatacagcgt ctcnccggag aactggatgt gtccgtgcac 360
ggtccgctcg cggtcaccgg gcagcacggg gcgtaacatc agttgagtcc cgtcggcaag 420
ccgtaccgga atcggggaga cga 443

<210> SEQ ID NO 374
<211> LENGTH: 445
<212> TYPE: DNA
<213> ORGANISM: Mycobacterium tuberculosis

<400> SEQUENCE: 374
caagatgatc gccggtgcca ccccgatccg tgcctcggtc agcgcgaacg tgctttccgg 60
tccggcgacc accatgtcgc acgcaccgac caggccgaac ccgccggccc gcacatgccc 120
gttgatggcg ccgaccaccg gcagcggcga ctcgacgatg gcgcgcaaca gcgccgtcat 180
ttcccgcgcc cgcgccaccg ccatccggta cggatcacca ccaccaccgc cggcctcgct 240
gaggtccgcg ccggcgcaga acgttccgcc ggtatgcccc agcacgacca gccgcaccgc 300
cggatctgct tcggccgcac tcagcccttg atgtagttgg ctgaccagcg tgctcgacag 360
cgcgttgcgg ttgtgcggag agttcagtgt cagcctggcg aaggggccgc cgcaggcggc 420
cgggccagcg tagtcgacgg ggctg 445

<210> SEQ ID NO 375
<211> LENGTH: 308
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 375
ctcaagcttc gatcgacagt actcccgcct tgggtctggt cttcgagctg gtcggtcatg 60
gtcggacctg ctggtagtgg ggatctaacg caacatggtc gggattcatc atggtgtacc 120
cgtgataccc attcgcagct gccggtgaaa ccccgcgatg ccgggatttc cagccgcact 180
aggatgtcta gccggccagc cgctgccgcc ggacttcggg atgttcggta taccaccgat 240
cggcaatctt gcntatccgc cgatgctcga acgctagcca ccccaaacca accactgtga 300 cnacaatc 308

<210> SEQ ID NO 376
<211> LENGTH: 239
<212> TYPE: DNA
<213> ORGANISM: Mycobacterium tuberculosis

<400> SEQUENCE: 376
tgaatttccc gatcccacaa tctcggttca gatacaggtc gccatacccc ttacttcggc 60
aacgctgggc ggattggccc tgccgctgca gcagaccatc gacgccatcg aattgccggc 120
aatctcgttc agccaatcca tacccatcga cattccgccg atcgacatcc cggcctccac 180
tatcaacgga atttcgatgt cggaggtcgt gccgatcgat gtgtccgtcg acattccgg 239

<210> SEQ ID NO 377
<211> LENGTH: 431
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 377
tactcaagct tgaacgctgc gagcgagccc atgtagagcg tttggtacca aaccgatcgg 60
tgggccaact tgccatgggc tcacagcggc tatcgcgagc gtgtagccga tcatcggcca 120
ggcgacggtg gcctgagcgg caggggttgc cttatccatc ctcttgcggc atggttgccg 180
cagggagtgc cggtaagtct ggtcggcaac ctggcccgct gcgggttggg ttcggattcc 240
ctcggctagt aaggtgctcg cctggtgtta caacgaatcg ctagacagct cttatcggga 300
gtggccgtcg cgatcgttgc gctgccgctg gcgatcgcgt tcggcnttac cgccaccgga 360
acgtcccaag gtgcgctcat cgggctctac ggcgccatct tcgccggatt cttcccngcc 420
gtgttcggtg g 431

<210> SEQ ID NO 378
<211> LENGTH: 334
<212> TYPE: DNA
<213> ORGANISM: Mycobacterium tuberculosis
<220> FEATURE:

<221> NAME/KEY: unsure
<222> LOCATION: (various positions within the sequence)
<223> OTHER INFORMATION: applicants are uncertain of bases designated
as "n"

<400> SEQUENCE: 378
gcggtgtctg aacttcgccc gttccctcca gcgcattgag cttcagcccg accggcaggt 60
agggagtcgg catgcggtcc ttcgccccga ccccgctggc taaatagcca cccccgagcg 120
cggtcacggt ctttgcaccg ggacgacggc ataccggcag cgcgaacatc gccgcgggct 180
gcagcgtgaa cgtcgaatac gagtcgaaca gtgtcggcgc gtaaaaaccc gagccggcgg 240
tcgcttcggt aatcaacggc tcctgcgcaa ccagctgcaa ntcnccggtg ccaccggcgt 300
tgacaatctt gatntcggcg acctcgcgca ccan 334

<210> SEQ ID NO 379
<211> LENGTH: 302
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 379
tactcagctt cggctcaggt ggtgctgctg gtaaagttcn ctgaacggtg caggtttcga 60
caatgtggtg ccggttcggc gggtactgcc atcgagacac tggcgcaggc tatcgcaccc 120
gttatcggct acaaacaaat cgcggtatgc gttcttgagc atgagtcggc gaccgtcgtc 180
atggtcgaca cccacgacgg aaagacgcag atcgccgtca agcntgtgtg ccgcggatta 240
tcaggactga cctcctggct gaccggcntg tttggtcncg atgcctggcg cccggccggc 300
gt 302

<210> SEQ ID NO 380
<211> LENGTH: 240
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 380
catcacctgg ttcatgaaac tggaagcagc gcagcgcttc cttttcggcc gcaacatgag 60
ccagcctctc gtcggcggtc gggtgcaggt gctcgggcag ctcggccgcg acagccgcct 120
gaccctgaaa ccagcttcca tatcccgcga cgaacgacgc cagtccgcta cgtaacccct 180
ccgcgactgt ccatggacaa cancgcgttc tccaccgacc gggcccgggt gtggggtgtt 240

<210> SEQ ID NO 381
<211> LENGTH: 362
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 381
ctcaagcttc ccggcggcca gtaccgaaag cgcgaacagc tcgcggcagc ccacaacntg 60

-continued

```
ctgcgtcgga ttgccggcgg cganatcaat tccaggcagc tcccggacaa tgcggctctg    120

ctggcccgca acgaaggact cgaggtcacc ccggtgcccg gggtcgtggt gcacctgccg    180

atcgcacagg ttggcccaca accggccgct tgatgcccgg tcggcaagcc cggcagttgc    240

caaacccagc gtgatcaggc tcggctcgcg agttcggcga agaagtggct cgcctgatca    300

cctaccatcg gccaggatct gcgtgtcatc acnacgctcg ccaaggaggt tgttgtggtg    360

ct                                                                   362
```

<210> SEQ ID NO 382
<211> LENGTH: 411
<212> TYPE: DNA
<213> ORGANISM: Mycobacterium tuberculosis

<400> SEQUENCE: 382

```
gccacgtttc gcgccgcccg gcatacggcg gcgtaccgat ctccgcgtca tacacccgcg     60

ggtaatcgcc gacggtgccg gttcgcgagc cgaaggtgac gacgctgatt gaatcgagtt    120

ccaggtccag cgggtggcgc agcaacggcg cgagctcaac gacgtcaatc acgttgtcgc    180

tttctacggt caccgacccg gtgaccgtag tcgcccggtg cgctcggccg agaagttgca    240

ccgccaccac cgcgacaccg tcttgcacgc ggacgccacc cccggatcgg ttgttggcca    300

aggtaattgg gtcattccat ttgacgggac gccgaccccg cagccccagt accgcccacg    360

accacgccgg ctgaccccac cactgtacga acaccaaggc gacgccgacc a             411
```

<210> SEQ ID NO 383
<211> LENGTH: 331
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 383

```
ctcaagcttg atgccgccta aaccgaagcg tgagcacgcc gccacccacc acgcgcgggt     60

cgggcgccgg gcccgggccg ccaggctgct ccgctcggtg atggcacgcc accgcgacac    120

cacccggctg cgctacgtca agccataccg ggcggagcta catcggctcg gccgcccagt    180

gttcgggccc tctttcgagg tcnaggtcna taccgatttg cgcatccgca gccgcaccct    240

ggacgacaga accgtgccct acgagtgctt gtcgggcggg gccaaagaac ancttggcat    300

cctggcgcga ttggccggcg cggtcctggt c                                   331
```

<210> SEQ ID NO 384
<211> LENGTH: 254
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 384

```
ctcgggtacg cttcggtcgc agtgtgcgag tgatagatga cgaccgggac ctcgtcggca     60

tcttccatag cccgccacac cttcagttgc tcaccggaat ccaaccggta naangtcggc    120

gagcgctcgg cattggtcat cgggatatgc cgctcgggac ggtcagagcc ctcgggtccg    180

gccagcactc cgcaggcttc gtcggggtgg tcgcgacncg catgggccac catcgcattc    240
```

accaggtctg cgcg 254

<210> SEQ ID NO 385
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 385
ctcaagcttc aattcctcca cgacgcgttc ccaaatgaat ttcccgatcc cacaatctcg 60
gttcagatac aggtcgccat accccttact tcggcaacgc tgggcggatt ggccctgccg 120
ctgcagcaaa ccatcgacgc catcgaattg ccggcaatct cgttcagcca atccataccc 180
atcgacattc cgccgatcga catcccggcc tccactatca acggaatttc gatgtcggag 240
gtcgtgccga tcgatntntc cgtcnacatt ccggnggtca ccatcaccgg caccagnatc 300
gacccgattc cgctgaactt cgacgttctc agcagcgccg gaacca 346

<210> SEQ ID NO 386
<211> LENGTH: 287
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 386
ttaacccccg tggcctctac gccgcctncg ggtcgaacat gcatcccgag canatgctcg 60
agcgcgcacc ccactcgccg atggccggaa ccggctggtt acccgggtgg cggctgacgt 120
tcggcggcga ggacatcggc tgggaagggg cgcttgccac cgtcgtcgaa gacccagatt 180
cgaaggtgtt cgtcgtgctc tacgacatga ccccggcgga cgagaagaac cttgaccggt 240
gggaaggctc cgagttcggc atccaccana agatccgatg ccgcgtt 287

<210> SEQ ID NO 387
<211> LENGTH: 370
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 387
ctcaagcttg attttgatca tcatggatga tcatcacccg aagtgtggta gccgcagtgg 60
ttatcgtggg taccgtcgtg ctttccatgg gcgcctcttt cgggctttcc gtattggtct 120
ggcaggacat tctgggtatc gagttgtact ggatggtgtt ggcgatgtcg gtgatcctgc 180
tcctggcggt gggatccgac tacaatctgc tgctgatttc ccggttgaaa aangaaattg 240
gggccggatt gaacaccgga attatccgtg ccatggctgg taccggggga gtggtgacgg 300
ctgccggcat ggtgttcgcc gttaccatgt cgttgtttgt gttcagcgat ttgcgaatta 360
ttggtcagat 370

<210> SEQ ID NO 388
<211> LENGTH: 330

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 388
cgnccaaccc gaattggttt tcggcgccnt cggtgaggac ggcgtgcggg tgctcaacga 60
cgacgtcgtc cgcgggacac acctcgatgc tgccgccatg gacgcggtcg aacgcaagca 120
gctgatcgag ctacaacgcc gcgcggaacg cttccgccnc nggcgttacc gcatcccgtt 180
gaccgggcgg atcgcggtga tcgtcgatga cggcatcgcc accggagcga cggccaaggc 240
ggcgtgccag gtcgcccggg cgcacggtgc ggacaaggtg gtgctggcgg tcccgatcgg 300
cccanacgac atcgtggcga gattcgccgg 330

<210> SEQ ID NO 389
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 389
cgtgactgcc accggggcca ctccgcagaa tctgtacccg accaagatct acaccatcga 60
atacgacggc gtcgccgact ttccgcggta cccgctcaac tttgtgtcna ccctcaacgc 120
cattgccggc acctactacg tgcactccaa ctacttcatc ctgacgccgg aacaaattga 180
cncagcggtt ccnctgacca atacggtcgg tcccacgatg acccantact acntcattcg 240
cacgganaac ctgccgctgc tagagccact gcgatcggtg ccgatcgtgg ggaacccact 300
ggcgaacctg gttcaaccaa acttgaaggt gattgttaac ctgggg 346

<210> SEQ ID NO 390
<211> LENGTH: 355
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 390
tcgctcaagc gcntgaggcc gaancggctg gttacgactc cctgtttgtg atggaccact 60
tctaccaact gcccatgttg gggacgcccg accagccgat gctggaggcc tacacggccc 120
ttggtgcgct ggccacggcg accgagcggc tgcaactggg cgcgttggtg accggcaata 180
cctaccgcag cccgaccctg ctggcaaaga tcatcaccac gctcgacgtg gttagcgccg 240
gtcgagcgat cctcggcatt ggagccggtt ggtttgagct ggaacaccgc cagctcggct 300
tcgagttcgg cactttcagt gaccggttca accggctcga aaaggcgcta canat 355

<210> SEQ ID NO 391
<211> LENGTH: 403
<212> TYPE: DNA
<213> ORGANISM: Mycobacterium tuberculosis
<220> FEATURE:
<221> NAME/KEY: unsure
<222> LOCATION: (various positions within the sequence)

<223> OTHER INFORMATION: applicants are uncertain of bases designated as "n"

<400> SEQUENCE: 391
atactcaagc ttccgctggg gcctgttcaa ccatggcgat cccgttggtc ccggacatcc 60
cgaacgagga caccgcgacc cncttcggtg tgtgatcatt accgttgggc cactgcgtaa 120
ccgcttgcgg cacaaagagc ccggtctcga cgtcggaaag ctcatcgggc acccgattga 180
aatgcagcag cggcggcacc accccgtgcc gcagtgacag aattgccttg atcagcccga 240
cggtccccgc cgatgccgtg ctgtgcccca tgttgctctt ggccgatcca agcgcgcagg 300
gggtgcccgc gccatacacc cgcgccaggc tgcggtactc aatcgggtcg ccgattggcg 360
taccggtgcc gtgcgcctcc accacaccga ccgtttcggg ctg 403

<210> SEQ ID NO 392
<211> LENGTH: 440
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 392
caacagcgtt ccagcggcat accaccgcac atgccgtgca cccggcgccg ggcggagtcg 60
ccgcataaca cangtacacc ttgggaatcg gtgtgcgcca gggattcnac cgcggggtgg 120
ggccggcgat cgcgcgccag gtcgagttgg cgccgaccgt gatntcaccg ccgacgtagt 180
tggcgttgtg gtccgccatc cgcgcggcgg gcacggcgcg ggccgccacc acgatgtcac 240
ggaagccggg ggcgaacgct cgacgacctg gttaccgtct cngtcgcntc nancgtggac 300
ccgacngcac gtgggcatat gtccanaacg gacgnggccg gtttcntcga tgcngccggg 360
gtccgcgacn tgcggacncn cngncacacc atccgccagt ccgcgtggcg tcccgccgcg 420
actctgcctc ggccgcgcca 440

<210> SEQ ID NO 393
<211> LENGTH: 353
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 393
ctcaagcttt gncgacgatc gggcgatgtc gatganagga aaccccagcg cacaaccgac 60
nattttggcg tagccggcgg acntctgctc gattccgatc acgtcggcgc tcgcatcgag 120
catggcgccg gcgacggcta gcagcgatcc gccgtcgtcg aggaacacga cacgagccgt 180
acgcccggcc gtaagccgcg cccaggattc ggcgaaaaac cgttctacgt ggcgggtgta 240
ctgggtgtcc aatgattcgt ggggtgcgta ggcgtcgctg caatcgtcga cataaatgcc 300
gtcggcccgc atcgcgtcaa caactcccgg gtgagtggaa tancacttgc cga 353

<210> SEQ ID NO 394
<211> LENGTH: 340
<212> TYPE: DNA
<213> ORGANISM: Mycobacterium tuberculosis

<400> SEQUENCE: 394
tccaacgcgg tgacagattt gtctatcctg gacctgacgg tgaggtcgaa gttttccagg 60
aattcggcaa aatcggtaag agcctgaaga attcggtatc gccggacgaa atctgcgacg 120
catacggggc agatacgctt cgggtttacg agatgtcgat ggggccgctg gaggcttcac 180
gtccatgggc cacaaaggat gttgtcggcg cgtaccgttt tctgcagcgg gtgtggcgct 240
tggtcgtcga cgagcacacc ggcgaaactc gggtggctga cggcgtggaa ctcgacatcg 300
atacgctacg ggcgttgcac cgcaccatcg tcggcgtgtc 340

<210> SEQ ID NO 395
<211> LENGTH: 362
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 395
ctcgtccttg actacgccca gtatcgaaan cctcctgtgc cggtncgcta aacacccggc 60
ggacactcan acggtgctgg tggtgcggca tggcaccgcg ggcagcaaag cgcacttctc 120
cggggacgac agcaagcgac cgctagacaa gaggggtcgt gcgcaggcag aagcgttggt 180
accacagctg ctggcgttcg gcgccaccga tgtttatgcc gccgaccggg tgcgctgcca 240
ccanacnatg gagccactcg ccgcggaact gaacgtgacc atacacaacg agcccncccct 300 gaccgaagag tcctacgcca acaaccccaa acgcggccga caccgagtgc tgcagatctt 360
cg 362

<210> SEQ ID NO 396
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 396
gtatcgcctc cncctttggc caccagcagc cacagcgcgg ttcgcggacc gaacgtggac 60
atcaatagcc cggaatcggt gtgtgcaagt tggtaaacgg tgttgatccc aagctttgcc 120
agccttttcg tagtcttggg ccccacaccc cacagtgctt cgacggtacg gtcacccatg 180
atggccatcc agttggcatc ggtgagctga tagatgccag ctggtttcgc caacccggta 240
gcgatcttgg cgcgctgctt gttgtcactg atacctatcg agcaagacag cccggtttgc 300
gacaagatga cttttcggat ctcttcngcg aacttccaat gggggtctcc gggant 356

<210> SEQ ID NO 397
<211> LENGTH: 350
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 397
ctcaagcttt tggtctagcc ggccgagcac gatacgggtg tccttggcca ccggcggcgg 60
ctgtccggga aatggcgggt ccccggtggt tttgctgang antgctgaac cgtagtcgaa 120
gtgggcggcg tcagactcca cccagccagc aggcagcgcg aagctgaatc ctccaaccgg 180
gttgtcgatc cggacaggtt ggggtgcgtt tggggcaatg acaggtggcg gcggtgcgtt 240
cgggtcggcc ggcggaggtg ctgcgttggg atcncccggc tgggcattcg gcntnttggc 300
ggcggccggt ggtggggggg caacangtgt cccggtgcgg gtggcgctgc 350

<210> SEQ ID NO 398
<211> LENGTH: 355
<212> TYPE: DNA
<213> ORGANISM: Mycobacterium tuberculosis

<400> SEQUENCE: 398
atctgtaccc gaccaagatc tacaccatcg aatacgacgg cgtcgccgac tttccgcggt 60
acccgctcaa ctttgtgtcg accctcaacg ccattgccgg cacctactac gtgcactcca 120
actacttcat cctgacgccg gaacaaattg acgcagcggt tccgctgacc aatacggtcg 180
gtcccacgat gacccagtac tacatcattc gcacggagaa cctgccgctg ctagagccac 240
tgcgatcggt gccgatcgtg gggaacccac tggcgaacct ggttcaacca aacttgaagg 300
tgattgttaa cctgggctac ggcgacccgg cctatggtta ttcgacctcg ccgcc 355

<210> SEQ ID NO 399
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 399
ctcaagcttg caatgcgggt cgggatgccc atggttggaa natggtcgcc ctggcgtcna 60
atacgcgcga gcgcatgagc tcaccggttc ggaacaacgt atcgaaaaac gtcgcactgc 120
tggcagatgg tatctccgat gtggttgtaa tttgtatccc aactctaact gtgctatcgg 180
atcagcgtga atatcganat attgcgaatg cgatgacagg ccgccattcg gtttattcgc 240
ttacgcttcc cgggttcgat tcgtctgatg cactgccgca aaacgcggat atgattgttg 300
aaaccgtatc taacgcaatt attgatgtgg taggcggcag ctgccgtttt gtgctgtcgg 360

<210> SEQ ID NO 400
<211> LENGTH: 272
<212> TYPE: DNA
<213> ORGANISM: Mycobacterium tuberculosis

<400> SEQUENCE: 400
caaatacacg ccggacgcac aggcggacat cgccatcccg agcacaccca aaacgggata 60
caggatggag gccaacgcca cggccgcgcc caggatcacc aaccacaccg gcttggtcag 120
cttgtcggcg gcggtatagg catcgggccg ctgcaacgca gcatgcacaa acgcgtacac 180
cgctgtcacc aagacggcga ccagcaatac cagcatgacg gtacccacga ggtggctcac 240
gcattcagac tatgcggttt gcatccaaca cg 272

<210> SEQ ID NO 401
<211> LENGTH: 306
<212> TYPE: DNA
<213> ORGANISM: Mycobacterium tuberculosis

<400> SEQUENCE: 401
ctcgtccttc ggcctcgctg caggagtggg agccgcaggg ctggaaatcc gaaaaacgag 60
ccggtgatcg cactgtcgcc gatcggcgcc gcacctggtt ggtgttacgg atgaatccgc 120
agcgaaatgt ggctgcggtg gcgtgtcgtg actcgttggc gtcgacgctg gtggcagcca 180
ccgagcggtt ggtccaggat ctggatgggc aaagttgtgc ggcccggccg gtgacggccg 240
atgagctgac cgaggtcgac agcgccgtgt tggctgactt ggaaccgaca tggagtcgcc 300
ccggtt 306

<210> SEQ ID NO 402
<211> LENGTH: 300
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 402
gtctagnccg ccgaacacga tacgggtgtc attggccacc ggcggcggct gtccgggaaa 60
tggcgggtcc ccggtggttt tgctgaagan tgctgaaccg tagtcgaagt gggcggcgtc 120
agactccacc cagccagcag gcagcgcgaa gctgaatcct ccaaccgggt tgtcgatccg 180
gacaggttgg ggtgcgtttg gggcaatgac aggtggcggc ggtgcgttcg ggtcggccgg 240
cggaagtgct gcgttgggat cgcccggctg ggcattcggc gtgttggcgg cggccggtgg 300

<210> SEQ ID NO 403
<211> LENGTH: 396
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 403
actcaagctt gagattggcg tcaacgggtg tcggcaccgg cgtcctgcag ttggtaggcc 60
tgcagtttgt gcatcaggcc gatgccgcgg ccctcgtggc cacgcatgta cancaccacg 120
ccgcgcccct cacgggcgac catcgccagc gcggcgtcca gctgaggccc gcaatcgcag 180
cggcgtgacc caaacacatc gccggtcaag cactccgaat gcacccggac cagcacgtcg 240
tcaccgtcgg cgttgggccc ggcgatctcg ccgcggacca gcgcgacatg ttccacgtcc 300
tcgtaaatgc tggtgtancc gatggcgcga aactccccat gacaantcgg aatcccgcgc 360
ctcggcgacc ccgctcaatg ttgcttctcn tgcttg 396

<210> SEQ ID NO 404
<211> LENGTH: 352
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 404
tcgacnagca ttcttgacng ttgttttggc tcggcatggt tagccaaggt tctgcggtcc 60
caccagatca tcttggtccg gtagcgctcg tccgggtatg ctgccgccgg gattctcgct 120

```
gctattactc cccccgaaga acgccaccgg tccagcgcgt gggccgccgc ggtccccatc    180

acaaactgaa cccccaacag gggacatgct tagcggtagg gcgcgcgcca aggcggcagc    240

aatcgcatca ctgcgctgcg cgtcactatt aacccacccg gacttcactt ccacgacccc    300

gaatggcgcc cggtcattga tcatcttgcg caccgcggat aatccgggat tg             352


<210> SEQ ID NO 405
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 405

accggggcca ctccgcacaa tctgtacccg accaanatct acaccatcga atacgacggc     60

gtcgccgact ttccgcggta cccgctcaac tttgtgtcna ccctcaacgc cattgccggc    120

acctactacg tgcactccaa ctacttcatc ctgacgccgg aacaaattga cgcngcggtt    180

ccgctgacca atacggtcgg tcccacnatg acccantact acatcattcg cacgganaac    240

ctgccgctgc taaagccact gcgatcggtg ccgatcgtgg ggaacccact ggcgaacctg    300

gttcaaccaa acttgaaggt nattgttnac ctgggctacg gcganccggc ctntggttat    360

tccacctcnc cgcccaatgt ttgcnactcc cgttcggggt tgttcccnna aggtcaaccc    420


<210> SEQ ID NO 406
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 406

cgctcaagcg cntgaggccg aancggctgg ttacgactcc ctgtttgtga tggaccactt     60

ctaccaactg cccatgttgg ggacgcccga ccagccgatg ctggaggcct acacggccct    120

tggtgcgctg gccacggcga ccgagcggct gcaactgggc gcgttggtga ccggcaatac    180

ctaccgcagc ccgaccctgc tggcaaagat catcaccacg ctcgacgtgg ttagcgccgg    240

tcgagcgatc ctcggcattg gagccggttg gtttganctg gaacaccgcc agctcggctt    300

cgagttcggc actttcagtg accggttc                                       328


<210> SEQ ID NO 407
<211> LENGTH: 315
<212> TYPE: DNA
<213> ORGANISM: Mycobacterium tuberculosis

<400> SEQUENCE: 407

ctcaagcttg cgttcgatga agtagtcgtc ggtcagcgcc gcctcttcga gctccttggc     60

gatgcccagc aaggagtcat cgccgccgag cttggccagg atcttgtcgg cctgttcctt    120

gacgatgcgg gcccgcggat cgtagttctt gtagacacga tgaccgaaac ccatcaattt    180

gaccccggcc tcgcggttct tgaccttgcg tacaaactcg ctgacgtcgt cgccgctgtc    240

gcgaatgccc tcgagcatct ccaggacagc ctgattggcg ccgccatgaa gcggacccca    300

tagtgcgttg atgcc                                                     315
```

<210> SEQ ID NO 408
<211> LENGTH: 329
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 408

```
ggtcaggccg agcaggcgcg aggaacgacg aacccaacaa gccatggtgg ttggcgccgt     60

cgagaggtcg gcggtcgcca caacgggaag atcgccttga gcgtcgctcg accgccgcct    120

cgagttgggt cataacgaag tagctgatgc cgatcatgtc gacgtttccg tcgcatcagc    180

gtgcagcggc gacccactcn acgaggtctc ggtgccgccg cggccagggc accagcagtg    240

acgagtccag gcgccgtcgg gccaagcagt cgcggtgcca nccgtggtgg gtcgggcgat    300

ggttgggtgt gctcatttcg ggaacgcca                                      329
```

<210> SEQ ID NO 409
<211> LENGTH: 294
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 409

```
ctcgaagctt taacagcatc aaccccgccc cgcaccagca ccgacacnat gtcgatgcca     60

tcgaggtgaa tgtcgaactg gcgcaaacca tcggcgaccg cgaccaccgg caacatgggt    120

accggcgatt tccggtgcca atgccgaccc gacgggccgc tctcaccgca ggtgacctcg    180

atcaccgaga ccanccggcc gttntnntca cgcaccccta ccgtgtcacg cccaaaacgg    240

cgctggtggt cgattgccgg agtgcacccc ncacccagtg tcgtgcccgg atcc          294
```

<210> SEQ ID NO 410
<211> LENGTH: 288
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 410

```
tgatgccgca cccgatcgac ggtcgttggt cggggttgac tggccgcccg gcgaagcagg     60

gcgtcgaccg cggcccggac gtcggcggcc gtcaccggtc ggccattgcc cgggcgggag    120

tcgtcgagct gaccacggta gacaagtcgg cgctggccgt cgaagacnaa cgtgtcgggt    180

gtgcaggccg cggagaaggc gcgggcgacn tcttgggttt cgtcgtanag atacgggaac    240

gtccagccgt ggcggcgggc ctcggcgacc atctgatcgg gcccgtcc                288
```

<210> SEQ ID NO 411
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 411
tttcgggcga ggcggtatan cttcccntcg taccggcgac cgccagccga naagctcgtt 60
ttcccagtgt tgctggggat tctcacgctg ctgctgantg cgtgccaaac cgcttccgct 120
tcgggttaca acgagccgcg gggctacnat cgtgcgacgc tgaagttggt gttctccatg 180
gacttgggga tgtgcctgaa ccggttcacc tacnactcca agctggcgcc gtctcgtccg 240
caggtcgttg cttgcgatag ccgggaggcc cggatccgca atgacggatt ccntgccanc 300
gctccgagtt gcntgcggat cgactacnaa ttgatcaccc anaaccatcg ggcgtnttac 360
tgcctgaagt acctggtgcg ggtcggatac tgctatccgg cggtgacaac cccggcaagc 420

<210> SEQ ID NO 412
<211> LENGTH: 378
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 412
gttttggctc ggcatggtta gccaaggttc tgcggtccca ccagatcatc ttggtccggt 60
agcgctcgtc cgggtatgct gccgccggga ttctcgctgc tattactccc cccgaagaac 120
gccaccggtc cagcgcgtgg gccgccgcgg tccccatcac aaactgaacc cccaacaggg 180
acatgcttag cggtagggcg cgcgccaagg cggcagcaat cgcatcactg cgctgcgcgt 240
cactattaac ccacccggac ttcacttcca cgaccccgaa tggcgcccgg tcattgatca 300
tcttgcgcac cgcggataat ccgggattgc cagcccattc nactaccgca tgcgagtcat 360
cggctgaccg cagcggtc 378

<210> SEQ ID NO 413
<211> LENGTH: 347
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 413
tcgcctaggc gggcttcccc ttccgtccga gcngtcagaa gctcctatga caatgcacta 60
cccgagacna tcaacggcct atgcaatacc nagctgatca aacccggcaa gccctggcgg 120
tccatcgagg atgtcgagtt ggccaccgcg cgctgggtcg actggttcaa ccatcgccgc 180
ctctaccggt actgcggcga catcccgccg gtctaactcg acgccgcctc actacgctca 240
acgccagaga ccanccgccg gctgacgtct cagatcagag agtctccgga ctcaccgggg 300
cggttcatcc ccactgtcga tagcgtctgt ggataacttt gtctgca 347

<210> SEQ ID NO 414
<211> LENGTH: 165
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 414
gcgcgtngaa ctgataggtg cggcccggct cgagcangcc ggccatttgt tcgatgcggt 60
taccgaagat ctcttcggtg acctgcccgc cgccggccag ctcggcccag tgcccggcgt 120
tggccgccgc ggcgacaatc ttggcgtcca cggtggtctg ggtca 165

<210> SEQ ID NO 415
<211> LENGTH: 317
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 415
ctcaagcttc aatacagagt tataaactgt gataatcaac cctcatcaat gatgacnaac 60 taaccccga tatcaggtca catgacgaag ggaaagagaa ggaaatcaac tgtgacaaac 120
tgccctcaaa tttggcttcc ttaaaaatta cagttcaaaa agtatgagaa aatccatgca 180
ggctgaagga aacagcaata actgtgacaa attaccctca gtaggtcaga acaaatgtga 240
cgaaccaccc tcaaatctgt gacagataac cctcagacta tcctgtcgtc atggaagtga 300
tatcgcggaa ggaaaat 317

<210> SEQ ID NO 416
<211> LENGTH: 379
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 416
ctcaagcttc gatcgacatt actcccgcct tgggtctggt ctccgagctg gtcggtcatg 60
gtcggacctg ctggtagtgg ggatctaacg caacatggtc gggattcatc atggtgtacc 120
cgtgataccc attcgcagct gccggtgaaa ccccgcgatg ccgggatttc cagccgcact 180
aggatgtcta gccggccagc cgctgccgcc ggacttcggg atgttcggta taccancgat 240
cggcaatctt gcgtatccgc cgatgctcga acgctancca cgccaaacca accactgtga 300
cnacaatcgc caccacacca aaggtcatgc cctcggcgtg atgtccggtg ccgaaagccg 360
caagagctcc gacgccgcc 379

<210> SEQ ID NO 417
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 417
cattcccaat tgaatttccc natcccacaa tctcggttca gatacaggtc gccatacccc 60
ttacttcggc aacgctgggc ggattggccc tgccgctgca gcanaccatc gacgccatcg 120
aattgccggc aatctcgttc agccaatcca tacccatcga cattccgccg atcgacatcc 180
cggcctccac tatcaacgga atttcgatgt cggaggtcgt gccgatcgat gtgtccgtcg 240
acattccggc ggtcaccatc accggcacca ggatcgaccc gattccgctg aacttcgacg 300
ttctcagcag cgccggaccc atcaacatct cgatcatcga cattccggcg ctgccgggct 360
ttggcaactc gaccgagctg ccgtcgtcgg gcttcttcaa caccggcggc ggtggcggct 420

<210> SEQ ID NO 418
<211> LENGTH: 255
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 418
ctcaagcttt cggcggagac ggacannttg cgaacattga tgacaaaata gaaatcattg 60
atggtttgag tcaccaggcc gatcaagcct tcgccgagcc aaattccaat caagaggccc 120
aagcccgtac caatcagccc ggcaacgagg gattccgtca ttatcagcca aaataactgc 180
tctcgggtta cacccaaaca gcgcaatatg gcgaaaaacg gtcgccgttg cacgacatta 240
aatgtcacgg tattg 255

<210> SEQ ID NO 419
<211> LENGTH: 359
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 419
agcttaactg ctccctaata cctggggctg tgcctgcggt gtatgcacgg catacggaca 60
tccntcccct gagacccncg gtctaatcag ccacgtgtcc accatcaggg gtcaaccccg 120
gccaagggcg acggcacccc aagttcgccg accgttaacc tattgctgtg agcttcattt 180
gctgcgagca aaacagttgg tcggccgtta ggaactgaat tgacactcaa ccgatttggt 240
gccnccgtag gtgtcctggc tgcgggtgcg ctggtgttgt ccgcgtgtgg taacgaccac 300
aatgtgaccg ggggaggtgc aaccactggc cacgcgtccg cgaatgtcta ttgcggggg 359

<210> SEQ ID NO 420
<211> LENGTH: 314
<212> TYPE: DNA
<213> ORGANISM: Mycobacterium tuberculosis

<400> SEQUENCE: 420
ctcaagcttg gggtggcgct gtcggtcggt gtgcttggcg gcgtcggtat caacaccgcc 60
cacgaaatgg ggcacaagaa ggattcgctg gagcggtggc tgtccaaaat caccctcgcc 120
cagacctgct acgggcactt ctacatcgag cacaaccgtg gccatcacgt ccgggtgtcc 180
acaccggagg acccggcgtc ggcgcggttc ggcgaaacgt tgtgggagtt cctgccccgc 240
agtgttatcg gcggcttgcg ctcggccgtt catttggagg cccaacggct gcgtcggctc 300
ggcgtcagcc ccct 314

<210> SEQ ID NO 421
<211> LENGTH: 280
<212> TYPE: DNA

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 421
gcaccaaggc cccacacgtc accctgtgac ctcctgcgcc gaccccgccc gaggtcctgg 60
ccgttaccac ctgaacgggc gagccgggag tctggtacgc atcgaacaaa gagcaaggtg 120
catgggcgga gttgttccgc cacttcgtcg atgacggggt cnatccattc gaggtccgtc 180
gccgcgtcgg tcgagtggcg gtcacactcc aggtactcga cctcacagac gagaggactc 240
gatcccatct aggtgtggac gaaacagatc ttctgtccga 280

<210> SEQ ID NO 422
<211> LENGTH: 230
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 422
tcgcctccgc atatgggtcg acgccaagcg ggtccggatt tctgggcttc atcgctcgcg 60
ccgtcgcgac aaacagcgcg gtcgaaccga cactcgttgt gatgtcccag ctatcacctt 120
cggtacgcac ccaatcgacc ctacncggct atctcagccg cgatctccag gctccgccga 180
gccaggtgca tcccggtccg gatcccacta acccggcacc attggcgtcn 230

<210> SEQ ID NO 423
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 423
gtcctcgagt gccgccgtcg ncacncccag cgcccgcgcg gccacttgga tgcgacccgt 60
ttcaagtccc ttcatcatct gcgaaaagcc ttgacccatg gctccgccca ggatcgccga 120
gaccggcacc cggaggttgt cgaacgacag ctcgcaggat tcgacgccct tgtaacccaa 180
cttcggcaag tcccgcgaca ccgtgagtcc cggcccgggt tcgacgagca cgatcgacat 240
gccttggtgc cgcggtgtgg cgttcgggtc gg 272

<210> SEQ ID NO 424
<211> LENGTH: 423
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 424
ggcataccaa tgtggacttc tgctcaccca cgatatccgt ggtctgatcc gctgctgcgg 60
cgggctgcna cctgcntctc ngcggcaccc gtnactacat ggcncgcgcc gcacgcatac 120
gtcgcggcgg gacccactcc nactggtcga cggtgctggc cgcgtgtccg cangtcccna 180
acccggccgc accgacgaaa ccggccgccg tccgttctgg accaacgctc atgtgccgtc 240
ggggtccatg ctcgacgcca tcgagaccgt aaccagcgtc ctcgagcggt tcgcctccgg 300
cttccgtgac atcttcgtgg ctgctcgcgc cgtgccgccg cgcggatggt cgaccacaac 360
gccaaccacc tcggcggtga catcaccgtc cgcgccactc gacctggcgc gcgatcgcgg 420
ccc 423

<210> SEQ ID NO 425
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 425
gtgagcagac ctacgccncc tggttgcgcc aactcggtac cgatcatggc gcgcngcctg 60
tcgtcaccga tacccagcga acaagacagc ccggtccgcg acaagatgac tttcccgatc 120
tcttcggcga cttccatggg gtcgtccgga gtcccgggcg ccaccgcgag gtaaccctcg 180
tctcagtccc atacgcgacc gggtatccac gtcgcgcaac aacgccacca cctccccaga 240
cgccncgttg tacgcggctg ggttccacng caataagtgg cctcanggca tcgtccggcg 300
gcggtccnca acgca 315

<210> SEQ ID NO 426
<211> LENGTH: 335
<212> TYPE: DNA
<213> ORGANISM: Mycobacterium tuberculosis

<400> SEQUENCE: 426
ctcaagcttg aggttaactt tgaacggatc gagctggacg ttcgagacgg tgatcgggcc 60
gaacctgaat tgtccggtaa tgcccaacgc aaaaagcagg gtggtggccg gggcggtgaa 120
accggcgtcg gcggcaccgt cgaaatctat gtggattgcc ggaatgggga tgtccggcac 180
ggcgaaaccg tagttcgctt gtcccgtgag gcccaggtgg atggggggaa agatcctggt 240
gtccgggata ataatggggc cgatgccgcc ggttgaagtc cactggatcg ggaattccgg 300
aatcttgatc cgacgttcag gccgaacagg ccctc 335

<210> SEQ ID NO 427
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 427
cggcgacgtc gcgatacgcc gagcagttgg gaatcgctct gcagcaaacc aatattctgc 60
gcgacgttcg agaggacttt ttgaatggac ggatctacct gccgcgcgac gagctggacc 120
gattaggcgt acgcctccgc ctggacgaca ccggggcact cgatgacccc gacggacggc 180
tcgcggcnct gctgcggttc agtgccgacc gcgccgcaga ctggtnttcg ctgggactgc 240
ggctgattcc acacctcgac cgccgcagcg ctgcctgctg tgcggccatg tctggcatct 300
accgccgtca gctcgccttg atcagagcat cgccggcggt cgtcta 346

<210> SEQ ID NO 428
<211> LENGTH: 332
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 428
ctataaaata ctcaagcttg atgccgccga aaccgagcgt gagcacgccg ccagccacca 60
cgcgcgggtc gggcgccggg cccgggccgc caggctgctc cgctcggtga tggcacgcca 120
ccgcgacacc acccggntgc gctacgtcna gccataccgg gcggagctac atcggctcgg 180
ccgcccagtg ttcgggccct ctttcgaggt cnaggtcnat accgatttgc gcatccgcag 240
ccgcaccctg aacnacanaa ccgtgcccta ctattgcttg tcnggcgggg ccaaaaaaca 300
gcttggcatc ctggcccnat tggccggcgc gg 332

<210> SEQ ID NO 429
<211> LENGTH: 276
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 429
cttcggtcgc agtgtgcgag tgatagatga cgaccgggac ctcgtcggca tcttccatag 60
cccgccacac cttcagttgc tcaccggaat ccaaccggta gaaggtcggc gagcgctcgg 120
cattggtcat cgggatatgc cgctcgggac ggtcagagcc ctcgggtccg gccagcactc 180
cgcaggcttc gtcggggtgg tcgcgacgcg catgggccac catcgcattc accaggtctg 240
cgcgaatcnc cancacgtan acngttcctt tcctaa 276

<210> SEQ ID NO 430
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 430
ctggcaccaa ggccccacac gtcaccctgt gacctcctgc gccgaccccg cccgaggtcc 60
tggccgttac caccgaacgg gcgagccggg agtctggtnc gcatcgaaca aanagcaagg 120
tgcatgggcg gagttgttcc gccacttcgt cgatgacggg gtcnatccat tcgaggtccg 180
tcgccgcgtc ggtcnagtgg cggtcacact ccaggtactc gacctcacag acnaaaggac 240
tcnatcccat ctaggtgtgg acnaaacaga tcttctgtcc gacnactaca ccaccaccca 300
ggccatcgcc gccgcccgcg atgccaactt cgacgccgta ctggccccgg cggggggcgc 360
tccccggttg tcaacacttg ccgtgttcnt tcacgcnctg ccccacatcc aaccccaacg 420

<210> SEQ ID NO 431
<211> LENGTH: 130

<212> TYPE: DNA
<213> ORGANISM: Mycobacterium tuberculosis

<400> SEQUENCE: 431
gttcttgggc ccatgcggag gtatcgccgt ttccaccacg cggtcggggt ggcgttgcat 60
tagctcaccg atggtgcgct tgtgcaggcc gccgggatac cccgagtgcc ggtaaaccat 120
cttgtgctgc 130

<210> SEQ ID NO 432
<211> LENGTH: 215
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 432
caatactcaa gcttggcgtg ccgttccaac ccgaattggc tttcggcgcc atcggtgagg 60
acggcgtgcg ggtgctcaac nacnacgtcg tccgcgggac acacctcgat gctgccgcca 120
tggacgcggt cgaacgcaag cagctgatcg agctacaacg ccgcgcggaa cgcttccgcc 180
gcgggcgtga ccgcatcccg ttgaccgggc ggatc 215

<210> SEQ ID NO 433
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 433
cntcatgatg atcatcaccc gaagtgtggt agccgcagtg gttatcgtgg gtaccgtcgt 60
gctttccatg ggcgcctctt tcgggctttc cgtattggtc tggcaggaca ttctgggtat 120
cgagttgtac tggatggtgt tggcgatgtc ggtgatcctg ctcctggcgg tgggatccga 180
ctacaatctg ctgctgattt cccggttgaa agaggaaatt ggggccggat tgaacaccgg 240
aattatccgt gccatggctg gtaccggggg agtggtgacg gctgccggca tggtgttcgc 300
cgttaccatg tcgttgtttg tgttcagcga tttgcgaatt attggtcaga tcggtaccac 360

<210> SEQ ID NO 434
<211> LENGTH: 265
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 434
atactcaagc ttttacggtg atcgcncatc acctggttca tgaactggaa gcagcgcagc 60
gcttcctttt cggccgcaac atgagccagc ctctcgtcgg cggtcgggtg caggtgctcg 120
ggcagctcgg ccgcnacagc cgcctgaccc tgaaaccagc ttccatatcc cgcgannaac 180
gacgccagtc cgctacgtna cccctccgcg actgtccatg gacaacagcg cgttctccac 240
cgaccgggcc cgggtgtggg gtntt 265

<210> SEQ ID NO 435
<211> LENGTH: 264
<212> TYPE: DNA
<213> ORGANISM: Mycobacterium tuberculosis

<400> SEQUENCE: 435
gctggtagag tcgctgaccg gtgcaggttt cgacaatgtg gtgccggttc ggcggctacg 60
tgccatcgag acactggcgc aggctatcgc acccgttatc ggctacgagc aaatcgcggt 120
atgcgttctt gagcatgagt cggcgaccgt cgtcatggtc gacacccacg acggaaagac 180
gcagatcgcc gtcaagcatg tgtgccgcgg attatcagga ctgacctcct ggctgaccgg 240
catgtttggt cgcgatgcct ggcg 264

<210> SEQ ID NO 436
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 436
gctttccgcc gatacccgcc atgtcncgca catccaggac ttctgggggg atccgctgac 60
agcggcggga tcccaaagtg cggatgatcg ggccgcctac gtcgtggtgt acctcgtcgg 120
taacaacgaa accgaagcgt atgactcggt ccacgcggtg cggcacatgg tggacaccac 180
accgccaccg cacggggtga aggcctatgt caccggtccg gcancactca atgccgacca 240
ggccgaggcc gganacaaaa ntatcgctaa ggtcaccgcg atcacnagca tggtgatcgc 300
agcaatgttg ctagtgatct atcgctccgt aatta 335

<210> SEQ ID NO 437
<211> LENGTH: 304
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 437
cttccaaccc gaattggctt tcggcgccat cggtgaggac ggcgtgcggg tgctcaacga 60
cgacgtcgtc cgcgggacac acctcgatgc tgccgccatg gacgcggtcg aacgcaagca 120
gctgatcgag ctacaacgcc gcgcggaacg cttccgccgc gggcgtgacc gcatcccgtt 180
gaccgggcgg atcgcggtga tcgtcgatga cggcatcgcc accggagcga cggccaaggc 240
ggcgtgccan gtcgcccggg cgcacggtgc ggacaaggtg gtgctggcgg tcccgatcgg 300
ccca 304

<210> SEQ ID NO 438
<211> LENGTH: 223
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 438
tactcaagct tcgcgagatc cggatggcac tcacgctgga caagaccttc acaaaatctg 60
aaatcctgac ccgatacttg aacctggtct cgttcggcaa taactcgttc ggcgtgcagg 120
acgcggcgca aacgtncttc ggcatcaacg cgtccganct gaattggcag caagcggcgc 180
tgctggccgg catggtgcaa tcnaccagca cgctcaaccc gta 223

<210> SEQ ID NO 439
<211> LENGTH: 263
<212> TYPE: DNA
<213> ORGANISM: Mycobacterium tuberculosis

<400> SEQUENCE: 439
cccacgactt tctcctcgat cagttggatt tgtacgaaga ggcaacgaaa gcagtgatcc 60
tcgggatggt cgacgcctac atcgacccgc cgttcacgcc gcacagcctg ctagatgcgc 120
tgggcgagca ggtcccacag ttcgccgcta aggcacggcg tctgttcccg tccggatcgc 180
cattcggcct cggcgtcctg ctcccattcg atcaataggg ctggcagctc cgtcggcagg 240
ggcctacgcc tcaccccgtc acg 263

<210> SEQ ID NO 440
<211> LENGTH: 301
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 440
ctcaagctta tgcgcgccgg ccgaggtctg ctcacggcaa cccctgaagt ttaggggacn 60
acctactcag cgcaaaattt cgctaatgtg agtccgcccc accaggggna natcaaccca 120
tgtcgatcat gatctacccg gataccggat tggcggtagc gcccacgatc gtcnaaatnt 180
ccgcctgaat catcggatag ctgatccggc gtcaacgcgt tttganttca ccgcgcaaca 240
gccgccaggc cggcccgcan cganccgatc tcntcgggcc gcatgggccc caatcttntc 300
g 301

<210> SEQ ID NO 441
<211> LENGTH: 90
<212> TYPE: DNA
<213> ORGANISM: Mycobacterium tuberculosis

<400> SEQUENCE: 441
gtgtgtggtg gaacccatct gagcagtgtg ccaaaccggg gcagacagct cccaattgac 60
gtgagcccgc tcacttgctg ggtaagcgtc 90

<210> SEQ ID NO 442
<211> LENGTH: 183
<212> TYPE: DNA
<213> ORGANISM: Mycobacterium tuberculosis

<400> SEQUENCE: 442
ctttacactt cctgcatccg gctcgtatgt tgtgtggaat tgtgagcgga taacaatttc 60
acacaggaaa cagctatgac catgattacg ccaagctatt taggtgacac tatagaatac 120
tcaagcttgg gcgtgacggc caccggggcc actccgcacc atctgtaccc gaccaagatc 180
tac 183

<210> SEQ ID NO 443
<211> LENGTH: 348
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 443
caggcatgca agctttagct gcccgaatgc gtcaccccga tgcgcccaga tcggggcttc 60
gcagataaag cacgaacagg cgggcaaaac gtcnatctcg gagccggaag ggcaatcagc 120
cgaccgtcga cgaacgacac cggcgagacc acttaggcag tgacggccgg cccgaacatt 180
acgcgctcgt tgattaggcg ttcggtctcg tccgcggtca tgccgagcag cttgcggcag 240
atctgaacgc tgtcctgtcc gggcagcggc gccgggcgtt ggggtgcctg cccgaatgtg 300
acgaaacgga gccggacccg tctcggcggg ccgcggacgg cgatccgc 348

<210> SEQ ID NO 444
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 444
cncaagcttg cggatgttac ccctgacagc ctgaactatg tcnaaacaca cggcaccgga 60
acggtgttgg gggaccccat cganttcgag tcgctggcgg ccacttatgg cctgggtaaa 120
ggccagggcn anagcccgtg cgcattgggg tcggtcaaaa ccaacatcgg ccacctggag 180
gcggccgccg gtgtggctgg atncatcaag gcggtgctgg cggtgcaacg tgggcacatt 240
ccccgcaact tgcacttcac ccggtggaac ccggccatcn acgcgtcggc nacgcggctg 300
ttcgtgccna ccnaaaaccc cccgtggccg gcggc 335

<210> SEQ ID NO 445
<211> LENGTH: 289
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 445
ggaaccggta accagatcag ctcgtcgacc tcactgccgg gggtgaattc cccaccggtg 60
ctgcgcgctg cccagtagtg caccttcttg acgcctcgaa aaggggagtc ggtcgggtag 120
gtcaccgtca ggagccgcct acccaggttg gcgcnatagc cggtctcctc gagtatctcc 180
cgcaccgccc ccaccggtgc ggtctcaccc anatccactt tgcccttggg cagcgaccag 240
tcgtcgtanc nggggcggtg aatgacaacg atctcgaccg gcccttccn 289

<210> SEQ ID NO 446
<211> LENGTH: 263
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 446
tactcaagct tcagaacagg cctgttgtgg gcncacccgg ctcgccgagt tctgcacgca 60
ccgcctcaag tgcggcccgc accgccggca tctcccggtc acgcagggcc gcggcccgcg 120
ccgcagcgac ggcgtgttcg cgcagttcgc cgtcaatgat gctgacctga tcggccaccc 180
gggcgttctc ggcgtcgtcg cgttcactaa tcgcggtgct cagcagcgtc tcgacagcca 240
ccacccgagt ggcgaccagc tgc 263

<210> SEQ ID NO 447
<211> LENGTH: 279
<212> TYPE: DNA
<213> ORGANISM: Mycobacterium tuberculosis

<400> SEQUENCE: 447
taatgtcttg ccaacgtcac cacaatcgcg atgaattcaa tcatgccgcc cagggcggcc 60
aacccaatgg tggccgcgag cggcagctcg atcgcagcgc ggaggttgcc ggccgccagt 120
tgattcacga acagggtgag gtcataggcg ggcaggatag tgacgaaggc aagacctata 180
tctgccgtcg gaagaagaat cgagtagccg gtcgacacaa cggaagcgaa agtgtccgcg 240
atgttgatga gcgtcgccgg ttgtggcggc ggtggcggc 279

<210> SEQ ID NO 448
<211> LENGTH: 295
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 448
tactcaagct ttcgtcagtt catcgcgcca gcagaccaac aagagcatcg ggacatacgg 60
agtcaactac ccggccaacg gtgatttctt ggccgccgct gacggcgcga acgacgccag 120
cgaccacatt cagcanatgg ccagcgcgtg ccgggccacg aggttggtgc tcggcggcta 180
ctcccagggt gcggccgtga tcgacatcgt caccgccgca ccactgcccg gcctcgggtt 240
cacgcagccg ttgccgcccg cagcgganna tcacatcgcc gcgatcgccc tgttc 295

<210> SEQ ID NO 449
<211> LENGTH: 280
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 449
ccacccgtgt aatttgggat gggcnaaaag gcnaagcacc gcgtggccac gaacgccggg 60
agggacaatc tcgggcggct agggcttctc gcgggaaggc ccgaacgtac ggcgtttcaa 120
cacgtcgcgt cgccctccga ccgcgaacat tcggggatgg cagcaacctg gtagcaccct 180
ggccgggcga tgatctgcag cgtcgccgcg ggtagtcgcc gcccgggcgg ctacagtctg 240
aaacgcgatg accatcgatg tgtggatgca gcatccgacg 280

<210> SEQ ID NO 450
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 450
tcaagcttta gctgcccgaa tccgtcancc cgatgcnccc agatcggggc ttcgcanata 60
aagcacnaac aggcgggcaa aacgtcnatc tcggagccgg aagggcaatc anccgaccgt 120
cnacaaacga caccggcgan accacttagg cagtgacggc cggcccgaac attacncgct 180
cgttgattag gcgttcggtc tcgtccgcgg tcatgccgag cagcttgcgg canatctgaa 240
cgctgtcctg tccgggcagc ggcgccgggc gttggggtgc ctgcggaatg tgacnaaacg 300
gagccggacc cntctcggcg 320

<210> SEQ ID NO 451
<211> LENGTH: 203
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 451
ccggggccac tccgcacaat cngtaccnna ccaanatcta caccatcgaa tacgacggcg 60
tcgccgantt tccgcggtac ccgctcaact ttgtgtcgac cctcaacgcc attgccggca 120
cctactacgt gcactccaac tacttcatcc tgacgccgga acaaatngac gcntcggttc 180
cgctgaccaa tacggtcggt ccc 203

<210> SEQ ID NO 452
<211> LENGTH: 287
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 452
nctggccttt ggtccacact aanacaatac tcaagcttcc ggccgcagag ccgccaactc 60
acgatatcgt taaccgatat cccgagccga tagctggcgg gctcgggtgg tggccagcgg 120
cgctgcgacn aaaggtgtga ccgtcatgaa acagacacca ccggcggccg tcggccgtcg 180
tcacctgctc ganatctcag catccgcagc cggtgtgatc gcgctttcgg cgtgtngtgg 240
gtcnccgccc gagcccggca aaggccggcc cgacacaacc ccggaac 287

<210> SEQ ID NO 453
<211> LENGTH: 272
<212> TYPE: DNA
<213> ORGANISM: Mycobacterium tuberculosis

<400> SEQUENCE: 453
catctgccca ccacacggac cgcggtgcgg acgcggctga cgcgcctggt ggtcagcatc 60
gtggccggtc tgctgttgta tgccagcttc ccgccgcgca actgctggtg ggcggcggtg 120
gttgcgctcg cattgctggc ctgggtgctg acccaccgcg cgacgacacc ggtgggtggg 180
ctgggctacg gcctgctatt cggcctggtg ttctacgtct cgttgttgcc gtggatcggc 240
gagctggtgg gccccgggcc ctggttggca ct 272

<210> SEQ ID NO 454
<211> LENGTH: 364
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 454
gacaatactc aagcttgact ggccacccac cggcatgacc accgacaggc ccgactggtc 60
gtaccactcg aacgccgggg tgttgatgtc ccagccgctg aantcgtcct gcgcgcgcag 120
gccgtcnaac aggtacaggg cgggcgaatt ggcaccacca ctttggaatt ggaccttgat 180
gtcacggccc atcgacggcg acggcacctg caggtactcc accggcaagc ccggccggga 240
aaatgccccc gcggtcnccg tgccaccgac ggcgccganc aaacccgaca ctagggccgc 300
gccnacggcc ccgaccacna ntcnacgcga catacccgtg acggcgccac naaccctgtc 360
aaca 364

<210> SEQ ID NO 455
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 455
cctccaactc ggcggggaag cgacnccagc ctaccgagct tggagtccan gacgccagcg 60
gcggcgtcgg tctgcgtcgt ggtgccgccg gggtggcgtt ggctggcaac gatctccacc 120
cagccggtcg ggttacccac gatctcggca tanacgcggg ccgaggccgg tgcgataccg 180
tattgcgtca attgggacgc ggttgtgcat tcggctagct cggttgccac acccgtcagg 240
ggttcgacgt tggcgggttc ggcgggcccc ancaccgctg tcaccatgcc cgccaagccg 300
acctgcggcg ccaccaactg cagcaccanc atgtcgccgt cgcgcgccgc gatcacatgg 360

<210> SEQ ID NO 456
<211> LENGTH: 311
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 456
ctcaagcttt ttgagcgtcg cgcggggcan cttcgccggc aattctacta ncgagaantc 60
tggcccgata cggatctgac cgaantcgct gcggtgcanc ccaccctcat tggcgatggc 120
gccgacnatg gcgcctggac cgatcttgtg ccgcttgccg acggcgacgc ggtaggtggt 180
caagtccggt ctacgcttgg gcctttgcgg acggtcccga cgctggtcgc ggttgcgccg 240
cnaaagcggc gggtcgggtg ccatcaggaa tgcctcnccg ccgcggcact gcacggccag 300
tgccgcggcg a 311

<210> SEQ ID NO 457
<211> LENGTH: 288
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 457
cnccagcttg attggtctgg ttgcattggc cagctgcgcg agcctggctc acttcaacta 60
cgacgaccgc aaacaattgc cgccttcgga tccgagttcg gttgggtacg cggcaatgga 120
gcaccatttc tcggtgaatc agactattcc tgagtacttg atcatccact ctgcacacga 180
cctgcgaacc ccgcgcggcc ttgccgacct ggagcagctg gcgcaacgtg tgagccagat 240
cccaggcgtt gccatggttc gcggtgtgac ccggccaaac ggggaaac 288

<210> SEQ ID NO 458
<211> LENGTH: 256
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 458
caatactcaa gcttgactgg gcccgcacct tcggcgccac ccacaccgtc aacgcccgcg 60
aagtcnacgt cgtccaggcc atcggcggcc tcacggatgg attcggcgcg gacgtggtga 120
tcgacgccgt cggccgaccg gaaacctacc agcaggcctt ctacgcccgc gatctcgccg 180
gaaccgttgt gctggtgggt gttccnacgc ccgacatgcg cctggacatg ccgctggtcn 240
acttcttctc tcacgg 256

<210> SEQ ID NO 459
<211> LENGTH: 327
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 459
tcgacggttt ggcggcctta aatgcactga ggtcgtcaat tgaccccaca gcggaaatgc 60
cgactattcg caggcctcct tcgccttggc tgccggagag gggctccgcg ggaaccgcat 120
gcaggtatat gacctcggtt tctcgggtgc taccgcgtgc cttgtntang atnanctcgg 180
cgttggaatt gtccagccgg cccaattcat cgagcgcana ttcgtacacn tggccggcgg 240
cgacatacgc ttcaccgtgg atctgctcca cacggaccgc cctgtcggga tcctgctcac 300
gggtaangga acttacgtgg cactcgg 327

<210> SEQ ID NO 460
<211> LENGTH: 100
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 460
gaccacgcca ggctaatcac gtgacgctac cgaataccct ncctagtggt gcaggctccc 60
gctggaaatg gccctgtacc aactcgcgca ccggtgccag 100

<210> SEQ ID NO 461
<211> LENGTH: 114
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 461
cggcacccga cccctttgag ccgtccgccg tggccgcggt ggaactggcc gacgagggac 60
tgatcgtgct gggcaaattg gtcgatggca cgctggccgc cgatctgaag gtcn 114

<210> SEQ ID NO 462
<211> LENGTH: 287
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 462
ctcaagcttg ccgttacccc gacttccgga gggacaccat gagcaccgcc agccgagcac 60
gaggccaaac tccgccgacg caggccggtt ggacttgtcg tgctggacaa ggggtttagc 120
cgccgaagca gtgacgtaca tcggcgaaaa gcagttcgcc tgtcgaccga cggngcnnac 180
cgtgaggcta gggaagcgag gagcacatgg ccgccgaccc gcaatgtaca cgctgcaagc 240
aaaccatcga acccggatgg ctatncntca ccgcccatcg ccgcggt 287

<210> SEQ ID NO 463
<211> LENGTH: 288
<212> TYPE: DNA
<213> ORGANISM: Mycobacterium tuberculosis

<400> SEQUENCE: 463
catgtcgcgc acatccagga cttctggggg gatccgctga cagcggcggg atcccaaagt 60
gcggatgatc gggccgccta cgtcgtggtg tacctcgtcg gtaacaacga aaccgaagcg 120
tatgactcgg tccacgcggt gcggcacatg gtggacacca caccgccacc gcacggggtg 180
aaggcctatg tcaccggtcc ggcagcactc aatgccgacc aggccgaggc cggagacaaa 240
agtatcgcta aggtcaccgc gatcacgagc atggtgatcg cagcaatg 288

<210> SEQ ID NO 464
<211> LENGTH: 255
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 464
atactcaagc ttcggtacgg tggcgggccg tgctgctggc cgcggtcgcg gcgtgcgcgg 60
cctgcggtct cgtttacnag ctcgcgctgc tgacactggc ggcnagcctg aacggcggcg 120
ggatcgtggc cacctccctg atcgtcgcgg gctacatagc cgcgctggga gcaggcgcct 180
tgctgatcaa gccgctactt gcacacgcgg ccatcgcgtt catcgccgtg gaggcggtgc 240
tgggcatcat cggcg 255

<210> SEQ ID NO 465
<211> LENGTH: 288
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 465
tgtcaagtcc tttcagatct cntttttatg acatgactgg agatctgtct agattgcagc 60
tcctgtgagc gtgggtaccg gattcaagcc ggtcggtcac gccgcggtgg taccggcttt 120
gcggcagtgc tcggcctcga gttcggcgat cgcgcgcgaa gtgcgttcgc gcagcaagat 180
cgcggccgta atgccggcga tgaccgcgat gaccagcgcg atccaggaga accgttccaa 240
ccagtgctgg gcggccatcc cggcgaagta gaccagtgca gtggtgcc 288

<210> SEQ ID NO 466
<211> LENGTH: 224
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 466
caatactcaa gcttcaaaac aggcctgttg tgggcgcacc cggctcgccg agttctgcac 60
gcaccgcctc aantgcggcc cgcaccgccg gcatctcccg gtcacgcagg gccgcggccc 120
gcgccgcanc gacggngtgt tcgcgcagtt cgccgtcaat gatgctgacc tgatcggcca 180
cccgggcgtt ctcggcgtcg tcncgttcac taatcgcggt gctc 224

<210> SEQ ID NO 467
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 467
tacgctggcg ctggagggag ccanntacaa catccacgcc aatgctcttg ccccgatcgc 60
ggcgaccagg atgacccagg acatcctgcc gcccgaagta ctggaaaagc tcacacccga 120
gttcgtcgca ccggtggtgg cctacctgtg caccgaggag tgtgccgaca acgcatcggt 180
gtacgtcgtc ggtggtggca aggtgcagcg agttgcgctg tttggcaacg acggcgccaa 240
cttcgacaaa ccgccgtcgg tacaagatgt tgcggcgcgg tgggccgaga tcaccgatct 300
gtccggtgcg aaaattgctg 320

<210> SEQ ID NO 468
<211> LENGTH: 303
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 468
gcttttcccg tccgtcnncg ctcaaccgcg tgaggccgaa gcggntggtt acgactccct 60
gtttgtgatg gaccacttct accaactgcc catgttgggg acncccgacc agccgatgct 120
ggaggcctac acggcccttg gtgcgctggc cacggcgacc gancggctgc nnntgggcgc 180
gttggtgacc ggcaatacct accgcagccc gaccctgctg gcaaanatca tcaccacgct 240
cgacgtggtt agcgccggtc gagcgatcct cggcattgga gccggttggt ttganctgga 300
aca 303

<210> SEQ ID NO 469
<211> LENGTH: 391
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 469
cngcttttta atggccttga cntgggcgng ccggccaccg gggccactcc gcacaatctg 60
tacccgacca agatctacac catcgaatac gacggcgtcg ccgactttcc gcggtacccg 120
ctcaactttg tgtcgaccct caacgccatt gccggcacct actacgtgca ctccaactac 180
ttcatcctga cgccggaaca aattgacgca gcggttccgc tgaccaatac ggtcggtccc 240
acgatgaccc agtactacat cattcgcacg gagaacctgc cgctgctaga gccactgcga 300
tcggtgccga tcgtggggaa cccactggcg aacctggttc aaccaaactt gaaggtgatt 360
gttaacctgg gctacggcga cccggcctat g 391

<210> SEQ ID NO 470
<211> LENGTH: 343
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 470
ctcaagcttg ccgggagggt gcatggccga ctcggattta cccaccangg ggcgccaacg 60
cggtgtccgc gccgtcnagc tgaacgttgc tgcccgcctg gagaacctgg cgctgctgcg 120
caccctggtc ggcgccatcg gcaccttcga ggacctggat ttcgacgccg tggccgacct 180
gaggttggcg gtggacgagg tgtgcacccg gttgattcgc tcggccttgc cggatgccac 240
cctgcgcctg gtggtcgatc cgcgaaaana cgaanttgtg gtggaggctt ctgctgcctg 300
cgacacccac nacgtggtgg caccgggcag ctttagctgg cat 343

<210> SEQ ID NO 471
<211> LENGTH: 303
<212> TYPE: DNA
<213> ORGANISM: Mycobacterium tuberculosis

<400> SEQUENCE: 471
ccgacgccgt cgtggccacc aacaccgcga ccagcaccgt gacccggacc ggggtgccgc 60
gcgaaccggt cttggccaat tgccgcggca ccaagccgtc gcgcgccatg gcgaacagca 120
cgcggcattg cccgagcatc aacaccatca ccaccgtggt aagcccggcc agcgcgccga 180
cggagatgat gccgctggcc cagtacaccc cgttggcctg gaacgcggtg gccagatttg 240
ccggcccgcg gcccggtacg gtccgcagtt gggtgtatgg aaccatgccc gacagcacca 300
ccg 303

<210> SEQ ID NO 472
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 472
ttnactggcc tttggtccac actagacaat actcaagctt ccaggacatc gtcatcgcga 60
ccaaaaccgc gagctaggtc ggcatccggg aagcatcgcg acaccgtggc gccgagcgcc 120
gctgccggca ggccgattag gcgggcaaat tagcccgccg cggctcccgg ctccgantac 180
ggcgccccga atggcgtcac cggctggtaa ccacgcttgc gcgcctgggc ggcggcctgc 240
cggatcaggt ggtaaatgcc gaca 264

<210> SEQ ID NO 473
<211> LENGTH: 280
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 473
ngacgtcttc catccgcgcg tcgttttggc gggttggcca cagcagcccg ccggtgacgg 60
cgacgatgct gggctggttg cggccctgcg ccaccgcggc ttgcatgctg gttggctgtc 120
ttgggacgat cccgaaatag tccacgcgga tctggtgatt ttgcgggcta cccgcgatta 180
ccccgcgcgg ctcgacgagt ttttggcctg gactacccgc gtggccaatc tgctgaactc 240
gcggccggtg gtggcctgga atgtcgagcg ccgttaccta 280

<210> SEQ ID NO 474
<211> LENGTH: 153
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 474
cttcctcctg agtaccnccc gtntactttg ggatgggtaa aaaggcgaat cnccgtttgg 60
tcacgaacgc cgggagggac aatctcgggc ggctggggcc tctcgcggga angcccgaat 120
gtacggtgtc tcgacacttc ccntccccct ccg 153

<210> SEQ ID NO 475
<211> LENGTH: 247
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 475
gagcatcggg acntacggag tcaactaccc ggccaacggt gatttcttgg ccgccgctga 60
cggcgcgaac gacgccngcg accacattca gcagatggcc agcgcgtgcc gggccacgag 120
gttggtgctc ggcggctact cccagggtgc ggccntgatc nacatcgtca ccgccgcacc 180
actgcccggc ctcgggttca cgcagccgtt gccgcccnca gcggacgatc acntcgccgc 240
gatcgcc 247

<210> SEQ ID NO 476
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 476
tactcatgan catcctttaa tcanngcttt gcgttttttt attaaatctt gcaatttact 60
gcaaagcaac aacaaaatcg caaagtcatc aaaaaaccgc aaagttgttt aaaataagag 120
cancactaca aaaggagata agaagagcac atacctcagt cacttattat cactagcgct 180
cgccgcagcc gtgtaaccga gcatagcgag cgaactggcg aggaagcaaa gaagaactgt 240
tctgtcagat agctcttacg cnca 264

<210> SEQ ID NO 477
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 477
ctcaagcttc aggtcaatgt gcnccaagcc ctgacgctgg ccgaccaggc caccgccgcc 60
gganacnctg ccaaggccac cgaatacaac aacgccgccg aggcgttcgc ancccagctg 120
gtgaccgccg agcanancgt caaaaacctc aagacgctgc atgaccaggc gcttancncc 180
gcanctcagg ccaagaaggc cgtcnaacga aatgcgatgg tgctgcacca naagatcgcc 240
gagcgaacca agctgctcag ccng 264

<210> SEQ ID NO 478
<211> LENGTH: 352
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 478
catggtggca ctgtagcgac gtgctgcaat caaggtcatg cccgactctg gtcagctcgg 60
anccgctgac accccgctaa ggctgctcag ctcggtgcat tacctcaccg acggcgaact 120
cccccagctt tacgactatc cggatgacgg cacctggttg cgggcgaact tcatcatcag 180
cttggacggc ggcgctaccg tcgatggcac cagcggggcg atggccgggc ccggcgaccg 240
attcgtcttc aacctgttgc gtgaacttgc cgacgtcatc gtggtcggcg tgggcaccgt 300
gcgcattgag ggctactccg gcgtccggat gggtgtcgtc cagcgccagc ac 352

<210> SEQ ID NO 479
<211> LENGTH: 207
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 479
tactcaagct tgcgggtgat cgccttggtc aacggcaccg tgatcggatc ggggtcnacc 60
gcacaaatgg actggagctt cggcgaantc atcgcctatg cctcgcgggg ggtgacgctg 120
accccgggtg acntgttcgg ctcgggcacg gtgcccacct gcacgctcgt ctatcacctc 180
nggccaccgg aatcattccc gggctgg 207

<210> SEQ ID NO 480
<211> LENGTH: 256
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 480
gttggngcct cgtcggcgaa cagttctcgc acgatttccg gattagcggg actggtcacc 60
agttgggtat gcgggaaggc gctgacgttc gccgcgatta gctgtttgat ggacgcggtg 120
gtgatgttct gatcacggaa ctggctgtaa tagcccaggg tcgccacgct ttcatccggg 180
cccggacccg gcgcaccgag cgtgtcgcgc aggtatgcga cgtgattttc gctgaagtcc 240
ccgtacccgg agaact 256

<210> SEQ ID NO 481
<211> LENGTH: 397
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 481
tgcttccggc tcgtatgttg tgtggaattg tgancggata acaatttcac acaggaaaca 60
gctatgacca tgattacgcc aagctattta ggtgacacta tagaatactc aagctccagg 120
tcaatgtgcg ccaagccctg acgctggccg accaggccac cgccgccgga gacgctgcct 180
ttgtcaccga atacaacaac gccgccgagg cgttcgcagc ccagctggtg accgccgagc 240
agagcgtcga agacctcaag acgctgcatg accaggcgct tagcgccgca gctcaggcca 300
agaatgccgt cgaacgaaat gcgatggtgc tgcggcataa gatcgccgag cgaaccaagc 360
tgctcagcca gctcgagcag gcgaagatgc acgagca 397

<210> SEQ ID NO 482
<211> LENGTH: 379
<212> TYPE: DNA
<213> ORGANISM: Mycobacterium tuberculosis

<400> SEQUENCE: 482
caggcatgca agcttcggag gcagacccgt gcatggtggc actgtagcga cgtgctgcaa 60
tcaaggtcat gcccgactct ggtcagctcg gagccgctga caccccgcta aggctgctca 120
gctcggtgca ttacctcacc gacggcgaac tcccccagct ttacgactat ccggatgacg 180
gcacctggtt gcgggcgaac ttcatcagca gcttggacgg cggcgctacc gtcgatggca 240
ccagcggggc gatggccggg cccggcgacc gattcgtctt caacctgttg cgtgaacttg 300
ccgacgtcat cgtggtcggc gtgggcaccg tgcgcattga aggctactcc ggcgtccgga 360
tgggtgtcgt ccatcgcca 379

<210> SEQ ID NO 483
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 483
tactcaagct tggggtggcg ctgtcggtcg gtgtgcttgg cggcgtcggt atcaacaccg 60
cccacgaaat ggggcacaag aaggattcgc tggagcggtg gctgtccaaa atcaccctcg 120
cccanacctg ctacgggcac ttctacatcg agcacaaccg tggccatcac gtccgggtgt 180
ccacaccgga ggacccggcg tcggcgcggt tcggcnaaac gttgtgggan ttcctgcccc 240
gcantgttat cggcggcttg cgct 264

<210> SEQ ID NO 484
<211> LENGTH: 351
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 484
ggccatcgcc accgcnccgc ggcgaacgct caaaggcacc tactggcacc aaggccccac 60
acgtcaccct gtgacctcct gcgccgaccc cgcccgaggt cctggccgtt accaccgaac 120
gggcgagccg ggagtctggt acgcatcgaa caaagagcaa ggtgcatggg cggagttgtt 180
ccgccacttc gtcgatgacg gggtcgatcc attcgaggtc cgtcgccgcg tcggtcgagt 240
ggcggtcaca ctccangtac tcgacctcac agacgagagg actcgatccc atctaggtgt 300
ggacgaaaca gatcttctgt ccgacgacta caccaccacc caggccatcg c 351

<210> SEQ ID NO 485
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
    as "n"

<400> SEQUENCE: 485

```
gcttgcgggt gatcgccttg gtcaacggca ccgtgatcgg atcggggtcn accgcncaga      60

tggactggan cttcggcgaa ntcntcgcct atgcctcgcg gggggtgacc ctgaccccgg     120

gtgacntgtt cggctcgggc acggtgccca cctgcacgct cgtcaagcac ctcnggccac    180

cggaatcatt cccgggctgg ctgcacnacg gcgacntggt cnccctccag gtcgaagggc    240

tgggcnaaac aangcagacc gtccggacaa ncggcactcc ttttccgttg gctcttcggc    300

cgaatccgga cgccnaaccc gaccggcg                                        328
```

<210> SEQ ID NO 486
<211> LENGTH: 344
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
    as "n"

<400> SEQUENCE: 486

```
gttctcgcac gatttccgga ttagcgggac tggtcaccag ttgggtatgc gggaaggcgc      60

tgacgttcgc cgcgattagc tgtttgatgg acgcggtggt gatgtnctga tcacggaact    120

ggctgtaata ncccagggtc gccncgcttt catccgggcc cggacccggc gcaccgagcg    180

tgtcgcgcag gtatgcgacg tgattttcgc tgaagtcccc gtacccggag aactcgaaca    240

cgctgaggcg ctcgtcaccg tcgtnncggc gaccaagcgc ggcgagcaac tgcgcaaaat    300

cgttaagana ggtcgaatcg ttgaaattcg gcaccacctg cacc                      344
```

<210> SEQ ID NO 487
<211> LENGTH: 285
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
    as "n"

<400> SEQUENCE: 487

```
cacaagacaa tactcaagct tcaggtcaat gtgcnccaag ccctgacgct ggccgaccag      60

gccaccgccg ccgganacgc tgccaaggcc accgaataca acaacgccgc cgaggcgttc    120

gcagcccagc tggtgaccgc cgagcananc gtcnaaaacc tcaagacgct gcatgaccag    180

gcgcttancg ccncagctca ggccaagaag gccgtcgaac gaaatgcgat ggtgctgcag    240

canaanatcg ccgancgaac caagctgctc agccagctcg agcag                     285
```

<210> SEQ ID NO 488
<211> LENGTH: 280
<212> TYPE: DNA
<213> ORGANISM: Mycobacterium tuberculosis

<400> SEQUENCE: 488

```
ccacccgtgc atggtggcac tgtagcgacg tgctgcaatc aaggtcatgc ccgactctgg     60

tcagctcgga gccgctgaca ccccgctaag gctgctcagc tcggtgcatt acctcaccga    120

cggcgaactc ccccagcttt acgactatcc ggatgacggc acctggttgc gggcgaactt    180

catcagcagc ttggacggcg gcgctaccgt cgatggcacc agcggggcga tggccgggcc    240

cggcgaccga ttcgtcttca acctgttgcg tgaacttgcc                          280


<210> SEQ ID NO 489
<211> LENGTH: 160
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 489

gctttccgcc gatacccncc atgtcccgca catccaggac ttctgggggg atccgctgac     60

agcggcggga tcccaaagtg cggatgatcg ggccgcctac gtcgtggtgt acctcgncgg    120

taacaacgaa accgaancgt atgactcngt ccacgcggtg                          160


<210> SEQ ID NO 490
<211> LENGTH: 176
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 490

caacccgant tggctttcgg cgccntcggt gaggacggcg tgcgggtgct caacgacgac     60

gtcgtccgcg ggacacacct cgatgctgcc gccatggacg cggtcgaacg caagcagctg    120

atcgatctac nacgccgngn ggaacgcttc ngccgcgggc gtgaccgcnt cccgtt        176


<210> SEQ ID NO 491
<211> LENGTH: 216
<212> TYPE: DNA
<213> ORGANISM: Mycobacterium tuberculosis

<400> SEQUENCE: 491

gggatgggca aaaaggcgaa gcaccgcgtg gccacgaacg ccgggaggga caatctcggg     60

cggctagggc ttctcgcggg aaggcccgaa cgtacggcgt ttcaacacgt cgcgtcgccc    120

tccgaccgcg aacattcggg gatggcagca acctggtagc accctggccg ggcgatgatc    180

tgccagcgtc cccgcgggta gtcgccgccc gggcgg                              216


<210> SEQ ID NO 492
<211> LENGTH: 163
<212> TYPE: DNA
<213> ORGANISM: Mycobacterium tuberculosis

<400> SEQUENCE: 492

cagcagacca acaagagcat cgggacatac ggagtcaact acccggccaa cggtgatttc     60

ttggccgccg ctgacggcgc gaacgacgcc agcgaccaca ttcagcagat ggccagcgcg    120

tgccgggcca cgaggttggt gctcggcggc tactcccacg gtt                      163


<210> SEQ ID NO 493
```

<211> LENGTH: 80
<212> TYPE: DNA
<213> ORGANISM: Mycobacterium tuberculosis

<400> SEQUENCE: 493
ctcaagcttg actggccacc caccggcatg accaccgaca ggcccgactg gtcgtaccac 60
tcgaacgccg gggtgtttga 80

<210> SEQ ID NO 494
<211> LENGTH: 248
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 494
ttggtgcccg gaatggcgag tcccatttan tcgctgattt gtttgaacag cgacgaaacc 60
ggtgttgaaa atgtcgcctg ggtcggggat tccctctcca agcaagagta actggcccca 120
aataaagtta ctcgtcgtct tgcaaagacc gctacccgat gccatttatg tgtttcctta 180
cgctcnnnnt tccggtgcgc catcattatc tgcacctttg cactgcacat tgagcttagc 240
agcgctcg 248

<210> SEQ ID NO 495
<211> LENGTH: 341
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 495
gaattngctt tcggcgccat cggcccagga ccgcgtgcgg gtgctcaacg acgacgtcgt 60
ccgcgggaca cacctcgatg ctgccgccat ggacgcggtc gaacgcaagc agctgatcga 120
gctacaacgc cgcgcggaac gcttccgccg cgggcgtgac cgcatcccgt tgaccgggcg 180
gatcgcngtg atcgtcgatg acggcatcgc caccggagcg acggccaagg cggcgtgcca 240
ggtcgcccgg gcgcacggtg cggacaaggt ggtgctggcg gtcccgatcg gcccagacga 300
catcgtggcg agattcgccg ggtacgccga tgaagtggtg t 341

<210> SEQ ID NO 496
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 496
taaagctttc gtcagttcat ngngcccccg gaccaacaaa agcatcggga catacggagt 60
caactacccg gccaacggtg atttcttggc cgccgctgac ggcgcnaacg acgccagcga 120
ccacattcag cagatggcca gcgcgtgccg ggccacgagg ttggtgctcg gcggctactc 180
ccagggtgcg gccgtgatcn acatcgtcac cgccgcacca ctgcccggcc tcgggttcac 240
gcagccgttg ccgcccgcag cggacgatca cntcgccgcg atcgccctgt tcgggaatcc 300
ctcgggccgc gctggcgggc tgatgagcgc cctgacccct caattcgggt ccaanaccat 360
cnacctctgc aacaacggcg acccgatttg ttcggacggc aaccggtggc gancgcacct 420

<210> SEQ ID NO 497
<211> LENGTH: 135
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 497
ccgggaggga ccatcncggg cggctncggc ttctctccgg aaggttctan ngtnnngcgt 60
ttcnacnctt cccgtcgccc tgcgaccgcc gaacattcgg ggtatggnng cancctgtna 120
gcatccnggc cgggc 135

<210> SEQ ID NO 498
<211> LENGTH: 277
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 498
ctcaagcttc cgcatcagat cgctatagaa ccggtgcgcg tccccaccga gtggctggtc 60
gccttccagc acgatcgtta ccgcgttatc ggaatcaaac tcnccgaaca cctgaccaac 120
gcgcttgatc gcctgaatcg atgcggcgtc gctggggctc atcgataccg agtgtgcttt 180
tccgaccact tccagttgcg gtacggcgag attgacaaag gcggtgaagc ccagccagag 240
caggacgatc accnccgcaa accggcggat ttgcccg 277

<210> SEQ ID NO 499
<211> LENGTH: 323
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 499
gcttggcagc ctgcggctgg gcgccctnga gctcttcgat ctggatctcc ggactcgaga 60
tgctcacttg cccggccgtg gacgtaccca ttgcggccgg gaccccagcg ccccaggtga 120
ccagcgagtt gggctgcacg ctgaccggcc cgtcggggtc gacgccggta acggtcagca 180
gctccgangt ccnnctgatc ccgaccgcag ctgccaatgc gcggctggca gccgacgtgg 240
atgtgccggg gcctagatcg cggggcagca gcgagaccgc gtcaccgacg gtcatcacct 300
tgccgagttt nggcctgccg can 323

<210> SEQ ID NO 500
<211> LENGTH: 148
<212> TYPE: DNA
<213> ORGANISM: Mycobacterium tuberculosis
<220> FEATURE:
<221> NAME/KEY: unsure
<222> LOCATION: (various positions within the sequence)

<223> OTHER INFORMATION: applicants are uncertain of bases designated
as “n”

<400> SEQUENCE: 500
gcttccggct cgtatgttgt gtggaattgt gagcggataa caattncaca caggaaacag 60
ctatgaccat gattacgcca agctatctag gtgacactat agaatactca agcttgagcc 120
atcgggctat cagctggttg atgtcccg 148

<210> SEQ ID NO 501
<211> LENGTH: 242
<212> TYPE: DNA
<213> ORGANISM: Mycobacterium tuberculosis

<400> SEQUENCE: 501
caggcatgca agcttgtcgt ctatcacatc cgaccaccaa ccgcccgacg gctcggcaga 60
acgcctccgc atatgggtcg acgaccagcg ggtcggactt ctgggctgcc agcgctcgcg 120
ccgtcgcgac aaacagcgcg gtcgaaccga cactccttgt gatgtcccac ctatcacctt 180
cggtacgcac ccaatcgacc ctacgcggct agctcagccc cgatcttcca gagctccgcc 240
cg 242

<210> SEQ ID NO 502
<211> LENGTH: 230
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 502
gctttttgag cgtcgcgcgg ggcggcttcc ccggcaattc tactagcgag aagtctggcc 60
cgatacggat ctgaccgaag tcgctgcggt gcagcccacc ctcattggcg atggcgccga 120
cnatggcgcc tggaccgatc ttgtgccgct tgccgacggc gacgcggtag gtggtcaatt 180
ccggtctacg cttgggcctt tgcggacggt cccgacgctg gtcgcggttg 230

<210> SEQ ID NO 503
<211> LENGTH: 235
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 503
cgancctgtt cgacggctac ctgaatcacc ccgatnccac cgccgcggcg ttcgacgccg 60
acagctggta ccgcaccggc gacgtcgcgg tggtcgacgg cagtgggatg caccgcatcg 120
tgggacgcga gtcggtcgac ttgatcaagt cgggtggata ccgggtcggc gccggtgaaa 180
ttgaaacggt gctgctcggg catccggacg tggcggaggc ggcagtcgtc ggggt 235

<210> SEQ ID NO 504
<211> LENGTH: 152
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 504
naagctttgt cacaccaagt gtttcnacca gncgctccat ccggcgaagt ggatactccc 60
agcaggtagc aggtcgccac cacgctggtc agtgcgcgtt cagctcgctt gcggcgctgc 120
agcagccagt ccgggaaata gctgccctgg cg 152

<210> SEQ ID NO 505
<211> LENGTH: 192
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 505
cgctggncgc cggcgctggg ctgcggtaac caattaccac aacacttttc ggtagccgaa 60
cagcggcgcg taccagcgaa atggcacagc caccgcagtc gccgacatcc cgcgaagatg 120
tggcagattt tcgtgcggtc gagccggcga aggcctagcg tcattgttgc ctggcaaggt 180
tgctgggccc gg 192

<210> SEQ ID NO 506
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 506
ctcaagcttc ttctgcccct tgccgttncg gatnacatcc cgcagcgact cggcttcggc 60
gtcgatgtcg aagttctcga tcagcttctg gatcgactcc gcgcccatgg caccggtgaa 120
gtactcgccg tagcggtcga cnagttcgcg gtagaggttt tcgtcnacna tcagctgctt 180
gggcgccanc ttggtgaaag tgctccaaat gtcctccaac cggtccagct cacgctgcgc 240
gcggtcacgg atctggcgca tctcgcgctc gccgccgtcg cgaacttgcg ccgcgcatcg 300
gccttggggc cc 312

<210> SEQ ID NO 507
<211> LENGTH: 296
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 507
gttcacacct acctactatg ccncaattcn ccgacacggg tggcatcaac acgggcgata 60
aggtggaaat cgctggggtg aacgtcgggc tggtgcgctc gctggcaatc cgcggcaacc 120
gcgtgttgat cggattctcg ttgcccggca agacaatcgg gatgcaaagc cgggcagcaa 180
ttcncnccna caccattctt ggccgtaaga acctggagat cgaaccccgc ggttcggagc 240
cgttgaaacc caacggtttc ctgccgttgg cgcanaccac tacgccatac caaatc 296

<210> SEQ ID NO 508
<211> LENGTH: 208
<212> TYPE: DNA
<213> ORGANISM: Mycobacterium tuberculosis

<400> SEQUENCE: 508
ctcaagcttt acgccgacgc cggcctacac aacaccaagg aaacgattgc ctactgccga 60
atcggggaac ggtcctcgca cacctggttc gtgttgcggg aattactcgg acaccaaaac 120
gtcaagaact acgacggcag ttggacagaa tacggctccc tggtgggcgc cccgatcgag 180
ttgggaagct gatatgtgct ctggaccc 208

<210> SEQ ID NO 509
<211> LENGTH: 278
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 509
tcccncatgg gataacgggt ttagatttcn acaacggcac cgtgtttctc aacaagccgg 60
tcatcagctg ggccggcgac aacggtatct acttcacccg ctttcgcccg tacaagaaaa 120
accactaggc caccatcgag tccaagaaca accacctggt ccgcaagtac gcgttctact 180
accgctatga caccgccgag gaacgcgccg tgctcaaccg gatgtggaag ctggtcaacg 240
accgcctcaa ctacctcacc ccgaccatca aaccgatc 278

<210> SEQ ID NO 510
<211> LENGTH: 177
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 510
ctcaagcttg ggtgttgccg atcaccggaa gccncatgat cagccacgtt tcgcgccgcc 60
cggcatacgg cggcgtaccg atctccgcgt catacacccg cgggtaatcg ccgacggtgc 120
cggttcgcga gccgaaggtg acaacgctga ttgaatcnag ttccangtcc agcgggt 177

<210> SEQ ID NO 511
<211> LENGTH: 296
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 511
tnaacagctc gcggcagccc acgacctgct gcgtcggatt gccggcggcg agatcaattc 60
caggcagctc ccggacaatg cggctctgct ggcccgcaac gaangactcg aggtcacccc 120
ggtgcccggg gtcgtggtgc acctgccgat cgcacaggtt ggcccacaac cggccgcttg 180
atgnnnngtc ggcaagcccg gcagtngcca aacccagcgt gatcangctc ggctcgcgag 240
ttcggcgaan aagtggctcg cctgatcacc taccatcggc cangatctgc gtgtca 296

<210> SEQ ID NO 512
<211> LENGTH: 223
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 512
gccanccggc ttggcgtcga ctcccgttcn gcacatcata cggtccccgg tactgtccaa 60
ctgcgccggt gcgctagcca aacgtcacga ctctcagtga tcccagttcg tgatccggcc 120
ggtggcgccg ctgcggcggg ggctnatnta cttcggactn attatctcat ccaaaggaca 180
ccgggccggt ggctggaatc ccatggtgcg atcggccaca can 223

<210> SEQ ID NO 513
<211> LENGTH: 147
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 513
ccgacctggt atcttccgat agcgcgcgtt gatatccggt ctgatctcct gcccttaacg 60
ccggatctca gcaggtcccc atgcaaagat ccgaggtgtc ccngatctag gggtcctcgt 120
cctccagatg atggagcaag tcggccc 147

<210> SEQ ID NO 514
<211> LENGTH: 149
<212> TYPE: DNA
<213> ORGANISM: Mycobacterium tuberculosis

<400> SEQUENCE: 514
ctcaagcttc ggctcaggcg gcgctgccgg taacgtcgct gaccggtgca ggtttcgaca 60
atgtggtgcc ggttcggcgg ctacgtgcca tcaagacact ggcgcaggct atcgcacccg 120
ttatcggcta caaacaaatc gcggtatgc 149

<210> SEQ ID NO 515
<211> LENGTH: 238
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 515
catcacctgn ttcatgaact ggaagcaccg cagcgcttcc ttttcggccg caacatgagc 60
cagcctctcg tcggcggtcg ggtgcaggtg ctcgggcagc tcggccgcga cagccgcctg 120
accctgaaac cagcttccat atcccgcgac gaacgacgcc agtccgctac gtaacccctc 180
cgcgactgtc catggacaac agcgcgttct ccaccgaccg ggcccgggtg tggggtgt 238

<210> SEQ ID NO 516
<211> LENGTH: 175
<212> TYPE: DNA
<213> ORGANISM: Mycobacterium tuberculosis

<400> SEQUENCE: 516
agcttagctt cccgccccgg caatagggct ccagctcatc cggtgtgacc agataggggc 60
ccagggtgat accgctgtct ttgcccttgg cctgtccgat gcgcagctgg ccctccagca 120
tctgcaggtc ccgtgcggac cagtcgttga aaatggtata gccgatgatc gaccg 175

<210> SEQ ID NO 517
<211> LENGTH: 144
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 517
ccngaacaga agcggnggtt cctaccgcgg tgtgcggccg gcgcgatatc ggccttttta 60
ctaaccgaac ccgatgtggg ctccgatccg gcgcgcatgg catcgacggc gacgccgatc 120
gatgaccgcc aggcttacca cctt 144

<210> SEQ ID NO 518
<211> LENGTH: 174
<212> TYPE: DNA
<213> ORGANISM: Mycobacterium tuberculosis

<400> SEQUENCE: 518
ctcaagcttg cgcgactcga caagcattct tgacagttgt tttggctcgg catggttagc 60
caaggttctg cggtcccacc agatcatctt ggtccggtag cgctcgtccg ggtatgctgc 120
cgccgggatt ctcgctgcta ttactccccc cgaagaacgc caccggtcca gcgc 174

<210> SEQ ID NO 519
<211> LENGTH: 187
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 519
gcnaggcggt atagcttccc gtcgtaccgg cgaccgccag ccgagaagct cgttttccca 60
gtgttgctgg ggattctcac gctgctgctg agtgcgtgcc agaccgcttc cgcttcgggt 120
tacaacgagc cgcggggcta cgatcgtgcg acgctgaagt tggtgttctc catggacttg 180
gggatgt 187

<210> SEQ ID NO 520
<211> LENGTH: 215
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 520
gtgtggaacc gtgagcggat aacaatttca cacaggaaac agctntgacc ttgattacgc 60
caagctattt aggtgaggct atattaatac tcaagattgc ggtcgagcac atcggcccaa 120
gaaccgccga aggcacggcg gaacgcctgc ggcacatggg gcgacgacca gcgggtcgga 180
cttctgggct gtccagccgg atcgcgccgt cgcga 215

<210> SEQ ID NO 521
<211> LENGTH: 406
<212> TYPE: DNA
<213> ORGANISM: Mycobacterium tuberculosis

<400> SEQUENCE: 521
cactgtcagt acatatgcgc cgctcctcct catcgctgcg ctcggcatcg tcgccggcgg 60
tcatggcgtc accctaccca agccgaacgc gaaacgagaa cgtgttccat tattagggtg 120
tgagcaccaa taccagattg ctcaccagga actcacgcag caccgggacg gatgtcagcc 180
accacgccca tctggggtgg tagcggggaa atacggctaa cgcggctccg gtgccggcag 240
cccagcgcag accctcggcg gcggacacgg caaacaacga cgacccatag ttgttctttg 300
ccggatggcc gtgtttgcgg acatatcggg cggcggcgcg ggcgccgccg aggtagtggc 360
tgaggcccat ctcgtgcccg ccgaatggcc ccagccaaac cgtgta 406

<210> SEQ ID NO 522
<211> LENGTH: 180
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 522
ctcaagcttt tacggtgatc gcgcatcacc tggttcatga actggaagca gcgcagcgct 60
tccttttcgg ccgcaacatg agccancctc tcgtcggcgg tcgggtgcag gtgctcgggc 120
agctcggccg cgacagccgc ctgaccctga aaccagcttc catatcccgc gacnaacgac 180

<210> SEQ ID NO 523
<211> LENGTH: 69
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 523
ctcagaagcc gctagctggt agagtcgctg accggtgcac gtggcgncaa tgtgcgctgc 60
cggttcgcg 69

<210> SEQ ID NO 524
<211> LENGTH: 168
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 524
ctcaagcttg cgctcatcaa gcgcgaacag cagggcggtc ggctggtcgc catgacgggt 60
gacgggacca atgacgcacc cgcgctcgcg caagccgatg tcggggtggc natnaatacc 120
ggcacccagg cggcccggga agccggcaac atggtcnatc tccactcc 168

<210> SEQ ID NO 525
<211> LENGTH: 83
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 525
acttctattt cgactggtgt gctgtggcgc gatccgactg ccggcgtggt caaggccggc 60
cagttgtggg atnccacagg cac 83

<210> SEQ ID NO 526
<211> LENGTH: 173
<212> TYPE: DNA
<213> ORGANISM: Mycobacterium tuberculosis

<400> SEQUENCE: 526
gcttgtcgta ttccgtggca ctgtcagaca tatgcgccgc tcctcctcat cgctgcgctc 60
ggcatcgtcg ccggcggtca tggcgtcacc ctacccaagc cgaacgcgaa acgagaacgt 120
gttccattat tagggtgtga gcaccaatac cagattgctc accaggaact cac 173

<210> SEQ ID NO 527
<211> LENGTH: 38
<212> TYPE: DNA
<213> ORGANISM: Mycobacterium tuberculosis

<400> SEQUENCE: 527
cgatattcgt cggccgcgtt gtctcgactg ggtcgcgt 38

<210> SEQ ID NO 528
<211> LENGTH: 136
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 528
gacctcggcc accaagccgg acgcgaccgt cgaggtggcg atccggcttg gcgtcgaccc 60
gcgtaaggca gaccacatgg tccgcggcac ggccancctg ccacacggca ctggtaagac 120
tgcccgcgtc gcggcn 136

<210> SEQ ID NO 529
<211> LENGTH: 114
<212> TYPE: DNA
<213> ORGANISM: Mycobacterium tuberculosis

<400> SEQUENCE: 529
ccggaagtct aggggacgac ctactcagcg caaaatgtcg ctaatgtgag tccgccccac 60
cagggcagat caacccatgt cgatgatgac ctacccggat accggattgg cggt 114

<210> SEQ ID NO 530
<211> LENGTH: 119
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 530
agcttcagtt cctccacgac gcgttcccaa atgaatttcc cgatcccaca atctcggttc 60
agatacaggt cgccataccc cttacttcgg naacgctggg cggattggcc ctgccgctg 119

<210> SEQ ID NO 531
<211> LENGTH: 99
<212> TYPE: DNA
<213> ORGANISM: Mycobacterium tuberculosis

<400> SEQUENCE: 531
ccgcctacgg gtcgaacatg catcccgaga ccgatgctcg agcgcgcacc ccactcgccg 60
atggccggaa ccggctggtt acccgggtgg cggctgacc 99

<210> SEQ ID NO 532
<211> LENGTH: 308
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 532
gcggctggtt acgactccct gtttgtgatg gaccacttct accaactgcc catgttgggg 60
acgcccgacc agccgatgct ggaggcctac acggcccttg gtgcgctggc cacggcgacc 120
gagcggctgc aactgggcgc nttggtnacc ggcaatacct accgcagccc gaccctgctg 180
gcaaagatca tcaccacgct cgacgtggtt agcgccggtc gagcgatcct cggcattgga 240
gccggttggt ttgagctgga acaccgccag ctcggcttcg agttcggcac tttcagtgac 300 cggttcan 308

<210> SEQ ID NO 533
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 533
gcctttccgc acaatctgta ccccaggacc ntctaaaaaa tcgaatacga cggcgtcgcc 60
gactttccgc ggtacccgct caactttgtg tcgaccctca acgccattgc cggcacctac 120
tacgtgcact ccaactactt catcctgacg ccggaacaaa ttgacgcagc ggttccgctg 180
accantnntg tcggtcccac gatgacccag tactacatca ttcgcacgga gaacctgccg 240
ctgctagagc cactgcgatc ggtgccgatc gtggggaacc cactggcgaa cctggttcaa 300
ccaaacttga aggtgattgt taacctgg 328

<210> SEQ ID NO 534
<211> LENGTH: 75
<212> TYPE: DNA
<213> ORGANISM: Mycobacterium tuberculosis

<400> SEQUENCE: 534
gcagaccaac aagatgcatc gggatcatac gccgtcaact acccggccaa cggtgatttc 60
ttggccgccg cccac 75

<210> SEQ ID NO 535
<211> LENGTH: 319
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 535
ctcaagcttg ccaaagagac ctcgtccacc aagcnggacg cgaccgtcna ggtggcgatc 60
cggcttggcg tccacccgcg taaggcanac canatggttc gcggcacggt caacctgcca 120
cacggcactg gtaanactgc ccgcgtcgcg gtattcgcgg ttggtgaaaa ggccgatgct 180
gccgttgccg cgggggcgga tgttgtcggg agtgacaatc tgatcganag gattcagggc 240
ggctggctgg aattcgatgc cgcgatcgcg acaccggatc agatggccaa agtcggtcnc 300
atcgctcggg tgctgggtc 319

<210> SEQ ID NO 536
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 536
ccacggcgtg gatcaaggta ccggccggga tgttgcgcaa tggcaggttg ttgcccggct 60
tgatgtcggc gttagcgccg gattccacca catccccttg cgaaagtccg ttgggtgcaa 120
tgatgtagcg cttctcccca tcgagatagt ggagcaacgc aatccgtgcg gtacggttcg 180
ggtcntactc gatgtgcgcg accttggcgt tgacaccatc tttgtcattg cggcgaaagt 240
cgatcatccg gtaagcgcgc ttatgaccgc cgcctttgtg ccgggtggta atccggccat 300
gcgcgttgcg tc 312

<210> SEQ ID NO 537
<211> LENGTH: 105
<212> TYPE: DNA
<213> ORGANISM: Mycobacterium tuberculosis

<400> SEQUENCE: 537
ggcggctgcg tcggcgagat gatcgcccgg tgccaccccg atccgtgcct cggtcagcgc 60
caacgtgctt tccggtccgg cgaccaccat gtcgcatgcg ccgac 105

<210> SEQ ID NO 538
<211> LENGTH: 144
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 538
gcaatcgcct tggcggtcgc cgggttgtca ccggtgatca tcncggngcg gatgctcatn 60
cggcgcattt cgtcnaatcg ttcccgtatg cccaccttga cgatgtcctt catatggacc 120
acgccgatgg cccncgcgct nctg 144

<210> SEQ ID NO 539
<211> LENGTH: 431
<212> TYPE: DNA
<213> ORGANISM: Mycobacterium tuberculosis

<400> SEQUENCE: 539
ccggctcgta tgttgtgtgg aattgtgagc ggataacaat ttcacacagg aaacagctat 60
gaccatgatt acgccaagct atttaggtga cactatagaa tactcaagct tccacatcgg 120
tatgccaaag cattgcgccg ctatcgattt cgcgctggca tcgccaaggt ggacttcttg 180
ctcagcgacg agatcccgtg gtcggatccg cggctgcggc gggctgcgac cctgcatctc 240
ggcggcaccc gtgaccagat ggcgcgcgcc gaggcagacg tcgcggcggg acgccacgcc 300
gactggccga tggtgctggc cgcgtgtccg cacgtcgccg accccggccg catcgacgaa 360
accggccgcc gtccgttctg gacctatgcc cacgtgccgt cggggtccac gctcgacgcg 420
accgagaccg t 431

<210> SEQ ID NO 540
<211> LENGTH: 462
<212> TYPE: DNA
<213> ORGANISM: Mycobacterium tuberculosis

<400> SEQUENCE: 540
cgcgtccacc gcagcgtgag attggtggcg ccattcgtcg tggtgtagct gctgttggcg 60
gcgtcgccgt attgtgcggg ccagccttgt gcgggggccg cttctaccca cgagtcggca 120
cttccgcaac cgcccagctc gaccgcgatt acggcggccg caacggccgc cggaaggcgt 180
ctcgcaagcg ccttatcctt tcgcaggttc ccagatcctt ccgctacgtg ggtcgctcat 240
cggcgggccc ggccgaatga gtacaggtga gggtaaccgc tacaaatgaa gttggtcagt 300
gctggccaac tgtgtaatgg ttgcccggct cgggtcacca cgtacattct ggcaaggcgg 360
gcgagattcg gttcctcgcg tccttggccg gtggcggttc ccggttgtcc gtgggcgtgt 420
cgtgtacgtg gtgtaagtgt cgtgaactcc tcagtttggg ct 462

<210> SEQ ID NO 541
<211> LENGTH: 307
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 541
ctcaagcttg cgctggatct ggcggctgag cctgttcttg ggcaacatgc cgagggatcg 60
ccttttccac cacgcggtcg gggtggcgtt gcattagctc accgatggtg cgcttgtgca 120
ggccgccggg ataccccgag tgccggtaaa ccatcttgtg ctgcagtttg tcgccgctga 180
tggcgacctt gtcggcgttg atcacnatga cnaagtcacc gccatcgaca ttgggggcga 240
acgtcggctt gtgcttgccg cgcagcaggt tggccgccgc gacggcaagg cggccaanca 300
ccacgtc 307

<210> SEQ ID NO 542

<211> LENGTH: 333
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 542
tttgggatgg gcaaaaaggc gaagcnccgc gtggccacga acgccgggag ggacaatctc 60
gggcggctag ggcttctcgc gggaaggccc gaacgtacgg cgtttcaaca cgtcgcgtcg 120
ccctccgacc gcgaacattc ggggatggca gcaacctggt agcaccctgg ccgggcgatg 180
atctgcagcg tcgccgcggg tagtcgccgc ccgggcggct acagtctgaa acgcgatgac 240
catcgatgtg tggatgcagc atccgacgca acggttccta cacggcgata tgttcgcctc 300
gctgcgccgg tggaccggtg ggtctatccc gga 333

<210> SEQ ID NO 543
<211> LENGTH: 234
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 543
ctcaagcttc gtcataagac catggtgcgc tttctttcac ccgtccanag tcgggggcat 60
ccgcaccggc tcgcatcgca tcatcctccc acgacgggcc gctcatcagc ttgggccatt 120
tcaatgtact tgataccccg cgctgcgggt aggccactgc nacaattcaa acacggtgtc 180
acacggtgaa tantgtcnan atgggctctg atcaaccgtc ncaaacccgg tttc 234

<210> SEQ ID NO 544
<211> LENGTH: 440
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 544
gaattctgcg tgcaccgcta tgggttgcag cagcggctgg cgccgcacac cccactggcc 60
cgggtgtttt cgccccgaac ccggatcatg gtgagcgaaa aggagattcg cctgttcgat 120
gctgggattc gccaccgcga ggccatcgac cgattactcg ccaccggggt gcgagaggtg 180
ccgcagtccc gctccgtcga cgtctccgac gatccatccg gcttccgccg tcgggtggcg 240
gtagccgtcg atgaaatcgc tgccggccgc taccacaagg tgattctgtc ccgttgtgtc 300
gaagtgcctt tcgcgatcga ctttccgttg acctaccggc tggggcgtct gcacaacacc 360
ccggtgaggt cgtttttgtt gcagttgggc ggaatccgtg ctctgggtta cagccccgaa 420
ctcgtcncgg cggtgcgcgc 440

<210> SEQ ID NO 545
<211> LENGTH: 425
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 545
gcagttggga atcgctctgc agcaaaccan tattctgcgc gacgttcgag aggactnttt 60
gaatggacgg atctacctgc cgcgcgacga gctggaccga ttaggcgtac ncctccgcct 120
ggacgactcc ggggcactcg atgaccccga cggacggctc gcggcactgc tgcggttcan 180
tgccnaccgc gccgcanact ggtattcgct gggactgcgg ctgattccac acctcgaccg 240
ccgcagcgct gcctgctgtg cggccatgtc tggcatctac cgccgtcngc tcgccttgat 300
cagaccatcg ccggcggtcg tctaccatcg gcgaatctct ctgttcggga ctgaanaang 360
cccaagtggc ggcggcagca ctggnctctt cggtaacctg cngaccgccc attggaccgc 420
taccg 425

<210> SEQ ID NO 546
<211> LENGTH: 401
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 546
ttgatctgga cgtctgagac ggtgatcggn ccgaacctga attgtccggt aatgcccagc 60
gcagaaagca nggtggtggc cggggcggtg aanccggcgt cggcggcacc gtcgaagtcg 120
atgtggattg ccggaatggg gatgtccggc acggcgaagc cgtagttcgc ttgtcccgtg 180
aggcccangt ggatgggggg aaggatcgtg gtgtccggga tgataatggg gccgatgccg 240
ccggttgaag tccagtggat cgggaattcg ggaatcgtga tgccgacgtt caggccgaac 300
aggccctcca agttgcctcg ccacnagatg ccgttgctga agttgcccga catgagggcg 360
ccggtgtcca cattgcccga attggcgacg ccggtgttgg c 401

<210> SEQ ID NO 547
<211> LENGTH: 391
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 547
cacgtaggcg ccgtccataa atnactccgc cgcgcttcgc acatcctcgt ancgatcctt 60
ggcgagcagg tcaaccgggc gctgcccgtc naggagccgg tttttggcgt gcagccactg 120
gccgacacct cggggggtaa gcgaatccga gagcaggagg acnaggtcac gaanctgcgc 180
cagccggtcg taccgctcag ggcggatgtc gccggtccgc cacccgcgta ccgcccgatc 240
ggacacctgt atgaccgcgg cgacntcgac ctgggtgacg ccgaagggtt tcagggcatc 300
nacnatctcg ctggcctcga ccgcccggtc cagggtgacc gccatcgtgg ttcctccgca 360
acttccggtt ctactaccgt aaacgctacc g 391

<210> SEQ ID NO 548
<211> LENGTH: 369
<212> TYPE: DNA

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 548
cggggaacgg tcctcgcaca cctggttcgt gttgcgggaa ttactcggac ancaaaacgt 60
caagaactac gacggcagtn ggacagaana cggctccctg gtgggcgccc cgatcgagtt 120
gggaagctga tatgtgctct ggacccaagc aaggactgac attgccggcc agcgtcgacc 180
tggaaaaaga aacggtgatc accggccgcg tagtggacgg tgacggccag gccgtgggcg 240
gcgcgtttcg tgcggctgct gggacncctc cgacgagttc accgccggga ggtcgtcgcg 300
tcggccaccg ggcgaatttc cggttcttcg ccgcgccccg ggatcctggg accgcnggcg 360
cgcgctgtt 369

<210> SEQ ID NO 549
<211> LENGTH: 85
<212> TYPE: DNA
<213> ORGANISM: Mycobacterium tuberculosis

<400> SEQUENCE: 549
ctcaagcttt gtccgacaag cgttcccggg cggtcagcaa gcgaacgtcg gttggcccac 60
tgcgggtcga tattgccgcc aggga 85

<210> SEQ ID NO 550
<211> LENGTH: 101
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 550
cgtcagcacg gcgacgtcgc gntacgccga gcagttacac aatcgctctg cagcaaacca 60
atattctgcg cgacgttcga gaggacttct tgattggact g 101

<210> SEQ ID NO 551
<211> LENGTH: 458
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 551
ctgcatccgg ctcgtatgtt gtgtggaatt gtgagcggat aacaatttca cacaggaaac 60
agctatgacc atgattacgc caagctattt aggtgacact atagaatact caagcttcgc 120
gcagcggcgg gttgacccgg ttcacgccgt catagctggc caatctggca tcgtcgatca 180
ncatgtggtg gggggtgacc tcggcggtga tcgaaatacc ctggtcctta tcccatttca 240
ggatttcgac ggtgcccgcg gccgacgcgt gacagatgtg cacccgggcg ccggcgtcac 300
gggccagcaa ggcgtcgcgg gcgacgatcg attcctcggc ggcccgcggc catcccgcca 360
ggcccagccg cgccgccatg ggtccctcgt gcgcgacggc gccgaccgtc agccggggct 420
cctcggcgtg ctgggcgatc agcacgccca aaccggtg 458

<210> SEQ ID NO 552
<211> LENGTH: 463
<212> TYPE: DNA
<213> ORGANISM: Mycobacterium tuberculosis

<400> SEQUENCE: 552
ccgacgcgca ctacgtgctg gtgtccaccc gcgacccgca ccggcacgag ctacgcagct 60
accgcatcgt cgatggcgct gtcaccgagg aacctgtcaa tgtcgtcgag cagtactgaa 120
ccgttccgag aaaggccagc atgaacgtca ccgtatccat tccgaccatc ctgcggcccc 180
acaccggcgg ccagaagagt gtctcggcca gcggcgatac cttgggtgcc gtcatcagcg 240
acctggaggc cagctattcg ggcatttccg agcgcctgat ggacccgtct tccccaggta 300
agttgcaccg cttcgtgaac atctacgtca acgacgaaga cgtgcggttc tccggcggct 360
tggccaccgc gatcgctgac ggtgactcgg tcaccatcct ccccgccgtg gccggtgggt 420
gagcggacac atgacacgat acgactcact gttgcatgcc ttg 463

<210> SEQ ID NO 553
<211> LENGTH: 453
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 553
tgcttccggc tcgtatgttg tgtggaattg tgagcggata acaatttcac acaggaaaca 60
gctatgacca tgattacgcc aagctattta ggtgacacta tagaatactc aagcttgccg 120
ggagggtgca tggccgactc ggatttaccc accaaggggc gccaacgcgg tgtccgcgcc 180
gtcgagctga acgttgctgc ccgcctggag aacctggcgc tgctgcgcac cctggtcggc 240
gccatcggca ccttcgagga cctggatttc gacgccgtgg ccgacctgag gttggcggtg 300
gacgangtgt gcacccggtt gattcgctcg gccttgccgg atgccaccct gcgcctggtg 360
gtcgatccgc gaaaagacga agttgtggtg gaggcttctg ctgcctgcga cacccacgac 420
gtggtggcac gggcagcttt agctggcatt cct 453

<210> SEQ ID NO 554
<211> LENGTH: 466
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 554
ggaaacaccg ncgccgtcgt ggccaccaac accgcgacca gcaccgtgac ccggaccggg 60
gtgccgcgcg aaccggtctt ggccaattgc cgcggcacca agccgtcgcg cgccatggcg 120
aacagcacgc ggcattgccc gagcatcaac accatcacca ccgtggtaag cccggccagc 180
gcgccgacgg agatgatgcc gctggcccag tacaccccgt tggcctggaa cgcggtggcc 240
agatttgccg gcccgcggcc cggtacggtc cgcagttggg tgtatggaac catgcccgac 300
agcaccaccg ataccgcgac gtagagaagg gtcacgaccc ccagcgacgc gagaatccct 360
cgagggacgt ctcgttgagg acgcttggtc tcctcggcca tggtggccac gatgtcaaac 420
ccgataaacg cgaagaacac gatcgatgcc cggccagcac gccgta 466

<210> SEQ ID NO 555
<211> LENGTH: 466
<212> TYPE: DNA
<213> ORGANISM: Mycobacterium tuberculosis

<400> SEQUENCE: 555
cctgcttccg gctcgtatgt tgtgtggaat tgtgagcgga taacaatttc acacaggaaa 60
cagctatgac catgattacg ccaagctatt taggtgacac tatagaatac tcaagcttgt 120
cctcgggcgt ggcctcggcc aagaaatcgt cgacgccggc ctcctgtgca atcgccttgg 180
cggtcgccgg gttgtcaccg gtgatcatca cggtgcggat gctcattcgg cgcatttcgt 240
cgaagcgttc ccgtatgccc accttgacga tgtccttcag atggacgacg ccgatggccc 300
gcgcgctgct gttatcggtc cattccgcaa cgactagggg tgtccccccg ccggagctga 360
tgccgtcgac aatggcaccc acctcctcag tggggtggcc accgtgatcg caaaaccact 420
tcatcaccgc agccgcggca ccttgcggat ccgaacggat gcgctc 466

<210> SEQ ID NO 556
<211> LENGTH: 467
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 556
ttcgttcgat ggcgccgccc cggctacggt ttgacctgtg ggtgtcgaat tggggtcaaa 60
ttccgaggtc ggcgcgctaa gagtggtcat cctgcaccgc ccgggggccg aactgcgccg 120
gctcacaccg cgcaacaccg accagctgct gttcgacggc ctgccctggg tatcccgcgc 180
gcatgacgag cacgacgaat tcgccgagct gctggcttcc cgcggtgcgg aagtgctgtt 240
gctgtcggac ctgttgactg aggcactaca tcacagcggg gccgcccgca tgcaggggat 300
cgccgctgcc gtcgacgcac cgcggctggg actgccgctg gcgcaagaac tttcggccta 360
cctgcgtatc tcgacccaag cangttggcg catgtgctga cgccggcatg acttcaacga 420
actcccntcc gacacgccga acgaagtgtc gttggtgttg cgtatgc 467

<210> SEQ ID NO 557
<211> LENGTH: 142
<212> TYPE: DNA
<213> ORGANISM: Mycobacterium tuberculosis

<400> SEQUENCE: 557
gcggcgagtg tggtgggtgc cgaacacgaa tccaacgacg cactggcgga gagataccac 60
ttgctgtact ggaagcacgt gctgatgatc tcccgtggaa tgtgcctcgc cgccgtctat 120
cgaaaacagt gagcatgctg cg 142

<210> SEQ ID NO 558
<211> LENGTH: 217
<212> TYPE: DNA
<213> ORGANISM: Mycobacterium tuberculosis

<400> SEQUENCE: 558
caaccgcgct cggcgcgtct gggccttccg ccggctccgc cgacaattct atctctggat 60
cagcggggct ctccgggccg gcctccgcga actcaacagg ccgcgccttc cggccgaaac 120
attccctagc catatatgat cgcacctcga tacacgatct ggcggcaaca ccgcaaagcg 180
tccgacgggc ccaacctccg caattcaggt atccggg 217

<210> SEQ ID NO 559
<211> LENGTH: 147
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 559
gaaggtcggc gaaggtgtgg ctggntgccg atcacgaatc caatgatgca gtggtcggaa 60
gatattagcc acttgctgtt ctggagacag gtgctgatga tctcccgtgg aatgtccctc 120
gactccgtct atcgaaatct gtgaaca 147

<210> SEQ ID NO 560
<211> LENGTH: 177
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 560
tcctgcgctc tgggccattc tcgggtctgc cgacaattct atctctggat ctgtggggct 60
ctcttggccg gcctcngcga tctcttcang gcgcgccttc cggccgaaac attccctatc 120
catatatgat cgcacctcta tacaccgttt ggcggcaaca ccgcaaagtg tctgtcg 177

<210> SEQ ID NO 561
<211> LENGTH: 128
<212> TYPE: DNA
<213> ORGANISM: Mycobacterium tuberculosis

<400> SEQUENCE: 561
agctttacgc tggcgtatca gcgttggggc cgctgccatt tcggtcgccc aacgcgttgc 60
cagctccctg cgctgtcagg gcttgcgcgc caaactggcc accgcaacaa acttggctga 120
gcttgatc 128

<210> SEQ ID NO 562
<211> LENGTH: 142
<212> TYPE: DNA
<213> ORGANISM: Mycobacterium tuberculosis

<400> SEQUENCE: 562
ctctatctgg cgtcacattc gcaatcttta gattgcagat atcgataaaa tcacccgcgc 60
gacaagaccg ccatgtcatc ctttcgatgt tatttcgccg gcctggggaa agcgcaacga 120
cgttgcctac acgttccgcc gt 142

<210> SEQ ID NO 563
<211> LENGTH: 406
<212> TYPE: DNA
<213> ORGANISM: Mycobacterium tuberculosis
<220> FEATURE:
<221> NAME/KEY: unsure
<222> LOCATION: (various positions within the sequence)

<223> OTHER INFORMATION: applicants are uncertain of bases designated as “n”

<400> SEQUENCE: 563
agctttncct tgcatctgca ccccgatcca cgtcagccac gtcggcgttc tccaccaaga 60
agttgcgggc attctccttg ccctggccga gctgctcgcc ctcgtaggtg aaccaggcac 120
ccgacttgcg gatgaggccc tgatccacac ccatgtcgat cagcgagccc tccctgctga 180
ttcccttgcc gtagaggatg tcgaactcgg cctgcttgaa ggggggcgaa cagttgtgca 240
cgacaacccc ttcggcgacg agggtgtgca gttcctcgac ctcgaggtcg aacgttcgtg 300
cccgccgcgt tggcagcact tctcggatca cggaatagcg ganttcttcc gccagcatgt 360
cgtgcaggaa tttgtcatcc agggcatccg cgagcgcctg cacgcg 406

<210> SEQ ID NO 564
<211> LENGTH: 311
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 564
actgtcnagg gaatgcttcg cagcatctac ctgcagtcgc ttgtgcataa gcggacggcc 60
cnacctgttc gtgttccggg acaccagacg cgggagcacc ggcagtacgg cgaaaggttt 120
gagcggaagg agttgcgcaa atcggggcgc cccaacaccc gtccgcaaga cgcggtcaac 180
gacctgtttc aggcgatcag ggtcaccgac tcacctgcac tgagaacaag cgatctgctg 240
atctgccaga agatggacat gaatgtccac ggcaagcctg atggcctgcc gctcttccgg 300
gaatgtttgg c 311

<210> SEQ ID NO 565
<211> LENGTH: 310
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 565
tgaattatga tcccgacaca actgcatcan tttagccgcg tcgngatgct atccgccgac 60
ggtttgganc nggtccgtgt cgttcgtgtt gatctcaccc gaagttgtgt ccgccgccgc 120
cggggatcta gcgaacgtgg gatcgacaat cagcgccgcc aacaaggcgg cagcggctgc 180
gaccacgcag gtgctggccg cgggcgccga tnaggtgtca gcgcgcatcg cggcgctgtt 240
tggtatgtac ggcctgnaat atccggcgat cagtgcgcaa gttgccgcgt atcaccanca 300
gtccgtgcag 310

<210> SEQ ID NO 566
<211> LENGTH: 326
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 566
aacggggacc ncaagaaacc attcaanaac gaggggtcgt caccaacgtc gaaaccgacg 60
gttgccagcc ggcccacgat attgcgtgct cgagggtccg ctgtaccctc accgaacgtg 120
agtcccacac cgcggaggcg ggcgactctg gcgtcgttag cagccgagct caaggtgtcc 180
cgcaccactg tctcgaatgc ttttaaccga ccggatcagc tctccgccga tctacgtgaa 240
cgagtgcttg ccacggccaa gcgactgggc tatgccggac cggatccggt ggcgcgatcg 300
ttgcggaccc gcaaagccgg tgcggt 326

<210> SEQ ID NO 567
<211> LENGTH: 374
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 567
agctttggag ccncnccgan ccnccggtac gccccgccac cgccgtaccc ggcacccgac 60
ccctttgagc cgttcgccgt ggccgcggtg ganctggccg acgagggact gatcgtgctg 120
ggcaaagtgg tcgatggcac gctggccgcc gatctgaagg tcggcatgga gatggagctg 180
acgaccatgc cgctgttcgc cgacnacgac ggtgtgcagc gcatcgtcta cgcgtggcgg 240
atcccatcgc gcgccggcga cnatgcanag cgcancgatg ctgaggagcg gcgccgatga 300
ggatgagcgc gccggaaccc gtttacntcc tgggtgccgg tatgcacccg tgggggaaat 360
ggggtaatga cttc 374

<210> SEQ ID NO 568
<211> LENGTH: 422
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 568
ttctcncatc gttcgtactn ngatgggacg ctgctgcccg aggcgatcct ggccaaccgg 60
ctctcgccgg cgctgacctt cggcggggcg aacctgaact tctttccgat gggcgcttgg 120
gccaaacgta ccggggctat cttcattcgg cgtcagacga aagatattcc cgtctaccgc 180
ttcgtattac gtgcttacgc cgcgcagctg gtgcaaaacc atgtcaacct cacctggtcg 240
atcgaagggg gtcggaccag aacgggcaag ctacggccac cggtgttcgg gatcctgcgt 300
tacatcaccg atgcggtcga cgaaatcgac ggtcccgaag tgtatttggt gccgacctcg 360
atcgtgtacg aacagctgca cgaagtggaa gccatgacca ccgaagccta tggcgccgtg 420
aa 422

<210> SEQ ID NO 569
<211> LENGTH: 300
<212> TYPE: DNA
<213> ORGANISM: Mycobacterium tuberculosis

<400> SEQUENCE: 569
ttcttccggg taccgctgat cggcggcacc atcacgcacc cggtgcaggg cgaggcggcc 60
gccggtgtgg tgttgctacg gccggccagc ccgggtaccg gtgtgatcgc cggtggtgcg 120
gcccgcgcgg tgctggaatg tgcgggggtg cacgacatct tggccaagtc gctgggcagt 180
gacaacgcga tcaatgtggt gcacgccacc gtggccgcgc tcaagctgct gcaccgtccg 240
gaggaggtgg cggcgcgccg cggtttgcca atagaagacg tccccccggc cgggatgctg 300

<210> SEQ ID NO 570
<211> LENGTH: 343
<212> TYPE: DNA
<213> ORGANISM: Mycobacterium tuberculosis

<400> SEQUENCE: 570
gtcgaaagtg accatctcta ccttgagtgc cataccgccc gaccctatgc ctcggatagc 60
tcggcggaaa gaaacgcttg cagtgccgcc gaataggcgg ctacgtcgtg agcgcccatc 120
aactctcgcg cggagtgcat cgccagctgg gcggcgccga cgtcgaccgt ggggattccg 180
gtgcgcgccg cggccaacgg cccgatcgtc gacccgcacg gcagatcggc gcgatgttcg 240
taacgctgca taggcactcc cgcgcgctgg caggccagtt gcgaaacgcc cccgccgggt 300
gccttccgtc ggttggcttt accgcaaatt tggggttgcc cct 343

<210> SEQ ID NO 571
<211> LENGTH: 220
<212> TYPE: DNA
<213> ORGANISM: Mycobacterium tuberculosis

<400> SEQUENCE: 571
aaagccacgg aaacgattgc ctactgccga atcggggaac ggtcctcgca cacctggttc 60
gtgttgcggg aattactcgg acaccaaaac gtcaagaact acgacggcag ttggacagaa 120
tacggctccc tggtgggcgc cccgatcgag ttgggaaact gatatgtgct ctggacccaa 180
gcaaggactg acattgccgg ccagcgtcta cctggaaaaa 220

<210> SEQ ID NO 572
<211> LENGTH: 254
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 572
tttcgccacc gcnaggtcgt gcgcgttcca gaaaagcgtg gtttcgccgg gcgcgaggat 60
tcgacggtcc aactgaccag ccggtcccgc cacccgttag gcaggatcgc ggtgtctata 120
tgttcgccct cggcataaac gccattgctg cggtgaaaat cggacatctc gccgattgcc 180
acgtctacat gatccgcttt gtcccgcgcc gggtcgttga caaacgcgat gtcngcctcc 240
tgggaagcgg tggc 254

<210> SEQ ID NO 573
<211> LENGTH: 329
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 573
tcgccaagtg gattcgtgct caccnacgag atccgtggtc ggatccgcng ctgcggcggg 60
ctgcgaccct gcatctcggc ggcacccgtg accaaatggc gcgcgccgaa gcagacgtct 120
cggcgggacg ccacgccgac tggccgatgg tgctggccgc gtgtccgcnc gtcnccgacc 180
ccggccgcat cnaccaaacc ggccgccgtc cgttctggac ctatcccacg tgccntcggg 240
gtccacgctc gacgcgaccg anaacgtaac cagcgtcctc gancggttcg cccccggctt 300
ccgtgacatc gtggtggcgg ccgcgccgt 329

<210> SEQ ID NO 574
<211> LENGTH: 297
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 574
gtaccgtcac catgatcgcc cccatcggca tcggtgagct gatagatccc agccggtttc 60
gccaaccccg gagcgatctt ggcgcgctgc tngtngtcnc tganacntag ccaccaacag 120
agcccggtgt gcgacaagan gactgatcgg atctctccgg acacntcgag ggggtcntca 180
ggagnccggg cgccaccccg aggtaagcct ccgcccagcc tcacaccgcg accgggtatc 240
ncaagtcgcg caataanccc accacctcct cggaccccac gttgtatgcg gctgggt 297

<210> SEQ ID NO 575
<211> LENGTH: 401
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 575
atactcaagc ttagacctca ctgatgtggc gggacgcggg agataaccgc ggttcgagcc 60
gttcaacagt ggtggttccc acaccagttg tttgcctttg cgaagtaaag cgattcgatt 120
tgctcgaaaa gagggctggc tgctcgtgag ggacatccat ggccgatacc tcagcgatct 180
caacggtcaa gcgactgcat gtttggcgca aggtatcgct aagcataggt tcgtgacgga 240
tttgacagca agagctttcc aaagattgct gtccacatan tgattcgcat ctctacacct 300
cttcgccggt gctgtcaaga gccattcgaa tcagttatct cgctcgtgct tggaanaaat 360
tttcccagcc tgcgttggac aaaccgcgtc gccaaagcgg t 401

<210> SEQ ID NO 576
<211> LENGTH: 453
<212> TYPE: DNA
<213> ORGANISM: Mycobacterium tuberculosis

<400> SEQUENCE: 576
agcttcccga gaaacagtgc attccctaag cagcccgttg tcacgccgat gagtgaagag 60
tgcacgcaat cgccggaatc cggcaaagcc ctgcacaagc gaaatcaacc cggaggctga 120
caaggcaacg tcggtgatcc gtaccgcctg gttggacaaa cggcagaagg cggcctcgtc 180
cggtccatct acgccgagca cactggtgat agcgcgcatc ggcatcggtg cggccacggt 240
ggagacgacg tccgcgggcg tctgggtcag taacccgccg accagttctc gggcaagctg 300
gtcgaccatc gggcgccacg tctccaacgc gccacgcgcc atacctggtg ccagttgctt 360
gcgcatccgg gtgtgcgccg gcggatcgga cgtcgcagaa acgcagccac cccgtgagaa 420
gtgacccacg gcgctggaca cgtgtctggt tac 453

<210> SEQ ID NO 577
<211> LENGTH: 474
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 577
cggccgggat gtgcgcaatg gcaggttgtc gcccggcttg atgtcggcgt tagcgccgga 60
ttccaccaca tccccttgcg aaagtccgtt gggtgcaatg atgtancgct tctccccatc 120
gagatagtgg agcaacgcaa tccgtgcggt acggttcggg tcgtactcga tgtgcgcgac 180
cttggcgttg acaccatctt tgtcatggcg gcgaaagtcg atcatccggt aagcgcgctt 240
atgaccgccg cctttgtgcc nggtggtaat ccggccatgc gcgttgcgtc caccgcgacc 300
gtgcagcggg cgcaccagcg acntctccgg ggttgaccgg gtgatctcgg cgaaatcaga 360
tacgctggcg ccgcgacgac caggcgtcgt gggcttgtac ttgcgaattg ccatggtcta 420
atcaggtctt tctctcacct ctcgtcgccg ggctagggcg cattgcctgc tcct 474

<210> SEQ ID NO 578
<211> LENGTH: 357
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 578
tagcggtgta accaactccc gggtcaccac ccgcaaacct cttgcggcaa cagcaccgtc 60
gacgcgtcaa ccgggctgcc cggaatcctg tggatgggca tcgagtgcat ggtcacgacg 120
tccccgacgc ggccggtggc aacgacaagt ggcccggatg caccacaaat gacggccgca 180
caccggtggg gacggccagc acgagagccg tgtcgccgaa gtcgacgcta atgccgtagg 240
cattggccgt cacaacaggc gacgccccgc gtaccaccga gtccacggng gttgggcggt 300
ctcctcggcc aaccaggcgt gaacccggcg gatccgaatg cagcaagacc cgtgggc 357

<210> SEQ ID NO 579
<211> LENGTH: 269
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 579
ccattggtcg gtgtgcgcat accantacna cgcgccgggc acctgacgcg gcggccgcaa 60
ccattcggtg gccatcgcca tcgtctgcca cccggtcaac ggacgcacct tctcctggcc 120
gacctagtgc gcccacccgc cgccgttgcg tcccatcgat ccggtcaaca tgagcagcgc 180
caacaccgag cggtacatga catctgctgt ggaaccagtg acanattccg ccgcccatga 240
tgatcntcga ccgtcctccg gattcggtc 269

<210> SEQ ID NO 580
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 580
gccggcctgg tcaaaggggc gtccgaagga nccgggctgg gtaacaagtt cctggctcat 60
atccgcgaat gcgacgccat ttgtcaggtg gtgcgggtgt tcgtcgacga cnacgtgact 120
catgtcaccg gacgggtcga tccccagtcc gacattgagg tcgtcgagac cgagctgatc 180
ctggcagatc tgcaaaccct ggagcgggcc acgggccggc tggagaanga agcncgcacc 240
aacaaggcgc gcaagccggt ctacgacccg gc 272

<210> SEQ ID NO 581
<211> LENGTH: 373
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 581
gatccactga ccacgatgac atatcgaaat gctcgacgat tccgatggcg atcaaggcca 60
cgatgccctg gccgttgggc ggtatctggt ggatggtgta cccgcggtag gttcccgtga 120
tcgtgtcgac ccagtccacg cgatgggcgg cgaggtcgtc ggcacgcatc accccgccgt 180
ntgccgccga gtgcgcctcg agtttggcgg ccagctctcc ccggtagaac tctcaccgtt 240
ggtcgccgcg atcttctcta ncgtcgccgc gtggtcagga aaggtaaaca gctcaccggg 300
tttcggcgct cgtccgccgg gcatgaacgc atctgcgaat ccgggctggg atgcgaacaa 360
cggacctgtg ccg 373

<210> SEQ ID NO 582
<211> LENGTH: 314
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 582
tctactgccg aatcggggaa cggtcctcgc ccaccnggtt cgtgttgccg gaattactca 60
ggacaccgaa acgtcgagaa ctacgagcgg agttggacan aataccgctc ccnggtgggc 120
gcccccatcg anttgggaag cngaaatgtg ctctggaccc cacccaagaa tgacattgcc 180
ggccgccctc caactggaaa tagaaacngt gatcacccgc cgcgttcttg gaaggaatgg 240
catgccctgg gccgggcgtt ccttccgctg ccggactcct cccaccaatt caccgccgaa 300
ggcgtcccgt ctgc 314

<210> SEQ ID NO 583

-continued

<211> LENGTH: 135
<212> TYPE: DNA
<213> ORGANISM: Mycobacterium tuberculosis

<400> SEQUENCE: 583
atactcaagc ttctgtcacc gaaatcccgc atgggataac gggtttagat ttcgacaacg 60
ggaccgtgtt tctcaacaag ccggtcatca gctgggccgg cgacaacggt atctacttca 120
cccgctttcg cccgt 135

<210> SEQ ID NO 584
<211> LENGTH: 221
<212> TYPE: DNA
<213> ORGANISM: Mycobacterium tuberculosis

<400> SEQUENCE: 584
ctggctcaag cgctcggcgc gcaggtgaac tcggaccggc tcgacgtcgc cgaacgcgag 60
gcggtgctgg cccacgccga cgccgtcgtc gcacatatcg gcaccgtgca caagtctaca 120
acaacgccgg catcgcgtac aacggcaacg tcgacaagtc ggagttcaag gacatcgagc 180
gcatcatcga cgtcgacttc tggggcgtcc tccacgggcc c 221

<210> SEQ ID NO 585
<211> LENGTH: 70
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 585
ccgccctccg cattatgggt caagaaccat cgggtcggac ttctgggctt ccaacgctcg 60 cgccgtcccn 70

<210> SEQ ID NO 586
<211> LENGTH: 241
<212> TYPE: DNA
<213> ORGANISM: Mycobacterium tuberculosis

<400> SEQUENCE: 586
ccgtggcact gtcagacata tgcgccgctc ctcctcatcg ctgcgctcgg catcgtcgcc 60
ggcggtcatg gcgtcaccct acccaagccg aacgcgaaac gagaacgtgt tccattatta 120
gggtgtgagc accaatacca gattgctcac caggaactca cgcagcaccg ggacggatgt 180
cggccaccac gcccatctgg ggtggtagcg gggaaatacc gctaacgcgg ctccggtgcc 240
g 241

<210> SEQ ID NO 587
<211> LENGTH: 492
<212> TYPE: DNA
<213> ORGANISM: Mycobacterium tuberculosis

<400> SEQUENCE: 587
tactcaagct tgtccaaata tcgaagcgtc gggtcgcgag gctcggtcgg cagctccagc 60
aaaacccgct ccacccctag atgccggtat ccctcaaggt ctttatccgc cgcttcaccc 120
cactggcaca cggtcaccgg cacgtcgccc ccggccatgg cgcgcaaccg ctgaagcgga 180
cccgacagcc gctgcggtga tggactgatc gcgatccacc cggcattgag ccgggctatc 240
cgcgggaagt tcgccggtcc cccgcccaca tacagcggag gatagggctt tgtcaccggc 300

```
ttcggccagc agtagatcgg atcgaagtcc acatatgtcc catggaattc cgcctgctcc    360

tgcgttcaga tctcgattat cgcgcgcaac cgctcatcga tcacacgtcc gcgcaccgca    420

gggtccacac catggttggc gacttcttcg cgcaaccagc cacacccacg ccgaaacgaa    480

accgtccctg cg                                                        492
```

<210> SEQ ID NO 588
<211> LENGTH: 313
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 588

```
caggcatgca agcttggcca actcctcatc ggacttgaag gtgccgtcct cgttggcggc     60

cctgctccac ggcacgttga tggcaccagg aatgtgtccg ggccgctggc tttgttcctg    120

cggcaggtgc gcgggggcca ggatcttgcc ggagaactcg tcgggagagc gcacgtcgat    180

gaggttcttg acgttgatgg ccgccaggac ctcgtcgcgg aatgcccgaa tcgtgttatc    240

cggcggggan gcggtgtagg aagtcaccgg ccggctgacc gggtcgctgg acagcgggcg    300

tccgtcgagc tcc                                                       313
```

<210> SEQ ID NO 589
<211> LENGTH: 305
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 589

```
atactcaagc ttcaaaacag gcctgttgtg ggcgcacccg gctcgccgag ttctgcacgc     60

accgcctcaa gtgcggcccg caccgccggc atctcccggt cacgcagggc cgcggcccgc    120

gccgcagcga cggcgtgttc gcgcagttcg ccgtcaatga tgctgacctg atcggccacc    180

cgggcggtct cggcgtcgtc ccgttcacta atcgcggtgc tcagcagcgt ctcgacagcc    240

accacccgag tggagaccag atgcnccacc acggaccgca gcgatgccag tcacctcacc    300

cgtcc                                                                305
```

<210> SEQ ID NO 590
<211> LENGTH: 394
<212> TYPE: DNA
<213> ORGANISM: Mycobacterium tuberculosis

<400> SEQUENCE: 590

```
caggcatgca agctttgcag ttgctgagta atgtcggcca acgtcaccac aatcgcgatg     60

aattcaatca tgccgcccag ggcggccaac ccaatggtgg ccgcgagcgg cagctcgatc    120

gcagcgcgga ggttgccggc cgccagttga ttcacgaaca gggtgaggtc ataggcgggc    180

aggatagtga cgaaggcaag acctagatct gccgtcggaa gaagaatcga gtatccggtc    240

gacacaacgg aagcgaaagt gtccgcgatg ttgatgagcg tcgccggttg tggcggcggt    300

ggcggcggta gcaccgtccg cacataccgc gggaacgcgg gcatccgaat ttggggcagg    360

gtgttcaagg cggctggcaa ctcaccatga atct                                394
```

<210> SEQ ID NO 591
<211> LENGTH: 457
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 591
ccggctcgta tgttgtgtgg aattgtgacc ggataacaat ttcacacagg aaacagctat 60
gaccatgatt acgccaagct atttaggtga cactatagaa tactcaagct tggccgcagg 120
gccgagtcga ttggtcgcgg tcgcctcgac agttagctta tgcaatgcta acttcggggc 180
aaagttcagg cggatcggcc gatggcgggc gtaggtgaag gagacagcgg aggcgtggag 240
cgtgatgaca ttggcatggt ggccgcttcc cccgtcgcgt ctcgggtaaa tggcaaggta 300
gacgctgacg tcgtcggtcg atttgccacc tgctgccgtg ccctgggcat cgcggtttac 360
cagcgtaaac gtccgccgga cctggctgcc gcccggtctg gtttcgccgc gctgacccgc 420
gtcgcccatg acagtgcgac cctgnaccgg gctggcc 457

<210> SEQ ID NO 592
<211> LENGTH: 438
<212> TYPE: DNA
<213> ORGANISM: Mycobacterium tuberculosis

<400> SEQUENCE: 592
gtgtgctgtc aattcagagc tgagcctgat gcactcaact tactgagcat gctaacgctg 60
gtcgtgcggg tcttgttccc gcgtgtcggc agggcacacg ctcggggcgt agctgggaga 120
ggccccggtc aagcccggag agcagtgctc agtccgccag cttgaccgac tttcgatgag 180
aacgcgcttc tcgccgtatt gaactggcgt gctgacggtc gctgagcagc gctcgccgag 240
tgcggccgct gattctttca tcgagccagg aggcgcattc gtgttcggcc gcctgcgggt 300
cggccccatc gtcgacgcga tccgtcaccc actcctcgat caggtctgcc tcatcgaacg 360
ggccaacggt gctgtcggag taagtgtgcg tgggcacgcg agccgggtgc tgtggtacac 420
ccaccgttgc atgaacaa 438

<210> SEQ ID NO 593
<211> LENGTH: 220
<212> TYPE: DNA
<213> ORGANISM: Mycobacterium tuberculosis

<400> SEQUENCE: 593
atactcaagc ttcaccaggc gccggcgggc cgcggcgcca agccaggcag ccgcgctcgg 60
cgcgtcgggg ccttccgccg gctcggccga cagttcgatc tctggatcgg cggggctctc 120
cgggccggcc tcggcgacct cagcgggccg cgccttccgg ccgaaccatt ccctagccat 180
agataaccgc acctcaatgc acggtttggc ggcaacccgg 220

<210> SEQ ID NO 594
<211> LENGTH: 266
<212> TYPE: DNA
<213> ORGANISM: Mycobacterium tuberculosis

<400> SEQUENCE: 594
agcttccgtc acgacccgcc ctcgccggtg ccggcgccat cggtcatcgg atctcatgac 60
gacgtcacgt aggcccgcta gccgcgagcg ggcgcggtca actggcgagg cggcggcgac 120
gtgactgagc tggccgagct ggaccggttc accgcggaac taccgttctc gctcgacgac 180
tttcagcagc gggcttgcag cgcgctggaa cgcggccacg gtgttgctgg tgtgcgcgcc 240
gaccggcgct ggcaagacgg tggtcg 266

<210> SEQ ID NO 595
<211> LENGTH: 105
<212> TYPE: DNA
<213> ORGANISM: Mycobacterium tuberculosis

<400> SEQUENCE: 595
atactcaagc ttgccgggac cgcggaacag aaccggcggt tcctaccgcg gtgtgcggcc 60
ggcgcgatat cggcctcccg actaaccgaa cccgatgtgg gctcc 105

<210> SEQ ID NO 596
<211> LENGTH: 141
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 596
acgttggctc tgccggaacg tatttccagc ggcacgcatt cggcgtgggt gccgggcgcc 60
gagttgcgtc gctgggatca cgcagcagtc gccggcggct gccgtcgggc tatgaattgc 120
accgagccgg aaaatccnca c 141

<210> SEQ ID NO 597
<211> LENGTH: 234
<212> TYPE: DNA
<213> ORGANISM: Mycobacterium tuberculosis

<400> SEQUENCE: 597
atactcaagc ttgtcgtatt ccgtggcact gtcagacata tgcgccgctc ctcctcatcg 60
ctgcgctcgg catcgtcgcc ggcggtcatg gcgtcaccct acccaagccg aacgcgaaac 120
gagaacgtgt tccattatta gggtgtgagc accaatacca gattgctcac caggaactca 180
cgcagcaccg ggacggatgt cagccaccac ccccatctgg ggtggtagcg ggga 234

<210> SEQ ID NO 598
<211> LENGTH: 184
<212> TYPE: DNA
<213> ORGANISM: Mycobacterium tuberculosis

<400> SEQUENCE: 598
cgttggtagc ccgatatgca tagtgtatct tactgaacat gatttccatt atggagcccg 60
gggtgccggc agcgcgaacg gtgcgccgtc agacgcgggc ggcactgacc agggtgttgc 120
gggcgaacat cggcccggct tcggattccg gtccgggtac cgggcgaccc accgcttcga 180
ggta 184

<210> SEQ ID NO 599
<211> LENGTH: 351
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 599
atactcaagc ttggccaact cctcatcgga cttgaaggtg ccgtcctcgt tggcggccct 60
gctccacggc acgttgatgg caccaggaat gtgtccgggc cgctggcttt gttcctgcgg 120
caggtgcgcg gggccatga tcttgccgga aaactcgtcg ggagagcgca cgtcgatgag 180
gttcttgacg ttgatggccg ccaggacctc gtcgcggaat gcccgaatcg tgttatccgg 240
cggggaggcg gtgtatgagg tcaccggccg gctgaccggg tcgctggaca gcgggcgtcc 300
gtccagctcc cacttcttgc gggcgccgtc caacnacttg acttctcctg g 351

<210> SEQ ID NO 600
<211> LENGTH: 438
<212> TYPE: DNA
<213> ORGANISM: Mycobacterium tuberculosis

<400> SEQUENCE: 600
atatcttaag cgtcgggtcc cgaggctcgg tcggcagctc cagcaaaacc cgctccaccc 60
ctagatgccg gtatccctca aggtctttag ccgccgcttc accccactgg cacacggtca 120
ccggcacgtc gcccccggcc atggcgcgca accgctgaag cggacccgac agccgctgcg 180
gtgatggact gatcgcgatc cacccggcat tgagccgggc tatccgcggg aagttcgccg 240
gtcccccgcc cacatacagc ggaggatagg gctttgtcac cggcttcggc cagcagtaga 300
tcggatcgaa gtccacatat gtcccatgga attccgcctg ctcctgcgtc cagatctcga 360
ttatcgcgcg caaccgctca tcgatcacac gtccgcgcac cgcagggtcc acaccatggt 420
tggcgacttc ttcgcgca 438

<210> SEQ ID NO 601
<211> LENGTH: 410
<212> TYPE: DNA
<213> ORGANISM: Mycobacterium tuberculosis

<400> SEQUENCE: 601
atactcaagc ttgtcgcggt aaacccgcag cagggcggtg ggtgcggtgt caaaaacaac 60
cacacttctt tgcggttcgg tgatctcgac accggccgcg agccgaccac catgcgcgcg 120
taaatcggcg atcagcgcgt cggctatcgc ctgggtgccg cccaccggaa tcggccagcc 180
gaccgaatgg gccagcgttg ccagcatcag tccggcgccg gccgacacca gtgacggcaa 240
cggtgaaatc gcgtgggcgg caacgccggt gaacaacgcg cgggcatcct cgcccgccag 300
cgaccgccag gcaggggtgc cctgggccag catccgcagc ccgagacgca ggaccgagcc 360
cagtgcagta ggcaaagacc gcttgtcgga gacatgaact ccacgaccgt 410

<210> SEQ ID NO 602
<211> LENGTH: 456
<212> TYPE: DNA
<213> ORGANISM: Mycobacterium tuberculosis

<400> SEQUENCE: 602
agcttattga accgcgggtc gcaggcaaag tggacctcat aacgactcgg gtccagcgac 60
cgcgccaaca cgaacggccg gacgacgtgg gccagggtcg cggcctcccc tacaaacagg 120
atccgttgcc tgcgagcgac aggctccggt gcggcgttgg gcgccgtgct cgtcccagcg 180
tccggtcccg ggtcgccggc gacgcttgtt tcctccatac tcgccccta atctcgaggc 240 agcccgtacc cgcaggcaac ctcccaaaaa tgcaatcccc caaaatgcaa tgcgtcgagc 300
tatttctcac accgaccgct agttgcggat cagaaatccg ttgggcgcgg aagtccagcc 360
gaatttgttc tcccgctccg catcatgctt gtaatcgttt ggaaattcat cctcatatgc 420
ctcgatcgct tcatagggtc caggccaaac cgggca 456

<210> SEQ ID NO 603
<211> LENGTH: 217
<212> TYPE: DNA
<213> ORGANISM: Mycobacterium tuberculosis

<400> SEQUENCE: 603
cttccggctc gtatgttgtg tggaattgtg agcggataac aatttcacac aggaaacagc 60
tatgaccatg attacgccaa gctatttagg tgacactata gaatactcaa gcttggccac 120
ctcgcggtgt gtggtggaac ccatctgagc agtgtgccaa accggggcag acagctccca 180
attgacgtga gcccgctcac ttgctgggta agcgtcg 217

<210> SEQ ID NO 604
<211> LENGTH: 478
<212> TYPE: DNA
<213> ORGANISM: Mycobacterium tuberculosis

<400> SEQUENCE: 604
tagcgccccc tcccgggcgg agctccacgg cgtggatcaa ggtaccggcc gggatgttgc 60
gcaatggcag gttgttgccc ggcttgatgt cggcgttagc gccggattcc accacatccc 120
cttgcgaaag tccgttgggt gcaatgatgt agcgcttctc cccatcgaga tagtggagca 180
acgcaatccg tgcggtacgg ttcgggtcgt actcgatgtg cgcgaccttg gcgttgacac 240
catctttgtc attgcggcga aagtcgatca tccggtaagc gcgcttatga ccgccgcctt 300
tgtgccgggt ggtaatccgg ccatgcgcgt tgcgtccacc gcgaccgtgc agcgggcgca 360
ccagcgactt ctccggggtt gaccgggtga tctcggcgaa atcagatacg ctggcgccgc 420
gacgaccaag cgtcgtgggc ttgttcttgc gaattgcatg tctaatcagg tctttctc 478

<210> SEQ ID NO 605
<211> LENGTH: 459
<212> TYPE: DNA
<213> ORGANISM: Mycobacterium tuberculosis

<400> SEQUENCE: 605
tgaaactata taatactcaa gcttgccaaa gaagacctcg tcgaccaagc aggacgcgac 60
cgtcgaggtg gcgatccggc ttggcgtcga cccgcgtaag gcaaaccaga tggttcgcgg 120
cacggtcaac ctgccacacg gcactggtaa gactgcccgc gtcgcggtat tcgcggttgg 180
tgaaaaggcc gatgctgccg ttgccgcggg ggcggatgtt gtcgggagtg acgatctgat 240
cgaaaggatt cagggcggct ggctggaatt cgatgccgcg atcgcgacac cggatcagat 300
ggccaaagtc ggtcgcatcg ctcgggtgct gggtccgcgc ggcctgatgc ccaacccgaa 360
aaccggcacc gtcaccgccg acgtcgccaa ggccgtcgcg gacatcaagg gcggcaagat 420
caacttccgg gttgacaagc aggccaacct gcacttctc 459

<210> SEQ ID NO 606
<211> LENGTH: 464
<212> TYPE: DNA
<213> ORGANISM: Mycobacterium tuberculosis

<400> SEQUENCE: 606
gctgagctcc acggcgtgga tcaaggtacc ggccgggatg ttgcgcaatg gcaggttgtt 60
gcccggcttg atgtcggcgt tagcgccgga ttccaccaca tccccttgcg aaagtccgtt 120
gggtgcaatg atgtagcgct tctccccatc gagatagtgg agcaacgcaa tccgtgcggt 180
acggttcggg tcgtactcga tgtgcgcgac cttggcgttg acaccatctt tgtcattgcg 240
gcgaaagtcg atcatccggt aagcgcgctt atgaccgccg cctttgtgcc gggtggtaat 300
ccggccatgc gcgttgcgtc caccgcgacc gtgcagcggg cgcaccagcg acttctccgg 360
ggttgaccgg gtgatctcgg cgaaatcaga tacgctggcg ccgcgacgac caggcgtcgt 420
gggcttgtac ttgcgaattg ccatgtctaa tcaggtcttt ctct 464

<210> SEQ ID NO 607
<211> LENGTH: 205
<212> TYPE: DNA
<213> ORGANISM: Mycobacterium tuberculosis

<400> SEQUENCE: 607
atactcaagc ttgttggtga cctcgccggc gaacagttct cgcacgattt ccggattagc 60
gggactggtc accagttggg tatgcgggaa ggcgctgacg ttcgccgcga ttagctgttt 120
gatggacgcg gcggtgatgt cctgatcacg gaactggctg taatagccca gggtcgccac 180
gcttccatcc gggcccggac ccggc 205

<210> SEQ ID NO 608
<211> LENGTH: 244
<212> TYPE: DNA
<213> ORGANISM: Mycobacterium tuberculosis

<400> SEQUENCE: 608
gatgatcgcc ggtgccaccc cgatccgtgc ctcggtcagc gcgaacgtgc tttccggtcc 60
ggcgaccacc atgtcgcacg caccgaccag gccgaacccg ccggcccgca catgcccgtt 120
gatggcgccg accaccggca gcggcgactc gacgatggcg cgcaacagcg ccgtcatttc 180
ccgcgcccgc gccaccgcca tccggtacgg atcaccacca cctccgccgg cctcgctgag 240
gtcc 244

<210> SEQ ID NO 609
<211> LENGTH: 289
<212> TYPE: DNA
<213> ORGANISM: Mycobacterium tuberculosis

<400> SEQUENCE: 609
atactcaagc ttgccgcaat cgaaaccaac ctgtttgtgc cgcaagaaat tacgccgtgg 60
cccggcgccg atcaagaaac gccccggcgc gcggcggtgt cgtcgtatgg catgacgggc 120
accaatgtgc acgccattgt cgagcaggca ccggtgccag cccccgaatc cggtgcacca 180
ggcgacaccc cggccacacc cggtatcgac ggcgcgctgc tgttcgcgct gtcggccagc 240
tcgcaggacg cgctgcggca aaccgccgcg cggctggccg attgggtct 289

<210> SEQ ID NO 610
<211> LENGTH: 282
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 610
ttggcgggtt ggccacanca ncccgccggt gacggcgacg atgctgggct ggttgcggcc 60
ctgcgccacc gcggcttgca tgctggttgg ctgtcttggg acgatcccga aatagtccac 120
gcggatctgg tgattttgcg ggctacccgc gattaccccg cgcggctcga cgagtttttg 180
gcctggacta cccgcgtggc caatctgctg aactcgcggc cggtggtggc ctggaatgtc 240
cancgccgtt cacctacgtg accttgatgg gatccggggg nt 282

<210> SEQ ID NO 611
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 611
ncgtggacac cggtgtcgan cgccaccagc cgcatgtctg cangtcnatt ccgtcctcgg 60
caacatcttg aatgccgagc agcgcctggg cgtgatcggc aaccggggat gaccgctcgc 120
cgatccgctc gacaatcccg gcggcacgtg acatgccggc ggacggctcg acgagctgga 180
acttcagcga cgacgatccg gaattgatca ccagcacggt gctactcatg gacccctgcg 240
cctgaatccc gtgatggcca cggtgttgac tattcgtcga cagtgcaccc gagatagtct 300
tcacggctgc gt 312

<210> SEQ ID NO 612
<211> LENGTH: 349
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 612
catgtattgc cgtgctcacg gcgccacgct cgatggtttc tcgaagtctc cgggctggtg 60
tacagcttct cgttgatctc gttcgccacg ccgtcctctt cccgccgacg acccgatctc 120
gatctccana atgatcttgg cggccgccgc cgccttgagc agctcctggg cgatggccag 180
gttctcatcg atgggcactg ccgaccgtcc cacatgtgcg acggaacaaa gatgtcacct 240
tgctcacgcg tgcgcnagat cncanaaggg ccggacatac tgtcnacttg tccttgggca 300
gtggtccgtg tcagcccacg tgacgggtac ttggcgcgat aacgtggtg 349

<210> SEQ ID NO 613
<211> LENGTH: 350
<212> TYPE: DNA
<213> ORGANISM: Mycobacterium tuberculosis

<400> SEQUENCE: 613
gccaccacga cccggccgta actctgctca cggaaatgcg gccaggccgc gcgtagcacg 60
tggtatccgc cataaaggtg caccttaagc acggcgtccc aattctcgaa cgacatcttg 120
tggaaggtgc cgtcgcgcaa gatcccggcg ttgctcacca caccgtgcac ggcgccgaat 180
tcgtcaagcg cggtcttgat gatgttcgct gcgccgtcct cggtggcgac gctgtcctta 240
gttggcgacc gcccggcccc ccttgtcgcg aatctcggcg acgacctcat cggccatcgc 300
cgaacggcgc ccgtgcccgt cgcgggcgcc accgaggtcg ttgaccacga 350

<210> SEQ ID NO 614
<211> LENGTH: 126
<212> TYPE: DNA
<213> ORGANISM: Mycobacterium tuberculosis

<400> SEQUENCE: 614
caggcatgca acctttgtcc acacggcgtc tactccgtgc aaggtccgac cgcttccacg 60
tcccgccgtg acggtgctcc atctccctca gcaacgcgtg aagtggtccg atcccgcggc 120
ttcagg 126

<210> SEQ ID NO 615
<211> LENGTH: 395
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 615
gttgagacgc aaccagcgca caacgacgat ttggcgtagc ggcggacgtc tgctcgattc 60
gatcacgtcg cgctcgcatc gagcatggcc cgcgacgcta cacgatcgcc gtcgtcgatg 120
acacgaccga gccgtacgcc ggccgtaagc cgcgccagga ttcggcgaaa aacgtctacg 180
tggcgggtgt actgggtgtc gaatgattcg tggggtgcgt atgcgtcctg caatcgtcga 240
catagatccg tcgccgcatc gcgtcgacaa ctccgggtga gtggaataca cttgccgatc 300
acgcgacgtg cgcggatcga tgccgaccga aatacgacca catggctctt gttgcncagt 360
gttggcggca tcaaataccc tcagtgccgt ccgac 395

<210> SEQ ID NO 616
<211> LENGTH: 371
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 616
ttnccgcctt nacgcctact ccnagacgat gctcgacgcg tgtgagcaca cggcgctgct 60
gtagacggca cggcgcagct ggatcgcgct tggtgcaccc aagcctctac gcgcgtcgct 120
gcgtcgtcat cgggtaccga acatattccg gtcgttgcgc agagtgtgca tgtgcggctc 180
ttgtgaacga acatagcaaa gcgtatatgt ctgtggcggc tctgcagata tcgcgataat 240
acgtatatac ataaggtggc gcgcgatcta tcggtatatc cgttatggcg gacgtgcgtg 300
agcgtgagtc gcggcgcatc gcgcacttcg cgatcgcgtg actggtcctc gcgactgcgc 360
gcatgcgtag c 371

<210> SEQ ID NO 617
<211> LENGTH: 423
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 617
ggtgatgacg cacttgcttc gaatgagtca ttgactactc ccgtggttgt cctgcgatgg 60
tggagtgccg cgcagccttg cccgangtcg cgatcgcgtc gcgggcttcg gggagcagac 120
tgacctgcag atggaagtcg tgccacatgc ccgcgaacgg cgagctcgat gcttgttttc 180
gaagngcgca ngcggtttcg atcttgtccg cgtcaacgca gatcggatct cgccgcggtc 240
tgcatgacga tgggcgcagg cccgctcatg tcccgtagac ggggagatac gggcagccgc 300
ggatcgagac ctacgtagcg cggcgcccat cgtgccatcg acgaagaatg acggatcgcg 360
cagcgccgtc gcgtcgcttc gatgtcacgc gagatcgcca cggcagatca gcgatgcgcg 420
ggc 423

<210> SEQ ID NO 618
<211> LENGTH: 354
<212> TYPE: DNA
<213> ORGANISM: Mycobacterium tuberculosis

<400> SEQUENCE: 618
cggtacgccg gcaacaaacg ccttgtgacg agcgcgtccg agcggtcatc ggcctccacc 60
gtcatgcaca gctccttctc caggtctacg ccgacgtcgc ggtccacatt ggtgagcttg 120
gcgaatgcct cggcaacctc gtcgaaatgc gcctccgcgt ccgcatcgaa ggtcgccatg 180
tcaaagatca actcgacgta gtagctagtt accgcatcag gtcagtgttt gctggcctcg 240
gagtccggcc gaacaatggc catttcccgc gactctagaa tccagtcatc gtctcggtga 300
cgacgccttg ccgatcacat agctcgaccg gatcggagag aatctggttc tcgt 354

<210> SEQ ID NO 619
<211> LENGTH: 128
<212> TYPE: DNA
<213> ORGANISM: Mycobacterium tuberculosis

<400> SEQUENCE: 619
atactcaagc ttaagcgcag cagtaccggc ggtgcctggg catcccagca aaacggggag 60
ctcaacgaac gattcctgaa cgaagggtcg tccaccaacc tccaaaccga acggttgcca 120
gccccggc 128

<210> SEQ ID NO 620
<211> LENGTH: 295
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 620
gcaagtccgc tcaatgtggt tgtgatcaca ngactacgtc gcctcaatca gctcaaacgt 60
caccccgtgg cgtgctgcgc agcatgaagg tcggcgcccg cacgatgtgg gcgaagcaac 120
aggtaataac tggtcggcat gggtcaaccc tcattgggcc gttgcggatc gggtgcacgc 180
ccggagtgcc ggtcgaactc aacaccgcct tcaccgatct tttcgtcgaa aatggcggtc 240
gtgtcggggt atacgtccgc gatcccacga ggcggaatcc gctgagccgc actga 295

<210> SEQ ID NO 621
<211> LENGTH: 361
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 621
atactcaagc ttcgcgccct caagcggctg aaggtggttc cggcgtncca acngtcgggc 60
aactcgccga tgggcatggt gctcgacncc gtcccggtga tcccgccgga gctgcgcccg 120
atggtgcagc tcgacggcgg ccggttcgcc ncgtccgact tgaacgacct gtaccgcagg 180
gtgatcaacc gcnacnncnn gntgaaaagg ctgatcgatc tgggtgcgcc ggaaatcatc 240
gtcaacaacn agaancggat gctgcnggaa tccgtggacg cgctgttcga caatggccgc 300
cgcggccggc ccgtcaccgg gccgggcaac cgtccgctca agtcgctttc cgatctgctc 360
a 361

<210> SEQ ID NO 622
<211> LENGTH: 361
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 622
tgcgcatggc agttgttgcc ggcttgagtc gcgttagcgc ggattccacc acatcccttg 60
cgaagtcgtg ggtgcaatga tgtagcgctt ctcccatcga gatagtggag caacgcaatc 120
cgtgcgtacg ttgggtcgta ctcgagtgcg cancttggcg ttgacaccat ctttgtcatt 180
gcggcgaagt cgatcatccg gtaagcgcgc ttatcgacgc cgcctctgtg ccgggtggta 240
atccggccat gcgcttgcgt ccaccgcgac gtgcagcggg cgcacaccga cttctccggg 300
tgacgggtga tctcggcgaa tcagaacctg gcgcgcgaca cagcgtcgtg gctgtacttg 360
c 361

<210> SEQ ID NO 623
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 623
tgggtgatca gatactggct agttggtcgg gtggggtgat cgaagatcgc ggtggccggc 60
agcgttactg cggtgacgct gttaagcggt tacgtactcc acggcactca angaattana 120
tcccgaatcg gcaaaccctg gccagcgtcg agtccgcagc gccgtcgcgc cccccaccgc 180
tgcggcatgc tcacatacca cctcgatcgc tgcgggagtt gctcgtcggc cgaccgaccg 240
gccagccggg cggcaaaccg gaggacccaa gattcagcac caccatcgct agcccgatct 300
ggccgcgcgt gg 312

<210> SEQ ID NO 624
<211> LENGTH: 454
<212> TYPE: DNA
<213> ORGANISM: Mycobacterium tuberculosis
<220> FEATURE:
<221> NAME/KEY: unsure
<222> LOCATION: (various positions within the sequence)

<223> OTHER INFORMATION: applicants are uncertain of bases designated as "n"

<400> SEQUENCE: 624
tcgtagcggt tgcgaccant ccgcggacag ctccgccacg cgacgggtcg ggatcaccgc 60
ggtcaaacca ccgagcggcg aggatctctg gccgtcgacg tgaccgcgca cggccgcggt 120
gatggccagt cccgaccgcc gttccacttg gcgtacgcgc tggatgtgtt gtgccgcaac 180
ggaatcccac ctcaattatg acctcgttgt gggcgagcgc ggtatcgtac gcccgaccag 240
gaatcgtcga tgctatctca cgtcaccgaa ggcctctccc agcacaccgc atccagaacg 300
tgcacacngt cgacatgtct cggcggatcc gcctgcagaa cgaacgccan gtgcgctgtg 360
cgacacgggt cgcgatcacc gctcgcacgc ggagatcggc acacgcgcag cgcatcgatc 420
ataatctctc gatgcggtct ccaccaccga acag 454

<210> SEQ ID NO 625
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 625
atactcaagc ttcgctgagg tggtggggca cgatcacgtc accgcaccgc tgtcggtggc 60
gctggatgcc ggccggatca accacgcgta cctgttctct gggccgcgtg gctgcggaaa 120
gacgtcgtca gcgcgtatcc tggcncggtc gttgaactgt gcgcagggcc ctaccgccaa 180
cccgtgcggg gtctgcgaat cctgcgtttc gttggcgccc aacgcccccg gcagcatcga 240
cgtggtagag ctggatgccg ccagccacgg cggcgtggac gacacccgcg agctgcggga 300
ccgcgcgttc tatgcgccgg tccactcacg gtaccgggta tttatcgtcg acgaggcgca 360
catggt 366

<210> SEQ ID NO 626
<211> LENGTH: 363
<212> TYPE: DNA
<213> ORGANISM: Mycobacterium tuberculosis

<400> SEQUENCE: 626
gcactcacgc tggtacaaga ccttcacaaa atctgaaatc ctgacccgat acttgaacct 60
ggtctcgttc ggcaataact cgttcggcgt gcaggacgcg gcgcaaacgt acttcggcat 120
caacgcgtcc gacctgaatt ggcagcaagc ggcgctgctg gccggcatgg tgcaatcgac 180
cagcacgctc aacccgtaca ccaaccccga cggcgcgctg gcccggcgga acgtggtcct 240
cgacaccatg atcgagaacc ttcccgggga ggcggaggcg ttgcgtgccg ccaaggccga 300
tccgctgggg gtactgccgc agcccaatga gttgccgcgc ggctgcatcg cggccggcga 360
ccg 363

<210> SEQ ID NO 627
<211> LENGTH: 367
<212> TYPE: DNA
<213> ORGANISM: Mycobacterium tuberculosis

<400> SEQUENCE: 627
atactcaagc ttgtataaaa agatcggtga gcgcatcgat tcgctccgcc gggtttgccg 60

```
ctgcggcggc ggagctgccg tgaccgtcta tttgggtgat cagatactgg gctagttcgg    120

tcggggtggg gtgatcgaag atcgcggtgg ccggcagcgt tactgcggtg acggctgtta    180

agcggttacg tacctccacg gcactcaagg aattaaatcc cgaatcggca aacgcctggc    240

cagcgtcgaa tccggcagcg ccgtcgcgcc ccagcaccgc tgcggcatgc tcacatacca    300

cctccatcgc tgcggcgaat tgctcgtcgg ccgaccgacc ggccagccgg gcggcaaacc    360

cggaaga                                                              367


<210> SEQ ID NO 628
<211> LENGTH: 518
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 628

cctcatcata tgccgataga gctctacata ttcaggagat caccatggct cgtgcggtcg     60

ggatcgactc gggaccacca actccgtcgt ctcggttctg gaangtggcg accnggtcgt    120

cgtcgccaac tccggagggc tccaggacca cccgtcaatt gtcgcgttcg cccgcaacgg    180

tgaggtgctg gtcngccagc ccgccaagaa caggcagtga ccaacgtcga tcgcaccgtg    240

cgctcggtca agcgaccatg ggcagcgact ggtccataga gattgacgca agaaatacac    300

gcccggagat ctcgccgcat tctgatgaac tgaacgcgac ccgaggctac tcggtganga    360

catnacgacg cgttatcaca ccccgcctnc ttcaatgacc ccacgtcngg caccaaggac    420

ccggcaatcg cggctcactt gngcgatngt cnacaaccaa cgcgncgcct ggctacgggc    480

tcaacaaggc anaagacaca atccgctctc gattggtg                           518


<210> SEQ ID NO 629
<211> LENGTH: 435
<212> TYPE: DNA
<213> ORGANISM: Mycobacterium tuberculosis

<400> SEQUENCE: 629

atactcaagc ttatcgaggc ggcgcatacc gaagcgtggg aaatccagac cgaataccgc     60

gacgtgctgg acactttggc cggcgagctg ctggaaaagg agaccctgca ccgacccgag    120

ctggaaagca tcttcgctga cgtcgaaaag cggccgcggc tcaccatgtt cgacaacttc    180

ggtggccgga tcccgtcgga caaaccgccc atcaagacac ccggcgagct cgcgatcgaa    240

cgcggcgaac cttggcccca gccggtcccc gagccggcgt tcaaggcggc gattgcgcat    300

gctacccaag ccgctgaggc cgcccggtcc gacccggcca aaccgggcac ggcgccaacg    360

gttcgcccgc cggcaccacc ggtccggtga ccgcagtacg gtccccccag cctgactacc    420

gtgccccggc gggct                                                     435


<210> SEQ ID NO 630
<211> LENGTH: 398
<212> TYPE: DNA
<213> ORGANISM: Mycobacterium tuberculosis

<400> SEQUENCE: 630

tggccgggct ggtagcccgc gtatggcaag gttccgctca atgtggttgt gatgcagcag     60

gactacgttc gcctcaatca gctcaaacgt cacccccgtg gcgtgctgcg cagcatgaag    120

gtcggcgccc gcacgatgtg ggcgaaggca acaggtaaga acctggtcgg catgggtcga    180
```

gccctcattg ggccgttgcg gatcgggttg cagcgcgccg gagtgccggt cgaactcaac 240
accgccttca ccgatctttt cgtcgaaaat ggcgtcgtgt ccggggtata cgtccgcgat 300
tcccacgagg cggaatccgc tgagccgcag ctgatccggg ctcgccgcgg cgtgatcctg 360
gcctgtggtg gtttcgagca taacgagcag atgcgaat 398

<210> SEQ ID NO 631
<211> LENGTH: 464
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 631
gtccagtcaa gcatcggtcc tctccgacta cgccaagant ggcgacgtgt cagtgcanac 60
agcgganatg gtggcgccta tgcgtcgacg ctcacaaacn gcggtgancg cgttctggtc 120
gtgcaccatc gagccgtgcc agcccggccg cgtgccgtca gccgcatcca ctggatgcct 180
tctcggngtt tcaatcangt acangcgacg ttcgccacca tcgtgccggg gcacggttag 240
cgagaaaccg ccgacttcac cgattgcctc ggtgatgccg tcgaacagat cgggcctatt 300
gtcgacagcc agtgtgatnc gtatttgccg ccgtgctcct cgtcgcaacg atgcgaacac 360
agatccgtgg nggacgatag cggctgacaa ngtgggggca acacaatcac atgccacatt 420
tcttcatttc acgcccacaa cccagacttc gtctcgatgn gccg 464

<210> SEQ ID NO 632
<211> LENGTH: 499
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 632
cacgcggtct ggcccgatcc gaagatccct ttgccggcgt ggcggctctg ctcggcggtg 60
ttgtacactt ctcgaacacc tcggcaccga caccaccacc gtngcttgaa caccgccaac 120
atcggcagca gatcttgatg gtcctggtga atcccacggt gactttggag tggaaggcgc 180
catactgatc gccgcgccag cacatgagct agcggcagga aaaccagcag ccgctcacct 240
tgcgcagcag cgtcnggtga tatgcctggc gcccttaatc tcgtgaacca gttggattgg 300
gtcaactggc agccttgggt ctccggtggt gccgangtgt anataagctc ccgggtccgt 360
caacgtantg cgcaggcggc ggttactcgg cgggtcaacg agccccgctc gtgagcnatc 420
agcctttgga ccgaacggga ttcatactcc gcaggcggcc ctccgaaatc ggcacatgtc 480
ctttgatcgt tcgcaacan 499

<210> SEQ ID NO 633
<211> LENGTH: 343
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 633
ggccatgtca catcggtggt acaggtaaac cgcgccgtgt gcgcggtctc ggagatcaga 60
acgtggtcgc agttgaaccg cgggctttca gccagtcgcg ataatcggcg gaagtcggcg 120
cctgccgccc caactagcgc gactcgccac ctagcacacc gatggcgaag gccatgtntc 180
cggccacgcc gccgcggtgc atcaccaagt catcgactag gaagctaagc gacancttgt 240
gcaggtgttc gggcagtagc tgctcggaaa atcggctgga aaccgcatca aatggtcggt 300
ccaatcgaac cggttacccg atcgtcacaa aaatctccgt cct 343

<210> SEQ ID NO 634
<211> LENGTH: 192
<212> TYPE: DNA
<213> ORGANISM: Mycobacterium tuberculosis

<400> SEQUENCE: 634
gggtctacaa ccaccgggtc tgacttctgg gcttccaccg ctcgcgccgt cgcgacaaac 60
agcgcggtcg aaccgacact cgttgtgatg tcccagctat cacctccggt aggcacccaa 120
tcgaccctac ccggctatct cacccccgat ctccaggctc cgccgatcca tgcgcatccc 180
ggtccggatc cc 192

<210> SEQ ID NO 635
<211> LENGTH: 376
<212> TYPE: DNA
<213> ORGANISM: Mycobacterium tuberculosis

<400> SEQUENCE: 635
caggcatgca agcttgtcgt attccgtggc actgtcagac atatgcgccg ctcctcctca 60
tcgctgcgct cggcatcgtc gccggcggtc atggcgtcac cctacccaag ccgaacgcga 120
aacgagaacg tgttccatta ttagggtgtg agcaccaata ccagattgct caccaggaac 180
tcacgcagca ccgggacgga tgtcagccac cacgcccatc tggggtggta gcggggaaat 240
acggctaacg cggctccggt gccggcagcc cagcgcagac cctcggcggc ggacacggct 300
aacaacgacg acccatagtt gttctttgcc ggatggccgt gtttgctgac atatcgggcg 360
cggcgccggc gccgcc 376

<210> SEQ ID NO 636
<211> LENGTH: 83
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 636
nctacgctgc tgaatgttgt gcgccggagg anctcaagac ccacgcggtt gtacgcggac 60
ntgcgacatg ttcaaccgcc gga 83

<210> SEQ ID NO 637
<211> LENGTH: 319
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 637
ctaaccaaca agccatggtg gttggcgccg tcgagaggtc ggcggtcgcc acaacgggaa 60
gatcgccttg agcgtcgctc gaccgccgcc tcgagttggg tcataacgaa gtactgatgc 120
cgatcatgtc gacgtgtccg tcgcatcagc gtgcagcggc gacccctcga cgagcctcgg 180
tgccgccgcg gccagggcac cagctgtttt agcgcattgt gctccgccgg taataaagga 240
ngtcggtcgc ctccgctgct gtggttgcgg aataacatct tcccttcctg caacaggatg 300
agaatggttt taattgctc 319

<210> SEQ ID NO 638
<211> LENGTH: 94
<212> TYPE: DNA
<213> ORGANISM: Mycobacterium tuberculosis

<400> SEQUENCE: 638
ctaagctttc gggtccgccg ccactagtac cgcgttgccg gccccgccga cctagaatgt 60
tccgcccatt gccgtttcct cccgccgccg ggtt 94

<210> SEQ ID NO 639
<211> LENGTH: 122
<212> TYPE: DNA
<213> ORGANISM: Mycobacterium tuberculosis

<400> SEQUENCE: 639
tctggtgccg ggtgtgccga cgggtccgtc cgcctctgct tcagtgattc tgtgatgcga 60
ccggcaacgt cctcgttgtt cggtgtctat gtggtccgtc tctccttgtt ccgcatacga 120
tt 122

<210> SEQ ID NO 640
<211> LENGTH: 210
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 640
gcgatcgntn accacaaggg cgcaaccgtt cgcgcgtcga ctgaacgtgc tgccgcctgg 60
agaactggcg ctgctgccac ctggtcggcg catcggcact tcgaggactg gatttcgacg 120
cgtggcccga cctgangtng gcggtggacn ngtgtgcacc cggttgattc ctcggccttg 180
ccgggatgcc acctgcgcct ggtggtcgat 210

<210> SEQ ID NO 641
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 641
cgtgaccgga cggggtgccg cgcgaaccgg tcttggccaa ttgccgggga ctggggctgg 60
agtataaagc gggcctgttg ccggaagata aagtcaaagc ggtgaccgag ctgaatcaac 120
atgcgccgct ggcgatggtc ggtgacggta ttaacgaccg ccagcgatga aagctgccgc 180
catcgggatt gcaatgggta gcggcacaga ctggcgctgg aaaccgccga cgcacattaa 240
ccataaccac ctgcgcggct ggtgcaaatg attgaactgg cacgnccact cacgccaata 300
tccgccagaa catcactatt gcgctggg 328

<210> SEQ ID NO 642
<211> LENGTH: 553
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 642
atactcaagc ttcttaccca nagcatgaac cccgccgtcc aatgccgcca ccgtggtgct 60
gtcggccggc cgggtgcggg cacaatcgcc gagttcggcg aacagatcct cgaaggtctt 120
cacggccagc gattgttgca cgtgtcagcc agccaagtca cggtggtttg acgccacacg 180
ttcgccaccg ccgcgccgcg cattagggca tcctaatata ggttaggcta ccctanttat 240
tcctgtggtc naaggaggca gccgaacgtg accttcccga tgtggttcgc agttccgccg 300
gaagtgccgt cagcatggct gtccaccggc atgggccccg gtccgctgct ggccgcggcc 360
agggcgtggc acgcgctggc cgcgcaatac accgaaattg caacggaact cgcaagcgtg 420
ctcgctgcgg tgcaggcaac tcgtggcagg ggcccagcgc cgacggttcg tcntccccat 480
caaccgttcc gtattggcta accacctgca cggtggcacc gcacaacgcc gccacaaacg 540
cgccccggta tac 553

<210> SEQ ID NO 643
<211> LENGTH: 486
<212> TYPE: DNA
<213> ORGANISM: Mycobacterium tuberculosis

<400> SEQUENCE: 643
ggccgaactt aatcggttgt tggcggctgc cgagttgggt cactcggggg gtgtgcactg 60
gcacatggtg ggccggattc aacgcaacaa agccgggtcg ctggctcgct gggcgcacac 120
cgctcactcg gtggacagct cgcggttggt gaccgcgctg gatcgggcgg ttgttgcggc 180
gctggccgaa caccgtcgtg gcgagcggct gcgggtttac gtccaggtca gcctcgacgg 240
tgacggatcc cggggcggcg tcgacagcac gacgcccggc gccgtagacc ggatttgcgc 300
gcaggtgcag gagtcagagg gcctcgaact ggtcgggttg atgggcattc cgccgctgga 360
ttgggacccg acgaagcctt tgaccggctg caatcggagc acaaccgggt gcgtgcgatg 420
ttcccgcacg cgatcggtct gtcgcgggca tgtccaacaa cttgaaatcc cgtcaacatg 480
gtcgac 486

<210> SEQ ID NO 644
<211> LENGTH: 146
<212> TYPE: DNA
<213> ORGANISM: Mycobacterium tuberculosis

<400> SEQUENCE: 644
gcttcccctg atactcgacc agccccactc gggccaatac gtgaatgtcc tagcattttt 60
cacccgttca cgggctagtc gagtagtaga cgattgatta gcctgaacgt acctccgacg 120
gccagctgac gaacgggttt gacgga 146

<210> SEQ ID NO 645
<211> LENGTH: 204
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 645
tcagctgtct gtagaagggc tggcgatact gtgcactgtc tgatatcgcn ncgtngtggg 60
actatncagn ccatnangat gcggttcngn nnntgcagag natcctggna cacatncggt 120
tcacgttaat cancatcgcg anttnctncg tnttcgatta nttctgctaa cgnntctnnn 180
agtgcctgcg ggtcgactct agag 204

<210> SEQ ID NO 646
<211> LENGTH: 209
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 646
nctctgccgg gcnagagcgc agagtcggac ggcttcgtcg atcgtgaagc gaccntgcga 60
tgancagata tcgntnacac tgctcanaaa cttcggatca tcgntgatac acaggccaac 120
gggtagcggt tgtccaaccg cttcgtcaac ganatgggat cgtgacganc ctacgctcgc 180
aggatatgtc gcngaccngn tctaganan 209

<210> SEQ ID NO 647
<211> LENGTH: 183
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 647
cacttcatgc tcgtgcgttg gcntcgattt gcncgagngg ttagctcctc gagtgngtga 60
cgtatcactc cggcngacta nccgtatcng cgtcccgcac cggtcaactg gtctagccac 120
accggggaga atncncgacc ggngctatcg accnatcacg gcttgtcgnn aagatagnca 180
gcc 183

<210> SEQ ID NO 648
<211> LENGTH: 154
<212> TYPE: DNA
<213> ORGANISM: Mycobacterium tuberculosis

<400> SEQUENCE: 648
atactcaagc ttgccaaccg ccaccctgca tccggggggc gagcactgct ccgccgacca 60
gtacgaacca acctgcggtg cccaggccat tgacaatgtg ctggtcggcg cccgcgagtt 120
ctagcacagc aacgccgcgg ccaccacagg ggcg 154

<210> SEQ ID NO 649
<211> LENGTH: 219
<212> TYPE: DNA

<213> ORGANISM: Mycobacterium tuberculosis

<400> SEQUENCE: 649
cggtcggtgt gcttggcggc gtcggtatca acaccgccca cgaaatgggg cacaagaagg 60
attcgctgga gcggtggctg tccaagatca ccctcgccca gacctgctac gggcacttct 120
acatcgagca caaccgtggc catcacgtcc gggtgtccac accggaagac ccggcgtcgg 180
cgcggttcgg caaaactttg tgggatttcc cgccccccc 219

<210> SEQ ID NO 650
<211> LENGTH: 307
<212> TYPE: DNA
<213> ORGANISM: Mycobacterium tuberculosis

<400> SEQUENCE: 650
aatactcaag cttcgcggag gtggtggggc aggagcacgt caccgcgccg ctgtcggtgg 60
cgctggatgc cggccggatc aaccacgcgt acctgttctc tgggccgcgt ggctgcggaa 120
agacgtcgtc agcgcgtatc ctggcgcggt cgttgaactg tgcgcagggc cctaccgcca 180
acccgtgcgg ggtctgcgaa tcctgcgttt cgttggcgcc caacgccccc ggcagcatcg 240
acgtggtaga gctggatgcc gccagccacg gcggcgtgga gcaaccccgc gagctgcggg 300
accgccc 307

<210> SEQ ID NO 651
<211> LENGTH: 252
<212> TYPE: DNA
<213> ORGANISM: Mycobacterium tuberculosis

<400> SEQUENCE: 651
gatggcactc acgctggaca agaccttcac aaaatctgaa atcctgaccc gatacttgaa 60
cctggtctcg ttcggcaata actcgttcgg cgtgcaggac gcggcgcaaa cgtacttcgg 120
catcaacgcg tccgacctga aattggcagc aaaccggcgc tgctgggccg ggcatggtgc 180
aatccgaaca agcacgctca acccgtacac caaccccgaa gggccgctgg cccggcggaa 240
ccttgtcctc ca 252

<210> SEQ ID NO 652
<211> LENGTH: 402
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 652
aacagctatg accatgatta cgccaagcta tttaggtgac actatagaat actcaagctt 60
ctgggcgtcg tggtgcccgg cctgccggtg caggaactgg attttactgc catctctcgc 120
gaccctgagg tggtccaggc ttacaacacc gacccactcg tgcaccacgg acgggttccg 180
gccgggattg gccgcgcgct gctgcangtg ggcgagacca tgccgcggcg ancaccggca 240
ttgaccgcgc cgctgctagt gctgcacggc accgatgacc ggctgatccc catcgaaggc 300
agccgtcgcc tggtcnaatg tntnggatcn gccgacgtgc anctgaanga ntatccccgg 360
ctgtnccacn aggtgttcaa cgaaccggan cgcaaccaag tg 402

<210> SEQ ID NO 653
<211> LENGTH: 429

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 653
caaggcatac gccaagaccc aagggatcgc agtcacctcc gtcaacggcc tggtcgccgg 60
ccacgggtcc gtgcaggaga cgtggctggc catgcaaagc gccgccgcct tatcaggaac 120
gccccggctt gtcggctttt cctgcatcga cacatttccg gaggtgttgt ggttggcgca 180
ncgcgcgaga caggcctggg atggcgtgcg catcgtcatc gggaatgcga tggcaacact 240
gaactacgag cgcatcctgc gccagcatga ctgtttcgac tacgtcgtcg ttggcgacgg 300
ggangtagcg ttcaccaagc tggccttggc cctggcgaat gacctgcggt tgacgactcc 360
cgggactaac ccgccgtant gagcaaggac agattctgcg cacaccctcc tcgctggtcg 420
accttgaca 429

<210> SEQ ID NO 654
<211> LENGTH: 353
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 654
aacagctatg accatgatta cgccaagcta tttaggtgac actatagaat actcaagctt 60
gccggtgatc tgggtggcca actcggcggg caccatctcc atcacgacng caaacgctcc 120
ggcttcggcg acagcgatcg cgtctgcgat ngtttgttcg gcggcgtctc cgcggccctg 180
cacccggaag ccgcccaagg tgttgacnct ttgcggggtg aagccgatgt gtgccatcac 240
cgggatnccc gccgcggtca gacangcgat ttgctcggcc acccgctcac cgccctcgan 300
cttgacngca tgtgcgccgc cgtccttgaa gaaaccggtg gcggnggcaa ccc 353

<210> SEQ ID NO 655
<211> LENGTH: 464
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 655
cgttgagatc cagctgcgca ctgtgcagcg cctcggtggt ctgctcggcc tgccgggata 60
actcgttgag cttggccagc gcgtcgtcgg ccggatcagc cagcacattc gcggccagga 120
cgccggagga gacggtgaag ctcgcaaaga aacctatggc ggaccgcatg attacacgcg 180
cgatcaacca cctctggtcg agcctcaaaa tttgcttcct taaacgggcc atcgacggat 240
gacgtcgagc tggtttaggt ctcaaacagg ttacgaaacg atctcggaat tgtccaaaag 300
gggaagttaa gaaaatggat agatttctac catttcgctg tggacgatcg tacttctgct 360
atagggctcc aggggcatcg acacgcaacg accttacgcg acaccggatc cgcgctggcg 420
gcggaacggc accangcgca accgaagggc caatccgaca tcgg 464

<210> SEQ ID NO 656
<211> LENGTH: 515
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 656
atactcaagc ttatctaggc gccagcttga ttggtctggt tgcattggcc agctgcgcga 60
gcctggctca cttcaactac aacaaccgca aacaattgcc gccttcggat ccgagttcgg 120
ttgggtacgc ggcaatggan caccatttct cggtgaatca gactattcct gagtacttga 180
tcatccactc tgcacacgac ctgcgaaccc cgcgcggcct tgccgacctg gagcagctgg 240
cgcaacgtgt gagccanatc ccaggcgttg ccatggttcg cggtgtgacc cggccaaacg 300
gggaaaccct tgaacaggcc cgggcgacat accaagccgg ccaagttggc aaccggctgg 360
gcggcgcgtc gcgaatgatc gatgagcgca ccggcgacct gaatcggctg gcatcgggtg 420
ccaacctgtt ggccgacaat ctcggtgact tcgcggtcaa gtcagccggg ccgttgcggg 480
tgtccgcagc cttgtccagc ccctcgctta ctcca 515

<210> SEQ ID NO 657
<211> LENGTH: 403
<212> TYPE: DNA
<213> ORGANISM: Mycobacterium tuberculosis

<400> SEQUENCE: 657
caggcatgca agctttttga gcgtcgcgcg gggcagcttc gccggcaatt ctactagcga 60
gaagtctggc ccgatacgga tctgaccgaa gtcgctgcgg tgcagcccac cctcattggc 120
gatggcgccg acgatggcgc ctggaccgat cttgtgccgc ttgccgacgg cgacgcggta 180
ggtggtcaag tccggtctac gcttgggcct ttgcggacgg tcccgacgct ggtcgcggtt 240
gcgccgcgaa agcggcgggt cgggtgccat caggaatgcc tcaccgccgc ggcactgcac 300
ggccagtgcc cgcggcgatt cagccatcgg gacatcatgc tcgcttcata ctcctcgacc 360
agtcggcgga acagctcgat tcccggaacg cccacgcatg gtg 403

<210> SEQ ID NO 658
<211> LENGTH: 444
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 658
aacagctatg accatgatta cgccaagcta tttaggtgac actatagaat actcaagctt 60
gtagaaaaag atcggtgagc gcatcgattc gctccgccgg gtttgccgct gcggcggcgg 120
agctgccgtg accgtctatt tgggtgatca gatactgggc tagttcggtc ggggtggggt 180
gatcgaagat cgcggtggcc ggcagcgtta ctgcggtgac agctgttaag cggttacgta 240
tctccacggc actcaaggaa ttaaatcccg aatcggcaaa cgcctggcca gcgtcnagtc 300
cggcagcgcc gtcncgcccc agcaccgctg cggcatgctc acataccacc tcgatcgctg 360
cggcganttg ctcgtcngcc gaccgaccgg ccanccgggc ggcaaacccn gaagacccaa 420
gaattcatca ccaccatcgc tagc 444

<210> SEQ ID NO 659
<211> LENGTH: 437
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 659
ccttcttgac acccacctcg ccatcgacct tgagcactcc gtcgtagttg gtgaacatgt 60
gaccggcgat cgggcgggtg aacgcgtact gggtgtcggt gtcgacgttc atcttcacca 120
cgccgtagcg cagcgcctcc tcgatctccg acttaagcga acccgagccg ccgtggaaca 180
cgaaatcnaa cggcttggcg tcngccggca gtccgagctt ggccgccgcc acctgttgcc 240
cttgcgcaag gatgtcnggg cgaancttga cgttgccggg cttgtanacg ccatgcacgt 300
tgccgaacgt cncggccagc angtatttgc cgtgctcacc ggcgcccanc gcctcgatgg 360
ttttctcgaa gtcctccggg ctggtgtaca gcttctcgtt gatctcgttc gccacgccgt 420
cctcttcgcc gccgacg 437

<210> SEQ ID NO 660
<211> LENGTH: 422
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 660
aacagctatg accatgatta cgccaagcta tttaggtgac actatagaat actcaagctt 60
ggaaaggaga tccccgggaa cctggtggca accccgccat tggggttgtt gggattgccg 120
atcagcgtga angaaagctc gtctggagac agcgggtcgg ccgaagccgc aagattggcc 180
atcactagtg acganatcgt ggcgctctgc gagtanccna agacagtgac gttgttnccg 240
gcggcaattt gctgccgaat cgcactttcg agaatgacng caccctgcgc caccgangaa 300
tcnaaagtga ggttcttgat cacgaccacc gggtngagcc cttggggcgt gaagancgcc 360
tgcgcnataa cacccgggac gctgccactc atgtncagcg cgttcgcgan ctcnacatat 420
ct 422

<210> SEQ ID NO 661
<211> LENGTH: 412
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 661
tcctggtgat cganggccgc ggttccggcc gaaaatccgg ttcgggttcg ggtcgcggtt 60
ccaacttgan cgcggtccgc agctgattca ccgtggcaac gccggccaac tgcgcataat 120
gcgcatccga accctcaccc gcccgccccg cgatcacccc aacctgatcc aacgacaacc 180
gcccctcccg catacccccgg gcgcagcgcg gaaactccgg caaccgccgc gccaccgtgg 240
cgatcgtgtg ggcgttgcct gacgaacanc ccatcttcca ggccaccaac cccgccaccg 300
accgcgcccc cgtcacaccc cacaacccgt cgcgatccag ctcagccacg atctccacaa 360
tgcgcccatc aatcgcattg cgctgaacgg gcaactccgc caactcctcc aa 412

<210> SEQ ID NO 662
<211> LENGTH: 467
<212> TYPE: DNA
<213> ORGANISM: Mycobacterium tuberculosis

<400> SEQUENCE: 662
aacagctatg accatgatta cgccaagcta tttaggtgac actatagaat actcaagatc 60
tggtacccat ccgtgataca ttgaggctgt tccctgggg tcgttacctt ccacgagcaa 120
aacacgtagc cccttcagag ccagatcctg agcaagatga acagaaactg aggttttgta 180
aacgccacct ttatgggcag caaccccgat caccggtgga aatacgtctt cagcacgtcg 240
caatcgcgta ccaaacacat cacgcatatg attaatttgt tcaattgtat aaccaacacg 300
ttgctcaacc cgtcctcgaa tttccatatc cgggtgcggt agtcgccctg ctttctcggc 360
atctctgata gcctgagaag aaaccccaac taaatccgct gcttcaccta ttctccagcg 420
ccgggttatt ttcctcgctt ccgggctgtc atcattaaac tgtgcaa 467

<210> SEQ ID NO 663
<211> LENGTH: 452
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 663
aacagctatg accatgatta cgccaagcta tttaggtgac actatagaat actcaagctt 60
ancgccacct cccgggcgga actccacggc gtggatnaag gtaccggccg ggatgttgcg 120
caatggcagg ttgttgcccg gcttgangtc cgcgttagcg ccggattcca ccacatcccc 180
ttgcgaaant ccgttgggtn cnatgatgtn ncgcttctcc ccntcnanat aatggancaa 240
cgcnatccgt gcggtacggt tcgggtcnta ctccatgtnc gcgaccttgg cgttganacc 300
atctttgtca ttgcggcgaa agtcnatcat ccggtnagcn cgcntatgan cgccgccttt 360
gtgccgggtg gtaatccggc catgcgcntt gcgtccaccg cgaacgtgca acgggggcnc 420
caacganttc tccngggttg aaccggtnat ct 452

<210> SEQ ID NO 664
<211> LENGTH: 93
<212> TYPE: DNA
<213> ORGANISM: Mycobacterium tuberculosis

<400> SEQUENCE: 664
tgtgtgtggt ggtaacccat ctgagcagtg tgccaaaccg gggcagccag ctcccaattg 60
acgtgagccc gctcacttgc tgggtaagcg tcg 93

<210> SEQ ID NO 665
<211> LENGTH: 352
<212> TYPE: DNA
<213> ORGANISM: Mycobacterium tuberculosis
<220> FEATURE:
<221> NAME/KEY: unsure
<222> LOCATION: (various positions within the sequence)

<223> OTHER INFORMATION: applicants are uncertain of bases designated as "n"

<400> SEQUENCE: 665
aacagctatg accatgatta cgccaagcta tttaggtgac actatanaat actcaagctt 60
gcgggtnatn gccttggtca acggcaccgt gatcggatcn gggtctaccg cacacatnga 120
ctggagcttc ggcgaantca tcgcctatgc ctcgcggggg gtgacgctga ncccnggtga 180
cntgttcngc tcnggcacgg tgcccacctg cacgctcntc naacacctca ngccaccgga 240
atcattcccn ggctggctgc acganagcga nnttgtcncc ctccaagtct aaaggctggg 300 cganananaagc anaacgtccc gacnaacggc actccttttc cntttgctct tc 352

<210> SEQ ID NO 666
<211> LENGTH: 448
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 666
gaaatcattg atggtttgag tcaccaggcc gatcaagcct tcgccgagcc aaattccaat 60
caagaggccc aagcccgtac caatcagccc ggcaacgagg gattccgtca ttatcagcca 120
aaataactgc tctcgggtta cacccaaaca gcgcaatatg gcgaaaaacg gtcgccgttg 180
cacgacatta aatgtcacgg tattgtagat taaaaagata cccaccaaca angcaatcaa 240
actgagagcg gttaaattga ccgtaaaagc gtccgtcatc tgtttgacng tgtcccgttg 300
ggtatccgac gtttccatac gcacaccggc cggcagtctt tgttggatgc gtnttgcaat 360
ggcctcatct ttgatgatca aatcgatgtn gctcagtctt ccgggcatat ggaacaactc 420
ttgggccgtg gaaatatcag caatgata 448

<210> SEQ ID NO 667
<211> LENGTH: 386
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 667
ctttcgccca ggccggcgcg gatgtcctca tcgcttcacg aacatcatcc gagcttgacg 60
ctgtcgccga acagatccgc gctgccggcc gccgcgccca caccgttgcc gccgatctgg 120
cccatcccga ggtgaccgcg cagctggctg gtcaggccgt cggagctttc gggaagctcg 180
acatcgtcgt caacaacgtt ggcggcacca tgcccaacac gctgctaagc acctcgacca 240
angacctcgc ggacgccttc gccttcaacg tgggcaccgc ccacgcgctg accgtcgcgg 300
cggtgccgtt gatgctggaa cactccggcg gcggcagcgt gatcaacatc agctccacca 360
tgggccggct ggcggcgcgg ggtttc 386

<210> SEQ ID NO 668
<211> LENGTH: 378
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 668
tgtgggctcc gatccggcgc gcatggcatc gacggcgacg ccgatcgatg acggccaggc 60
ttacgagctt gagggtgtga agttgtggac caccaacggt gtggtagcgg acctgctagt 120
ggttatggcg cgggtaccgc gcagtgaagg gcnccgaggg ggaatcancg cctttgtcgt 180
cgaggctgat tcgcccggga tcaccgtgga gcggcgcaac aagttcatgg gactgcgtgg 240
catcgaaaac ggcgtgaccc ggcttcntcg cgtcagggtg cccaaagaca acttgatcgc 300
anggaagcga cggtctgaag atcgcgctga ccacactcaa cgccggacgg ctgtccctac 360
cggcgatcca accggagt 378

<210> SEQ ID NO 669
<211> LENGTH: 344
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 669
gagctggccg agctggaccg gttcaccgcg gaactaccgt tctcgctcga cgactttcag 60
cagcgggctt gcagcgcgct ggaacgcggc cacggtgtgc tggtgtgcgc gccgaccggc 120
gctggcaaga cagtggtcgg cgagttcgcc gtgcacctgg cgctggcggc cggcagtaaa 180
tgtttctaca ccacgccgct gaaagccctg agcaaccaaa agcacaccga tctcacagca 240
cgctacggcc gtgaccagat ctggctgctg accggtgacc tgtcngtcaa cggcaaccgc 300
cggtggtggt gatgaccacc gaaatgctgc gcaacatgct ctac 344

<210> SEQ ID NO 670
<211> LENGTH: 411
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 670
gatctctgga tcggcggggc tctccgggcc ggcctcggcg acctcagcgg gccgcgcctt 60
ccggccgaac cattccctag ccatagatga ccgcacctcg atgcacggtt tggcggcaac 120
gcggcaaggc gtcngtcggg cccagccgcg gcaatgcggg tacccgggag cgcgggtcng 180
tanaccancg ctggactgcg tcgcgcggtg cgtcnacntc aaagtccccg gcgtcccata 240
tcgcgtatga cgcgggcgcg cccggcacca ngggtgccga tccggccgtc tcgaacacca 300
ccggcccgcc agccgccgcg ggtccggcag cnaacccgcc cgcgccgata cccgctgccc 360
gcgtgcgtga ttgaccgccg cgcgcacgct ggccanggat caaagcccgt g 411

<210> SEQ ID NO 671
<211> LENGTH: 473
<212> TYPE: DNA
<213> ORGANISM: Mycobacterium tuberculosis
<220> FEATURE:
<221> NAME/KEY: unsure
<222> LOCATION: (various positions within the sequence)

<223> OTHER INFORMATION: applicants are uncertain of bases designated as "n"

<400> SEQUENCE: 671
ggacgcgtag cccgccaggc cggtcagggt gcccttccag tccacgccgc tgtggtcggc 60
gaaccgctta tcttcaatcg agacgatcgc cagcttcatc gtgttggcga tcttgtccga 120
gggcacctcg aaccggcgct gcgagtncag ccacgcgatc gtgttgccct tcgcgtcgac 180
catcgtcgat accgcaggca cttgcccctc gagcagctgg gccgagccgt tggcaacgac 240
ctcagangca cgattggaca tcagccctag cccgcctgcg aacgggaacg tcagcgcagt 300
ggcgacgaca ctggccaaca gacagcaccc agccagcttc agaacggtga tcgcggccgg 360
gaagcgctcg ggcatgcgtn ctacagtagc gacctcctgt cactccacgt gccgctcggt 420
ccaatagaat ctttccgcgg gcgggtgaat ctctgcngga tcggggcngg cgc 473

<210> SEQ ID NO 672
<211> LENGTH: 357
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 672
gctcgttgcc ggcggcgatc tcgtcgagct cgtcttccat cgccgcggtg aagtcgtagt 60
cgacgagccg accgaaatgc tgctcgagca gaccggttac cgcgaacgcc acccatgacg 120
gcaccagtgc actgcccttc ttgtgcacgt ngccgcgatc ctggatggtc ttgatgatcg 180
acgantaggt cgacgggcgg ccgatgccca gctcctcgag cgctttgacc agcgacgcct 240
cngtgtnncg ggccggcggg ttggtggcat ggccgtctgg ggtcaactcg acnatgtcca 300
accgttgacc cggggtcaga tggggcagtc gccgctcggc atcgtcagcc tcgccgc 357

<210> SEQ ID NO 673
<211> LENGTH: 402
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 673
gtctttcgat ggctgcttct tcggcgctga cgctggcgat ctatcacccc cagcagttcg 60
tctacgcggg agcgatgtcg ggcctgttgg acccctccca ggcgatgggt cccaccctga 120
tcggcctggc gatgggtgac gctggcggct acaaggcctc cgacatgtgg ggcccgaagg 180
aggacccggc gtggcagcgc aacgacccgc tgttgaacgt cnggaanctg atcgccaacn 240
acacccncgt ctgggtgtac tgcggcaacn gcaagccgtc ggatctgggt ggcaacaacc 300
tgccggccaa gttcctcgag ggcttcgtgc ggaccatcaa catcaagttc caagacgcct 360
acaacgccng tggcggccac aaccgcgtgt tcgacttccc gg 402

<210> SEQ ID NO 674
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 674
gccaggtcga ggtcccatgc gcgtgggcca ttgatgctga tcgccaggac gtcaaanatt 60
tggtccggcg tcagctgggc gaaaaacgtg ggccccagga cttgcccgga gctgcccggg 120
ttcccgtcgc gcagctcggc ggccccggtc agaaanaaat tgcgccaggt cgcacactcc 180
gcgccgtang ccagctgctc cagggtgtcg gcatagagcc cgcgggccgc agcgtgctcg 240
ctgtcggcga acaccgcatg gtcgagaagc gttgccgccc aacggaaatc acctgcgtcn 300
aangcttcgc gggccaactc cagcactcgg tcgatg 336

<210> SEQ ID NO 675
<211> LENGTH: 405
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 675
naaacgttcc ggcttnggtg ccgggcgctt atttgcgtct ctgggatcac nctcagtcgc 60
cggcggctgc cgttgggcta tnanttgcac cganccggaa aatccgcacn anaactgcna 120
gtagcggcct gcagaantgc atcctcggcg aancngacta ccggtggaca ncnacaagcg 180
ccgccgaaca acgcactggc ccgagggatn ggcgtctatc ggccccgccc gtcgaactng 240
gaacagacng tgcggttcta ccgtgatctg gtgggaatgc tcnaccanac cttccccnann 300 gctacggaac nacggcgcga tattcngccn tcccanctcg agcctgacnc tngatatcgt 360
cgannctcac catcncgatc ngctgtgccg gtnttgctcg gactn 405

<210> SEQ ID NO 676
<211> LENGTH: 389
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 676
cgaacgacga acnccncaag ccatggtggt tggcgccgtc aaaaggtccg cggtcgccac 60
tactggaaaa tcgccttgag cgtcnctcga ccnccgcctc gagttgggtc ntaacgaaat 120
acctgatgcc gatcangtcn acgtctccgt cgcnncaacg tgcagcggcg acccactcta 180
cnangtctcg gtnccgccnc ggccagngca ccaccagtga cnaatccntg cgccntcggg 240
ccnagcantc ccggtgcnac cgnggtgggt ccggcgatgg tngggtgtnc tcnntacngg 300
aacgccagcg cnatcancat cggcanactc ncgtcgatgt gccgcggcgc aaccatcccc 360
cacaatgatc nggtgcgtct gatcaggcn 389

<210> SEQ ID NO 677
<211> LENGTH: 135
<212> TYPE: DNA
<213> ORGANISM: Mycobacterium tuberculosis

<400> SEQUENCE: 677
ttaggcgtga cggccaccgg ggccactccg cacaatctgt acccgaccaa gatctacacc 60
atcgaatacg acggcgtcgc cgactttccg cggtacccgc tcaactttgt gtcgaccctc 120
aacgccattg ccggc 135

<210> SEQ ID NO 678
<211> LENGTH: 140
<212> TYPE: DNA
<213> ORGANISM: Mycobacterium tuberculosis

<400> SEQUENCE: 678
cgtcaccccg atgcgcccag atcggggctt cgcagataaa gcacgaactg gcgggcaaaa 60
cgtcgatctc ggagccggaa gggcaatcag ccgaccgtcg acgaacgaca ccggcgagac 120
cacttaggca gtgacggcct 140

<210> SEQ ID NO 679
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 679
cttttcncga tgtctcatga tnccnangga gaacnntgcn ancncngccg ctgacntngc 60
ncaccgctnt ggcngnggtg acattggtgg tggttgcggg ctgcnacgcc cgactcgang 120
ccganccatn tnttgcggcc gaccgcntnt cgtctcnacc gcannccena tctcngccgc 180 ncccggtgga nctacngctn cttcgccatc tctcgccnat ggctccngcg nntcgcncaa 240
cgtntggttt ggtnanctgc ctacctggtc nt 272

<210> SEQ ID NO 680
<211> LENGTH: 507
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 680
gctgcgccag tcgttcggtg cggtcatgcc gttggaccna ccatcggagt tagttgccga 60
accgcggacc accgcaagca cccggtcctg gtcgcgcacc gcgtcggcca accgcttgag 120
caccaccacg ccgcagccct cgccgcgcac gaatccatcc gcgttggcgt cnaanctgtn 180
gcatcggtcg gtcggtgaca gcgccgacca cttggacagc gcgatggcgg tgaacggtna 240
ntaggtgacc tgccnccncg cccgccaatg cccacctccg cttcacncat gcgaatggtc 300
tgacacgccn agtgaattgc caccagcgac aacaaaaatc ggtatctncn gcgacggcgg 360
acacgcnatc ccnactgata ctcgatccgc cccaccgctt gnanctccgg gttccngtgc 420
tcatgtaccn tcatgtcggt ctgcgcncga tattgacgat cgtgtttccc acgannanag 480
ancctcatca cgccggttcg agtgccg 507

<210> SEQ ID NO 681
<211> LENGTH: 470
<212> TYPE: DNA
<213> ORGANISM: Mycobacterium tuberculosis
<220> FEATURE:

<221> NAME/KEY: unsure
<222> LOCATION: (various positions within the sequence)
<223> OTHER INFORMATION: applicants are uncertain of bases designated as “n”

<400> SEQUENCE: 681
ctgtgtgcgg ncggcgcgat atcggccttt ttactaaccg aacccgatgt gggctccgat 60
ccggcgcgca tggcatctac ngcgacgccg atcgatgacg gccaggctta cgagcttgag 120
ggtgtgaant tgtggaccnc caacggtgtg gtagcggacc tgctantggt tatggcgcgg 180
gtaccgcgca gtgaanggca ccgagggga atcancgcct ttgtcgtcta ngctgattct 240
cccgggatca ccntggagcg cnccncnant tcatgggact gcgtggcatc caanacggcg 300
tgaccggctt catccntcng ggtgcccaaa gacaacttga tcngcnngga agcgacgtct 360
gaanatcgcg ctgatcncac tcaacgccgg acgctgtcct accggcgatc gcaccggant 420
tgccaanccg cgctnannat ncgcgngaat gnccgtccac nantgcatgg 470

<210> SEQ ID NO 682
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 682
tggggtgccg ggcgccgagt tgcgtccctg ggatcacgca gagtcgccgg cggctgccgt 60
tgggctatga attgcaccga gccggaaaat ccgcancaaa actgcgagta gcggcctgca 120
gaagtgcanc ctcggcgaaa cggagtacgg tggacaacga aaagcgccgc cgaacnacgc 180
actggcccga gggattggcg tcaatcggcc ccgcccgtcg aacttggaag anacantgcg 240
gttctaccgt gatctggtgg gaatgctcca acnnaccttc nccgaaagct acggaagcna 300
cggcgcgatn ttcggccttc ccagctcgac ctgacgctgg aaatcg 346

<210> SEQ ID NO 683
<211> LENGTH: 453
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 683
nggcngggaa gttaatgccc tactggttcn atgctcncac ntcnccngtg acnncctgcn 60
ccgacccgcc gaggtcctgn ccgtnaccac cgancnggcg atccgggact ctngtacgca 120
tccaacanng ancaacgtgc acgggcggag tngtnccgcc acttcgncna tgacggggtc 180
gatccnttcg acgtccgtcg ccgcgtcggt cgagtggcgg tcacnctccn ngtactcgac 240
cncacngacg agaggactcg ancccatcta cgtgtggacg aaacanatct tctgtccnac 300
gactacacca ccacccaggc catcgccgnc gcccgcgang cccccttcgac gccntactgg 360 tccngnggng gcgctctccg gttgtctnnc ncntgncgtg ttccttcacn cactgcccna 420
catcganccc gagcnatncn angtccgtca atc 453

<210> SEQ ID NO 684
<211> LENGTH: 382

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 684
ggacactgtt cgcgtgcccc tcgtcaaagc cggagtggtc gtgctgcgcc ggacccgacc 60
cgaccttcag cgggggttca cagctccgtg ggtgccgtta cttccgatcg ccgcagtgtg 120
cgcgtgcctg tggctgatgc tgaacctcac cgcgttgact tggatccggt tcgggatctg 180
gctggtggcc ggaaccgcga tttatgtcng ctacgggcgc cggcactcgg cgcatggcct 240
tcggcaagcn cnananaacg cgacccggag gtgttgaact agcttcgccg cgtatttaca 300
aattgcntta tatgtctaca cataagacgc aaactgctct attgtcaant cccancgtgg 360
tgtggcncat gaagatgttt gg 382

<210> SEQ ID NO 685
<211> LENGTH: 408
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 685
tccttctcgg tatcggtttg ggctgtcacc ancagttggt agttcttcac gtnctgttgt 60
tcgagcgtcn agccgtcgcg cgtgtcnang tcnccggacg cgtatcccgc caggccggtc 120
anggtgccct tccantccac gccgctgtgg tcggcgaacg ctnatcttca atcgagacca 180
tcgccagctt catcntgttg gcgatcttgt cnnacggcac ctcnaaccgg cgctnctagt 240
acnccacncn atcntgttnc cttcncgtcn acatcctcga tnccncntgc actttccctc 300
gancncctgg gccgagccgt tggcantnac ctcngagccc cattggacat cancccancc 360
cgcctgcgaa cgggaacgtc agcncnctgg cgacaacctg gccaacan 408

<210> SEQ ID NO 686
<211> LENGTH: 372
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 686
cacnccgtga tcgcnagccc cngtagaaat ngttgagcca gttggtgcgg cgctcgttgc 60
cggcggtnat ctcgtcgagc tcntcttcca tcgccgcggt gaagtcgtac tcgacnagcc 120
gaccnaaatg ctgctcnagc agaccggtta ccnnnaacnc cncctcntga cngcaccagt 180
gcnctgccct tcttgtgcac gtacccgcna tcctggatgg tcttgatgat cnactantnt 240
gtcgacgggc ggccgatgcc catctcctcn agcgctttga ccagcgacnc ctcggtgtat 300
cgggccggcg ggttngtggc atggccgtct ggggtcanct cnacnatntt canccgttga 360
cccggggtca ca 372

<210> SEQ ID NO 687

<211> LENGTH: 403
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 687
tggccttctt gncangggcn nacatnngct atngcgagcg tgtaaccgat catcntccng 60
gcgactgtgg cctgancggc aagggtngcc tnattcntcc tcctgnggca tggttnccac 120
acggaatgnc ggtaagtctg gtcggcaacc tggcccgctg cgggttgggt tcggattcgc 180
tcggctanta aggtgctcgc ctggtgtnac nactaatcnc natatacnct tancgggagt 240
ngncgtcccg atcctngccc tgccgcnggc gatcncgttc gcancaccgc caccggaact 300
cncaangtgc gctcatcggg ctctacgcgc catcttcccc ggattcttcg cggcngngtn 360
ccgngggacc ccggactgtg acnggcccaa cggctcatca tcg 403

<210> SEQ ID NO 688
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 688
ccggatagcg gtgtctgaac ttcgcccgtt ccctccancg cattgagctt cagcccgacc 60
ggcaggtnng gagtcggcat gcggtccttc gccccgaccc cgctggctaa atanccaccc 120
ccgagcgcgg tcacggtctt tgcaccggga cgacgcatac cggcagcgcg aacatcnccg 180
cgggctgcag cntgaacgtc caataccant cnaacagtgt ccgcgcgtna aaacccganc 240
cggcggtcgc ttcngtaatc aacggctcct gcgcaaccag ctgcaagtcg ccggtgccac 300
cggcgttgac gatcttgatg tctgcganct cgcgcaccag ctcgacggcc cgggca 356

<210> SEQ ID NO 689
<211> LENGTH: 439
<212> TYPE: DNA
<213> ORGANISM: Mycobacterium tuberculosis

<400> SEQUENCE: 689
cctcccgacc acatacaggc aaagtaatgg cattaccgcg agccattact cctacgcgcg 60
caattaacga atccaccatc ggggcagctg gtgtcgataa cgaagtatct tcaaccggtt 120
gagtattgag cgtatgtttt ggaataacag gcgcacgctt cattatctaa tctcccagcg 180
tggtttaatc agacgatcga aaatttcatt gcagacaggt tcccaaatag aaagagcatt 240
tctccaggca ccagttgaag agcgttgatc aatggcctgt tcaaaaacag ttctcatccg 300
gatctgacct ttaccaactt catccgtttc acgtacaaca ttttttagaa ccatgcttcc 360
ccaggcatcc cgaatttgct cctccatcca cggggactga gagccattac tattgctgta 420
tttggtaagc aaaatacgt 439

<210> SEQ ID NO 690
<211> LENGTH: 442
<212> TYPE: DNA
<213> ORGANISM: Mycobacterium tuberculosis
<220> FEATURE:

<221> NAME/KEY: unsure
<222> LOCATION: (various positions within the sequence)
<223> OTHER INFORMATION: applicants are uncertain of bases designated
      as "n"

<400> SEQUENCE: 690
cttcacntcc gtacggctcg ggtacgcttc ggtcncattg tgcgagtgat agatgacgac 60
cgggacctcg tcggcatctt ccatagcccg ccacaccttc agttgctcac cggaatccaa 120
ccggtanaag gtcggcganc gctcngcatt ggtcatcggg atatgccgct cgggacggtc 180
anagccctcg ggtccggcca gcactccgca ggcttcgtcg gggtggtcgc gacgcgcatg 240
ggccaccatc gcattcacca ggtctgcgcg aatcaccagc acgtanacgg ttcctttcct 300
aagcaacacc gaantttcag gacccgaatg ctccgggaaa catgtcacgg taggtcggta 360
ttccggctac cggctganca ttgagcacgc cggccagcac cgcacgaacc aggcaatcag 420
ccgccgccgc acccgaccgc gg 442

<210> SEQ ID NO 691
<211> LENGTH: 365
<212> TYPE: DNA
<213> ORGANISM: Mycobacterium tuberculosis

<400> SEQUENCE: 691
caggcatgca agcttgatgc cgccgaaacc gagcgtgagc acgccgccag ccaccacgcg 60
cgggtcgggc gccgggcccg ggccgccagg ctgctccgct cggtgatggc acgccaccgc 120
gacaccaccc ggctgcgcta cgtcgagcca taccgggcgg agctacatcg gctcggccgc 180
ccagtgttcg ggccctcttt cgaggtcgag gtcgataccg atttgcgcat ccgcagccgc 240
accctggacg acagaaccgt gccctacgaa ttgcttgtcg ggcggggcca aagaacagct 300
tggcatcctg gcgcgattgg ccggcgcggc gctggtcgcc aaggaagacc cgttccggtg 360
ctgat 365

<210> SEQ ID NO 692
<211> LENGTH: 307
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 692
aagntcgggt ttccacacgc gcggtttgac cctagtcata tgtaatcatg tgtaccatgt 60
gcgggcgctt ttcgacggcc gcgaaccacc gganatttcc tgtgatttca ctgcatgcgt 120
accatctggc acaattgagc anttgtctnt cgcggtggtc ggncgggttg cgtgccgcct 180
gctgcganat gcaccantaa gcccgaaccc accggcttgg tgaccaccgc acgctgcgtg 240
tggggggtaa ccactccgcg accccaagga tggtcatttc caatgaaccg gctggacttc 300 gtccana 307

<210> SEQ ID NO 693
<211> LENGTH: 414
<212> TYPE: DNA
<213> ORGANISM: Mycobacterium bovis

<400> SEQUENCE: 693
gtcgcggttc gatcgacccg atcttcacct cgtaacctcg atgcttagca ggatccagct 60
tgaccgcgtt tggctctacc cactctttga gtggcgccgt cgcctgtgcc ccatcggtgt 120
tcatgacgaa cgcttcgaaa gacttcctct tgtgagccgg aatgtctgcg taaagaagtt 180
ccatgtccgg gaagtagacc cggtcgccct ccacgtggta ctccttcgag gtccgcttct 240
cgccggatcc gataaacacc ggccccaggc accgcagcgt gagttcgaac ggcttcaggt 300
aggtgttcat gcggcggact ccgggagtgc gagaaatagc ggtcgcgcgt agctgtagac 360
cggatggttt ccgcccaggc tgacgtcgaa gatgcctcct tggaaggggc gcga 414

<210> SEQ ID NO 694
<211> LENGTH: 256
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 694
aactcaagtt tttacggtga tcgcgcatca cctggttcat gaactggaag cagcgcagcg 60
cttccttttc ggccgcaaca tgagccagcc tctcgtcggc ggtcgggtgc aggtgctcgg 120
gcagctcggc cgcgacagcc gcctgaccct gaaaccagct tccatatccc gcgacnaacg 180
acgccagtcc gctacgtaac ccctccgcga ctgtccatgg acaacagcgc gttctccacc 240
gaccgggccc gggtgt 256

<210> SEQ ID NO 695
<211> LENGTH: 328
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 695
gtgcaggttt cgacaatgtg gtgccggttc ggcggctacg tgccatcgag acactggcgc 60
angctatcgc acccgttatc ggctgcgagc aaatcgcggt atgcgttctt gagcatgagt 120
cggcgaccgt cgtcatggtc gacacccacg acggaaagac gcagatcgcc gtcaagcatg 180
tgtgccgcgg attatcagga ctgacctcct ggctgaccgg catgtttggt cgcgatgcct 240
ggcgcccggc cggcgtggtc gtggtcggct cggatagcga ggtcagcgaa ttctcgtggc 300
agctcgaaag ggtcctgccg gtgccggt 328

<210> SEQ ID NO 696
<211> LENGTH: 278
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 696
ttcgagtcat gcgcccgcct cgaccacgaa natgcacgtc gnggttcgat cgacccgatc 60
ttcacctcgt aacctcgatg cttagcagga tccagcttga ccgcgtttgg ctctacccac 120
tctttgagtg gcgccgtcgc ctgtgcccca tcggtgttca tgacgaacgc ttcgaaagac 180
ttcctcttgt gagccggaat gtctgcgtaa agaagttcca tgtccgggaa gtagacccgg 240
tcgccctcca cgtggtactc cttcgaggtc cgcttctc 278

<210> SEQ ID NO 697
<211> LENGTH: 264
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 697
gtcatgtgta ccatttgcgg gcgcttttcg acggccgcga aacaccggag atttcctgtg 60
atttcactgc atgcgtaccg tctggcacaa ttgagcagtt gtctgtcgcg gtggtcggcc 120
gggttgcgtg ccgcctgctg cgagatgcac caataagccc gaacccaccg gcttggtgac 180
caccgcacgc tgcgtgtggg gggtaaccac gccgcgaccc caaggatggt catttccaat 240
gaaccggctg gacttcntca acaa 264

<210> SEQ ID NO 698
<211> LENGTH: 169
<212> TYPE: DNA
<213> ORGANISM: Mycobacterium bovis

<400> SEQUENCE: 698
aacagcgcgg ttgaactgat aggtgcggcc cggctcgagc aggccgggcc atttgttcga 60
tgcggttacc gaaagatctc ttcggtgacc tgcccgccgc cggccagctc ggcccagtgc 120
ccggcgttgg ccgccgcggc gacgatcttg gcgtccacgg tggtcgggg 169

<210> SEQ ID NO 699
<211> LENGTH: 256
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 699
gcatctgggc tggcggtggt tcgccgctcc gaagccgtcg aacaccatcg ccagcgcggc 60
ttccacatca acgaccattt cggccagctt gcggcgcatc agcggcttgt cgatgagcgc 120
cccaccgaat gcccgccgct gcccggcgta ncacagcgat tcgaccagcg cgcggcgcgc 180
gttgccgagg gcgaacgaag cggtgcccaa ccgcaatctg ttggtcagct ccatcatgcg 240
ggtgagtccc ttgccg 256

<210> SEQ ID NO 700
<211> LENGTH: 291
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 700
atcggtttcc agcaacagcc gatcgacggc ttcgcccagg ccgctcccgg gcgacccgac 60
cattgctgtc gccgcgtaac gccatcacgg atgacgcgca gttcgtcgct gtctagctcc 120

```
accatcgcct gcacaccggc ggccagnacc cattggccgt cgcactcgta nagcaggtaa    180

tcctcgtcga cggactcggt aaccaccgcc gccagctccg ctgccaggtc ggcggggttg    240

acaccggcgg gcatcgggat ggacgacgac gcggtgctga cggcgcctgt c             291


<210> SEQ ID NO 701
<211> LENGTH: 315
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 701

agcggtttcc cangcgggat gtgctgtgag cgccgcacca ccagcgccga cgctaaggat     60

ggaacgcacg gcatcttctg acgcgtaacc gcgttgtgat cgcgagctga ggagacggta    120

tgggggaggg ttctcggagg ccatctggga tgttgatgtc tgtcgatctt gagccggtgc    180

aactcgtcgg cccggacggt acgccgacgg ccgaacgccg ctaccaccgt gaccttcctg    240

aggaaacgct gcgttggctc tacgagatga tggtggtcac ccgcgagctg gataccgaat    300

tcgtcaatct gcacg                                                     315


<210> SEQ ID NO 702
<211> LENGTH: 328
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 702

caagcttcca caggtaggga tcgaggaaca gcgcgttgaa ctgataggtg cggcccggct     60

cgagcaggcc ggccatttgt tcgatgcggt taccgaaaat ctcttcggtg acctgcccgc    120

cgccggccag ctcggcccag tgcccggcgt tggccgccgc ggcaacgatc ttggcgtcca    180

cggtggtcgg ggtcatgccc gcgagcagga tcggcgagcg gccggtcagc cgggtgaact    240

tcgtcgaaag cttgaccctg ccgtcgggga ggcgaaccac ggtcggtgcg tanctccacc    300

aagcccgggc aacctcgggg gtggcgcc                                       328


<210> SEQ ID NO 703
<211> LENGTH: 352
<212> TYPE: DNA
<213> ORGANISM: Mycobacterium bovis

<400> SEQUENCE: 703

tggacctcat gacaacgcgg cggcgattac ccccgctacc gccagcagca tgacggcggt     60

agcgaacacc gccggatgca gcgcaggtgc gtcgatgtgc tcacggaatc gccccggcac    120

cgcgatctcg aggatcacca gtgccacccc ctgcagcgcg acaccgacga ttccgtacac    180

cgccacgccg atcaggccct gggccagctg gcgtatatgg cggcgatggt gacgatggcc    240

agcgccacat acattgtggc ggccagaacc acggcgttgg ggcggcggtc gatgaacact    300

aggcgacgca gatcgcccgg ggtcaacagg ttgaccatca gaaagcctgc ga            352


<210> SEQ ID NO 704
<211> LENGTH: 315
<212> TYPE: DNA
```

<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 704
tttggtgcgg ccggcaatca acttcngctc ncagcggttt cccaggcggg atgtgctgtg 60
agcgccgcac caccagcgcc gacgctaagg atggaacgca cggcatcttc tgacgcgtaa 120
ccgcgttgtg atcgcgagct gaggagacgg tatgggggag ggttctcgga ggccatctgg 180
gatgttgatg tctgtcgatc ttgagccggt gcaactcgtc ggcccggacg gtacgccgac 240
ggccgaacgc cgctaccacc gtgaccttcc tgaggaaacg ctgcgttggc tctacgatat 300
gatggtggtc acccg 315

<210> SEQ ID NO 705
<211> LENGTH: 390
<212> TYPE: DNA
<213> ORGANISM: Mycobacterium bovis

<400> SEQUENCE: 705
cgcccagggc cgctcccggg cgacccgacc attgctgtcg ccgcgtaacg ccatcacgga 60
tgacgcgcag ttcgtcgctg tctagctcca ccatcgcctg cacaccggcg gccaggaccc 120
attggccgtc gcactcgtag agcaggtaat cctcgtcgac ggactcggta accaccgccg 180
ccagctccgc tgccaggtcg gcggggttga caccggcggg catcgggatg gacgacgacg 240
cggtgctgac ggcgcctgtc gcgacgctga gctcggacac agctagtaaa tgtagcctaa 300
cctacttaat gggtcgcagc cccccggggt cgtcgcatgt ccaacgttgc tcgactggaa 360
gaaaatgctc gtcggggagc aaatggcacc 390

<210> SEQ ID NO 706
<211> LENGTH: 322
<212> TYPE: DNA
<213> ORGANISM: Mycobacterium bovis

<400> SEQUENCE: 706
aatactcaat cttgatcggt ttccagcaac agccgatcga cggcttcgcc cagggccgct 60
cccgggcgac ccgaccattg ctgtcgccgc gtaacgccat cacggatgac gcgcagttcg 120
tcgctgtcta gctccaccat cgcctgcaca ccggcggcca ggacccattg gccgtcgcac 180
tcgtagagca ggtaatcctc gtcgacggac tcggtaacca ccgccgccag ctccgctgcc 240
aggtcggcgg ggttgacacc ggcgggcatc gggatggacg acgacgcggt gctgacggcg 300
cctgtcgcga ctctgagctc gg 322

<210> SEQ ID NO 707
<211> LENGTH: 398
<212> TYPE: DNA
<213> ORGANISM: Mycobacterium bovis

<400> SEQUENCE: 707
ggatgtgctg tgagcgccgc accaccagcg ccgacgctaa ggatggaacg cacggcatct 60
tctgacgcgt aaccgcgttg tgatcgcgag ctgaggagac ggtatggggg agggttctcg 120
gaggccatct gggatgttga tgtctgtcga tcttgagccg gtgcaactcg tcggcccgga 180
cggtacgccg acggccgaac gccgctacca ccgtgacctt cctgaggaaa cgctgcgttg 240
gctctacgag atgatggtgg tcacccgcga gctggatacc gaattcgtca atctgcagcg 300
ccagggggaa gctggcgttg tacacgccct gtcgcgggca ggaagccgcg caggtgggtg 360
cggcggcttg cctacgcaaa accgactggt tgttcccc 398

<210> SEQ ID NO 708
<211> LENGTH: 175
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 708
atcacgacaa cagcgacggt gtgtcggatc agcggccccc gttgccgggc aatgttgagg 60
cgtttctgcg tctggttgag gccggctggg acnccgaggt ggctcgtcgg ccacatgggc 120
agcacaccac cgtggtgatg catctagacg tgcaggaccg tgccgctggc ctgca 175

<210> SEQ ID NO 709
<211> LENGTH: 210
<212> TYPE: DNA
<213> ORGANISM: Mycobacterium bovis

<400> SEQUENCE: 709
gcggctacgt gccatcgaga cactggcgca ggctatcgca cccgttatcg gctgcgagca 60
aatcgcggta tgcgttcttg agcatgagtc ggcgaccgtc gtcatggtcg acacccacga 120
cggaaagacg cagatcgccg tcaagcatgt gtgccgcgga ttatcaggac tgacctcctg 180
gctgaccggc atgtttggtc gcgatgcctg 210

<210> SEQ ID NO 710
<211> LENGTH: 312
<212> TYPE: DNA
<213> ORGANISM: Mycobacterium bovis

<400> SEQUENCE: 710
tacaagcggc acctcgccgg tgaactgacc gttcgcacgc tgcgcaccgc cgccgggcgc 60
gtgctcggcg cgccggcggc ccccgaggcc tgagagggga accaaccatg caggtgaaca 120
tgacggtaaa cggcgagccc gtcaccgccg aggtcgaacc ccggatgctg ctggtccatt 180
ttctccgtga tcagctgcgg ctcaccggaa ctcactgggg ctgtgatacc agcaactgcg 240
ggacatgcgt ggtggaggtc gacggcgtgc cggtgaaatc ctgcacgatg ctcgccgtga 300
tggcctccgg gc 312

<210> SEQ ID NO 711
<211> LENGTH: 255
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 711
agcggctggt tacgactccc tgtttgtgat ggaccacttc taccaactgc ccatgttggg 60
gacgcccgnc cntccgatgc tggaagccta cactgccctt ggtgcgctgg ccncngcgac 120
cgagcggctg caactgggcg cnttggtgac cngcaatacc taccgcaccc cnaccctgct 180
ggncaaanat catcaccacg ctcgacttgg ttagcgccgg tcgancgatc ctcggcattg 240
gaaccggttg gtttn 255

<210> SEQ ID NO 712
<211> LENGTH: 304
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 712
acgcgcgccg atcatatctg ctatggatgt acaattcagc tcttgctgtt ataccagtat 60
atggtgtact atttgatcta tgctgacgtg tgagatgcgg gaatcggccc tggctcgact 120
cggccgggct ctggctgatc cgacgcggtg ccggattctg gtggcgttgc tggatggcgt 180
ttgctatccc ggccagctag ctgcgcacct cgggttgacc cgatcgaatg tgtccaacca 240
tctgtcgtgt ttgcggggct gcgggctggt antcccaacc tatgagggcc ggcaggttcg 300
gtat 304

<210> SEQ ID NO 713
<211> LENGTH: 352
<212> TYPE: DNA
<213> ORGANISM: Mycobacterium bovis

<400> SEQUENCE: 713
ccgcgctgct gctgacgtcg gtcgaacgtg cgacacgtct gcgaataccg gccgaacgct 60
gggtttatcc acaggctggc accgacgccc acgacacacc ggccgtcgcc gaccgccacc 120
gactgcatcg gtcgacggcc attcggatcg ccggtgcccg ggcgctggaa ctggctgggc 180
tggggctcga tgacatcgaa tacgtcgacc tgtattcgtg ctttccctcc gctgtccaag 240
tcgccgcaat cgaactcggc ctggacaccg acgatcctgc ccgcccgctg accgtcaccg 300
ggggcctgac cttcgccggc gggccgtgga gcaattacgt cacgcactcc at 352

<210> SEQ ID NO 714
<211> LENGTH: 233
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 714
caggcgtgca atgacctgca ctgcgccgga nantccctaa cccactaaac cggggccgct 60
cacaagccgt gcagctcggt cagcgtcagg tgcgcgacca ggaantaaat gagcagaccc 120
gtgccgtcaa cgatggtggc gatcatcggc cccgaaacga tggccgggtc natgcgcaac 180
ttcttcagca gcggcggaag gacggcancc accagcgacn accacaccac gat 233

<210> SEQ ID NO 715
<211> LENGTH: 335
<212> TYPE: DNA
<213> ORGANISM: Mycobacterium bovis

<400> SEQUENCE: 715
gcgaacactt cgtcaacttc cagggctgcc cgcaccaagt atttcgacga gtatttccgt 60
cgggccgccg ccgccggcgc gcggcaggtg gtcatcctgg cggcggggct ggactcgcgc 120
gcgtaccggc tgccttggcc cgacgggacc acggtttttg agctggaccg cccgcaggtc 180
cttgatttca agcgcgaggt gctcgccagc cacggtgccc aaccgcgcgc cctgcgccgc 240
gagatcgccg tcgacctgcg tgacgattgg ccacaagcct tgcgggacag tggtttcgat 300
gcggctgcac cgtcggcatg gattgccgaa gggct 335

<210> SEQ ID NO 716
<211> LENGTH: 274
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 716
ttgggcnttg cccncaatan ggccccaatc aaaagccgag caggtggaac ctanncgcat 60
tcgcctcntc gtntgtgcac ccgagccatc gcacgcgcgg gaattcccgg atntcnccgt 120
attctccggc ggccgggcta acccatccca ngccgaacgg ttggctcntg ccgtgggtcc 180
cgtgttggcc gatcggggcg tcaccggggg tgctcgggtg cggntgacca tggcnaactg 240
ccccnatggg ccgaccctgg tgcagataaa cctg 274

<210> SEQ ID NO 717
<211> LENGTH: 327
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 717
tggtggaggt ccccaccaan acccggccgt aactctgctc acggaaatgc ggncaggccg 60
cgcgtagcac gtggtatccg ccataaaggt gcaccttaag cacggcgtcc caattctcga 120
acgacatctt gtggaaggtg ccgtcgcgca agatcccggc gttgctcacc acaccgtgca 180
cggcgccgaa ttcgtcaagc gcggtcttga tgatgttcgc tgcgccgtcc tcggtggcga 240
cgctgtcggt anttggcgac cgcccggccc cccttgtcgc gaaatctcgg cgacgacctc 300
atcggccatc gccgaaccgg gcgcccg 327

<210> SEQ ID NO 718
<211> LENGTH: 344
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 718
gccggccaaa ctggccggcg gggttgctgt cntcaaggtg ggttccgcca ccaanaccnc 60
actcaaggat cgcaaggaaa gcntcaagga tgcggtcgcg gccgccaagg ccgcggtcaa 120
ggagggcatc gtccctggtg gggganccte cctcatccac caggcccgca aggcgctgac 180
cgaactgcnt gcgtcncnga ccggtgacaa ngtcctcggt gtccacgtgt nctccgaagc 240
ccttgccgct ccgttgttct ggatcnccnc caacnctggc ttggacggct cngtggtggt 300
caacaaggtc agcgagctac ccgccgggca tgggctgaac gtga 344

<210> SEQ ID NO 719
<211> LENGTH: 271
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 719
cgaacctnaa ttgtcctgta atgcccagct caccaangca tggctggtgg ccggggcggt 60
gaagccggcg tctgcggcac cgtccaactc natgtggatn gccggaatgg ggatgtccgg 120
nacggcgaat ccgtanttcg cttgtcccgt gaggcccagg tggatggggg gaaggatcnt 180
ggtgtccggg atgatnatgg ggccgatgcc gccggttgaa gtccactgga tcgggaattc 240
gggaatcgtg atnccgacgt tcaggccgaa c 271

<210> SEQ ID NO 720
<211> LENGTH: 302
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 720
ctaacggaat gaaagccctg gtggccgtnt cggcggtggc cgtcgtcgca ctgctcggtg 60
tatcttccgc ccaagctgat cccgaggcgg atcccggcgc aggtgaggcc aactatggtg 120
gccccccaag ttccccacgt cttgtcgatc acaccgaatg ggcgcantgg ggaattctgc 180
ccagcctccg ggtctacccg tcccaagttg ggcgtacanc ctcccgccgc ctcgggatgg 240
ccgctgccga cccggcctgg gccnaggttc tcgcgctgtc accggaagcc gacactgccg 300
gc 302

<210> SEQ ID NO 721
<211> LENGTH: 303
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 721
ccgcgggaca cncctcnatg ctgccgccat ggacgcggtc gaacgcaagc agctgatcga 60
gctacaacgc cgcgcggaac gcttccgccg cgggcgtgac cgcatcccgt tgaccgggcg 120
gatcgcggtg atcgtcgatg acggcatcgc caccggagcg acggccaagg cggcgtgcca 180
ggtcgcccgg gcgcacggtg cggacaaggt ggtgctggcg gtcccgatcg gcccanacga 240
catcgtggcg aagattcgcc gggtacgccg atgatgtggt gtgtttggcg acgccggcgt 300
tgt 303

<210> SEQ ID NO 722
<211> LENGTH: 280
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 722
ctctgggacc ggccacggtg ccnccggcgt tcccggacgt gctgcgccag gtgtccggcg 60
gccgcgtgca tggtgttccc ggatcggccg ctggccagag cccaccggtg aatctggcgc 120
ctggccgacc accgtgcgcc gtaggcttgc gatcgtgcag cgctggcgtg gccaggacga 180
gatcccgacg gattggggca gatgcgtgct caccatcggg gtatttgacg gcgtgcaccg 240
cgggcacgcc gaactgatcg cgcacgcggt caaaggcggc 280

<210> SEQ ID NO 723
<211> LENGTH: 333
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 723
aatactcaag ctttcgtcag ttcattgcgc cagcagacca acaanagcat cgggacatac 60
ggantcaact acccggccaa cggtgatttc ttggccgccg ctgacggcgc gaacgacgcc 120
agcgaccacn ttcagcaaat ggccancgcg tgccgggcca cgaggttggt gctcggcggc 180
tactcccagg gtgcggccgt gatcnacatc ntcaccgccg caccactgcc cggcctcggg 240
ttcacgcagc cgttgccgcc cgcagcggac natcacatcg ccgcgatcgc cctgttcggg 300
aatccctcng gccgcgctgg cgggctgatt aac 333

<210> SEQ ID NO 724
<211> LENGTH: 320
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 724
tgccgcggat ttggctggct gcccaatatt cagaatcggg cctttctttt tgcgcgacaa 60
taaggtcaca gtaaaccctc gttttgtgag atgcggggcg ggccgggcga antcgacctc 120
gagtgaatgg atctcgagtg aatggacagg gcatcgccta cgagtcgcat ccccatccaa 180
cagaccggtg ctcttgcatc ggaccctgaa ggtcccgcac ggagggtgtg gttgccggcg 240
cggggtcacg gtgcggtagc gacgtagtgt ttgaacgaat ttcttgatgc tccaacctgt 300
ttggtgttca atccagttct 320

<210> SEQ ID NO 725
<211> LENGTH: 296
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 725
aancttgcgc gctcggccgg gtcnagcatc cagctgctcg gcaaggaggc cagctacncn 60
tcgctgcgta tgcccagcgg tgagatccgc cgggtcnacg tccgctgccg cgcgaccgtc 120
ggcgaagtgg gcaatgccga gcaggcaaac atcaactggg gcaaggccgg tcggatgcgg 180
tggaagggca agcgcccgtc ggtccggggc gtggtgatna acccggtcna ccacccgcac 240
ggcggtggtg agggtaaaac ctccggcggc cgtcacccgg ttagcccgtg gggcaa 296

<210> SEQ ID NO 726
<211> LENGTH: 304
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 726
antcgaaagt gaccatctct accttgagtg ccataccgcc cgaccctatg cctcggatag 60
ctcggcggaa agaaacgctt gcagtgccgc cgaataggcg gctacgtcgt gagcgcccat 120
caactctcgc gcggagtgca tcgccagctg ggcggcgccg acgtcgaccg tggggattcc 180
ggtgcgcgcc gcggccaacg gcccgatcgt cgacccgcac ggcagatcgg cgcgatgttc 240
gtaacgctgc ataggcactc ccgcgcgctg gcaggccagt gcgaacgccg ccgcggtgcg 300
tccg 304

<210> SEQ ID NO 727
<211> LENGTH: 318
<212> TYPE: PRT
<213> ORGANISM: Mycobacterium sp.

<400> SEQUENCE: 727

Pro Thr Gln Thr Leu Thr Gly Arg Pro Leu Ile Gly Asn Gly Thr Pro
1 5 10 15

Gly Ala Val Gly Ser Gly Ala Thr Gly Ala Pro Gly Gly Trp Leu Leu
20 25 30

Gly Asp Gly Gly Ala Gly Gly Ser Gly Ala Ala Gly Ser Gly Ala Pro
35 40 45

Gly Gly Ala Gly Gly Ala Ala Gly Leu Trp Gly Thr Gly Gly Ala Gly
50 55 60

Gly Ala Gly Gly Ser Ser Ala Gly Gly Gly Gly Ala Gly Gly Ala Gly
65 70 75 80

Gly Ala Gly Gly Trp Leu Leu Gly Asp Gly Gly Ala Gly Gly Ile Gly
85 90 95

Gly Ala Ser Thr Val Leu Gly Gly Thr Gly Gly Gly Gly Gly Val Gly
100 105 110

Gly Leu Trp Gly Ala Gly Gly Ala Gly Gly Ala Gly Gly Thr Gly Leu
115 120 125

Val Gly Gly Asp Gly Gly Ala Gly Gly Ala Gly Gly Thr Gly Gly Leu
130 135 140

Leu Ala Gly Leu Ile Gly Ala Gly Gly Gly His Gly Gly Thr Gly Gly
145 150 155 160

Leu Ser Thr Asn Gly Asp Gly Gly Val Gly Gly Ala Gly Gly Asn Ala
165 170 175

Gly Met Leu Ala Gly Pro Gly Gly Ala Gly Gly Ala Gly Gly Asp Gly
180 185 190

```
Glu Asn Leu Asp Thr Gly Gly Asp Gly Gly Ala Gly Gly Ser Ala Gly
        195                 200                 205

Leu Leu Phe Gly Ser Gly Gly Ala Gly Gly Ala Gly Gly Phe Gly Phe
    210                 215                 220

Leu Gly Gly Asp Gly Gly Ala Gly Gly Asn Ala Gly Leu Leu Leu Ser
225                 230                 235                 240

Ser Gly Gly Ala Gly Gly Phe Gly Gly Phe Gly Thr Ala Gly Gly Val
                245                 250                 255

Gly Gly Ala Gly Gly Asn Ala Gly Trp Leu Gly Phe Gly Gly Ala Gly
            260                 265                 270

Gly Val Gly Gly Ser Ala Gly Leu Ile Gly Thr Gly Gly Asn Gly Gly
        275                 280                 285

Asn Gly Gly Thr Gly Ala Asn Ala Gly Ser Pro Gly Thr Gly Gly Ala
    290                 295                 300

Gly Gly Leu Leu Leu Gly Gln Asn Gly Leu Asn Gly Leu Pro
305                 310                 315


<210> SEQ ID NO 728
<211> LENGTH: 334
<212> TYPE: PRT
<213> ORGANISM: Mycobacterium sp.

<400> SEQUENCE: 728

Pro Thr Gln Thr Leu Thr Gly Arg Pro Leu Ile Gly Asn Gly Thr Pro
  1               5                  10                  15

Gly Ala Val Gly Ser Gly Ala Thr Gly Ala Pro Gly Gly Trp Leu Leu
            20                  25                  30

Gly Asp Gly Gly Ala Gly Gly Ser Gly Ala Ala Gly Ser Gly Ala Pro
        35                  40                  45

Gly Gly Ala Gly Gly Ala Ala Gly Leu Trp Gly Thr Gly Gly Ala Gly
     50                  55                  60

Gly Ile Gly Gly Ala Ser Thr Val Leu Gly Gly Thr Gly Gly Gly Gly
 65                  70                  75                  80

Gly Val Gly Gly Leu Trp Gly Ala Gly Gly Ala Gly Gly Ala Gly Gly
                 85                  90                  95

Thr Gly Leu Val Gly Gly Asp Gly Gly Ala Gly Gly Ala Gly Gly Thr
            100                 105                 110

Gly Gly Leu Leu Ala Gly Leu Ile Gly Ala Gly Gly Gly His Gly Gly
        115                 120                 125

Thr Gly Gly Leu Ser Thr Asn Gly Asp Gly Gly Val Gly Gly Ala Gly
    130                 135                 140

Gly Asn Ala Gly Met Leu Ala Gly Pro Gly Gly Ala Gly Gly Ala Gly
145                 150                 155                 160

Gly Asp Gly Glu Asn Leu Asp Thr Gly Gly Asp Gly Gly Ala Gly Gly
                165                 170                 175

Ser Ala Gly Leu Leu Phe Gly Ser Gly Gly Ala Gly Gly Ala Gly Gly
            180                 185                 190

Phe Gly Phe Leu Gly Gly Asp Gly Gly Ala Gly Gly Asn Ala Gly Leu
        195                 200                 205

Leu Leu Ser Ser Gly Gly Ala Gly Gly Phe Gly Gly Phe Gly Thr Ala
    210                 215                 220

Gly Gly Val Gly Gly Ala Gly Gly Asn Ala Gly Trp Leu Gly Phe Gly
225                 230                 235                 240

Ala Gly Gly Ile Gly Gly Ile Gly Gly Asn Ala Asn Gly Gly Ala Gly
                245                 250                 255
```

```
Gly Asn Gly Gly Thr Gly Gly Gln Leu Trp Gly Ser Gly Gly Ala Gly
            260                 265                 270

Val Glu Gly Gly Ala Ala Leu Ser Val Gly Asp Thr Gly Gly Ala Gly
        275                 280                 285

Gly Val Gly Gly Ser Ala Gly Leu Ile Gly Thr Gly Gly Asn Gly Gly
    290                 295                 300

Asn Gly Gly Thr Gly Ala Asn Ala Gly Ser Pro Gly Thr Gly Gly Ala
305                 310                 315                 320

Gly Gly Leu Leu Leu Gly Gln Asn Gly Leu Asn Gly Leu Pro
                325                 330


<210> SEQ ID NO 729
<211> LENGTH: 650
<212> TYPE: DNA
<213> ORGANISM: Mycobacterium sp.

<400> SEQUENCE: 729

gcggccgcaa ggggttcgcg tcagcgggtg ttggcgggtg tcggggctgg cttaactatg      60

cggcatcaga gcagattgta ctgagagtgc accatatgcg gtgtgaaata ccgcacagat     120

gcgtaaggag aaaataccgc atcaggcgcc attcgccatt caggctgcgc aactgttggg     180

aagggcgatc ggtgcgggcc tcttcgctat tacgccagct ggcgaaaggg ggatgtgctg     240

caaggcgatt aagttgggta acgccagggt tttcccagtc acgacgttgt aaaacgacgg     300

ccagtgaatt gtaatacgac tcactatagg gcgaattcga gctcggtacc cggggatcct     360

ctagagtcga cctgcaggca tgcaagcttg agtattctat agtgtcacct aaatagcttg     420

gcgtaatcat ggtcatagct gtttcctgtg tgaaattgtt atccgctcac aattccacac     480

aacatacgag ccggaagcat aaagtgtaaa gcctggggtg cctaatgagt gagctaactc     540

acattaattg cgttgcgctc actgcccgct ttccagtcgg gaaacctgtc gtgccagctg     600

cattaatgaa tcggccaacg cgaacccctt gcggccgccc gggccgtcga                650


<210> SEQ ID NO 730
<211> LENGTH: 8
<212> TYPE: PRT
<213> ORGANISM: Mycobacterium sp.
<220> FEATURE:
<221> NAME/KEY: Unsure
<222> LOCATION: (1-8)
<223> OTHER INFORMATION: applicants are uncertain of residues designated
      as “xaa”

<400> SEQUENCE: 730

Asn Xaa Gly Xaa Gly Asn Xaa Gly
  1               5


<210> SEQ ID NO 731
<211> LENGTH: 9
<212> TYPE: PRT
<213> ORGANISM: Mycobacterium sp.
<220> FEATURE:
<221> NAME/KEY: Unsure
<222> LOCATION: (1-9)
<223> OTHER INFORMATION: applicants are unsure of residues designated
      as “xaa”

<400> SEQUENCE: 731

Gly Xaa Xaa Ser Val Pro Xaa Xaa Trp
  1               5


<210> SEQ ID NO 732
<211> LENGTH: 29
```

<212> TYPE: PRT
<213> ORGANISM: Mycobacterium sp.

<400> SEQUENCE: 732

```
Gly Gly Ala Gly Gly Ala Gly Gly Ser Ser Ala Gly Gly Gly Gly Ala
  1               5                  10                  15

Gly Gly Ala Gly Gly Ala Gly Gly Trp Leu Leu Gly Asp
             20                  25
```

<210> SEQ ID NO 733
<211> LENGTH: 45
<212> TYPE: PRT
<213> ORGANISM: Mycobacterium sp.

<400> SEQUENCE: 733

```
Gly Ala Gly Gly Ile Gly Gly Ile Gly Gly Asn Ala Asn Gly Gly Ala
  1               5                  10                  15

Gly Gly Asn Gly Gly Thr Gly Gly Gln Leu Trp Gly Ser Gly Gly Ala
             20                  25                  30

Gly Val Glu Gly Gly Ala Ala Leu Ser Val Gly Asp Thr
         35                  40                  45
```

<210> SEQ ID NO 734
<211> LENGTH: 21
<212> TYPE: DNA
<213> ORGANISM: Mycobacterium sp.

<400> SEQUENCE: 734
agttagctca ctcattaggc a 21

<210> SEQ ID NO 735
<211> LENGTH: 21
<212> TYPE: DNA
<213> ORGANISM: Mycobacterium sp.

<400> SEQUENCE: 735
ggatgtgctg caaggcgatt a 21

<210> SEQ ID NO 736
<211> LENGTH: 27
<212> TYPE: DNA
<213> ORGANISM: Mycobacterium sp.

<400> SEQUENCE: 736
aaacagctat gaccatgatt acgccaa 27

<210> SEQ ID NO 737
<211> LENGTH: 24
<212> TYPE: DNA
<213> ORGANISM: Mycobacterium sp.

<400> SEQUENCE: 737
tcctctagag tcgacctgca ggca 24

<210> SEQ ID NO 738
<211> LENGTH: 18
<212> TYPE: DNA
<213> ORGANISM: Mycobacterium sp.
<220> FEATURE:
<221> NAME/KEY: variation
<222> LOCATION: (1-18)
<223> OTHER INFORMATION: bases designated as “n” may be A,T,C or G

<400> SEQUENCE: 738

-continued

```
tctagannnn nntccggc                                                 18


<210> SEQ ID NO 739
<211> LENGTH: 18
<212> TYPE: DNA
<213> ORGANISM: Mycobacterium sp.
<220> FEATURE:
<221> NAME/KEY: variation
<222> LOCATION: (1-18)
<223> OTHER INFORMATION: bases designated as "n" may be A, T, C or G

<400> SEQUENCE: 739

tctagannnn nngggccc                                                 18


<210> SEQ ID NO 740
<211> LENGTH: 20
<212> TYPE: DNA
<213> ORGANISM: Mycobacterium sp.
<220> FEATURE:
<221> NAME/KEY: variation
<222> LOCATION: (1-20)
<223> OTHER INFORMATION: bases designated as "n" may be A, T, C, or G

<400> SEQUENCE: 740

cgtttaaann nnnwaggccg                                               20


<210> SEQ ID NO 741
<211> LENGTH: 21
<212> TYPE: DNA
<213> ORGANISM: Mycobacterium sp.
<220> FEATURE:
<221> NAME/KEY: variation
<222> LOCATION: (1-21)
<223> OTHER INFORMATION: bases designated as "n" may be A, T, C, or G

<400> SEQUENCE: 741

ggtactagtn nnnnwtccgg c                                             21


<210> SEQ ID NO 742
<211> LENGTH: 22
<212> TYPE: DNA
<213> ORGANISM: Mycobacterium sp.

<400> SEQUENCE: 742

acgacctcat attccgaatc cc                                            22


<210> SEQ ID NO 743
<211> LENGTH: 23
<212> TYPE: DNA
<213> ORGANISM: Mycobacterium sp.

<400> SEQUENCE: 743

gcatctgttg agtacgcact tcc                                           23
```

METHOD FOR ISOLATING A POLYNUCLEOTIDE OF INTEREST FROM THE GENOME OF A MYCOBACTERIUM USING A BAC-BASED DNA LIBRARY: APPLICATION TO THE DETECTION OF MYCOBACTERIA

This is a division of application Ser. No. 10/259,678, filed Sep. 30, 2002, now U.S. Pat. No. 6,991,904, which is a continuation of application Ser. No. 09/670,314, filed Sep. 26, 2000, now U.S. Pat. No. 6,492,506, which is a division of application Ser. No. 09/060,756, filed Apr. 16, 1998, now U.S. Pat. No. 6,183,957, which are each herein incorporated by reference.

I. BACKGROUND OF THE INVENTION

The present invention pertains to a method for isolating a polynucleotide of interest that is present in the genome of a mycobacterium strain and/or is expressed by said mycobacterium strain and that is absent or altered in the genome of a different mycobacterium strain and/or is not expressed in said different mycobacterium strain, said method comprising the use of at least one clone belonging to a genomic DNA library of a given mycobacterium strain, said DNA library being cloned in a bacterial artificial chromosome (BAC). The invention concerns also polynucleotides identified by the above method, as well as detection methods for mycobacteria, particularly *Mycobacterium tuberculosis*, and kits using said polynucleotides as primers or probes. Finally, the invention deals with BAC-based mycobacterium DNA libraries used in the method according to the invention and particularly BAC-based *Mycobacterium tuberculosis* and *Mycobacterium bovis* BCG DNA libraries.

Radical measures are required to prevent the grim predictions of the World Health Organisation for the evolution of the global tuberculosis epidemic in the next century becoming a tragic reality. The powerful combination of genomics and bioinformatics is providing a wealth of information about the etiologic agent, *Mycobacterium tuberculosis*, that will facilitate the conception and development of new therapies. The start point for genome sequencing was the integrated map of the 4.4 Mb circular chromosome of the widely-used, virulent reference strain, *M. tuberculosis* H37Rv and appropriate cosmids were subjected to systematic shotgun sequence analysis at the Sanger Centre.

Cosmid clones (Balasubramanian et al., 1996; Pavelka et al., 1996) have played a crucial role in the *M. tuberculosis* H37Rv genome sequencing project. However, problems such as under-representation of certain regions of the chromosome, unstable inserts and the relatively small insert size complicated the production of a comprehensive set of canonical cosmids representing the entire genome.

II. SUMMARY OF THE INVENTION

In order to avoid the numerous technical constraints encountered in the state of the art, as described hereabove, when using genomic mycobacterial DNA libraries constructed in cosmid clones, the inventors have attempted to realize genomic mycobacterial DNA libraries in an alternative type of vectors, namely Bacterial Artificial Chromosome (BAC) vectors.

The success of this approach depended on whether the resulting BAC clones could maintain large mycobacterial DNA inserts. There are various reports describing the successful construction of a BAC library for eucaryotic organisms (Cai et al., 1995; Kim et al., 1996; Misumi et al., 1997; Woo et al., 1994; Zimmer et al., 1997) where inserts up to 725 kb (Zimmer et al., 1997) were cloned and stably maintained in the *E. coli* host strain.

Here, it is shown that, surprisingly, the BAC system can also be used for mycobacterial DNA, as 70% of the clones contained inserts in the size of 25 to 104 kb.

This is the first time that bacterial, and specifically mycobacterial, DNA is cloned in such BAC vectors.

In an attempt to obtain complete coverage of the genome with a minimal overlapping set of clones, a Bacterial Artificial Chromosome (BAC) library of *M. tuberculosis* was constructed, using the vector pBeloBAC11 (Kim et al., 1996) which combines a simple phenotypic screen for recombinant clones with the stable propagation of large inserts (Shizuya et al., 1992). The BAC cloning system is based on the *E. coli* F-factor, whose replication is strictly controlled and thus ensures stable maintenance of large constructs (Willets et al., 1987). BACs have been widely used for cloning of DNA from various eucaryotic species (Cai et al., 1995; Kim et al., 1996; Misumi et al., 1997; Woo et al., 1994; Zimmer et al., 1997). In contrast, to our knowledge this report describes the first attempt to use the BAC system for cloning bacterial DNA.

A central advantage of the BAC cloning system over cosmid vectors used in prior art is that the F-plasmid is present in only one or a maximum of two copies per cell reducing the potential for recombination between DNA fragments and, more importantly, avoiding the lethal overexpression of cloned bacterial genes. However, the presence of the BAC as just a single copy means that plasmid DNA has to be extracted from a large volume of culture to obtain sufficient DNA for sequencing and it is described here in the examples a simplified protocol to achieve this.

Further, the stability and fidelity of maintenance of the clones in the BAC library represent ideal characteristics for the identification of genomic differences possibly responsible for phenotypic variations in different mycobacterial species.

As it will be shown herein, BACs can be allied with conventional hybridization techniques for refined analyses of genomes and transcriptional activity from different mycobacterial species.

Having established a reliable procedure to screen for genomic polymorphisms, it is now possible to conduct these comparisons on a more systematic basis than in prior art using representative BACs throughout the chromosome and genomic DNA from a variety of mycobacterial species.

As another approach to display genomic polymorphisms, the inventors have also started to use selected H37Rv BACs for "molecular combing" experiments in combination with fluorescent in situ hybridization (Bensimon et al., 1994; Michalet et al., 1997). With such techniques the one skilled in the art is enabled to explore the genome of mycobacteria in general and of *M. tuberculosis* in particular for further polymorphic regions.

The availability of BAC-based genomic mycobacterial DNA libraries constructed by the inventors have allowed them to design methods and means both useful to identify genomic regions of interest of pathogenic mycobacteria, such as *Mycobacterium tuberculosis*, that have no counterpart in the corresponding non-pathogenic strains, such as *Mycobacterium bovis* BCG, and useful to detect the presence of polynucleotides belonging to a specific mycobacterium strain in a biological sample.

By a biological sample according to the present invention, it is notably intended a biological fluid, such as plasma, blood, urine or saliva, or a tissue, such as a biopsy.

Thus, a first object of the invention consists of a method for isolating a polynucleotide of interest that is present in the genome of a mycobacterium strain and/or is expressed by said mycobacterium strain and that is absent or altered in the genome of a different mycobacterium strain and/or is not expressed in said different mycobacterium strain, said method comprising the use of at least one clone belonging to a genomic DNA library of a given mycobacterium strain, said DNA library being cloned in a bacterial artificial chromosome (BAC).

The invention is also directed to a polynucleotide of interest that has been isolated according to the above method and in particular a polynucleotide containing one or several Open Reading Frames (ORFs), for example ORFs encoding either a polypeptide involved in the pathogenicity of a mycobacterium strain or ORFs encoding Polymorphic Glycine Rich Sequences (PGRS).

Such polynucleotides of interest may serve as probes or primers in order to detect the presence of a specific mycobacterium strain in a biological sample or to detect the expression of specific genes in a particular mycobacterial strain of interest.

The BAC-based genomic mycobacterial DNA libraries generated by the present inventors are also part of the invention, as well as each of the recombinant BAC clones and the DNA insert contained in each of said recombinant BAC clones.

The invention also pertains to methods and kits for detecting a specific mycobacterium in a biological sample using either at least one recombinant BAC clone or at least one polynucleotide according to the invention, as well as to methods and kits to detect the expression of one or several specific genes of a given mycobacterial strain present in a biological sample.

III. BRIEF DESCRIPTION OF THE FIGURES

In order to better understand the present invention, reference will be made to the appended figures which depicted specific embodiments to which the present invention is in no case limited in scope with.

FIG. 1: PCR-screening for unique BAC clones with specific primers for 2 selected genomic regions of the H37Rv chromosome, using 21 pools representing 2016 BACs (Panel A) and sets of 20 subpools from selected positive pools (Panel B).

Figure 2:
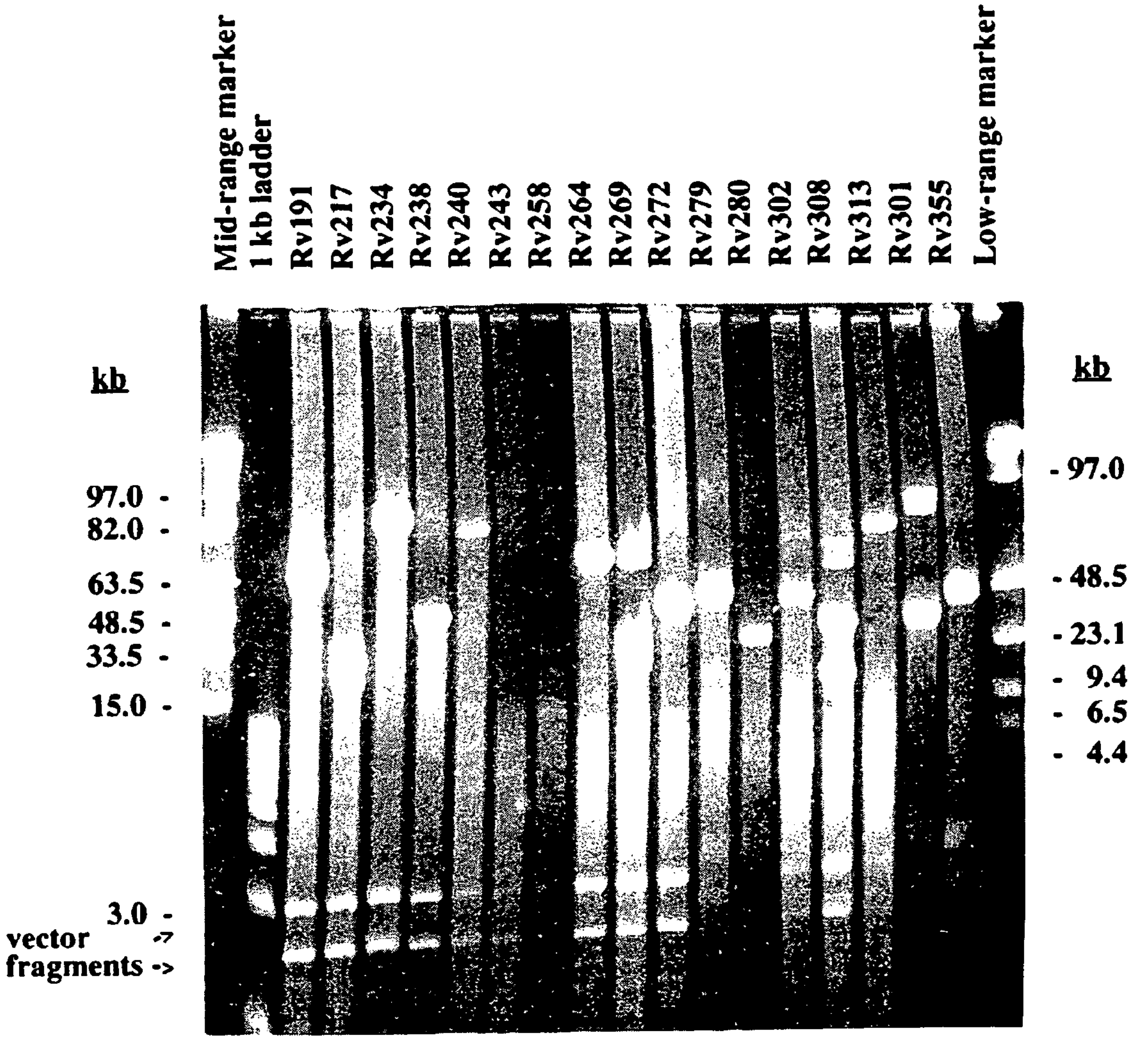
Figure 3A:
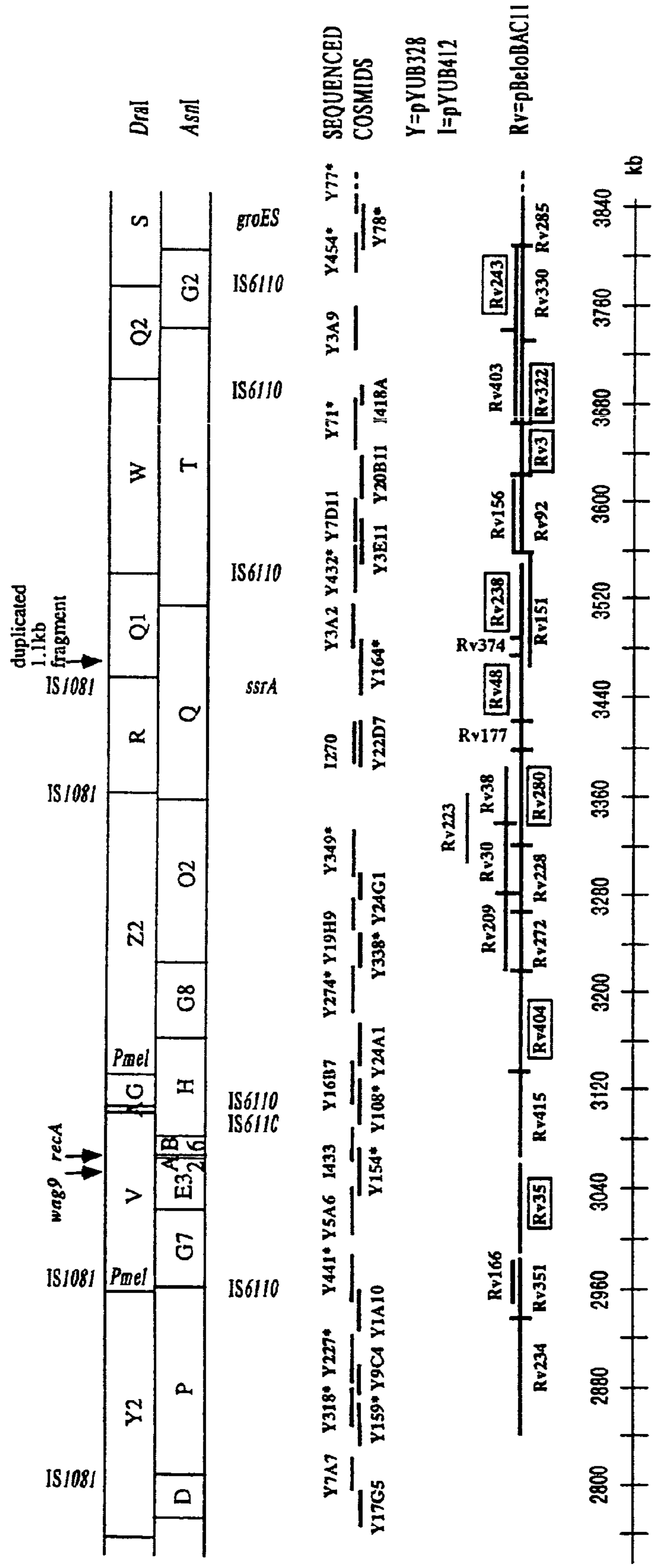
Figure 3B:
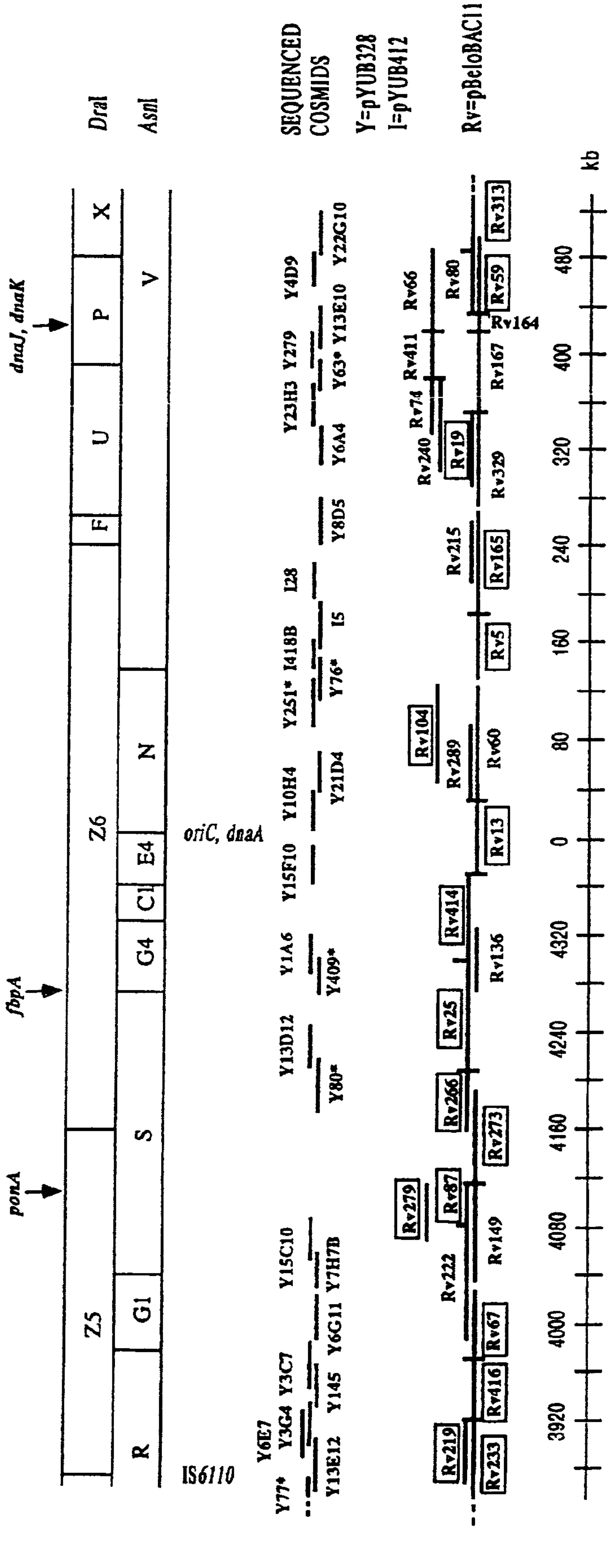
Figure 3C:
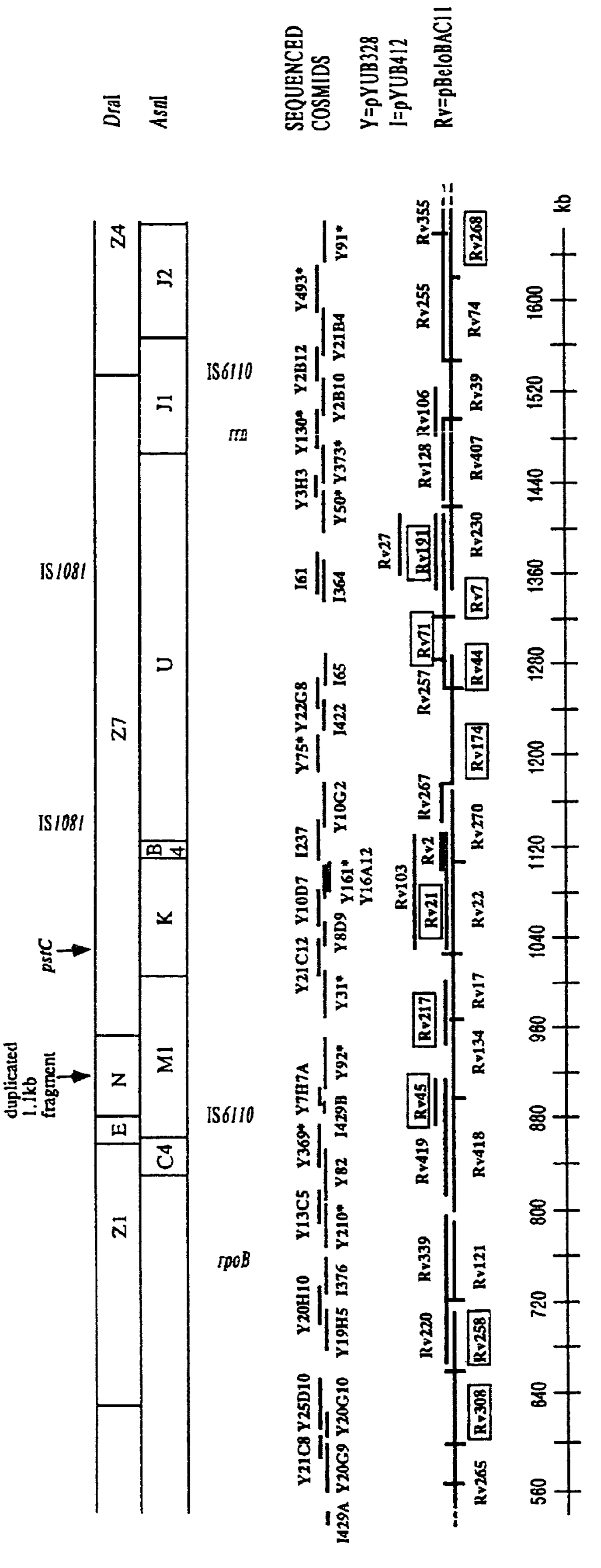
Figure 3D:
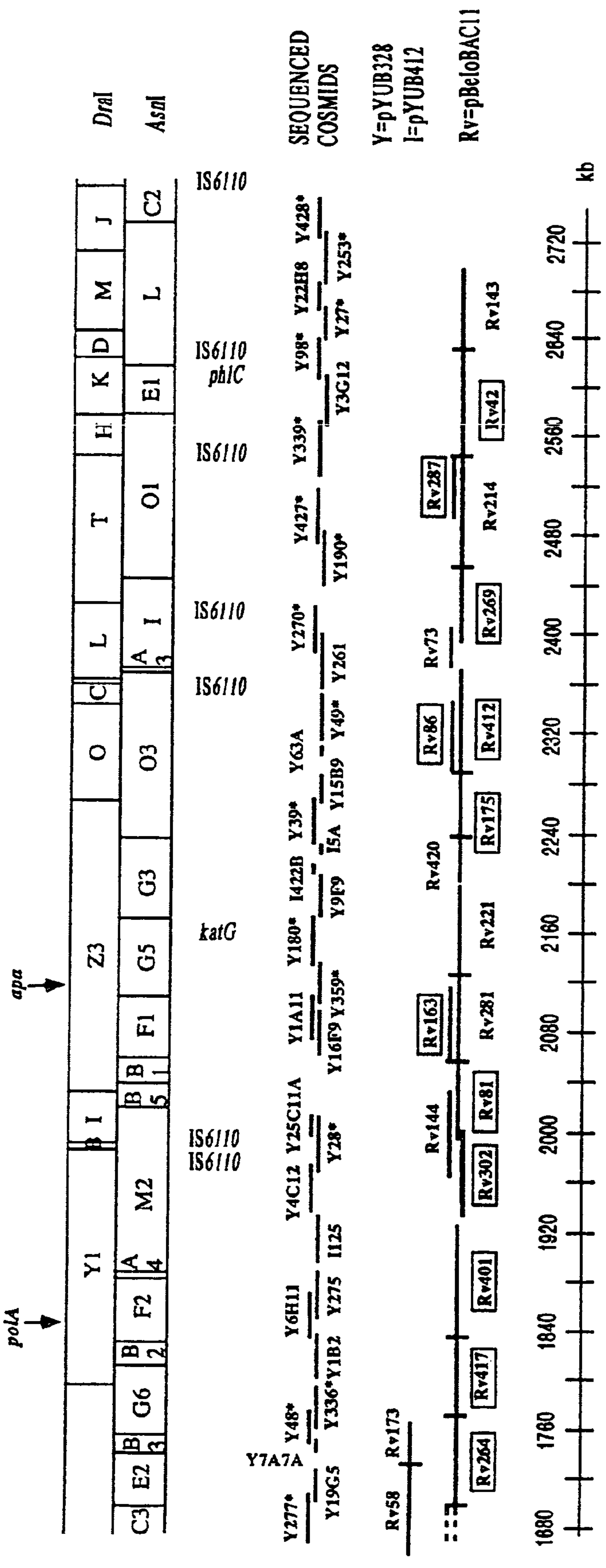

FIG. 2: Pulsed-field gel electrophoresis gel of DraI-cleaved BAC clones used for estimating the insert sizes of BACs.

FIG. 3: Minimal overlapping BAC map of *M. tuberculosis* H37Rv superimposed on the integrated physical and genetic map established by Philipp et al. (18). Y- and I-numbers show pYUB328 (2) and pYUB412 (16) cosmids which were shotgun sequenced during the H37Rv genome sequencing project Y-cosmids marked with * were shown in the integrated physical and genetic map (18). Rv numbers show the position of representative BAC clones relative to sequenced Y- and I-clones. Squared Rv numbers show BACs which were shotgun sequenced at the Sanger Centre.

Figure 4A:
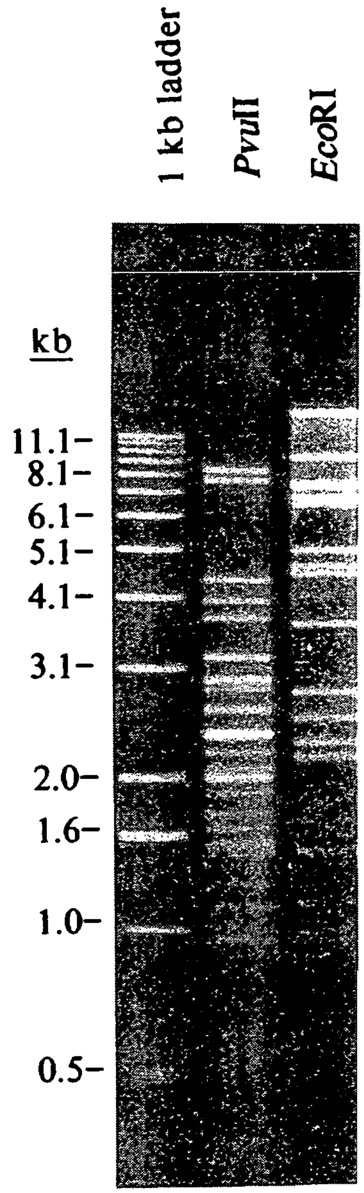
Figure 4B:
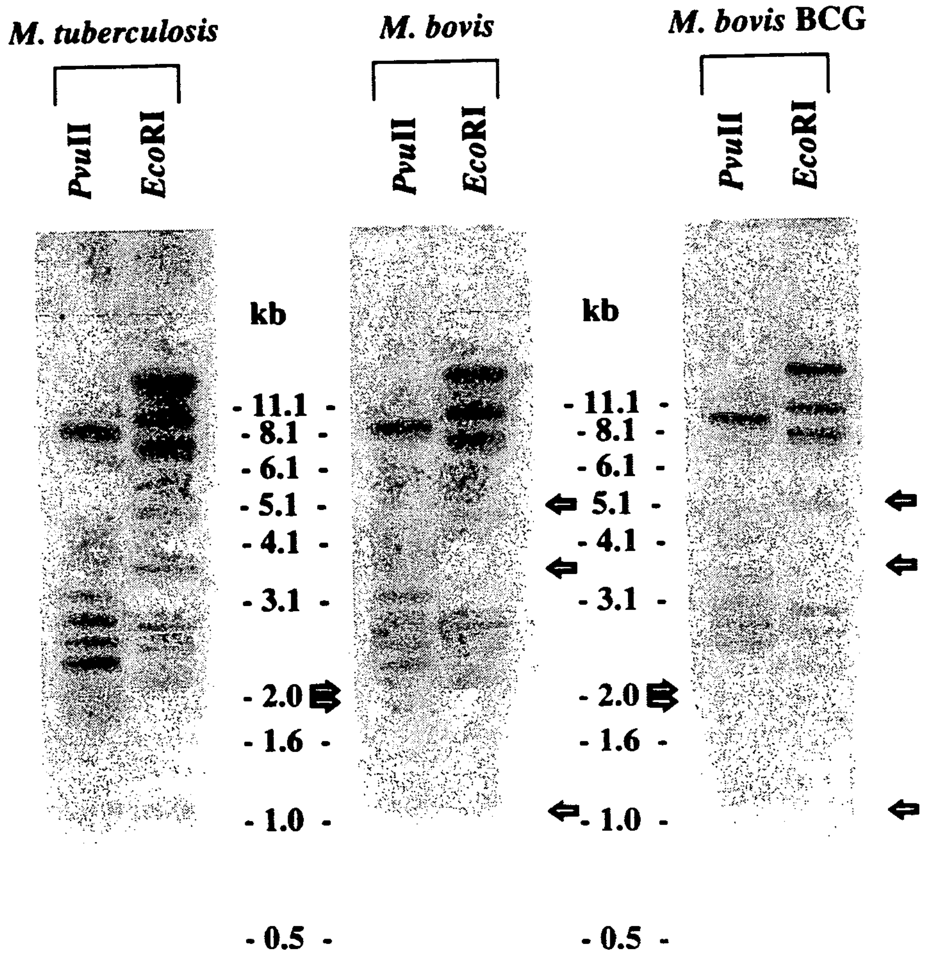

FIG. 4: Ethidium bromide strained gel (Panel A) and corresponding Southern blot (PanelB) of EcoRI and PvuII digested Rv58 DNA hybridized with $^{32}P$ labeled genomic DNA preparations from *M. tuberculosis* H37Rv, *M. bovis* ATCC 19210 and *M. bovis* BCG Pasteur.

Figure 5:
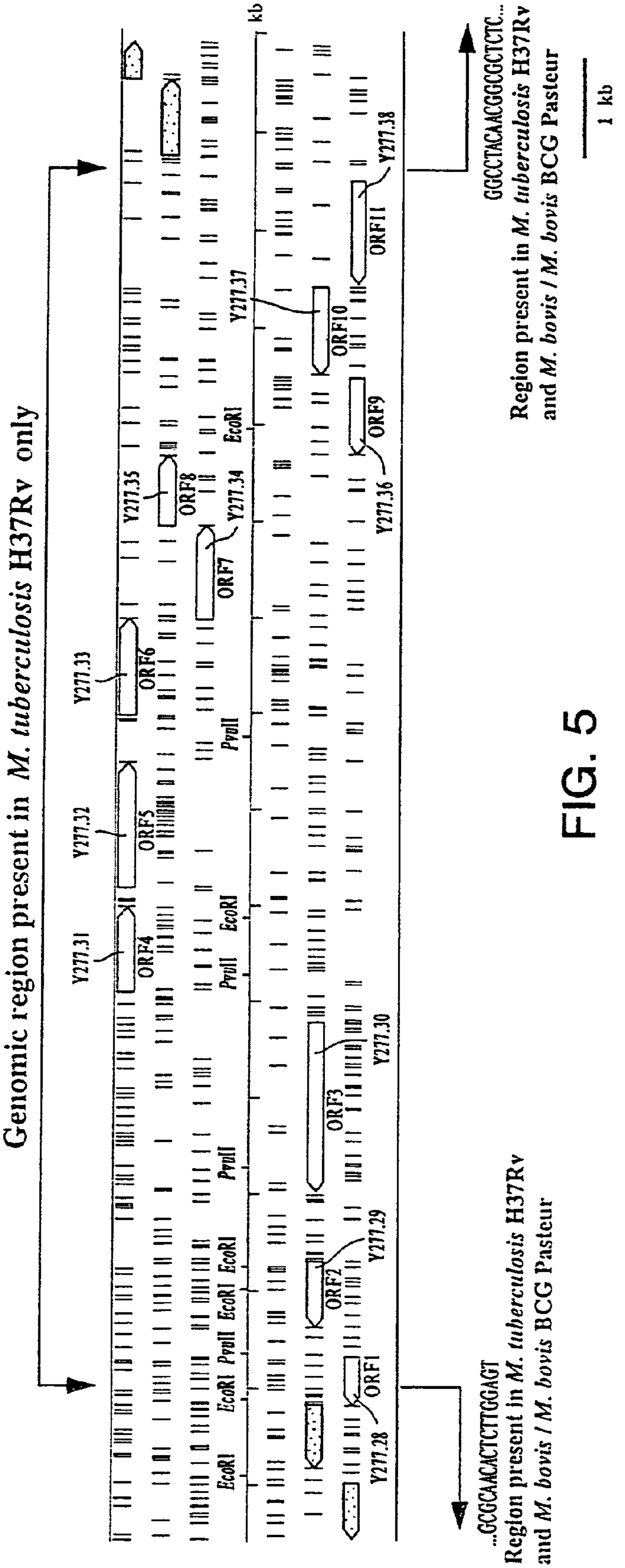

FIG. 5: Organisation of the ORFs in the 12.7 kb genomic region present in *M. tuberculosis* H37Rv but not present in *M. bovis* ATCC 19210 and *M. bovis* BCG Pasteur. Arrows show the direction of transcription of the putative genes. Positions of EcoRI and PvuII restriction sites are shown. Vertical dashes represent stop codons. The 11 ORFs correspond to the ORFs MTCY277.28 to MTCY277.38/accession number Z79701-EMBL Nucleotide Sequence Data Library. The junction sequences flanking the polymorphic region are shown.

FIG. 6: Variation in the C-terminal part of a PE-PGRS open reading frame in *M. tuberculosis* strain H37Rv relative to *M. bovis* BCG strain Pasteur. The numbers on the right side of the Figure denote the position of the end nucleotides, taking as the reference the *M. tuberculosis* genome.

FIG. 7: Polynucleotide sequence next to the HindIII cloning site in the BAC vector pBeloBAC11 (Kim et al., 1996) used to clone the inserts of the BAC-based myobacterial genomic DNA library according to the invention.

NotI: location of the NotI restriction sites.

Primer T7-BAC1: nucleotide region recognized by the T7-BAC1 primer shown in Table 1.

T7 promoter: location of the T7 promoter region on the pBeloBac11 vector.

Primer T7-Belo2: nucleotide region recognized by the T7-Belo2 primer shown in Table 1.

Hind III: the HindIII cloning site used to clone the genomic inserts in the pBeloBAC11 vector.

SP6-Mid primer: nucleotide region recognized by the SP6 Mid primer shown in Table 1.

SP6-BAC1 primer: nucleotide region recognized by the SP6 BAC1 primer shown in Table 1.

SP6 promoter: location of the SP6 promoter region on the pBeloBac11 vector.

IV. DETAILED DESCRIPTION OF THE PREFERRED EMBODIMENTS

As already mentioned hereinbefore, the present invention is directed to a method for isolating a polynucleotide of interest that is present in the genome of a mycobacterium strain and/or is expressed by said mycobacterium strain and that is absent or altered in the genome of a different mycobacterium strain and/or is not expressed in said different mycobacterium strain, said method comprising the use of at least one clone belonging to a genomic DNA library of a given *mycobacterium* strain, said DNA library being cloned in a bacterial artificial chromosome (BAC).

For this purpose, the inventors have constructed several BAC-based mycobacterial genomic DNA libraries that may be used in order to perform the above described method.

Because it is the first time that mycobacterial genomic DNA has been successfully cloned in BA type vectors, and because these DNA libraries are then novel and nonobvious, an object of the present invention consists in a myobacterial genomic DNA library cloned in such a BAC type vector.

As an illustrative example, a BAC-based DNA library of *Mycobacterium tuberculosis* has been realized. Forty-seven cosmids chosen from the integrated map of the 4.4 Mb circular chromosome (Philipp et al., 1996a) were shotgun-sequenced during the initial phase of the H37Rv genome sequence project The sequences of these clones were used as landmarks in the construction of a minimally overlapping BAC map. Comparison of the sequence data from the termini of 420 BAC clones allowed us to establish a minimal overlapping BAC map and to fill in the existing gaps between the sequence of cosmids. As well as using the BAC library for genomic mapping and sequencing, we also tested the system in comparative genomic experiments in order to uncover differences between two closely related mycobacterial species. As shown in a previous study (Philipp et al., 1996b), *M. tuberculosis, M. bovis* and *M. bovis* BCG, specifically BCG Pasteur strain, exhibit a high level of global genomic conservation, but certain polymorphic regions were also detected. Therefore, it was of great interest to find a reliable, easy and rapid way to exactly localize polymorphic regions in mycobacterial genomes using selected BAC clones. This approach was validated by determining the exact size and location of the polymorphisms in the genomic region of DraI fragment Z4 (Philipp et al., 1996b), taking advantage of the availability of an appropriate BAC clone covering the polymorphic region and the H37Rv genome sequence data. This region is located approximately 1.7 Mb from the origin of replication.

The Bacterial Artificial Chromosome (BAC) cloning system is capable of stably propagating large, complex DNA inserts in *Escherichia coli*. As part of the *Mycobacterium tuberculosis* H37Rv genome sequencing project, a BAC library was constructed in the pBeloBAC11 vector and used for genome mapping, confirmation of sequence assembly, and sequencing. The library contains about 5000 BAC clones, with inserts ranging in size from 25 to 104 kb, representing theoretically a 70 fold coverage of the *M. tuberculosis* genome (4.4 Mb). A total of 840 sequences from the T7 and SP6 termini of 420 BACs were determined and compared to those of a partial genomic database. These sequences showed excellent correlation between the estimated sizes and positions of the BAC clones and the sizes and positions of previously sequenced cosmids and the resulting contigs. Many BAC clones represent linking clones between sequenced cosmids, allowing full-coverage of the H37Rv chromosome, and they are now being shotgun-sequenced in the framework of the H37Rv sequencing project. Also, no chimeric, deleted or rearranged BAC clones were detected, which was of major importance for the correct mapping and assembly of the H37Rv sequence. The minimal overlapping set contains 68 unique BAC clones and spans the whole H37Rv chromosome with the exception of a single gap of 150 kb. As a post-genomic application, the canonical BAC set was used in a comparative study to reveal chromosomal polymorphisms between *M. tuberculosis, M. bovis* and *M. bovis* BCG Pasteur, and a novel 12.7 kb segment present in *M. tuberculosis* but absent from *M. bovis* and *M. bovis* BCG was characterized. This region contains a set of genes whose products show low similarity to proteins involved in polysaccharide biosynthesis. The H37Rv BAC library therefore provides the one skilled in the art with a powerful tool both for the generation and confirmation of sequence data as well as for comparative genomics and a plurality of post-genomic applications.

The above described BAC-based *Mycobacterium tuberculosis* genomic DNA library is part of the present invention and has been deposited in the Collection Nationale de Cultures de Microorganismes (CNCM) on Nov. 19, 1997 under the accession number I-1945.

Another BAC-based DNA library has been constructed with the genomic DNA of *Mycobacterium bovis* BCG, Pasteur strain, and said DNA library has in the Collection Nationale de Cultures de Microorganismes (CNCM) on XX XX, 1998 under the accession number I-XXXX.

Thus, as a specific embodiment of the above described method for isolating a polynucleotide of interest said method makes use of at least one BAC-based DNA library that has been constructed from the genomic DNA of *Mycobacterium tuberculosis*, more specifically of the H37Rv strain and particularly of the DNA library deposited in the accession number I-1945.

In another specific embodiment of the above described method for isolating a polynucleotide of interest said method makes use of at least one BAC-based DNA library has been constructed from the genomic DNA of *Mycobacterium bovis* BCG, more specifically of the Pasteur strain and particularly of the DNA library deposited in the accession number I-X.

In more details, the method according to the invention for isolating a polynucleotide of interest may comprise the following steps:

a) Isolating at least one polynucleotide contained in a clone of a BAC-based DNA library of mycobacterial origin;

b) Isolating:

at least one genomic or cDNA polynucleotide from a mycobacterium, said mycobacterium belonging to a strain different from the strain used to construct the BAC-based DNA library of step a); or alternatively at least one polynucleotide contained in a clone of a BAC-based DNA library prepared from the genome of a mycobacterium that is different from the mycobacterium used to construct the BAC-based DNA library of step a);

c) Hybridizing the at least one polynucleotide of step a) to the at least one polynucleotide of step b);

d) Selecting the at least one polynucleotide of step a) that has not formed a hybrid complex with the at least one polynucleotide of step b);

e) Characterizing the selected polynucleotide.

Following the above procedure, the at least one polynucleotide of step a) may be prepared as follows:

1) Digesting at least one recombinant BAC clone by an appropriate restriction endonuclease in order to isolate the polynucleotide insert of interest from the vector genetic material;

2) Optionally amplifying the resulting polynucleotide insert;

3) Optionally digesting the polynucleotide insert of step 1) or step 2) with at least one restriction endonuclease.

The above method of the invention allows the one skilled in the art to perform comparative genomics between different strains or species of mycobacteria cells, for example between pathogenic strains or species and their non pathogenic strains or species counterparts, as it is the illustrative case for the genomic comparison between *Mycobacterium tuberculosis* and *Mycobacterium bovis* BCG that is described herein in the examples.

Restriction digests of a given clone of a BAC library according to the invention may be blotted to membranes, and then probed with radiolabeled DNA form another strain or another species of mycobacteria, allowing the one skilled in the art to identify, characterize and isolate a polynucleotide of interest that may be involved in important metabolically and/or physiological pathways of the mycobacterium under testing, such as a polynucleotide functionally involved in the pathogenicity of said given mycobacteria for its host organism.

More specifically, the inventors have shown in Example 6 that when restriction digests of a given clone of the library identified by the CNCM accession number I-1945 are blotted to membranes and then probed with radiolabeled total genomic DNA from, for example, *Mycobacterium bovis* BCG Pasteur, it is observed that restriction fragments that fail to hybridize with the *M. bovis* BCG Pasteur DNA are absent from its genome, hence identifying polymorphic regions between *M. bovis* BCG Pasteur and *M. tuberculosis* H37Rv.

Thus, a further object of the present invention consists in a polynucleotide of interest that has been isolated according to the method described herein before.

In Example 6, a polynucleotide of approximately 12.7 kilobases has been isolated that is present in the genome of *M. tuberculosis* but is absent of the genome of *M. bovis* BCG. This polynucleotide of interest contains 11 ORFs that may be involved in polysaccharide biosynthesis. In particular, two of said ORFs are of particular interest, namely ORF6 (MTCY277.33; Rv1511) that encodes a protein that shares significant homology with bacterial GDP-D-mannose dehydratases, whereas the protein encoded by ORF7 (MTCY277.34; Rv1512) shares significant homology with a nucleotide sugar epimerase. As polysaccharide is a major constituent of the mycobacterial cell wall these deleted genes may cause the cell wall of *M. bovis* BCG to differ from that of *M. tuberculosis*, a fact that may have important consequences for both the immune response to *M. bovis* BCG and virulence. Detection of such a polysaccharide is of diagnostic interest and possibly useful in the design of tuberculosis vaccines.

Consequently, the polynucleotide of interest obtained following the method according to the invention may contain at least one ORF, said ORF preferably encoding all or part of a polypeptide involved in an important metabolically and/or physiological pathway of the mycobacteria under testing, and more specifically all or part of a polypeptide that is involved in the pathogenicity of the mycobacteria under testing such as for example *Mycobacterium tuberculosis*, and more generally mycobacteria belonging to the *Mycobacterium tuberculosis* complex.

The *Mycobacterium tuberculosis* complex has its usual meaning, i.e. the complex of mycobacteria causing tuberculosis which are *Mycobacterium tuberculosis, Mycobacterium bovis, Mycobacterium africanum, Mycobacterium microti* and the vaccine strain *Mycobacterium bovis* BCG.

An illustrative polynucleotide of interest according to the present invention comprises all or part of the polynucleotide of approximately 12.7 kilobases that is present in the genome of *M. tuberculosis* but is absent from the genome of *M. bovis* BCG disclosed hereinbefore. This polynucleotide is contained in clone Rv58 of the BAC DNA library I-1945.

Generally, the invention also pertains to a purified polynucleotide comprising the DNA insert contained in a recombinant BAC vector belonging to a BAC-based mycobacterial genomic DNA library, such as for example the I-1945 BAC DNA library.

Advantageously, such a polynucleotide has been identified according to the method of the invention.

Such a polynucleotide of interest may be used as a probe or a primer useful for specifically detecting a given mycobacterium of interest, such as *Mycobacterium tuberculosis* or *Mycobacterium bovis* BCG.

More specifically, the invention then deals with a purified polynucleotide useful as probe or a primer comprising all or part of the nucleotide sequence SEQ ID No1:

```
ACCTGCGCTT GCAGAGATCA AATAGGGCGC ATGGGTCAGC ATAGTACAGG TCGTCGCGCA      60
TCTTTGATGC ATCGGAATAA GATGTCAGGC AATTAAAAGA GAAGCCACGG CGACTCGCGG     120
CATTCAGCAT GTCGAGCGTC GCTTCGATGT GAGCGCACCA TTCCGTGTCC AACGATTTCA     180
GACGAACATT GAATATTCCA CTCGCGACGC TATAGTCCGC CTCCCGATCT ATGCGCGCCG     240
CGCAGATGAA GTCTGCGTTC GCCCGACCTT CGAAACGTAG TGCGGCCGCG CGCACCATTT     300
CGGGGGAGAC GTCGATGCCG GTGTAATCAG TTTTGAAGCC ACGCGCATCT AGGTAGTCCA     360
GTAGAGCCCC ATAGCCACAG CCTAGATCGT TGATCGAAAA TGGGTCCGCC GCATTGACAA     420
TGCGCACCAG CTGGTCAAAG CGCAACGCCT GCCCGGCTTC GCCGTTCCAA TCGACGCCGC     480
GCGGGTGCCG TGTGCTTCGA GTTTCGATGC GTAGTAACGG GCCACGTCAG CGAGCATGGT     540
CGTTGCGTCT TCCGCCATGA AGCTGCCTCA CGATTTGTGT GTGTGGGCGT CGGTGCGTGG     600
GTCCGAGACT ATACCTTCAA CAGTTGCATG CCGAGGCTGC GGCGGGCAAT GACCCAAAAA     660
CCCGCCGGCA CGGTTCGCCG AGCAAGGAAG CGTGGAGACG ATAGATAATT TCACTGGCGA     720
CAGTACCTCA AATAGTCCGG AGCCTCGGCT CCGACGTTAA AGAGCAGATC CAGAATCGAC     780
ACGGCGGGCT CGAACCCTCC CCACAATTGC TTATAATCGC GGTAGCCGTC ATAATCGAAC     840
CAAGTTACCC GGATGCTAAG TTCGTCGAAC ACGCGCTCAT CGACATACGA ACGGGCTGAG     900
GGGCCAGAGA CATATTCGGT CGCTGCGGCC TGTTGGCAGA GGTTGGCCAG TCTCTCGGTC     960
TTGCCGTCGG CTAATTCGTA GTCCCACGAA TTTGCCAGTC GCGTGCTGAT ACCGAGATAA    1020
CTGCAAATCG CATTCAATAG ACGCCTGTTG AGTAAGGAAA GATTCGTGTG CTGTTCTTCG    1080
AGGTAAATCG GCGCGAGCCA GTCAGCGATC TCCGCAAAAT GAGCGGCCGC GCTGTAGTTG    1140
AATTCTAGTG CCCGCCAGTG CGCTTTCGCC CAATCGGTGC CGTCGATCAG CGTCTCACGT    1200
ATCTTTTGAT GGAAACGTCC CTTCACCTGG ACGGGAACAG TTATCCACTG TAACCCCTGG    1260
CTCGTTTTGA TCCGATTTCT GTTTCGCCAA TCACGCTTGG TATATTGCAT GTCATCATAG    1320
ATGATGAATT CATCGACGAA TGCAATCAGG TCAAAATATC CTCGCCAAGG TATGTAATTT    1380
GATTGAACAA TCGCGACTTT CTTCAACGCG GTGTCTCCAA TTTAGAATAA CAAATACGTC    1440
GCGCCCGCGA CAGCTCCGCT GGAGCGAGTT CAAGCGATTC TGCGACATAT TCAATATGGT    1500
```

-continued

```
GCTCGGGAAG GCCAGGATGG GCCGCGACCC GGGGCGTCCG GTGCGCGATG AACGTCGCAT    1560
CGTCTCCTGT GAGATAATTG CATCCGATCA TATAGGGCTG GCTGCGGCTA GGTTGCTGGC    1620
AAAAAGATAT CGCGGCCGAT CCGTTTCTGG TTTTGTCTTG ATGATCAAAT CCGCTTCCGT    1680
TCACGAGATC GATTCCTGGT CTTCCCCCAG CGTCGCGATG TCGATAGGTG TCGCGCTTTG    1740
TTCGTACCCG CACTACGCGG CGGCGAGAAC CTCGCCACCG AATCGGGATT GGGGGGAGGA    1800
TACCACTCGG TCGAGGCCCG TCACCGGCCT TCTAGCGGGT TGACCATCAG TGTTTGCAGG    1860
GCCCTATCCC GGTATGGCGC ACCACGGGAT CGGCAGCGTT CCGGTTGCTG GCGTGGTACC    1920
TCGTTGTGGC GCCGTGGTCC ATGTCGATTG AGTGCGTGGA TCAGTGTAAA CCGTTGCGCG    1980
CCATGTTCTG TAGGCACTGG TTCGGGTTGT GGTTAGGCTG CACGGTTGGC AGGTTACCAA    2040
CCACTGAGCC CCTGGGCGGA TGTGAGCTCG GACTCCGCCT ATGGGGTGTA ATTTTGGCAG    2100
ATTGGGCCGG GTCCCCGTGG TGAGGACTCC TCAACCGGAT TGGGTAAGCA TGAGGTGGTG    2160
CTGGCAGCGG TGTCCTGGTC GCTCTCCCGA GTAGGCCCGT TGTGACTGTC ATGTGGGCGA    2220
GCGGGTTTGC GCGCGTAGGA GACGATGATT ACTACGCACG TGACCAACCA CAAGAACGGT    2280
GCCCATGTCA CCGTGGTGAA AACGAGTGGC GTGGTACCGA CTACCCCTTT GGCTCCCAGC    2340
TGTCCATAGA GCGGCACGTA GAACGGCTGG CCCGGGACCG CGACGTTGAC GATGCTCAGC    2400
GCCACGGCCA AACTCACGCA GACGCCGACC GCGCGGCGGC GGTCTCCATG GGCTGCGAGT    2460
TGGTCGAATA TCCCAGCACC AGGAGGCCCG TTGGGGTCTC GGGCTACCAG TGCAGCGATT    2520
GGCAAGACGA AAACGAGATA GTAGAAGGCG ACGTCCGCGG GGGAGAAGGT GGCGGTGGCG    2580
AGCAACACAA TCCCCACCAT GACAGGCGGG ATACGGCGTC CGAGCGCCAG CACGGCGACC    2640
ACGACTATGA CTAGGACAGC AAACCCGATC TGCGTTCGCG GACCAGTGAG GAAACCCTCT    2700
GGGATCTTGC CCGATTGATA GTTCTTGATG CTATCGGGGA TCAGCAGGAG TGCCTTGCCA    2760
AAGGACACGT TCCGCGGGTC TCGAAGCCCT CCGAACGAAC TATTGAACTT GATGATGCCG    2820
TGGATCGACT GTGCGATCGT CCCCGGGAAG CCTCGTGGCC ACAACAGAAA GGCTGCGATA    2880
TTGGACACCA CCACGCCGGT GATCCCGATA CCAGCCCACC GCCATTCTCG AGCCGCCAAC    2940
AACACCACGC CGAGAACGAC GAACTGCGGC TTTACCAGGA CGGCCAAGAT CACCGTGATG    3000
GTGGCGAGGC CCCACCGCTG TCGGGACAAC GCCACGAAGT AAGCCAGCGC GATCGGTACC    3060
ACGAACCCTG TCGAGTTGCC TCGATCGATG ACCCCCCACG CCGGGATGGC CGCGGCGCCC    3120
AGTGTCACGA AGATGACCAC TCGCTCCAGA CCACGTGCCC CCCGGGCCGC CCAGATGGCG    3180
GGAGATATGA CCGCCATCGT TAGGGCGACC AGGTAACAGA TCAGCCCCAA GCGCGGCGCA    3240
CCCAGCCAAT GGCTGGGTAG TCCGAAAATC GCATACGGTA TGCGGGCGGG GGCCCATGCA    3300
GCAACCGCGG TCGGCTGGTA ATCGGCGGGT AGCGAGATCA GGTAGTCCGC GGGATTGGGT    3360
TGAATCCCGG CGGCGGCGAC CATGGCGTAG TCGCTGAAGC AGTGCCGACC GATATTCATG    3420
CCCCAATCAA GCCAACAGTC CCCAGGGACT ACCAAAAGAG TGGAAAAGAC GTCGACCGCG    3480
TACCACTGAC TGAGGGCGTA CGCCGTCGCC GCCGAAATCA CCGACGCCAG CAGGATGGTG    3540
CCGAGCATGA GGGTGCGCTC GGATTGGGAG CCGATCGCCC AGAGCCGCTC CCGGCTCGCG    3600
GTCACGGCAC CGCGCAACAC CTCCGGGGGT CGCTTCATCT GGATTCTCCT CGGTTCTGCG    3660
CGAAACGGTA GCAGAGCGCC ATGGTTGCCA ACGCGGTCGC CGGGCAGTCT AGACCGGATC    3720
TTCCTCGTGG CAACCGACAA CAGGACGTCG TTGCCGAAAG GGCGCTGGGC ACCGACATCT    3780
AGGATGAACC CACAGCCACG CCCCGACGTT ATGCCATGGC GAAGAGCGAC CGGCAGGAGC    3840
GGGAACCCAG TGAAGCGAGC GCTCATCACC GGAATCACAG GACCGGACGG CTCGTATCTC    3900
GCTAAGCTCC CGCTGAAGGG ATATGTGGCC GCTGGTAGCC CGGCCGAGGT CTATTTCTGC    3960
```

-continued

```
TGGGCGACAC GGAATTATCG CGAATTGTAT GGGTTGCTCG CGGTCAACAG CATCTGGTTC    4020
AATCACGAAT CACCGCGTCA CGGCGAGACA TTCATGACTC GTAATCCTGC ACCATATCGC    4080
GGTCGGCAAC GAGGCGCTGA TCGATGCGCA GACGCTGATG CGCCGGCCCA CCCGGATAGG    4140
TATCAGTATT GGGGCGTTCC GGCCAGCGTA CGAGGCGTGA TCGACCGCGC AATGGGTGTT    4200
TGCGTTGAGT AATAATCTGA ACCGTGTGAA CGCATGCATG GATGGATTCC TTGCCCGTAT    4260
CCGCTCACAT GTTGATGCGC ACGCGCCAGA ATTGCGTTCA CTGTTCGATA CGATGGCGGC    4320
CGAGGCCCGA TTTGCACGCG ACTGGCTGTC CGAGGACCTC GCGCGGTTGC CTGTCGGTGC    4380
AGCATTGCTG GAAGTGGGCG GGGGGGTACT TCTGCTCAGC TGTCAACTGG CGGCGGAGGG    4440
ATTTGACATC ACCGCCATCG AGCCGACGGG TGAAGGTTTT GGCAAGTTCA GACAGCTTGG    4500
CGACATCGTG CTGGAATTGG CTGCAGCACG ACCCACCATC GCGCCATGCA AGGCGGAAGA    4560
CTTTATTTCC GAGAAGCGGT TCGACTTCGC CTTCTCGCTG AATGTGATGG AGCACATCGA    4620
CCTTCCGGAT GAGGCAGTCA GGCGGGTATC GGAAGTGCTG AAACCGGGGG CCAGTTACCA    4680
CTTCCTGTGC CCGAATTACG TATTCCCGTA CGAACCGCAT TTCAATATCC CAACATTCTT    4740
CACCAAAGAG CTGACATGCC GGGTGATGCG ACATCGCATC GAGGGCAATA CGGGCATGGA    4800
TGACCCGAAG GGAGTCTGGC GTTCGCTCAA CTGGATTACG GTTCCCAAGG TGAAACGCTT    4860
TGCGGCGAAG GATGCGACGC TGACCTTGCG CTTCCACCGT GCAATGTTGG TATGGATGCT    4920
GGAACGCGCG CTGACGGATA AGGAATTCGC TGGTCGCCGG GCACAATGGA TGGTCGCTGC    4980
TATTCGCTCG GCGGTGAAAT TGCGTGTGCA TCATCTGGCA GGCTATGTTC CCGCTACGCT    5040
GCAGCCCATC ATGGATGTGC GGCTAACGAA GAGGTAATGA CATGGCGCAA GCGACATCGG    5100
GCATTCGCGC GGCACTTTCG CAACCTGCTG TGTATGAGGC GTATCAGCGG ATTGCGGGCG    5160
CTAAAAGCGG GCTTGCGTGG ATCACAACCG ACCCCATCCA GTCGTTGCCA GGCATGCGTA    5220
CTCTCGACCT CGGTTGCTGG CCAGCGGTGA TACACAGCTC CCCGCCAGTG GACGTGACAT    5280
GTACGAGAGA CGGCATGAGC GCGGAATGTG CGACCGTGCC GTCGAGATGA CCGACGTCGG    5340
CGCTACGGCA GCCCCCACCG GACCTATCGC GCGGGGCAGC GTCGCTCGGG TCGGCGCGGC    5400
GACCGCGTTG GCCGTTGCCT GCGTCTACAC GGTCATCTAT CTGGCGGCCC GCGACCTACC    5460
CCCGGCTTGT TTTTCGATAT TCGCGGTGTT TTGGGGGGCG CTCGGCATTG CCACCGGCGC    5520
CACCCACGGC CTCCTGCAAG AAACGACCCG CGAGGTCCGC TGGGTGCGCT CCACCCAAAT    5580
AGTTGCGGGC CATCGTACCC ATCCGCTGCG GGTGGCCGGG ATGATTGGCA CCGTCGCGGC    5640
CGTCGTAATT GCGGGTAGCT CACCGCTGTG GAGCCGACAG CTATTCGTCG AGGGGCGCTG    5700
GCTGTCCGTG GGGCTACTCA GCGTTGGGGT GGCCGGGTTC TGCGCGCAGG CGACCCTGCT    5760
GGGCGCGCTG GCCGGCGTCG ACCGGTGGAC ACAGTACGGG TCACTGATGG TGACCGACGC    5820
GGTCATCCGG TTGGCGGTCG CCGCGGCAGC GGTTGTGATC GGATGGGGTC TGGCCGGGTA    5880
CTTGTGGGCC GCCACCGCGG GAGCGGTGGC GTGGCTGCTC ATGCTGATGG CCTCGCCCAC    5940
CGCGCGCAGC GCGGCCAGCC TGCTGACGCC CGGGGGAATC GCCACGTTCG TGCGCGGTGC    6000
CGCTCATTCG ATAACCGCCG CGGGTGCCAG CGCGATTCTG GTAATGGGTT TCCCAGTGTT    6060
GCTCAAAGTG ACCTCCGACC AGTTAGGGGC AAAGGGCGGA GCGGTCATCC TGGCTGTGAC    6120
CTTGACGCGT GCGCCGCTTC TGGTCCCACT GAGCGCGATG CAAGGCAACC TGATCGCGCA    6180
TTTCGTCGAC CGGCGCACCC AACGGCTTCG GGCGCTGATC GCACCGGCGC TGGTCGTCGG    6240
CGGCATCGGT GCGGTCGGGA TGTTGGCCGC AGGGCTTACC GGTCCCTGGT TGCTGCGTGT    6300
TGGATTCGGC CCCGACTACC AAACTGGCGG GGCGTTGCTG GCCTGGTTGA CGGCAGCGGC    6360
```

-continued

```
GGTAGCTATC GCCATGCTGA CGCTGACCGG CGCCGCCGCG GTCGCGGCCG CACTGCACCG    6420
GGCGTATTTG CTGGGCTGGG TCAGCGCGAC GGTGGCGTCG ACGCTGTTGC TGCTGCTGCC    6480
GATGCCGCTG GAGACGCGCA CCGTGATCGC GCTGTTGTTC GGTCCAACGG TGGGAATCGC    6540
CATCCATGTG GCCGCGTTGG CGCGGCGACC CGACTGATTT GTGCCCCAGG TCGACAAATC    6600
ACGCCGTCTC GTCAGTGAGC ACTCCGTCCT CGGGTCCGAT CCTTCCAGGA GACGTTGCAA    6660
CCTGATTTGG CTCAAATTGG TGCGCACCGA GGGTCGGGCA CATCGTAGGG TCGCAACAGT    6720
CACATGTGTC ACTGCACCGG GCGACACCCG ATGTCCCGGC TCTCAGCGAC AGCTGTCTGA    6780
CCTGTGGTTT TGTTCCCAAG TTGGTCGTGG CTGTGCGGGA TTGGAGGTGG CGTGGGGGTC    6840
GCGTCGTATG GATTCTCCTC CTCGGTTCCG CGCGAAACGG CCGCAGGCGC AATGGTCACC    6900
AACTTGGCCG CGGTGGAGTC TAGCCTCACA TTTTCCTGGT CGCCCCCGAC AACCAGGAGG    6960
TCGCTGCAGA ACGGGCGTTC CCTACCCACA TCTACTATGA AGCGACAGCG GCGCCCCGCT    7020
GTGATGGCTG AGCATGACCG ACAGAGGCGG GAAGACAGTG AAGCGAGCGC TCATCACCGG    7080
AATCACCGGC CAGGACGGCT CGTATCTCGC CGAACTGCTG CTGGCCAAGG GGTATGAGGT    7140
TCACGGGCTC ATCCGGCGCG CTTCGACGTT CAACACCTCG CGGATCGATC ACCTCTACGT    7200
CGACCCGCAC CAACCGGGCG CGCGGCTGTT TCTGCACTAT GGTGACCTGA TCGACGGAAC    7260
CCGGTTGGTG ACCCTGCTGA GCACCATCGA ACCCGACGAG GTGTACAACC TGGCGGCGCA    7320
GTCACACGTG CGGGTGAGCT TCGACGAACC CGTGCACACC GGTGACACCA CCGGCATGGG    7380
ATCCATGCGA CTGCTGGAAG CCGTTCGGCT CTCTCGGGTG CACTGCCGCT TCTATCAGGC    7440
GTCCTCGTCG GAGATGTTCG GCGCCTCGCC GCCACCGCAG AACGAGCTGA CGCCGTTCTA    7500
CCCGCGGTCA CCGTATGGCG CCGCCAAGGT CTATTCGTAC TGGGCGACCC GCAATTATCG    7560
CGAAGCGTAC GGATTGTTCG CCGTTAACGG CATCTTGTTC AATCACGAAT CACCGCGGCG    7620
CGGTGAGACG TTCGTGACCC GAAAGATCAC CAGGGCCGTG GCACGCATCA AGGCCGGTAT    7680
CCAGTCCGAG GTCTATATGG GCAATCTGGA TGCGGTCCGC GACTGGGGGT ACGCGCCCGA    7740
ATACGTCGAA GGCATGTGGC GGATGCTGCA GACCGACGAG CCCGACGACT TCGTTTTGGC    7800
GACCGGGCGC GGTTTCACCG TGCGTGAGTT CGCGCGGGCC GCGTTCGAGC ATGCCGGTTT    7860
GGACTGGCAG CAGTACGTGA AATTCGACCA ACGCTATCTG CGGCCCACCG AGGTGGATTC    7920
GCTGATCGGC GACGCGACCA AGGCTGCCGA ATTGCTGGGC TGGAGGGCTT CGGTGCACAC    7980
TGACGAGTTG GCTCGGATCA TGGTCGACGC GGACATGGCG GCGCTGGAGT GCGAAGGCAA    8040
GCCGTGGATC GACAAGCCGA TGATCGCCGG CCGGACATGA ACGCGCACAC CTCGGTCGGC    8100
CCGCTTGACC GCGCGGCCCG GGTCTACATC GCCGGGCATC GCGGCCTGGT CGGGTCCGCG    8160
CTGCTACGCA CGTTTGCGGG CGCGGGGTTC ACCAACCTGC TGGTGCGGTC ACGCGCCGAG    8220
CTTGATCTGA CGGATCGGGC CGCGACGTTC GACTTCGTTC TCGAGTCGAG GCCGCAGGTC    8280
GTCATCGACG CGGCGGCCCG GGTCGGCGGC ATCCTGGCCA ACGACACCTA CCCGGCCGAT    8340
TTCCTGTCGG AAAACCTCCA GATCCAGGTC AACCTGCTGG ATGCCGCCGT GGCGGCGCGG    8400
GTGCCGCGGC TGCTGTTCCT GGGCTCGTCG TGCATCTACC CGAAACTCGC CCCGCAGCCG    8460
ATCCCGGAGA GCGCGCTGCT CACCGGTCCG TTGGAGCCGA CCAACGACGC GTACGCGATC    8520
GCCAAAATCG CCGGCATCCT TGCGGTCCAG GCGGTGCGCC GCCAACATGG CCTGCCGTGG    8580
ATCTCGGCGA TGCCCACCAA CCTGTACGGG CCAGGCGACA ACTTTTCGCC GTCCGGCTCG    8640
CATCTGCTGC CGGCACTCAT CCGCCGCTAT GACGAGGCCA AAGCCAGTGG CGCGCCCAAC    8700
GTGACCAACT GGGGCACCGG CACGCCCCGA CGGGAGTTGC TGCACGTCGA CGACCTGGCG    8760
AGCGCATGCC TGTATCTGCT GGAACATTTC GACGGGCCGA CCCATGTCAA CGTGGGAACC    8820
```

-continued

GGCATCGACC ACACCATCGG CGAGATCGCC GAGATGGTCG CCTCGGCGGT AGGCTATAGC 8880

GGCGAAACCC GCTGGGATCC AAGCAAACCG GACGGAACAC CACGCAAACT GCTGGATGTT 8940

TCGGTGCTAC GGGAGGCGGG ATGGCGGCCT TCGATCGCGC TGCGCGACGG CATCGAGGCG 9000

ACGGTGGCGT GGTATCGCGA GCACGCGGGA ACGGTTCGGC AATGAGGCTG GCCCGTCGCG 9060

CTCGGAACAT CTTGCGTCGC AACGGCATCG AGGTGTCGCG CTACTTTGCC GAACTGGACT 9120

GGGAACGCAA TTTCTTGCGC CAACTGCAAT CGCATCGGGT CAGTGCCGTG CTCGATGTCG 9180

GGGCCAATTC GGGGCAGTAC GCCAGGGGTC TGCGCGGCGC GGGCTTCGCG GGCCGCATCG 9240

TCTCGTTCGA GCCGCTGCCC GGGCCCTTTG CCGTCTTGCA GCGCAGCGCC TCCACGGACC 9300

CGTTGTGGGA ATGCCGGCGC TGTGCGCTGG GCGATGTCGA TGGAACCATC TCGATCAACG 9360

TCGCCGGCAA CGAGGGCGCC AGCAGTTCCG TCTTGCCGAT GTTGAAACGA CATCAGGACG 9420

CCTTTCCACC AGCCAACTAC GTGGGCGCCC AACGGGTGCC GATACATCGA CTCGATTCCG 9480

TGGCTGCAGA CGTTCTGCGG CCCAACGATA TTGCGTTCTT GAAGATCGAC GTTCAAGGAT 9540

TCGAGAAGCA GGTGATCGCG GGTGGCGATT CAACGGTGCA CGACCGATGC GTCGGCATGC 9600

AGCTCGAGCT GTCTTTCCAG CCGTTGTACG AGGGTGGCAT GCTCATCCGC GAGGCGCTCG 9660

ATCTCGTGGA TTCGTTGGGC TTTACGCTCT CGGGATTGCA ACCCGGTTTC ACCGACCCCC 9720

GCAACGGTCG AATGCTGCAG GCCGATGGCA TCTTCTTCCG GGGCAGCGAT TGACGCGCCG 9780

GCGCGTCAAT CTATTTCGAC ATTCGCGTGA AGACGTTTTC CCAGAATCGA CTGTTGTAGG 9840

CGTAGAACTC CCGGCCGCGT AGGTAGGCAT GTGATATTCG CCTTCCCCCG AACGGGTAGC 9900

GGCGATGAAG GTCGCCCATG CGGCGCAGAT CACCGAAGAC CGCGCTTGGT TCCCGGTGCG 9960

AGCCGACGCC CGTGGTGTCG AACTCGCACA GCACACACCG AATCGTGACC GGCTCGCATA 10020

CCAGCGCGGC CCGCAATATG AATTCCTGGT CGGCGGCGAT CCCGAAATCA AGGTCGTAGC 10080

CACCGATCTT GGCCACCAGC GATGATCCGA AGAACGATGC TTGATGCGGA ACAACCTGCT 10140

TGCCGGCCAG GAATTTGCGC AGGCTGAAAG GTATCGGGCC GCGCACCCGA TCGAGCCCGA 10200

CGAGACGATC CATCCCGAAG CCCCACAATT CGGACACCGG TCCCTTGCCG GATAGCGCCT 10260

CCACGGCCTG GGCTACCACG TCGGGCCCGG AAAAACGATC GGCGGAGTGC AAGAACCACA 10320

ACAGATCACC CGATGCGTGC GCGATGCCCT GGTTCATCGC GTCGTACCGC CCGCCGTCGG 10380

GCTCGGACTG CCAATACGCG AAGCCTGGTT CACACCCGGA CAGGTATGCC ACCACGTCGT 10440

CGCCGCTGCC ACCGTCGATT ACGATGTGCT CGATGCGTCC CCGGTAGCGT TGCGCCCGCA 10500

CACTTTTCAC CGTGCGCTGC AACCCGTCGA GGTCGTTGAA CGAGATCGTT ATCACCGAGA 10560

CGGTCGGAGC AGACGTCACC GAGTTCCCCT AGGTTGCTGG CGGCGATTGT GGATCACCGG 10620

GTCTTGATAC CGATGAAGGT GCCTCGAAGA TTCGCCGCAT AGGAACCTCC GAGCAACGAC 10680

TCGGCGATGC TTGGTTCCAA GTTGTCGTAC TCCTCCATCA CCAGGTCGAC GCCGACGTCT 10740

TTGATGGCCT GAAGTAGGTG CTCGCGTTGA ATCCAGAATG ACCGGCGATT GTCCCAGGAC 10800

GCCCATTTTG CGGTGTCGCG CTGGCCAAAC GAGCGGTCGT CGGAAAACTC GGTAAACCAC 10860

CTACCGGGAA GTCCCTCATG TTCGGTGGGC GCCGAGAGCA TGAACTTCAC CGGCGCCGGC 10920

CGCCGCAGCA ACCGATCGGT CAATTGTCGT GCCGTCGTGG GCAACCGGAG CCATTTATCG 10980

CTCCGGTTGA TGATCGAGAA GTGCGTCTGG AGAATCAGCA GCTTGTTCGT TACCGACGAG 11040

AGGGTTTCCA GGTATTGCTT CGGATTCTCC AGGTGGTAGA AGAGGCCGCA GCAGAAGACG 11100

GTATCGAAGA GCCCGTGGTT GGCGATGTTG AGGGCGTTGT CGTGGACGAA CCGGAGATTC 11160

GGCAGGTTGG TCTTCGATTT GATGTAGTTG CAGGCCGCCA TGTTCAGCTC GCGAACCTCG 11220

-continued

```
ATCCCGAGGA CCTGAAATCC CATGCGCGCG AACCCGACCG CGTACCCGCC TTCCAAGCAG   11280

CCGACATCGG CCAGGCGTAG GTGGCTCTTG TCCCCGGGAA AGACGGTTTC CAGAATCCCG   11340

CGCGCCGAGA TGAACCAGGA CGATTCGTCT AACGTGCGCG AGGACTCCGG TATCGTCAAG   11400

GTTCCGTCGT CGAGGCGAAC GTTGTGGGCG GTGAATTGTA CCGCGCCGGC CGAATGTTCC   11460

TGTGCCATCA CTTGGTTAGC CCCTTCGGCT GGTCCTGGGT TTGTCGACAT GGTCAGGCTC   11520

GACAGCCGCG TCGGAGCCGG GAGGGCCACA CATCCACGAG CCCCCTGCGG CTCGGCGTCG   11580

CGGCGGCGAG CTTGCGCCAC TGGGTCTTGA GCCGCCGCGC GGGTGTCGCC CCGCGGTGCT   11640

GCAGCGCCAG CATGGCGATC CGGGGATGGC GCGCGATGGT TTCCTGCAGC GCGGCGCGCC   11700

CCTCCGGGCC TGGAACGTTG GCGATCTGGC GAAGGATCCA GTCGGCCATG ACGGCGATGA   11760

GCTCCTCGCG CGCGGGGTCT CCCGGGAACA GGTCGAGCAT CGCGTCAAAC GTCGCCGCAT   11820

GCCCCGGACC CTGCGTCAAC CAGAACTTTG GCGGGTCCAC CACCTGGTTG TGCCACATGC   11880

CTTGGGCGTG GCGGCGATAC ACGGCCATGG TGTCGGGCAA CATGGCGATG TCGCCATGCA   11940

CCGCGTGCCG GACGTGCAGA TACCAGTCCA GGGGCATGAC GTCGGCAGGA ATGTCGTCGT   12000

AGCGCTCGAG GCGACGGTAC ACGGCCGAGT TGGTCTGGAT GAAGTTCATC AAGATCAACG   12060

CATCCAGGCT CAAGTTGCCC CGCACCCGAA CCGGGGGGAA CTTCGAGTCC TTGGCATGGC   12120

CGTCCTCCCA TATCACTCGG ACGGGATGGA AGCACACCGT CGTCTTGGGG TGCCGGTCGA   12180

GGAATGCGAC CTGTTTGCTT AGCTTCAGCG GATCGATCCA GTAGTCGTCC GCCTCGCACA   12240

ACGCGACGTA CTCGCCGCGA GCGGCCGACA GGGCGCCGGT CAGGTTCCCA TTGAGGCCGA   12300

GGTTTTCGGT CCTGAAGATC GGCCGGAACA CGTGCGGGTA CCGCTCGGCG TACTCACGGA   12360

TGATCGCCGG GGTGGCATCG GTCGACGCGT CGTCGGCGAC GATGATCTCC ACCGGGAAGT   12420

CGGTTTGCTG GTCGAGAAAG CTGTCGAAGG CCTGACGGGC GTAGCCCGCC TGGTTGTGAG   12480

TGGTCGAGAC GATGCTCACC TTGGGGCAAA GCTGGGGACT CACCGTCGGC CCTTTTCCTG   12540

CGCGGCCGCA AGGGTATTGC GATGGCGAAC GTGAATCGCC TGTGCCCGCC GGCCGTCGGC   12600

CGTCGTGGCC TGGTGGTCGG CGGACGTACG GCACACGCTG GCGAAGTATA GCGAGGGTGC   12660

ACTGACGTTG GGCTCGAACC GCGTGGCGCG CGGTGTGGGC GCACCGTCTC GAGTCGGTGC   12720

TGGTTGGCTC GC                                                       12732
```

The location, on the *Mycobacterium tuberculosis* chromosome, of the above polynucleotide of sequence SEQ ID No1 has now been ascribed to begin, at its 5'end at nucleotide at position nt 1696015 and to end, at its 3'end, at nucleotide at position nt 1708746.

For diagnostic purposes, this 12.7 kb deletion should allow a rapid PCR screening of tubercle isolates to identify whether they are bovine or human strains. The primers listed in Table 1 are flanking the deleted region and give a 722 bp amplicon in *M. bovis* or *M. bovis* BCG strains, but a fragment of 13,453 bp in *M. tuberculosis* that is practically impossible to amplify under the same PCR conditions. More importantly, assuming that some of the gene products from this region represent proteins with antigenic properties, it could be possible to develop a test that can reliably distinguish between the immune response induced by vaccination with *M. bovis* BCG vaccine strains and infection with *M. tuberculosis* or that the products (e.g. polysaccharides) are specific immunogens The invention also provides for a purified polynucleotide useful as a probe or as a primer, said polynucleotide being chosen in the following group of polynucleotides:

a) a polynucleotide comprising at least 8 consecutive nucleotides of the sequence SEQ ID No1.

b) a polynucleotide whose sequence is fully complementary to the sequence of the polynucleotide defined in a);

c) a polynucleotide that hybridizes under stringent hybridization conditions with the polynucleotide defined in a) or with the polynucleotide defined in b).

For the purpose of defining a polynucleotide or oligonucleotide hybridizing under stringent hybridization conditions, such as above, it is intended a polynucleotide that hybridizes with a reference polynucleotide under the following hybridization conditions:

The hybridization step is realized at 65° C. in the presence of 6×SSC buffer, 5× Denhardt's solution, 0.5% SDS and 100 μg/ml of salmon sperm DNA.

For technical information, 1×SSC corresponds to 0.15 M NaCl and 0.05M sodium citrate; 1× Denhardt's solution corresponds to 0.02% Ficoll, 0.02% polyvinylpyrrolidone and 0.02% bovine serum albumin.

The hybridization step is followed by four washing steps:

two washings during 5 min, preferably at 65° C. in a 2×SSC and 0.1% SDS buffer;

one washing during 30 min, preferably at 65° C. in a 2×SSC and 0.1% SDS buffer, one washing during 10 min, preferably at 65° C. in a 0.1×SSC and 0.1% SDS buffer A first illustrative useful polynucleotide that is included in the polynucleotide of sequence SEQ ID No1 is the following polynucleotide of sequence SEQ ID No2 that corresponds to the Sp6 endsequence of SEQ ID No1:

```
ATACTCAAGC TTGCCGCAAT CGAAACCAAC CTGTTTGTGC CGCAAGAAAT TACGCCGTGG   60

CCCGGCGCCG ATCAAGAAAC GCCCCGGCGC GCGGCGGTGT CGTCGTATGG CATGACGGGC  120

ACCAATGTGC ACGCCATTGT CGAGCAGGCA CCGGTGCCAG CCCCCGAATC CGGTGCACCA  180

GGCGACACCC CGGCCACACC CGGTATCGAC GGCGCGCTGC TGTTCGCGCT GTCGGCCAGC  240

TCGCAGGACG CGCTGCGGCA AACCGCCGCG CGGCTGGCCG ATTGGGTCT              289
```

A second illustrative useful polynucleotide that is included in the polynucleotide of sequence SEQ ID No1 is the following polynucleotide of sequence SEQ ID No3 that corresponds to the T7 endsequence of SEQ ID No1, located on the opposite strand:

```
TTGGCGGGTT GGCCACACAC CCGCCGGTGA CGGCGACGAT GCTGGGCTGG TTGCGGCCCT   60

GCGCCACCGC GGCTTGCATG CTGGTTGGCT GTCTTGGGAC GATCCCGAAA TAGTCCACGC  120

GGATCTGGTG ATTTTGCGGG CTACCCGCGA TTACCCCGCG CGGCTCGACG AGTTTTTGGC  180

CTGGACTACC CGCGTGGCCA ATCTGCTGAA CTCGCGGCCG GTGGTGGCCT GGAATGTCCA  240

CGCCGTTCAC CTACGTGACC TTGATGGGAT CCGGGGGT                         278
```

The polynucleotide of sequence SEQ ID No1 contains 11 ORFs, the respective locations of which, taking into account the orientation of each ORF on the chromosome, on the sequence of the *Mycobacterium tuberculosis* chromosome, is given hereafter:

The location of ORF1 is comprised between nucleotide at position nt 1695944 and nucleotide at position nt1696441.

The location of ORF2 is comprised between nucleotide at position nt 1696728 and nucleotide at position nt1697420.

The location of ORF3 is comprised between nucleotide at position nt 1698096 and nucleotide at position nt1699892. ORF3 probably encodes a protein having the characteristics of a membrane protein.

The location of ORF4 is comprised between nucleotide at position nt 1700210 and nucleotide at position nt1701088.

The location of ORF5 is comprised between nucleotide at position nt 1701293 and nucleotide at position nt1702588. ORF5 encodes a protein having the characteristics of a membrane protein.

The location of ORF6 is comprised between nucleotide at position nt 1703072 and nucleotide at position nt1704091. ORF6 encodes a protein having the characteristics of a GDP-D-mannose dehydratase.

The location of ORF7 is comprised between nucleotide at position nt 1704091 and nucleotide at position nt1705056. ORF7 encodes a protein having the characteristics of a nucleotide sugar epimerase involved in colonic acid biosynthesis.

The location of ORF8 is comprised between nucleotide at position nt 1705056 and nucleotide at position nt1705784.

The location of ORF9 is comprised between nucleotide at position nt 1705808 and nucleotide at position nt1706593. ORF9 encodes a protein having the characteristics of colonic acid biosynthesis glycosyl transferase.

The location of ORF10 is comprised between nucleotide at position nt 1706631 and nucleotide at position nt1707524.

The location of ORF11 is comprised between nucleotide at position nt 1707530 and nucleotide at position nt1708648. ORF11 encodes a protein similar to a spore coat polysaccharide biosynthesis.

A polynucleotide of interest obtained by the above-disclosed method according to the invention may also contain at least one ORF that encodes all or part of acidic, glycine-rich proteins, belonging to the PE and PPE families, whose genes are often clustered and based on multiple copies of the polymorphic repetitive sequences. The names PE and PPE derive from the fact that the motifs ProGlu (PE, positions 8, 9) and ProProGlu (PPE, positions 7 to 9) are found near the N-terminus in almost all cases. The PE protein family all have a highly conserved N-terminal domain of ~110 amino acid residues, that is predicted to have a globular structure, followed by a C-terminal segment which varies in size, sequence and repeat copy number. Phylogenetic analysis separated the PE family into several groups, the larger of which is the highly repetitive PGRS class containing 55 members whereas the other groups share very limited sequence similarity in their C-terminal domains. The predicted molecular weights of the PE proteins vary considerably as a few members only contain the ~110 amino acid N-terminal domain while the majority have C-terminal extensions ranging in size from 100 up to >1400 residues. A striking feature of the PGRS proteins is their exceptional glycine content (up to 50%) due to the presence of multiple tandem repetitions of GlyGlyAla or GlyGlyAsn motifs or variations thereof.

Like the PE family, the PPE protein family also has a conserved N-terminal domain that comprises ~180 amino acid residues followed by C-terminal segments that vary considerably in sequence and length. These proteins fall into at least three groups, one of which constitutes the MPTR class characterised by the presence of multiple, tandem copies of the motif AsnXGlyXGlyAsnXGly. The second subgroup contains a characteristic, well-conserved motif around position 350 (GlyXXSerValProXXTrp), whereas the other group contains proteins that are unrelated except for the presence of the common 180-residue PPE domain. C-terminal extensions may range in size from 00 up to 3500 residues One member of the PGRS sub-family, the WHO antigen 22T (Abou-Zeid et al., 1991), a 55 kD protein capable of binding fibronectin, is produced during disease and elicits a variable antibody response suggesting either that individuals mount different immune responses or that this PGRS-protein may not be produced in this form by all strains of *M. tuberculosis*. In other words, at least some PE_PGRS coding sequences encode for proteins that are involved in the recognition of *M. tuberculosis* by the immune system of the infected host Therefore, differences in the PGRS sequences could represent the principal source of antigenic variation in the otherwise genetically and antigenically homogeneous bacterium.

By performing the method of the invention using the *M. tuberculosis* BAC based DNA library 1-1945, the inventors have discovered the occurrence of sequence differences between a given PGRS encoding ORF (ORF reference on the genomic sequence of *M. tuberculosis* Rv0746) of *M. tuberculosis* and its counterpart sequence in the genome of *M. bovis* BCG.

More precisely, the inventors have determined that one ORF contained in BAC vector No Rv418 of the *M. tuberculosis* BCG I-1945 DNA library carries both base additions and base deletions when compared with the corresponding ORF in the genome of *M. bovis* BCG that is contained in the BAC vector No X0175 of the *M. bovis* BCG I-XXXX DNA library. The variations observed in the base sequences correspond to variations in the C-terminal part of the amino acid sequence of the PGRS ORF translation product.

As shown in FIG. 6, an amino acid stretch of 29 residues in length is present in this *M. tuberculosis* PGRS (ORf reference Rv0746) and is absent from the ORF counterpart of *M. bovis* BCG, namely the following amino acid sequence:

$NH_2$-GGAGGAGGSSAGGGGAGGAGGAGGWLLGD-COOH.

Furthermore, FIG. 6 shows also that an amino acid stretch of 45 residues in length is absent from this *M. tuberculosis* PGRS and is present in the ORF counterpart of *M. bovis* BCG, namely following amino acid sequence:

$NH_2$-GAGGIGGIGGNANGGAGGNGGTGGQLWGSGGAGVEGGAALSVGDT-COOH.

Similar observations were made with PPE ORF Rv0442, which showed a 5 codon deletion relative to a *M. bovis* amino acid sequence.

Given that the polymorphism associated with the PE-PGRS or PEE ORFS resulted in extensive antigenic variability or reduced antigen presentation, this would be of immense significance for vaccine design, for understanding protective immunity in tuberculosis and, possibly, explain the varied responses seen in different BCG vaccination programmes.

There are several striking parallels between the PGRS proteins and the Epstein-Barr virus-encoded nuclear antigens (EBNA). Both polypeptide families are glycine-rich, contain Gly-Ala repeats that represent more than one third of the molecule, and display variation in the length of the repeat region between different isolates. The Gly-Ala repeat region of EBNA1 has been shown to function as a cis-acting inhibitor of antigen processing and MHC class I-restricted antigen presentation (Levitskaya et al., 1995). The fact that MHC class I knock-out mice are extremely susceptible to *M. tuberculosis* underlines the importance of MHC class I antigen presentation in protection against tuberculosis. Therefore, it is possible that the PE/PPE protein family also play some role in inhibiting antigen presentation, allowing the *bacillus* to hide from the host's immune system.

As such the novel and nonobvious PGRS polynucleotide from *M. bovis* which is homolog to the *M. tuberculosis* ORF Rv0746, and which is contained in the BAC clone No X0175 (See Table 4 for SP6 and T7 endsequences of clone no X0175) of the I-XXXX *M. bovis* BCG BAC DNA library is part of the present invention, as it represents a starting material in order to define specific probes or primers useful for detection of antigenic variability in mycobacterial strains, possible inhibition of antigen processing as well as to differentiate *M. tuberculosis* from *M. bovis* BCG.

Thus, a further object of the invention consists in a polynucleotide comprising the following sequence SEQ II No4:

```
CCGACCCAGA CACTGACCGG GCGACCGCTG ATCGGCAACG GCACCCCCGG GGCGGTCGGC    60
AGCGGGGCCA CCGGGGCCCC CGGTGGGTGG CTGCTCGGCG ACGGCGGGGC CGGCGGGTCC   120
GGCGCGGCGG GCTCGGGCGC GCCCGGCGGG GCGGGCGGGG CTGCCGGGCT GTGGGGTACC   180
GGCGGGGCCG GCGGGATCGG CGGAGCCAGC ACCGTACTCG GCGGCACCGG CGGGGGAGGC   240
GGGGTCGGTG GGCTGTGGGG CGCCGGTGGG GCCGGCGGGG CCGGTGGAAC CGGCCTTGTT   300
GGTGGCGACG GCGGGGCCGG TGGGGCCGGC GGGACCGGCG GACTGCTGGC CGGGCTGATC   360
GGTGCCGGCG GAGGTCACGG CGGGACCGGC GGGCTCAGCA CTAATGGCGA CGGCGGGGTT   420
GGCGGGGCCG GCGGGAATGC CGGAATGCTC GCCGGGCCGG GCGGCGCCGG CGGAGCCGGC   480
GGTGACGGCG AAAACCTGGA CACCGGTGGG GACGGCGGGG CCGGCGGTAG CGCAGGGCTG   540
CTGTTCGGCA GCGGCGGCGC CGGCGGCGCC GGCGGATTTG GTTTCCTCGG TGGGGACGGC   600
GGGGCCGGTG GCAACGCCGG GCTGCTGTTG TCCAGCGGCG GGGCCGGCGG GTTCGGCGGG   660
TTCGGCACCG CCGGTGGGGT CGGTGGGGCC GGCGGCAATG CCGGCTGGCT GGGCTTCGGC   720
GGGGCCGGGG GCATCGGCGG AATCGGCGGT AACGCTAACG GGGGCGCCGG TGGGAACGGC   780
GGCACCGGCG GTCAGTTATG GGGTAGCGGC GGCGCCGGCG TCGAAGGCGG CGCAGCCTTA   840
AGCGTCGGCG ACACCGGCGG GGCCGGTGGC GTCGGCGGCA GCGCCGGGCT GATCGGCACC   900
```

-continued

```
GGCGGCAACG GCGGCAACGG CGGCACCGGC GCCAACGCCG GCAGCCCCGG AACCGGCGGC    960

GCCGGCGGGT TGCTGCTGGG CCAAAACGGG CTCAACGGGT TGCCGTAGCC GGGCGGCACG   1020

GCATGGCTTC CGGGCGTCAA CCACTCGCCG GTGATGCAGA TCGGCTGCGG AGCGGGCCGC   1080

CAAAATGGGG GCCGCCGCGC CAGGTATCTC GGCGAAGATC CCCGGCGCTC GAGCGCTTTG   1140

TCAGAGGCCC GTCGCGGGTC GTCGTGACGA CGGCTATCCG GGCGGTGCGG GTTTCGCGGC   1200

GCGCCCTGTG CCCGGCACCG CCGCCCGTTT GTCGGCAACG CCGCCGCGAC CCGTGAGCCG   1260

TCCAGCAGCT GGCGCCTGCG                                               1280
```

Polynucleotides of interest have been defined by the inventors as useful detection tools in order to differentiate *M. tuberculosis* from *M. bovis* BCG. Such polynucleotides are contained in the 45 amino acid length coding sequence that is present in *M. bovis* BCG but absent from *M. tuberculosis*. This polynucleotide has a sequence beginning (5'end) at the nucleotide at position nt 729 of the sequence SEQ ID No4 and ending (3'end) at the nucleotide in position nt 863 of the sequence SEQ D No4.

Thus, part of the present invention is also a polynucleotide which is chosen among the following group of polynucleotides:

a) A polynucleotide comprising at least 8 consecutive nucleotides the following nucleotide sequence SEQ ID No5:

```
GGGCATCGGC GGAATCGGCG GTAACGCTAA CGGGGGCGCC GGTGGGAACG GCGGCACCGG    60

CGGTCAGTTA TGGGGTAGCG GCGGCGCCGG CGTCGAAGGC GGCGCAGCCT TAAGCGTCGG   120

CGACACC                                                             127
```

b) A polynucleotide which sequence is fully complementary to the sequence of the polynucleotide defined in a);

c) A polynucleotide that hybridizes under stringent hybridization conditions with the polynucleotide defined in a) or with the polynucleotide defined in b).

The stringent hybridization conditions for the purpose of defining the above disclosed polynucleotide are defined herein before in the specification.

The invention also provides for a BAC-based *Mycobacterium tuberculosis* strain H37Rv genomic DNA library that has been deposited in the Collection Nationale de Cultures de Microorganismes on Nov. 19, 1997 under the accession number I-1945.

A further object of the invention consists in a recombinant BAC vector which is chosen among the group consisting of the recombinant BAC vectors belonging to the BAC-based DNA library I-1945.

Generally, a recombinant BAC vector of interest may be chosen among the following set or group of BAC vectors contained in the BAC-based DNA library I-1945: Rv101; Rv102; Rv103; Rv104; Rv105; Rv106; Rv107; Rv108; Rv109; Rv10; Rv110; Rv111; Rv112; Rv113; Rv114; Rv115; Rv116; Rv117; Rv118; Rv119; Rv11; Rv120; Rv121; Rv122; Rv123; Rv124; Rv126; Rv127; Rv128; Rv129; Rv130; Rv132; Rv134; Rv135; Rv136; Rv137; Rv138; Rv139; Rv13; Rv140; Rv141; Rv142; Rv143; Rv144; Rv145; Rv146; Rv147; Rv148; Rv149; Rv14; Rv150; Rv151; Rv152; Rv153; Rv154; Rv155; Rv156; Rv157; Rv159; Rv15; Rv160; Rv161; Rv162; Rv163; Rv164; Rv165; Rv166; Rv167; Rv169; Rv16; Rv170; Rv171; Rv172; Rv173; Rv174; Rv175; Rv176; Rv177; Rv178; Rv179; Rv17; Rv180; Rv181; Rv182; Rv183; Rv184; Rv185; Rv186; Rv187; Rv188; Rv18; Rv190; Rv191; Rv192; Rv193; Rv194; Rv195; Rv196; Rv19; Rv1; Rv201; Rv204; Rv205; Rv207; Rv209; Rv20; Rv214; Rv215; Rv217; Rv218; Rv219; Rv21; Rv220; Rv221; Rv222; Rv223; Rv224; Rv225; Rv226; Rv227; Rv228; Rv229; Rv22; Rv230; Rv231; Rv232; Rv233; Rv234; Rv235; Rv237; Rv240; Rv241; Rv243; Rv244; Rv245; Rv246; Rv247; Rv249; Rv24; Rv251; Rv252; Rv253; Rv254; Rv255; Rv257; Rv258; Rv259; Rv25; Rv260; Rv261; Rv262; Rv263; Rv264; Rv265; Rv266; Rv267; Rv268; Rv269; Rv26; Rv270; Rv271; Rv272; Rv273; Rv274; Rv275; Rv276; Rv277; Rv278; Rv279; Rv27; Rv280; Rv281; Rv282; Rv283; Rv284; Rv285; Rv286; Rv287; Rv288; Rv289; Rv28; Rv290; Rv291; Rv292; Rv293; Rv294; Rv295; Rv296; Rv29; Rv2; Rv301; Rv302; Rv303; Rv304; Rv306; Rv307; Rv308; Rv309; Rv30; Rv310; Rv311; Rv312; Rv313; Rv314; Rv315; Rv316; Rv317; Rv318; Rv319; Rv31; Rv32; Rv322; Rv327; Rv328; Rv329; Rv32; Rv330; Rv331; Rv333; Rv334; Rv335; Rv336; Rv337; Rv338; Rv339; Rv33; Rv340; Rv341; Rv343; Rv344; Rv346; Rv347; Rv348; Rv349; Rv34; Rv350; Rv351; Rv352; Rv353; Rv354; Rv355; Rv356; Rv357; Rv358; Rv359; Rv35; Rv360; Rv361; Rv363; Rv364; Rv365; Rv366; Rv367; Rv368; Rv369; Rv36; Rv370; Rv371; Rv373; Rv374; Rv375; Rv376; Rv377; Rv378; Rv379; Rv37; Rv381; Rv382; Rv383; Rv384; Rv385; Rv386; Rv387; Rv388; Rv389; Rv38; Rv390; Rv391; Rv392; Rv393; Rv396; Rv39; Rv3; Rv40; Rv412; Rv413; Rv414; Rv415; Rv416; Rv417; Rv418, Rv419; Rv41; Rv42; Rv43; Rv44; Rv45; Rv46; Rv47; Rv48; Rv49; Rv4; Rv50; Rv51; Rv52; Rv53; Rv54; Rv55; Rv56; Rv57; Rv58; Rv59; Rv5; Rv60; Rv61; Rv62; Rv63; Rv64; Rv65; Rv66; Rv67; Rv68; Rv69; Rv6; Rv70; Rv71; Rv72; Rv73; Rv74; Rv75; Rv76; Rv77; Rv78; Rv79; Rv7; Rv80; Rv81; Rv82; Rv83; Rv84; Rv85; Rv86; Rv87; Rv88; Rv89; Rv8; Rv90; Rv91; Rv92; Rv94; Rv95; Rv96; Rv9.

The end sequences of the polynucleotide inserts of each of the above clones corresponding respectively to the sequences adjacent to the T7 promoter and to the Sp6 promoter on the BAC vector are shown in Table 3.

It has been shown by the inventors that the minimal overlapping set of BAC vectors of the BAC-based DNA library I-1945 contains 68 unique BAC clones and practically spans almost the whole H37Rv chromosome with the exception of a single gap of approximately 150 kb.

More specifically, a recombinant BAC vector of interest is chosen among the following set or group of BAC vectors from the BAC-based DNA library I-1945, the location of which vector DNA inserts on the chromosome of *M. tuberculosis* is shown in FIG. 3:

Rv234; Rv351; Rv166; Rv35; Rv415; Rv404; Rv209; Rv272; Rv30; Rv228; Rv233; Rv38; Rv280; Rv177; Rv48; Rv374; Rv151; Rv238; Rv156; Rv92; Rv3; Rv403; Rv322; Rv243; Rv330; Rv285; Rv233; Rv219; Rv416; Rv67; Rv222; Rv149; Rv279; Rv87; Rv273; Rv266; Rv25; Rv136; Rv414; Rv13; Rv289; Rv60; Rv104; Rv5; Rv165; Rv215; Rv329; Rv240; Rv19; Rv74; Rv44; Rv167; Rv56; Rv80; Rv164; Rv59; Rv313; Rv265; Rv308; Rv220; Rv258; Rv339; Rv121; Rv419; Rv418; Rv45; Rv217; Rv134; Rv17; Rv103; Rv21; Rv22; Rv2; Rv270; Rv267; Rv174; Rv257; Rv144; Rv71; Rv7; Rv27; Rv191; Rv230; Rv128; Rv407; Rv268; Rv58; Rv173; Rv264; Rv417; Rv401; Rv144; Rv302; Rv81; Rv163; Rv281; Rv221; Rv420; Rv175; Rv86; Rv412; Rv73; Rv269; Rv214; Rv287; Rv42; Rv143.

The polynucleotides disclosed in Table 3 may be used as probes in order to select a given clone of the BAC DNA library I-1945 for further use.

The invention also provides for a BAC-based *Mycobacterium bovis* strain Pasteur genomic DNA library that has been deposited in the Collection Nationale de Cultures de Microorganismes on XXXX XX, 1998 under the accession number I-XXXX.

A further object of the invention consists in a recombinant BAC vector which is chosen among the group consisting of the recombinant BAC vectors belonging to the BAC-based DNA library I-XXXX. This DNA library contains approximately 1600 clones. The average insert size is estimated to be ~80 kb.

Generally, a recombinant BAC vector of interest may be chosen among the following set or group of BAC vectors contained in the BAC-based DNA library I-XXXX:

X0001; X0002; X0003; X0004; X0006; X0007; X0008; X0009; X0010; X0012; X0013; X0014; X0015; X0016; X0017; X0018; X0019; X0020; X0021; X0175.

The endsequences of the polynucleotide inserts of each of the above clones, corresponding respectively to the sequences adjacent to the T7 promoter and to the Sp6 promoter on the BAC vector are shown in Table 4.

The polynucleotides disclosed in Table 4 may be used as probes in order to select a given clone of the BAC DNA library I-XXXX for further use.

Are also part of the invention the polynucleotide inserts that are contained in the above described BAC vectors, that are useful as primers or probes.

These polynucleotides and nucleic acid fragments may be used as primers for use in amplification reactions, or as nucleic probes.

PCR is described in the U.S. Pat. No. 4,683,202. The amplified fragments may be identified by an agarose or a polyacrylamide gel electrophoresis, or by a capillary electrophoresis or alternatively by a chromatography technique (gel filtration, hydrophobic chromatography or ion exchange chromatography). The specificity of the amplification may be ensured by a molecular hybridization using, for example, one of the initial primers as nucleic probes.

Amplified nucleotide fragments are used as probes in hybridization reactions in present invention or in order to detect mutations in the genome of the given mycobacterium of interest, specifically a mycobacterium belonging to the *Mycobacterium tuberculosis* complex and more specifically *Mycobacterium tuberculosis* and *Mycobacterium bovis* BCG.

Are also part of the present invention the amplified nucleic fragments (<<amplicons>>) defined herein above.

These probes and amplicons may be radioactively or non-radioactively labeled, using for example enzymes or fluorescent compounds.

Other techniques related to nucleic acid amplification may also be used and are generally preferred to the PCR technique.

The Strand Displacement Amplification (SDA) technique (Walker et al., 1992) is an isothermal amplification technique based on the ability of a restriction enzyme to cleave one of the strands at his recognition site (which is under a hemiphosphorothioate form) and on the property of a DNA polymerase to initiate the synthesis of a new strand from the 3'OH end generated by the restriction enzyme and on the property of this DNA polymerase to displace the previously synthesized strand being localized downstream. The SDA method comprises two main steps:

a) The synthesis, in the presence of dCTP-alpha-S, of DNA molecules that are flanked by the restriction sites that may be cleaved by an appropriate enzyme.
b) The exponential amplification of these DNA molecules modified as such, by enzyme cleavage, strand displacement and copying of the displaced strands. The steps of cleavage, strand displacement and copy are repeated a sufficient number of times in order to obtain an accurate sensitivity of the assay.

The SDA technique was initially realized using the restriction endonuclease HincII but is now generally practised with an endonuclease from *Bacillus stearothermophilus* (BSOBI) and a fragment of a DNA polymerase which is devoid of any 5'→3'exonuclease activity isolated from *Bacillius cladotenax* (exo-Bca) [=exo-minus-Bca]. Both enzymes are able to operate at 60° C. and the system is now optimized in order to allow the use of dUTP and the decontamination by UDG. When using this technique, as described by Spargo et al. in 1996, the doubling time of the target DNA is of 26 seconds and the amplification rate is of $10^{10}$ after an incubation time of 15 min at 60° C.

The SDA amplification technique is more easy to perform than PCR (a single thermostated waterbath device is necessary) and is faster than the other amplification methods.

Thus, another object of the present invention consists in using the nucleic acid fragments according to the invention (primers) in a method of DNA or RNA amplification according to the SDA technique. For performing SDA, two pairs of primers are used: a pair of external primers (B1, B2) consisting of a sequence specific for the target polynucleotide of interest and a pair of internal primers (S1, S2) consisting of a fusion oligonucleotide carrying a site that is recognized by a restriction endonuclease, for example the enzyme BSOBI.

The operating conditions to perform SDA with such primers are described in Spargo et al. 1996.

The polynucleotides of the invention and their above described fragments, especially the primers according to the invention, are useful as technical means for performing different target nucleic acid amplification methods such as:

TAS (Transcription-based Amplification System), described by Kwoh et al. in 1989;

SR (Self-Sustained Sequence Replication), described by Guatelli et al. in 1990.

NASBA (Nucleic acid Sequence Based Amplification), described by Kievitis et al. in 1991.

TMA (Transcription Mediated Amplification).

The polynucleotides according to the invention are also useful as technical means for performing methods for amplification or modification of a nucleic acid used as a probe, such as:

LCR (Ligase Chain Reaction), described by Landegren et al. in 1988 and improved by Barany et al. in 1991 who employ a thermostable ligase.

RCR (Repair Chain Reaction) described by Segev et al. in 1992.

CPR (Cycling Probe Reaction), described by Duck et al. in 1990.

Q-beta replicase reaction, described by Miele et al. in 1983 and improved by Chu et al. in 1986, Lizardi et al. in 1988 and by Burg et al. and Stone et al. in 1996.

When the target polynucleotide to be detected is a RNA, for example a mRNA, a reverse transcriptase enzyme will be used before the amplification reaction in order to obtain a cDNA from the RNA contained in the biological sample. The generated cDNA is subsequently used as the nucleic acid target for the primers or the probes used in an amplification process or a detection process according to the present invention.

The non-labeled polynucleotides or oligonucleotides of the invention may be directly used as probes. Nevertheless, the polynucleotides or oligonucleotides are generally labeled with a radioactive element ($^{32}P$, $^{35}S$, $^{3}H$, $^{125}I$) or by a non-isotopic molecule (for example, biotin, acetylaminofluorene, digoxigenin, 5-bromodesoxyuridin, fluorescein) in order to generate probes that are useful for numerous applications.

Examples of non-radioactive labeling of nucleic acid fragments are described in the french patent No FR-7810975 or by Urdea et al. or Sanchez-Pescador et al., 1988.

In the latter case, other labeling techniques may be also used such as those described in the french patents FR-2,422,956 and 2,518,755. The hybridization step may be performed in different ways (Matthews et al., 1988). The more general method consists of immobilizing the nucleic acid that has been extracted from the biological sample onto a substrate (nitrocellulose, nylon, polystyrene) and then to incubate, in defined conditions, the target nucleic acid with the probe. Subsequently to the hybridization step, the excess amount of the specific probe is discarded and the hybrid molecules formed are detected by an appropriate method (radioactivity, fluorescence or enzyme activity measurement).

Advantageously, the probes according to the present invention may have structural characteristics such that they allow the signal amplification, such structural characteristics being, for example, branched DNA probes as those described by Urdea et al. in 1991 or in the European patent No EP-0225,807 (Chiron).

In another advantageous embodiment of the probes according to the present invention, the latters may be used as <<capture probes>>, and are for this purpose immobilized on a substrate in order to capture the target nucleic acid contained in a biological sample. The captured target nucleic acid is subsequently detected with a second probe which recognizes a sequence of the target nucleic acid which is different from the sequence recognized by the capture probe.

The oligonucleotide probes according to the present invention may also be used in a detection device comprising a matrix library of probes immobilized on a substrate, the sequence of each probe of a given length being localized in a shift of one or several bases, one from the other, each probe of the matrix library thus being complementary to a distinct sequence of the target nucleic acid. Optionally, the substrate of the matrix may be a material able to act as an electron donor, the detection of the matrix positions in which an hybridization has occurred being subsequently determined by an electronic device. Such matrix libraries of probes and methods of specific detection of a target nucleic acid is described in the European patent application No EP-0713,016 (Affymax technologies) and also in the U.S. Pat. No. 5,202,231 (Drmanac).

Since almost the whole length of a mycobacterial chromosome is covered by a BAC-based genomic DNA libraries according to the present invention (i.e. 97% of the *M. tuberculosis* chromosome is covered by the BAC library I-1945), these DNA libraries will play an important role in a plurality of post-genomic applications, such as in mycobacterial gene expression studies where the canonical set of BACs could be used as a matrix for hybridization studies. Probing such matrices with cDNA probes prepared from total mRNA will uncover genetic loci induced or repressed under different physiological conditions (Chuang et al., 1993; Trieselmann et al., 1992). As such, the H37Rv BAC library represents a fundamental resource for present and future genomics investigations.

The BAC vectors or the polynucleotide inserts contained therein may be directly used as probes, for example when immobilized on a substrate such as described herein before.

The BAC vectors or their polynucleotide inserts may be directly absorbed on a nitrocellulose membrane, at predetermined locations on which one or several polynucleotides to be tested are then put to hybridize therewith.

Preferably, a collection of BAC vectors that spans the whole genome of the mycobacterium under testing will be immobilized, such as, for example, the set of 68 BAC vectors of the I-1945 DNA library that is described elsewhere in the specification and shown in FIG. 3.

The immobilization and hybridization steps may be performed as described in the present Materials and Methods Section.

As another illustrative embodiment of the use of the BAC vectors of the invention as polynucleotide probes, these vectors may be useful to perform a transcriptional activity analysis of mycobacteria growing in different environmental conditions, for example under conditions in which a stress response is expected, as it is the case at an elevated temperature, for example 40° C.

In this specific embodiment of the invention, Genescreen membranes may be used to immobilize the restriction endonuclease digests (HindIII digests for the BAC DNA library I-1945) of the BAC vectors by transfer from a gel (Trieselmann et al., 1992).

Alternatively, the BAC vectors may be immobilized for dot blot experiments as follows. First, the DNA concentration of each BAC clone is determined by hybridization of blots of clone DNAs and of a BAC vector concentration standard with a BAC vector specific DNA probe. Hybridization is quantified by the Betascope 603 blot analyzer (Betagen Corp.), which collects beta particles directly from the blot with high efficiency. Then, 0.5 µg of each clone DNA is incubated in 0.25 M NaOH and 10 mM EDTA at 65° C. for 60 min to denature the DNA and degrade residual RNA contaminants. By using a manifold filtration system (21 by 21 wells), each clone DNA is blotted onto a GeneScreen Plus nylon membrane in the alkaline solution. After neutralization, the blots are baked at 85° C. for 0.2 h under vacuum. Positive and negative controls are added when necessary. In order to perform this procedure, it may be referred to the article of Chuang et al. (1993).

For RNA extractions, cells grown in a suitable volume of culture medium may, for example, be immediately mixed with an equal volume of crushed ice at −70° C. and spun at 4° C. in a 50 ml centrifugation tube. The cell pellet is then suspended in 0.6 ml of ice-cold buffer (10 mM KCl, 5 mM MgCl, 10 mM Tris; pH 7.4) and then immediately added to 0.6 ml of hot lysis buffer (0.4 M NaCl, 40 mM EDTA, 1% beta-mercaptoethanol 1% SDS, 20 mM Tris; pH 7.4) containing 100 μl of water saturated phenol. This mixture is incubated in a boiling water bath for 40 s. The debris are removed by centrifugation. The supernatant is extracted with phenol-chloroform five times, ethanol precipitated, and dried. The dried RNA pellet is dissolved in water before use.

Then labeled total cDNA may be prepared by the following method. The reaction mixture contains 15 μg of the previously prepared total RNA, 5 μg of pd($N_6$) (random hexamers from Pharmacia Inc.), 0.5 mM dATP, 0.5 mM dGTP and 0.5 mM DTTP, 5 μM dCTP, 100 μCi of [α-$^{32}$P]dCTP (3,000 Ci/mmol), 50 mM Tris-HCl (pH 8.3), 6 mM $MgCl_2$, 40 mM Kcl, 0.5 U of avian myeloblastosis virus reverse transcriptase (Life Science Inc.) in a total volume of 50 μl. The reaction is allowed to continue overnight at room temperature. EDTA and NaOH are then added to final concentrations of 50 mM and 0.25 M, respectively, and the mixture is incubated at 65° C. for 30 min to degrade the RNA templates. The cDNA is then ready to use after neutralization by adding Hcl and Tris buffer.

The hybridization step may be performed as described by Chuang et al. (1993) and briefly disclosed hereinafter. The DNA dot blot is hybridized to $^{32}$P-labeled total cDNA in a solution containing 0.1% polyvinylpyrrolidone, 0.1% Ficoll, 0.1% sodium $Pp_i$, 0.1% bovine serum albumin, 0.5% SDS, 100 mM NaCl, and 0.1 mM sodium citrate, pH 7.2, at 65° C. for 2 days and then washed with a solution containing 0.1% SDS, 100 mM NaCl, and 10 mM Na-citrate, pH 7.2. The same dot blot is used for hybridization with both control and experimental cDNAs, with an alkaline probe stripping procedure (soaked twice in 0.25M NaOH-0.75 M NaCl at room temperature, 30 min each, neutralized, and completely dried at 65° C. for at least 30 min) between the two hybridizations. Quantification may be done with the Betascope 603 blot analyzer (Betagen Corp.).

As it flows from the above technical teachings, another object of the invention consists in a method for detecting the presence of *mycobacteria* in a biological sample comprising the steps of:

a) bringing into contact the recombinant BAC vector or a purified polynucleotide according to the invention with a biological sample.

b) detecting the hybrid nucleic acid molecule formed between said purified polynucleotide and the nucleic acid molecules contained within the biological sample.

The invention further deals with a method for detecting the presence of mycobacteria in a biological sample comprising the steps of:

a) Bringing into contact the recombinant BAC vector or a purified polynucleotide according to the invention that has been immobilized onto a substrate with a biological sample.

b) Bringing into contact the hybrid nucleic acid molecule formed between said purified polynucleotide and the nucleic acid contained in the biological sample with a labeled recombinant BAC vector or a polynucleotide according to the invention, provided that said polynucleotide and polynucleotide of step a) have non-overlapping sequences.

Another object of the invention consists in a method for detecting the presence of mycobacteria in a biological sample comprising the steps of:

a) Bringing into contact the nucleic acid molecules contained in the biological sample with a pair of primers according to the invention.

b) Amplifying said nucleic acid molecules;

d) detecting the nucleic acid fragments that have been amplified, for example by gel electrophoresis or with a labeled polynucleotide according to the invention.

In one specific embodiment of the above detection and/or amplification methods, said methods comprise an additional step wherein before step a), the nucleic acid molecules of the biological sample have been made available to a hybridization reaction.

In another specific embodiment of the above detection methods, said methods comprise an additional step, wherein, before the detection step, the nucleic acid molecules that are not hybridized with the immobilized purified polynucleotide are Also part of the invention is a kit for detecting mycobacteria in a biological sample comprising:

a) A recombinant BAC vector or a purified polynucleotide according to the invention;

b) Reagents necessary to perform a nucleic acid hybridization reaction.

The invention also pertains to a kit for detecting a mycobacteria in a biological sample comprising:

a) A recombinant BAC vector or a purified polynucleotide according to the invention that is immobilized onto a substrate.

b) Reagents necessary to perform a nucleic acid hybridization reaction.

c) A purified polynucleotide according to the invention which is radioactively or non-radioactively labeled, provided that said polynucleotide and the polynucleotide of step a) have non-overlapping sequences.

Moreover, the invention provides for a kit for detecting mycobacteria in a biological sample comprising:

a) A pair of purified primers according to the invention;

b) Reagents necessary to perform a nucleic acid amplification reaction;

c) Optionally, a purified polynucleotide according to the invention useful as a probe.

The invention embraces also a method for detecting the presence of a genomic DNA, a cDNA or a mRNA of mycobacteria in a biological sample, comprising the steps of:

a) Bringing into contact the biological sample with a plurality of BAC vectors according to the invention or purified polynucleotides according to the invention, that are immobilized on a substrate;

b) Detecting the hybrid complexes formed.

The invention also provides a kit for detecting the presence of genomic DNA, cDNA or mRNA of a mycobacterium in a biological sample, comprising:

a) A substrate on which a plurality of BAC vectors according to the invention or purified polynucleotides according to the invention have been immobilized;

b) Optionally, the reagents necessary to perform the hybridization reaction.

Additionally, the recombinant BAC vectors according to the invention and the polynucleotide inserts contained therein may be used for performing detection methods based on <<molecular combing>>. Said methods consist in methods for aligning macromolecules, especially DNA and are applied to processes for detecting, for measuring intramolecular distance, for separating and/or for assaying a macromolecule, especially DNA in a sample.

These <<molecular combing>> methods are simple methods, where the triple line S/A/B (meniscus) resulting form the contact between a solvent A and the surface S and a medium B is caused to move on the said surface S, the said macromolecules (i.e. DNA) having a part, especially an end, anchored on the surface S, the other part, especially the other end, being in solution in the solvent A. These methods are particularly fully described in the PCT Application no PCT/FR 95/00165 files on Feb. 11, 1994 (Bensimon et al.).

When performing the <<molecular combing>> method with the recombinant BAC vectors according to the inventions or their polynucleotide inserts, the latters may be immobilized (<<anchored>>) on a suitable substrate and aligned as described in the PCT Application no PCT/FR 95/00165, the whole teachings of this PCT Application being herein incorporated by reference. Then, polynucleotides to be tested, preferably under the form of radioactively or non radioactively labeled polynucleotides, that may consist of fragments of genomic DNA, cDNA etc. are brought into contact with the previously aligned polynucleotides according to the present invention and then their hybridization position on the aligned DNA molecules is determined using any suitable means including a microscope or a suitable camera device.

Thus, the present invention is also directed to a method for the detection of the presence of a polynucleotide of mycobacterial origin in a biological sample and/or for physical mapping of a polynucleotide on a genomic DNA, said method comprising:

a) Aligning at least one polynucleotide contained in a recombinant BAC vector according to the invention on the surface of a substrate;
b) Bringing into contact at least one polynucleotide to be tested with the substrate on which the at least one polynucleotide of step a) has been aligned;
c) detecting the presence and/or the location of the tested polynucleotide on the at least one aligned polynucleotide of step a).

The invention finally provides for a kit for performing the above method, comprising:

a) a substrate whose surface has at least one polynucleotide contained in a recombinant BAC vector according to the invention;
b) optionally, reagents necessary for labeling DNA;
c) optionally, reagents necessary for performing a hybridization reaction.

In conclusion, it may be underlined that the alliance of such BAC-based approaches such as described in the present specification to the advances in comparative genomics by the availability of an increased number of complete genomes, and the rapid increase of well-characterized gene products in the public databases, will allow the one skilled in the art an exhaustive analysis of the mycobacterial genome.

Materials and Methods

1. DNA-preparation. Preparation of *M. tuberculosis* H37Rv DNA in agarose plugs was conducted as previously described (Canard et al., 1989; Philipp et al., 1996b). Plugs were stored in 0.2 M EDTA at 4° C. and washed 3 times in 0.1% Triton X-100 buffer prior to use.
2. BAC vector preparation. pBeloBAC11 was kindly provided by Dr. Shizuya, Department of Biology, California Institute of Technology (Pasadena, Calif.). The preparation followed the description of Woo et al., 1994 (Woo et al., 1994).
3. Partial digestion with HindIII. Partial digestion was carried out on plugs, each containing approximately 10 µg of high molecular weight DNA, after three one hour equilibration steps in 50 ml of HindIII IX digestion buffer (Boehringer Mannheim, Mannheim, Germany) plus 0.1% Triton X-100. The buffer was then removed and replaced by 1 ml/plug of ice-cold HindIII enzyme buffer containing 20 units of HindIII (Boehringer). After two hours incubation on ice, the plugs were transferred to a 37° C. water bath for 30 minutes. Digestions were stopped by adding 500 µl of 50 mM EDTA (pH 8.0).
4. Size selection. The partially digested DNA was subjected to contour-clamped homogenous electric field (CHEF) electrophoresis on a 1% agarose gel using a BioRad DR III apparatus (BioRad, Hercules, Calif.) in 1×TAE buffer at 13° C., with a ramp from 3 to 15 seconds at 6 V/cm for 16 hours. Agarose slices from 25 to 75 kb, 75 to 120 kb and 120 to 180 kb were excised from the gel and stored in TE at 4° C.
5. Ligation and transformation. Agarose-slices containing fractions from 25 to 75 kb, 75 to 120 kb and 120 to 180 kb were melted at 65° C. for 10 minutes and digested with Gelase (Epicentre Technologies, Madison, Wis.), using 1 unit per 100 µl gel-slice. 25-100 ng of the size-selected DNA was then ligated to 10 ng of HindIII digested, dephosphorylated pBeloBAC11 in a 1:10 molar ratio using 10 units of T4 DNA ligase (New England Biolabs, Beverly, Mass.) at 16° C. for 20 hours. Ligation mixtures were heated at 65° C. for 15 minutes, then drop-dialysed against TE using Millipore VS 0.025 mM membranes (Millipore, Bedford, Mass.). Fresh electrocompetent *E. coli* DH10B cells (Sheng et al., 1995) were harvested from 200 ml of a mid-log ($OD_{550}$=0.5) culture grown in SOB medium. Cells were washed three times in ice-cold water, and finally resuspended in ice-cold water to a cell density of $10^{11}$ cells/ml ($OD_{550}$=150). 1 µl of the ligation-mix was used for electroporation of 30 µl of electrocompetent DH10B *E. coli* using a Eurogentec Easyject Plus electroporator (Eurogentec, Seraing, Belgium), with settings of 2.5 kV, 25 µF, and 99½, in 2 mm wide electroporation cuvettes. After electroporation, cells were resuspended in 600 µl of SOC medium, allowed to recover for 45 minutes at 37° C. with gentle shaking, and then plated on LB agar containing 12.5 µg/ml chloramphenicol (CM), 50 µg/ml X-gal, and 25 µg/ml IPTG. The plates were incubated overnight and recombinants (white colonies) were picked manually to 96 well plates. Each clone was inoculated 3 times (2×200 µl and 1×100 µl of 2YT/12.5 µg/ml CM per clone) and incubated overnight. One of the microtiter plates, containing 100 µl culture per well, was maintained as a master plate at −80° C. after 100 ml of 80% glycerol were added to each well while minipreps (Sambrook et al., 1989) were prepared from the remaining two plates to check for the presence of inserts. Clones containing inserts were then designated "Rv" clones, repicked from the master plate to a second set of plates for storage of the library at −80° C.
6. Preparation of DNA for sizing, direct sequencing and comparative genomics. A modified Birnboim and Doly protocol (Birnboim et al., 1979) was used for extraction of plasmid DNA for sequencing purposes. Each Rv clone was inoculated into a 50 ml Falcon polypropylene tube containing 40 ml of 2 YT medium with 12.5 µg/ml of CM and grown overnight at 37° C. with shaking. Cells were harvested by centrifugation and stored at −20° C. The frozen pellet was resuspended in 4 ml of Solution A (50 mM glucose, 10 mM EDTA, 25 mM Tris, pH 8.0) and 4 ml of freshly prepared solution B (0.2 M NaOH, 0.2% SDS) was then added. The solution was gently mixed and kept at room temperature for 5 minutes before adding 4 ml of ice-cold solution C (3M Sodium Acetate, pH 4.7). Tubes were kept on ice for 15 min, and centrifuged at 10,000 rpm for 15 min. After isopropanol precipitation, the DNA pellet was dissolved in 600 µl RNase solution (15 mM Tris HCl pH 8.0, 10 µg/ml RNase A). After 30 minutes at 37° C. the DNA solution was extracted with chloroform:isoamylalcohol (24:1) and precipitated from the aqueous phase using isopropanol. The DNA pellet was then rinsed with 70% ethanol, air-dried and dissolved in 30 µl distilled water. In general, DNA prepared by this method was clean and concentrated enough to give good quality results by automatic sequencing (at least 300 bp of sequence). For a few DNA preparations, an additional polyethylene glycol (PEG) precipitation step was necessary, which was performed as follows. The 30 µl of DNA solution were diluted to 640, mixed gently and precipitated using 16 µl 4M NaCl and 80 µl of 13% PEG 8000. After 30 min on ice the tubes were centrifuged at 4° C., the pellet carefully rinsed with 70% ethanol, air-dried and diluted in 20 µl of distilled water.

7. Sizing of inserts. Insert sizes were determined by pulsed-field gel electrophoresis (PFGE) after cleavage with DraI (Promega). 100-200 ng of DNA was DraI-cleaved in 20 µl total reaction volume, following the manufacturer's recommendations, then loaded onto a 1% agarose gel and migrated using a pulse of 4 s for 15 h at 6.25 V/cm at 10° C. on an LKB-Pharmacia CHEF apparatus. Mid-range and low-range PFGE markers (New England Biolabs) were used as size standards. Insert sizes were estimated after ethidium bromide straining of gels.
8. Direct sequencing. For each sequencing reaction 7 µl BAC DNA (300-500 ng), 2 µl primer (2 µM), 8 µl reaction mix of the Taq DyeDeoxy Terminator cycle sequencing kit (Applied Biosystems) and 3 µl distilled water were used. After 26 cycles (96° C. for 30 sec; 56° C. for 15 sec; 60° C. for 4 min) in a thermocycler (MJ-research Inc., Watertown, Mass.) DNA was precipitated using 70 µl of 70% ethanol/0.5 mM $MgCl_2$, centrifuged, rinsed with 70% ethanol, dried and dissolved in 2 µl of formamide/EDTA buffer. SP6 and T7 samples of 32 BAC clones were loaded onto 64 lane, 6% polyacrylamide gels and electrophoresis was performed on a Model 373A automatic DNA sequencer (Applied Biosystems) for 12 to 16 hours. The sequences of oligonucleotides used as primers are shown in Table 1.
9. DOP-PCR. As an alternate procedure we used partially degenerate oligonucleotides in combination with vector-specific (SP6 or T7) primers to amplify insert ends of BAC clones, following a previously published protocol for P1 clones (Liu et al., 1995). The degenerate primers Deg2, Deg3, Deg4, Deg6 (Table 1) gave the best results for selected amplification of insert termini.

TABLE 1

| Primers used for PCRs and sequencing |
|---|
| Vector specific Primers for DOP PCR- first amplification step: |
| SP6-BAC1:<br>AGT TAG CTC ACT CAT TAG GCA |
| T7-BAC1:<br>GGA TGT GCT GCA AGG CGA TTA |
| Vector specific Primers (direct sequencing, nested primer for second PCR step) |
| SP6 Mid:<br>AAA CAG CTA TGA CCA TGA TTA CGC CAA |
| T7-Belo2:<br>TCC TCT AGA GTC GAC CTG CAG GCA |
| Degenerate Primers: |
| Deg2:<br>TCT AGA NNN NNN TCC GGC |

TABLE 1-continued

| Primers used for PCRs and sequencing |
|---|
| Deg3:<br>TCT AGA NNN NNN GGG CCC |
| Deg4:<br>CGT TTA AAN NNN NWA GGC CG |
| Deg6:<br>GGT ACT AGT NNN NNW TCC GGC |
| Primers used for the amplification of *M. bovis* DNA in polymorphic chromosomal region of Rv58: |
| Primer 1:<br>ACG ACC TCA TAT TCC GAA TCC C |
| Primer 2:<br>GCA TCT GTT GAG TAC GCA CTT CC |

Figure 1B:
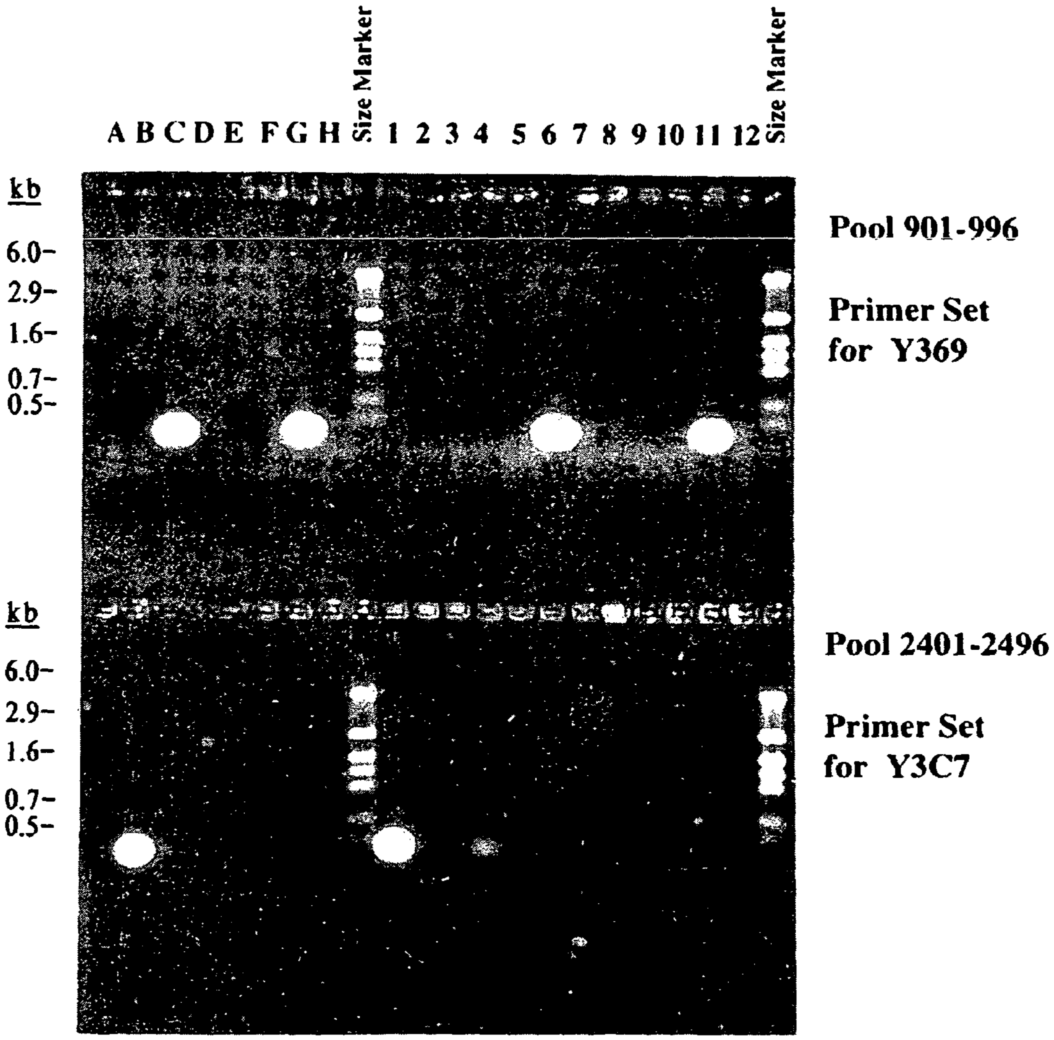

10. Screening by pooled PCR. To identify particular clones in the library which could not be detected by random end-sequencing of the 400 BAC clones, PCR-screening of DNA pools was performed. Primers were designed for regions of the chromosome where no BAC coverage was apparent using cosmid- or H37Rv whole genome shotgun sequences. Primers were designed to amplify approximately 400-500 bp. Ninety-six-well plates containing 200 µl 2 YT/12.5 µg/ml CM per well were inoculated with 5 µl of −80° C. glycerol stock cultures each from the master plates and incubated overnight. The 96 clones of each plate were pooled by taking 20 µl of culture from each well and this procedure was repeated for 31 plates. Pooled cultures were centrifuged, the pellets were resuspended in sterile water, boiled for 5 minutes, centrifuged and the supernatants kept for PCRs. As an initial screening step, the 31 pools of a total of 2976 BACs, representing about two thirds of the library were tested for the presence of a specific clone using appropriate PCR primers. PCR was performed using 10 µl of supernatant, 5 µl of assay buffer (100 mM b-mercaptoethanol, 600 mM Tris HCl (pH 8.8), 20 mM $MgCl_2$, 170 mM $(NH_4)_2SO_4$), 5 µl of Dimethylsulfoxide (DMSO), 5 µl of dNTPs (20 mM), 5 µl of water, 10 µl primer (2 µM), 10 µl inverse primer (2 µM) and 0.2 units of Taq DNA polymerase (Boehringer). 32 cycles of PCR (95° C. for 30 s, 55° C. for 1 min 30 s, 72° C. for 2 min) were performed after an initial denaturation at 95° C. for 1 min. An extension step at 72° C. for 5 min finished the PCR. If a pool of 96 clones yielded an appropriate PCR product (FIG. 1A), subpools were made to identify the specific clone. Subpools representative for lane A of a 96 well plate were made by pooling clones 1 to 12 from lane A into a separate tube. Subpools for lanes B to H were made in the same way. In addition, subpools of each of the 12 rows (containing 8 clones each) were made, so that for one 96 well plate, 20 subpools were obtained. PCR with these 20 subpools identified the specific clone (FIG. 1B, lower gel portion). If more than one specific clone was present among the 96 clones of one plate (FIG. 1B, upper gel portion), additional PCR reactions had to be performed with the possible candidates (data not shown).
11. Genomic comparisons. DNA from the BAC clone Rv58 was digested with the restriction endonucleases EcoRI and PvuII, and resolved by agarose gel electrophoresis at low voltage overnight (1.5 V/cm). DNA was transferred via the method of Southern to nitrocellulose membranes (Hybond C extra, Amersham) following standard protocols (Sambrook et al., 1989), then fixed to the membranes at 80° C. for 2 hours. The blot was hybridized with $^{32}P$ labelled total genomic DNA from *M. tuberculosis* H37Rv, *M. bovis* type strain (ATCC 19210) or *M. bovis* BCG Pasteur. Hybridization was performed at 37° C. overnight in 50% formamide hybridization buffer as previously described (Philipp et al., 1996b). Results were interpreted from the autoradiograms.

12. Computer analysis. Sequence data from the automated sequencer ABI373A were transferred as binary data to a Digital Alpha 200 station or Sun SparcII station and analysed using TED, a sequence analysis program from the Staden software package (Dear et al., 1991). Proof-read sequences were compared using the BLAST programs (Altschul et al., 1990) to the *M. tuberculosis* H37Rv sequence databases of the Sanger Centre, containing the collected cosmid sequences (TB.dbs) and whole-genome shotgun reads (TB_shotgun_all.dbs) (http://www.sanger.ac.uk/). In addition, local databases containing 1520 cosmid endsequences and the accumulating BAC endsequences were used to determine the exact location of end-sequenced BACs on the physical and genetic map. MycDB (Bergh et al., 1994) and public databases (EMBL, Genbank) were also used to compare new sequences, but to a lesser extent. The organization of the open reading frames (ORFs) in the polymorphic region of clone Rv58 was determined using the DIANA software established at the Sanger Centre.

EXAMPLES

Example 1

Construction of a pBeloBAC11 Library of *M. tuberculosis* H37Rv

Partial HindIII fragments of H37Rv DNA in the size range of 25 to 180 kb were ligated into pBeloBAC11 and electroporated into strain *E. coli* DH10B. While cloning of fractions I (25 to 75 kb) and II (75 to 120 kb) gave approximately $4\times10^4$ transformants (white colonies), cloning of fraction III (120 to 180 kb) repeatedly resulted in empty clones. Parallel cloning experiments using partial HindIII digests of human DNA resulted in stable inserts for all three fractions (data not shown), suggesting that the maximum size of large inserts in BAC clones is strongly dependent on the source of the DNA. Analysis of the clones for the presence of inserts revealed that 70% of the clones had an insert of the appropriate size while the remaining 30% of white colonies represented empty or lacZ'-mutated clones. Size determination of randomly selected, DraI-cleaved BACs via PFGE showed that the insert sizes ranged for the majority of the clones between 40 kb and 100 kb with an average size of 70 kb. Clones with inserts of appropriate size were designated with "Rv" numbers, recultured and stored at −80° C. for further use.

Example 2

Direct DNA Sequence Analysis of BACs

To characterize the BAC clones, they were systematically subjected to insert termini sequencing. Two approaches, direct sequencing of BAC DNA and PCR with degenerate oligonucleotide primers (DOP), adapted to the high G+C content of mycobacterial DNA, were used. In a first screening phase, 50 BAC clones designated Rv1 to Rv50 were analysed using both methods in parallel. Except for two clones, where the sequences diverged significantly, the sequences obtained by the two methods only differed in length. Sequences obtained directly were on average about 350 bp long and for 95% of the clones both the SP6 and T7 endsequences were obtained at the first attempt. Sequences obtained by DOP-PCR were mostly shorter than 300 bp. For 40% of the BACs we obtained only very short amplicons of 50 to 100 base pairs from one end. In two cases the sequence obtained with the DOP-PCR differed from the sequences obtained by direct sequencing, and in these cases *E. coli* or vector sequences were amplified (data not shown). Taking the advantages and disadvantages of both methods into account, we decided to use direct termini sequencing for the systematic determination of the SP6 ad T7 end-sequences.

Example 3

Representativity of the Library

After having determined the end-sequences of 400 BACs a certain redundancy was seen; The majority of clones were represented at least 3 to 4 times. Maximum redundancy was seen in the vicinity of the unique rrn operon, as 2.5% of the clones carried identical fragments that bridge the cosmids Y50 and Y130 (FIG. 3, approximate position at 1440 kb). The majority of clones with identical inserts appeared as two variants, corresponding to both possible orientations of the HindIII fragment in pBeloBAC11. This suggests that the redundancy was not the result of amplification during library construction, but due to the limited number of possible combinations of partial HindIII fragments in the given size-range of 25 to 120 kb. To detect rare BAC clones, a pooled PCR protocol was used. Primers were designed on the basis of the existing cosmid sequences and used to screen 31 pools of 96 BAC clones. When positive PCR products of the correct size were obtained, smaller subpools (of 8 or 12 clones each) of the corresponding pool were subsequently used to identify the corresponding clone (FIG. 1). With this approach 20 additional BACs (Rv401-Rv420) were found for the regions where no BACs were found with the initial systematic sequencing approach. The endsequences of these BACs (Rv401-420) were determined by direct sequencing, which confirmed the predicted location of the clones on the chromosome. A 97% coverage of the genome of H37Rv with BAC clones was obtained. Only one region of ~150 kb was apparently not represented in the BAC library as screening of all pools with several sets of specific primers did not reveal the corresponding clone. This was probably due to the fact that HindIII fragments of mycobacterial DNA larger than 110 kb are very difficult to establish in *E. coli* and that a HindIII fragment of ~120 kb is present in this region of the chromosome (data not shown).

Example 4

Establishing a BAC Map

Using all endsequence and shotgun-sequence data from the H37Rv genome sequencing project, most of the BAC clones could then be localized by sequence comparison on the integrated map of the chromosome of *M. tuberculosis* strain H37Rv (Philipp et al., 1996b) and an ordered physical map of the BAC-clones was established. PCR with primers from the termini sequences of selected BACs were used for chromosomal walking and confirmation of overlapping BACs (data not shown). The correct order of BACs on the map was also coded more recently, using 40,000 whole genome shotgun reads established at the Sanger Centre. In addition, pulsed-field gel electrophoresis of DraI digests of selected BACs was performed (FIG. 2) in order to see if the approximate fragment size and the presence or absence of DraI cleavage sites in the insert were consistent with the location of the BACs on the physical map (FIG. 3). Comparison of the sequence-based BAC-map with the physical and genetic map, established by PFGE and hybridization experiments (Philipp et al., 1996b), showed that the two maps were in good agreement. The positions of 8 genetic markers previously shown on the physical and genetic map were directly confirmed by BAC-endsequence data (Table 2, FIG. 3). The position of 43 from 47 Y-clones (91%) shown on the physical and genetic map, which were later shotgun sequenced, was confirmed by the BAC endsequences and shotgun sequence data. Four clones (Y63, Y180, Y251, and Y253) were located to different positions than previously thought and this was found to be due to book keeping errors or to chimeric inserts. Their present approximate location relative to the oriC is shown in FIG. 3: Y63 at 380 kb, Y63A at 2300 kb, Y180 at 2160 kb, Y251 at 100 kb, and Y253 at 2700 kb. A total of 48 BACs, covering regions of the chromosome, not represented by cosmids were then shotgun sequenced (Cole et al., 1997), and these are squared in FIG. 3. No chimeric BACs were found, which is consistent with the observations of other research groups for other BAC libraries (Cai et al., 1995; Zimmer et al, 1997). The absence of chimeric BACs was of particular importance for the correct assembly of the *M. tuberculosis* H37Rv sequence. The exact position of the BAC termini sequences on the chromosome will be available via the world wide web (http://www.pasteur.fr/MycDB).

TABLE 2

Identities of genetic markers previously shown on the integrated and genetic map of H37Rv (Phlipp et al., 1996b) wich showed perfect sequence homology with BAC ens sequences.

| Locus | BAC end sequence | Description of genetic marker | Organism | GenBank Accession n° |
|---|---|---|---|---|
| apa | Rv163SP6 | Secreted alanine-proline-rich antigen | *M. tuberculosis* | X80268 |
| dnaJ, dnaK | Rv164T7 | DnaJ hsp | *M. leprae* | M95576 |
| fop-A | Rv136T7 | Fibronectin binding protein | *M. tuberculosis* | M27016 |
| polA | Rv401T7 | DNA polymerase I | *M. tuberculosis* | L11920 |
| ponA | Rv273T7 | Penicillin binding protein | *M. leprae* | S82044 |
| pstC | Rv103T7 | Putative phosphate transport receptor | *M. tuberculosis* | Z48057 |
| recA | Rv415SP6 | Homologous recombination | *M. tuberculosis* | X58485 |
| wag9 | Rv35SP6 | 35-kDa antigen | *M. tuberculosis* | M69187 |

Example 5

Repetitive Endsequences

Repetitive sequences can seriously confound mapping and sequence assembly. In the case of the BAC endsequences, no particular problems with repetitive sequences were observed. Although nine clones with one end in an IS1081 (Collins et al., 1991) sequence were identified, it was possible to correctly locate their position on the map using the sequence of the second terminus. Moreover, these BACs were used to determine the exact locations of IS1081 sequences on the map. Five copies of this insertion sequence, which harbors a HindIII cleavage site, were mapped on the previous physical and genetic map. In contrast, BAC endsequence data revealed an additional copy of IS1081 on the *M. tuberculosis* H37Rv chromosome. The additional copy was identified by six clones (Rv27, Rv118, Rv142, Rv160, Rv190, Rv371) which harbored an identical fragment linking Y50 to I364 (FIG. 3, at ~1380 kb). This copy of IS1081 was not found by previous hybridization experiments probably because it is located near another copy of IS1081, localized on the same DraI fragment Z7 and AsnI fragment U (FIG. 3, at ~1140 kb). Furthermore, the position of a copy of IS1081 previously shown in DraI fragment Y1 (FIG. 3, at ~1840 kb) had to be changed to the region of Y349 (FIG. 3, at ~3340 kb) according to the endsequences of BAC Rv223. The positions of the four other IS1081 copies were confirmed by the sequence data and therefore remained unchanged. In total 6 copies of IS1081 were identified in the H37Rv genome in agreement with the findings of others (Collins et al., 1991).

In addition, a sequence of 1165 bp in length containing a HindIII site was found in two copies in the genome of H37Rv in different regions. The endsequences of BAC clones Rv48 and Rv374, covering cosmid Y164, as well as Rv419 and Rv45, that cover cosmid Y92, had perfect identity with the corresponding parts of this 1165 bp sequence (FIG. 3, at ~3480 kb and ~900 kb). Analysis of the sequence did not reveal any homology with insertion sequences or other repetitive elements. However, as each of the two locations showed appropriate BAC coverage, chimerism of the sequenced cosmids Y164 and Y92 can be ruled out as the probable cause.

Example 6

Using BAC Clones in Comparative Genomics

The minimal overlapping set of BAC clones represents a powerful tool for comparative genomics. For example, with each BAC clone containing on average an insert of 70 kb, it should be possible to cover a 1 Mb section of the chromosome with 15 BAC clones. Restriction digests of overlapping clones can then be blotted to membranes, and probed with radiolabelled total genomic DNA from, for example, *M. bovis* BCG Pasteur. Restriction fragments that fail to hybridize with the *M. bovis* BCG Pasteur DNA must be absent from its genome, hence identifying polymorphic regions between *M. bovis* BCG Pasteur and *M. tuberculosis* H37Rv. The results of such an analysis with clone Rv58 (FIG. 3, at ~1680 kb) are shown here. This clone covers a previously described polymorphic genomic region between *M. tuberculosis* and *M. bovis* BCG strains (Philipp et al., 1996a). EcoRI and PvuII digests from clone Rv58, fixed on nitrocellulose membranes, were hybridized with $^{32}$P-labelled total genomic DNA from *M. tuberculosis* H37Rv, *M. bovis* (ATCC 19120), and *M. bovis* BCG Pasteur. FIG. 4 presents the results of this analysis, where it is clear that several restriction fragments from clone Rv58 failed to hybridize with genomic DNA from either *M. bovis* or *M. bovis* BCG Pasteur. On the basis of the various missing restriction fragments, a restriction map of the polymorphic region was established and compared to the H37Rv sequence data. The localization of the polymorphism could therefore be estimated, and appropriate oligonucleotide primers (Table 1) were selected for the amplification and sequencing of the corresponding region in *M. bovis*. The alignment of *M. bovis* and *M. tuberculosis* H37Rv sequences showed that 12,732 bp were absent from the chromosomal region of the *M. bovis* type strain and *M. bovis* BCG Pasteur strain. The G+C content of the polymorphic region is 62.3 mol %, which is the same as the average genome G+C content of the *M. tuberculosis* genome, hence indicating that this region is not a prophage or other such insertion. Subsequent PCR studies revealed that this segment was also absent from the Danish, Russian, and Glaxo substrains of *M. bovis* BCG, suggesting that this polymorphism can be used to distinguish *M. bovis* from *M. tuberculosis*. Analysis of this sequence showed that 11 putative open reading frames (ORFs) are present in *M. tuberculosis*, corresponding to ORFs MTCY277.28 to MTCY277.38/accession number Z79701—EMBL Nucleotide Sequence Data Library (FIG. 5). FASTA searches against the protein and nucleic acid databases revealed that the genes of this region may be involved in polysaccharide biosynthesis. Among these putative genes, the highest score was seen with ORF 6 (MTCY277.33), whose putative product shows a 51.9% identity with GDP-D-Mannose dehydratase from *Pseudomonas aeruginosa* (accession number U18320—EMBL Nucleotide Sequence Data Library) in a 320 amino acid overlap. The novel *M. bovis* sequence of the polymorphic region was deposited under accession number AJ003103 in the EMBL Nucleotide Sequence Data Library.

As it appears from the teachings of the specification, the invention is not limited in scope to one or several of the above detailed embodiments; the present invention also embraces all the alternatives that can be performed by one skilled in the same technical field, without deviating from the subject or from the scope of the instant invention.

TABLE 3

End sequences of the polynucleotide inserts cloned in the named recombinant BAC vectors contained in the I-1945 *M. tuberculosis* H37Rv genomic DNA library.

RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081
repetitive sequence (Insertion element)
The character << - >> denotes an uncertain base residue.

Clone Rv101
::::::::::::::Rv101SP6.seq::::::::::::::
AATACTCAAGCTTGCCCAGCCGTCGATGACAAGAAATATGTCCGCAAAAGACTCAGCGGCCGACTTTGCTCGCAGCTGGCGGTACCGCGCCACCGATTCTAT
GCCGTGGTCGCGGAAAAATGCCTCCCGAAATCGCACGGCCGACTCCAGTTCGGCGAGCATCCGCGATGCCAGCTGCGGCTGCGCCCTGCCGGCCACGGCACC
CACATGCGGCAGTTCGTCCACCTGGGCCAGCGCCCCGCCGCCGAATTCCAAACAATAGAACTGCACCCGGCCCGCATCGTGGGTAACAGCCAACGCCATGAT
CAGCGTCCGCAGCGCGGTTGACTTGCCCGTTTGCGGTGCACCTACGAACGCGACATTGCCTGCGGCCCCGGACAAGTCGATCGTGCGCGGCACCCGTGACTG
CTCTAACGGGCGATTGAAATTCCGAT ::::::::::::::Rv101T7.seq::::::::::::::
CCACCCGTGTAATTTGGGATGGGCAAAAAGGCGAAGCACCGCGTGGCCACGAACGCCGGGAGGGACAATCTCGGGCGGTTAGGGCTTCTCGCGGGAAGGCCC
GAACGTACGGCGTTTCAACACCTCGCGTCGCCCTCCGACCGCGAACATTCGGGGATGGCAGCAACCTGCTGGCACCCTGGCCGGGCGATGATCTGCAGCGTC
GCCGCGGGTAGTCGCCGCCCGGGCGGCTACACTCTGAAACGCGATGACCATCGATGTGTGGATGCAGCATCCCGACGCAACGGTTCCTACACCGCGATATGT
TCGCCTCGCTGCCCCGGTGGACCGGT Clone Rv102
::::::::::::::Rv102SP6.seq::::::::::::::
AATACTCAAGCTTTCCGCCGATACCCGCCATGTCGCGCACATCCAGGACTTCTGGGGGGATCCGCTGACAGCGGCGGGATCCCAAAGTGCGGATGATCGGGC
CGCCTACGTCGTGGTGTACCTCGTCGGTAACAACGAAACCGAAGCGTATGACTCGGTCCACGCGGTGCGGCACATGGTGGACACCACACCGCCACCGCACGG
GGTGAAGGCCTATGTCACCGGTCCGGCAGCACTCAATGCCGACCAGGCCGAGGGCGGAGACAAAAGTATCGCTAAGGTCACCGCGATCACCAACATGGTGAT
CGCAGCAATGTTGCTAGTGATCTATCGCTCCGTAATTACCGCGGTTCT ::::::::::::::Rv102T7.seq::::::::::::::
GTGCCGTTCCAACCCGAATTGGCTTTCGGCGCCATCGGTGAGGACGGCGTGCGGGTGCTCAACGACGACGTCGTCCGCGGGACACACCTCGATGCTGCCGCC
ATGGACGCGGTCGAACGCAAGCAGCTGATCGAGCTACAACGCCGCGCGGAACGCTTCCGCCGCGGGCGTGACCGCATCCCGTTGACCGGGCGGATCGCGGTG
ATCGTCGATGACGGCATCGCCACCGGAGCGACGGCCAAGGCGGCGTGCCAGGTCGCCCGGGCGCACGGTGCGGACAAGGTGGTGCTGGCGGTCCCGATCGGC
CCAGACGACATCGTGGCGAGATTCGCCGGGTACGCCGATGAGGTGGT Clone Rv103
::::::::::::::Rv103SP.seq::::::::::::::
AATACTCAAGCTTTCGGCGGAAACGGACACATTGCGAATATTGATGACAAAATAAAAATCATTGATGGTTTGAGTCACCAGGCCGATCAAGCCTTCGCCGAG
CCAAATTCCAATCAAGAGGCCCAAGCCCGTACCAATCAGCCCGGCAACGAGGGATTCCGTCATTATCAGCCAAAATAACTGCTCTCGGGTTACACCCAAACA
GCGCAATATGGCGAAAAACGGTCGCCGTTGCACGACATTAAATGTCACGGTATTGTAGATTAAAAAGATACCCAC ::::::::::::::Rv103T7.seq::::::::::::::
TGCTCCCGAAACCTGGGGGTGTGCCTGCTCTGTATGCACGGCATACGGACATCCTTCCCCTGAGACCCGCGGTCGAACCAGCCACGTGTCCATCATAGNGGG
TCAACCCCGGCCAAGGGCGACGGCACGCCAAGTTCGCCGACCGTTAACCTAGTGCTGTTAGCTTCATTTGCTGCGATCAAAACAGCTGGTCGGCCGTTAGGA
ACTGAATTGAAACTCAACCGATTTGGTGCCGCCGTAGGTGTCCTGGCTGCGGGTGCGCTGGTGTTGTCCGCGTGTGGTAACGACGACAATGTGACCGGGGGA
GGTGCAACCACTGGCCAGGCGTCGGCAAAGGTCGATTGCGGGGGGAAGAAGACACTCAAAGCCAGTGGGT Clone Rv104
:::::::::::::Rv104SP6.seq:::::::::::::
ATACTCAAGCTTTGCCGACGAGCGGGCGATGTTGATGACGGGAAACCCCAGCGCACAACCGACGATTTTGGCGTAGCCGGCGGACGTCTGCTCGATTCCGAT
CACGTCGGCGCTCGCATCGAGCATGGCGCCGGCGACGGCTAGCAGCGATCCGCCGTCGTCGAGGAGCACGACACGAGCCGTACGCCCGGCCGTAAGCCGCGC
CCAGGATTCGGCGAAAAACCGTTCTACGTGGCGGGTGTACTGGGTGTCGAATGATTCGTGGGGTGCGTAGGCGTCGCTGCAATCGTCGACATAGATGCCGTC
GGGCCGCATCGCGTCGACAACTCCGGGTGAGTGGAATAGCACTTGCCGATGACCGCGACGTTGCGCGGATGAGGCCGAACCCGAATA :::::::::::::Rv104T7.seq:::::::::::::
TCCTATGTCCCTGCCGAGCANGTGATCGAACGCGGTGACAGATTTGTCTATCCTGGACCTGACGGTGAGGTCGAAGTTTTCCAGGAATTCGGCAAAATCGGT
AAGAGCCTGAAGAATTCGGTATCGCCGGACGAAATCTGCGACGCATACGGGGGCATATACGCTTCGGGTTTACGAGATGTCGATGGGGCCGCTGGAGGCTTC
ACGTCCATGGGCCACAAAGGATGTTGTCGGCGCGTACCGTTTTCTGCAGCGGGTGTGGCGCTTGGTCG :::::::::::::Rv105SP6.seq:::::::::::::
ATACTCAAGCTTGATTCCGCCGAAACCGACCGTGAGCACCCCGCCAGCCACCACGCTCGGGTCGGGCGCCGGGCCCGGGCCGCCAGGCTGCTCCGCTCGGTG
ATGGCACGCCACCGCGACACCACCCGGCTGCGCTACGTCTAACCATTCCAGGCGGAGCTACATCAGCTCGGCCGCCCAGTGTTCGGGCCCTCTTTCCAGGTC TABLE 3-continued End sequences of the polynucleotide inserts cloned in the named recombinant BAC vectors contained in the I-1945 *M. tuberculosis* H37Rv genomic DNA library.

GAAGTCTATACCGATATGCGCATCCGCAGCCGCCACCCTGGAGAACAGAACGATGCCCTACTAATGCTTGTCTGGCGGGGCC

:::::::::::::Rv105T7.seq:::::::::::::
GGTACGCTTCGGTCGCAGTCTGCGAGTGATGCATGACGACCGGGACCTCGTCGGCATCCTCCATAGCCCGCCACACCTTCAGTTGCTCACCGGAATCCAACC
GGTAGAAGGTCGGCGAGCGCTCGGCATTGGTCATCGGGATATGCCGCTCGGGACGGTCAGAGCCCTCGGGTCCGGCCAGCACTCCGCAGGCTTCGTCGGGGT
GGTCGCGACGCGCATGGGCCACCATCGCATTCACCAGGTCTGCGCGAATCACCAGCACGTAGACGGTTCCTTTCCTAAGCAACACCGAAGTTTCAGGACCCG
AATGCTCCGGGAAACATGTCACGGTAGGTCGGTATTCCGGCTACCGGCTGA Clone Rv106
:::::::::::::Rv106SP6.seq:::::::::::::
GGCGTCAACGGTGTCGGAACCCGCGTCAAGCAATTGGTAGGCCTGCAGTCTGTGAATCAGGCCGACGCTGTGGCCGCCGCGGC :::::::::::::Rv106T7.seq:::::::::::::
GGCTNGCGTACCCGGTACCGGCCGCGGGCCTACCACGTGCCGGAACTGGAAGCGCAGTAAGCCCTCAACGCGCCACCGCTTTGGCCCGCGCGCCCGGCGTAG
GCGCATCGGCGGTGGCCGTGGGGCGGCGCACTGCGACCTCACCAGCGGCTTTCGAGCTTTGTTCGATCAACCGGCCAGCATGGTCGANGATGCATTCGAGAC
CATATTCGAAATTGGTTTCATCGGGGGCCCCGATCCGATGCCCCCTCCCAGTTGCGTGAGCAANCAGCGGAGTCNTCGCGGGATCGATGGCCACGGGGTGTT
CAATGGCGGATGGTCCGCTGCCCGCCGACTGGCTCTTGCGGGAGAACCGATCTAGCACCACCGATCCGCGCACGTNG Clone Rv107
:::::::::::::Rv107T7D4.seq:::::::::::::
CGTAATNTCGCGCACANCCANGACTTCTGGGGGGATCNGCTGACAGTGGTNGGATCCCAAATTGCGGATGATCGGGCCGCCNACGTCGTTGTGTACCTCNTC
NGTCACAACNAANCCGAANCGTATGACTCGGTCCACGCGGTGCGGCACATGGTGGACACCACACCGCCACCGCNCGGGGTGAAGGCCTATGTCACCGGTCCG
GCAACACTCAATGCCGACCAGGCCGANGCCGGACACNANAGTATCNCTAACGTCACCGCGATCACGAGCATGGTGATCGNNCAATGTTNCTANTGATCTATC
GCTCCGTAATTACCGCGGTTCTCGTCTTGATCATGGTCGCANCGAACTCCGGCGCAATCCGCGGATTCATCGNCTTGCTCGCCGATCACATATTTTCAGCCT
TTCACATTGCAACNAACCTGCTCGTCTCATGGNGATGCGGCGACACGGACTACCGATATCATGCTCGCCGTTACACAATCNCGCCACGCCGCGAAGACNGGA
AACGCTTCTACACAATNTTCNCGGGACGCCACTNAACTTGGTTCNGGTTTGACATTGCGCGCATGTNTGCCCAGCTTTGCCGGCTCCCCTTA Clone Rv108
:::::::::::::Rv108T7D4.seq:::::::::::::
TGAATTTCCCGATCCCACAATCTCGGTTCAGATACAGGTCGCCATACCCCTTACTTCGGCAACGCTGGGCGGATTGGCCCTGCNGCTGCAGCANACCATCGA
CGCCATCGAATTGCCGGCAATCTCGTTCAGCCAATCCATACCCATCGACATTCCGCCGATCGACATCCCGGCCTTCNCCCTTTAACGG Clone Rv109
:::::::::::::Rv109SP6.seq:::::::::::::
AACAGCTATGACCATGNTTACGCCAAGCTATTTAGGTAACACTATANAATACTCAAGCTTTTACGGTGATCGCGCATCACCTGGTTCATGAACTGGAAGCAG
CGCANCGCTTCCTTTTCGGCCGCAACATGAGCAGCCTCTCGTCCGCGGTCNGGTGCAGGTGCTCGGGCAGCTCGGCCGCGACAGCCGCCTGACCCTGAAAC
CAGCTTCCATATCCCGCGACNAACNACNCCAGTCCGCTACGTAACCCCTCCGCGACTGTCCATGGACAACAGCGCGTTCTCCACCGACCGGGCCCGGGTGTG
GGGTGTTTCGGCGACCGGCAGCCAGGTGGTCCACACTGCCGACGGGCGCCGCGAGCCGTTCACCGACCAAGCCGCCGAACAAGTCCGCCCGATCGCATACTC
CAACCGGTTGCGGTACTGCAGGTCAGCTGGCGTACCTCCTCNTCNCGCTCGGCGAAGTCTTGCTCCANCACGTCGCAGAACGGCAAGGAACACGTTCA :::::::::::::Rv109T7.seq:::::::::::::
GACCGNNCCATGTTTCCACAATGTGGTGCCAGTNCGGNGGCTACGTGCCATCNANACACTGGCGCAGGCTATCGCACCCGTTATCNGCTACGAACAAATCNC
GGTATGCGTTCTTTANCATGAGTCGGCGACCGNCGATCATGGTCGACACCCACGACNGAAATACGCAGATCGCCNTCNAGCNTGTGTGCCGCGGATTATCAN
GACTGACCTCCTGGCTGACCGGNNTGTNTGGTCGCGATGCCTGGCGCCCGGCCGGCGTGNTCGTGGTCGGCTCGGATAGCGAAGTCAGCTAATTCTCGTGGC
AGCTCGAAAGGGTCCTGCCGGTGCCGGTCTTTGCGCAAACCATGCNCATGTTACGGTCCCTCGGGTGCGGCCTGGCGGCGGC Clone Rv10
:::::::::::::Rv10SP6D2.seq:::::::::::::
GGGATGGGCGGGCCCGCTAAACTCTTCGTGTTCCACTAACTCCGGGAGGGNCAATCTCGGGCCGTTATGGCTCACGTCGCGTCGCCCTCCGACCGCGAACAT
TCGGAGTTGGCAGCAACCTGGTAGCACCCTGGCCGG :::::::::::::Rv10T7D4.seq:::::::::::::
NCCGTCGTTGACAAGTAAATATGTCCGCAAAAGTCTCAGCGGCCGACTTTGCTCGCAGGTGGCGGTACCGCGCCACCGAGTCGATGCCGTGGTCGCGGAAGA
ATGCCTCCCGAAATCGCACGGCCTTCCCNNTTTAAACGGA Clone Rv110
:::::::::::::Rv110SP6.seq:::::::::::::
TTTAGGTGACACTATAGAATACTCAAGCTTTTGGTCTAGCCGGCCGAGCACGATACGGGTGTCATTGGCCACCGGCGGCGGCTGTCCGGGAAATGGCGGGTC
CCCGGTGGTTTTGCTGATGAGTGCTGAACCGTANTCGAAGTGGGCGGCGTCAGACTCCACCCANCCAGCAGGCAGCGCGAAGCTGAATCCTCCAACCGGGTT
GTCNATCCGGACAAGTTGGGGTGCGTTTGGGGCAATGACAGGTGGCNGCGGTGCGTTCGGGTCCGCCGGCGGAAGTGCTGCGTTGGGATCNCCCGCTGGGCA
TTCGGCNTTTTTGCGGCGGCCGGTGGTNGGGGGGCAACAGGTNTCCCNGTGCGGGTGGCGCTCAACGGTCNACGGCGCAAGCCGCCGTTGTTGGTACCNGGG
GCGCTGGCTCCGGATCGCGTTGGCGGTCNCCGG :::::::::::::Rv110T7.seq:::::::::::::
CTACACCATCGAATACGACGGCGTCGCCNACTTTCCGCGGTACCCGCTCAACTTTGTGTCGACCCTCAACGCCATTGCCGGCACCTACTACGTGCACTCCAA
CTACTTCATCCTGACGCCGGAACAAATTGACGCAGCGGTTCCGCTGACCAATACGGTCGGTCCCACGATGACCCAGTACTACATCATTCGCACGGANAACCT
GCCGCTGCTAGAGCCACTGCGATCGGTGCCGATCGTGGGGAACCCACTGGCGAACCTGGTTCAACCAAACTTGAANGTGATTGTTAACCTGGGCTACNGCGA
CCCGGCCTATGGTTATTCNACCTCNCCGCCCAATGTTGCGACTCCGTTCGGGTTGTTCCCANAAAGTCNNCCCGGTCGTCATCGCCGAANCTCCNTCCCGGG
ACCCACAGGGAATCNGCNATTTCNCCTACAAATCANCCACCTCCA Clone Rv111
:::::::::::::Rv111T7.seq:::::::::::::
GCATGATCGGCCACCTTTCGGGCCGCCCGGCATACGGCGGCGTACCGATCTCCGCGTCATACACCCGCGGGTAATCGCCGACGGTGCCGGTTCGCGAGCCGA
AGGTGACGACTCTGATTGAATCGAGTTCCAGGTCCAGCGGGTGGCGCACCAACGGCGCGAGCTCAACGACGTCAATCNCGTTGTCGCTTTCTACGGTCACCG
ACCCTGGTGACCGTAGTTCNCCCG TABLE 3-continued End sequences of the polynucleotide inserts cloned in the named recombinant BAC vectors contained in the I-1945 *M. tuberculosis* H37Rv genomic DNA library.

Clone Rv112
::::::::::::Rv112SP6.seq::::::::::::
GACACTATAGAATACTCAAGCTTGCCAACCGCCAGCCTGCATCCGGCGGCGANCACTGCTCCGCCGACCAGTACGAACCAACCTGCGGTGCCCAGGCCATTG
ACGATGTGCTGGTCGGCGCCCGCGAGTCCGCGCACCATCAACGCCGCGGGCACCACCANGGCGGCCCCACCCTGCACGGCGACGATCATTCCGGCGCCGCTC
ACGGCGGGCGGGGCTCGAACANGCACAGCATCAACGTNGTCACCCGGCCGTGACCGGCCCGCATCGTCACACCACCCAAGCCCATTGCCGTCCTCCTCAACN
GGGCGACCCGGCCCGCATCGTCACGGNCTAAGGCATTGCCGTCCTCCT ::::::::::::Rv112T7.seq::::::::::::
TCGGCGCCATCGGCACCTTCGAGGACCTGTATTTCGACGCCGTGGCCNACCTGAGGTTGGCGGTGGACNAAGTGTGCACCCGGTTGATTCGCTCGGCCTTGC
CGGATGCCACCCNGCGCCTGGTGGTCGATCCGCNAANAGACAANTTGTGGTGGANGCTTCTGCTGCCTGCGACACCCACNACGTGGTGGCACCGGGCAGCTT
TAGCTGGCATGTCCTGACCGCGCTGGCCGACNACTCCAGACNTTCCACNAANGGTCGCCNNCCCAATGTNCCGNANTGTCTCCGGNTCCCTTTACCNCCCAA
TGGGCNGNTTCCACNGGTTACGGGCCCCNTNCCGGCGGGTCTNCCTCCCAANCTACCAAATACGCCCGACNTTCCGGA Clone Rv113
::::::::::::Rv113SP6.seq::::::::::::
ATACTCAAGCTTTTATGGTGATCGCGCATCACCTGGTTCATGAACTGGAAGCAGCGCAGCGCTTCCTTTTCGGCCGCAACATGAGCCAGCCTCTCGTCGGCG
GTCGGGTGCAGGTGCTCGGGCAGCTCGGCCGCGAACAGCCCGGCTTGAACCCTGAAAACCNGCTTTCCATATCCCGCGACGAAAGAACGCCAGTTCCGCTAC
TTAACCCCTCCGCGAACCGTCCATGGACAACAGCGCGTTCTCCACCAACCGGGCCCGGGTGT ::::::::::::Rv113T7.seq::::::::::::
TCGGCTCAGGCCGCGCTGCTGGTAGAGTCGCTGACCGGTGCAGGTTTCGACAATGTGGTGCCGGTTCGGCGGCTACGTGCCATCGAGACACTGGCGCAGGCT
ATCGCACCCGTTATCGGCTACGAAGCAAATCGCGGTATGCGTTCTTGAGCATGAGTCGGCGACCGTCGTCATGGTCGACACCCACGACGGAAAGACGCAGAT
CGCCGTCAAGCATGTGTGCCGCGGATTATCAGGACTGACCTCCTGGCTGACCGGCATGTTTGGTCGCGATGCCTGGCGCCCGGCCGGCGTGGTCGTGGTCGG
CTCGGATAGCGAGGTCAGCGAATTCTCGTGGCAGCTCGAAAGGGTCCTGCCGGTGCCGGTCTTTGCGCAAACAATAGCGCAGGTTACGGTCGCGCGGGGTGC
GGCCTGGCGGCGGCC Clone Rv114
::::::::::::Rv114SP6.seq::::::::::::
CAAGCTATTTAGGTGACACTATAGAATACTCAAGCTTCGCGTCTACGCCGGCCCGGAGCATCCGCACAGCGCTCAGCAGCCGGTTCCGTACGANCTCAAGCA
GGTGGCGCAATGACCGAAACCACCCCAGCCCCGCAAACCCCGGCGGCCCCGGCCGGGCCCGCACAATCGTTCGTGTTGGAGCGGCCCATCCANACCGTTGGG
CGCCGTAAGGANGCCGTGGTACGAATGCGGCTGGTGCCCGGCACCGGCAAGTTCGACCTCAACGGCCGCAGCTTGGANGACTACTTCCCAAACAAGGTGCAC
CAGCAGTTGATCAAGGCAGGGGTGGTCACCGTGGATCGGGTGGAAAGTTTCGACATCTTTGCCCACCTGGGCGGCGGCGGCCGTCCGGTCAGGCCGGGCCTG
CCCTGGGTATCGCCCGGGCATTGATTCTGGTATCCCCNGAAGAACCG ::::::::::::Rv114T7.seq::::::::::::
CGGTTGGCCACCGCTTCTCGGTGCCGCCGCCGTCGACAATGACCGTGTCGTCCTTGCTGACCACCACGCGTCGGGCCGAGCCCAGCACCTCCAAGCCCACC
TCGCGCAGCACCATGCCGGCGTCGGGGTTGACCACCTGGCCACCCGTCACCACCGCCAGGTCCTCAAGGAAACGCCTTACGGCGGTCACCGAAGTACGGCCC
CTTGACCGCGACCGCTTTCAACGTCTTGCGAATCGCGTTGACGACCAGCGTCGCCAACGCTTCGCCCTCCACGTCTTCAGCCACGATCAGTAGTGGCTTACC
CGTTCCTGCAACCTTTTCCAGCAATGGCAACAGATCGGGAAGCGANCTGATCTTGTCTTGGTGCN Clone Rv115
::::::::::::Rv115SP6.seq::::::::::::
CCAAGCTATTTAGGTGACACTATAGAATACTCAAGCTTTTGGCTGGGTCGCCTTCGAATTCNGCGTGCACCGCTATGGGTTGCANCAGCGGCTGGCGCCGCA
CACCCCACTGGCCCGGGTGTTTTCGCCCCGAACCCGGATCATGGTGAGCGAAAAGGANATTCNCCTGTTCGATGCTGGGATTCGCCACGCCAAGGCATCTAN
CGATTACTCTCCNCGGGGTGGGAAAAGTGCCCAATCCCCCTCCCTCCAACTTTCCNAACAATCATTCCGGTTCCNCCNTCCGGTTGGNGGTAACCNNCCAAT
AAAACCCCTGCCCG ::::::::::::Rv115T7.seq::::::::::::
GCCCGCNCATGGCCAATCCCCGAAGACATCATTGGCCAGTGGCCGGGCGCTAACAGGTTCCAGCCCCCCACCANTGCCGCTCGAACATGCGGTGCAACCCAT
TCGCAGGCCGGCAGGGAAAGCACCGCGGAAGCCGCAAAGGGCTGCAGTTCCGCGCCCAATAATGTCGTCCGCAACCAGATGCGCTCNAAAACCNCNCCGGCA
GTCAGCGCACCCGACGCGANGTCGAAAGACGTCNTCAGCGCGCCCACATGGGGTGCCAATCGGCACGGCAGGTATGCCGCGCGCAACCCGAGCGCGTGGTGC
ATGCCCACGGTCCGCANGANGCGCANCACCCGCCAATGCCGAANCCCACGAAACATCGGGCGCATCCACCTTCAACC Clone Rv116
::::::::::::Rv116SP6.seq::::::::::::
ATACTCAAGCTTGCCCAGCCGTCGATGACAAGAAATATGTCCGCAAAAGACTCAGCGGCCGACTTTGCTCGCAGCTGGCGGTACCGCGCCACCGAGTCGATG
CCGTGGTCGCGGAAGAATGCCTCCCGAATTCGCACGGCCAATTCCATTCCGGGAAGCATCCGCAATGCCAGCTGCGGTTGCCCCCTGCCGGCCACGGCACCC
ACTTGCGGCATTGCGTCCACCTGGGCCAGCGCCCCGCCGCCAAATTCCAAACAATAAAAATTGCACCCGGC ::::::::::::Rv116T7.seq::::::::::::
CCACCGTGTATTTTGGGATGGGCAAAAAGGCGAAGCACCGCGTGGCCACGAACGCCGGGAGGGACAATCTCGGGGCGGCTAGGGCTTCTCGCGGGAAGGCCC
GAACGTACGGCGTTTCAACACGTCGCGTCGCCCTCCGACCGCGAACATTCGGGGATGGCAGCAACCTGGTAGCACCCTGGCCGGGCGATGATCTGCAGCGTC
GCCGCGGGTAGTCGCCGCCCGGGCGGCTACAGTCTGAAACGCGATGACCATCGATGTGTGGATGCAGCATCCGACGCAACGGTTCCTACACGGCGATATGTT
CGCCTCCCTGCCCCGT Clone Rv117
::::::::::::Rv117SP6D2.seq::::::::::::
CTGCCCATGTTTGGGGACGCCCGACCAGCCGATGCTGGAGGCCTACACGGCCCTTGGTGCGCTGGCCACGGCGACCGAGCGGCTGCAACTGGGCGCGTTGGT
GACCGGCAATACCTACCGCAGCCNGACCCCTNTCNCAANAGGATNTTGTTCGCCGGACCCCNCTC ::::::::::::Rv117T7D4.seq::::::::::::
CCGACTTTCCGCGGTACCCGCTCAACTTTGTGTCGACCCTCAACGCCATTGCCGGCACCTACTACGTGCACTCCAACTACTTCATCCTGACGCCGGAACAAA
TTGACGCAGCGGTTCCGCTGACCAATACGGTCGGTCCCACGATGACCCAGTACTACATCATTCGCACGGAGAACCTGCCGCTGCTAGAGCCACTGCGATCGG
TGCCGATCGTGGGGAACCCACTGGCGAACCTGGTTCAACCAAACTTGAAGGTGATTGTTAACCTGGGCTACGCGACCGCCTTT TABLE 3-continued End sequences of the polynucleotide inserts cloned in the named recombinant BAC vectors contained in the I-1945 *M. tuberculosis* H37Rv genomic DNA library.

Clone Rv118
::::::::::::Rv118SP6.seq::::::::::::
ATACTCAAGCTTTGTCACACCAAGTGTTTCGACCAGGCGCTCCATCCGGCGAGTGGATACTCCCAGCAGGTAGCAGGTCGCCACCACGCTGGTCAGTGCGCG
TTCAGCTCGCTTGCGGCGCTGCAGCAGCCATTCGGGGAAATACCTGCCCTGGCGCAGCTGGGGGATCCCAACTTCAATGGTTGCGGCACGGGTGTCAAATTC
ACGGTGGCGGTAGCCGTTGCCCTAATTGGACCGCTCATCGCTGCTTTCGCGGTACCCCGCCCCGCACAGGGCTTCGGCTTCAGCCCCCATCAGGGCGGCAAT
AAACTTCAAGAGCACC ::::::::::::Rv118T7.seq::::::::::::
GAGGCAGCTTCGCCGGCAATTCTACTAGCGAGAAGTCTGGCCCGATACGGATCTGACCGAAGTCGCTGCGGTGCAGCCCACCCTCATTGGCGATGGCGCCGA
CGATGGCGCCTGGACCGATCTTGTGCCGCTTGCCGACGGCGACGCGGTAGGTGGTCAAGTCCGGTCTACGCTTGGGCCTTTGCGGACGGTCCCGACGCTGGT
CGCGGTTGCGCCGCGAAAGCGGCGGGTCGGGTGCCATCAGGAATGCCTCACCGCCGCGGCACTGCACGGCCAGTGCCGCGGCGATGTCAGCCATCGGGACAT
CATGCTCGCGTTCATACTCCTCGACCAGTCGGCGGAACAGCTCGATTCCCGGACCGCCCAGCGCATTGGTGATGGAATCGGCGAACTTGGCCACCCGCTGGG
TGTTGACATCCTCGACGGTGGGCAATTGCGCCTCGGTAAGCTTTGCCGCGTAGCCTTTTCATC Clone Rv119
::::::::::::Rv119SP6.seq::::::::::::
ATACTCAAGCTTCACTGACAAGGGACGAATTCGTCGGCCGCCTGTTCGACTGGGTGGTGGCCGAGCTGGTCGCCACCACTCAGGCCGCGGTCACGGCGGTAC
CGGCGCGGGAGCAAACTCGCGCGGGCATGGCCAACTTCTTGCGGACCATCACCGCAGACGCCCGCTTCGGACCCCTGCTGTCCACCACACAGTTGGCCAACG
CATTAATCACCCGCAAGCTTGCGGAATCCACCGCCCTGTTCGC ::::::::::::Rv119T7.seq::::::::::::
TCCATCACCCGATGTGGCNGGAGCACTGCCATGTCGATCTCAACTACCACCTCCGGCCGTGGCGGTTGCGCGCCCCGGGGGGTCCGCGCGAACTCGACGAGG
CGGTCGGAGAAATCGCCANCACCCCGCTGAACCGCGACCACCCGCTGTGGGAGATGTACTTCGTTGAGGGGCTTGCCAACCACCGGATCGCGGTGGTTGCCA
AAATTCACCATGCGTTGGCTGACGGTGTTGCCTCGGCAAACATGATGGCACGGGGGATGGATCTGCCGCCGGGACCGGAGGTCGGCCGCTATGTGCCTGACC
CCGCTCCTACCAAGCGGCA Clone Rv11
::::::::::::Rv11SP6.seq::::::::::::
AGCTTTGCAGTTGCTGAGTAATGTCGGCCAACGTCACCACAACCGCGATGAATTCAATCATGCCGCCCAGGGCGGCCAACCCAATGGTGGCCGCGAGCGGCA
GCTCGATCGCAGCGCGGAGGTTGCCGGCCGCCAGTTGATTCACGAACAGGGTGAGGTCATAGGCGGGCAGGATAGTGACGAAGGCAAGACCTCCATCTGCCG
TCGGAAGAAGTATCGAG ::::::::::::Rv11T7.seq::::::::::::
AGCTTCAGAACAGGCCTGTTGTGGGCGCACCCGGCTCGCCGAGTTCTGCACGCACCGCCTCAAGTGCGGCCCGCACCGCCGGCATCTCCCGGTCACGCAGGG
CCGCGGCCCGCGCCGCAGCGACGGCGTGTTCGCGCAGTTCGCCGTCAATGATGCTGACCTGATCGGCCACCCGGGCGTTCTCGGCGTCGTCGCGTTCACTAA
TCGCGGTGCTCAGCAGCGTCTCGACAGCCACCACCCGAGTGGCGACCAGCTGCTCCACCACGGACCGCAGCGATGCCCGTC Clone Rv120
::::::::::::Rv120SP6.seq::::::::::::
ATACTCAAGCTTCAGTTCCTCCACGACGCGTTCCCAAATGAATTTCCCGATCCCACAATCTCGGTTCAGATACAGGTCGCCATACCCCTTACTTCGGCAACG
CTGGGCGGATTGGCCCTGCCGCTGCACCAAACCATCAACGCCTTCAAATTGCCGGCAATCTCGTTCAGCCAATCCAT ::::::::::::Rv120T7.seq::::::::::::
GCTCTACGCCGCCTACGGGTCGAACATGCATCCCGAGCAGATGCTCGAGCGCGCACCCCACTCGCCGATGGCCGGAACCGGCTGGTTACCCGGGTGGCGGCT
GACGTTCGGCGGCGAGGACATCNGCTGGGAAGGGGCGCTTGCCACCGTCGTCNAAGACCCAAATTCGAAGGTGTTCGTCGTGCTCTACGACATGACCCCGGC
GGACGAGAAGAACCTTGACCGGTGGGAAGGCTCCGAGTTCGGTATCCACCAGAAGATCCGATGCCGCGTGGAGCGCATTTCCTCGGACACCACAACGGGATC
CCGTCCTCG Clone Rv121
::::::::::::Rv121SP6.seq::::::::::::
ATACTCAAGCTTGCCAAAGAGACCTCGTCCACCAAGCAGGACGCGACCGTCGAGGTGGCGATCCGGCTTGGCGTCGACCCGCGTAAGGCAAACCAGATGGTT
CGCGGCACGGTCAACCTGCCCACACCGGCACTGGTTAAGAACTGCCCGCGTCGCGGTTTTCGCGGTTGGTGAAAAGGCCAATGCCTGCGTTTGCCGTGGGGG
CGGATGTTGTCGGGAGTGACAATCTGATGAAAAGGATTCAGGGCGGTTGGCTGGAATTCAATGCCGCAATCGCGACACCGG ::::::::::::Rv121T7.seq::::::::::::
CCACGGCGTGGATCAAGGTACCGGCCGGGATGTTGCGCAATGGCAGGTTGTTGCCCGGCTTGATGTCGGCGTTAGCGCCGGATTCCACCACATCCCCTTGCG
AAAGTCCGTTGGGTGCAATGATGTAGCGCTTCTCCCCATCGAGATAGTGGAGCAACGCAATCCGTGCGGTACGGTTCGGGTCGTACTCGATGTGCGCGACCT
TGGCGTTGACACCATCTTTGTCATTGCGGCGAAAGTCGATCATCCGGTAAGCGCGCTTATGACCGCCGCCTTTGTGCCGGGTGGTAATCCGGCCATGCGCGT
TGCGTCCACCGCGACGTGCAGCGGGCGCACCAGCGACTTCTCCGGGGTTGACCGGGTNATCTC Clone Rv122
::::::::::::Rv122SP6D2::::::::::::
GCAGCATGACGGCGGTAGCGAACACCGCCGGATGCAGCGCAAGTAGCGTCGATGTGCTCACGGAATCGCCCCGGCACCGCGATCTCGANGATCACCAGTGCC
ACCCCCTGCAGCGCNACACCGACGATTCCGTACACCGCCACGCCGATCAGGCCCTGGGCCATCTGATTGGAGCTGGCGTANATGGCGGCGATGGTGACGATG
GCCAGCGCCACATACATTGTGGCGGCCAGAACCACGGCGTTGGGGCGGCGGTCGATGAACACTAGGCGACGCAGATCGCCCGGGGTCAACAGGTTGACCATC
AGAAAGCCTGCGACTAGCACGGCGGCGCCACTAGGAAGTACAAGAANGTGGCCACCACCCCATGCAGGATCGGGGTAAGGCTGATGGTCCCGAAATCGACTC
CGGCCTAATACATGACTCTCTCCTTTGCGTCATCGCCTTACTTGTGCGCGGAA Clone Rv
::::::::::::Rv123SP6D2.seq::::::::::::
GGGACACACCTCGATGCTGCCGCNATGGACGCGGTCGAACGCAAGCAGCTGATCGAGCTACAACGCCGCGCGGAACGCTTCCGCCGCGGGCGTGACGCATCC
CGTTGACCGGCCGGANCNCTCTCTA ::::::::::::Rv123T7D4.seq::::::::::::
TGGGCGCCTCTTTCGGCCTTCCCNNTTTAAACGNAGCANGACATTCTGGGTATCGAGTTGTACTGGATGGTGTTGGCGATGTCGGTGATCCTGCTCCTGGCG
GTGGGATCCGACTACAATCTGCTGCTGATTTCCCGGTTGAAAGAGGAAATTGGGGCCGGATTGAACACCGGAATTATCCGTGCCATGGCTGGTACCGGGGGA
GTGGTGACGGCTGCCGGCATGGTGTTCGCCGTTACCATGTCGTTGTTTGTGTTCAGCGATTTGCGAATTATTGGTCAGATCGGTACCACCATCGCCTTCCC TABLE 3-continued End sequences of the polynucleotide inserts cloned in the named recombinant BAC vectors contained in the I-1945 *M. tuberculosis* H37Rv genomic DNA library.

Clone Rv124
:::::::::::::Rv124SP6D2.seq:::::::::::::
CCGATCGGCGCCGCANCTGGTTGGTGTTNCGGATGAATCCGCAGCGAAAATGTAGCTGCGGTGGCGTGTCGTGACTCGTNGGCGTCGACGCTCGTGGCAGCC
ACCGANCGGTTGGTCCAGGATCTGGATGGGCAAAGTTGTGCGGCCCGGCCGGTGACGGCCGATGAGCTGACCGAGGTCGACAGCGCCGTGTTGGCTGACTTG
GAACCGACATGGAGTCGCCCCGGTTGGCGTCACCTCAAGCATTTCAATGGTTATGCGACCAGTTTTTGGGTTACGCCGTCAGACATCACGTCGGAGACTTGG
ATGAGCTGTGTCTGCCAGATAGCCCCGAATCGGGACGACCGTGGTCACGGTGCGTCTGACCACTCGGGTCGGGTCGCCCGCGCTATCGGCATGGGTGCGTNA
TCACAGCGACACGCGCCTGCCCAAGGANGTNCGGNCGGACC :::::::::::::Rv124T7D4.seq:::::::::::::
CGGGTTGCGGATCCACGCGTGCGGGTTGTCAGCAGCTACGGCACTGAACCGCGCCCACAGCTCGCCGATCCGCTTTCGGTGGTTCTCGATCGACTCGCCGTA
GGCGATGCGCAGCGCCTGCTCGAATATCGGGTACACGTAGGCCGGCCTTCCCNCTTTA Clone Rv126
:::::::::::::Rv126SP6.seq:::::::::::::
CTTGATTTTGATCATCATGACGATCATCACCCTAATTTTGCTACCCGCACTGGTTATCGTGGGTACCGTCGTGCTTTCCATGGGCGCCTCTTTCGGGCTTTC
CGTATTGGTCTGGCAGGACATTCTGGGTATCGATTTGTACTGGATGGTGTTGGCGATGTCGGTGATCCTGCTCCTGGCGGTGGGATCCGACTACAATCTGCT
GCTGATTTCCCGGTTGAAAAAGGAAATTGGGGCCGGATTGAACACCGGAATTATCCGTGCCATGGCTGGTACCGGGGGAGTGGTGACGGCTGCCGGCATGGT
GT :::::::::::::Rv126T7.seq:::::::::::::
GGGGATCCCTAGATCGACCTGCAGGCATGCAAGCTTGGCGTGTCGTTCCAACCCGAATTGGCTTTCGGCGCCATCGGTGAGGCGGGACACACCTCGATGCTG
CCGCCATGGACGCGGTCGAACGCAAGCAGCTGATCGAGCTACAACGCCGCGCGGAACGCTTCCGCCGCGGGCGTGACCGCATCCCGTTGACCGGGCGGATCG
CGGTGATCGTCGATGACGGCATCGCCACCGGAGCNACTGTCAAGGCGGCGTGCCAGGTCGCCCGGGCGCACGGTGCGGACAAGGTGGTGCTGGCGGTCCCGA
TCGGCCCAGACGACATCGTGGCGAGATTCGNCGGGTACGCCGATGAGGTGGTGTGTTTGGCGACGCCGGCGTNGTTCTTCGCCGNCGGGCANGGTTACCGCA
ACTTCACCCAGACCTCCGACGACGAGGTGGTGGCGTCTCCTGGATCGTGCTC Clone Rv127
:::::::::::::Rv127SP6.seq:::::::::::::
AAGGCTGCAGGTCGAAGCGGNTGGTTACGACTCCCTGTGTGTGATGGACCAGTTCTACTATCTGCGTCTACACGGCCCTTGGTGCGCTGGCCACGGCGACCG
AGCGGCTGCAACTGGGCGCGTTGGTGACCGGCAATACCTACCGCAGCCCCGACCCTGCTGGCAAAGATNATCACCACGCTCGACGTGGTTAGCGCCGGTCGA
GCGATCCTCGGCATTGGAGCCGGCGGGTTTGAACTGGAACACCGCCAGCTCGGCTTCGAGTCCGGCACTTCCAGTGACCGGTTCAACCGGCTCGA :::::::::::::Rv127T7.seq:::::::::::::
CTTTCCGCGGTACCCGCTCAACTTTGTGTCGACCCTCAACGCCATTGCCGGCACCTACTACGTGCACTCCAACTACTTCATCCTGACGCCGGAACAAATTGA
CGCNGCGGTTCCGCTGACCAATACGGTCGGTCCCACGATGACCCAGTACTACATCATTCGCACGGAGAACCTGCGCGTGCTACAGCCACTGCGATCGGTGCC
GATCGTGGGGAACCCACTGGCGAACCTGGTTCAACCAAACTTGAAGGTGATTGTTAACCTGGGCTACGGCGACCCGGCCTATGGTTATTCGACCTCGCCGNC
CAATGTTGCGACTCCGTTCGGGTTGTTCCAGANGTCAGCCCGGTCGTCATCGCCGACGCTCTCGTCN Clone Rv128
:::::::::::::Rv128SP6.seq:::::::::::::
CGGTCATAGCCCTCGGGTCCGGCCAGCACTCCGCAGGCTTCGTCGGGGTGGTCGCGACGCGCATGGGCCACCATCGCATTCACCAGGTCTGCGCGAATCACC
AGCACGTAGACGGTTCCTTTCCTAAGCAACACCGAAGTTTCACGACCCGAATGCTCCGGGAAACATGTCACGGTAGGTCGGTATTCCGGCTACCGGCTGAGC
ATTGAGCACGCCGGCCAGCACCGCACGAGCCAGGCAATCAGCCGCCGCCGCACCGATCGCGGTGACCAGCTGAGTCTCCGGAGACAATGCGGCCGGCACGCC
GGNCTCCGGCGGCACCGCTACNGCGCCCGTGG :::::::::::::Rv128T7.seq:::::::::::::
GTGATGGCACGCCACCGCGACACCACCCGGCTGCGCTACNTCGAGCCATACCGGGCGGAGCTACATCGGCTCGGCCGCCCAGTGTTCGGGCCCTCTTTCGAG
GTCGAGGTCGATACCGATTTGCGCATCCGCANCCGCNCCCTGGACGACAGAACCGTGCCCTACGAGTGCTTGTCGGGCGGGGCCAAAGAACAGCTTGGCATC
CTGGCGCGATTGGCCGGCGCGGCGCTGGTCGCCAAGGACGACGCCGTTCCGGTGCTGATCGACGACGCGCTGGGGTTCACCGATCCGGAGCGACTATCAAGA
TGGGGGAGGTCTCTGACACCATCGGCCCCNACGGACATGTGATCGTGCCGACGTGCAGTCCCACCCCG Clone Rv129
:::::::::::::Rv129SP6.seq:::::::::::::
GCGAAAGTCCGTTGGGTGCAATGATGTAGCGCTTCTCCCCATCGAGATAGTGGAGCAACGCAATCCGTGCGGTACGGTTCGGGTCGTACTCGATGTGCGCGA
CCTTGGCGTTGACACCATCTTTGTCATTGCGGCGAAAGTCGATCATCCGGTNNGCGCGCTTATGACCGCCGCCTTTGTGCCGGGTGGTAATCCGGCCATGCG
CGTTGCGTCCACCGCGACCGTGCAGCGGGCGCACCAGCGACTTCTCCGGGGTTGACCGGGTGATCTCGGCGAAATCAGATACGCTGGCGCCGCGACGACCAG
GCGTCGTGGGCTTGTNCTTGCGAATTGNCATGTCTAATCANGTCTTTCTCTCACGCTCTCGTCGCCGGGCTAGGCCGCATTGCCCTGCTCCTCCTCATCGCT
TCGCTCTGCATCGTCCCCGGGCTAAGCCCGTGCCCCGAAA :::::::::::::Rv129T7.seq:::::::::::::
GATGGTTCGCGGCACGGTCAACCTGCCACACGGCACTGGTAAGACTGCCCGCGTCGCGGTATTCGCGGTTGGTGAAAAGGCCGATGCTGCCGTTGCCGCGGG
GGCGGATGTTGTCGGGAGTGACGATCTGATCGAGAGGATTCAGGGCGGCTGGCTGGAATTCGATGCCGCGATCGCGAACACCGGATCAGAATGGCCAAAGTC
GGTCGCATCGCTCGGGTGCTGGGTCCGCGCGGCCTGATGCCCAACCCGAAAACCGGCACCGTCACCGCCGACTCCCCATGGCGTCCCGGATATCAAGGGCCG
GCAAATCAACTTCCCGGTTCATCAGCAAGGCAACCTGCTTCCNCCTCCGG Clone Rv130
:::::::::::::Rv130SP6.seq:::::::::::::
ATACTCAAGCTTCGTCATAAGACCATGGTGCGCTTTCTTTCACCCGTCCAGAGTCGGGGGCATCCGCACCGGCTCGCATCGCATCATCCTCCCACGACGGGC
CGCTCATCAGCTTGGGCCATTTCAATGTACTTGATACCCCGCGCTGCGGGTAGGCCACTGCGACAATTCAAACACGGTGTCACACGGTGAATAGTGTCGAGA
TGGGCTCTGATCAACCGTCGCAAACCCGGTTTCGCATCAATAGCGGAATCCCACCGGGTTGCATGGAGGCTGCTGACCTTGGAAAACAAAATTTTTTCATTA
CAACAAAACAACCGCCNCGGAAACTTTGCA :::::::::::::Rv130T7.seq:::::::::::::
CGAATTCGGCGTGCACCGCTATGGGTTGCAGCAGCGGCTGGCGCCGCACACCCCACTGGCCCGGGTGTTTTCGCCCCGAACCCGGATCATGGTGAGCGAAAA
GGAGATTCGCCTGTTCGATGCTGGGATTCGCCACCGCGAGGCCATCGACCGATTACTCGCCACCGGGGTGCGAGAGGTGCCGCAGTCCCGCTCCGTCGACGT
CTCCGACGATCCATCCGGCTTCCGCCGTCGGGTGGCGGTAGCCGTCGATGAAATCGCTGCCGGCCGCTACCTGCAAGGTGATTCTGTCCCGTTGTGTCGAAG TABLE 3-continued End sequences of the polynucleotide inserts cloned in the named recombinant
BAC vectors contained in the I-1945 *M. tuberculosis* H37Rv genomic DNA library.

TGCCTTTCGCGATCGACTTTCCGTTGACCTACCGGCTGGGGCGTCGGCACAACACCCCGGTGAGGTCGTTTTTGTTGCAGTTGGGCGGAATCCGTGCTCTGG
GTTACAGCCCCGAACTCGTCACGGCGGTGCGCGCCGACGGAGTTGTTATCACCGATCCGTTGGCCGTACCGCGCCTTGGGC

Clone Rv132
:::::::::::::Rv132SP6.seq:::::::::::::
TCAGACTCCACCCAGCCAGCAGGCAGCGCGAAGCTGAATCCTCCAACCGGGTTGTCGATCCGGACAGGTTGGGGTGCGTTTGGGGCAATGACAGGTGGCGGC
GGTGCGTTCGGGTCGGCCGGCGGAGGTGCTGCGTTGGGATCGCCCGGCTGGGCATTCNGCGTGTTGGCGGCGGCCGGTGGTGGGGGGGCAACAGGTGTCGCC
GGTGCGGGTGGCGCTGCAGCGGTCGACGGCGGCGAAGCGGCCGTTGTGGGTACCGGGGGCGCTGGCTCCGGATCGGCGTTGGCGGTCGCGGGCACCGCAACG
GTCACCAAGCTGGCGCTGGCCATCGCCGCGATAGCCAGTGCCGCCAATCGTCCCTTGCGACGTGTCAAGTNGGGGTCCACCTGATGCATGGCCAAAGAACCT
ACCGTGTTAACGGCNCAACNCAAGGACCGCGCCGGTCGCN :::::::::::::Rv132T7.seq:::::::::::::
TTTCCGCGGTACCCGCTCAACTTTGTGTCNACCCTCAACGCCATTGCCGGCACCTACTACGTNCACTCCAACTACTTCATCCTGACGCCGGAACAAATTGAC
GCAGCGGGTCCGCTGAACAATTCGGTCCGTCCCACGAAAGAACCAGTTTTNCNTCTTTCNCACGGAGAACCTGCCGCTGCTAGAGCCACTGCGATCGGTGCC
GATCGTGGGGAACCCACTGGCGAACCTGTGTTTCAACCAACACTTAGAGTGTAATTGTAAACCTGGGCTAGGGGAAACCGGCTCTAGTTTTTCCACCNTCTC
CGCCCCNTGTTTCGAATACTCCGTTCGGGTTGTCCCCAAA Clone Rv134
:::::::::::::Rv134SP6.seq:::::::::::::
GCTTCCGGCTCGTATGTTGTGTGGAATTGTGACCGGATACCAATTTCACACAGGAAACAGCTATGACCATGATTACGCCAAGCTAGTTAGGTGACACTATAC
AATACTCAAGCTTGCCGGCTGGTGGGCCGACCACTTCGATGGCACGACCCGTGAACTGCTGCCCGGCCAATTCTTCTTGGTCGCCCGGACCGATGGACCGCG
GCTGGGATTCCAGAAGGTGCCCGATCCCGCCCCTGGGAAAAACCGCGTGCACCTCTACTTCACGACCAACGAC :::::::::::::Rv134T7.seq:::::::::::::
CCGATCGACTGATGCGCCGACAACCACGCCCCAACAACTGGAATGAACCGTCGTGACCATCATCAGCACGCGGTTGTAGGCGACTTGCGACATGTTCAACCC
GCCGTACTCGGACGGAATCTTCAAACCGAAACAGCCCAGCTCGGCCAGGCCTTTCACGTACTCGTCGGGGATCTGGGCACCACGCTCGAGGACGCTGCCGTC
CACGGTGTCTAGGAATTCCCGCAGTTTGACCAGAAACGCCTCGGTTCGGGCCTCCTCGGCGTCCGACGGCTTGGGAAATGGGTGTATGAGCCCTACGGGAAA
CCGGCCCACAAAGAGTTCTTTGGCGAAGGACGGTTTATCCCAACCACTTTCGCGAGATTCCTCGGCAAGGGCCCGCGCTTGCTCCTCGGTGACCTGAGTTTG
CTGTGCCATCGCCGCCTCCTCCCTGA Clone Rv135
:::::::::::::Rv135SP6.seq:::::::::::::
TGCATCCGGCTCGTATGTTGTGTGGAATTGTGAGCGGATAACAATTTCACACAGGAAACAGCTATGACCATGATTACGCCAAGCTATTTAGGTGACACTATA
GAATACTCAAGCTTTTACGGTGATCGCGCATCACCTGGTTCATGAACTGGAAGCAGCGCAGCGCTTCCTTTTCGGCCGCAACATGAGCCAGCCTCTCGTCGG
CGGTCGGGTGCAGGTGCTCGGGCAGCTCGGCCGAGACAGCCGCCTGACCCTGAAACCAGCTTCCATATCCCGCGACGAACGACGCCAGTCCGCTACGTAACC
CCTCCGCGACTGTCCATGGACAACAGCGCGTTCTCCACCGACCGGGCCCGGGTGTGGGGTGTTTCGGCGACCGGCAGCCAGGTGGTCCACACTGCCGACGGG
CGCCGCGAGCCGTTCACCGACCAGGCCGCCGAGCAAGTCCGCCCGATCGCATACTCC :::::::::::::Rv135T7.seq:::::::::::::
GGGGGCGCTGCTGGTATAGTCGCTGACCGGTGCAGGTTTCGACAATGTGGTGCCGGTTCGGCGGCTACGTGCCATCGAGACACTGGCGCAGGCTATCGCACC
CGTTATCGGCTACGAGCAAATCGCGGTATGCGTTCTTGAGCATGAGTCGGCGACCGTCGTCATGGTCGACACCCACGACGGAAAGACGCAGATCGCCGTCAA
GCATGTGTGCCGCGGATTATCAGGACTGACCTCCTGGCTGACCGGCATGTTTGGTCGCGATGCCTGGCGCCCGGCCGGCGTGGTCGTGGTCGGCTCGGATAG
CGAGGTCAGCGAATTCTCGTGGCAGCTCGAAAGGGTCCTGCCGGTGCCGGTCTTTGCGCAAACGATGGCGCAGGTTACGGTCGCGCGGGGTGCGGCCTGGCG
GCGGCCAGAGCACGAGTTCACCGATGCGCAGCTAGTGGCGACAGCGTCAGCCAAC Clone Rv136
:::::::::::::Rv136SP6.seq:::::::::::::
TGCTTCCGGCTCGTATGTTGTGTGGAATTGTGAGCGGATAACAATTTCACACAGGAAACAGCTATGACCATGATTACGCCAAGCTATTTAGGTGACACTATA
GAATACTCAAGCTTCCGTACAGGTCGCCTCCAACACGGCGGGGAAGCGACACCAGCCTACCGAGCTTGGAGTCCAGGACGCCAGCGGCGGCGTCGGTCTGCG
TCGTGGTGCCGCCGGGGTGGCGTTGGCTGGCAACGATCTCCACCCAGCCGGTCGGGTTACCCACGATCTCGGCATAGACGCGGGCCGAGGCCGGTGCGATAC
CGTATTGCGTCAATTGGGACGCGGTTGTGCATTCGGCTAGCTCGGTTGCCACACCCGTCAGGGGTTCGACGTTGGCGGGTTCGGCGGGCCCCAGCACCGCTG
TCACCATGCCCGCCAAGCCGACCTGCGGCGCCACCAACT :::::::::::::Rv136T7.seq:::::::::::::
CGGCATGACCACCGACAGGCCCGACTGGTCGTACCACTCGAACGCCGGGGTGTTGATGTCCCAGCCGCTGAAGTCGTCCTGCGCGCGCAGGCCGTCGAGCAG
GTACAGGGCGGGCGAGTTGGCACCACCACTTTGGAATTGGACCTTGATGTCACGGCCCATCGACGGCGACGGCACCTGCAGGTACTCCACCGGCAAGCCCGG
CCGGGAAAATGCCCCCGCGGTCGCCGTGCCACCGACGGCGCCGACCAGACCCGACACTAGGGCCGCGCCGACGGCCCCGACCACGAGTCGACGCGACATACC
CGTGACGGCGCCACGAACCCTGTCAACAAGCTGCATTCTTGCTTCCCTCATCCTCATCTCAACGCATCCATGCATGTTTGGGCGCATCCTGAATTANGTCAG
ACTGCAGGCGCTGGGCCGGCAGTGCTCGTGTATCAACCACAACTTCGGGCGT Clone Rv137
:::::::::::::Rv137SP6.seq:::::::::::::
TTCCAACCCTAATTGGCTTTCGGCCCCATCCGTGAGGACGGGGTGCGGGTGCTCAACAACAACGTCGTCCGCGGGACACACCTCTATGCTGCCGCCATGGAC
GCGGTCCAACGCAAGCAGCTGATCGAGCTACAACCCCGCGCGGAACGCTTCCGCCGCGGGCGTGACCGCATCCCGTTGACCGGGCGGATCGCGGTGATCGTC
GATGACGGCATCGCCACCGGAGCGACGGCCAAGGCGGCGTGCCACGTCGCCCGGGCGCACGGTGCGGACAAGGTGGTGCTGGCGGTCCCGATCGGCCCAAAC
GACATCGTGGCGAGATTCGCCGGGTACGCCGATGAGGTGGTGTGTCTGGCGACGCCGGCGTTGTTCTTCGCCCTCGGGCAGGGTTACCGCAACTTCAC :::::::::::::Rv137T7.seq:::::::::::::
CAGGCATGCAAGCTTTCCGCCGATACCCGCCATGTCGCGCACATCCAGGACTTCTGGGGGGATCCGCTGACAGCGGCGGGATCCCAAAGTGCGGATGATCGG
GCCGCCTACGTCGTGGTGTACCTCGTCGGTAACAACGAAACCGAAGCGTATGACTCGGTCCACGCGGTGCGGCACATGGTGGACACCACACCGCCACCGCAC
GGGGTGAAGGCCTATGTCACCGGTCCGGCAGCACTCAATGCCGACCAGGCCGAGGCCGGAGACAAAAGTATCGCTAAGGTCACCGCCGATCACNAGCATGGT
GATCGCAGCAATGTTGCTAGTGATCTATCGCTCCGTAATTACCGCGGTTCTCGTCTTGATCATGGTCGGCATCGACTCGGCCAATCCGCGGATTCATCGCCT
TGCTCGCCGAACACAACATTTTCACCTTTCACATTTGCACCAACCTGCTCTTCTCAT TABLE 3-continued End sequences of the polynucleotide inserts cloned in the named recombinant BAC vectors contained in the I-1945 *M. tuberculosis* H37Rv genomic DNA library.

Clone Rv138
:::::::::::::Rv138SP6.seq:::::::::::::
CACTACTCAAGCTCTCTCNTCATTACCACCCCTGTAATTTGGGATGGGCAAAAAGGCGAAGCACCGCTTGGCCACNAACGCCGGGAGGGACAATCTCGGGCG
GCTATGGCTTCTCCCGGGAAGGCCCCAACGTACGGCGTTTCAACACGTCGCGTCGCCCTCCGACCGCGAACATTCGGGGATTGGCACCAACCTGNTACCACC
CTGGCCGGGCGATGATCTGCAGCGTCGCCGCGGGTAGTCCCCGCCCGGGCGGCTACAGTCTGAAACCCCGATGACCATCGATGTGTGGATGCAGCATCCGAC
GCAACGGTTCCTACACGGCGGATATGTTCTCCTCGCTGCGCCGGTGGACCGGTGGGTCTATCCCCTGAAACCGACATCCCN :::::::::::::Rv138T7.seq:::::::::::::
CAGGCATGCAAGCTTTCGTCAGTTCATTGCGCCAGCAGACCAACAAGAGCATCGGGACATACGGAGTCAACTACCCGGCCAACGGTGATTTCTTGGCCGCCG
CTGACGGCGCGAACGACGCCAGCGACCACATTCAGCAGATGGCCAGCGCGTGCCGGGCCACGAGGTTGGTGCTCGGCGGCTACTCCCAGGGTGCGGCCGTGA
TCGACATCGTCACCGCCGCACCACTGCCCGGCCTCGGGTTCACGCAGCCGTTGCCGCCCGCAGCGGACGATCACATCGCCGCGATCGCCCTGTTCGGGAATC
CCTCGGGCCGCGCTGGCGGGCTGATGAGCGCCCTGACCCCTCAATTCGGGTCCAAGAACATCAACCTCTGCAACAACGGCGACCCATTTGTTCGGACGGCAA
CCGGTGGCAACGCACCTAAGCTACTTGCCCGGGATGA Clone Rv139
:::::::::::::Rv139SP6.seq:::::::::::::
GTTTATGCACTGGTTAGGTGTTTCCATGAGTTTCATTCTGAACATCCTTTAATCATTGCTTTGCGTTTTTTTATTAAATCTTGCAATTTACTGCAAAGCAAC
AACAAAATCGCAAAGTCATCAAAAAACCGCAAAGTTGTTTAAAATAAGAGCAACACGTACACAAGGAGATAAGAAGAGCACATACCTCAGTCACTTATTATC
ACTAGCGCCCGCCGCAGCCGTGTAACCGAGCATAGCGAGCGAACTGGCGAGGAAGCAAAGAAGAACTGTTCTGTCAGATAGCTCTTACGCTCAGCGCAAGAA
GAAATATCCACCGTGGGGAAAAACTCCAGGTAGAGGTAC Clone Rv13
:::::::::::::Rv13SP6.seq:::::::::::::
ATACTCAAGCTTGGGTGTAGCCGATCACCGGAAGTCNCATGATCAGCCACGTTCCGCGCCGCCCGGCATACGGTGGTGTACCGATCTCCGCGTCATACACCC
GCGGGTAATCGCCGACGGTGCCGGTTCGCGAGCCGAA :::::::::::::Rv13T7.seq:::::::::::::
AGCTTTATCGAAAGCGCGAACAGCTCGCGGCGGCCCACGACGTGCTGCGTCGGATTGCCGGCGGCGAGATCAATTCCAGGCAGCTCCCGGACAATGCGGCTC
TGCTGGCCCGCAACGAAGGACTCGAGGTCACCCCGGTGCCCGGGGTCGTGGTGCACCTGCCGATCGCACAGGTTGGCCCACAACCGGCCGCTTGATGCCCGG
TCGGCAAGCCCGGCAGTTGCCAAACCCATCGTGATCAGGCTCGGCTCGCGAGTTCGGCGAAGAAATGGTTCGCCTGATCACCTACCATCGGCCA Clone Rv140
:::::::::::::Rv140SP6.seq:::::::::::::
TCAACACGCCGCCAGCCACCACGCGCGGGTCGGGCGCCGGGCCCGGGCCTCCAGGCTNCTCCGCTCGGTGATGGCACGCCACCGCGACACCACCCGGCTGCG
CTACGTCGAGCCATACCGGGCGGAGCTACATCGGCCCGGCCGCCCAGTGTTCGGGCCCTCTCGCCCAGGTCGAGGTCGACACCGATTTGCGCATCCGCAGCC
GCACCCTGCGACGACAGAACCGCGGCCCTACCCACTGCTTGTCGGGCGGGGGCCAAAGAACCAGCTTGNCATCCTGCCACAATTGGCCGGCGCCCG :::::::::::::Rv140T7.seq:::::::::::::
CAGGCATGCAAGCTTCACGTCCGTACGGCTCGGGTACGCTTCGGTCGCAGTGTGCGAGTGATAGATGACGACCGGGACCTCGTCGGCATCTTCCATAGCCCG
CCACACCTTCAGTTGCTCACCGGAATCCAACCGGTAGAAGGTCGGCCAGCGCTCGGCATTGGTCATCGGGATATGCCGCTCGGGACGGTCAGAGCCCTCGGG
TCCGGCCAGCACTCCGCAGGCTTCGTCGGGGTGGTCGCGACGCGCATGGCCACCATCGCATTCACCAGGTCTGCGCGAATCACCAGCACGTAGACGGTTCC
TTTCCTAAGCAACAC Clone Rv141
:::::::::::::Rv141SP6.seq:::::::::::::
AATATTCAAGCTTTCGGCGGAAACGGACNCCTTGCGAACATTGATAACAAAATAGAAATCATTGATGGTTTGAGTCACCAGGCCGATCAAGCCTTCGCCGAG
CCAAATTCCAATCAAGAGGCCCAAGCCCGTACCAATCAGCCCGGCAACGAGGGATTCCGTCNTTATCAGCCNAAATAACTGCTCTCGGGTACCACCCAAACA
GCGCAATATGGCGAAAAACGGTCGCCGTTGCACAACATTAAATGTCTCGGTATTGTTGATTAAAAAGATACCCACCACCAGGGCAATCCAACTGAGAGCGGT
TAAATTGACCGTAAAAACCTCCCGTCATCTGTTT :::::::::::::Rv141T7.seq:::::::::::::
CAGGCATGCAAGCTTGCTGCATCTTCCTGTGACTGCTCCCGAAACCTGGGGGTGTGCCTGCTGTGTATGCACGGCATACGGACATCCTTCCCCTGATACCCG
CGGTCGAACCAGCCACGTGTCCATCATCAGGGGTCAACCCCGGCCAAGGGCGACGGCACGCCAAGTTCGCCGACCGTTAACCTAGTGCTGTTAGCTTCATTT
GCTGCGAGCAAAACAGCTGGTCGGCCGTTAGGAACTGAATTGAAACTCAACCGATTTGGTGCCGCCGTAAGTGTCCTGTCTGCGGGTGCGCTGGTGTTGTCC
GCGTGTGGTAACGACGACAATGTGACCGGGGGAGGTGCAACCACTGGCCAGGCGTCCGCGAAAGTCCATTGCNGGGGGAAGAAGACAC Clone Rv142
:::::::::::::Rv142IS1081.seq:::::::::::::
GAAAGTGCCCCAAGGTGTTGGTGAAACTCGCTGGACGGTCCCCAGGATGTTGGCAGCACATTCACCGGACATGACCGGAGCAAGACCGGACATCCTCCCATA
CCGTCGTCGCCGTGTACATCCGTAGCCCGTCCTGGCAGGTGCTGGGTTGAACAAAATCAGCCCAACACCTGCCACGACGAAGAAGCGGGTTGCGCTGGCATG
TCTTGTCGGCTCGGCGATCGAATTCTACGAATTCCTTATCTACGGGACCGCTGCGGCGCTGGTGTTTCCCACCGTGTTCTTCCCACACCTGGATCCCACGGT
GGCCGCCGTGGCCTCCAAGGGGACATTTGCTGTGGCGTTCCTATCCCGGCCGTTCGGCGCGGCCGTCTTTGGATACTTTGGAGACCGCCTCGGCCGCCAGAA
GACCCTGGTCGCCACACTGTTGATCATGGGCCTGGCAACCGTGACTGTTGGGCTGGTTCCACGACAGTGGCCATCGCGC :::::::::::::Rv142SP6.seq:::::::::::::
ATATTCAAGCTTTGTCACACCAAGTGTTCCGACCAANCGCTCCATCCGGCGAGTGGATACTCCCAGCAGGTAGCAGGTCGCCACCACGCTGGTCAGTGCGCG
TTCATCTCGCTTGCGGCGCTGCAGCAGCCAGTCCGGGAAATAGCTGCCCTGGCGCAGCTTGGGGATCGCGACGTCGATGGTTGCGGCACGGGTGTCGAAATC
ACGGTGGCGGTAGCCGTTGCGCTGATTGGACCGCTCATCGCTGCGTTCGCGGTAGCCCNCCCCGCACAGGGCGTCGGCTTCAGCCCCCATCCAAGGCGGCGA
TGAACGTCGAGAGCAGCCCGCGCAGCAAATCCGGGCTCGCCTGTGCGAGTTGGTCAGCCAGAAGCTGCTCGGTGTCATAAGATGAGAAGAGGTCAGTGCGTC
CTTTCCTTCG :::::::::::::Rv142T7.seq:::::::::::::
CAGGCATGCAAGCTTTTTGAGCGTCTCGCGGGGCAGCTTCGCCGGCAATTCTACTAGCGAGAAGTCTGGCCCGATACGGATCTGACCGAAGTCGCTGCGGTG
CAGCCCACCCTCATTGGCGATGGCGCCGACGATGGCGCCTGGACCGATCTTGTGCCGCTTGCCGACGGCGACGCGGTAGGTGGTCAAGTCCGGTCTACGCTT
GGGCCTTTGCGGACGGTCCCGACGCTGGTCGCGGTTGCGCCGCCAAAGCGGCGGGTCGGGTGCCATCATGAATGCCTCACCGCCGCCGCACTGCACGGCCAG
TGCCCCGGCGATGTCAGCCATCGGGCATCATGCTCGCGTTCATACCTCGACCAGTCCGCCGAACAGCTCCATTCCCGGACCGCCCAACGC TABLE 3-continued End sequences of the polynucleotide inserts cloned in the named recombinant BAC vectors contained in the I-1945 *M. tuberculosis* H37Rv genomic DNA library.

Clone Rv143
:::::::::::::Rv143SP6.seq:::::::::::::
ATACTCAAGCTTTTGGCTGGGTCGCCTTCCAATTCAGCGTGCACCGCTATGGGTTGCAGCAGCGGCTGGCNCCGCACACCCCACTGGCCCGGGTGTTTTCGC
CCCGAACCCGGATCATGGTGAGCGAAAAGGAGATTCNCCTGTTCGATGCTGGGATTCGCCACCGCGAGGCCATCGACCGATTACTCGCCACCGGGGTGCGAG
AGGTGCCGCAGTCCCGCTCCGTCGACGTCTCCGACGATCCATCCGGCTTCCGCCGTCGGGTGGCGGTAGCCGTCGATGAAATCGCTGCCGGCCGCTACCACA
AGGTGATTCTGTCCCGTTGTGTCCAAGTGCCTTTCGCGATCGACTTTCCGTTGACCTACCGGCTGGGGCGTCGGCACAACACCCCGGTGAGGTCGTTTTTGT
TGCAGTTGGGCGGAATCCGTGCTCTGGGTTACAGCCCCGAACTCGTCACGGCGGTGCGCCGCCGAC :::::::::::::Rv143T7.seq:::::::::::::
CAGGCATGCAAGCTTCAACCTATTGACGCATTGTGCGAACTGACGGCGCCCGCGCATGGCCAATCCGGAAGACCATCATTGGCCAGTGGCCGGGCGCTAACA
GGTTCCAGCCCCCCACCAGTGCCGCTCGAACATGCGGTGCAACCCATTCGCAGGCCGGCAGGGAAAGCACCGCGGAAGCCGCAAAGGGCTGCAGTTCCGCGC
CCAATAGTGTCGTCCGCAACCAGATGCGCTCGAAAACCGCCGCCGGCAGTCAGCGCACCCGACGCGAGGTCGAGAGACGTCGTCAGCGCGCCCACATGGGGT
GCCAATCGGCACGGCAGGTAGGCCGCGCGCAACCCCAACGCGTGGTGCATGCCACGGTCCGCAGGAGGCCACCACCC Clone Rv144
:::::::::::::Rv144SP6.seq:::::::::::::
ATACTCAAGCTTCCCGGCCGCAGGTGACGGCGCGGCCTAGCGCCACTTGATGCCGCACCCGATCGACGGNCGTTGGTCGGGGTTGACTGGCCGCCCGGCGAG
CAGGGCGTCAACCGCGGCCCGGACGTCGGCGGCCGTCACCGGTCGGCCATTGCCCGGGCGGGAGTCGTCGAGCTGACCACGGTAGACAAGTCGGCGCTGGCC
GTCGAAGACAAACGTGTCGGGTGTGCAGGCCGCGGAGAAGGCGCNGGCGACGTCTCGGGTTTCGTCGTAGAGATACGGGAACGTCCAGCCGTGGCGGCGGGC
CTCGGCGACCATCTGATCGGGCCCGTCCTGCGGGTAGGTGACCACGTCCTTACTGGAGATACCGACCATCGGGACCCTTTGATCGGCGAGGTCCCGGCCGAC
CGTGGCCAATCCGGCGGCGACGTGTCGCCCGTACCGGCCAGTGGTTC :::::::::::::Rv144T7.seq:::::::::::::
CAGGCATGCAAGCTTTANCANCATCAACCCCGCCCCGCACCAGCACCGACACGATGTCGATGCCATCGAGGTGAATGTCGAACTGGCNCAAACCATCTGGCG
ACCGCGACCACCGGCAACATGGGTACCGGCGATTTCCGGTGCCAATGCCGACCCGACGGGCCGCTCTCACCGCAGGTGACCTCGATCACCGAGACCAGCCGG
CCGTTATACTCACGCACCCCTACCGTGTCACGCCCAAAACGGCGCTGGTGGTCGATTGCCGGAGTGCACCCCGCACCCAGTGTCGTGCCCGGATCCGCCGAC
CAATCCCGCACCCACGTCGCCAAACCCGAAATCACCGTGATGCCGTGGTAACTGACCACCGACAGTAACGTCACTACGGCCGCCACGCCGACGCCGAACCAC
CACGCACATGATGATCGGCTG Clone Rv145
:::::::::::::Rv145SP6.seq:::::::::::::
ATATTCAACCTTGCACACATTGACGATACCTTGGTCACGAGACCCCAAAAGCTGGCCTCCACCGCGCGCCGGGGACCACGGTCATACCTTGANNCNGCTTTC
GATCGTTGATGCTGCGTCTTGGTCCGCGGAAACCGCAGGCTGGCATATGCACGTGGGCGCACTGGCGATCTGCGATCCCCACCGATTCGCCCGAATACAGCT
TTCAGCGGCTCCCCAAGTTGATCATCGACCGGCTGCCGGATATCCCGCACTTGCGGTGGCGGGTCACCGGCGCCCCGCTCGGACTGGACCGGCCGTGGTTCG
TCGAGGACCACGAAC :::::::::::::Rv145T7.seq:::::::::::::
CAGGCATGCAAGCTTCATGCCCGCGGCATGATAGCCACATGCACGCAATCGAACTCAGCGAAACCGGCGGGCCAGGCGTCTTACGCCACCTCACCAGCGCGC
AACCTCAACCCGGCCACGGAGACCTCCTGATC Clone Rv146
:::::::::::::Rv146SP6.seq:::::::::::::
ATACTCAAGCTTGATTTTGATCATCATGATGATCATCACCCGAATTGTGGTAGCCGCAGTGGTTATCGTGGGTACCGTCGTGCTTTCCATGGGCGCCTCTTT
CGGGCTTTCCGTATTGGTCTGGCAGGACATTCTGGGTATCGAGTTGTACTGGATGGTGTTGGCGATGTCGGTGATCCTGCTCNTGGCGGTGGGATCCGACTA
CAATCTGCTGCTGATTTCCCGGTTGAAAGAGGAAATTGGGGCCGGATTGAACACCGGAATTATCCGTGCCATGGCTGGTACCGGGGGAGTGGTGACGGCTGC
CGGCATGGTGTTCGCCGTTACCATGTCGTTGTTTGTGTTCAGCGATTTGCGAATTATTGGTCAGATCGGTACCACCATCGGCCTGGGCTTGCTGTTCGACAC
CCTCGTCGTGCCTCGTTCATGAAACCGTCCATTGCTGCCCTGCTGGGACCTGGTTCTGGTGGCCGCTACGGGTGCGCCCGCGCCCGGCAGTCAAATCTTCCG
CCG :::::::::::::Rv146T7.seq:::::::::::::
CAGGCATGCAAGCTTGGCGTGCCGTTCCAACCCGAATTGGCTTTCGGCGCCATCGGTGAGGACGGCGTGCGGGTGCTCAACGACGACGTCGTCCGCGGGACA
CACCTCGATGCTGCCGCCATGGACGCGGTCGAACGCAAGCAGCTGATCGAGCTACAACGCCGCGCGGAACGCTTCCGCCGCGGGCGTGACCGCATCCCGTTG
ACCGGGCGGATCGCGGTGATCGTCGATGACGGCATCGCCACCGGAGCGACGGCCAAGGCGGCGTGCCAGGTCGCCCGGGCGCACGGTGCGGACAACGTGGTG
CTGGCGGTCCCCATCGGCCCAGACGACATCGTGGCGAGA Clone Rv147
:::::::::::::Rv147SP6.seq:::::::::::::
ATACTCAAGCTTTTACGGTGATCGCGCATCACCTGGTTCATGAACTGGAAGCAGCGCAGCGCTTCCTTTTCGGCCGCAACATGAGCCAGCCTCTCGTCGGCG
GTCGGGTGCAGGTGCTCGGGCAGCTCGGCCGCGACAGCCGCCTGACCCTGAAACCAGCTTCCATATCCCGCGACGAACGACGCCAGTCCGCTACGTAACCCC
TCCGCGACTGTCCATGGACAACAGCGCGTTCTCCACCGACCGGGCCCGGGTGTGGGGTGTTTCGGCGACCGGCAGCCANGTGGTCCACACTGCCGAAG :::::::::::::Rv147T7.seq:::::::::::::
TAGTCGCTGACCGGTGCAGGTTTCGACNATGTGGTGCCGGTTCGGCGGCTACGTGCCATCGAGACACTGGCGCAGGCTATCGCACCCGTTATCGGCTACGAG
CAAATCGCGGTATGCGTTCTTGAGCATGAGTCGGCGACCGTCGTCATGGTCGACACCCACGACGGAAAGACGCAGATCGCCGTCTANCNTGTGTGCCGCGGA
TTATCAGGACTGACCTCCTGGCTGACCGGCATGTTTGGTCGCGATGCCTGGCGCCCGGCCGGCGTGGTCGTGGTCGGCTCGG Clone Rv148
:::::::::::::Rv148SP6.seq:::::::::::::
ATACTCAAGCTTTCCGCCGATACCCGCCATGTCGCGCACATCCAGAACTTCTGGGGGGATCCGCTGACAGCGGCGGGATCCCAAAGTGCGGATGATCGGGCC
GCCTACGTCGTGGTGTACCTCGTCGGTAACAACGAAACCGAAGCGTATGACTCGGTCCACGCGGTGCGGCACATGGTGGACACCACACCGCCACCGCACGGG
GTGAAGGCCTATGTCACCGGTCCGGCAGCACTCAATGCCGACCAGGCCGAGGCCGGAGACAAAAGTATCGCTAAGGTCACCGCGATCACGAGCATGGTGATC
GCAGCAATGTTGCTAGTGATCTATCGCCCCGTAATTACCGCGGTTCTCGTCTTGATCATGGTCGGCATCGACCTCGGCGCAATCCGCGGATTCNTCGCCTTG
CTCGCCGACCACAACATTTTCAGCCTTTCAACATTTGCGACAACCTGCTCGTTCTCATGGCGATTGCNGCGAAC :::::::::::::Rv148T7.seq:::::::::::::
CAGGCATGCAAGCTTGGCGTGCCGTTCCAACCCGAATTGGCTTTCGGCGCCATCGGTGAGGACGGCGTGCGGGTGCTCAACGACGACGTCGTCCGCTGGACA
CACCTCGATGCTGCCGCCATGGACGCGGTCGAACGCAAGCAGCTGATCGAGCTACAACGCCGCGCGGAACGCTTCCGCCGCGGGCGTGACCGCATCCCGTTG TABLE 3-continued End sequences of the polynucleotide inserts cloned in the named recombinant BAC vectors contained in the I-1945 *M. tuberculosis* H37Rv genomic DNA library.

ACCGGGCGGATCGCGGTGATCGTCGATGACGGCATCGCCACCGGAGCGACGGCCAAGGCGGCGTGCCAGGTCGCCCGGGCGCACGGTGCGGACAAGGTGGTG
CTGGCGGTCCCGATCGGCCCAGACGACATCGTGGCGAGATTCGCCGGGTACGCCGATGAAGTGGTGTTGTTTGGCGACCCGGCGTTGTT

Clone Rv149
:::::::::::::Rv149SP6.seq:::::::::::::
ATACTCAAGCTTTGGCATTGTGCACATTTTCCACCCGTGCTCTATTAATGCTGAGCCGCTAATTGTGACCCCAGTCGGGAAACACGCGGAGCACCAAATTCA
CCGCAGCGGCCGGGGCGGTTCAACTCACCATGGATCGCTCTCGTCGTCTGGTGCTGGACAATCGTCGCTGTAGCGCGTCGCGAACACCTCAGCTTCTGCTGC
CGCGGCTTCTTCCGGCGATGGTAACCCCCAGGTTTCGCCCACGGTCTTACGTAGCAGTGCGACGCGGTGTTCATCTGCATCGACCTGTTGACTCATCCTGTC
AAGGATGAAGGCGTACTGGGCCGACTGCGCCTTCTGCCGCGCCAGGTCGGCAATCACCAGGATCTCAGAAACGAGCTGCGACTCACTCTTCCAGGCCACCCT
GGCCGAAAGCTCGACATGGTCAATCCGGCCG :::::::::::::Rv149T7.seq:::::::::::::
CAGGCATGCAAGCTTGCGGGCCGGAGTGGTTTCGACGGCCGCTCGCTTCTCGGCATCGGTTTGGGCTGTCACCAGCAGTTGGTAGTTCTTCACGTACTGTTG
TTCGAGCGTCGAGCCGCCGCGCGTGTCGAGGTCGCCGGACGCGTATCCCGCCAGGCCGGTCAGGGTGCCCTTCCAGTCCACGCCGCTGTGGTCGGCGAACCG
CTTATCTTCAATCGAGACGATCGCCAGCTTCATCGTGTTGGCGATCTTGTCCGAGGGCACCTCGAACCGGCGCTGCGAGTACAGCCACGCGATCGTGTTGCC
CTTCGCGTCGACCATCGTCGATACCGCAGGCACTTGCCCCTC Clone Rv14
:::::::::::::Rv14SP6.seq:::::::::::::
ATACTCAAGCTTCCCGGCGGCCAGTACCGAAAGCGCGAACAGCTCGCGGCAGCCCACGACGTGCTGCGTCGGATTGCCGGCGGCGAAATCAATTCCAGGCAG
CTCCCGGACAATGCGGCTCTGCTGGCCCGCAACGAAGGACTCGAGGTCACCCCGGTGCCCGGGGTCGTGGTGCACCTGCCGATCGCACAGGTTGGCCCACAA
CCGGCCGCTTGATGCCCGGTCGGCAAGCCCGGCAGTTGCCAAACCCAGCGTGATCAGGCTCGGCTCGCGAGTTCGGCGAAGAAGTGGCTCGCCTGATGACCT
ACCATCGGCCAGGATCTGCGTGTCATCACAACGCTCGCCAAGGAGGTTGTTGTGGTGCTATCGACGGCCTTTAGCCAGATGTTCGGAATCGACTATCCGATA
GTGTCCGCGCCAATGGACTTGATCGCCG :::::::::::::Rv14T7.seq:::::::::::::
AGCTTCGGTGTAGCCGATCACCGGAAGCCGCATGATCAGCCACGTTTCGCGCCGCCCGGCATACGGCGGCGTACCGATCTCCGCGTCATACACCCGCGGGTA
ATCGCCGACGGTGCCGGTTCGCGAGCCGAAGGTGACGACGCTGATTGAATCGAGTTCCAGGTCCAGCGGGTGGCGCAGCAACGGCGCGAGCTCAACGACGTC
AATCACGTTGTCGCTTTCTACGGTCACCGACCCGGTGACCGTAGTCGCCCGGTGCGCTCGGCCGAGAAGTTGCACCGCCACCACCGCGACACCGTCTTGCAC
GCGGACGCCACCCCCGGATCGGTTGTTGGCCAAGGTAATTGGGTCATTCCATTTGACGGGACGCCGACCCCGCAGCCCCAGTACCGCCCACGACCACGCCGG
CTGACCCACCACTGTACGAACACCAAGGCGACGCCGA Clone Rv15
:::::::::::::Rv150SP6.seq:::::::::::::
ATACTCAAGCTTCGGTGGCTTCGCCCGCCCTGCCGGGTGGACTTCATGACAACGCGGGGGCGATTACCCCCGCTACCGCCAGCAGCATGACGGCGGTACCTA
ACACCGCCCGGATGCCTCGCACGTGCCTCGATGTGCTCACGGAATCGCCCCGGCACCGCGATCTCGAGGATCACCAGCGTTACCCCCGGCAGCGCGACACCG
ACAATTCCGTACACCGCCACGCCGATCCGGCCCTGGGCCAGCTGATTGGAGCTGGCG :::::::::::::Rv150T7.seq:::::::::::::
CAGGCATGCAAGCTTCCACATGTACGGATCCACGAACATCCCGTTGAACTGACAGGTGCGGCCCGGCTCGATCAGGCCGGCCACTTGTTCTACGCGGTTACC
GAAGATCTCTTCGGTGACCTGCCCGCCGCCGGCCAGCTCGGCCCAGTGCCCGGCGTTGGCCGCCGCGGCGACGATCTTGGCGTCCACGGTGGTCCGGGTCTT
GCCCGCTAGCACGATCCGCGAGTCGGCCGGTCACCCGGGT Clone Rv151
:::::::::::::Rv151SP6.seq:::::::::::::
ATACTCAAGCTTTCCAAGTCCCAAGTGTCGATCATGGCCAAAGAGCTCGACAAAGCCGTAGAGGCGTTTCGGACCCGCCCGCTCGATGCCGGCCCGTATACC
TTCCTCGCCGCCGACGCCCTGGTGCTCAAGGTGCGCGAGGCAGGCCGCGTCGTCGGGGTGCACACCTTGATCGCCACCGGCGTCAACGCCGAGGGCTACCGA
AAGATCCTGGGCATCCAGGTCACCTCCGCCGAAGACGGGGCCGGCTGGCTGGCGTTCTTCCGCGACCTGGTCGCCCGCGGCCTGTCCGGGGTCGCGCTGGTC
ACCAGCGACGCCCACGCCGGCCTGGTGGCCGCGATCGGGGCCACCCTGCCCGCAGCGGCCTGGCAGCGCT :::::::::::::Rv151T7.seq:::::::::::::
CAGGCATGCAAGCTTCACACGTAGGCGCCGTCGATAAATGACTCCGCCGCGCTTCGCACATCCTCGTAGCGATCCTTGGCGAGCAGGTCAACCGGGCGCTGC
CCGTCGAGGAGCCGGTTTTTGGCGTGCAGCCACTGGCCGACACCTCGGGGGGTAAGCGAATCCGAGAGCAGGAGGACGAGGTCACGAAGCTGCGCCAGCCGG
TCGTACCGCTCAGGGCGGATGTCGCCGGTCCGCCACCCGCGTACCGCCCGATCGGACACCTGTATGACCGCGGCGACGTC Clone Rv152
:::::::::::::Rv152SP6.seq:::::::::::::
CGCGGCGGCGCATTACCCCCGCTACCGTCAGCAGCTTGACGGCGGTAGCGAACACCGCCGGATGCAGCGCAGGTGCGTCTATGTGCACACGGAATCGCCCCG
GCACCGCGATCTCGAGGATCACCAGTGCCCGCCCCCTG :::::::::::::Rv152T7.seq:::::::::::::
GGGATCGAGGAACAGCGCGTTGAACTGATAGGTGCGGCCCGGCTCGAGCAGGCCGGCCATTTGTTCGATGCGGTTACCGAAGATCTCTTCGGTGACCTGCCC
GCCGCCGGCCAGCTCGGCCCAGTGCCCGGCGTTGGCCGCCGCGGCGACGATCTTGGCGTCCACGGTGGTCGGGGTCATGCCCGCGAGCAGGATCGGCGAGCG
GCCGGTCAGCCGGGTGAACTTCGTCGAGAGCTTGACCCTGCCGTCGGGGAGGCGAACCACGGTCGGTGCGTATCTCGACCAGGCCCGGGCAACCTCGGGGGT
GGCGCCGACGGTGAACAGGTTGCGCTGGCCACCGCGGGTAGCCGCCGGCACTATGCCGATGCCCAGGCCGCGGATCACCGGTGCGGTCAGTCGGGTCAGGAT
GTCGCCCGGCCCCAGGTCGAAGATCCAGCGGGCGCCGGCCGCGTGGACACNGGTGATCTCGTCCACCATCGACTTTCTGATCA Clone Rv153
:::::::::::::Rv153SP6.seq:::::::::::::
TAACTCAAGGCTTGCGTTGAGGCCCCAGGCCCATCGACGGTTTGGCGGCCTTAAATGACATGAGGTCGTCAATTGACCCCACAGCGGAAATGCCGACTATTC
GCAGGCCTCCTTCGCCTTGGCTGCCGGAGAGGGGCTCCGCGGGAACCGCATGCAGGTATATGACCTCGGTTTCTCGGGTGCTACCGCGTGCCTTGTCGAGGA
TGAACTCGGCGTTGGAATTGTCCAGCCGGCCCAATTCATCGAGCGCAGATTCGTACACATGGCCGGCGGCGACATACGCTTCACCGTGGATCTGCTCCACAC
GGACCGCCCTGTCGGGATCCTGCTCACGGGTAAAGGAACTTACNTGGCNCTCGGTGCC :::::::::::::Rv153T7.seq:::::::::::::
CCTTCTGCGCCACCCACACCGTCAACGCCCGCGAAGTCGACGTCGTCCAGGCCATCGGCGGCCTCACGGATGGATTCGGCGCGGACGTGGTGATCGACGCCG
TCGGCCGACCGGAAACCTACCAGCAGGCCTTCTACGCCCGCGATCTCGCCGGAACCGTTGTGCTGGTGGGTGTGCCGACGCCCGACATGCGCCTGGACATGC TABLE 3-continued End sequences of the polynucleotide inserts cloned in the named recombinant BAC vectors contained in the I-1945 *M. tuberculosis* H37Rv genomic DNA library.

CGCTGGTCGACTTCTTCTCTCACGGCGGTGCGCTGAAGTCGTCGTGGTACGGCGATTGCCTGCCCGAAAGCGACTTCCCCACGCTGATCGACCTTGACCTGC
ATGGCCGGCTGCCGCTGCAGCGGTTCGTTTCCGAACGCATCGGGCTCGAAGACGTCGAGGAGGCGTTCCACAAGATGCATGGCGGCAAGGTATTGCGTTCGG
TGGTGATGTTGTGATGGCCGCCATCGAGCGCGTCATCACCCACGG

Clone Rv154
::::::::::::Rv154SP6.seq::::::::::::
ATACTCAAGCTTGATTTTGATCATCATGATGATCATCACCCGAAGTGTGGTAGCCGCAGTGGTTATCGTGGGTACCGTCGTGCTTTCCATGGGCGCCTCTTT
CGGGCTTTCCGTATTGGTCTGGCAGGACATTCTGGGTATCGAGTTGTACTGGATGGTGTTGGCGATGTCGGTGATCCTGCTCCTGGCGGTGGGATCCGACTA
CAATCTGCTGCTGATTTCCCGGTTGAAAAAAGAAATTGGGGCCGGATTGAACACCGGAATTATCCGTGCCATGGCTGGTACCGGGGGAGTGGTTACCGCTGC
CGGCATGGTGTTCGCCGTTACCA ::::::::::::Rv154T7.seq::::::::::::
ATTGNCTTTCGGCGCCATCGGTGAGGACGGCGTGCGGGTGCTCAACGACGACGTCGTCCGCGGGACACACCTCGATGCTGCCGCCATGGACGCGGTCGAACG
CAAGCAGCTGATCGAGCTACAACGCCGCGCGGAACGCTTCCGCCGCGGGCGTGACCGCATCCCGTTGACCGGGCGGATCGCGGTGATCGTCGATGACGGCAT
CGCCACCGGAGCGACGGCCAAGGCGGCGTGCCAGGTCGCCCGGGCGCACGGTGCGGACAAGGTGGTGCTGGCGGTCCCGATCGGCCCAGACGACATCGTGGC
GAGATTCGCCGGGTACGCCGATGAGGTGGTGTGTTTGGCGACGCCGGCGTTGTTCTTCGCCGTCGGGCAGGGTTACCGCAACTTCACCCAGACCTCCGACGA
AGAAGTGGTGGCGTTTTCTGGATCGTGCTC Clone Rv155
::::::::::::Rv155SP6.seq::::::::::::
ATACTCAAGCTTTTCCCGTCCGTCATCGCCCAAGCGCGTGAGGCCGAAGCGGCTGGTTACGACTCCCTGTTTGTGATGGACCACTTCTACCAACTGCCCATG
TTGGGGACGCCCGACCAGCCGATGCTGGAGGCCTACACGGCCCTTGGTGCGCTGGCCACGGCGACCGAGCGGCTGCAACTGGGCGCGTTGGTGACCGGCAAT
ACCTACCGCAGCCCGACCCTGCTGGCAAAGATCATCACCACGCTCGACGTGGTTAGCGCCGGTCGAGCGATCCTCGGCATTGGAGCCGGTTGGTTTGAGCTG
GAACACCGCCAGCTCGGCTTCGAGTTCGGCACTTTCAGTGACCGGTTCAACCGGCTCGAANAGGCGCTACAGATCCTCGAGCCAATGGTCAAGGGTGAGCGC
CAACGTTTTTCGGCGATTGGTACCCACCGA ::::::::::::Rv155T7.seq::::::::::::
CGGCCACCGGGGCCACTCCGCACAATCTGTACCCGACCAAGATCTACACCATCGAATACGACGGCGTCGCCGACTTTCCGCGGTACCCGCTCAACTTTGTGT
GTCCCACGCGACCCTCAACGCCATTGCCGGCACCTACTACGTGCACTCCAACTACTTCATCCTGACGCCGGAACAAATTGACGCAGCGGTTCCGCTGACCAA
TACGGTCGATGACCCAGTACTACATCATTCGCACGGAGAACCTGCCGCTGCTAGAGCCACTGCGATCGGTGCCGATCGTGGGGAACCCACTGGCGAACCTGG
TTCAACCAAACTTGAAGGTGATTGTTAACCTGGGCTACGGCGACCCGGCCTATGGTTATTCGACCTCGCCGCCCAATGTTGCGACTCCGTTCGGGTTGTTCC
CAGAGGTCAGCCCGGTCGTCATCGCCGACGCTCTCGTCGCCGGGACCAGCAGGGAATCGGCGATTTCGCCTACA Clone Rv156
::::::::::::Rv156SP6.seq::::::::::::
ATACTCAAGCTTGGGGTGGCGCTGTCGGTCGGTGTGCTTGGCGGCGTCGGTATCAACACCGCCCACGAAATGGGGCACAAGAAGGATTCGCTGGAGCGGTGG
CTGTCCAAAATCACCCTCGCCCAGACCTGCTACGGGCACTTCTACATCGAGCACAACCGTGGCCATCACNTCCGGGTGTCCACACCGGAGGACCCGGCGTCG
GCGCGGTTCGGCGAAACGTTGTGGGAGTTCCTGCCCCGCAGTGTTATCGGCGGCTTGCGCTCGGCCGTTCATTTGGAGGCCCAACGGCTGCGTCGGCTCGGC
GTCAGCCCCTGGAATCCCATGACGTATCTGCGCAACGACGTGCNCAACNCGTGGCTGATGTCNGTGGTGTTGTGGGGTGGGC ::::::::::::Rv156T7.seq::::::::::::
TCGCCACCGCACCGCGGCGAACGCTCAAAGGCACCTACTGGCACCAAGGCCCCACACGTCACCCTGTGACCTCCTGCGCCGACCCCGCCCGAGGTCCTGGCC
GTTACCACCGAACGGGCGAGCCGGGAGTCTGGTACGCATCGAACAAAGAGCAAGGTGCATGGGCGGAGTTGTTCCGCCACTTCGTCGATGACGGGGTCGATC
CATTCGAGGTCCGTCGCCGCGTCGGTCGAGTGGCGGTCACACTCCAGGTACTCGACCTCACAGACGAGAGGACTCGATCCCATCTAGGTGTGGACGAAACAG
ATCTTCTGTCCGACGACTACACCACCACCCAGGCCATCGCCGCCGCCCGCGATGCCAACTTCGACGCCGTACTGGCCCCGGCGGCGGCGCTCCCCGGTTGTC
AAACACTTTGCCGTGTTCGTTCACGCACTGCCCAACATCGAGCCCGA Clone Rv157
::::::::::::Rv157SP6.seq::::::::::::
ATGAAATAAGAAGAGCACATCCCTCAGTCGGTTATCATCACTAGCGCTCGCCGCACCCGTGTAACCGATCATAGCGAGCGAACTGGCGAGGAAGCAAAGAAT
ATCTGTTCTGTCAGATAGCTCTTACGCTCAGCGCAAGAAGAAATATCCCCCGCGGGAACAACTCCAGGTAGAGGTACACACGCGGATAGCCAATTCAGAGTA
ATAAACTGTGACACTCACACCCTCATCAATGATGACGAACTACACCCCGATATCCGGTCACATGACGAAGGGAAAGAGAAGGATATCATCTGTGACAAACTG
CCCTCAAATTTGGCTTCCTTAA Clone Rv159
::::::::::::Rv159SP6.seq::::::::::::
ATACTCAAGCTTGTCGAACTCCTTCTTGAATACCGGCCGGCCATCCACAGATGCCCGGAAGAACTTCCAGGTACCCATGGCGGCTGGATCAGGGGGCGGCAC
AGTTGGTCTTGTCCTGCCTCGAGTGGCGTCGTTGTCCGGCTTGGACGGGGCTCCGACGGTACCGGAGGGCAGCGACAAAACACTTATGCACTTGGGCGACCC
GCCGAGACGGTGCGACACCCATCCCGACGGCACAAGCTCAGCCGCGGCCGCTCTTGTTCTTCGTCGGATCGACATTCACCCACTTCTGACCGGGCTTGGGCG
AAGGAAGCAGAA ::::::::::::Rv159T7.seq::::::::::::
GGTATAGTCGCTGACCGGTGCAGGTTTCGACAATGTGGTGCCGGTTCGGCGGCTACGTGCCATCGAGACACTGGCGCAGGCTATCGCACCCGTTATCGGCTA
CGAGCAAATCGCGGTATGCGTTCTTGAGCATGAGTCGGCGACCGTCGTCATGGTCGACACCCACGACGGAAAGACGCAGATCGCCGTCAAGCATGTGTGCCG
CGGATTATCAGGACTGACCTCCTGGCTGACCGGCATGTTTGGTCGCGATGCCTGGCGCCCGGCCGGCGTGGTCGTGGTCGGCTCGGATAGCGAGGTCAGCGA
ATTCTCGTGGCAGCTCGAAAGGGTCCTGCCGGTGCCGGTCTTTGCGCAAACGATGGCGCAGGTTACGGTCGCGCGGGGTGCGGCCCTGGCGGCGGCCCA Clone Rv15
::::::::::::Rv15SP6D2.seq::::::::::::
GACACTATATNATACTCAAGCTTCAGGTCAATGTGCGCCAAGCCCTGACGCTGGCCGACCAGGCCACCGCCGCCGGANCCCTNTCTAGA ::::::::::::Rv15T7.seq::::::::::::
CTGTAGCCACCTGTTGCCATCCCCGTCATGCCCGACTCTGGTCATCTCGGATCCGCTGACACCCCGCTAAGGCTGCTCCTCTCGGTGCATTACCTCACCGAC
GGCGAACNCCCCCAGCTTTACGACTATCCGGATGACGGCACCTGGTTGCCGGCTAACTTCACCGTCAGCTTGGACGGCGGCGCTACCGTCGATGGCGCCAGC
GGGGCGATGGCCGGGCCCGGCGACCGATTCGTCNTCANCCTGTCGCGTGAACTTGCCGACGTCATCGTGGTCGGTGTGGGCACCGTGCGCATTGAGGGCTAC
TCCGGCGTCCGGATGGGTGTCGTCAAGCGCCCGCACCGGCAGGCCCGA TABLE 3-continued End sequences of the polynucleotide inserts cloned in the named recombinant BAC vectors contained in the I-1945 *M. tuberculosis* H37Rv genomic DNA library.

Clone Rv160
::::::::::::Rv160SP6.seq::::::::::::
ATACTCAAGCTTCGCACGCTCGGCGCGCGCGGTACCGCCCAGGTCGCCCAACAGATCGTCGATGTTCGCGTCGTCCGCCTCGCGCACGTGGTCTGTCACCAG
TCAACGTTAACGCCGCCGCACATGTCCTGCGGCCGGGCAAAAACGTGAAAAACGAGCGGGCGACTGCNATGTCATGACACCGACGGCCGCCGATGGGCCCAG
GGTCTGGCAAATTCGATCTGTGCGGCCAGTGCCAGCAGCGTCGCCTCGTCATACGGCCGGCCGACGAGTTGAACCGACATGGGCAGGCCGTCGCCGTCGAAG
TCCCACGGCACCACGGGCGCGGGCTGGCCGGTCAGATTCCAAAATTGAAAGTACGGAACCGCTGCACCACCAA ::::::::::::Rv160T7.seq::::::::::::
ATCGTTTCGACCAGGCGCTCCATCCGGCGAGTGGATACTCCCAGCAGGTAGCAGGTCGCCACCACGCTGGTCAGTGCGCGTTCAGCTCGCTTGCGGCGCTGC
AGCAGCCAGTCCGGGAAATAGCTGCCCTGGCGCAGCTTGGGGATCGCGACGTCGATGGTTGCGGCACGGGTGTCGAAATCACGGTGGCGGTAGCCGTTGCGC
TGATTGGACCGCTCATCGCTGCGTTCGCGGTAGCCCGCCCCGCACAGGGCGTCGGCTTCAGCCCCCATCAAGGCGGCGATGAACGTCGAGAGCAGCCCGCGC
AGCAGATCCGGGCTCGCCTGTGCGAGTTGGTCAGCCAGAAGCTGCTCGGTGTCGATAAGATGANAAGAAGTCATTGCGTTATTTCCT Clone Rv161
::::::::::::Rv161SP6.seq::::::::::::
ATACTCAAGCTTGGGTGTTGCCGATCACCGGAAGCCGCATGATCAGCCACGTTTCGCGCCGCCCGGCATACGGCGGCGTACCGATCTCCGCGTCATACACCC
GCGGGTAATCGCCGACGGTGCCGGTTCGCGAGCCGAAGGTGACGACGCTGATTGAATCGAGTTCCAGGTCCAGCGGGTGGCGCAGCAACGGCGCGAGCTCAA
CNACGTCAATCACGTTGTCGCTTTCTACGGTCACCGACCCGGTGACCGTAGTCGCCCGGTGCGCTCGGCCGAGAAGTTGCACCGCCACCACCGCGACAACGT
CTTGCACGCGGACGCCACCCCCCGGAT ::::::::::::Rv161T7.seq::::::::::::
GCGCNAACAGCTCGCGGCAGCCCACGACGTGCTGCGTCGGATTGCCGGCGGCGAGATCAATTCCAGGCAGCTCCCGGACAATGCGGCTCTGCTGGCCCGCAA
CGAAGGACTCGAGGTCACCCCGGTGCCCGGGGTCGTGGTGCACCTGCCGATCGCACAGGTTGGCCCACAACCGGCCGCTTGATGCCCGGTCGGCAAGCCCGG
CAGTTGCCAAACCCAGCGTGATCAGGCTCGGCTCGCGAGTTCGGCGAAAAAGTGGCTCGCCTGATCACCTACCATCGGCCAGGATCTGCGTGTCATCACGAC
GCTCGCCAAGGAGGTTGTTGTGGTGCTATCGACGGCCTTTAGCCAGATGTTCGGAATCGACTATCCGATAGTGTCCGCGCCAATGGACTTGATCGCCGGCGG
TGAGCTGGCTGCCGCNGT Clone Rv162
::::::::::::Rv162SP6.seq::::::::::::
ATACTCAAGCTTTCTCCGATACCCGCCATGTCGCGCACATCCAGGACTTCTGGGGGGATCCGCTGACAGCGGCGGGATCCCAAAGTGCGGATGATCGGGCCG
CCTACGTCGTGGTGTACCTCGTCGGTAACAACGAAACCGAAGCGTATGACTCGGTCCACGCGGTGCGGCACATGGTGGACACCACACCGCCACCGCACGGGG
TGAAGGCCTATGTCACCGGTCCGGCAGCACTCAATGCCGACCAGGCCGAGGCCGGAAACAAAAGTATCGCTAAGGTCACCGCGATCACGAACATGGTGATCG
CAGCAATGTTGCTAGTGATCTATCGCTCCG ::::::::::::Rv162T7.seq::::::::::::
CCATGAGCACCGCCAGCCGAGCACGAGGCCAAACTCCGCCGACGCAGGCCGGTTGGACTTGTCGTGCTGGACAAGGGGTTTAGCCGCCGAAGCAGTGACGTA
CATCGGCGAAGAGCAGTTCGCCTGTCGACCGACGGCGCAAACCGTGAGGCTAGGGAAGCGAGGAGCACATGGCCGCCGACCCGCAATGTACACGCTGCAAGC
AAACCATCGAACCCGGATGGCTATACATCACCGCCCATCGCCGCGGTCAAGCCGGGATCGTCGATGACGGCGCAGTACTGATTCACGTGCCCGGTGAATGCC
GCACCCCGGGGAGCACTTTCCGCCAAAACTAACCGGTTGG Clone Rv163
::::::::::::Rv163SP6.seq::::::::::::
CGGGTGTCATTGGCCACCGGCGGCGGCTGTCCGGGAAATGGCGGGTCCCCGGTGGTTTTGCTGAGGAGTGCTGAACCGTAGTCGAAGTGGGCGGCGTCAGAC
TCCACCCAGCCAGCAGGCAGCGCGAANCTGAATCCTCCAACCGGGTTGTCNATCCGGACAGGTTGGGGTGCGTTTGGGGCAATNACAGGTGGCGGCGGTGCG
TTCGGGTCGGCCGGCGGAGGTGCTGCNTTGGGATCCCCGGCTGGGCATTCGGCNTGTTGGCGGCGGCCGGTGGTGGGGGGGGCAACACGTGTCNCCGGTGCG
GGTGGCCCT ::::::::::::Rv163T7.seq::::::::::::
CCAAGATCTACACCATCGAATACGACGGCGTCGCCGACTTTCCGCGGTACCCGCTCAACTTTGTGTCGACCCTCAACGCCATTGCCGGCACCTACTACGTGC
ACTCCAACTACTTCATCCTGACGCCGGAACAANTTGACGCAGCGGTTCCGCTGACCAATACGGTCGGTCCCACGATGACCCAGTACTACATCATTCGCACGG
AGAACCTGCCGCTGCTAGAGCCACTGCGATCGGTGCCGATCGTGGGGANACCCACTGGCGAACCTGGGTTCAACCAAACTTGAAGGTGATTGTTAACCTGGG
CTACGGCGACCCGGCCTATGGTTATTCGACCTCGCCGCCCAAATGTTG Clone Rv164
::::::::::::Rv164SP6.seq::::::::::::
AGCTTCCCGAGTTCGGCTTTGGATCAAGACCCCAGTCCGCGGGCGCGATCCGGCNGCTCGGTGACTACATCAAGCCACAAATCGACGGCTTTCGGGGTGCCG
ATACCGATGACGTGGCGGATGTCGAGTGTTGAGTTCTCGGCGGGGCGGATGCTCACCTGGCGATCACCTGCCTCTCGTTGACGATCGATCGTCTATGCCGCC
GTCTCTGCGGGAACAGGCCNCCAGTACATCGCCACAGACGGGATCCACCCGCATTTCGGCTACGGTTGCTCGTTTCGGTGTTCGGACTAGTCGGTCCTGGTG
ACGTGCCGGTGATGCGGACCGGTCCTAGCACTGACCAATGGCCAAAATGCGGGC ::::::::::::Rv164T7.seq::::::::::::
CGGGGGGCCTCTTAATAGTGTAGGAAAGAAGCTCTACATATTCAGGAGGATTCACCATGGCTCGTGCGGTCGGGATCGACCTCGGGACCACCAACTCCGTCG
TCTCGGTTCTGGAAGGTGGCGACCCGGTCGTCGTCGCCAACTCCGAGGGCTCCAGGACCACCCCGTCAATTGTCGCGTTCGCCCGCAACGGTGAGGTGCTGG
TCTGCCAGCCCGCCAAGAACCAGGCAGTGACCAACGTCGATCGCACCGTGCGCTCGGTCAAGCGACACATGGGCAGCGACTGGTCCATAGAGATTGACGGCA
AGAAATACACCGCGCCGGAGATCAGCGCCCGCATTCTGATGAAGCTGAAGCGCGACGCCGAGGCCTACCTCGGTGAGGACATTACCGACGCGGTTATCACGA
CGCCCGCCTACTTCAATGACGCCCAGCGTCAGGCCACCAAGGACCCGGCCAGATCGCCGGTCTCACGTGCTGCGG Clone Rv165
::::::::::::Rv165SP6.seq::::::::::::
ATACTCAAGCTTCATAACAGGCCTGTTGTGGGCGCACCCGGCTCGCCGAGTTCTGCACGCACCGCCTCAAGTGCGGCCCGCACCGCCGGCATCTCCCGGTCA
CGCAGGGCCGCGGCCCGCGCCGCAGCGACGGCGTGTTCGCGCAGTTCGCCGTCAATGATGCTGACCTGATCGGCCACCCGGGCGTTCTCGGCGTCTTCGCGT
TCACTAATCGCGGTGCTCAGCAGCGTCTCGACAGCCACCACCCGAGTGGCGACCAGCTGCTCCACCACGGACCGCAGCGATGCCGTCACCTCACCCGTCCAG
CGGTCCACCACGACACGGTCGTGCACCAGCGCGCGGGCATTCACCACCCAGGCGGTCACCGCCAGGCCGATCGCCACACCCGCCACCATCCCCGATGCAGCC
AGGCCGGGAGTAAGA TABLE 3-continued End sequences of the polynucleotide inserts cloned in the named recombinant
BAC vectors contained in the I-1945 *M. tuberculosis* H37Rv genomic DNA library.

::::::::::::Rv165T7.seq:::::::::::::
CTGGTGCTGGACGGAGCCTAGTACAACTTCCTCTCCAATGCTCTTGCCCCGATCGCGGCGACCAGGATGACCCAGGACATCCTGCCGCCCGAAGTACTGGAA
AAGCTCACACCCGAGTTCGTCGCACCGGTGGTGGCCTACCTGTGCACCGAGGAGTGTGCCGACAACCCATCGGTGTACGTCGTCAGTGGTGGTTAGGTGCAG
CGAGTTGCGCTGTTTGGCAACGACGGCGCCAACTTCGACAAACCGCCGTCNGTACAAGATGTTGCGGCGCGGTGGGCCGAGATCNCCGATCTGTCCGGTGCG
AAAATTGCTGGATTCAAGTTGTAGAACTAAAT Clone Rv166
:::::::::::::Rv166SP6.seq:::::::::::::
ATACTCAAGCTTTTCCGGCGTCGTCCACCTGACCCAAAAAGCGCAGGTGCGCCGCCAAACGGCCCGCCTGGCCGCGCAACTGGTCGGCGTCGCCGTGGCCGA
CAATCAGTAGCTGGACATCCGGAAACCGCTGCACCACCTTCGGCAGCGCGTCAAGCAAAAACGGCCATTCC :::::::::::::Rv166T7.seq:::::::::::::
TTTCAGATCTCATTTTTATGACATGACTGGAGATCTGTCTAGATTGCAGCTCCTGTGAGCGTGGGTACCGGATTCAAGCCGGTCGGTCACGCCGCGGTGGTA
CCGGCTTTGCGGCAGTGCTCGGCCTCGAGTTCGGCGATCGCGCGCGAAGTGCGTTTCGCGCACCAAGATCGCGGCCTAATGGCCGGCGATGACCGCGATGAC
CAGCGCGATCCAGGAAAAACCGTTCCAACCAGTGCTGGGCGGCCATCCCCG Clone Rv167
:::::::::::::Rv167SP6.seq:::::::::::::
ATACTCAAGCTTCCCGACCACAAGTTGAACAGCACCGATTTCGGCGAGCACTTCGTCAACTTCCAGGGTGCCCGCACCAAGTATTTCGACAAGTATTTCCGT
CGGGCCGCCGCCGCCGGCGCGCGGCAGGTGGTCATCCTGGCGGCGGGGCTGGACTCCCGCGCGTACCGGCTGCCTTGGCCCGACGGGACCACGGTTTTTGAG
CTGGACCGCCCGCAGGTCCTTGATTTCAAGCGCGAGGTGCTCGCCAGCCACGGTGCCCAACCGCGCGCCCTGCGCCCGCGA :::::::::::::Rv167T7.seq:::::::::::::
GTGTGCTGTCAATTCAGAGCTGAGCCTGATGCACTCAACTTACTGAGCATGCTAACGCTGGTCGTGCGGGTCTTGTTCCCGCGTGTCGGCAGGGCACACGCT
CGGGGCGTAGCTGGGAGAGGCCCCGGTCAAGCCCGGAGAGCAGTGCTCAGTCCGCCAGCTTGACCGACTTTCGATGAGAACGCGCTTCTCGCCGTATTGAAC
TGGCGTGCTGACGGTCGCTGAGCAGCGCTCGCCGAGTGCGGCCGCTGATTCTTTCATCGAGCCAGGAGGCGCATTCGTGTTCGGCCGCCTGCGGGTCGGCCC
CATCGTCGACGCGATCCGTCACCCACTCCTCGATCAGGTCTGCCTCATCGAACGGGCCAACGGTGCTGTCGGAGTATGTGTGCGTGGGCACGGCGAGCCGGG
TGCTGTGGTACACCCACCGTTGCATGACCAAGTTGACGCCTGACTGGCTGAGCACCGCGATCCGCTCACAGGTCGGAACGTTGGTG Clone Rv169
:::::::::::::Rv169SP6.seq:::::::::::::
ATACTCAAGCTTTTGGTCTAGCCGGCCGAGCCCGATACAGGTGTCATTGGCCACCGGCGGCGGCTGTCCGGGAAATGGCGGGTCCCCGGTGGTTTTGCTGAG
GAGTGCTGAACCGTATGCGAAGTGGGCGGCGTCAGACTCCACCCAGCCAGCAGGCAGCGCGAAACTGAATCCTCCAACCGGGTTGTCGATCCGGACAGGTTG
GGGTGCGTTTGGGGCAATGACAGGTGGCGGCGGTGCGTCCGGGTCGGCCGGCGGAAGTGCTGCGTTGGGATCGCCCGGCTGGGCATTCTGCGTGTTGGCGGC
GGCCGGTGGTGGGGGGGCAACAGGTGTCTCCGGTGCGGGTGGCGCTGCACC :::::::::::::Rv169T7.seq:::::::::::::
GGGGCCACTCCGCACAATCTGTACCCGACCAAGATCTACACCATCGAATACGACGGCGTCGCCGACTTTCCGCGGTACCCGCTCAACTTTGTGTCGACCCTC
AACGCCATTGCCGGCACCTACTACGTGCACTCCAACTACTTCATCCTGACGCCGGAACAAATTGACGCAGCGGTTCCGCTGACCAATACGGTCGGTCCCACG
ATGACCCAGTACTACATCATTCGCACGGAGAACCTGCCGCTGCTAGAGCCACTGCGATCGGTGCCGATCGTGGGGAACCCACTGGCGAACCTGGTTCAACCA
AACTTGAAGGTGATTGTTAACCTGGGCTACGGCGACCCGGCCTATGGTTATTCGACCTCGCCGCCCAATGTTGCGACTCCGTTCGGGTTGTTCCCAGAGGTC
AGCCCGGTCGTCATCGCCGACGCTCTCGTCGCCGGGACCCAGCACGGAAT Clone Rv16
:::::::::::::Rv16SP6.seq:::::::::::::
TTCTNTCTTCCCNNATTCGTNNNTCTCNTACTACCNGGGCCNCAAAACACCTTGGCNAACGCTCAAAGGCGNTACNGGCACCAAGGCCCCACACGTCACCCT
GTGACCTCCTGCGCCGACCCCGCCCGAGGTCCTGGCCGTTACCACTGAACGGGCGAGCCGGGAGTCTGGTACGCATCGAACAAAGAGCAAGGTGCATGGGCG
GAGTTGTTCCGCCNCTTTTTTTATGACGGGGTCGATCCATTCGAGGTCCGTCGCCGCGTCGGTCGAGTGGCGGTCACACTCCAGGTACTCGACCTCNCAGAC
GAGAGGACTCGATCCCATCTANGTGTGGACNAAACAGATCTTCTGTCCGACGACTACACACCACCCAGGCCATCGCCGCCGCCCGCGATGCCAACTTCNACN
CCGTNCTGGCCCCGGCGGCGGCGCTCCCCGGTTGTCAAACACCTGCCGTGTTCGTTCACNCACTGCCCAACATCNAGCCCGANCNATCCNAGGTCCGTCCAA
CGCCTCCGCGGCTCNCCAACCTNCTCCCNCTGATCNTCCGCACCAAACACATGCCCGACTCCNTGCNCCNATTGCTTGNATCCCT :::::::::::::Rv16T7.seq:::::::::::::
CCGCTATCGGTCGGTGTGCTTGGCGGCGTCGGTATCAACACCGCCCACGAAATGGGGCACAAGAAGGATTCGCTGGAGCGGTGGCTGTCCAAGATCACCCTC
GCCCAGACCTGCTACGGGCACTTCTACATCGAGCACAACCGTGGCCATCACGTCCGGGTGTCCACACCGGAGGACCCGGCGTCGGCGCGGTTCGGCGAGACG
TTGTGGGAGTTCCTGCCCCGCAGTGTTATCGGCGGCTTGCGCTCGGCCGTCTTCATTTGGAGGCCCAACGGCTGCGTCGGCTCGGCGTCAGCCCCTGGAATCCC
ATGACGTATCTGCGCAACGACGTGCTCAACGCGTGGCTGATGTCGGTGGTGTTGTGGGGTGGGCTGATCGCGGTCTTCGGCCCGGCGCTGATCCCGTTCGTC
ATCATCCAGGCAGTCTTCGGCTTCAG Clone Rv170
:::::::::::::Rv170SP6.seq:::::::::::::
ATACTCATGCTTGCCGAAGTTCCGATGGGTCGCGCCGGCGANCCCAGCGAAGTCGCTAGCGTGGCCGTGTTCTTGGCTTCGGATCTATCCTCGTACATGACC
GGCACCGTGTTGGACGTGACTGGCGGCCGGTTCATATGACACCGAGATCATTGCCACGGTACGGCAATTCGTCAAGAAGGAAATCTTTCCCAATGCACCGGC
CCTCGAACGTGGCAACAGCTACCCGCAAGAAATCGTCGATCGGCTGGGTGTTATTGGCTTGCTCGGTCGCCGGCTGCAAGGGTATCGACACCACCGAGTTCA
TTCTCCGGGCGTGCC :::::::::::::Rv170T7.seq:::::::::::::
GGCGTCAACGGTGTCGGCACCGGCGTCCTGCAGTTGGTAGGCCTGCAGTTTGTGCATCAGGCCGATGCCGCGGCCCTCGTGGCCACGCATGTACAGCACCAC
GCCGCGCCCCTCACGGGCGACCATCGCCAGCGCGGCGTCCAGCTGAGGCCCGCAATCGCAGCGGCGTGACCCAAACACATCGCCGGTCAAGCACTCCGAATG
CACCCGGACCAGCACGTCGTCACCGTCGGCGTTGGGCCCGGCGATCTCGCCGCGGACCAGCGCGACATGTTCCACGTCCTCGTAGATGCTGGTGTAGCCGAT
GGCGCGAATCTCCCATGACGAGTCGGAATCCGCGCCTCGGCG Clone Rv171
:::::::::::::Rv171SP6.seq:::::::::::::
ATACTCAAGCTTCGGCCTCGCTGCAGGAGTGGGAGCCGCAGGGCTGGAAATCCGAAAAACGAGCCGGTGATCGCACTGTCGCCGATCGGGGCCGCACCTGGT
TGGTGTTACCGATGAATCCGCACCCAAAATGTGGCTGCGGTGGCGTTTCTTGACTCCTTGGCGTCGACTCTTGTGGCAGCCACCGAGCGGTTGGTCCAGGAT TABLE 3-continued End sequences of the polynucleotide inserts cloned in the named recombinant BAC vectors contained in the I-1945 *M. tuberculosis* H37Rv genomic DNA library.

CTGGATGGGCAAAGTTGTGCGGCCCGGCCGGTGACGGCCGATGAGCTGACCGAGGTCGACAGCGCCGTGTTGGCTGACTTGGAACCGACATGGATTCGCCCC
GGTTGGCGTCACCTCAAGCATTTCAATGGTTAT

::::::::::::Rv171T7.seq::::::::::::
ATGCGTCACCCCGATGCGCCCAGATCGGGGCTTCGCAAATAAAGCACGAACAGGCGGGCAAAACGTCTATCTCGGAGCCGGAAGGGCAATCAGCCGACCGTC
GACGAACGACACCGGCGATAACCACTTAGGCGTTGAACGGCCGGCCCAAACATTACGCCTCCGTTGATAAGGCTTTCGGTCTCTTCCCCGGTCATCCCAAGC
ACCTTGCGGCAAATTTGAACGCTTTCCTGTCCGGGCACCGGCCCCGGGCTTTGGGGTCCNTCCGA Clone Rv172
::::::::::::Rv172SP6.seq::::::::::::
ATACTCAAGCTTCAATCGCGCCGCCACAATCCAAATATGCGTCTAGCGTCTCGATGAGCGTCGGTCCGGCATCGGCTAGGGGCCGCATCACGTCGGTATGCA
GGGCCACGATCGCCCAAGGCGTCGAAAATCAAGGGCGCGTTCGGGCAAAAATTCCCCTATCCAGCACGGGCCGCGGCGCTCCGCNCCAGCCGGCGACGGCGT
TCATCCCGGAGATCGCCTCGCTAGCGCTGCGGTGCGCCGCGGTCAGCATGGGCGCCGTGGGGCCGATGACCACCGGGGCGT ::::::::::::Rv172T7.seq::::::::::::
TTCGGCGGGTCTGTAGATTGCGGTCGGCCACCCCACAGGCACTCATGAACCGCAGCCCACGATCGATCTCGGTGG Clone Rv173
::::::::::::Rv173SP6.seq::::::::::::
GCGCACCATCGCCAGTAGGTGCCCGTGGTCGGGCGCGTCGAGCCACCCGAGCGGAAACGCGAGTCCGAACAGCAACAGCAGGACGGGCGCAACCAGGGCGGT
GACCATGCCCCCGGCGCTGAACATCAACCACAGGAAGGGCTCCGCCGAGCGTCCGCGCGACC ::::::::::::Rv173T7.seq::::::::::::
CATCGTCGAACTTCGGTCCGGGTTGNTAGNACCGCAGCACCAAACGCACCCACCGACCCCCACGCTTCACGCCAACCCTTTAGTTCATTGGCGTGAACAGCA
GCGTAGCCGGTTGCCCCGATATATGTGGAAAAATCGTTCGGACGTACAAAAAAAGTTCCTGACGCTGGCGTCAACTCGAAACTGCCTCGGAAGTCAATGATG
ATCCATCAGTCAATATTAAAGTCG Clone Rv174
::::::::::::Rv174SP6.seq::::::::::::
ATACTCAAGCTTGTCTGCTGCCTCAGCGTATGCATCCAACAGCGCATCGCGATCAACGATCAGGCGCGCCGATTTCGGGCCGCGGGCAGTGGCACTGGCCAG
ATGGCCGTTTTTTTCGAGAAACTTCAACGCCTGAGCGCTGCTTCCCATCGAGAGACCGGTGGCCTCTACAACCGATGCGACAGTTGGACCGGCGATGTTCGC
CAGCAGCGCTTCACATACGGCAAGTNTGGCGCGG ::::::::::::Rv174T7.seq::::::::::::
TTGTCCAGGCGGGGAATCGGGCAGGGAGACGACACCTTCGTTCGGTTCGATCGTCGCGAACGGGTAGTTGGCCGCGACCACGTTGTTTCGGGTCAGCGCGTT
GAAAAGTGTCGACTTGCCGACGTTGGGCAGGCCCACGATCCCCAGGCTCAAGCTCACAGA Clone Rv175
::::::::::::Rv175SP6.seq::::::::::::
ATACTCATGCTTGGCGCCTGGGTGGCAGCCCACCTGCCCACCACACGGACCGCGGTGCGGACGCGGCTGACGCGCCTGGTGGTCAGCATCGTGGCCGGTCTG
CTGTTGTATGCCAACTTCCCGCCGCGCAACTGCTGGTGGGCGGCGGTGGTTGCGCTCGCATTGCTGGCCTGGGTGCTGACCCNCCGCNCNACAACACCGGTG
GGTGGGCTGGGCTACGGCCTGCTATTCGGCCTGGTGTTCTACGTCTCGTTGTTGCCGTGGATCGGCGAGCTGGTGGGCCCCGGGCCCTGGTTGGCACTGGCG
ACGACGTNCGCGCTGTTCCCCGGCATCTTCGGTCTGTTCGCCGTCGTGGTACCCTGTTGCCGGGTTGGCCC ::::::::::::Rv175T7.seq::::::::::::
CGCCAATTCACGATATCGTTAACCGATATCCCGAGCCGATAGCTGGCGGGCTCGGGTGGTGGCCAGCGGCGCTGCGACGAAAGGTGTGACCGTCATGAAACA
GACACCACCGGCGGCCGTCGGCCGTCGTCACCTGCTCGAGATCTCAGCATCCGCAGCCGGTGTGATCGCGCTTTCGGCGTGTAGTGGGTCGCCGCCCGACCC
CGGCAAAGGCCGGCCCGACACAACCCCGGAACAGGAAGTCCCGGTCACCGCGCCCGAAGNACTTGATGCGCGAACNCGGAGTGCTCCAAACGCATCCTGCTG
AT Clone Rv176
::::::::::::Rv176SP6.seq::::::::::::
ATACTCAAGCTTGGGCACTGACTTCGGTACCCCCTCCGCCTTTGGCCAGCAGCAGCCACAGCGCGGTTCGCGGACCGAACGTGGACATCAATAGCCCGGAAT
CGGTGTGTGCAAGTTGGTAAACGGTGTTGATCCCAAGCTTTGCCAGCCTTTTCGTAGTCTTGGGCCCCACACCCCACAGTGCTTCGACGGTACGGTCACCCA
TGATGGCCATCCAGTTGGCATCGGTGAGCTGATAAATGCCAGCTGGTTTCGCCAACCCGGTAGCGATCTTGGCGCGCTGCTTGTTGTCACTGATACCTATCG
AGCAAGACAGCCCGGTTTGCGACAAAATGACTTTTCGGATCTCTTCGGCGACTTCGATGGGGTCGTCGGGA ::::::::::::Rv176T7.seq::::::::::::
AAAGTCCTGTGCCGGTTCGCTAAACACCCGGCGGACACTCAGACGGTGCTGGTGGTGCGGCATGGCACCGCGGGCAGCAAAGCGCACTTCTCCGGGGGACGA
CAGCAAGCGACCGCTAGACAAGAGGGGTCGTGCGCAGGCAGAAACGTTGGTACACAGCTGCTGGCGTTCGGCGCCACCGATGTTTATGCCGCCGACCGGGTG
CGCTGCCACCAGACGATGGAGCCACTCGCCGCGGAACTGAACGTGACCATACACA Clone Rv177
::::::::::::Rv177SP6.seq::::::::::::
ATACTCAAGCTTGGGTTCCACGCCCGCGCAGCCACGCCGTCACCTTTCCACGAGACCTCACCTGCCGATCCGAAATGGAATCGGCCGTGACGGAATTGGCGC
ACCGAACACCCAACGAGGTGGTGGCTTCGTCGCGAACCGTCACCCGAGTCGCGGCCACCGTGCGCACGGCGACGTTCTACACCCGCACCAAGATCCGAAAGC
TGCAAGCTCCCAGCACCGATCCCGACGTCATCACCGCTGCCGCCCGGCACGTCCTTGACCTATTCGAGCTGGATCGGCCCGTCCGGTTGCTGGGAGTGCGGT
TAGAACTGGCCTAGAACCGGCGGGCACACCGCNCCTGGGCGGGGCGAATTCTTGACCGCNCCGGCC ::::::::::::Rv177T7.seq::::::::::::
CGCGGTTGGCGTAGTTGGACGGGTCGCCCTCCGAGGCCAATGATGACGATGACCACGCCGATCACGATGGCCACCGAGAGGGACAACAACAGAAAGCTGACG
AATCCCTCCTTGGCGGCCGGGGCTTTGTGGTCGCCGGTCGCGATGGGCGCGAATTTACGGCCCGCTCCCCCAGGCCGCCGCGAAGCAGGGTCCCCAGCCAGT
TGGCGTAGGCGGAATTAACGATCAGCGCCACCGCGATAACCTGCCATGCCTCGGGCATATCGATGTGCGGCCAGAACAGGCCGAAC TABLE 3-continued End sequences of the polynucleotide inserts cloned in the named recombinant BAC vectors contained in the I-1945 *M. tuberculosis* H37Rv genomic DNA library.

Clone Rv178
:::::::::::::Rv178SP6.seq:::::::::::::
CCAACAAGAGCATCGGGACATACGGAGTCAACTACCCGGCCAACGGTGATTTCTTGGCCGCCGCTGACGGCGCGAACGACGCCAGCGACCACATTCAGCAGA
TGGCCAGCGCGTGCCGGGCCACGAGGTTGGTGCTCGGCGGCTACTCCCAGGGTGCGGCCGTGATCGACATCGTCACCGCCGCACCACTGCCCGGCCTCGGGT
TCACGCAGCCGTTGCCGCCCGCAGCGGACGATCACATCGCCGCGATCGCCCTGTTCGGGAATCCCTCGGGCCGCGCTGGCGGGCTGATGAGCGCCCTGACCC
CTCAATTCGGGTCCAAGACCATCANCCTCTGCAACAACGGCGACCCGATTTGTTCNGACGGCAACCGGTGGCGAGCGCACCTAGGCTACGTGCCCGGGATGA
CCAACCAGGCGGCGCGTTTCGTCGCGAGCAGGATCTAACCGCGAGCCGCCCATAGATTCCCG :::::::::::::Rv178T7.seq:::::::::::::
TAANACCCGTGTAATTTGGGATGGGCAAAAGGCCAAGCACCGCGTGGCCACGAACGCCGGGAGGGACAATCTCGGGCGGCTAGGGCTTCTCGCGGGAAGGC
CCGAACGTACGGCGTTTCAACACGTCGCGTCNCCCTCCGACCGCGAACATTCGGGGATGGCAGCAACCTGGTAGCNCCCTGGCCGGGCGATGATCTGCAGCG
TCGCCGCGGGTAGTCGCCGCCCGGGCGGCTACAGTCTGAAACGCGATGACCATCGATGTGTGGATGCAGCATCCGACGCAACGGTTCCTACACGGCGATATG
TTCGCCTCGCTGCGCCGGTGGACCGGTGGGTCTATCCCGGAGACCGACNTCCCGATCGAAGCGACCGTCTCCTCGATGGACGCCGGCGGCGTCACCCTGGGT
TTGCTCACCGCCTGGCGTGGCCCCAA Clone Rv179
:::::::::::::Rv179SP6.seq:::::::::::::
GTCCGCAAAAGACTCAGCGGCCGACTTTGCTCGCAGCTGGCGGTACCGCGCCACCGATTCGATGCCGTGGTCGCGGAAGAATGCCTCCCGAAATCGCACGGC
CGACTCCAGTTCGGCGAGCATCCGCGATGCCAGCTGCGGCTGCGCCCTGCCGGCCACGGCACCCACATGCGGCAGTTCGTCCACCTGGGCCAGCGCCCCGCC
GCCGAAGTCCAAACAATAGAACTGCACCCGGCCCGCATCGTGGGTAGCAGCCAACGCCATGATCAGCGTCCGCAGCGCGGTTGACTTGCCCGTTTGCGGTGC
ACCTACGACCGCGACATTGCCTGCGGCCCCGGACAAGTCGATCGTCAGCGGCACCCN :::::::::::::Rv179T7.seq:::::::::::::
CGTGGCCACGAACGCCGGGAGGGACANTCTCGGGCGGCTAGGGCTTCTCGCGGGAAGGCCCGAACGTACGGCGTTTCAACACGTCGCGTCGCCCTCCGACCG
CGAACATTCGGGGATGGCAGCAACCTGGCAGCTACCTGGCCGGGCGATGATCTGCAGCGTCGCCGCGGGTAGTCGCCGCCCGGGCGGCTACAGTCTGAAACG
CGATGACCATCGATGTGTGGATGCATCATCCGACGCAACGGTTCCTACACGGCGATATGTTCNCCTCGCTGCGCCGGTGGACCGGTGGGTCTATCCC Clone Rv17
:::::::::::::Rv17SP6.seq:::::::::::::
ATACTCAAGCTTTGCGGCGGGCGCCGAAATGTGAACGCACCAAACCCGCCCGCTGCGGGTCGGCGGGCCACTCGACCTCGAATTTCGCCGCCGTGACCATCC
AGCCCGACGGCAGTTGGGCACCCGGCCCCCCGGTCGCGGCATAACTGTTGGCGTCGCCGTCATAAAGCTCGAACAGCACCGAAACCGACTCCACCACCGGCC
GGTGCGCCTCAAAATCCACGCCGATCTCCACATACCGGGAAAACGTCGGTGTCCCATCGGGTTTCGGCTTGCCCGCCAGCTGCACACCACCGGTGGCCTCGG
CCACCTTCGCGGCCTGAGCGCAGCTACNCATCCTGACGATCATCACCCCGCCCCCGGCTCACGCTTGGCCTCCGTGACCGCACGCATCGCCCGGTTGCGCGC
ACCGCGACGCCCGTACAGCCGCGCGCAC :::::::::::::Rv17T7.seq:::::::::::::
AGCTTGCCGGGACTGCGGAACAGAAGCGGCGGTTCCTACCGCGGTGTGCGGCCGGCGCGATATCGGCCTTTTTACTAACCGAACCCGATGTGGGCTCCGATC
CGGCGCGCATGGCATCGACGGCGACGCCGATCGATGACGGCCAGGCTTACGAGCTTGAGGGTGTGAAGTTGTGGACCACCAACGGTGTGGTAGCGGACCTGC
TAGTGGTTATGGCGCGGGTACCGCGCAGTGAAGGGCACCGAGGGGGAATCAGCGCCTTTGTCGTCGAGGCTGATTCGCCCGGGATCACCGTGGAGCGGCGCA
ACAAGTTCATGGGACTGCGTGGCATCNAAAACGGCGTGACCCGGCTTCATCGCGTCNGGGTGCCCAAAGACAACTTGATCGGCA Clone Rv180
:::::::::::::Rv180SP6.seq:::::::::::::
CTCAAGCTTGGCGATGCGGGCTGGCCAAAACTGGCCGGGCGGGGGTTGGCTTGTTCAATCAAGGGTGGGTTGCCG :::::::::::::Rv180T7.seq:::::::::::::
CCGAAGGCCCGTTCCCGGGCGTTCAGCAAGCGATCGTCGGTTGGCCCACTGCGGGTCGAATCTTGCGGCCGCGCCGGTCGTGGAACGCCCAGGTCACCCGGC
GGCGTACC Clone Rv181
:::::::::::::Rv181SP6.seq:::::::::::::
ATACTCAAGCTTTTTTCTGCTCATGAAGGTTAGATGCCTGCTGCTTAAGTAATTCCTCTTTATCTGTAAAGGCTTTTTGAAGTGCATCACCTGACCGGGCAA
ATAGTTCACCGGGGTGAGAAAAAAGAGCAACAACTGATTTAGGCAATTTGGCGGTGTTGATACAGCGGGTAATAATCTTACGTGAAATATTTTCCGCATCAG
CCAGCGCAGAAATATTTCCAGCAAATTCATTCTGCAATCGGCTTGCATAACGCTGACCACGTTCATAAGCACTTGTTGGGCGATAATCGTTACCCAATCTGG
ATAATGCAGCCATCTGCTCATCATCCAGCTCGCCAACCAGAACACGATAATCACTTTCGGTAAGTGCAGCAGCTTTACGACGGCGACTCCCATCGGCAATTT
CTATGACACCAGATACTCTTCGACCGAACGCCGGTGTCTGTTGACCA Clone Rv182
:::::::::::::Rv182SP6.seq:::::::::::::
CTCAAGCTTGGTGCCGACATGGCCGGGCTGGAGCCCGCGTATGGCAAGGTTCCGCTCAATGTGGTTGTGATGCAGCAGGACTACGTTCGCCTCAATCAGCTC
AAACGTCACCCCCGTGGCGTGCTGCGCAGCATGAAGGTCGGCGCCCGCACGATGTGGGCGAAGGCAACAGGTAAAAACCTGGTCGGCATGGGTCGAGCCCTC
ATTGGGCCGTTGCGGATCGGGTTGCACCGCGCCGGAGTGCCGGTCGAACTCAACACCGCCTTCACCGATCTTTTCGTCAAAAATGGCGTCGTGTCCGGGGTA
TAC :::::::::::::Rv182T7.seq:::::::::::::
CCGAAGCGTGGGAAATCCTGACCGAATACCGCGACGTGCTGGACACTTTGGCCGGCGAGCTGCTGGAAAAGGAGACCCTGCACCGACCCGAGCTGGAAAGCA
TCTTCGCTGACGTCTAAAAGCGGCCGCGGCTCACCATGTTCGACGACTTCGGTGGCCGGATCCCGTCGGACAAACCGCCCATCAAGACACCCGGGGGAGATC
GCGATCGAAACGCGGCGAAACTTGGGCC :::::::::::::Rv183SP6.seq:::::::::::::
CGACTCGACAAGCATTCTTGACAGTTGTTTTGGCTCGGCATGGTTAGCCAAGGTTCTGCGGTCCCACCAGATCATCTTGGTCCGGTAGCGCTCGTCCGGGTA
TGCTGCCGCCGGGATTCTCGCTGCTATTACTCCCCCCGAAAAACGCCACCGGTCCAGCGCGTGGGCCGCCGCGGTCCCCATCACAAACTGAACCCCCAACAG
GGGACATGCTTAGCGGTAGGGCGCGCGCCAAGGCGGCAGCAATCGCATCACTGCGCTGCGCGTCACTATTAACCCACCCGGACTTCACTTCCACGACCCCGA
ATGGCGCCCGGTCATTGATCATCTTGCGCACCGCGGATAATCCGGGATTGCCAGCCCATTCGACTACCGCATGCGAGTCATCGGCTGACCGCAGCGGTCCGA
TTACCCGAGCGCCCCGANTACATCTCCTCCAATATCAATGGGCGCAA TABLE 3-continued End sequences of the polynucleotide inserts cloned in the named recombinant BAC vectors contained in the I-1945 *M. tuberculosis* H37Rv genomic DNA library.

Clone Rv183
:::::::::::::Rv183T7.seq:::::::::::::
GCGGTNTAGCTTCCCGTCGTACCGGCGACCGCCAGCCGAGAAGCTCGTTTTCCCAGTGTTGCTGGGGATTCTCACGCTGCTGCTGAGTGCGTGCCAGACCGC
TTCCGCTTCGGGTTACAACGAGCCGCGGGGCTACGATCGTGCGACGCTGAAGTTGGTGTTCTCCATGGACTTGGGGATGTGCCTGAACCGGTTCACCTACGA
CTCCAAGCTGGCGCCGTCTCGTCCGCAGGTCGTTGCTTGCGATAGCCGGGAGGCCCGGATCCGCAATGACGGATTCCATGCCAACGCTCCGAGTTGCATGCG
GATCGACTACGAATTGATCACCCAGAACCATCGGGCGTATTACTGCCTGAAGTACCTGGTGCGGGTCGGATACTGCTATCCGGCGGTGACGACCCCCGGCAA
GCCGCCATCCGTGCTGCTGT Clone Rv184
:::::::::::::Rv184SP6.seq:::::::::::::
CTCAAGCTTGGGCGTGACGGCCACCGGGGCCACTCCGCACAATCTGTACCCGACCAAGATCTACACCATCGAATACGACGGCGTCGCCGACTTTCCGCGGTA
CCCGCTCAACTTTGTGTCGACCCTCAACGCCATTGCCGGCACCTACTACGTGCACTCCAACTACTTCATCCTGACGCCGGAACAAATTGACGCAGCGGTTCC
GCTGACCAATACGGTCGGTCCCACGATGACCCAGTACTACATCATTCGCACGGAGAACCTGCCGCTGCTAAAGCCACTGCGATCGGTGCCGATCGTGGGGAA
CCCACTGGCGAACCTGGTTCAACCAAACTTGAAGGTGATTGTTAACCTGGGCTACGGCGACCCGGCCTATGGTTATTCC :::::::::::::Rv184T7.seq:::::::::::::
CGGGTGTCATTGGCCACCGGCGGCGGCTGTCCGGGAAATGGCGGGTCCCCGGTGGTTTTGCTGAGGAGTGCTGAACCGTAGTCGAAGTGGGCGGCGTCAGAC
TCCACCCAGCCAGCAGGCAGCGCGAAGCTGAATCCTCCAACCGGGTTGTCGATCCGGACAGGTTGGGGTGCGTTTGGGGCAATGACAGGTGGCGGCGGTGCG
TTCGGGTCGGCCGGCGGAGGTGCTGCGTTGGGATCGCCCGGCTGGGCATTCGGCGTGTTGGCGGCGGCCGGTGGTGGGGGGGCAACANGTGTCGCCGGTGCG
GGTGGCGCTGCA Clone Rv185
:::::::::::::Rv185SP6.seq:::::::::::::
NCTTGATATTGGCGTCAACGGTGTCGGCACCGGCGTCCTGCAGTTGGTAGGCCTGCAGTTTGTGCATCAGGCCGATGCCGCGGCCCTCGTGGCCACGCATGT
ACAGCACCACGCCGCGCCCCTCACGGGCGACCATCGCCAGCGCGGCGTCCAGCTGAGGCCCGCAATCGCAGCGGCGTGACCCAAACACATCGCCGGTCAAGC
ACTCCGAATGCACCCGGACCAGCACGTCGTCACCGTCGGCGTTGGGCCCGGCGATCTCGCCGCGGACCAGCGCGACATGTTCCACGTCCTCGTAGATGCTGG
TGTAGCCGATGGCGCGAAACTCCCCATGACGAGTCGGAATCCGCGCCTCGGCGACCCGCTCAATGTGCTTCTCGTGCTTGCGCCGCCATTCGATCAAGTCAG
CAATGGTGATCAGCGCCAGACCGTGCTCNTCGGCG :::::::::::::Rv185T7.seq:::::::::::::
CATAAGGGCCGGCGTACCCGGTACCGGCCGCGGGCCTACCACGTGCCGGAACTGGAAGCGCAGTAAGCCCTCAACGCGCCACCGCTTTGGCCCGCGCGCCCG
GCGTAGGCGCATCGGCGGTGGCCGTGGGGCGGCGCACTGCGACCTCACCAGCGGCTTTCGAGCTTTGTTCGATCAACCGGCCAGCATGGTCGAGGATGCATT
CGAGACCATATTCGAAATTGGTTTCATCGGGGGCCCCGATCCGATGCCCCCTCCCAGTTGCGTGAGCAAGCAGCGGAGTCGTCGCGGGATCGATGGCCACGG
GGTGTTCAATGGCGGATGGTCCGCTGCCCGCCGACTGGCTCTTGCGGGAGAGCCGATCTAGCACCACCGATCCGCGCACGTGGACCGAAACCGCCGAGTAGA
TGTCGAAAGCGT Clone Rv186
:::::::::::::Rv186SP6.seq:::::::::::::
CGTCCTTTTCCCCAAGATAGAAAGGCAGGAGAGTGTCTTCTGCATGAATATGAAGATCTGGTACCCATCCGTGATACATTGAGGCTGTTCCCTGGGGGTCGT
TACCTTCCACNAGCAAAACACGTAGCCCCTTCAGAGCCNNATCCTGAGCAANATGAACAGAAACTGAGGTTTTGTAAACGCCACCTTTATGGGCAGCAACCC
CGATCACCGGTGGAAATACGTCTTCAGCACGTCGCAATCGCGTACCAAACACATCACGCATATGATTAATTTGTTCAATTGTATAACCAACACGTTGCTCAA
CCCGTCCTCGAATTTCCATATCCGGGTGCG Clone Rv187
:::::::::::::Rv187SP6.seq:::::::::::::
CTCAAGCTTCATGTCCGTACGGCTCGGGTACGCTTCCGTCGCAGTGTGCGAGTGATAAATGACGACCGGGACCTCGTCGGCATCTTCCATAGCCCGCCACAC
CTTCAGTTGCTCACCGGAATCCAACCGGTAGAAGGTCGGCGAGCGCTCGGCATTGGTCATCGGGATATGCCGCTCGGGACGGTCAGAGCCCTCGGGTCCGGC
CAGCACTCCGCAGGCTTCGTCGGGGTGGTCGCGACACGCATGGGCCACCATCGCATTCAC :::::::::::::Rv187T7.seq:::::::::::::
NCGCCGCCAGCCACCACGCGCGGGTCGGGCGCCGGGCCCGGGCCGCCAGGCTGCTCCGCTCGGTGATGGCACGCCACCGCGACACCACCCGGCTGCGCTACG
TCGAGCCATACCGGGCGGAGCTACATCGGCTCGGCCGCCCAGTGTTCGGGCCCTCTTTCGAGGTCGAGGTCGATACCGATTTGCGCATCCGCAGCCGCACCC
TGGACGACAGAACCGTGCCCTACGANTGCTTGTCGGGCGGGGCCAAAGAACAGCTTGGCATCCTGGCGCGATTGGCCGGCGCGGCGCTGGTCTCCAAAGAAG
ACGCCCTTCCGGTGCTGAT Clone Rv188
:::::::::::::Rv188SP6.seq:::::::::::::
CGCCACGTTCATGGGCAACAACCCCGATCACCGGTGGAAATACGTCTTCAGCACGTCGCAATCGCGTACCAAACACATCACGCATATGATTAATTCGTCCAA
TTGTATAACCAACACGTTGCTCAACCCGTCCTCGAATTTCCATATCCGGGTGCGGTAGTCGCCCTGCTTTCTCGGCATCTCTGATAGCCTGAGAAGAAACCC
CAACTAAATCCGCTGCTTCNCCTATTCTCCAGCGCCGGG Clone Rv189
:::::::::::::Rv18SP6.seq:::::::::::::
ATACTCAAGCTTCAACCGATTGACGCATTGTGCGAACTGACGGCGCCCGCGCATGGCCAATCCGGAAGACCATCATTGGCCAGTGGCCGGGCGCTAACAGGT
TCCAGCCCCCCACCAGTGCCGCTCGAACATGCGGTGCAACCCATTCGCAGGCCGGCAGGGAAAGCACCGCGGAAGCCGCAAAGGGCTGCAGTTCCGCGCCCA
ATAGTGTCGTCCGCAACCAGATGCGCTCGAAAACCGCGCCGGCAGTCAGCGCACCCGACGCGAGGTCGAGAGACGTCGTCAGCGCGCCCACATGGGGTGCCA
ATCGGCACGGCAGGTAGGCCGCGCGCAACCCGAACGCGTGGTGCATGCCCACGGTCCGCAGGAGGCGCAGCACCCGCCAATGCCGAAGCCCACGAAACATCG
GGCGCATCCACGCTTCAACCTC Clone Rv18
:::::::::::::Rv18T7.seq:::::::::::::
AGCTTTTGGCAGGGTCTCCTTCGAATTCGGCGTGCACCGCTATGGGTTGCAGCAGCGGCTGGCGCCGCACACCCCACTGGCCCGGGTGTTTTCGCCCCGAAC
CCGGATCATGGTGAGCGAAAAGGAGATTCGCCTGTTCGATGCTGGGATTCGCCACCGCGAGGCCATCGACCGATTACTCGCCACCGGGGTGCGAGAGGTGCC
GCAGTCCCGCTCCGTCGACGTCTCCGACGATCCATCCGGCTTCCGCCGTCGGGTGGCGGTAGCCGTCGATGAAATCGCTGCCGGCCGCTACCACAAGGTGAT
TCTGTCCCGTTGTGTCGAAGTGCCTTTCGCGATCGACTTTCCGTTGACCTACCGGCTGGGGCGTCGGCACAACACCCCGGTGAGGTCGTTTTTGTTGCAGTT
GGGCGGAATCCGTGCTCTGGGTTACAGCCCGAATCGTCAC TABLE 3-continued End sequences of the polynucleotide inserts cloned in the named recombinant BAC vectors contained in the I-1945 *M. tuberculosis* H37Rv genomic DNA library.

Clone Rv190
::::::::::::Rv190SP6.seq::::::::::::
ATACTCAAGCTTTGTCACACCAACTGTTTCCACCAGGCGCTCCATCCGGCGAGTGGATACTCCCAGCAGGTAGCAGGTCGCCACCACGCTGGTCAGTGCGCG
TTCAGCTCGCTTGCGGCGCTGCAGCAGCCAGTCCGGGAAATAGCTGCCCTGGCGCAGCTTGGGGATCGCGACTTCTATGGTTGCGGCACGGGTGTCGAAATC
ACGGTGGCGGTAGCCGTTGCGCTGATTGGACCGCTCATCGCTGCGTTCGCGGTAGCCCGCCCCGCACAGGGCGTCGGCTTCAGCCCCCATCAAGGCGGCGAT
GAACGTCGAGAGCAGCCCGCGCAGCAGATCCGGGCTCGCCTGTGCGAGTTGGTCAGCCAGAACTGCTCGGTGTC ::::::::::::Rv190T7.seq::::::::::::
CCTTAAGCCCCGCAGGGCCCGGCACGCGCGGTACCGCCCAGGTCGCCCAACAGATCGTCGATGTTCGCGTCGTCCGCCTCGCGCACGTGGTCTGTCACCAGT
CAACGTTAACGCCGCCGCACATGTCCTGCGGCCGGGCAAAAACGTGAAAAACGAGCGGGCGACTGCAATGTCATGACACCGACGGCCGCCGATGGGCCCAGG
GTCTGGCAGATTCGATCTGTGCGGCCAGTGCCAGCAGCGTCGCCTCGTCATACGGCCGGCCGACGAGTTGAACCGACATGGGCAGGCCGTCGCCGTCGAAGT
CCCACGGCACCACGGCCGCGGGCTGGCCGGTCAGATTCCAGACTTGAAAGTACGGAACCCGCTGCACCACCAGCAGCAACGTCGAAACTGCACCCCGGCGTT
GGTAGGCGCCGATGCGGGACGGGCCGGTCGCGGCGCCTGGCGTCACAACTACGTCGACATCGTCGAAGATCGACTGGATCGGCTGCTCACACCACTCGGCGG
CCGCAGGCCGCCATCCGCCGTC Clone Rv191
::::::::::::Rv191SP6.seq::::::::::::
AGCTTTTTGAGCGTCGCGCGGGGCAGCTTCGCCGGCAATTCTACTAGCGAGAAGTCTGGCCCGATACGGATCTGACCGAAGTCGCTGCGGTGCAGCCCACCC
TCATTGGCGATGGCGCCGACGATGGCGCCTGGACCGATCTTGTGCCGCTTGCCGACGGCGACGCGGTGGGTGGTCAAGTCCGGTCTACGCTTGGGCCTTTGC
GGACGGTCCCGACGCTGGTCGCGGTTGCGCCGCGAAAGCGGCGGGTCGGGTGCCATCAGGAATGCCTCACCGCCGCGGCACTGCACGGCCAGTGCCGCGGCG
ATGTCAGCCATCGGGACATCATGCTCGCGTTCATACTCCTCGACCAGTCGGCGGAACAGCTCGATTCCCGGACCGCCCAGCGCATTGGTGATGGAATCGGCG
AACTTGGCCACCCGCTGGGTGTTGACATCCTCGACGGTGGGCAATTGCCCCCGGTAACGTTTGCCGCCT ::::::::::::Rv191T7.seq::::::::::::
CGGTCCGACCCTGTTCGACGGCTACCTGAATCAACCCGATGCCACCGCCGCGGCGTTCGACGCCGACAGCTGGTACCGCACCGGCGACGTCGCGGTGGTCGA
CGGCAGTGGGATGCACCGCATCGTGGGACGCGAGTCGGTCGACTTGATCAAGTCGGGTGGATACCGGGTCGGCGCCGGTGAAATTGAAACGGTGCTGCTCGG
GCATCCGGACGTGGCGGAGGCGGCAGTCGTCGGGGTGCCCGACGATGATCTAGGCCAGCGGATCGTTGCCTACGTAGTCGGCTCAGCGAATGTCGATGCGGA
CGGGCTTATCAACTTTGTTGCCCAACAACTTTCGGTGCACAAGCGCCCGCGCGAGGTGCGTATCGTANATGCGCTGCCGCGCAACGCCTTGGGGAAAGTGCT
CCAGAACATTGCTGTCAGAAGCTGANCTACGCGAATTATCGTGTTACGCTGGA Clone Rv192
::::::::::::Rv192SP6.seq::::::::::::
ATACTCAAGCTTGCCGAAGTTCCGATGGGTCGCGCCGGCGAGCCCAGCGAAGTCGCTACCGTGGCCGTGTTCTTGGCTTCGGATCTATCCTCGTTCATGACC
GGCACCGTGTTGGACGTGACTGGCGGCCGGTCCATATGACACCGAGATCATTGCCACGGTACGGCAATTCGTCAAGAAGGAAATCTTTCCCAATGCACCGGC
CCTCGAACGTGGCAACAGCTACCCGCAAGAAATCGTCGATCGGCTGGGTGTTATTGGCTTGCTCGGTCGCCGGCTGCAAGGGTATCGACACCACCGAGTTCA
TTCTCGGGCGTGCCGGCGCATTCGAGCTGGCGGTGCGCGCTGCCCAGCACCGTCATAGGTACTTGACGATGGTCCACGTCGGACGAGCGCCTCCACGTCGCT
GCCGAACGGTATGCATGGCGGCTACGATTCTC ::::::::::::Rv192T7.seq::::::::::::
CGGTGTCGGCACCGGCGTCCTGCAGTTGGTAGGCCTGCAGTTTGTGCATCAGGCCGATGCCGCGGCCCTCGTGGCCACGCATGTACAGCACCACGCCGCGCC
CCTCACGGGCGACCATCGCCAGCGCGGCGTCCAGCTGAGGCCCGCAATCGCAGCGGCGTGACCCAAACACATCGCCGGTCAAGCACTCCGAATGCACCCGGA
CCAGCACGTCGTCACCGTCGGCGTTGGGCCCGGCGATCTCGCCGCGGACCAGCGCGACATGTTCCACGTCCTCGTAGATGCTGGTGTAGCCGATGGCGCGAA
ACTCCCCATGACGAGTCGGAATCCGCGCCTCGGCGACCCGCTCAATGTGCTTCTCGTGCTTGCGCCGCCATTCGATCAAGTCAGCAATGGTGATCAGCGCCA
GACCGTGCTCATCGGCGAACACCGCAATTCATCGGTGTTGCGCCATCGAGCCCTGATCTTTTTGGCTGACGATCTCGCAAATCGCCCCCGCGGGTTGCAGCC
GGCAT Clone Rv193
::::::::::::Rv193SP6.seq::::::::::::
ATACTCAAGCTTTGGGTGAAAGCCGATCACCGGAAGCCGCATGATCAGCCACGTTTCGCGCCGCCCGGCATACGGCGGCGTACCGATCTCCGCGTCATACAC
CCGCGGGTAATCGCCGACGGTGCCGGTTCGCGAGCCGAAGGTGACGACGCTGATTGAATCGAGTTCCAGGTCCAGCGGGTGGCGCAGCAACGGCGCGAGCTC
AACGACGTCAATCACGTTGTCGCTTTCTACGGTCACCGACCCGGTGACCGTNCTCGCCCGGTGCGCTCGGCCGATAAGTTGCACCGCCACCACCGCGACACC
GTCTTGCACGCGGACCCACCCCCGGATCCGTTGTTGGCC ::::::::::::Rv193T7.seq::::::::::::
AGCTTGCTGGCATCCGCTCCAGTAGCGCCCCGCGCGTGGCTTCCAGCGCCCGCAGATGCTCCATGAGCCGGCCGGTCGAGTCGGCGCCGGCGTTCACCGCCA
CCCGCCAGGAGCTGGCGGCCAGCATCTCCGCCTTCACGCATTGCGCGATCACAGAGAGAATATACGTCTCATATTCGTTGGAGGTCGTCGCAGGCAATCGGT
CGATGACGGATTTGATGGCATCGAGCTGTGCTTCGGCGTAGCCCTCCAGCACGTCGGTATCGCTGTGGCGGTCCACGACGACCGCACCGGCGCGGCGGACAG
CCGTCGGGTTGGACGNTGTGCGGCGATCAGTCCGGCCAGCTCCGCCTCGGGATCAGCGGC Clone Rv194
::::::::::::Rv194SP6.seq::::::::::::
ATACTCAAGCTTGCTGCAGCTTCCTATGACTGCTCCCGAAACCTGGGGGTGTGCCTGCTGTGTATGCACGGCATACGGACATCCTTCCCCTGAGACCCGCGG
TCGAACCAGCCACGTGTCCATCATCAGGGGTCAACCCCGGCCAAGGGCGACGGCACGCCAAGTTCGCCGACCGTTAACCTAGTGCTGTTAGCTTCATTTGCT
GCGAGCAAAACAGCTGGTCGGCCGTTAGGAACTGAATTGAAACTCAACCGATTTGGTGCCGCCGTAGGTGTCCTGGCTGCGGGTGCGCTGGTGTTGTCCGCG
TGTGGTAACNACNACAATGTGACCGGGGGAGGTGCAACCACTGGCCAGGCGTCGGCGAAGGTCGATTGCGGGGGGAAGAAGAACTCAAAGCCAGTGGGTCGA
CGCGCAGGCCAACGC ::::::::::::Rv194T7.seq::::::::::::
AGCTTGACGCGGAGACGGACACATTGCGAACATTGATGACAAAATAGAAATCATTGATGGTTTGAGTCACCAGGCCGATCAAGCCTTCGCCGAGCCAAATTC
CAATCAAGAGGCCCAAGCCCGTACCAATCAGCCCGGCAACGAGGGATTCCGTCATTATCAGCCAAAATAACTGCTCTCGGGTTACACCCAAACAGCGCAATA
TGGCGAAAAACGGTCGCCGTTGCACGACATTAAATGTCACGGTATTGTAGATTAAAAAGATACCCACCAACAAGGCAATCAAACTGAGAGCGGTTAAATTGA
CCGTAAAAGCGTCCGTCATCTGTTTGACGGTGTCCCGTTGGGTATCCGACGTTTCCATACGCACACCGGCCGGCAGTCTTTGTTGGATGCGTGTTGCAGTGG
CCTCATCTTTGATGATCAAATCGATGTGGCTCAGTCTTCCGGGCA TABLE 3-continued End sequences of the polynucleotide inserts cloned in the named recombinant BAC vectors contained in the I-1945 *M. tuberculosis* H37Rv genomic DNA library.

Clone Rv195
:::::::::::::Rv195SP6.seq:::::::::::::
ATACTCAAGCTTCGGCTCAGGCGGCGCTGCTGGTAAAGTCGCTGACCGGTGCAGGTTTCGACAATGTGGTGCCGGTTCGGCGGCTACGTGCCATCGAGACAC
TGGCGCAGGCTATCGCACCCGTTATCGGCTACGAGCAAATCGCGGTATGCGTTCTTGAGCATGAGTCGGCGACCGTCGTCATGGTCGACACCCACGACGGAA
AGACGCAGATCGCCGTCAAGCATGTGTGCCGCGGATTATCAGGACTGACCTCCTGGCTGACCGGCATGTTTGGTCGCGATGCCTGGCGCCCGGCCGGCGTGG
TCGTGGTCCGCTCGGATAGCGAGGTCAGCGAATTCNCNTGGCAGCTCCAAAGGGTCCTGCCGGTGCCGGTCTTTGCGCAAACNAAGGCNCAGGTTA :::::::::::::Rv195T7.seq:::::::::::::
TGATCGCGCATCACCTGCTTCATAAACTGGAAGCAGCGCAGCGCTTCCTTTTCGGCCGCAACATGAGCCAGCCTCTCGTCGGCGGTCGGGTGCAGGTGCTCG
GGCAGCTCGGCCGCGACAGCCGCCTGACCCTGAAACCAGCTTCCATATCCCGCGACGAACGACGCCAGTCCGCTACGTAACCCCTCCGCGACTGTCCATGGA
CAACAGCGCGTTCTCCACCGACCGGGCCCGGGTGTGGGGTGTTTCGGCGACCGGCAGCCAGGTGGTCCACACTGCCGACGGGCGCCGCGAGCCGTTCACCGA
CCAGGCCGCCGAGCAAGTCCGCCCGATCGCATACTCCAACCGGTTGCGGTACTGCAGGTTCAGCTGGCGTACTCCTCGTCGCGCTCGGCGAGGTCTTGCTCC
AGCACGTCGCANACGGCAG Clone Rv196
:::::::::::::Rv196SP6.seq:::::::::::::
CAAAGCGCGAACTGCTCGCGGCAGCCCACGACGTGCTGCGTCGGATTGCCGGCGGCGAAATCAATTCCAGGCAGCTCCCGGACAATGCGGCTCTGCTGGCCC
GCAACGAAGGACTCGAGGTCACCCCGGTGCCCGGGGTCGTGGTGCACCTGCCGATCGCACAGGTTGGCCCACAACCGGCCGCTTGATGCCCGGTCGGCAAGC
CCGGCAGTTGCCAAACCCAGCGTGATCAGGCTCGGCTCGCGAGTTCCGGGAAGAAGTGGCTCCGCCTGATCACCTACCATCCGCCAGGATCTGCGTGTCTTC
ACCACGCCCGCCAAGGAGGTTGTTGTGGTGCTATCGACCGN :::::::::::::Rv196T7.seq:::::::::::::
CCGGAAGCCGCATGATCAGCCAAGTTTCGCGCCGCCCGGCATACGGCGGCGTACCGATCTCCGCGTCATACACCCGCGGGTAATCGCCGACGGTGCCGGTTC
GCGAGCCGAAGGTGACGACGCTGATTGAATCGAGTTCCAGGTCCAGCGGGTGGCGCAGCAACGGCGCGAGCTCAACGACGTCAATCACGTTGTCGCTTTCTA
CGGTCACCGACCCGGTGACCGTNGTCGCCCGGTGCGCTCGGCCGAAAANTTGCACCGCCACCACCGCGAAACCGTCTTGCACNCCGGAAGCCACCCCCGATC
CGTTGTTGGGCCAGGTTATTGGGT Clone Rv19
:::::::::::::Rv19SP6.seq:::::::::::::
CCGGAACCGCCGACGGCACGGTATAACGCCTCCGCATATGGGTCGACAACCAGCGGGTCGGACTTCTGGGCTTCTAGCGTTCGCGCNGTCGCGACAAACAGC
GCGGTCGAACCGACACTCGTTGTGATGTCCTAGCTATCACGTTCGGTACGCACCCAATCGAGTCTAGCGCGGGTAGNTCAGCCCCGATCTCCANGCTCCGCC
GAGCCAGGCGC :::::::::::::Rv19T7.seq:::::::::::::
CTGGTTTATGTCCCGTTGAAGTTCCATCACCCGATGTGGCGGGAGCACTGCCAGGTCGATCTCAACTACCACATCCGGCCGTGGCGGTTGCGCGCCCCGGGG
GGTCGGCGCGAACTCGACGAGGCGGTCGGAGAAATCGCCAGCACCCCGCTGAACCGCGACCACCCGCTGTGGGAGATGTACTTCGTTGAGGGGCTTGCCAAC
CACCGGATCGCGGTGGTTGCC Clone Rv1
:::::::::::::Rv1SP6D2.seq:::::::::::::
CCGAGCAGTTGGGAATCGCTCTGCANCAAACCAATATTCTGCGCGACGTCGCGCGACGAGCTGGACCGATTAGGCGTACGCCTCCGNCTGGACGACACCGGG
GCACTCGATGACCCCGACGCCTACGCTCGCAGGATATTGTTCGCCGGACCCCTCTCTAG :::::::::::::Rv1T7.seq:::::::::::::
TATATAATACTCAAGCTTGCCGACGCCAACGCTCGCGCGATGTTGTTAGCCCGACCCGGCTCTTACATGGCACCGGTGCCCCACACGTCAGCCTGTGACGTC
CTGCACCGCGACTCTTTACATAGAATGTGGATTGCCGGATTGGGGATGTCCGGCATCGCTCAATCTGTAGTCCGCGTTGTCCCGCGAGGGCCATGTGGATGG
GGGGAAGGATCCGTGGCGTCCGGGATCACCATGGGG Clone Rv201
:::::::::::::Rv201SP6.seq:::::::::::::
ATACTCAAGCTTGCCGAAGTTCCGATGGGTCGCGCCGGCGAGCCCAACGAAATCGCTAGCGTGGCCGTGTTCTTGGCTTCGGATCTATCCTCGTACATGACC
GGCACCGTGTTGGACGTGACTGGCGGCCGGTTCATATGACACCGAGATCATTGCCACGGTACGGAAATTCGTCCAGAAGGAAATCTTTCCCAATGCACCGGC
CCTCGAACGTGGCAACAGCTACCCGCAAGAAATCGTCAATCGGCTGGGTGTTATTGGCTTGCTCGGTCGCCGGCTGCGAGGGTTTCTACACCACCGAGTTCA
TTCTCGGGCGTGCCGGCGCATTCGAACTGGCGGTGCGCGCTG :::::::::::::Rv201T7.seq:::::::::::::
GCACCGGCGTCCTGCAGTTGGTAGGCCTGCAGTTTGTGCATCAGGCCGATGCCGCGGCCCTCGTGGCCACGCATGTACAGCACCACGCCGCGCCCCTCACGG
GCGACCATCGCCAGCGCGGCGTCCAGCTGAGGCCCGCAATCGCAGCGGCGTGACCCAAACACATCGCCGGTCAAGCACTCCGAATGCACCCGGACCAGCACG
TCTTCACCGTCGGCGTTGGGCCCGGCGATCTCGCCGCGGACCAACGCGACATGTTCCACGTCCTCGTAGATGCTGGTGTAGCCGATGGCGCGAAACTCCCCA
NGACAAGTCGGAATCCGCGCCTCGGCGAACCGCTCAATGTGCCTCTCGTGCTTGCGCCGCCATTC Clone Rv204
:::::::::::::Rv204SP6.seq:::::::::::::
TGGTCCGTGTGCGCATACCAATACAACGCGCCGGGCACCTGACGCGGCGGCCGCAACCAATCGGTGGCCATCGCCATCTTCTGCTACCCGGTCAACGGACGC
ACCTTCTCCTGGCCGACGTAGTGCGCCCACCCGCCGCCGTTGCGTCCCATCGATCCGGTCAAC Clone Rv205
:::::::::::::Rv205SP6.seq:::::::::::::
GGCGTGTTGGCCACCGGGGCCACTCCGCACAATCTGTACCCGACCAAGATCTACACCATCGAATACGACGGCGTCGCCGACTTTCCGCGGTACCCGCTCAAC
TTTGTGTCGACCCTCAACGCCATTGCCGGCACCTACTACGTGCACTCCAACTACTTCATCCTGACGCCGGAACAAATTGACGCAGCGGTTCCGCTGACCAAT
ACGGTCGGTCCCACGATGACCCAGTACTACATCATTCGCACGGAGAACCTGCCGCTGCTAAAGCCACTGGCGATCGGTGCCGATCGTGGGGAACCCACTGGC
GAACCTGGTTCAACCAAACTTGAAGGTGATTGTTTACCTGGGCTACGGCGACCCGGCCTATGGTTATTCGACCTCCCCGCCCAA :::::::::::::Rv205T7.seq:::::::::::::
CGTCCGTGNCCCCTCAANCGCGTGNNGCCGAAGCGGCTGGTTACGACTCCCTGTTTGTGATGGACACTTCTACCAACTGCCCATGTTGGGGACGCCCGACCA
GCCGATGCTGGAGGCCTACACGGCCCTTGGTGCGCTGGCCACGGCGACCGANCGGCTGCAACTGGGCGCGTTGGTGACCGGCAATACCTACCGCAGCCCGAC
CCTGCTGGCAAAGATCATCACCACGCTCGACGTGGTTAGCGCCGGTCGAGCGATCCTCGGCATTGGAGCCGGTTGGTTTGAGCTGGAAACACCGCCAGCTCG TABLE 3-continued End sequences of the polynucleotide inserts cloned in the named recombinant BAC vectors contained in the I-1945 *M. tuberculosis* H37Rv genomic DNA library.

GCTTCGAGTTCGGCACTTTCAGTGACCGGTTCAACCGGCTCGAAGAGGCGCTACAGATCCTCCAGCCAATGGTCAAGGGTGAGCGCCCAACGTTTTTCGGCG
ATTGGTACACCACCGAATC

Clone Rv207
:::::::::::::Rv207SP6.seq:::::::::::::
CCGCTTCCGTGTAACCGAGCANNGCGAGCGANCTGGCGAGGAAGCAAAGAAGAACTGTTCTGTCAGATAGCTCTTACGCTCAGCGCAAGAAGAAATATCCAC
CGTGGGAAAAACTCCAGGTAGAGGTACACACGCGGATAGCCAATTCAGAGTAATAAACTGTGATAATCAACCCTCATCAATGATGACGAACTATCCCCCGAT
ATCAGGTCACATGACGAAGGGAAAGAGAAGGAAATCAACTGTGACAAACTGCCCTCAAATTTGGCTTCCTTAAAAATTACAGTTCAAAAAGTATGAGAAAAT
CCATGCAGGCTGAAGGAAACAGCAAAACTGTGACAAATTACCCTCAGTAGGTCAGAACAAATGTGACGAACCNCCCTCAAATCTGTGACAGATAACCCTCAG
ACTATCCTGTCGTCATGGAAGTGATATCGCGGAAGGAAAATACGATNTGAGTCGTCTGGCGGCCTTTCTTTTTCTCAATGTATGAGAGCG Clone Rv209
:::::::::::::Rv209SP6.seq:::::::::::::
TGACACCCAACAGAGGGCACTTAAGATGGCAATGCGGCCGCCTACCTGCACGTTTTCGCGATGTCAGAGGATGCCGAGGGAGAACAATGCGAGCACGGCCGC
TGACNTTGCTCACCGCTTTGGCGGCGGTGACATTGGTGGTGGTTGCGGGCTGCNAGGCCCGANTCNAGGCCGAAGCATATAGCGCGGCCGACCGCATTTCGT
CTCGACCGCAAGCGCGACCTCAGCCGCAGCCGGTGGAGCTACTGCTGCGCGCCATCACGCC :::::::::::::Rv209T7.seq:::::::::::::
ACGGGCGACGCTGAGGTGGGCCCGCGGCTATTCATGCTGTCGTCCACGTCCAGCGACGCACTGCGCCAGACGGCCCGCCAACTAGCCACCTGGGTGGAAGAA
CACCAGGACTGCGTGGCGGCCTCGGATCTGGCCTACACGCTGGCGCGTGGCCGCGCGCACCGGCCGGTGCGCACCGCGGTGGTTGCCGCCAACCTGCCGGAG
CTCGTCGAGGGTTTGCGCGAGGTGGCCGACGGTGACCCCTCTATGACGCGGCGGTGGGACACTGTGATCTAAGACCGGTCTGGGTCTTCTCCGGGCAAGGGT
CTCAGTGGGCGGCGATGGGCACCCAATTGCTCGCCAGCGAACCAGTGTTCGCGGCCACCATCG Clone Rv20
:::::::::::::Rv20SP6.seq:::::::::::::
ATACTCAAGCTTCGCGAGATCCGGATGGCACTCACGCTGGACAAGACCTTCACAAAATCTGAAATCCTGACCCGATACTTGAACCTGGTCTCGTTCGGCAAT
AACTCGTTCGGCGTGCAGGACGCGGCGCAAACGTACTTCGGCATCAACGCGTCCGACCTGAATTGGCAGCAAGCGGCGCTGCTGGCCGGCATGGTGCAATCG
ACCAGCACGCTCAACCCGTACACCAACCCCGACGGCGCGCTGGCCCGGCGGAACGTGGTCCTCGACACCATGATCNAAAACTTCCCGGGGAGGCGGAGGCGT
TGCGTGCCGCCCAGGGCGAACCGCTGGGGGTTCTGCCGCAGCCCAATGATTGCCGCGCGGCTGCATCGCGGGCGGCGACCGCCATTCTTCTGCGAATACGTC
CAGGAGTACTGTCTCGGGGC :::::::::::::Rv20T7.seq:::::::::::::
AGCTTATGTGGCCGCCCACCTACCTTATCTAGCCTAGCTAACTAAATCCAGTGCCGACAGTGCGCGGCTGGCCACCCAGCATGAGGTTATGACCACGGCATA
TGCCAGCGCGCTGGCGGCGATGCCGACGCTGACCGAGTTGGCCGCTAATCACACCAGCCATGCGGTGTTGCTGGGAACGAATTTCTTTGGAATCAATACGAT
CCCGATCGCGCTCAATGAGGCCGACTATGCGCGGATGTGGATTCAGGCGGCCACCACGATGAGTATCTATGAGGGCACCTCCGATGCGGCGCTGGCGTCNGC
ACCGCAAACCACACCGGCTCCGGTACTGTTCAACGGCGGTGCTGGCGTTTGCCAGCGCCTGCCGGCGATCTC Clone Rv214
:::::::::::::Rv214SP6.seq:::::::::::::
ATACTCAAGCTTGCCACCCATGCCGAGCAAGGTCGACTCAGCGATGACGAATTGTTCTTCTTCGCGGTGTTGCTGCTGGTTGCGGGCTATGAGAGCACTGCT
CATATGATTAGCACNTTGTTTCTGACGCTGGCCGACTATCCAGATCAGCTGACACTCCTTGCGCAGCAACCAGACCTGATCCCGTCGGCGATCGAGGAGCAC
CTCCGCTTTATATCGCAATCCAAAACATCTGCCGCACAACGCGCGTCGACTATTCGGTCGGTCAAGCGGTCATCCCGGGA :::::::::::::Rv214T7.seq:::::::::::::
CCGGGGTAGAACGATGCGATCTGGGCCATGTCGACATCGGTGGTACAGGTAAACCGCGCCGTGTGCGCGGTCTCGGAGATCAGAACGTGGTCGCAGTTGACA
CCGCGGGCTTTCAGCCAGTCGCGATAATCGGCGAAGTCGGCGCCTGCCGCCCCAACTAGCGCGACCTCGCCACCTAGCACACCGATGGCGAAGGCCATGTTT
CCGGCCACGCCGCCGCGGTGCATCAACTC Clone Rv215
:::::::::::::Rv215SP6.seq:::::::::::::
ATACTCAAGCTTGGCGGCAACGCCACTACCGGGCTCACCAGGTCCTGTGCCGCCACCGCCGGCGCCGAAAGCACCATCAGGTCGTAGTTGTCTGGACGTTCG
ACACCGTAAGCGAACACAATGCCGCCGCCCATGCTGTGCCCGAGCACGATGCGCTTGCACCCGGGATATTCCCGGGTGGCGATCCCAACGAGGGTGTCGAAG
TCAGCGGTGTATCTGAGATGTCTCTCACTATCATCCGTTTGGCACCCGAGCGGGCATGCCCGCGGGGGGTCAAC :::::::::::::Rv215T7.seq:::::::::::::
GTCGACGGCATCAAGGTCCGCAGTGATGGTGTTCATCTCACCCAGGAAGGCGTGAAGTGGCTGATACCGTGGCTTGAGGATTCGGTGCGGGTCGCCAGTTAA
TCCGCCGTGTGCTCCGGATGAGCGCGACGGTAACCCTGGAATTGTGCTGTGTGCTGGCTGTGTCGTTGTGATGAGCCTGTCTAAGTGGTGCGTAACCGTTTG
ACGAGCCGCGGCCTCGCTGCAAACATTGAAGCCCGCACGTCTGGGTTTGTATTTACACAACGAGGGCGCTCCCCGATCTGGCGCGCGCAACGAGGTGCNCAC
TATCCATTCGAGGTGAACTGGACTCCTTGATGCTCATGCCGGTGCGGTTTTGTC Clone Rv217
:::::::::::::Rv217SP6.seq:::::::::::::
ATACTCAAGCTTGCGTTCGATGAAGTAGTCGTCGGTCAGCGCCGCCTCTTCGAGCTCCTTGGCGATGCCCAGCAAGGAGTCATCGCCGCCGAGCTTGGCCAG
GATCTTGTCGGCCTGTTCCTTGACGATGCGGGCCCGCGGATCGTAGTTCTTGTAGACACGATGACCGAAACCCATCAATTTGACCCCGGCCTCGCGGTTCTT
GACCTTGCGTTACAAACTCGCTGACGTCGTCGCCGCTGTCGCGAATGCCCTC :::::::::::::Rv217T7.seq:::::::::::::
NGTCAAGCCGAGCATGCGCGAGGNAACGACGAACCCAACAAGCCATGGTGGTTGGCGCCGTCGAGAGGTCGGCGGTCGCCACAACGGGAAGATCGCCTTGAG
CGTCGCTCGACCGCCGCCTCGAGTTGGGTCATAACGAAGTAGCTGATGCCGATCATGTCGACGTTTCCGTCGCATCAGCGTGCAGCGGCGACCCACTCGACG
AGGTCTCGGTGCCGCCGCGGCCAGGGCACCAGCAGTGACGATTCCAGGCGCCGTCGGG Clone Rv218
:::::::::::::Rv218SP6.seq:::::::::::::
CGATAATCGCTTCCGGTAAGTGCAGCAGCTTTACGACGGCGACTCCCATCGGCAATTTCTATGACACCAGATACTCTTCGACCGAACGCCGGTGTCTGTTGA
CCAGTCAGTAGAAAAGAAGGGATGAGATCTCCCCGTGCGTCCTCAGTAAGCAGCTCCTGGTCGCGTTCATTACCTGACCATACCCGAGAGGTCTTCTCAACA
CTATCACCCCGGAGCACTTCTAGAGTAAACTTCCCATCCCGACCACATATAGGCTAAGGTAATGGGCATTACCGCGAGCCATTACTCCTACGCGCGCAATTA
ACGAATCCACCATCGGGGCCGCTGGTGTCN TABLE 3-continued End sequences of the polynucleotide inserts cloned in the named recombinant BAC vectors contained in the I-1945 *M. tuberculosis* H37Rv genomic DNA library.

Clone Rv219
:::::::::::::Rv219SP6.seq:::::::::::::
NAATAGTCAAGCTTTCTCGTGATTACCACCCGTGTAATTTGGGATGGGCAAAAAGGCGAATCACCGCGTGGCCACAAACGCCGGGAGGGACAATCTCGGGCG
GCTAGGGCTTCTCGCGGGAAGGCCCGAACGTACGGCGTTTCAACACGTCGCGTCGCCCTCCGACCGCGAACATTCGGGGATGGCAGCAACCTGGTATCACCC
TGGCCGGGCAATGATCTGCAGCGTCGCCGCGGGTAGTGNCCGCCCGGGCGGCTAC :::::::::::::Rv219T7.seq:::::::::::::
CCAACTAGAGCATCGGGACATACGGAGTCAACTACCCGGCCAACGGTGATTTCTTGGCCGCCGCTGACGGCGCGAACGACGCCAGCGACCACATTCAGCAGA
TGGCCAGCGCGTGCCGGGCCACGATGTTGGTGCTCGGCGGCTACTCCCAGGGTGCGGCCGTGATCGACATCGTCACCGCCGCACCACTGCCCGGTCTCGGGT
TCACGCAGCCGTTGCCGCCCGCAGCGGACGATCACATCGCCGCGATCGCCCTGTTCGGGAATCCCTCGGGGCCGCGCTGGCGGGCTGATGATCGCCCTGACC
CCTCAATTCGGGTCCAAGA Clone Rv21
:::::::::::::Rv21SP6.seq:::::::::::::
ATACTCAAGCTTGCTGCAGCTTCCTGTGACTGCTCCCGAAACCTGGGGGTGTGCCTGCTGTGTATGCACGGCATACGGACATCCTTCCCCTGAGACCCGCGG
TCGAACCAGCCACGTGTCCATCATCAGGGGTCAACCCCGGCCAAGGGCGACGGCACGCCAAGTTCGCCGACCGTTAACCTAGTGCTGTTAGCTTCATTTGCT
GCGAGCAAAACAGCTGGTCGGCCGTTAGGAACTGAATTGAAACTCAACCGATTTGGTGCCGCCCGTAAGTGTCCTGGCTGCCGGTGCGCTGGTGTT :::::::::::::Rv21T7.seq:::::::::::::
AGCTTGCGCGGCGTGGCGATCGCGGTTCAAGGCGCGCTCTTCGAGCACAACGAGCGAAGACAGCTCGGCGACGGAGCCTTTATCGACATCCGTTCGGGCTGG
CTGACCGGCGGCGAAGAACTGCTGGACGCGTTGTTGTCGACGGTGCCGTGGCGAGCCGAGCGCCGTCAGATGTACGACCGGGTGGTCGATGTGCCGCGGCTG
GTGAGTTTTCACGACCTGACCATCGAAGATCCGCCGCATCCGCAGCTGGCGCGGATGCGCC Clone Rv220
:::::::::::::Rv220SP6.seq:::::::::::::
AATACTCAAGCTTGCGCACGACCAGGACGTCGAGTGGCGCTTGCAGTGACTTGGCGACCTCAAAGGCCACCGGTACCCCGCCGCGCGGCAAGCCAAGGACNA
CNACGGCCTTGCCGGATAGCTGCGCCAGGCGTTGCGCCAACTGGCGTCCAGCGTCGCCACGATCGTCAAAGAGCTTCATCTGCCGAGTGTGTCGCCATCTCA
TGGCTCCAAATATGGAATTAGGTCCCTGGGCCGACTGACGACAGTCCCTCAGCGACCGGATTGCGCATCCCGCCTTGTACGCTGCTCCGCAAATCCCGGGCT
TGCGTCCGCGGAAGCGAACTCGGCGGCGCTACGGTGGTGGCTCACTTCGGCCGTGC :::::::::::::Rv220T7.seq:::::::::::::
GGTTGGTGCGGTCCACCTTCGCGGCGGCGGCGCGATATGCCTTGCTGGTCTTGCTCATTTGATATCCAATCTATGGGTCGTGGTTACTCAGCGGGCCGAAGC
TGGCCCTCCCACGGGTAGGGCCCTATTCGACGGTGATGCCCATCGACCGAGCGGTACCGGCGATGATCTTGGCCGCAGCGTCGACGTCGTTGGCGTTGAGGT
CCGTCTTCTTGGTCTCGGCGATTTCGCGGACTTGATCCCAGGTGACTTTGGCGACCTTGGTCTTGTGCGGCTCCGCCGAACCCTTCGCCACACCAGCGGCCT
TAAGCAGCAGCTTGGCGGCGGGCGGCGTCTTCAGCGTGAAAGTGAAGCTACGGTCTTCATAAACGGTGATCTCCACCGGGATGACGTTGCCGCGCTGGTTCT
CCGTCGCGGCGTTGTACGCCTTGCAGAACTCCATGATGTTGACCCGTGCTGACCGAACGCGGGGCCCACTGGCGGGGC Clone Rv221
:::::::::::::Rv221SP6.seq:::::::::::::
ATACTCAAGCTTTTCGACCCGCAAGCCGGCGGTGCCCCTCCTCGTTCCGCTGCCCGGTCTGCTCGATCGGTTCGGGGTCGCCGCGCTAGGCCCAATTGCCCG
GCTCCTCCTCGGGCCGTTCCACAACCCGCATCGTCGCCGGGCTAGGTTCAAGCCATGCCGGTAAACCCCAGGACGCCAGTGCTGATCGGCTATGGACAGGTC
AACCACCGAGGCGACATCGACGCCNAAAATCAGTCCATCGAACCCGTCGACCTGATGGCCNCCGCGGCCCGGAAAGCCGCCGAGTCCACCGTGCTCGAAGCG
GTGGATTCCATCCGTGTGGTGCACATGCTGTCGGCGCATTACCGGAATTCCCGGGCGTCTCCTCGGC :::::::::::::Rv221T7.seq:::::::::::::
NCCTGGTTCATGAACTGGAAGCAGCGCAGCGCTTCCTTTTCGGCCGCAACATGAGCCAGCCTCTCGTCGGCGGTCGGGTGCAGGTGCTCGGGCAGCTCGGCC
GCGACAGCCGCCTGACCCTGAAACCAGCTTCCATATCCCGCGACGAACGACGCCAGTCCGCTACGTAACCCCTCCGCGACTGTCCATGGACAACAGCGCGTT
CTCCACCGACCGGGGCCGGGTGTTGGGGTGTTCGGCAACGGCAACCAAGTTGGTCCACACTGCCGACGGGCGCCGCAAATCCGTTCACCGAACCAGGCCGCC
NAAACAATTCCGCCCGATCCCATAT Clone Rv222
:::::::::::::Rv222SP6.seq:::::::::::::
ATACTCAAGCTTGTCGGGATCAATCTCGAGGGCATCCACGCACGAAAAGTAAACTCTATCAAGCTTTTTGACGACACCCACGGACGCCCCATATATGTTCGG
GTGGGCAAGAACGGTCCCTACCTGGAACGTTTGGTGGCCGGCGACACCGGTGAGCCCACGCCGCAGCGGGCCAACCTCAGCGACTCGATTACCCCGGACGAA
CTGACTCTACAGGTGGCCGAAGAGCTCTTTGCCACACCGCAACAGGGACGGACTTTGGGCTTGGACCCAGAAACCGGCCACGAAATCTTTGCCAGGGGAAGG
CCGGTTTGGGCCTTATGTTACCTATATCCTGCCGGAACCTGCGGCTGATGCGGCCGCGGCCGCTCAGGGAN :::::::::::::Rv222T7.seq:::::::::::::
AGCAGCTAGCCGCGCTCGCCGCGCTGGTCGGTGCGTGCATGCTCGCAGCCGGATGCACCAACGTGGTCGACGGGACCGCCGTGGCTGCCGACAAATCCGGAC
CACTGCATCAGGATCCGATACCGGTTTCAGCGCTTGAAGGGCTGCTTCTCGACTTGAGCCAGATCAATGCCGCGCTGGGTGCGACATCGATGAAGGTGTGGT
TCAACGCCAAGGCAATGTGGGACTGGAGCAAGAGCGTGGCCGACAAGAATTGCCTGGGCTATCGACGGTCCAGCACAGGAAAAGGTCTATGCCGGCACCGGG
TGGACCGCTATGCGCGGCCAACGGCTGGATGACAGCATCGATGACTCCAAGAAACGCGACCACTACGCCATTCAAGCGGTCGTCGGCTTCCCGACCGCACAT
GATGCCGAAGAATTCTACAGCTCCTCCG Clone Rv223
:::::::::::::Rv223IS1081N1400.seq:::::::::::::
CGCGACTGGCTCCCCGGNCGGCTGCTCGGGTCCGCCGATAGAGACCGGGATGTCGCCCGACGACGGGCAGCCGGGTTGCGTGGGACGGGGCGGGGGTCGGGC
AGCCCAAGCAACGGGCTAGTCCCCGAATCCTACGGAGCCGTCACCTACGCCTACGTAATAGTAGCTATCAATAACAGTTGACATACGCAACGATCTGTGAGA
TCAATATTGCCTGACGCATGTCAAGACAGGCGTCAAGACAGGTGTCAATAATTCGCTCCGCTGGTGACGGTAACCGGTCGTGCGGGTGTGTGACGCCTAAGG
AAGGAGTGTGGGTGGTGACGCTGAGAGTGGTTCCTGAGGGTTTGGCGGCCGCCAGTGCGGCGGTGGAGGCGTTGACCGCACGGCTGGCCGCCGCACACGCTG
GCGCGGCGCCGGCGATTACGGCGGTGGTGGCGCCCGCGGCGGATCCGGTGTCGTTGCAGAATGCGGTGGGGTTTAGCGCCTTAAGTAGCCAGCATGCCGCGA
TCGCCGGCGAAAGGGTCCAAGAACTGGGT :::::::::::::Rv223SP6.seq:::::::::::::
ATACTCAAGCTTATTGAACCGCGGGTCGCAGGCAAAGTGGACCTCATAACGACTCGGGTCCAGCGACCGCGCCAACACGAACGGCCGGACGACGTGGGCCAG
GGTCGCGGCCTCCCCTACAAACAGGATCCGTTGCCTGCGAACGACAGGCTCCGGTGCGGCGTTGGGCGCCGTGCTCGTCCCAGCGTCCGGTCCCGGGTCGCC TABLE 3-continued End sequences of the polynucleotide inserts cloned in the named recombinant
BAC vectors contained in the I-1945 *M. tuberculosis* H37Rv genomic DNA library.

GGCGACGCTTGTTTCCTCCATACTCGCCCCCTAATCTCGAGGCAGCCCGTACCCGCAGGCAACCTCCCAAAAATGCAATCCCGCAAAATGCAATGCGTCNAG
CTATTTCTCACACCGACCGCTAGTTGCGGATCAGAAATCCGTTGGGCGCGGAAGTCCAGCCGAATTTGTTCTCCCGCTCCGCATCATGCTTGTAATCGTTTG
GAAATTCATCCTCATATGCCTCGATCGCTTCATAGGGTCCAGGCCCAAACCCGGGCAGGACTGGGTGGCCGTTGATGTTGGAATCCTCCACTACTAGGTATT
CACCGGC

::::::::::::Rv223T7.seq::::::::::::
GTCTCGATCATGGCCAAAGAGCTCGACGAAGCCGTAGAGGCGTTTCGGACCCGCCCGCTCGATGCCGGCCCGTATACCTTCCTCGCCGCCGACGCCCTGGTG
CTCAAGGTGCGCGAGGCAGGCCGCGTCGTCGGGGTGCACACCTTGATCGCCACCGGCGTCAACGCCGAGGGCTACCGAGAGATCCTGGGCATCCAGGTCACC
TCCGCCGAGGACGGGGCCGGCTGGCTGGCGTTCTTCCGCGACCTGGTCGCCCGCGGCCTGTCCGGGGTCGCGCTGGTCACCGGCGACGCCCACGCCGGCCTG
GTGGCCGCGATCGGCGCCACCCTGCCCGCAGCGGCCTGGCAGCGCTGCAGAACCCACTACGCAGCCAATCTGATGGCAGCCACCCCGAAGCCCTCCTGGCCG
TGGGTGCGCACCCTGCTGCACTCCATCTACGACCAGCCCGACGCCGAATCAGTTGTTGCCAATATGATCGGGTTCTCGAC Clone Rv224
::::::::::::Rv224SP6.seq::::::::::::
ATACTCAAGCTTTCGTCAGTTCATGGCGCCAGCAGACCAACAAGAGCATCGGGACATACGGAGTCAACTACCCGGCCAACGGTGATTTCTTGGCCGCCGCTG
ACGGCGCGAACGACCCCAGCGACCACATTCAGCAAATGGCCAGCGCGTGCCGGGCCACGAGGTTGGTGCTCGGCGGCTACTCCCAGGGTGCGGCCGTGATCA
AGATCTTCACCGCCGCACCACTGCCCGGCCTCGGGTTCACGCATCCGTTTGGCCGCCGCC ::::::::::::Rv224T7.seq::::::::::::
GCCCCGTGTAATTTGGGATGGGCAAAAAGCGAAGCACCGCGTGGCCACGAACGCCGGGAGGGACAATCTCGGGCGGCTAGGGCTTCTCGCGGGAAGGCCCGA
ACGTACGGCGTTTCAACACGTCGCGTCGCCCTCCGACCGCGAACATTCGGGGATGGCAGCAACCTGGTAGCACCCTGGCCGGGCGATGATCTGCAGCGTCGC
CGCGGGTAGTCTCCGCCCGGGCCGC Clone Rv225
::::::::::::Rv225SP6.seq::::::::::::
ATACTCAAGCTTCCTTTGACCGAACGCGTCCACCGCACCGTGAGATTGGTGGCGCCATTCGTCGTGGTGTAGCTGCTGTTGGCGGCGTCGCCGTATTGTGCG
GGCCAGCCTTGTGCGGGGGCCGCTTCTACCCACAAGTCGGCACTTCCGCAACCGCCCAGCTCGACCGCGAATTACGGCGGCCGCAACGGCCGCCGGAAGGCG
TCACGCAATCGCTTATCCTTTCCAGGTTCCCAAATCCTCCGCTTACTTGGGTCCTTCATCGG ::::::::::::Rv225T7.seq::::::::::::
GGCAGCGGCGACAACCGGAACGTCCGCACGGTGCTCAATCACGGGTGCACGGTGTGCATCAGAATGGCGGGGGTTCGTTGTCGCGGTGAGGCGTTCGGCGAG
GAGGTAGTGTCTACCCCTTGCCCGCGGGTTCGTGCGGACTGAAAGGGATTTCATTGGGAACCCACGGCTGCGTATCGCAGGGCCTCGGTGACGTCTGCTTCC
TCNAGCTCAGGAAGTTCGGCGAGAATCTCGGTGGATGTTATTTGGTCCGCCTAC Clone Rv226
::::::::::::Rv226SP6.seq::::::::::::
ATACTCAAGCTTTCTCGGCTTCTCTGATAGCCTGAGAAGAAACCCCAAGTTAATCCGCTGCTTCACCTATTCTCCAGCGCCGGGTTATTTTCCTCGCTTCCG
GGCTGTCATCATTAAACTGTGCAATGGCGATAGCCTTCGTCATTTCATGACCAGCGTTTATGCACTGGTTAAGTGTTTCCATGAGTTTCATTCTGAACATCC
TTTATTCATTGTTTTGCGTT Clone Rv227
::::::::::::Rv227SP6.seq::::::::::::
ATACTCAAGCTTGGTGACCGGCACCGCGATACGTTGCGGCAGGCATCTGGGCTGGCGGTGGTTCGCCGCTCCGAAGCCGTCGAACACCATCGCCAGCGCGGC
TTCCACATCAACGACCATTTCGGCCAGCTTGCGGCGCATCAGCGGCTTGTCGATGAGCGCCCCACCGAATGCCCGCCGCTGCCCGGCGTATCACATCGATTC
GACCATCGCGCGGCGCGCGTTGCCGAGGGCGAACGAGGCGGTGCCCAACCGCAATCTGTTTGGTCAGCTCCCTCATGCGGGTTGATTCCTTGCCGTCCGGAC
GGGCCCGCGTCATGCGCTCGGTTCGCC ::::::::::::Rv227T7.seq::::::::::::
CCGTTGCGCAGCGTGAGCCGATAGTTGACATCCGGCTCGGTGAAGGTGAAATCGATGGCCAGGTCGAGGTCCCATGCGCGTGGGCCATTGATGCTGATCGCC
AGGACGTCAAAGATTTGGTCCGGCGTCAGCTGGGCGAAAAACGTGGGCGCCGGGACTTGCCCGGAGCTGCCCGGGTTCCCGTCGCGCAGCTCGGCGGCCCCG
GTCAGAAAGAAATTGCGCCAGGTCGCACACTCCGCGCCGTAGGCCAGCTGCTCCAGGGTGTCGGCATAGAGCCCGCGGGCCGCAGCGTGCTCGCTGTCGGCG
AACACCGCATGGTCGAGAAGCGTTGCCGCCCAACGGGAAATCACCTGCGTCGAAAGCTTCGCGGGCCAGCTCCAGCACTCGGTCGATGCCACCCAACGCGT Clone Rv228
::::::::::::Rv228SP6.seq::::::::::::
ATACTCAAGCTTGCGGATGTTACCCCTGACAGCGTGAACTATGTCNAAACACACGGCACCGGAACGGTGTTGGGGGACCCCATCGAGTTCGAGTCGCTGGCG
GCCACTTATGGCCTGGGTAAAGGCCAGGGCGAGAGCCCGTGCGCATTGGGGTCGGTCAAAACCAACATCGGCCACCTGGAGGCGGCCGCCGGTGTGGCTGGA
TTCATCAAGGCGGTGCTGGCGGTGCAACGTGGGCACATTCCCCGCAACTTGCACTTCACCCGGTGGAACCCGGCCATCAACACGTCGGCGACGCGGCTGTTC
GTGCCGACCGAAAGCGCCCCGTGGCCGGCGGCTGCCGGTCCACGCAGGGCTGCGGTGTCATCGTTCGGCCTCAGCGGGACCAA ::::::::::::Rv228T7.seq::::::::::::
CCGGTAACCAGATCAGCTCGTCGACCTCACTGCCGGGGGTGAATTCCCCACCGGTGCTGCGCGCTGCCCAGTAGTGCACCTTCTTGACGCCTCGAAAAGGGG
AGTCGGTCGGGTAGGTCACCGTCAGGAGCCGCCTACCCAGGTTGGCGCGGTGACCGGTCTCCTCGAGTATCTCCCGCACCGCCCCCACCGGTGCGGTCTCGC
CCGGATCCACTTTGCCCTTGGGCAGCGACCAGTCGTCGTAACGGGGGCGGTGAATGACAGCGATCTCGACCGGCCCTTCCGAATCGGCACTGCCGGGTCGCC
AGAACACCGCACCGGCGGCGTACACAATCCGGCCCGCCGAGCGCCGGCGGGCGGACGANTTCTGGATCGACACCTCAACTCCTGCAGGTCAATTCGGCCAAG
CTGCTCGCGGTCGTGGATGTGGTC Clone Rv229
::::::::::::Rv229SP6.seq::::::::::::
ATACTCAAGCTTGATGCCGCCGAAACCGAGCGTGAGCACGCCGCCACCCACCACGCGCGGGTCGGGCGCCGGGCCCGGGCCGCCAGGCTGCTCCGCTCGGTG
ATGGCACGCCACCGCGACACCACCCGGCTGCGCTACGTCGAGCCATACCGGGCGGAGCTACATCGGCTCGGCCGCCCAGTGTTCGGGCCCTCTTTCGAGGTC
GAGGTCTATACCGATTTGCGCATCCGCAGCCGCACCCTGGTCGTCTCGTACCGTGCCCTACCTCTGCTTGTCGGGCGGGGCCA ::::::::::::Rv229T7.seq::::::::::::
TCCGTACGGCCCGGGTACGCTTCGGTCGCAGTGTGCGAGTGATAGATGACGACCGGGACCTCGTCGGCATCTTCCATAGCCCGCCACACCTTCAGTTGCTCA
CCGGAATCCAACCGGTAGAAGGTCGGCGAGCGCTCGGCATTGGTCATCGGGATATGCCGCTCGGGACGGTCAGAGCCCTCGGGTCCGGCCAGCACTCCGCAG
GCTTCGTCGGGGTGGTCGCGACGCGCATGGGCCACCATCCATCCACCAGGTCTGCGCGAATCACCCGC TABLE 3-continued End sequences of the polynucleotide inserts cloned in the named recombinant BAC vectors contained in the I-1945 *M. tuberculosis* H37Rv genomic DNA library.

Clone Rv22
:::::::::::::Rv22SP6.seq:::::::::::::
GGACACATTGCGAACATTGATGACAAAATAGAAATCATTGATGGTTTGAGTCACCAGGCCGATCAAGCCTTCGCCGAGCCAAATTCCAATCAAGAGGCCCAA
GCCCGTACCAATCAGCCCGGCAACGAGGGATTCCGTCATTATCAGCCAAAATAACTGCTCTCGGGTTACACCCAAACAGCGCAATATGGCGAAAAACGGTCG
CCGTTGCACGACATTAAATGTCACGGTATTGTAAATTAAAAGATACCCACCAACAAGGCAATCAAACTGAGAGCGGTTAAATTGACCGTAAAAGCGTCCGT
CATCTGTTTGACGGTGTCCCGTTGGGTNTCCGACGTTTCCATACGCACACCGGCCGGCAGTCTTTGTTGGATGCGTGTTGCAGTGGCCTCATCTTTGATGAT
CA :::::::::::::Rv22T7.seq:::::::::::::
GCCTGGCCCAGGTGAAGGCCGACCTCGACGCCAAAGCCGCTGATCCGGCACATGAGTCGGTGGACTGGGACTTGAAGTCGCTGCGATGGGCGTGGAACCGAG
CCAAAGATGACGTGGCGCCGTGGTGGGCCGAGAATTCCAAGGAGTGCTACTCGTCGGGGTTGGCCGATCTGGCCCAGGGCCTGGCTAATTGGAAAGCTGGCA
AGAACGGGACCCGCAAAGGCCGGCGGGTGGGCTTCCCGCGATTCAAATCCGGGCGGCGTGATCCTGGCAGGGTGCGGTTCACCACCGGCACCATGCGCATAG
AGGATGACCGGCGCACGATCACGGTCCCGGTGATCGGGCCGCTGCGGGCCAAGGAGAACACCCGCCGGGTGCAACGCCACCTCGTGAGCGGGCGCGCGCAGA
TCCTGAACATGACCTTGTCGCAGCGGTGGGG Clone Rv230
:::::::::::::Rv230SP6.seq:::::::::::::
TAACTCAAGCTTCAAGTCCGCNGTCCGACCCTGTTCGACGGCTACCTGAATCAACCCGATGCCCCGCCGCGGCGTTCGACCCGACAGCTGGTACCGCACCGG
CGACGTCGCGGTGGTCGACGGCAGTGGGATGCACCGCATCGTGGGACGCGAGTCGGTCGACTTGATCAAGTCGGGTGGATACCGGGTCGGCGCCGGTGAAAT
TGAAACGGTGCTGCTCGGGCATCCGGACGTGGCGGANGCGGCAGTCGTCGGGGTGCTCGACTATTATCTAGGCCAGCGGATCGTTGCCTACGTAGTCGGCTC
AGCGAATGTCGATGCGGACGGGCTTATCAACTTTGTTGCCCAACAACTTT :::::::::::::Rv230T7.seq:::::::::::::
CCATGTCGCCCAACATATCGTCGATGTTCGCGTCGTCCGCCTCGCGCACGTGGTCTGTCACCAGTCAACGTTAACGCCGCCGCACATGTCCTGCGGCCGGGC
AAAAACGTGAAAAACGAGCGGGCGACTGCAATGTCATGACACCGACGCCGCCGATGGGCCCAGGGTCTGGCAGATTCGATCTGTGCGGCCAGTGCCAGCAGC
GTCGCCTCGTCATACGGCCGGCCGACGAGTTGAACCGACATGGGCATGCCGTCGCCGTCGAAGTCCCACGGCACCACGGCCGCGGGCTGGCCGGTCAGATTC
CANACTTGAAAGTACTGAAGCCGCTGCACCACCAG Clone Rv231
:::::::::::::Rv231SP6.seq:::::::::::::
CGAAAGCGTGAAACAGCTCGCGGCAGCCCCCGACGTGCTGCGTCGGATAGCCGGCGGGCGAAGATCAATTCCAGGCAGCTCCCGGACAATGCGGCTCTGCTG
GCCCGCAACGAAGGACTCGAGGTCACCCCGGTGCCCGGGGTCGTGGTGCACCTGCCGATCGCACAGGTTGGCCCACAACCGGCCGCTTGATGCCCGGTCGGC
AAGCCCGGCAGTTGCCAAACCCAGCGTGATCNTGCTCNGCTCTNTANTTCGGCGAAGAAGTGGCTCGCCTGATCACCTACCATCGGCCAGGATCTGCGTGTC
ATCACAACGCTCGCCAAGGAGGTTGTTGTG :::::::::::::Rv231T7.seq:::::::::::::
TCCGCCACGCTTCGCGCCGCCCGGCATACGGCGCGTACCGATCTCCGCGTCATACACCGCGGGTAATCGCCGACGGTGCCGGTTCGCGAGCCGAAGGTGACG
ACGCTGATTGAATCGAGTTCCAGGTCCAGCGGGTGGCGCAGCAACGGCGCGAGCTCAACGACGTCAATCACGTTGTCGCTTTCTACGGTCACCGACCCGGTG
ACCGTAGTCGCCCGGTGCGCTCGGCCGAGAAGCTGCACCGCCACCACCGCGACACCGTCTTGCACGCGGACCCACCCCGGATCGGTTGTTGGCCAAGGTAAT
TGGGTCATTCCATTTGACGGGACGCCGACCC Clone Rv232
:::::::::::::Rv232SP6.seq:::::::::::::
CATTCTTTAACAGTTGTTTTGGGCTCGGCATGGTTAGCCAACGTTCTGCGGTCCACCATATCATCTTGGTCCGGTAGCGCTCGTCCGGGGTATGCTGCCGCC
GGGATTCTCGCTGCTATTACTCCCCCCGAAGAACCGCCACCGGTCCAGCGCGTGGGCCGNCGCGGTCCCATCACAAACTGAACCCCCAACAGGGACATGCTT
ATCGGTAGGGCGCGCGCCAAGGCGGCAGCAATCGCATCACTGCGCTCTGCGCGTCACTATTAACCCACCCGGACTTCACTTCCACCACCCCGAATGGCGCCC
GGTCATTGATCATCTGGCGCACCGCGGATAA :::::::::::::Rv232T7.seq:::::::::::::
CGGTGTCCTGCAGTTGGTAGGCCTGCAGTTTGTGCATCATGCCGATGCCGCGGCCTCGTGGCCACGCATGTACAGCACCACGCCGCGCCCCTCACGGGCGAA
CATCGCCAGCGCGGCGTCCAGCTGAAGCCCGCAATCGCAGCGGCGTGACCAAACACATCGCCGGTCAAGCACTCCGAATGCACCGGACCAGCACGTCGTCAC
CGTCGGCGTTGGGCCCGGCGATCTCGCCGCGGACCATGCGCGACATGTTCCACGTCCTCGTANATGCTGGTGTAGCCGATGGCGCGAAACTCCCCATGACGA
GTCGGAATCCGCGCCTCGGCGACCCGCTCAATGTGCT Clone Rv233
:::::::::::::Rv233SP6.seq:::::::::::::
CGGCATCTGGCGGCTGAACCTGTTCTTGGGCAACATGCCGAGGATCGCCTCTTGGACCACGCGGTCGGGGTGGCGTTGCATTACCTCACCGATGGTGCGCTT
GTGCAGGCCGCCGGGATACCCCGAGTGCCGGTAAACCATCTTGTGCTGCAGTTTGTCGCCGCTGATGGCGACCTTGTCGGCGTTGATCACGATNACNAATCA
CCGCCANCGACATTGGGGGCGAACGTCGGCTCGTGCTTGCCGCGCAGCAGGCTGGCCGCCGCGACGCAAGGCGCCAACCACCACGTCCGTGGCGTCGATGAC
GTACCACCATCGCGTGGTGTCACCCGCCTTGGGC :::::::::::::Rv233T7.seq:::::::::::::
GCGGCAAAAATTGAAGCACTCNTGGCCACTNCCGCCGGGAGGGACAATCTCGGGCGGCTAGGGCTTCTCGCGGGAAGGCCCGAACGTACTGCGTTTCAACAC
GTCGCGTCGCCCTCCGACCGCGAACATTCTGGGATGGCAGCAACCTGTTAGCACCCTGGCCGGGCGATGATCTGCAGCGTCGCCGCGGGTAGTCGCCCCCGG
GCGGCTACAGTCTGAAACGCGATGACCATCGATGTGTGGACGCCGCATCCGACNCAACGGTTCCTACACTGTGATATGTTCGCCTCGCTGCGCCGGTGGACG
GTGGGTCTATCCCGGA Clone Rv234
:::::::::::::Rv234SP6.seq:::::::::::::
CGCGTTGAACTGAAGGGGTGCCGCCCGGCTCGAGCAGGCAAGCCATTTGTTCGATGCGGTTACCGAAGATCTCTTCGGTGACTGCCCGCCGCCGGCCAGCTC
GGCTCAGTGTCCGGCGTTGGTCGCCGCGGCGACAATCTTGGCGTCCACGGTGGTCGGGGTGATGCCCGCGAGCAGGATTGGCGAGCGGNCGGTCAGCCGGGT
GAACTTCGTCAAGAGCTGACGCTGCGGTTGGGGAGGCGAATCATGGTCGGTGCGTAGCCTCGACTAGGCCCGGG :::::::::::::Rv234T7.seq:::::::::::::
TGACAACGCGGCGGCGATTACCCCGCTACCGCAGCAGCATGACGCGGTAGCGAACACCGCCGGATGCAGCGCAGGTGCGTCGATGTGCTCACGGAATCGCCC
CGGCACCGCGATCTCGAGGATCACCAGTGCCACCCCCTGCAGCGCGACACCGACGATTCCGTACACCGCCACGCCGATCAGGCCCTGGGCCAGCTGATTGGA TABLE 3-continued End sequences of the polynucleotide inserts cloned in the named recombinant BAC vectors contained in the I-1945 *M. tuberculosis* H37Rv genomic DNA library.

GCTGGCGTATATGGCGGCGATGGTGACGATGGTCATCGCCTCTTACATTGTGGCGGCCAGAACCACGGCGTTGGGGCGGCGGTCGATGAACACTAGGCGACC
ANATCCCCGGGGTCAACAGGTTGACCATCC

Clone Rv235
:::::::::::::Rv235SP6.seq:::::::::::::
CGCGGACATCCCGAACGAGGACACGCGACCGCTTCGGTGTGTGATCTATCAGGGCTCGCACCACGCGCAACCGCTTCCGGCTACCTAGACGCGGT :::::::::::::Rv235T7.seq:::::::::::::
GCATGCGGGTGATGCCGTTCTCAGTGCGCAACAGCGTTCGACGCGGCATACCCAGCCGCACATGCCGTGCACGCCGGNGCCGGGGCGGGAATCT Clone Rv237
:::::::::::::Rv237SP6.seq:::::::::::::
CTCAAGCTTCAGNCCNTCTAAGCGGTCTGCGCGGCGATCGCAAAGATCGCCCTTTGCCGGCGTTGGGGGCTTCTGCTCGGGGGTGTTGTACACCTTCTCGAA
CACCTCGGCACCGACACCACCACCGTCGGCTTGAACACCGCCAACATCGGCAGCANATCTTGATGTCCTGGTGAATCCACGGTGACTTTGGAGTGGAAGGCG
GCCATACTGATCGCGCGCGCCACCACATGAGCTAGCGGCAGGAAAACCAGCAGCCGCTCACCCTTGCGCAGCAGCGTCGGGTGATATGCCTGGCGCCC :::::::::::::Rv237T7.seq:::::::::::::
AGTCGAANGTCAGTCCGGTCTCCTCTCCGACTACGGCCAAGAACTGGGGCGACGGTGTCAGTGCAGAACAGCGGAAACTGGTGGCGCCCTAGGCGAGCGAAC
GCTCACAAACGGCGGTGACCGCTTCTGGTCGTGCACCATCGAGCCGTGCCCAGCCCGGCCGCGTGCCGTCAGCCGCATCCACTGGATGCCCTTCTCGGCGGT
TTCAATCANGTACAGGCGACGTTCGCCACCATCGTGCCGGGGCACGGTTAGCGAGCCCCGCCGACTTCACCGATTGCCTCGGTGATGxxxxx Clone Rv23
:::::::::::::Rv23T7.seq:::::::::::::
AGCTTCGCGGCGTGGCGATCGCGGTTCAAGGCGCGCTCTTCGAGCACAACGAGCGAAGACAGCTCGGCGACGGAGCCTTTATCGACATCCGTTCGGGCTGGC
TGACCGGCGGCGAAGAACTGCTGGACGCGTTGTTGTCGACGGTGCCGTGGCGAGCCGAGCGCCGTCAGATGTNCGACCGGGTGGTCGATGTGCCCGCGGCTGG
TGAGTTTTCACGACCTGACCATCGAAGATCCGCCGCATCCGCAGCTGGCGCGGATGCGCCGGCGGCTCAACGACATCTACGGCGGCGAACTGGGTGAGCCCT
TCACCACCGCCGGGCTGTGCTACTACCGCGACGGCTCTGACAGCGTCGCCTGGCATGGCGACACCATTGGTCGCGGCAGCACTGAGGACACTATGGTGGCGA
TCGTCAGCCTCGGCGCCACCCGCGTCTTCGCGCTGCGGCCGCGTGG Clone Rv240
:::::::::::::Rv240SP6.seq:::::::::::::
AGCTTCAGCTGATACTCGACCAGCCCCACTCGGGCCAATACGTGAATGTCTAGCATCTTCACCCGTTCACGGGCTANTCGAGTAGTAGACATTGATTAGCCT
GAACGTACCTCCGACGCCAGCTGACGAACGGGTATGACGGATGGATTTCGTGGTGTCGCGCCCGAGGTCAATTCGTTACGGATGTATCTCGGGGCCGGATCG
GGGCCGATGTTGGCGGCCGCGGCGGCCTGGGACGGACTATCCGACGAACTGGCGGTGGCGGCGTCGTGGTTTGGGTCGGTGACCTCGGGCCTGGCGGATGCG
GCGTGGCGCGGCCCGCGGCGGTTGCGATGGCNCGCGCGGT :::::::::::::Rv240T7.seq:::::::::::::
CTGGTCATGGACGTTGCTCCGGTAGTGGCTCACTGCCGATCCTCCTCGTTGAGAGTGCCACCTCAGGGTTGGGTAGGGTTGGGTACTCGAAACCAAGTTACC
CACCAGTAACACCGTCAAAATATATCCGTTGCATAGGTCAATGCAAGTTGATGTGAGCTACATTGCACCAACTAACTAACCAACCGGTTGGGTTAGCGGTGA
TCCTGGCCGTGTCGGTCCTCTCACCTGCGGTGATAGCGATCAAATGAAGAATATGCGGAGTCTAGGGCGGCAGCGCCTGGCANCGTAGATCATCGGCTCACG
CGGATGCGGCCTCTTGGTACGGACATGCGCGCG Clone Rv241
:::::::::::::Rv241SP6.seq:::::::::::::
CTCGTGAGTAGCACCCCTGTAATTTGGGATCGGCAAAAAGGCGAATCACCGCGTGGCCACGACACGCCGGGAGGGACNATCTCGGGCGGCTAGGGCTTCTCG
CGGGAAGGCCCGAACGTACGGCGTTTCAACACGTCGCGTCGCCCTCCGACCGCGAACATTCGGGGATGGCAGCAACCTGG :::::::::::::Rv241T7.seq:::::::::::::
GGATCAACTACCGGCCAACGGTGATTCTTGGGCGCCGCTGACGCGCGAACGACCCAGCGACACATTCAGCAGATGGCCAGCGCGTGCCGGGCCACGATGTTG
GTGCTCGGCGGCTACTCCCATGGTGCGGCNCGTGATCGACATCGTCACCGCCGCACCACTGCCGGCCTCGGGTTCACGCAGCCGTTGCCGCCCGCAGCGGAC
GATCACATC Clone Rv243
:::::::::::::Rv243SP6.seq:::::::::::::
AGGACCGTCAGCACGGCGACGTGCTACTCGCCGAGCAGTGGGAATCGCTCTGCAGCAAACCATTACTCTGCGCGACGTTCGAGATGACCTTCTGAATGGACG
GATCTACCTGCCGCGCGACGACCTGGACCGCGTATGCGTCCGCCTCCGCCTGGACGACACCGGGGCACTCTATGACCCCGACGGACGGCTCGCGGTACTGCT
GCGGTTCACCGCCGACGCCCGCACGGTACGCGTCGGGACTGCGCTGAGTCCANCCTCGACGCCGTAGCGCTGCTGCTGTGCGGCCATGTCTGGCATCTACCG
CCGTCGCTCCCTTGA :::::::::::::Rv243T7.seq:::::::::::::
CGACTCTGTTGGCCACTGCGGGTCGATCTTGCGGCCGCCCCGGTCGTGGAACGCCCAGGTCACCCGGCGGCGCACCGCGGTCAGCGCGTCGTTGGCCAGCGT
GGTCACATGGAAGTGGTCGACGACGAGCTTGGCGTTGGGCAGCAGCCCGGGCGTGCGGATCGCCGAGGCGTATGCAGCGGCGGGGTCGATGGCCACCGTACT
GGATGCTCTCCCGGAACTGCGGTGTGCGCGCTTGCAGCCATGCCAGCACCGCCGCGCCGCCGCGGCCTTCATGCTGCCCATAAACCCTGATACCGGCCAGGT
CGACNAACCNGTATCCCACGGTCAACCC Clone Rv244
:::::::::::::Rv244SP6.seq:::::::::::::
CACACGGACGGCGGTGCGGACGCAGCTGACGCGCATGGTGGTCAGCATCGCGGCCGGTCTGCTGTTGTATGCCTACTTCGCGCCGCGCAAATGCTGGTGGGC
GGCGGTGGTGGCGCTCGCATGGCTGGGCTGGGTGCTGACCCAACTCTCGAACCACACCGGTGGGTGGGCTGGGCTATGGCCTGCCATATCGGCCTGGTGTTC
TACN :::::::::::::Rv244T7.seq:::::::::::::
CCGATATCCGAGCCGATAGCTGGCGGGCTCGGGTGGTNGCCAGCGGCGCTGCGACGAAAGTGTGACCGTCATGAAACAGACACCACCGGCGGCCGTCGGCCG
TCGTCACCTGCTCGAGATCTCAGCATCCGCAGCCGGTGTGATCGCGCTTTCGGCGTGTAGTGGGTCGCCGCCCGAGCCCGGCAAACGCCGGCCCGACACAAC
CCCGGAACAGGAAGTCCGGTCACCGCGCC TABLE 3-continued End sequences of the polynucleotide inserts cloned in the named recombinant BAC vectors contained in the I-1945 *M. tuberculosis* H37Rv genomic DNA library.

Clone Rv245
:::::::::::::Rv245SP6.seq:::::::::::::
GCTTCAGGACAAATTGNATCCCTATGCACCCGTTGTCACGCCGATGAGTGAAGACTGCACGCAATCGCCGGAATCCGGCAAAACCCTGCACAAGCGAAATCA
ACCGGAGGCTGACAAGGCAACGTCGGTGATCCGTACCGCCTGGTTGGACAAACGGCAGAAGGCGCCTCGTCCGGTCCATCTACGCCGAGCACACTGGTGATA
GCGCCATCGGCATCGGTGCGGCCACGGTGGAGACGAACGTCCGCNGGCGTCTGGGTCAGTAACCCGCCGACCAGTTCTCGGGCAAGCTGGTCAACATCGGGC
GCCACGTCTCCAAC :::::::::::::Rv245T7.seq:::::::::::::
GTTTGGCGGCCTTATTGCACTGAGGTCGTCAATTGACCCACAGCGGAAATGCCGACTATTCGCAGGCCTCCTTCGCCTTGGCTGCCGGAGATGGGCTCCGCG
GGAACCGCATGCAGGTATATGACCTCGGTTTCTCGGGTGCTACCGCGTGCCTTGTCGAGGATGAACTCGGCGTTGGAATTGTCCAGCCGGCCCAATTCATCG
AGCGCAGATTCGTACACATGGCCGGCGGCGACATACCTTCACCGTGGATCTGCTCCACACGGACCGCCCTGTCGGGATCTGCTCACGGGTAAAGGAATTA Clone Rv246
:::::::::::::Rv246SP6.seq:::::::::::::
GCGCACTCCTCCTTATCGCTCCGCTCTGCATCGTCGCGGCGCGGTCAGGTGCAAACGCCTTCGGGGGTGGGGGTCCTGCGGAGCACACCGGATACGGAGCGC
AACGCGTCGCGTTGTGCGGGCAAACAAGTGTGCAGGNNCCAATGCCATGTCCAGCAGCTTATCAGTGTCGAACGTGCGAACGTCGCGCCTTCGCCGGTGCCT
GAATCTCTACAAG :::::::::::::Rv246T7.seq:::::::::::::
CGCTGAAAGCCACCATTCGCGGGTCGGGCGCCGGGCTCGGGCCGCCAGGCTGCTCCGCTCGGTGATGGCACGCCACCGCGACACCACCCGGCTGCGCTACGT
CGAGCCATACCGGGCGGAGCTACATCGGCTCGGCCGCCTAGTGTTCGGGNCCTCTTTCGAGGTCGAGGTCGA Clone Rv247
:::::::::::::Rv247SP6.seq:::::::::::::
TGTAATTTGGGATGGGCAAAAAGCAAANCACCGCGTGGCCACAAACGCGGGGAGGGACAATCTCGGGCGGCTAGGGCTTCTCGCGGGAAGCCCGAAACGTAC
GGCGTTTCAACACGTCGCGTCGCCTCCGACGCGAAATTCGGG :::::::::::::Rv247T7.seq:::::::::::::
CTTGGGCAACATGCTGAGGATCGCCTTTTCACCACGCGGTCGGGGTGGCGTTGCATTAGCTCACCGATGGTGCGCTTGTTGCAGGCCGCCGGGATACCCGAG
TGCCGGTAAACCATCTTGTGCTGCAGTTTGTCCCGCTGATGGCGACCTTGTCGCGTTGATCACGATGACGAAGTCACCGCCATCGACATTGGGGGCGAACTC
GGCTTGTGCTTG Clone Rv249
:::::::::::::Rv249SP6.seq:::::::::::::
GCATGCTTCATTATCTAATCTCCAGCCGTGGTTTAATCAGACGATCGAAAATTCATGCAGACGGTCCCAAATAGAAAGACATTCTCCAGGCACCAGTTGAAG
AGGTTGATCAATGGTCTGTTCAAAAACAAGTTCTCATCCGGATTGAACTTTACCAACTTCATCCGTTTCATGTACAACATTTTTAGAANCATGCTTC Clone Rv24
:::::::::::::Rv24SP6.seq:::::::::::::
ATACTCAAGCTTGATGCCGCCGAAACCGAGCGTGAGCACGCCGCCAGCCACCACGCGCGGGTCGGGCGCCGGGCCCGGGCCGCCAGGCTGCTCCGCTCGGTG
ATGGCACGCCACCGCGACACCACCCGGCTGCGCTACGTCTATCCATACCGGGCGGAGCTACATCGGCTCGGCCGCCCATTGTTCNGGCCCTCTTTCGAGGTC
GAGGTCTATACCGATTTGCGCATCCG :::::::::::::Rv24T7.seq:::::::::::::
TCCGTACTGGTCGGGTACGCTTCGGTCGCAGTGTGCGAGTGATAGATGACGACCGGGACCTCGTCGGCATCTTCCATAGCCCGCCACACCTTCAGTTGCTCA
CCGGAATCCAACCGGTAGAAGGTCGGCGAGCGCTCGGCATTGGTCATCGGGATATGCCGCTCGGGACGGTCAGAACCTCGGGTCCG Clone Rv251
:::::::::::::Rv251SP6.seq:::::::::::::
GTTCTCGCACGATTTCGGATTAGCGGGATGGTCTCAATTGGGTATGCGGGGAAGGCGCTGACATTCGCCGCGATTAGCTGTTTGATGGACCGGGGGTGATTT
TTGATCACGGAAATGGGTGTTTATNCAGGTCGCACGCTTTCATCCGGGGCGGAACG :::::::::::::Rv251T7.seq:::::::::::::
GGGTGTGCCTGCTGTGTATGCACGGCATACGGACATCCTTCCCCTGAAGACCCGCGGTCGAACAGCCACGTGTCCATCATCANGGGGTCAACCCCGGCCAAG
GGCGACGGCACGCCAAGTTCGCCGACCGTTAACCTAGTGCTGTTAGCTTCATTTGCTGCGAGCAAAACAGCTGGTCGGNCGTTAGGAATGAATTGAAACTCA
ACCGATTTGGTGCCGCCGTAGGTGTCCTGGCTG Clone Rv252
:::::::::::::Rv252T7.seq:::::::::::::
ACTACCCGGCCAACGGTGATNTCTTGGCCGCCGCTGACNGCGCGAACGACGCCAGCGACCACATTCAGCAGATGGCCAGCGCGTGCCGGGCCACGANGTTGG
TGCTCGGCGGCTACTCCCANGGTGCGGNCGTGATCGACATCNTCACCGCCGCACCACTGCCCGGCCTCGGGTTCACCAGCCGTTGCCGCCCGCAGCGGACGA
TCACATCGCTTTTATTTNNTNTTCNGGAATCCCTCGGGCCGCGCTGGCGGGCTGATGA Clone Rv253
:::::::::::::Rv253SP6.seq:::::::::::::
ACGTCGGGANACTGTTCGCGTTCATCCTCGTCTCGGCGGATTGGTCTGCTGCGCCGGACCGACCGATCTTCAGCGGGGGGTCACGCTCCGTGGGGTGCCGTT
ACTTCCGATCGCCCAGTGTGCGCGTGCTGTGGCTGATGCTGAACCTCACCGCGTTGANTTGGATCGGTTCGGGATCTGGCTGGTGGCCGGAACGCNATTTAT
GTCGCTACGGGCGCCGGC :::::::::::::Rv253T7.seq:::::::::::::
GCTCAAAGGCACTACTGGCACCAAGGCCCACACGTCACCTGTGACTCCTGCGCCGACCCGCCCGAGGTCTGGCCGTTACACCGAACGGGCGAGCCGGGAGTT
GGTACCATCGAACAAGACAAGGTGCATGGGCGGAGTTGTTCCGCCACTTCGTCGATGACGGGTC Clone Rv254
:::::::::::::Rv254SP6.seq:::::::::::::
CGATACCGGCTGCTTACCGAGACATCCACCATGCCACCCGAATCACCGCACGCGCCGAAATCGCACAACAGCTTGACGCCTTGCAGGTTCCGCGATTGGAAT
TGCCGACGGTCTCTGACGGCGTCGACCTTGGCAGCCTCTACGAGCTCTCGGAATCACTTGCCCAGCAGGGGGTTCGATGAGTGTCACACCGAAGACCTCGAT TABLE 3-continued End sequences of the polynucleotide inserts cloned in the named recombinant BAC vectors contained in the I-1945 *M. tuberculosis* H37Rv genomic DNA library.

ATGGGCGCAATCCTGGCCGACACATCCAACCGGGTGGTTGTGTGCTGCGGCGCCGGTGGGGTCNGCAANACACTACCGCGGCCGCGCTGGCGTTGCGCGCGG
CCGAATATGGCCGCACTGTGGTCG

::::::::::::Rv254T7.seq::::::::::::
CGTCGTCGTCGTGGTATGCGATAGCCATCCCGTCGGGCTACTCGCCATCACCGATCAGCTTCGCCCCGAAGCCGCCGCGGCGATTTCCGCTGCGACCAAACT
GACCGGGGCCAAACCGGTATTGCTTACCGGCGACAACCGGGCCACCGCCGATCGGCTCGGTGTACANGTTGGCATCGACGACGTACGGGCCGGGCTACTGCC
GACGACAANGTCGCAGCCGTGCNGCNGCTGCAAGCTGGAGGTGCCAGATTGACCGTGGTCGGTGACGGTATCAACGACCTCCGGCCTTAGCGGCCGCGCATG
TCGCATCGCCATGGGCAGCGCCCGAC Clone Rv255
::::::::::::Rv255SP6.seq::::::::::::
GCACGCAATCGAAGTCACCCAAACCGGGCGGGCCAGGCGTCTNACGCCACGTCNACCAGCCGCAACCTCAACCCGGCCACGGCGAGCTCCTGATCAAGGCCG
AGGCCATCGGTGTCTACTTCATCGACACCRACTTCCGCTCCGGGCAATATCCGCGCGAACTCCCGTTCGTCATCTGCTCCGAAGTATGCGGCACGGTGGANG
CCGTCGGCCAGGGGTTAC ::::::::::::Rv255T7.seq::::::::::::
TCGACTGTGTGGCCACAGATCACGCCCCGCATGCCGAGCACGAGAAATGCGTCGAATTCGCCGCGGGCCGGCCGGCATGCTCGGGTTGCAGACGGCATTGTC
GGTGGTGGTGCATACAATGGTGGCGCCGGCTTGTTGANTTNGGCGCGATATCGCGCGGGTGATGAGTGANAACCGGCGTGCA Clone Rv257
::::::::::::Rv257SP6.seq::::::::::::
GAACCTGACACCCTGGTCACGGGTGAGCACGGACTTGATTTCTTCNCTATTGGTCGGCGCTGTTGAGCACACCACGCCGCTGACGGCCGTCGCGTCCTCGCT
GTGCTCGGTCTGGTGGAGCGCGCTGCCCGCGGCCNAACATCNTAAATCAAGCGTATTCGTCAACAGATATCATCAATGTCGGCGCTGGACTATTCAAATCAT
CGATATACTGGTGACCTGGTCCTTCGCCATCGATCAATGGCGATAGTCACGCAAATCGTCACGGACATCGTCGGCGTCCCAGCTGGCCCGTGCCAACAGATG
CTGCAACCCATCGGGGTGGTATCACCGCGGTGCTCGGCGATGGTCCACAATTCTTGCGGTCCAAGCCCNAAACATCCCGGGCATGAATTCACCGGCATGCGC
N ::::::::::::Rv257T7.seq::::::::::::
CTATCGTACCCGCGCCGGTCACCTTCTGGATATCGCCGGCCTGGTCAAGGGGGCGTCCGAGGGAGCCGGGCTGGGTNACAAGTTCCTGGCTCATATCCGCGA
ATGCGACGCCATTTGTCAGGTGGTGCGGGTGTTCGTCGACGACGACGTGACTCATGTCACCGGACGGGTCGATCCCCAGTCCGACATTGAGGTCGTCGAGAC
CGAGCTGATCCTGGCAGATCTGCAAACCCTGGAGCGGGCCACGGGCCGGCTGGAGAATGAAGCGCGCACCAACAAGGCGCGCAAGCCGGTCTACGAAGCGGC
ACTGCGTGCCCAGCANGTGCTCGACGCCGGGCAAGACGCTGTTCGCCGCGGGGGTGGATGCCGCCGCGTTGCGCGACTGAAACTGCTGACCACCAAGCCCTT
CCTGT Clone Rv258
::::::::::::Rv258SP6.seq::::::::::::
TACTCAAGCTTCAGGCCGCCACGTCCGCCGTCCGTCGGCGACGTGACCTCGAGCGCCGAGTTCGACTCGACATCGCCGCCGGCGCATGCCGACATGAACGCG
GCACTCACCGCAAGCCCGTCGGACGTCAGGTCGATCGACTCCGCTTCAAGCACCGGATCGTCCGGGCAACTCGCGGCCTCGGCCTGTGCGAACGGCACACCC
GTCGTGGCGGCNCCCCGCGCGGAACTGGGCTCATCACGGTCGTTGCGAGCCGGTCGCGTCACCGCGTACCGACGCCGTC ::::::::::::Rv258T7.seq::::::::::::
CCGACATCGAGTGGGCTCGCAGTGACTTGGCGACCTCCAAGCCACCGGTACCCGCCGCGCGGCAAGCCAAGGACGACGACGGCCTTGCCGGATAGCTGCGCC
AGGCGTTGCGCCAACTGGCGTCCAGCGTCGCCACGATCGTCAAAGAGCTTCATCTGCCGAGTGTGTCGCCATCTCATGGCTCCAAATATGGAATTAGGTCCC
TGGGCCGACTGACGACAGTCCCTCAGCGACCGGATTGCGCATCCCGCCTTGTACGCTACTCCGCAAATCCCGGGCTTGCGTCCGCGGAAGCGAACTCGGCGG
CGCTACGTGGTGGTTCACTTCGGCCGTGCGCACTCGGATCGACGGGCCGATGGTGGCCGGGCCCGCGCGCTTCTTGGTCATCCGATTGAGT Clone Rv259
::::::::::::Rv259SP6.seq::::::::::::
ATACTCAAGCTTGTCGCGGTAAACCGCACGCAGGGCGGTGGGTGCGGTGTCAAAGACACCCACACTTCTTTGCGGTTCGGTGATCTCGACACCGGCCGCGAG
CCGACCACCATGCGCGCGTAGATCGGCGATCAGCGCGTCGGCTATCGCCTGGGTGCCGCCCACCGGAATCGGCCAGCCGACCGAATGGGCCAGCGTTGCCAG
CATCAGTCCGGCGCCGGCCGACACCAGTGACGGCAACGGTGAAATCGCGTGGGCGGCAACGCCGGTGAACAACGCGCGGGCATCCTCGCCCGCCAACGACCG
CCAGGCAGGGTGCCTGGGCCATCATCCGCAGCCCGA ::::::::::::Rv259T7.seq::::::::::::
TGGACTCATAACGATCGGGTCAGCGACGCGCCAACACGAACGGCCGGACGAGTGGGCCAGGGTCGCGCCTCCCCTACAAACAGGATCCGTTGCCTGCGAGCG
ACAGGCTCCGGTGCGGCGTTGGGCGCCGTGCTCGTCCCAGCGTCCGGTCCCGGGTCGCCGGCGACGCTTGTTTCCTCCATACTCGCCCCCTAATCTCGAGGC
AGCCCGTACCCGCAGGCAACCTCCCAAAAATGCAATCCCCCAAAATGCAATGCGTCGAGCTATTTCTCACACCGACCGCTAGTTGCGGATCAGAAATCCGTT
GGGCGCGGAAGTCCAGCCGAATTTGTTCTCCCGCTCCGCATCATGCTTGTAATCGTTTGGAAATCATCCTCATATGCCTCGATCGCTTCATAGGTCAAGCCC
AAACCCGGCAGGATGGGTGGCC Clone Rv25
::::::::::::Rv25SP6.seq::::::::::::
CTTTACACTTTATGCTTCCGGCTCGTATGTTGTGTGGAATTGTGAGCGGATAACAATTTCACACAGGAAACAGCTATGACCATGATTACGCCAAGCTATTTA
GGTGACACTATAGAATACTCAAGCTTAGTGGTTGCGCACGTAAATTCGTCAGGTGACCGATCCCCTGCTGTCTCACTCGCCTCACAGCGACCACCACGGCTG
GCGCTCAAGGCGGGCACGTGCGGAGCAGATGAGGAATGTGCGACGTCTTGATGCAGCCTGTCAGAACACCGAGACCCTCGACGAACTTACGATCGAAACCGC
TTAGGCCAACCGGTGACGGGGGTGTCTTTCCGCGGCTAGGGCGCCTTATCGTCCGAAGGCCGTGGGTGGTGATCGCCTTCTGGGTCGCGCTTGCGGGTCTGC
TTGCGCCGACGGTGCCGTCCCTGGACCGATCTCCCAGCGGCATCCAGTGGCGATTCTGCCATCGG ::::::::::::Rv25T7.seq::::::::::::
CAGGCATGCAAGCTTGCGATGTATCAACACGCCGTTGCGCAGCGTGAGCCGATAGTTGACATCCGGCTCGGTGAAGGTGAAATCGATGGCCAGGTCGAGGTC
CCATGCGCGTGGGCCATTGATGCTGATCGCCAGGACGTCAAAGATTTGGTCCGGCGTCAGCTGGGCGAAAAACGTGGGCGCCGGGACTTGCCCGGAGCTGCC
CGGGTTCCCGTCGCGCAGCTCGGCGGCCCCGGTCAGAAAGAAATTGCGCCAGGTCGCACACTCCGCGCCGTAGGCCAGCTGCTCCACGGTGTCGGCATATAG
CCCGCGGGCCGCAGCGTGCTCGCTGTCGGCGAACACCGCATGGTCGAGAAGCGTTGCCGCCCAACGGAAATCACTGCGTCAAAGCTTCGCCGGGCCACTCCA
GCACTCCGTC TABLE 3-continued End sequences of the polynucleotide inserts cloned in the named recombinant BAC vectors contained in the I-1945 *M. tuberculosis* H37Rv genomic DNA library.

Clone Rv260
:::::::::::::Rv260SP6.seq:::::::::::::
ATACTCAAGCTTGACCGACGCTGATCGCACCGCACGCGGGAACCTCAAGGGCACTACTGGCACAAGGGCCCACACGTCAACCTGTTAACTCCTGCGCCGAC
CCGGCCGAAGTCCTTGGCGTTAACACCGAACGGGCCAACCCGGGAATTTGGGTTCCATCAAAACAAATAGCAGGTGCCTGGGCGGAGTGTTC :::::::::::::Rv260T7.seq:::::::::::::
GTCGTCGTGTGCTGGGGCGTCCGTATCAGCACGCCCACGAAATGGGGCACAAGAAGGATTCCTGGAACGGTGGCTGTCCAAGATCACCCTCGCCCAAAACTG
CTACGGGCACTTCTACATCGAGCACAACCGTGGCCATCACGTCCGCGGTGTCCACACCGGGAGG Clone Rv261
:::::::::::::Rv261SP6w.seq:::::::::::::
ATATGCCTTGCTGAGCTTTTCGGATCGCAGCGAGTCGTACCCGCGCCGGTCACCTTCGTGGATATCGCCGGCCTGGTCAAGGGGGCGTCCGAGGGAGCCGGG
CTGGGTAACAAGTTCCTGGCTCATATCCGCGAATGCGACGCCATTTGTCAGGTGGTGCGGGTGTTCGTCGACAACGACGTGACTCATGTCACCGGACGGGTC
GATCCCCAGTCCGACATTGAGGTCGTCGAGACCGAGCTGATCCTGGCAGATCTGCAAGCCCTGGAGCGGGCCACGGGGCGGCTNGAA :::::::::::::Rv261T7.seq:::::::::::::
GACACCCTGGTCACGGGTGAGCAGGACTCGATTTCTTCGCTATTGGTCGGCGCTGTTGAGGCACAGCACGCCGCTGAGGCCGTCGCGTCCTCGCTGTGCTCG
GTCTGGTGGAGCGCGCTGCCCGCGGCCGAACATCGTAAATCAAGCGTATTCGTCAACAGATATCATCAATGTCGGCGCTGGACTATTCAAATCATCGATATA
CTGGTGACCTGGTCCTTCGCCATCGATCAATGGCGATAGTCACGCAGATCGTCACGGACATCGTCTGCGTCCCAGCTGGCCCGTGCCAACAGATGCTGCAAC
CCATCGGGGTGGTATCNCCGCGGTGCTCGGCGATGGTCCAACAATTCTTGCGGTCCAAGCCCGAAACCATCCGGCCATGAGTTCACCGGCATGGCGCAACGG
CTGGTGCCGGGCAAAACGCGGCGCGATCGAATTC Clone Rv262
:::::::::::::Rv262SP6.seq:::::::::::::
TGTAGAAGGTGGGTCCCGTCCAACTTCGCGGCGGCGGCGCGATATGCCTTGCTGGTCTTGCTCATTTGATATCCAATCTATGGGTCGTGGTTACTCAACGGG
CCGAAGCTGGCCCTCCCACGGGTAGGGTCCTATTCGACGGTGATGTCC :::::::::::::Rv262T7.seq:::::::::::::
CCCGAATCCGGTGGCCGGCAGGGGGCCTGGCGACGTGGACACCTTCTAACTTGTCTTTACCGGTCACTGTTGCACCCCAACACCTTTAACGACGTGGACGGA
CGTTACATCGGATTCGACGGTGTCATCCACAGCGTTGCCATTGGGCACACCCACTACGCCAATTTCTCCGACTGGGACACCTACCGCAGCCTCGCCCCACTG
CAGGGACTGTTGTTCCCGCAACGGGCCATCGACATGATCCAGTCGTTGGTGACCGACGCGGAGCAGACTGGTGCGTATCCGCGTTGGGCGCTGGCGAAATTC
CGCCACCGGCATGAT Clone Rv263
:::::::::::::Rv263SP6.seq:::::::::::::
TTGAGATGCTGGTCGGGATGCCGATGGTTGGAACATGGTCCCCTGGCGTCGAATACGCGCGAGCGCATGAGCTCACCGGTTCGGAACAACGTATCGAAGAAC
TCGCACTGCTGGCAGATGGTATCTCCGATGTGGTTGTAATTTGTATCCCAACTCTAACTGTGCTATCGGATCTGCGTGAATA :::::::::::::Rv263T7.seq:::::::::::::
CGTAATCACGATCCCGCTGAGACACTTGACCTTACGGCCGAAGTGACTTCGCTGCTGCTATGCCGACACCCGATTTCCATACGCTGCTGTACACGACGGCCG
GGCCGGTGGCCTCCATCACGCTCAACCGCCCGGAACAGCTCAACACCATCGTCCCGCCCATGCCCGACGAGATCGAGGCCGCTATCGGGTTGGTCGAACGCG
ACCAGGACATCAAGGTCATCNTNCTGCGCGGTGGCGGGCGCGCCTTCTCCGGCGG Clone Rv264
:::::::::::::Rv264SP6.seq:::::::::::::
CAAGCTTAAGCTGGTTCCGGCCACTCCATGAGCCGTAGTGCAATGGTTCGTGCACGGCGAGGCCGAACTTGCCATAAACATCCCTGACGAAAGTCTCCGGCA
AGCCGATTGCTTCTTCGGGCCGCTTCTTGTGGATTGTCCGATAACCCGGTCCCTCATGCTGGAAGTTGTGCGCACTCTTTCCTTCCGCGATGTGGGCTAACG
ACTCGTCATTGAGCAAGAAGTACGTGCACAGGCATCGTCCGCCGGGCTTCAGCACGCGGGAGATCTCGTCCAGATAGTGCTCCACGTCCGGNGGGAAACATG
TGGGTGAACACCGAGGTNAGAAACACCNCATCCAACGACGCATCCGGGATATGGAAAGCGAAA :::::::::::::Rv264T7.seq:::::::::::::
TATGGTCTTCGTCGACCAGTACGTCGTAGGCGCCATGAGCCAGCGACTGAAGCCGCGCCATGCCTGCACGGCCCGCTCATCCAGCGAGGCGGCCATCTCCCG
CAGATAGCCTGCCGCCTCGGCGCGCACGCTGTCCGGATCGCGTCCGAGCTCGTCGGCCAGCGCACGCAGCCGCTCGTCATACCATCGGGCATCCAGCAGTTG
GGTAACCTCAACGGGGTCGGTCGCTAGCGGCGTCATTGATTCAGCAACAATACCGATGCGCTGCAGCAACTTTCGCAGTCCGATGCGGCCCACCTCCCGTGC
AGTCACTGGCTAGCCCCCGTCATGCCGGTTGTGTCGATGGCACGGCAGCGGGCTCGTAAACCTGCGGTCTCAGCTCGCTGG Clone Rv265
:::::::::::::Rv265SP6.seq:::::::::::::
GCTTAGCGGTCTTGCTCGAACCGACATTGCGTGCCACTCATGAGCGGGTGGCGGTCGCGGTGCTTACACATCT :::::::::::::Rv265T7.seq:::::::::::::
GTATCTGGCGCCTCTCGAATATCCTTGAACGTCCCGCGGTGCCACCCAGATAGATCGCAGCGCCCTGCAATGGAGTTCCCTTTATGGCCTCTCTAGCCTCCC
GCTTGATCGGCTCGACCCGAGAGATGCCCTCGGGCGTTGCGGGATCTCCCTCCA Clone Rv266
:::::::::::::Rv266SP6.seq:::::::::::::
CTTCACGCCGATCCGCGACCGCGAACGCGACGGTGACGGTGGGCGACAAGGTTCGGTTGGTCGCCGCGGCGCTGGGCGATATCAGCTCACCCGGTTTCGAGG
TGTTCGGCGACCGGACGGTGCTGCAGACATTCTTGAGCGTCCTCGACCGGCCCGATTCGGCCTTCAACATCGTGACGCCGTATTTCGGCGGTACCGCTCGGC
GCCGAGTCGAAGGCGGCCTGAGCTAAAGCCGGGCATTGCGCGAGTGGTAAACAAGTTCGGTGACTTCGGTTGACCGACTCGACGGGCTCGATCTGGGCGCGC
TGGACCGGTATCTGCGTTCGCTGGGGATCGGGCCNACCGCNANTTGCGTTGCGANCTGATTCCGGTGGAGCTCCAATCTGACTTCCGG :::::::::::::Rv266T7.seq:::::::::::::
GCAGCTACCGACCCTAGCGACGAGTGTGTTCGCAGCGTCGAATGTGAACGTTCGGCGTGATTCGGCGCGCGGGTTCCCGCTCTCAGCGCACGTTCGGCGCCG
AGGNGGCTAGTCCCTGGTTAAGCAATGTCTCGGTCGCCGCCAGCAGCGCGCATGTCGCCAACCCGTCNACCGCGTTGCGCATGTCCGGTACCGACGGAAACG
ACGGCGCGATCCGGATGTTCTTGTCGTCCGGATCCTTTCGATACGGGAACGACCCCCCGCCTCGGTCACCGCGATACCAACGTCCTTAGCCAANGCTACNGT
CCGGCGCGCGGTCCCGGGCAACACGTCGAAGCTGATGAANTAACCACCCTTGGGCTCGGTCCAAGANGCGATCTTGGACTCCTTAACCGCTGATNCAA TABLE 3-continued End sequences of the polynucleotide inserts cloned in the named recombinant BAC vectors contained in the I-1945 *M. tuberculosis* H37Rv genomic DNA library.

Clone Rv267
:::::::::::::Rv267IS1081N60.seq:::::::::::::
TCCCCATCGGCGCCGGACCGTTTGAAAGTCCAAGCACGGGTGGGATGGAATCGACGACAGTTGAGCGCCGTCGGTGGCCGTGGTCAGCAGCTGTTCGCGAAC
GCACCAGGTCACATCCCTTCGACATCTCACCGACGTGGCACGGGCGACATCAACAGGAAGATTGACGAATCCCTCGCAGGCGCGGCACGTCCGCAGGCCAAC
GCCAACTACGGGGCCACCAGCGATCCTCCGCTCACGCACCAGCCCAAGCCAGGCTCANCCACCCAAGTCGGCCCGCGCTCTCCCTCGCCCCCTGGTCTCCGG
GGCCTTGTTAAACAACTACCGGAAGTCCACCAATCCTCGCTGCATCTCGACACCGTCCGCCTCACTCCCTTCCTCCCGCCCCTCTCCACACNACACACCTCT
TGCATTAAGGTCACGGAGCGGTCACTTTTCGTCGGACGAAATTCGCAATCCGGCCGCTCGCCGCCAGAGAT :::::::::::::Rv267SP6.seq:::::::::::::
CGGAAAGTGGATACTCCCAGCAGGTAGCAGGTCGCCACCACGCTGGTCAGTGCGCGTTCAGCTCGCTTGCGGCGCTGCAGCAGCCAGTCCGGGAAATAGCTG
CCCTGGCGCAGCTTGGGGATCGCGACGTCGATGGTTGCGGCACGGGTGTCGCAAATCACGGTGGCGGTAGCCGTTGCGCTGATTGGACCGCTGATCGCTGCG
TTCGCGGTAGCCCGCCCCGCACAGGGCGTCGGCTTCAGCCCCCATCAAGGCGGCGA :::::::::::::Rv267T7.seq:::::::::::::
GGCCGAGTCCAGCACTTCGCACTATGTGCAGACCAAANACCCGGTGGTCGCCGCGCTGCGGCAGCGGCTGGCAACGGCGCCGGTGATCACCGAGTGGTGCGN
AGTTGCCGACCGGCAGTTCGCCGCGGGCTTACTACGAGAAGGGCCTGCGCGACGTCATCAGGTATCACGTGTCGATGACGTCGAGCGTTAACTTCCCCGACC
AGACGGCGACCTCGCCGATGGACCCCGCGTTGTACCTGGTGTGGGCGCAAGCTAACGCCGCCGCANGCTATCGGTACTCGGTCGAAGCGCAGCCGGGGTCGC
AAGCGCTAGCGGGCAAGGTCGCGACGATCTCGGTCACCTGGACCAACTACGGCGCTGCTGCCGCCACCGAATAGTGNGTGCCCGGCTACCGGCTGGTGGATT
CCACGGGACATGTGGTTCGGACCTGCCGGCAGCGGTGGAACTGAAGANGCTGGTCT Clone Rv268
:::::::::::::Rv268SP6.seq:::::::::::::
AGCTTCAAGGACATCGTCATCGCGACCAAAACCGCGAGCTAGGTCGGCATCCGGGAAGCATCGCGACACCGTGGCGCCGAGCGCCGCTGCCGGCAGGCCGAT
TAGGCGGGCAGATTAGCCCGCCGCGGCTCCCGGCTCCGATTACGGCGCCCCGAATGGCGTCACCGGCTGGTAACCACGCTTGCGCGCCTGGGCGGCGGCCTG
CCGGATCAGGTGGTATATGCCGACAAAGCCTGCGTGATCGGTCATCACCAACGGTGACAGCAGCCGGTTGTGCACCATCGCNAACGCCACCCCGGTCTCCGG
GTCTGTCAN :::::::::::::Rv268T7.seq:::::::::::::
GCTCGCGGTCCAGCAGCAGACGTGTCTGACCCCGACGCCCGGCCGCCGGTACCGAAACCGGATCGGCCCGCCGATGGCCGCGGCCACGGCGTCTGCCTTACC
CGGCCCGGATACCAGCAGCCACACCTCGCGGGAACGCTGAATCGCCGGCAGGGTCAAGGTGATTCGGCGTGGCGGCGGTTTCGCGAATCGTCCACCGCCACC
ACCATGCGGGTGCTCTCGAAGACGCGGGGCTGTGCGGGAACAGCGAGTTAATGTGGCCCTCGGGCCCCATGCCCAGCAGGTGGACGTCGAAATTCGGCCCGG
GTCACCTGGTGCGGCACTGGCGGCC Clone Rv269
:::::::::::::Rv269SP6.seq:::::::::::::
AGCTTGTCGATCGTCCGGCAGCGTCCGGCGAGTCAAGTCGAAGCCAGTCCGGTCTCCTCTCCGACTACGGCCAAGAACTGGGCGACGGTGTCAGTGCATACC
AGCGCANACTGGTGGCGCCCTAGGCGAGCGACCGCCTCACAAACGGCGGTGACCGCGTTCTGGTCGTGCACCATCGAGCCGTGCCCATCCCGGCCGCGTGCC
GTCAGCCGCATCCACTGGATGCCCTTCTCGGCGGTTTCAATCAGGTACAGGCGACGTTCGCCANCATCGTGCCGGGGCANGG :::::::::::::Rv269T7.seq:::::::::::::
TTGGTGATCATCGNCCCAACGACCCGAGGCGATGTTCTTGCACACCGAGGAGTGTCGCAAGCTGGGGTGGCCTTCGCCGCCGATCCGTCTCAGCAGCTGGC
GAACGCTGTCGGGGTGAGGAAATTCGCAGGCTCGTCAACGGTGCTGCTTACTTGTTCACCAACGACTACTAATGGGATCTGCTGCTGTCCAAGACCGGCTGG
TCAGANGCCGATGTGATGGCGCAGATCGACCTGCGGGTGACCACATTGGGTCCTAAGGGTGTCGATTTGGTAGAACCTGACGCACCACCATCCACGTCGGCG
TTGGTCCCCGAAACAGCCAGACCGA Clone Rv26
:::::::::::::Rv26SP6.seq:::::::::::::
GGCTCGTATGTTGTGTGGAATTGTGAGCGGATAACAATTTCACACAGGAAACAGCTATGACCATGATTACGCCAAGCTATTTAGGTGACACTATAGAATACT
CAAGCTTGATTTTGATCATCATGATGATCATCACCCGAAGTGTGGTAGCCGCAGTGGTTATCGTGGGTACCGTCGTGCTTTCCATGGGCGCCTCTTTCGGGC
TTTCCGTATTGGTCTGGCAGGACATTCTGGGTATCGAGTTGTACTGGATGGTGTTGGCGATGTCGGTGATCCTGCTCCTGGCGGTGGGATCCGACTACAATC
TGCTGCTGATTTCCCGGTTGAAAGAGGAAATTGGGGCCGGATTGAACACCGGAATTATCCGTGCCATGGCTGGTACCGGGGGAGTGGTGACGGCTGCCGGCA
TGGTGTTCGCCGTTACCATGTCGTTGTTTGTGTTCAGCGATTTGCGAATT :::::::::::::Rv26T7.seq:::::::::::::
CAGGCATGCAAGCTTGGCGTGCCGTTCCAACCCGAATTGGCTTTCGGCGCCATCGGTGAGGACGGCGTGCGGGTGCTCAACGACGACGTCGTCCGCGGGACA
CACCTCGATGCTGCCGCCATGGACGCGGTCGAACGCAAGCAGCTGATCGAGCTACAACGCCGCGCGGAACGCTTCCGCCGCGGGCGTGACCGCATCCCGTTG
ACCGGGCGGATCGCGGTGATCGTCGATGACGGCATCGCCACCGGAGCGACGGCCAAGGCGGCGTGCCAGGTCNCCCGGGCGCACG Clone Rv270
:::::::::::::Rv270SP6.seq:::::::::::::
GGCATCTTGGCCGCCATGTTAGCCACACTGCCACCGGCTATAGAAGCGATGCGCACCGTCCTGCCAGCACATTGCGGCGCTCCTCCCTGGAAAGCAAGATAA
CCAAGCTCATGCCGTGGTTGTGGGTGGCGTGGTTTGGTTTGGGTAACTTTGG :::::::::::::Rv270T7.seq:::::::::::::
TCGGCTAATAATCGTCGACGCCGGCCTCCTCTGCAATCGCCTTGGCGGTCGCCGGGTTGTCACCGGTGATCATCACGGTGCGGATGCTCATTCGGCGCATTT
CGTCGAATCGTTCCCGTATGCCCACCTTGACGATGTCCTTCAGATGGACGACGCCGATGGCCCGCGCGCTGCTGTTATCGGTCCATTCCGCAACGACTAGGG
GTGTCCCCCGCCGGAGCTGATGCCGTCGACAATGGCACCCACCTCCTCGGTGGGGTGGGCACCGTGATCGCGAACCCACTTCATCACCGCAGCCGCGGCACC
TTGCGGATTCGACGGATG Clone Rv271
:::::::::::::Rv271SP6.seq:::::::::::::
CTCAAGCTTGGAGGCGTGGCGATCGCGGTCCAAGGCGCGCTCTCCGAGCACAACGAGCGAAGACNGCTCGGCGACGGAGCCTTTATCGACNTCCGTTCGGGC
TGGCTGACGGCGGCNAAATAATGCTGGACTCGTTGTTGTCGACGGTGCCGTGGCGAGCCGAGCGCCGTCAGATGTACGACCGGGTGGTCTATGTGCCGCGGT
TGGTGAGTTTCCACGACCTGACCATCGAAGATCCGCCGCATCCGCTGCTGGCGCGGATGCGCCGGTGGCTCAACTAATTCTACGGCGGCGAACTGGGTNATC
CCTTCNCCACCGTCGG TABLE 3-continued End sequences of the polynucleotide inserts cloned in the named recombinant BAC vectors contained in the I-1945 *M. tuberculosis* H37Rv genomic DNA library.

::::::::::::Rv271T7.seq::::::::::::
CCTAGGTCAACCGTACCGTCATCGGATCGGGGTCGACCGCACAGATGGACTGGAGCTTCGGCGAGGTCATCGCCTATGCCTCGCGGGGGGTGACGCTGACCC
CGGGTGACGTGTTCGGCTCGGGCACGGTGCCCACCTGCACGCTCGTCGAAGCACCTCAGGCCACCGGAAATCATTCCCGGGCTGGCTGCACGACTGCGACGT
GGTCACCCTCCAGGTCGAAGGGCTGGGCGAGACGATGCAGACCGTCCGGACGAGCGGCACTCCTTTTCCGTTGGCTCTTCGGCCGAATCCGGACGCCGAACC
CGACCGGCGCGGGGTCAACCCGGCACCGACGCGGGTGCCGTTTACCCGCGGGCTGCACAAATCCCGACGGGTATGGGCTTTGACCTGCCGACGGGGA Clone Rv272
::::::::::::Rv272SP6.seq::::::::::::
AGCTTGGCGTGACACCAACACAGGGCACTTAAGATGGCAATGCGCCGCCTACCTGCACGTTTTCGCGATGTCAGAGGATGCCGAGGGGAGAACAATGCGAGC
ACGGCCGCTGACGTTGCTCACCGCTTTGGCGGCGGTGACATTGGTGGTGGTTGCGGGCTGCGAGGCCCGAGTCTAGGCCGAAGCATATAGCGCGGCCGACCG
CATTTCGTCTCGACCGCAAGCGCGACCTCAGCCGCAGCCGGTGGAGCTACTGCTGCGCGCCATCACGCCGCCTAGGGCTCCGGCGGCGTCGCCGAACGTCGG
GTTTGGCGAACTGCCTACCCGGGTCCGGCAGGCAACCGAT ::::::::::::Rv272T7.seq::::::::::::
TCATGCCGTTGGACCGACCATCGGAGTTAGTTGCCGAACCGCGGGACCACCGCAAGCACCCGGTCCTGGTCGCGCACCGCGTCGGCCAACCGCTTGAGCACC
ACCACGCCGCAGCCCTCGCCGCGCACGAATCCATCCGCGTTGGCGTCGAAGCTGTTGCATCGGCCGGTCGGTGACAGCGCCGACCACTTGGACAGCGCGATG
GCGGTGAACGGTGACAAGGTGAGCTGCACCCCGCCCGCCAATGCCACGTCGGTTTCACGCAGGCGAAGCTCTGACACGCCAAGTGAATTGCCACCAGCGACG
ACGAACAAGCGGTATCTACGGCGATGG Clone Rv273
::::::::::::Rv273SP6.seq::::::::::::
GGGTCGACTTTCTGCAAGGCGAGGCTACACCGTCGTCGTCGTGGTATGCGATAGCCATCCCGTCGGGCTACTCGCCATCACCGATCAGCTTCGCCCCGAAGC
CGCCGTGGTGATTTCCGCTGCGACCAAACTGAACGGGGCCAAACCGGTATTGCTTACCGGCGACAACCGGGCCACCGCCGATCGGCTCGGTGTTCAGGTTGG
CAT ::::::::::::Rv273T7.seq::::::::::::
AATCCGAAATCCTGACCGATACTTGAACCTGGTCTCGTTCGGCAATAACTCGTCGGCGTGCAGGACGCGGCGCAAACGTACTTCGGCATCAACGCGTCCGAC
CTGAATTGGCAGCAAGCGGCGCTGCTGGCCGGCATGGTGCAATCTAACAGCACGCTCTTCCCGTACACCAACCCCGACGGCGCGCTGGCCCGGGCGGAACGT
GGTCCTCGACACCATGATCGAAAAACCTTCCCGGGGAGGCGGATGC Clone Rv274
::::::::::::Rv274SP6.seq::::::::::::
TTCCGAATTTCGGGTCCNGGTCATATGACCCTCATGGAAGAAGAAGCGGCCGCCCCGCGCCCGTGCGACGGCGAATGAAAACCCTCACCCAGGCCGCATTGA
ACGCCGACAAGACGGTGGAGCAGGTCGAAGACGTCCTGGACGGTCTGGGTAAGACCATGGCCGAGCTGAACAGCTCGCTGTCACAGCTGAACAGCACCGTGG
AGCGCTTGGAGGACGGTCTGGACCATCTCGAAGGTACCCTGCACAGCCTGGACGATCTCGCGAAACGGCTCATCGTGTTGGTCGAGCCGGTGGAAGCCATCG
TCGATCGGATCGACTACATCGTGAGCCTCGGCGAAACGGTGATGTCACCGCTGTCGGTC ::::::::::::Rv274T7.seq::::::::::::
NCTCGATCTTGGGGTACGTTCGATGAGGCTGCTGACCAACAACCCGGCCAAGCGGGTGGGACTGGATGGATACGGATTGCACATCATCGAGCGCGTGCCGCT
GCCGGTGCGGGCCAACGCGGAAGAACATCCGTTACCTGATGACCAAGCGTGACAAATTGGGGCACGACTTGGCTGGGTTGGACGATTTTCACGAATCCGTGC
ATCTGCCCGGAGAATTCGGCGGTGCCTTGTGAAGGTGGCGCCGGGGTGCCGGATCTGCCGTCGCTGGATCGTCTGGTGTGCGGCTGGCGATTGTCGCCAGCA
GCTGGCACGGAAAGATCTGCGACGCGCTGTTGGACGGCGCCCGCAAGTGGCCGCCGGGTGTGGCCTCGATGACCGACTGTGGTTCGGGTGCTCCGCGCGATC
GATAT Clone Rv275
::::::::::::Rv275SP6.seq::::::::::::
TCATCCCGACCAAAACGCGAGCTAGGTCGGCATCCGGGAAGCATCGCGACACCGTGGCGCCGAGCGCGCTGCCGGCAGGCCGATTAGGCGGGCATATTATCC
CGCCGCGGCTCCCGGCTCCGAGTACGGCGCCCCGAATGGCGTCACCGGCTGGTAACCGCTCTTGCGCGCCTGGGCGGCGGCCTGCCGGATCAGGTGGTAGAT
GCCNACAAAGCCTGCGTGATCGGTCATCACCAACGGTGACAGCAGCCGGTTGTGCACCAAGCGCGAACGCCACCCCGGTCTCCGGGTCTGTGGAACCGATCG
ACCGCCCAAGCCCACATGAACAAACCCCGGCATCACGTTGCCGATCGGCATACCGTGA ::::::::::::Rv275T7.seq::::::::::::
TTGGCGGGTTGGCCCAGCAGCCCGCCGGTGACGGCGACGATGCTGGGCTGGTTGCGGCCCTGCGCCACCGCGGCTTGCATGCTGGTTGGCTGTCTTGGGACG
ATCCCGAAATAGTCCACGCGGATCTGGTGATTTTGCGGGCTACCCGCGATTACCCCGCGCGGCTCGACGAGTTTTTGGCCTGGACTACCCGCGTGGCCAATC
TGCTGAACTCGCGGCCGGTGGTGGCCTGGAATGTCGAGCGCCGTTACCTACGTGACCTGATGGATCGGGGGGTGCCGACCGTGCCCGGCGATGTGTATGTGC
CGGGANAGCCGGTCCGGTTGCCACGCAAAGGCCATGTCTTCGTCGGTCCGACCATCGGTACCGGGACACGGCGCTGTATTGCCCGGTTCGCTGCCGAGTTCG
TCGCGCAACTGCACGCNGGCGGGCCAGCGGTGCTCGTTGANCCCGGAGGTTCCGGTGACGATGATCGTGTTGGTCTCCCT Clone Rv276
::::::::::::Rv276SP6.seq::::::::::::
GTAGGAGAGAACAAAGACCGTCGATAGGACACGTGTTACGCCGGTAGCTGTCATTGGTATGGGGTGCCGCTGCCGGGGGGCATCTACTCACCCGATCGGTTG
TGGGAGGCGTTGCTGCGGGGCGACAATCTGGTCACCGAGATCCCCGCCGACCGCTGGGACATCTACGAGTACTACGACCCCGAACCCGGCGTGCCCGGACGC
ACCGACTGCAAATGGGGCGCGTACCTCGATAACGTCGGCGACTTTGATCCCGAGTTCTTCGGGATCGGGGAGAAAGAAACGATAGCGATCGATCCGCAGCAC
CGCTTGTTGCTGGAAACCTCCTGGGAAGCCATGGAACACGGCGGGCTAACACCGAACCATATGCCTCCCGACANGGGTTTTCGTGGGGTT ::::::::::::Rv276T7.seq::::::::::::
CGAACTGAGCCCATAGAAAGGCAGCGACTAATTCGCTGGGCAAATAGGAAGACCCTTTGTCCTGCCACGTATATTTGTCGACCTCGTTGCGAAGGAAGCGGC
TGCGATTGGTGCCCTTTTCCCTGGAGAATCTCTGCCCGGAGCAGGAAGTCTTATGAGTTGACAAGCAGGGGCGCCGCCTTCGCCGGAAATCACATTCTTGGT
CTCGTGAAATGAGAGCGCTCCCAGGTCGCCGATGCTGCCGAGCGCCCGCCCACGATACGACGCCATCGCGCCTTGGGCCGCGTCTTCGACCACCGCCAGGTT
GTGGTGCGTGGCGATCTTCATGATCGCGTCCATCTCGCAGGCCACCCGGCATAGTGAACGGGGACCATGGCCTCGGTTCGCGGGTGAA Clone Rv277
::::::::::::Rv277SP6.seq::::::::::::
CTTAGACGCCACCTCCGGGCCGAGCTCCACGGGGTGGATAAGTACGGCCGGATGTGGCCGCAATGGGAAGTTGTTGCCCGCTTGACTGTCCGGGTTAACGCC
GGATTCCACCACATCCCCTTGCGAAAGGCCGTTGGGTT TABLE 3-continued End sequences of the polynucleotide inserts cloned in the named recombinant
BAC vectors contained in the I-1945 *M. tuberculosis* H37Rv genomic DNA library.

::::::::::::Rv277T7.seq:::::::::::::
GATCGCGATCGTCGATGTGGCCATCCGGCTTGGCGTCGACCCGCGTAAGGCAGACCAGATGGTTCGCGGCACGGTCAACCTGCCACACGCACTGGTAAGACT
GCCCGCGTCGCGGTATTCGCGGTTGGTGAAAAGGCCGATGCTGCCGTTGCCGCGGGGGCTGATGCTGTCGGATCGACGATCTGATCGAGAGGATCAGGGCGG
CTGGCTGGAATTCGATGCCGCGATCGCGATACCGGATT Clone Rv278
:::::::::::::Rv278SP6.seq:::::::::::::
AGCTTACGCCGCTTTCGCTTCNGATTTGGGACGCCGCATCGAAAGCGCAGTTGGAAGCGCGGCGCCCGGCTGGTCGAGCTGCTCAAGCAGCCGCAATCCCAG
CCCATGCCCGTTGAGGAGCAAGTGGTTTCGATCTTCCTGGGCACCGGCGGTCACCTGGACTCGGTGCCCGTCAAGGATGTCGGCGGTTCGAAACCGAATTAC
TGGACCACATGCGGGC :::::::::::::Rv278T7.seq:::::::::::::
CGACGGGACCTCGTCGCATCTTCCATAGCCCGCCACACCTTCAGTTGCTCACCGGAATCCAACCGGTATAAGGTCGGCGAAGCGCTCGGCATTGGTCATCGG
GATATGCCGCTCGGGACGGTCAGATGCCCTCGGGTCCNGCCAGCACTCCTCAGGCTTCGTCGGGGTGGTCGCGACCGCATGGGCCACATCGCATTCACCAGG
TCTGCGCGAATCACCAGCACGTANACGGTTCCTTTCCTAAGCAACACCGAAATTTCAGGACCCGAATGCTCCGGGAAAACATGTCACGGTAAGTCCGGTATT
CCGGGTACCGGTTGAGCATTGA Clone Rv279
:::::::::::::Rv279SP6.seq:::::::::::::
CGGCATCGGTTTGGGCTGTCACCAGCAGTTGGTAGTTCTTCACTACTGTTGTTCGAGCGTCGAGCCGCCGCGCGTGTCGAGGTCGCCGGACGCGTACCCGCC
AGGCCGGTCAGGGTGCCCTTCCAGTCCACGCNGCTGTGGTCGGCTAACCGCTTATCTTCAATCGAGACNATCGCCAGCTTCATCGTGTTGGCGATCTTGTCC
GAGGGCACCTCGAACCGGCGCTGCGANTACAGCCACGCGATCGTGTTGCCCTTCGCGTCGACCATCGTCGATACCGCAGGCACTTGCCCCTCGAGCAGCTGG
GCCGATCCGTTGGCAACGACCTCAGAGGCACGATTGGACATCAGCCCTAGCCCGCCTGCG :::::::::::::Rv279T7.seq:::::::::::::
CCGTCGANGCCGCCGACTTGGCTTGACCGACACCAACATGGCCTGAGGGTGTTCAACAAGACCGTGGCCGACGGGCTGAACATCACCATGAGCGGCATGAGC
CACGCCACCGAGTTCATCATGTTGATCGCCGAAAACCATTGGCGGGTAGCGGAAGAACGGTCGAGGTGCTCTACACCGAGTATTCGAAGTCGAAAGGCCAAC
CGCTGCTCAACGGCGTCAACATCATTTTCGACGGGTTTCTGCGAGGGAGGATGCCACGATGAACTGGATCCAGGTGCTGTTGATCGCGTCGATCATCGGGTT
GCTGTTCTACCTGTTGCGGTCGCGCCGAAGCGCGCGGTCCGTGCCTGGGTCAAGGTGGGCTATGTCTTGTTCGTGCTCCCGGCATCTATGCCGTGCTGAGA Clone Rv27
:::::::::::::Rv27SP6.seq:::::::::::::
TTACACGNCCTGCTTCCGGCTCGTATGTTGTGTGGAATTGTGAGCGGATAACAATTTCACACAGGAAACAGCTATGACCATGATTACGCCAAGCTATTTAGG
TGACACTATAGAATACTCAAGCTTTTTGAGCGTCGCGCGGGGCAGCTTCGCCGGCAATTCTACTAGCGAGAAGTCTGGCCCGATNCGGATCTGACCGAAGTC
GCTGCGGTGCAGCCCACCCTCATTGGCGATGGCGCCGACNATGGCGCCTGGACCGATCTTGTGCCGCTTGCCGACGGNGACGCGGTANGTGGTCAAGTCCGG
TCTACNCTTGGGCCTTTGCGGACGGTCCCGACGCTGGTCGCGGTTGCGCCGCGGAAAGCGGCGGGTCGGGTGCCATCAGGAATGCCTCACCGCCGCGGCACT
GNACGGCCAGTGCCGCGGCGATGTCNGCCATCGGGACATCATGCTCGCGTTCATACTCCTCGACC :::::::::::::Rv27T7.seq:::::::::::::
CAGGCATGCAAGCTTTGTCACACCAAGTGTTTCGACCAGGCGCTCCATCCGGCGAGTGGATACTCCCAGCAGGTAGCAGGTCGCCACCACGCTGGTCAGTGC
GCGTTCAGCTCGCTTGCGGCGCTGCAGCAGCCAGTCCGGGAAATAGCTGCCCTGGCGCAGCTTGGGGATCGCGACGTCGATGGTTGCGGCACGGGTGTCGAA
ATCACGGTGGCGGTAGCCGTTGCGCTGATTGGACCGCTCATCGCTGCGTTCGCGGTAGCCCGCCCCGCACAGGGCGTCGGCTTCAGCCCCCATCAAGGCGG Clone Rv280
:::::::::::::Rv280SP6.seq:::::::::::::
AGCTTAGCCAGTTTTTCTACTCTTGGGCCCACACCCACAGTGCTTCGACGGTACGGTCACCCATGATGGCCATCCAGTTGGCATCGGTGAGCTGATAAATGC
CAGCTGGTTTCGCCAACCCGGTAGCGATCTTGGCGCGCTGCTTGTTGTCACTGATACCTATCGAGCAAGACAGCCCGGTTTGCGACAAGATGACTTTTCGGA
TCTCTTCGGCGACTTCGATGGGGTCGTCGGGAGTCCCGGGCGCCACCGCGAGGTAAGCCTCGTCCCAGCCCCATACCTCGACCGGGTATCCCAGGTCGCGCA
ATAACGCCACCACCTCCTCGGACGCCGCGTTGTAGGCGGCTGGGTTCGACGGCAAGAAGTGGCCTCAGGGCATCGTCGGCGCGGTCCCAACGGCNTGCCGGC
GCGCACACCGTAGGCGCGGGGCTC :::::::::::::Rv280T7.seq:::::::::::::
CCGGCGGAACTCAGACGTGCTGGTGGTGCGGCATGGCACCGCGGGCAGCAAAGCGCACTTCTCCGGGGACGACAGCAAGCGACCGCTAGACAAGAGGGGTCG
TGCGCAGGCAGAAGCGTTGGTACCACAGCTGCTGGCGTTCGGCGCCACCGATGTTTATGCCGCCGACCGGGTGCGCTGCCACCAGACGATGGAGCCACTCGC
CGCGGAACTGAACGTGACCATACACAACGAGCCCACCCTGACCGAAGAGTCCTACGCCAACAACCCCAAACGCGGCCGACACCGAGTGCTGCAGATCGTCGA
GCAAGTAGGCACACCCGTGATCTGCACGCAGGGCAAGGTCATTCCCGATCTGATCACGTGGTGGTGCGAGCGCGACCGTGTGCCCCCGACAGTCCCGCAATC
GCAAAGGCAGCACGTTGGTGT Clone Rv281
:::::::::::::Rv281SP6.seq:::::::::::::
GTATGGTCAGCTGTCCATCCGGCGCTGTCGGCCGAGCTGCCAGATCTCGTCAGCCGTAACCGGGTTGCGGGATCCACGCGTGCGGGTTGTCTAC :::::::::::::Rv281T7.seq:::::::::::::
CCGACTTTCCGCGGGTACCCGCTCAACTTTGTGTCNACCTCAACGCCATTGCCGGCACCTACTACGTGCACTCCAACTACTTCATCCTGACGCCGGAACAAA
TTGACGCAGCGGTTCCGCTGACCAATACGGTCGGTCCCACGATGACCCAGTACTACATCATTCGCACGGAGAACCTGCCGCTGCTAGAGCCACTGCGATCGG
TGCCGATCGTGGGGAACCCACTGGCGAACCTGGTTCAACCAAACTTGAAGGTGATTGTTAACCTGGGCTACGCGACCCGGCCTATGGTTATTCGACCTCGCC
GCCCAATGTTGCGACTCCGTTCGGTTGTTCCAGAANGTCAGCCCG Clone Rv282
:::::::::::::Rv282SP6.seq:::::::::::::
GCACCGATGTCGGCGAGCACTTCGTCAACTTCCAGGGGTGCCCGCACCAAGTATTTCGACGAGTATTTCCGTCGGGCCGCCGCCGCCGGTGCGCGGCAGGTG
GTCATCCTGGCGGCGGGGCTGGGACTCGCGCGCGTACCGGCTGCCTCGGC :::::::::::::Rv282T7.seq:::::::::::::
TGCACCCAACTTACTGAGCATGCTAACGCTGGTCGTGCGGGTCTTGTTCCCGCGTGTCGGCAGGGCACACGCTCGGGGCGTAGCTGGGAGAGGCCCCGGTCA
AGCCCGGAGAGCAGTGCTCAGTCCGCCAGCTTGACCGACTTTCGATGAGAACGCGCTTCTCGCCGTATTGAACTGGCGTGCTGACGGTCGCTGAGCAGCGCT
CGCCGAGTGCGGCCGCTGATTCTTTCATCGAGCCAGGACGCGCATTCGTGTTCGGCCGC TABLE 3-continued End sequences of the polynucleotide inserts cloned in the named recombinant BAC vectors contained in the I-1945 *M. tuberculosis* H37Rv genomic DNA library.

Clone Rv283
:::::::::::::Rv283SP6.seq:::::::::::::
AGCTTACGGCCGGTCGACGCGACGAGTGGTTCATGACACCACAAACCGTCAACGCCTACTACAACCCGGGGATGAACGAAATCGTCTTCCCGCAGCGATTTT
ACAGCCACCATTTTTCGATCCGCAGGCCGACGAGGCCGCCAACTACGGCGGGATCGGGGCGCGTGATCGGGCACGATGATCGGGCACGGTTTCGACGATAGG
GCGCCAAATACGANGGCGACGCAATCTGGTCNATTGGTGGATCGA :::::::::::::Rv283T7.seq:::::::::::::
ATGTCGTCACGTCACCACAATCGCGAGGACCCAATCATGCCGCCCAGGGCGGCCAACCCAATGGTGGCCGCGAAGCGGCAGCTCGATCGCAGCGCGGAGGTG
CCGGCCGCCAGTTGATTCACGAACAGGGTGAGGTCATAGGCGGGCAGGATAGTGACGAACGCAAGACCTATATCTGCCGTCGGAGTAAGAATCGAGTAGCCG
GTCGACCAACGGAAGCGAAAGTGTCCGCGATGTTGATGAGCGTCGCCGGTTGTGGCGGCGGTGGC Clone Rv284
:::::::::::::Rv284SP6.seq:::::::::::::
AGCTTCACCAGCGTGCCGATGCTGTTCGCNACACCTCCCTACTATGCGCAATTCGCCGACACGGGTGGCATCAACACGGGCGATAAGGTGGACATCGCTGGG
GTGAACGTCGGGCTGGTGCGCTCGCTGGCAATCCGCGGCAACCGCGTGTTGATCGGATTCTCGTTGCCCGGCAAGACAATCGGGATGCAAAGCCGGGCAGCA
ATTCGCACCGACACCATTCTTGGCCGTAAGAACCTGGAAATCGAACCCCGCGGTTCGGAGCCGTTGAAACCCAACGGTTTCCTGCCGTTGGCGCAGAACACT
ACGCCATACCAAATCTATGACGCGTTCGTC :::::::::::::Rv284T7.seq:::::::::::::
CTGCCGCGGTGGCGGTCAGCGCCTGGCAAGTCACCGCACCGCCGTCCGGTTCATCGGCAGGCTCCCCCGAAAAGGGCCCTGGCAACAGAAGGTGATCAATGA
GCTCCCGCAGACCTTCGCCGATCTGGGACCGACATACGTGAAGTTCGGCCAGATCATCGCGTCCAGCCCGGGAGCATTCGGTGAGTCGCTGTCGCGGGGAAT
TCCGCGGCCTGCTCGACCGGGTGCCGCCCGCAAAAACCGACGAGGTGCACAAGCTCTTCGTCGAGGAACTCGGCGACGAGCCGGCCCGGCTGTTCGCCTCCT
TCGAGGAAGAACCGTTCGCGTCTGCGTCCATCGCCCAAGTGCACTACGCGACCTGCGCAGCGGCGAAGAAGTGTGGTCAAGATCCACGGCCGGGCATCCGCC
GCCGCGTTT Clone Rv285
:::::::::::::Rv285SP6.seq:::::::::::::
GATCGTGCCGGCCCCCCGGCGGCAGTAGCAGATCAGCTCGTCGAAATCGCGGCAACCAGTCCAGTCGATTTCCATACGGGCGCCGTCAATCAACTCTGCGAA
CATCGCGATCGGCACCGGAAACCGGCGAGCCGCGTCAGCCAGCGCAACCAGCACCGGGATCGGATGAATCATCAATATTATCAAGTGATTTCCTGATGGCAT
CGAGCTCGGTGATCTTGGTCTCGGGGGCCAGCTCGCCGTCGGCGACGTCGTCGATCCGGCGGCCGAGCGCATAGACCGCAAATAGTGCCGCTCGCTTTTCGC
GCGGCAAGAGTCGGATGCCGTAATATANGTTTCTGGCGGCCGTGCGCGTGATCNACTCGGTGATTCGATACGCCTGTTCATCTCGGTCATGCCGTCCTC :::::::::::::Rv285T7.seq:::::::::::::
GGTGGCGCAATGACCGAAACCACCCCAGCCCCGCAAACCCCGGCGGCCCCGGCCGGGCCCGCACAATCGTTCGTGTTGGAGCGGCCCATCCAGACCGTTGGG
CGCCGTAAGGAGGCCGTGGTACGAGTGCGGCTGGTGCCCGGCACCGGCAAGTTCGACCTCAACGGCCGCAGCTTGGAGGACTACTTCCCAAACAAGGTGCAC
CAGCAGTTGATCAAGGCACCCCTGGTCACCGTGGATCGGGTGGAAAGTTTCGACATCTTTGCCCACCTGGGCGGCGGCGGCCCGTCGGGTCATGGCCGGCGC
GCTGCGCCTGGGTATCGCCCGGGCATTGATTCTNGTATCGCCGGATGACCGGCCCGCGCTGAATAANGCCGGCTTCTTGACCGTGATCCACGCGCCACCGAA
CGCAAA Clone Rv286
:::::::::::::Rv286SP6.seq:::::::::::::
CACAATAGATTACTCAAGCTTCGAACCAGCGGCCTTATCACGTATCCCCGCTGAGACCTTGACCCTTAGGGCCGAAGTGACTTCGCTGCTGCTATGCCGACA
CCCGATTTCCAGACGCTGCTGTTACACGACGGCCGGGCCGGTGGCCACCATCACGCTCAACCGCCCGGAACAGCTCAACACCATCGTCCCGCCCATGCCCGA
CGAGATCGAGGCCGCTATCGGGTTGGCCGAGCGCGACCAGGACATCAAGGTCATCGTGCTGCGCGGTGCCGGCCGCGCCTTCTCCGGCGGTTACAACTTCGG
CGGCGGGTTCCAACATTGGGGGCAT :::::::::::::Rv286T7.seq:::::::::::::
TCAGGACGCTTATGGTTGGCAGATGGTCGCCCTGGCGTCGAATACGCGCGAGCGCATGAGCTCACCGGTTCGGAACAACGTATCGAAGAACGTCGCACTGCT
GGCAGATGGTATCTCCGATGTGGTTGTAATTTGTATCCCAACTCTAACTGTGCTATCGGATCAGCGTGAATATCGAGATATTGCGAATGCGATGACAGGCCG
CCATTCGGTTTATTCGCTTACGCTTCCCGGGTTCGATTCGTCTGATGCACTGCCGCAAAACGCGGATATGATTGTTGAAACCGTATCTAACGCAATTATTGA
TGTGGTAGGCGGCAGCTGCCGTTTTGTGCTGTCGGGCTATTCATCGGGTGGGGGTGTTTGGCTATGCCCTCTGCTCCCAT Clone Rv287
:::::::::::::Rv287SP6.seq:::::::::::::
CGCAGCTGTCGCCGATCTGGTCCGGAATACCTAGCTCCAGGTTCTGAGTGGAGATGAGTGCGGCCATCGAAGTGTTGTCAATGTACTCCAGGATGTCAGGTG
CCAGGCCGCTGGCGAGGATCTTGGGCACCGCCGCCATGACTTGGTCGAAGTCGGCGAACGGGGCGAGCACGCTGGCGTCGTGGTC :::::::::::::Rv287T7.seq:::::::::::::
GTAGTTCGTTCATCCAAACACAGTGCGGTACCGGCTCAAGCGGATCACCGACTTCACCGGGCGCGATCCCACCCAGCCACGCGATGCCTATGTCCTTCGGGT
GGCGGCCACCGTGGGTCAACTCAACTATCCGACGCCGCACTGAAGCATCGACAGCAATGCCGTGTCATAGATTCCCTCGCCGGTCAGAGGGGGTCCAGCAGG
GGCCCCGGAAAAGATACCAGGGGCGCCGTCGGACCGA Clone Rv288
:::::::::::::Rv288SP6.seq:::::::::::::
TCCGCTCGCTTCTCCGAGAGGTTGAGTGCCAACGCTCTGCCGATGCCCGAAGCCGGCCCCGGTGATGACGGCGACCTTGCCTTCGAATGAGCTCATTTGACT
ACTCCCCGTGGTTGTCCCTGCGATTGGTGGAGGTGGCCGCGCAGCCTTGCCCCGAGGTCGGCGATCGCGTCTCGGGCTTCGGGGAGCAGACTGACCTGCAGA
TGGAAGTCGTGCCACATGCCCGCGAACCGGCGATGCTCGATGCTTGTTTTCGAAGCGGCGCAGGCGGTTTCGATCTTGTCCGCGTCAACACNGATCGGATCG
TCGCCCGCGGTCTGCATGACGAATGGGCG :::::::::::::Rv288T7.seq:::::::::::::
ATGGGAGGCCACCGATTACCATCTTGCACACACCGATTCCGGGCTATTGATGTCCACGTTCGGTCCGCGAACCGCGCTGTGGCTGCTGCTGGCCAAAGGCGG
AGGCGATACCGAAGTCAGTGCCCAAGCTTGGGTTCCACGCTCGCGCAGCCACGCCGTCACCTTTCCACGAGACCTCACCTGCCGATCCGAAATGGAATCGGC
CGTGACGGAATTGGCGCAGCGAACACTCAACGAGGTGGTGGCTTCGTCGCGAACCGTCACCCGAGTCGCGGTCACCGTGCGCACGGCGACGTTCTACACCCG
CACCAAGATCCGAAAGCTGCAAGCTCCCAGCACCGATCCCGACGTCATCACCGCTGCCGCCCGGCACGTTCTTGAACCTATTCGAGCTGGAATCGGCCGTCC
GGTTGCTGGGAATTGCNGTTAAGAACTGGGCCT TABLE 3-continued End sequences of the polynucleotide inserts cloned in the named recombinant BAC vectors contained in the I-1945 *M. tuberculosis* H37Rv genomic DNA library.

Clone Rv289
::::::::::::Rv289SP6.seq::::::::::::
GCTTTGCGCGCTTCTCCGAGAGGTTGGAGTGCCAACGCTCTGCCGATGCCCGAGCCGGCCCCGGTGATGACGGCGACCTTGCCTTCGAATGAGCTCATTTGA
CTACTCCCCGTGGTTGTCCCTGCGATTGGTGGAGGTGGCCGCGCAGCCTTGCCCCGAGGTCGGCGATCGCGTCGCGGGCTTCGGGGAGCAAACTGACCTGCA
GATGGAAGTCGTGCCACATGCCCGCGAACCGGCGATGCTCGATGCTTGTTTTCGAAGCGGCGCAGGCGGTTCGATCTTGTCCGCGTCAACGCAGATCGGATC
GTCGCCCGCGGGTCTGCATGAAGAAT ::::::::::::Rv289T7.seq::::::::::::
CTCACGCAGCCACGCCGTCACCTTTCCACGAAGACCTCACCTGCCGATCCGAAATGGAATCGGCCGTGACGGAAATTGGCGCAGCGAAACACTCAACGAGGT
GGTGGCTTCGTCGCGAACCGTCACCCGAGTCGCGGTCACCGTGCGCACGGCGACGTTCTACACCCGCACCAACATCCGAAAGCTGCAAGCTCCCAGCACCGA
TCCCGACGTCATCACCGCTGCCGCCCGGCACGTTCTTGACCTATTCGAGCTGGATCGGCCCGTCCGGTTGCTGGGAGTGCGGTTAGAAACTGGCCTAGAAAC
CGGCGGGCACACCGACCTGGCGGGGN Clone Rv28
::::::::::::Rv28SP6.seq::::::::::::
TGCTTCCGGCTCGTATGTTGTGTGGAATTGTGAGCGGATAACAATTTCACACAGGAAACAGCTATGACCATGATTACGCCAAGCTATTTAGGTGACACTATA
GAATACTCAAGCTTGATGCCGCCGAAACCGAGCGTGAGCACGCCGCCAGCCACCACNCGCGGGTCGGGCGCCGGGCCCGGGTCGCCANGCTGCTCCGCTCGG
TGATGGCACGCCACCGCGACACCACCCGGCTGCGCTACGTCGAGCCATACCGGGCGGAGCTACATCGGCTCGGCCGCCCAGTGTTCGGGCCCTCTTTCGAAG
TCGAAGTCGATACCGATTGCGCATCCGCNGCCGCA ::::::::::::Rv28T7.seq::::::::::::
CAGGCATGCAAGCTTCACGTCCGTACGGCTCGGGTACGCTTCGGTCGCAGTGTGCGAGTGATAGATGACGACCGGGACCTCGTCTGCATCTTCCATAGCCCG
CCACACCTTCAGTTGCTCACCGGAATCCAACCGGTAGAAGGTCGGCGAGCGCTCGGCATTGGTCATCGGGATATGCCGCTCGGGACGGTCAGAACCCTCGGG
TCCGGCCAGCACTCCGCAGGCTTCGTCGGGGTGGTCGCGACGCGCATGGGCCACC Clone Rv290
::::::::::::Rv290SP6.seq::::::::::::
GCTTGTCTATCGTCCCGGCCAGGTCCGGCCAGTCAAGGTCGAAGGCCAGTCCGGTCTCCTCTCCGACTACGGCCAAGAACTGGGCGACGGTGTCAGTGCAGA
CCAGCGGAAACTGGTGGCGCCCTAGGCGAGCGACCGCCTCACAAACGGCGGTGACCGCGTTCTGGTCGTGCACCATCGAGCCGTGCCCAGCCCGGCCGCGTG
CCGTCAGCCGCATCCACTGGATGCCCTTCTCGGCGGTTTCAATCAGGTACAGGCGACGTTCGCCACCATCGTGCCGGGGCACGGTTAGCGAGAAACCGCCGA
CTTCACGATTGCCTCGGTGATGCCGTCGAAACAGATCGGGCCT ::::::::::::Rv290T7.seq::::::::::::
GCGCGCCATGTTGAGGTTGTCCGACGGTGACGACGGTGAACCACAACTGTTTGACCTGTCCGCACACACCGTGTGGATCGGCGAGCGGACCCGACAAATCGA
TGGCGCGCACATCGCGTTTGCCCAGGTGATTGCTAATCCGGTCGGGGTCAAGTTGGGCCCCAACATGACCCCGGAACTGGCCGTGGAGTACGTCGAGCGGCT
CGACCCGCACAATAAGCCGGGCCGGCTGACTTGGTGAGCAGGATGGGCAACCACAAGGTCCGCGATCTGTTGCCACCGATCGTGGAGAACGTCCATGCCACC
GGGCATCAGGTCATCTGGC Clone Rv291
::::::::::::Rv291SP6.seq::::::::::::
TTGCCTTCCATGCCGAGCAAGGTCGACTCAGCGATGACGAATTGTTCTTCTTCGCGGGTGTTGCTGCTGGTTGCGGGCTATGAGAGCACTGCTCATATGATT
AGCACATTGTTTCTGACGCTGGCCGACTATCCAGATCAGCTGACACTCCTTGCGCAGCAACCAGACCTGATCCCGCCGGCGATCGAGGA ::::::::::::Rv291T7.seq::::::::::::
CGACGCTGGGCCCAACTGCGACCACCAGGTCCTGGTATGGCAGGACATGGCCGGGTTCAGCGGCGCCAATACCG Clone Rv292
::::::::::::Rv292SP6.seq::::::::::::
TAACGACTCGGGTCCAGCGACCGCGCCAACACNAACGGCCGGACNACGTGGGCCAGGGTCGCGGCCTCCCCTACAAACAGGATCCGTTGCCTGCGAACGACA
GGCTCCGGTGCGGCGTTGGGCGCCGTGCTCGTCCCAGCGTCCGGTCCCGGGTCGCCGGCGACGCTTGTTTCCTCCATACTCGCCCCCTAATCTCGAGGCAGC
CCGTACCCGCAGGCAACCTCCCAAAAATGCAATCCCCCAAAATGCAATGCGTCNAGCTATTTCTCACACCGACCGCTAGTTGCGGATCANAAATCCGTTGGG
CGCGGA ::::::::::::Rv292T7.seq::::::::::::
CNTGGCGGTGGGTGCGGTGTCGAACACGACCACACTTCTTTGCGGTTCGGTGATCTCGACACCGGCCGCGAGCCGACCACCATGCGCGCGTAGATCGGCGAT
CAGCGCGTCGGCTATCGCCTGGGTGCCGCCCACCGGAATCGGCCAGCCGACCGAATGGGCCAGCGTTGCCATCATCAGTCCGGCGCCGGCCGACACCAGTGA
CGGCAACGGTGAAATCNCGTGGGCGGCAACGCCGGTGAACAACGCGCGGGCATCCTCGCCCGCCAGCGACCGCCAGGCAGGGGTGCCCTGGGCCAGCATCCG
CAGCCCGAGACNCAGGACCGANCCCAGTG Clone Rv293
::::::::::::Rv293SP6.seq::::::::::::
GCTTTTCNGATCGCAGCGAGTCGTACCCGCGCCGGTCACCTTCGTGGATATCGCCGGCCTGGTCAAGGGGGCGTCCGAGGGAGCCGGGCTGGGTAACAAGTT
CCTGGCTCATATCCGCGAATGCNACGCCATTTGTCAGGTGGTGCGGGTGTTCGTCAACAACNACTTGACTCATGTCACCGGACGGGTCGATCCCCANTCCGA
CATTGAGGTCGTCGANACCGAGCTGATCCTGGCANATCTGCAAACCCTGGAGCGGGCCACGGGCCGGCTGGAGAAGGAANCGCGCACCAACAAGGCGCGCAA
GCCGGTCTACGACGCGGCACTGCGTGCCCAGCAGGTGCTCGACGCCGGCAANACGCTGTTCGCCGCGGGGGTGGATGCCG ::::::::::::Rv293T7.seq::::::::::::
GTCGTACGCCATTNGTCGGTGTGCGCATACCAGTACGACGCGCCGGGCACCTGACGCGGCGGCCGCGACCAGTCGGTGGCCATCGCCATCGTCTGCCACCCG
GTCAACGGACGCACCTTCTCCTGGCCGACGTAGTGCGCCCACCCGCCGCCGTTGCGTCCCATCNATCCGGTCAACATGAGCAGCGCCAACACCGAGCGGTAC
ATGACATCGCTGTGGAACCAGTGACAGATTCCGCCGCCCATGATGATCATCGACCGTCCTCCGGATTCGGTCGCGTTGCGGGCGAAATTCCTTGGCAAACCG
GATTGCCTGCGCGGCCGGCACACCGGTGATCGACTCCTGCCAGGCCGGGGTGTTCTGCTGGGTTCGGTCGTGGTACCGGT Clone Rv294
::::::::::::Rv294SP6.seq::::::::::::
GCGAGGCGGTATCGCTTCCCGTCGTACCGGCGACCGCCAGCCGAGAAGCTCGTTTTCCCAGTGTTGCTGGGGATTCTCACGCTGCTGCTGANTGCGTGCCAN
ACCGCTTCCGCTTCGGGTTACAACGAGCCGCGGGGCTACGATCGTGCGACGCTGAANTTGGTGTTCTCCATGGACTTGGGGATGTGCCTGAACCGGTTCACC TABLE 3-continued End sequences of the polynucleotide inserts cloned in the named recombinant BAC vectors contained in the I-1945 *M. tuberculosis* H37Rv genomic DNA library.

TACNACTCCAAGCTGGCGCCGTCTCGTCCGCAGGTCGTTGCTTGCGATAGCCGGGAGGCCCGGATCCGCAATGACGGATTCCATGCCAACGCTCCGAGTTGC
ATGCGGATCGAATACNAATTGATCACCCA

::::::::::::Rv294T7.seq::::::::::::
TGGGTCTTGCCGGCGAGCCCAGCGAAGTCGCTAGCGTGGCCGTGTTTCTTGGCTTCGGATCTATCCTCGTTACATGACCGGCACCGTGTTGGACGTGACTGG
CGGCCGGTTCATATGACACCGAGATCATTGCCACGGTACGGCAATTCGTCAAGAAGGAAATCTTTGGGNATGCACCGGCCCTCGAACGTGGCAACAGCTACC
CGCAAGAAATCGTCGATCGGCTGGGTGTTATTGGCTTGCTCGGTCGCCGGCTGCAAGGGTATCGACACCACCGAGTTCATTCTCGGGCGTGCCGGCGCATTC
GAGCTGGCGGTGCGCGCTGCCCAGCACCGTCATAAGTACTTGANGATGGTCAAACGTCGGACGAACCGCCACCACGTCGCTGCCGAACGG Clone Rv295
::::::::::::Rv295SP6.seq::::::::::::
TAGATGCCCAAGCTTGCCNTTANAGACCTCGTCGACCAAGCACGGACGCGACCGTCGAAGGTGGCGAATCCGGGCTTGGCGTCNACCCGCGTAAGGCAGACC
AGATGGTTCGCGGCACGGTCAACCTGCCACACGGCACTGGTAAGACTGCCCGCGTCGCGGTATTCGCGGTTGGTGAAAAGGCCGATGCTGCCGTTGCCGCGG
GGGCGGATGTTGTCGGGAGTGACGATCTGATCGAGAGGATTCAGGGCGGCTGGCTGGA ::::::::::::Rv295T7.seq::::::::::::
TCTCCACGGCGTGGATCAAGGTACCGGCCGGGATGTTGCGCAATGGCAGGTTGTTGCCCGGCTTGATGTCTGCGTTAGCGCCGGATTCCACCACATCCCCTT
GCGAAAAGTCCGTTGGGTGCAATGATGTAGCGCTTCTCCCCATCGAGATAGTGGAGCAACGCAATCCGTGCGGTACGGTTCGGGTCGTACTCGATGTGCGCG
ACCTTGGCGTTGACACCATCTTTGTCATTGCGGCGAAAGTCGATCATCCGGTAAGCGCGCTTATGACCGCCGCCTTTGTGCCGGGTNGGTAATCCGGCC Clone Rv296
::::::::::::Rv296SP6.seq::::::::::::
GCCCGGTTCGATCGGGCATGTCCGCAGTCGTCGTTACCGGAGGCGGTCGTGGCCGCGCTAATCGGCGTCGGCGCCGACAAGATGTGGGATATCCGCAATCGG
GGCGTCATCCCTGCGGGCGCGCTCCCCCGCGTCCGAGCCTTCGTCGACGCAATCGAGGCAAGTCACGACGCGGATGAGGGGCAGCAGTGAATTACAGCGAGG
TCGAGCTGTTGAGTCGCGCTCATCAACTGTTCGCCGGAAACAGTCGGCGACCGGGGTTGGATGCGGGCACCACACCCTACGGGGGATCTGCTGTCTCGGGCT
GCCGACCTGAATGTNGGTGCGGGCANCGCCGGTATCNACTCCCGTGGAACACAGCCGGGGC ::::::::::::Rv296T7.seq::::::::::::
CTCGGCGTGGATATCGGTGTAGCCGGCGCCGGTGAANGTCGGCTCCTTACGTCCACTCGACAACAGCTCATAGCGATCCAACCAGTANGCAACCGCCTTCAG
CAGTACAACCGCGCCGGCGAACACTGCGAGTTGAACGCGAGCTGCCTGGGTCAGCATGCCTCTGCCGGTTGTCAGCCGAAGGCCGCCGAACAGGTAATGCGT
CAACAGGCTCGCTAGAAACGCCAGAACCACGGCCACGAACAGCCAGTTCAGCACCGACCGGTAGAACGGCAGATCGAAGACGAAAAAACCCAATGTCATAGC
CGAATTCGGGGTCCACGATGCCAAAGGTGCCCCCGTGTACAACAACTGAACCTTCACCCA Clone Rv29
::::::::::::Rv29SP6.seq::::::::::::
TCCGGCTCGTATGTTGTGTGGAATTGTGAGCGGATAACAATTTCACACAGGAAACAGCTATGACCATGATTACGCCAAGCTATTTAGGTGACACTATAGAAT
ACTCAAGCTTCACGTCCGTACGGCTCGGGTACGCTTCGGTCGCAGTGTGCGAGTGATAGATGACGACCGGGACCTCGTCGGCATCTTCCATAGCCCGCCACA
CCTTCAGTTGCTCACCGGAATCCAACCGGTAGAAGGTCGGCGAGCGCTCGGCATTGGTCATCGGGATATGCCGCTCGGGACGGTCAGAGCCCTCGGGTCCGG
CCAGCACTCCGCAGGCTTCGTCGGGGTGGTCGCGACGCGCATGGGCCACCATCGCATTCACCAGGTCTGCGCGAATCACCAGCACGTAGACGGTTCCTTTCC
TAAGCAACACCGAAGTTTCAGGACCGAATGCTCCGGGAAACATGTCA ::::::::::::Rv29T7.seq::::::::::::
CAGGCATGCAAGCTTGATGCCGCCGAAACCGAGCGTGAGCACGCCGCCAGCCACCACGCCCGGGTCGGGCGCCGGGCCCGGGCCGCCAGGCTGCTCCGCTCG
GTGATGGCACGCCACCGCGACACCACCCGGCTGCGCTACGTCGAGCCATACCGGGCGGAGCTCCATCCGCTCGGCCGCCAGTGTCCGGGCCCTC Clone Rv2
::::::::::::Rv2SP6.seq::::::::::::
CCTGCATCCGGCTCGTATGTTGTGTGGAATTGTGANCGGATAACAATTTCACACAGGAAACAGCTATGACCATGATTACGCCAAGCTATTTAGGTGACACTA
TAGAATACTCAAGCTTCCAATCCCCCTGCCCTGATACGCGTCGGCAACCGTGAACGCGATCTCGGCGACCGTCGGATCGGTTTCATCCCGCACAAAACGCGC
GTCGGCTACGGGGTCGCTTCCGTCGGTCACCACCCAGACGAAGTGGTCGACGTAGTCGACTTCCGACAGGTAGTGCATCAACGCCGGACTGGGAACACNAGC
CGACATGAACCGTCGATACAGCGTCTCNCCGGAGAACTGGATGTGTCCGTGCACGGTCCGCTCGCGGTCACCGGGCAGCACGGGGCGTAACATCAGTTGAGT
CCCGTCGGCAAGCCGTACCGGAATCGGGGAGACGA ::::::::::::Rv2T7.seq::::::::::::
CAAGATGATCGCCGGTGCCACCCCGATCCGTGCCTCGGTCAGCGCGAACGTGCTTTCCGGTCCGGCGACCACCATGTCGCACGCACCGACCAGGCCGAACCG
GCCGGCCCGCACATGCCCGTTGATGGCGCCGACCACCGGCAGCGGCGACTCGACGATGGCGCGCAACAGCGCCGTCATTTCCCGCGCCCGCGCCACCGCCAT
CCGGTACGGATCACCACCACCACCGCCGGCCTCGCTGAGGTCCGCGCCGGCGCAGAACGTTCCGCCGGTATGCCCCAGCACGACCAGCCGCACCGCCGGATC
TGCTTCGGCCGCACTCAGCCCTTGATGTAGTTGGCTGACCAGCGTGCTCGACAGCGCGTTGCGGTTGTGCGGAGAGTTCAGTGTCAGCCTGGCGAAGGGGCC
GCCGCAGGCGGCCGGGCCAGCGTAGTCGACGGGGCTG Clone Rv301
::::::::::::Rv301SP6.seq::::::::::::
CTCAAGCTTCGATCGACAGTACTCCCGCCTTGGGTCTGGTCTTCGAGCTGGTCGGTCATGGTCGGACCTGCTGGTAGTGGGGATCTAACGCAACATGGTCGG
GATTCATCATGGTGTACCCGTGATACCCATTCGCAGCTGCCGGTGAAACCCCGCGATGCCGGGATTTCCAGCCGCACTAGGATGTCTAGCCGGCCAGCCGCT
GCCGCCGGACTTCGGGATGTTCGGTATACCACCGATCGGCAATCTTGCNTATCCGCCGATGCTCGAACGCTAGCCACCCCAAACCAACCACTGTGACNACAA
TC ::::::::::::Rv301T7.seq::::::::::::
TGAATTTCCCGATCCCACAATCTCGGTTCAGATACAGGTCGCCATACCCCTTACTTCGGCAACGCTGGGCGGATTGGCCCTGCCGCTGCAGCAGACCATCGA
CGCCATCGAATTGCCGGCAATCTCGTTCAGCCAATCCATACCCATCGACATTCCGCCGATCGACATCCCGGCCTCCACTATCAACGGAATTTCGATGTCGGA
GGTCGTGCCGATCGATGTGTCCGTCGACATTCCGG Clone Rv302
::::::::::::Rv302SP6.seq::::::::::::
TACTCAAGCTTGAACGCTGCGAGCGAGCCCATGTAGAGCGTTTGGTACCAAACCGATCGGTGGGCCAACTTGCCATGGGCTCACAGCGGCTATCGCGAGCGT
GTAGCCGATCATCGGCCAGGCGACGGTGGCCTGAGCGGCAGGGGTTGCCTTATCCATCCTCTTGCGGCATGGTTGCCGCAGGGAGTGCCGGTAAGTCTGGTC
GGCAACCTGGCCCGCTGCGGGTTGGGTTCGGATTCCCTCGGCTAGTAAGGTGCTCGCCTGGTGTTACAACGAATCGCTAGACAGCTCTTATCGGGAGTGGCC TABLE 3-continued End sequences of the polynucleotide inserts cloned in the named recombinant BAC vectors contained in the I-1945 *M. tuberculosis* H37Rv genomic DNA library.

GTCGCGATCGTTGCGCTGCCGCTGGCGATCGCGTTCGGCNTTACCGCCACCGGAACGTCCCAAGGTGCGCTCATCGGGCTCTACGGCGCCATCTTCGCCGGA
TTCTTCCCNGCCGTGTTCGGTGG

::::::::::::Rv302T7.seq::::::::::::
GCGGTGTCTGAACTTCGCCCGTTCCCTCCAGCGCATTGAGCTTCAGCCCGACCGGCAGGTAGGGAGTCGGCATGCGGTCCTTCGCCCCGACCCCGCTGGCTA
AATAGCCACCCCCGAGCGCGGTCACGGTCTTTGCACCGGGACGACGGCATACCGGCAGCGCGAACATCGCCGCGGGCTGCAGCGTGAACGTCGAATACGAGT
CGAACAGTGTCGGCGCGTAAAAACCCGAGCCGGCGGTCGCTTCGGTAATCAACGGCTCCTGCGCAACCAGCTGCAANTCNCCGGTGCCACCGGCGTTGACAA
TCTTGATNTCGGCGACCTCGCGCACCAN Clone Rv303
::::::::::::Rv303SP6.seq::::::::::::
TACTCAGCTTCGGCTCAGGTGGTGCTGCTGGTAAAGTTCNCTGAACGGTGCAGGTTTCGACAATGTGGTGCCGGTTCGGCGGGTACTGCCATCGAGACACTG
GCGCAGGCTATCGCACCCGTTATCGGCTACAAACAAATCGCGGTATGCGTTCTTGAGCATGAGTCGGCGACCGTCGTCATGGTCGACACCCACGACGGAAAG
ACGCAGATCGCCGTCAAGCNTGTGTGCCGCGGATTATCAGGACTGACCTCCTGGCTGACCGGCNTGTTTGGTCNCGATGCCTGGCGCCCGGCCGGCGT ::::::::::::Rv303T7.seq::::::::::::
CATCACCTGGTTCATGAAACTGGAAGCAGCGCAGCGCTTCCTTTTCGGCCGCAACATGAGCCAGCCTCTCGTCGGCGGTCGGGTGCAGGTGCTCGGGCAGCT
CGGCCGCGACAGCCGCCTGACCCTGAAACCAGCTTCCATATCCCGCGACGAACGACGCCAGTCCGCTACGTAACCCCTCCGCGACTGTCCATGGACAACANC
GCGTTCTCCACCGACCGGGCCCGGGTGTGGGGTGTT Clone Rv304
::::::::::::Rv304SP6.seq::::::::::::
CTCAAGCTTCCCGGCGGCCAGTACCGAAAGCGCGAACAGCTCGCGGCAGCCCACAACNTGCTGCGTCGGATTGCCGGCGGCGANATCAATTCCAGGCAGCTC
CCGGACAATGCGGCTCTGCTGGCCCGCAACGAAGGACTCGAGGTCACCCCGGTGCCCGGGGTCGTGGTGCACCTGCCGATCGCACAGGTTGGCCCACAACCG
GCCGCTTGATGCCCGGTCGGCAAGCCCGGCAGTTGCCAAACCCAGCGTGATCAGGCTCGGCTCGCGAGTTCGGCGAAGAAGTGGCTCGCCTGATCACCTACC
ATCGGCCAGGATCTGCGTGTCATCACNACGCTCGCCAAGGAGGTTGTTGTGGTGCT ::::::::::::Rv304T7.seq::::::::::::
GCCACGTTTCGCGCCGCCCGGCATACGGCGGCGTACCGATCTCCGCGTCATACACCCGCGGGTAATCGCCGACGGTGCCGGTTCGCGAGCCGAAGGTGACGA
CGCTGATTGAATCGAGTTCCAGGTCCAGCGGGTGGCGCAGCAACGGCGCGAGCTCAACGACGTCAATCACGTTGTCGCTTTCTACGGTCACCGACCCGGTGA
CCGTAGTCGCCCGGTGCGCTCGGCCGAGAAGTTGCACCGCCACCACCGCGACACCGTGTTGCACGCGGACGCCACCCCCGGATCGGTTGTTGGCCAAGGTAA
TTGGGTCATTCCATTTGACGGGACGCCGACCCCGCAGCCCCAGTACCGCCCACGACCACGCCGGCTGACCCCACCACTGTACGAACACCAAGGCGACGCCGA
CCA Clone Rv306
::::::::::::Rv306SP6.seq::::::::::::
CTCAAGCTTGATGCCGCCTAAACCGAAGCGTGAGCACGCCGCCACCCACCACGCGCGGGTCGGGCGCCGGGCCCGGGCCGCCAGGCTGCTCCGCTCGGTGAT
GGCACGCCACCGCGACACCACCCGGCTGCGCTACGTCAAGCCATACCGGGCGGAGCTACATCGGCTCGGCCGCCCAGTGTTCGGGCCCTCTTTCGAGGTCNA
GGTCNATACCGATTTGCGCATCCGCAGCCGCACCCTGGACGACAGAACCGTGCCCTACGAGTGCTTGTCGGGCGGGGCCAAAGAACANCTTGGCATCCTGGC
GCGATTGGCCGGCGCGGTCCTGGTC ::::::::::::Rv306T7.seq::::::::::::
CTCGGGTACGCTTCGGTCGCAGTGTGCGAGTGATAGATGACGACCGGGACCTCGTCGGCATCTTCCATAGCCCGCCACACCTTCAGTTGCTCACCGGAATCC
AACCGGTANAANGTCGGCGAGCGCTCGGCATTGGTCATCGGGATATGCCGCTCGGGACGGTCAGAGCCCTCGGGTCCGGCCAGCACTCCGCAGGCTTCGTCG
GGGTGGTCGCGACNCGCATGGGCCACCATCGCATTCACCAGGTCTGCGCG Clone Rv307
::::::::::::Rv307SP6.seq::::::::::::
CTCAAGCTTCAATTCCTCCACGACGCGTTCCCAAATGAATTTCCCGATCCCACAATCTCGGTTCAGATACAGGTCGCCATACCCCTTACTTCGGCAACGCTG
GGCGGATTGGCCCTGCCGCTGCAGCAAACCATCGACGCCATCGAATTGCCGGCAATCTCGTTCAGCCAATCCATACCCATCGACATTCCGCCGATCGACATC
CCGGCCTCCACTATCAACGGAATTTCGATGTCGGAGGTCGTGCCGATCGATNTNTCCGTCNACATTCCGGNGGTCACCATCACCGGCACCAGNATCGACCCG
ATTCCGCTGAACTTCGACGTTCTCAGCAGCGCCGGAACCA ::::::::::::Rv307T7.seq::::::::::::
TTAACCCCCGTGGCCTCTACGCCGCCTNCGGGTCGAACATGCATCCCGAGCANATGCTCGAGCGCGCACCCCACTCGCCGATGGCCGGAACCGGCTGGTTAC
CCGGGTGGCGGCTGACGTTCGGCGGCGAGGACATCGGCTGGGAAGGGGCGCTTGCCACCGTCGTCGAAGACCCAGATTCGAAGGTGTTCGTCGTGCTCTACG
ACATGACCCCGGCGGACGAGAAGAACCTTGACCGGTGGGAAGGCTCCGAGTTCGGCATCCACCANAAGATCCGATGCCGCGTT Clone Rv308
::::::::::::Rv308SP6.seq::::::::::::
CTCAAGCTTGATTTTGATCATCATGGATGATCATCACCCGAAGTGTGGTAGCCGCAGTGGTTATCGTGGGTACCGTCGTGCTTTCCATGGGCGCCTCTTTCG
GGCTTTCCGTATTGGTCTGGCAGGACATTCTGGGTATCGAGTTGTACTGGATGGTGTTGGCGATGTCGGTGATCCTGCTCCTGGCGGTGGGATCCGACTACA
ATCTGCTGCTGATTTCCCGGTTGAAAAANGAAATTGGGGCCGGATTGAACACCGGAATTATCCGTGCCATGGCTGGTACCGGGGGAGTGGTGACGGCTGCCG
GCATGGTGTTCGCCGTTACCATGTCGTTGTTTGTGTTCAGCGATTTGCGAATTATTGGTCAGAT ::::::::::::Rv308T7.seq::::::::::::
CGNCCAACCCGAATTGGTTTTCGGCGCCNTCGGTGAGGACGGCGTGCGGGTGCTCAACGACGACGTCGTCCGCGGGACACACCTCGATGCTGCCGCCATGGA
CGCGGTCGAACGCAAGCAGCTGATCGAGCTACAACGCCGCGCGGAACGCTTCCGCCNCNGGCGTTACCGCATCCCGTTGACCGGGCGGATCGCGGTGATCGT
CGATGACGGCATCGCCACCGGAGCGACGGCCAAGGCGGCGTGCCAGGTCGCCCGGGCGCACGGTGCGGACAAGGTGGTGCTGGCGGTCCCGATCGGCCCANA
CGACATCGTGGCGAGATTCGCCGG Clone Rv309
::::::::::::Rv309SP6.seq::::::::::::
CGTGACTGCCACCGGGGCCACTCCGCAGAATCTGTACCCGACCAAGATCTACACCATCGAATACGACGGCGTCGCCGACTTTCCGCGGTACCCGCTCAACTT
TGTGTCNACCCTCAACGCCATTGCCGGCACCTACTACGTGCACTCCAACTACTTCATCCTGACGCCGGAACAAATTGACNCAGCGGTTCCNCTGACCAATAC
GGTCGGTCCCACGATGACCCANTACTACNTCATTCGCACGGANAACCTGCCGCTGCTAGAGCCACTGCGATCGGTGCCGATCGTGGGGAACCCACTGGCGAA
CCTGGTTCAACCAAACTTGAAGGTGATTGTTAACCTGGGG TABLE 3-continued End sequences of the polynucleotide inserts cloned in the named recombinant
BAC vectors contained in the I-1945 *M. tuberculosis* H37Rv genomic DNA library.

::::::::::::Rv309T7.seq::::::::::::
TCGCTCAAGCGCNTGAGGCCGAANCGGCTGGTTACGACTCCCTGTTTGTGATGGACCACTTCTACCAACTGCCCATGTTGGGGACGCCCGACCAGCCGATGC
TGGAGGCCTACACGGCCCTTGGTGCGCTGGCCACGGCGACCGAGCGGCTGCAACTGGGCGCGTTGGTGACCGGCAATACCTACCGCAGCCCGACCCTGCTGG
CAAAGATCATCACCACGCTCGACGTGGTTAGCGCCGGTCGAGCGATCCTCGGCATTGGAGCCGGTTGGTTTGAGCTGGAACACCGCCAGCTCGGCTTCGAGT
TCGGCACTTTCAGTGACCGGTTCAACCGGCTCGAAAAGGCGCTACANAT Clone Rv30
::::::::::::Rv30SP6.seq::::::::::::
ATACTCAAGCTTCCGCTGGGGCCTGTTCAACCATGGCGATCCCGTTGGTCCCGGACATCCCGAACGAGGACACCGCGACCCNCTTCGGTGTGTGATCATTAC
CGTTGGGCCACTGCGTAACCGCTTGCGGCACAAAGAGCCCGGTCTCGACGTCGGAAAGCTCATCGGGCACCCGATTGAAATGCAGCAGCGGCGGCACCACCC
CGTGCCGCAGTGACAGAATTGCCTTGATCAGCCCGACGGTCCCCGCCGATGCCGTGCTGTGCCCCATGTTGCTCTTGGCCGATCCAAGCGCGCAGGGGGTGC
CCGCGCCATACACCCGCGCCAGGCTGCGGTACTCAATCGGGTCGCCGATTGGCGTACCGGTGCCGTGCGCCTCCACCACACCGACCGTTTCGGGCTG ::::::::::::Rv30T7PEG.seq::::::::::::
CAACAGCGTTCCAGCGGCATACCACCGCACATGCCGTGCACCCGGCGCCGGGCGGAGTCGCCGCATAACACANGTACACCTTGGGAATCGGTGTGCGCCAGG
GATTCNACCGCGGGGTGGGGCCGGCGATCGCGCGCCAGGTCGAGTTGGCGCCGACCGTGATNTCACCGCCGACGTAGTTGGCGTTGTGGTCCGCCATCCGCG
CGGCGGGCACGGCGCGGGCCGCCACCACGATGTCACGGAAGCCGGGGGCGAACGCTCGACGACCTGGTTACCGTCTCNGTCGCNTCNANCGTGGACCCGACN
GCACGTGGGCATATGTCCANAACGGACGNGGCCGGTTTCNTCGATGCNGCCGGGGTCCGCGACNTGCGGACNCNCNGNCACACCATCCGCCAGTCCGCGTGG
CGTCCCGCCGCGACTCTGCCTCGGCCGCGCCA Clone Rv310
::::::::::::Rv310SP6.seq::::::::::::
CTCAAGCTTTGNCGACGATCGGGCGATGTCGATGANAGGAAACCCCAGCGCACAACCGACNATTTTGGCGTAGCCGGCGGACNTCTGCTCGATTCCGATCAC
GTCGGCGCTCGCATCGAGCATGGCGCCGGCGACGGCTAGCAGCGATCCGCCGTCGTCGAGGAACACGACACGAGCCGTACGCCCGGCCGTAAGCCGCGCCCA
GGATTCGGCGAAAAACCGTTCTACGTGGCGGGTGTACTGGGTGTCCAATGATTCGTGGGGTGCGTAGGCGTCGCTGCAATCGTCGACATAAATGCCGTCGGC
CCGCATCGCGTCAACAACTCCCGGGTGAGTGGAATANCACTTGCCGA ::::::::::::Rv310T7.seq::::::::::::
TCCAACGCGGTGACAGATTTGTCTATCCTGGACCTGACGGTGAGGTCGAAGTTTTCCAGGAATTCGGCAAAATCGGTAAGAGCCTGAAGAATTCGGTATCGC
CGGACGAAATCTGCGACGCATACGGGGCAGATACGCTTCGGGTTTACGAGATGTCGATGGGGCCGCTGGAGGCTTCACGTCCATGGGCCACAAAGGATGTTG
TCGGCGCGTACCGTTTTCTGCAGCGGGTGTGGCGCTTGGTCGTCGACGAGCACACCGGCGAAACTCGGGTGGCTGACGGCGTGGAACTCGACATCGATACGC
TACGGGCGTTGCACCGCACCATCGTCGGCGTGTC Clone Rv311
::::::::::::Rv311SP6.seq::::::::::::
CTCGTCCTTGACTACGCCCAGTATCGAAANCCTCCTGTGCCGGTNCGCTAAACACCCGGCGGACACTCANACGGTGCTGGTGGTGCGGCATGGCACCGCGGG
CAGCAAAGCGCACTTCTCCGGGGACGACAGCAAGCGACCGCTAGACAAGAGGGGTCGTGCGCAGGCAGAAGCGTTGGTACCACAGCTGCTGGCGTTCGGCGC
CACCGATGTTTATGCCGCCGACCGGGTGCGCTGCCACCANACNATGGAGCCACTCGCCGCGGAACTGAACGTGACCATACACAACGAGCCCNCCCTGACCGA
AGAGTCCTACGCCAACAACCCCAAACGCGGCCGACACCGAGTGCTGCAGATCTTCG ::::::::::::Rv311T7.seq::::::::::::
GTATCGCCTCCNCCTTTGGCCACCAGCAGCCACAGCGCGGTTCGCGGACCGAACGTGGACATCAATAGCCCGGAATCGGTGTGTGCAAGTTGGTAAACGGTG
TTGATCCCAAGCTTTGCCAGCCTTTTCGTAGTCTTGGGCCCCACACCCCACAGTGCTTCGACGGTACGGTCACCCATGATGGCCATCCAGTTGGCATCGGTG
AGCTGATAGATGCCAGCTGGTTTCGCCAACCCGGTAGCGATCTTGGCGCGCTGCTTGTTGTCACTGATACCTATCGAGCAAGACAGCCCGGTTTGCGACAAG
ATGACTTTTCGGATCTCTTCNGCGAACTTCCAATGGGGGTCTCCGGGANT Clone Rv312
::::::::::::Rv312SP6.seq::::::::::::
CTCAAGCTTTTGGTCTAGCCGGCCGAGCACGATACGGGTGTCCTTGGCCACCGGCGGCGGCTGTCCGGGAAATGGCGGGTCCCCGGTGGTTTTGCTGANGAN
TGCTGAACCGTAGTCGAAGTGGGCGGCGTCAGACTCCACCCAGCCAGCAGGCAGCGCGAAGCTGAATCCTCCAACCGGGTTGTCGATCCGGACAGGTTGGGG
TGCGTTTGGGGCAATGACAGGTGGCGGCGGTGCGTTCGGGTCGGCCGGCGGAGGTGCTGCGTTGGGATCNCCCGGCTGGGCATTCGGCNTNTTGGCGGCGGC
CGGTGGTGGGGGGGCAACANGTGTCCCGGTGCGGGTGGCGCTGC ::::::::::::Rv312T7.seq::::::::::::
ATCTGTACCCGACCAAGATCTACACCATCGAATACGACGGCGTCGCCGACTTTCCGCGGTACCCGCTCAACTTTGTGTCGACCCTCAACGCCATTGCCGGCA
CCTACATACGTGCACTCCAATACTTCATCCTGACGCCGGAACAAATTGACGCAGCGGTTCCGCTGACCAATACGGTCGGTCCCACGATGACCCAGTACTACA
TCATTCGCACGGAGAACCTGCCGCTGCTAGAGCCACTGCGATCGGTGCCGATCGTGGGGAACCCACTGGCGAACCTGGTTCAACCAAACTTGAAGGTGATTG
TTAACCTGGGCTACGGCGACCCGGCCTATGGTTATTCGACCTCGCCGCC Clone Rv313
::::::::::::Rv313SP6.seq::::::::::::
CTCAAGCTTGCAATGCGGGTCGGGATGCCCATGGTTGGAANATGGTCGCCCTGGCGTCNAATACGCGCGAGCGCATGAGCTCACCGGTTCGGAACAACGTAT
CGAAAAACGTCGCACTGCTGGCAGATGGTATCTCCGATGTGGTTGTAATTTGTATCCCAACTCTAACTGTGCTATCGGATCAGCGTGAATATCGANATATTG
CGAATGCGATGACAGGCCGCCATTCGGTTTATTCGCTTACGCTTCCCGGGTTCGATTCGTCTGATGCACTGCCGCAAAACGCGGATATGATTGTTGAAACCG
TATCTAACGCAATTATTGATGTGGTAGGCGGCAGCTGCCGTTTTGTGCTGTCGG ::::::::::::Rv313T7.seq::::::::::::
CAAATACACGCCGGACGCACAGGCGGACATCGCCATCCCGAGCACACCCAAAACGGGATACAGGATGGAGGCCAACGCCACGGCCGCGCCCAGGATCACCAA
CCACACCGGCTTGGTCAGCTTGTCGGCGGCGGTATAGGCATCGGGCCGCTGCAACGCAGCATGCACAAACGCGTACACCGCTGTCACCAAGACGGCGACCAG
CAATACCAGCATGACGGTACCCACGAGGTGGCTCACGCATTCAGACTATGCGGTTTGCATCCAACACG Clone Rv314
::::::::::::Rv314SP6.seq::::::::::::
CTCGTCCTTCGGCCTCGCTGCAGGAGTGGGAGCCGCAGGGCTGGAAATCCGAAAAACGAGCCGGTGATCGCACTGTCGCCGATCGGCGCCGCACCTGGTTGG
TGTTACGGATGAATCCGCAGCGAAATGTGGCTGCGGTGGCGTGTCGTGACTCGTTGGCGTCGACGCTGGTGGCAGCCACCGAGCGGTTGGTCCAGGATCTGG
ATGGGCAAAGTTGTGCGGCCCGGCCGGTGACGGCCGATGAGCTGACCGAGGTCGACAGCGCCGTGTTGGCTGACTTGGAACCGACATGGAGTCGCCCCGGTT TABLE 3-continued End sequences of the polynucleotide inserts cloned in the named recombinant BAC vectors contained in the I-1945 *M. tuberculosis* H37Rv genomic DNA library.

::::::::::::Rv314T7.seq::::::::::::
GTCTAGNCCGCCGAACACGATACGGGTGTCATTGGCCACCGGCGGCGGCTGTCCGGGAAATGGCGGGTCCCCGGTGGTTTTGCTGAAGANTGCTGAACCGTA
GTCGAAGTGGGCGGCGTCAGACTCCACCCAGCCAGCAGGCAGCGCGAAGCTGAATCCTCCAACCGGGTTGTCGATCCGGACAGGTTGGGGTGCGTTTGGGGC
AATGACAGGTGGCGGCGGTGCGTTCGGGTCGGCCGGCGGAAGTGCTGCGTTGGGATCGCCCGGCTGGGCATTCGGCGTGTTGGCGGCGGCCGGTGG Clone Rv315
::::::::::::Rv315SP6.seq::::::::::::
ACTCAAGCTTGAGATTGGCGTCAACGGGTGTCGGCACCGGCGTCCTGCAGTTGGTAGGCCTGCAGTTTGTGCATCAGGCCGATGCCGCGGCCCTCGTGGCCA
CGCATGTACANCACCACGCCGCGCCCCTCACGGGCGACCATCGCCAGCGCGGCGTCCAGCTGAGGCCCGCAATCGCAGCGGCGTGACCCAAACACATCGCCG
GTCAAGCACTCCGAATGCACCCGGACCAGCACGTCG
TCACCGTCGGCGTTGGGCCCGGCGATCTCGCCGCGGACCAGCGCGACATGTTCCACGTCCTCGTAAATGCTGGTGTANCCGATGGCGCGAAACTCCCCATGA
CAANTCGGAATCCCGCGCCTCGGCGACCCCGCTCAATGTTGCTTCTCNTGCTTG ::::::::::::Rv315T7.seq::::::::::::
TCGACNAGCATTCTTGACNGTTGTTTTGGCTCGGCATGGTTAGCCAAGGTTCTGCGGTCCCACCAGATCATCTTGGTCCGGTAGCGCTCGTCCGGGTATGCT
GCCGCCGGGATTCTCGCTGCTATTACTCCCCCCGAAGAACGCCACCGGTCCAGCGCGTGGGCCGCCGCGGTCCCCATCACAAACTGAACCCCCAACAGGGGA
CATGCTTAGCGGTAGGGCGCGCGCCAAGGCGGCAGCAATCGCATCACTGCGCTGCGCGTCACTATTAACCCAGCCGGACTTCACTTCCACGACCCCGAATGG
CGCCCGGTCATTGATCATCTTGCGCACCGCGGATAATCCGGGAT
TG Clone Rv316
::::::::::::Rv316SP6.seq::::::::::::
ACCGGGGCCACTCCGCACAATCTGTACCCGACCAANATCTACACCATCGAATACGACGGCGTCGCCGACTTTCCGCGGTACCCGCTCAACTTTGTGTCNACC
CTCAACGCCATTGCCGGCACCTACTACGTGCACTCCAACTACTTCATCCTGACGCCGGAACAAATTGACGCNGCGGTTCCGCTGACCAATACGGTCGGTCCC
ACNATGACCCANTACTACATCATTCGCACGGANAACCTGCCGCTGCTAAAGCCACTGCGATCGGTGCCGATCGTGGGGAACCCACTGGCGAACCTGGTTCAA
CCAAACTTGAAGGTNATTGTTNACCTGGGCTACGGCGANCCGGCCTNTGGTTATTCCACCTCNCCGCCCAATGTTTGCNACTCCCGTTCGGGGTTGTTCCCN
NAAGGTCAACCC ::::::::::::Rv316T7.seq::::::::::::
CGCTCAAGCGCNTGAGGCCGAANCGGCTGGTTACGACTCCCTGTTTGTGATGGACCACTTCTACCAACTGCCCATGTTGGGGACGCCCGACCAGCCGATGCT
GGAGGCCTACACGGCCCTTGGTGCGCTGGCCACGGCGACCGAGCGGCTGCAACTGGGCGCGTTGGTGACCGGCAATACCTACCGCAGCCCGACCCTGCTGGC
AAAGATCATCACCACGCTCGACGTGGTTAGCGCCGGTCGAGCGATCCTCGGCATTGGAGCCGGTTGGTTTGANCTGGAACACCGCCAGCTCGGCTTCGAGTT
CGGCACTTTCAGTGACCGGTTC Clone Rv317
::::::::::::Rv317SP6.seq::::::::::::
CTCAAGCTTGCGTTCGATGAAGTAGTCGTCGGTCAGCGCCGCCTCTTCGAGCTCCTTGGCGATGCCCAGCAAGGAGTCATCGCCGCCGAGCTTGGCCAGGAT
CTTGTCGGCCTGTTCCTTGACGATGCGGGCCCGCGGATCGTAGTTCTTGTAGACACGATGACCGAAACCCATCAATTTGACCCCGGCCTCGCGGTTCTTGAC
CTTGCGTACAAACTCGCTGACGTCGTCGCCGCTGTCGCGAATGCCCTCGAGCATCTCCAGGACAGCCTGATTGGCGCCGCCATGAAGCGGACCCCATAGTGC
GTTGATGCC ::::::::::::Rv317T7.seq::::::::::::
GGTCAGGCCGAGCAGGCGCGAGGAACGACGAACCCAACAAGCCATGGTGGTTGGCGCCGTCGAGAGGTCGGCGGTCGCCACAACGGGAAGATCGCCTTGAGC
GTCGCTCGACCGCCGCCTCGAGTTGGGTCATAACGAAGTAGCTGATGCCGATCATGTCGACGTTTCCGTCGCATCAGCGTGCAGCGGCGACCCACTCNACGA
GGTCTCGGTGCCGCCGCGGCCAGGGCACCAGCAGTGACGAGTCCAGGCGCCGTCGGGCCAAGCAGTCGCGGTGCCANCCGTGGTGGGTCGGGCGATGGTTGG
GTGTGCTCATTTCGGGAACGCCA Clone Rv318
::::::::::::Rv318SP6.seq::::::::::::
CTCGAAGCTTTAACAGCATCAACCCCGCCCCGCACCAGCACCGACACNATGTCGATGCCATCGAGGTGAATGTCGAACTGGCGCAAACCATCGGCGACCGCG
ACCACCGGCAACATGGGTACCGGCGATTTCCGGTGCCAATGCCGACCCGACGGGCCGCTCTCACCGCAGGTGACCTCGATCACCGAGACCANCCGGCCGTTN
TNNTCACGCACCCCTACCGTGTCACGCCCAAAACGGCGCTGGTGGTCGATTGCCGGAGTGCACCCCNCACCCAGTGTCGTGCCCGGATCC ::::::::::::Rv318T7.seq::::::::::::
TGATGCCGCACCCGATCGACGGTCGTTGGTCGGGGTTGACTGGCCGCCCGGCGAAGCAGGGCGTCGACCGCGGCCCGGACGTCGGCGGCCGTCACCGGTCGG
CCATTGCCCGGGCGGGAGTCGTCGAGCTGACCACGGTAGACAAGTCGGCGCTGGCCGTCGAAGACNAACGTGTCGGGTGTGCAGGCCGCGGAGAAGGCGCGG
GCGACNTCTTGGGTTTCGTCGTANAGATACGGGAACGTCCAGCCGTGGCGGCGGGCCTCGGCGACCATCTGATCGGGCCCGTCC Clone Rv319
::::::::::::Rv319SP6.seq::::::::::::
TTTCGGGCGAGGCGGTATANCTTCCCNTCGTACCGGCGACCGCCAGCCGANAAGCTCGTTTTCCCAGTGTTGCTGGGGATTCTCACGCTGCTGCTGANTGCG
TGCCAAACCGCTTCCGCTTCGGGTTACAACGAGCCGCGGGGCTACNATCGTGCGACGCTGAAGTTGGTGTTCTCCATGGACTTGGGGATGTGCCTGAACCGG
TTCACCTACNACTCCAAGCTGGCGCCGTCTCGTCCGCAGGTCGTTGCTTGCGATAGCCGGGAGGCCCGGATCCGCAATGACGGATTCCNTGCCANCGCTCCG
AGTTGCNTGCGGATCGACTACNAATTGATCACCCANAACCATCGGGCGTNTTACTGCCTGAAGTACCTGGTGCGGGTCGGATACTGCTATCCGGCGGTGACA
ACCCCGGCAAGC ::::::::::::Rv319T7.seq::::::::::::
GTTTTGGCTCGGCATGGTTAGCCAAGGTTCTGCGGTCCCACCAGATCATCTTGGTCCGGTAGCGCTCGTCCGGGTATGCTGCCGCCGGGATTCTCGCTGCTA
TTACTCCCCCCGAAGAACGCCACCGGTCCAGCGCGTGGGCCGCCGCGGTCCCCATCACAAACTGAACCCCCAACAGGGACATGCTTAGCGGTAGGGCGCGCG
CCAAGGCGGCAGCAATCGCATCACTGCGCTGCGCGTCACTATTAACCCACCCGGACTTCACTTCCACGACCCCGAATGGCGCCCGGTCATTGATCATCTTGC
GCACCGCGGATAATCCGGGATTGCCAGCCCATTCNACTACCGCATGCGAGTCATCGGCTGACCGCAGCGGTC Clone Rv31
::::::::::::Rv31SP6.seq::::::::::::
TCGCCTAGGCGGGCTTCCCCTTCCGTCCGAGCNGTCAGAAGCTCCTATGACAATGCACTACCCGAGACNATCAACGGCCTATGCAATACCNAGCTGATCAAA
CCCGGCAAGCCCTGGCGGTCCATCGAGGATGTCGAGTTGGCCACCGCGCGCTGGGTCGACTGGTTCAACCATCGCCGCCTCTACCGGTACTGCGGCGACATC TABLE 3-continued End sequences of the polynucleotide inserts cloned in the named recombinant BAC vectors contained in the I-1945 *M. tuberculosis* H37Rv genomic DNA library.

CCGCCGGTCTAACTCGACGCCGCCTCACTACGCTCAACGCCAGAGACCANCCGCCGGCTGACGTCTCAGATCAGAGAGTCTCCGGACTCACCGGGGCGGTTC
ATCCCCACTGTCGATAGCGTCTGTGGATAACTTTGTCTGCA

:::::::::::::Rv31T7.seq:::::::::::::
GCGCGTNGAACTGATAGGTGCGGCCCGGCTCGAGCANGCCGGCCATTTGTTCGATGCGGTTACCGAAGATCTCTTCGGTGACCTGCCCGCCGCCGGCCAGCT
CGGCCCAGTGCCCGGCGTTGGCCGCCGCGGCGACAATCTTGGCGTCCACGGTGGTCTGGGTCA Clone Rv321
:::::::::::::Rv321SP6.seq:::::::::::::
CTCAAGCTTCAATACAGAGTTATAAACTGTGATAATCAACCCTCATCAATGATGACNAACTAACCCCCGATATCAGGTCACATGACGAAGGGAAAGAGAAGG
AAATCAACTGTGACAAACTGCCCTCAAATTTGGCTTCCTTAAAAATTACAGTTCAAAAAGTATGAGAAAATCCATGCAGGCTGAAGGAAACAGCAATAACTG
TGACAAATTACCCTCAGTAGGTCAGAACAAATGTGACGAACCACCCTCAAATCTGTGACAGATAACCCTCAGACTATCCTGTCGTCATGGAAGTGATATCGC
GGAAGGAAAAT Clone Rv322
:::::::::::::Rv322SP6.seq:::::::::::::
CTCAAGCTTCGATCGACATTACTCCCGCCTTGGGTCTGGTCTCCGAGCTGGTCGGTCATGGTCGGACCTGCTGGTAGTGGGGATCTAACGCAACATGGTCGG
GATTCATCATGGTGTACCCGTGATACCCATTCGCAGCTGCCGGTGAAACCCCGCGATGCCGGGATTTCCAGCCGCACTAGGATGTCTAGCCGGCCAGCCGCT
GCCGCCGGACTTCGGGATGTTCGGTATACCANCGATCGGCAATCTTGCGTATCCGCCGATGCTCGAACGCTANCCACGCCAAACCAACCACTGTGACNACAA
TCGCCACCACACCAAAGGTCATGCCCTCGGCGTGATGTCCGGTGCCGAAAGCCGCAAGAGCTCCGACGCCGCC :::::::::::::Rv322T7.seq:::::::::::::
CATTCCCAATTGAATTTCCCNATCCCACAATCTCGGTTCAGATACAGGTCGCCATACCCCTTACTTCGGCAACGCTGGGCGGATTGGCCCTGCCGCTGCAGC
ANACCATCGACGCCATCGAATTGCCGGCAATCTCGTTCAGCCAATCCATACCCATCGACATTCCGCCGATCGACATCCCGGCCTCCACTATCAACGGAATTT
CGATGTCGGAGGTCGTGCCGATCGATGTGTCCGTCGACATTCCGGCGGTCACCATCACCGGCACCAGGATCGACCCGATTCCGCTGAACTTCGACGTTCTCA
GCAGCGCCGGACCCATCAACATCTCGATCATCGACATTCCGGCGCTGCCGGGCTTTGGCAACTCGACCGAGCTGCCGTCGTCGGGCTTCTTCAACACCGGCG
GCGGTGGCGGCT Clone Rv327
:::::::::::::Rv327SP6.seq:::::::::::::
CTCAAGCTTTCGGCGGAGACGGACANNTTGCGAACATTGATGACAAAATAGAAATCATTGATGGTTTGAGTCACCAGGCCGATCAAGCCTTCGCCGAGCCAA
ATTCCAATCAAGAGGCCCAAGCCCGTACCAATCAGCCCGGCAACGAGGGATTCCGTCATTATCAGCCAAAATAACTGCTCTCGGGTTACACCCAAACAGCGC
AATATGGCGAAAAACGGTCGCCGTTGCACGACATTAAATGTCACGGTATTG :::::::::::::Rv327T7.seq:::::::::::::
AGCTTAACTGCTCCCTAATACCTGGGGCTGTGCCTGCGGTGTATGCACGGCATACGGACATCCNTCCCCTGAGACCCNCGGTCTAATCAGCCACGTGTCCAC
CATCAGGGGTCAACCCCGGCCAAGGGCGACGGCACCCCAAGTTCGCCGACCGTTAACCTATTGCTGTGAGCTTCATTTGCTGCGAGCAAAACAGTTGGTCGG
CCGTTAGGAACTGAATTGACACTCAACCGATTTGGTGCCNCCGTAGGTGTCCTGGCTGCGGGTGCGCTGGTGTTGTCCGCGTGTGGTAACGACCACAATGTG
ACCGGGGGAGGTGCAACCACTGGCCACGCGTCCGCGAATGTCTATTGCGGGGG Clone Rv328
:::::::::::::Rv328SP6.seq:::::::::::::
CTCAAGCTTGGGGTGGCGCTGTCGGTCGGTGTGCTTGGCGGCGTCGGTATCAACACCGCCCACGAAATGGGGCACAAGAAGGATTCGCTGGAGCGGTGGCTG
TCCAAAATCACCCTCGCCCAGACCTGCTACGGGCACTTCTACATCGAGCACAACCGTGGCCATCACGTCCGGGTGTCCACACCGGAGGACCCGGCGTCGGCG
CGGTTCGGCGAAACGTTGTGGGAGTTCCTGCCCCGCAGTGTTATCGGCGGCTTGCGCTCGGCCGTTCATTTGGAGGCCCAACGGCTGCGTCGGCTCGGCGTC
AGCCCCCT :::::::::::::Rv328T7.seq:::::::::::::
GCACCAAGGCCCCACACGTCACCCTGTGACCTCCTGCGCCGACCCCGCCCGAGGTCCTGGCCGTTACCACCTGAACGGGCGAGCCGGGAGTCTGGTACGCAT
CGAACAAAGAGCAAGGTGCATGGGCGGAGTTGTTCCGCCACTTCGTCGATGACGGGGTCNATCCATTCGAGGTCCGTCGCCGCGTCGGTCGAGTGGCGGTGA
CACTCCAGGTACTCGACCTCACAGACGAGAGGACTCGATCCCATCTAGGTGTGGACGAAACAGATCTTCTGTCCGA Clone Rv329
:::::::::::::Rv329SP6.seq:::::::::::::
TCGCCTCCGCATATGGGTCGACGCCAAGCGGGTCCGGATTTCTGGGCTTCATCGCTCGCGCCGTCGCGACAAACAGCGCGGTCGAACCGACACTCGTTGTGA
TGTCCCAGCTATCACCTTCGGTACGCACCCAATCGACCCTACNCGGCTATCTCAGCCGCGATCTCCAGGCTCCGCCGAGCCAGGTGCATCCCGGTCCGGATC
CCACTAACCCGGCACCATTGGCGTCN :::::::::::::Rv329T7.seq:::::::::::::
GTCCTCGAGTGCCGCCGTCGNCACNCCCAGCGCCCGCGCGGCCACTTGGATGCGACCCGTTTCAAGTCCCTTCATCATCTGCGAAAAGCCTTGACCCATGGC
TCCGCCCAGGATCGCCGAGACCGGCACCCGGAGGTTGTCGAACGACAGCTCGCAGGATTCGACGCCCTTGTAACCCAACTTCGGCAAGTCCCGCGACACCGT
GAGTCCCGGCCCGGGTTCGACGAGCACGATCGACATGCCTTGGTGCCGCGGTGTGGCGTTCGGGTCGG Clone Rv32
:::::::::::::Rv32SP6.seq:::::::::::::
GGCATACCAATGTGGACTTCTGCTCACCCACGATATCCGTGGTCTGATCCGCTGCTGCGGCGGGCTGCNACCTGCNTCTCNGCGGCACCCGTNACTACATGG
CNCGCGCCGCACGCATACGTCGCGGCGGGACCCACTCCNACTGGTCGACGGTGCTGGCCGCGTGTCCGCANGTCCCNAACCCGGCCGCACCGACGAAACCGG
CCGCCGTCCGTTCTGGACCAACGCTCATGTGCCGTCGGGGTCCATGCTCGACGCCATCGAGACCGTAACCAGCGTCCTCGAGCGGTTCGCCTCCGGCTTCCG
TGACATCTTCGTGGCTGCTCGCGCCGTGCCGCCGCGCGGATGGTCGACCACAACGCCAACCACCTCGGCGGTGACATCACCGTCCGCGCCACTCGACCTGGC
GCGCGATCGCGGCCC :::::::::::::Rv32T7.seq:::::::::::::
GTGAGCAGACCTACGCCNCCTGGTTGCGCCAACTCGGTACCGATCATGGCGCGCNGCCTGTCGTCACCGATACCCAGCGAACAAGACAGCCCGGTCCGCGAC
AAGATGACTTTCCCGATCTCTTCGGCGACTTCCATGGGGTCGTCCGGAGTCCCGGGCGCCACCGCGAGGTAACCCTCGTCTCAGTCCCATACGCGACCGGGT
ATCCACGTCGCGCAACAACGCCACCACCTCCCCAGACGCCNCGTTGTACGCGGCTGGGTTCCACNGCAATAAGTGGCCTCANGGCATCGTCCGGCGGCGGTC
CNCAACGCA TABLE 3-continued End sequences of the polynucleotide inserts cloned in the named recombinant BAC vectors contained in the I-1945 *M. tuberculosis* H37Rv genomic DNA library.

Clone Rv330
:::::::::::::Rv330SP6.seq:::::::::::::
CTCAAGCTTGAGGTTAACTTTGAACGGATCGAGCTGGACGTTCGAGACGGTGATCGGGCCGAACCTGAATTGTCCGGTAATGCCCAACGCAAAAAGCAGGGT
GGTGGCCGGGGCGGTGAAACCGGCGTCGGCGGCACCGTCGAAATCTATGTGGATTGCCGGAATGGGGATGTCCGGCACGGCGAAACCGTAGTTCGCTTGTCC
CGTGAGGCCCAGGTGGATGGGGGGAAAGATCCTGGTGTCCGGGATAATAATGGGGCCGATGCCGCCGGTTGAAGTCCACTGGATCGGGAATTCCGGAATCTT
GATCCGACGTTCAGGCCGAACAGGCCCTC :::::::::::::Rv330T7.seq:::::::::::::
CGGCGACGTCGCGATACGCCGAGCAGTTGGGAATCGCTCTGCAGCAAACCAATATTCTGCGCGACGTTCGAGAGGACTTTTTGAATGGACGGATCTACCTGC
CGCGCGACGAGCTGGACCGATTAGGCGTACGCCTCCGCCTGGACGACACCGGGGCACTCGATGACCCCGACGGACGGCTCGCGGCNCTGCTGCGGTTCAGTG
CCGACCGCGCCGCAGACTGGTNTTCGCTGGGACTGCGGCTGATTGGACACCTCGACCGCCGCAGCGCTGCCTGCTGTGCGGCCATGTCTGGCATCTACCGCC
GTCAGCTCGCCTTGATCAGAGCATCGCCGGCGGTCGTCTA Clone Rv331
:::::::::::::Rv331SP6.seq:::::::::::::
CTATAAAATACTCAAGCTTGATGCCGCCGAAACCGAGCGTGAGCACGCCGCCAGCCACCACGCGCGGGTCGGGCGCCGGGCCCGGGCCGCCAGGCTGCTCCG
CTCGGTGATGGCACGCCACCGCGACACCACCCGGNTGCGCTACGTCNAGCCATACCGGGCGGAGCTACATCGGCTCGGCCGCCCAGTGTTCGGGCCCTCTTT
CGAGGTCNAGGTCNATACCGATTTGCGCATCCGCAGCCGCACCCTGAACNACANAACCGTGCCCTACTATTGCTTGTCNGGCGGGGCCAAAAAACAGCTTGG
CATCCTGGCCCNATTGGCCGGCGCGG :::::::::::::Rv331T7.seq:::::::::::::
CTTCGGTCGCAGTGTGCGAGTGATAGATGACGACCGGGACCTCGTCGGCATCTTCCATAGCCCGCCACACCTTCAGTTGCTCACCGGAATCCAACCGGTAGA
AGGTCGGCGAGCGCTCGGCATTGGTCATCGGGATATGCCGCTCGGGACGGTCAGAGCCCTCGGGTCCGGCCAGCACTCCGCAGGCTTCGTCGGGGTGGTCGC
GACGCGCATGGGCCACCATCGCATTCACCAGGTCTGCGCGAATCNCCANCACGTANACNGTTCCTTTCCTAA Clone Rv333
:::::::::::::Rv333SP6.seq:::::::::::::
CTGGCACCAAGGCCCCACACGTCACCCTGTGACCTCCTGCGCCGACCCCGCCCGAGGTCCTGGCCGTTACCACCGAACGGGCGAGCCGGGAGTCTGGTNCGC
ATCGAACAAANAGCAAGGTGCATGGGCGGAGTTGTTCCGCCACTTCGTCGATGACGGGGTCNATCCATTCGAGGTCCGTCGCCGCGTCGGTCNAGTGGCGGT
CACACTCCAGGTACTCGACCTCACAGACNAAAGGACTCNATCCCATCTAGGTGTGGACNAAACAGATCTTCTGTCCGACNACTACACCACCACCCAGGCCAT
CGCCGCCGCCCGCGATGCCAACTTCGACGCCGTACTGGCCCCGGCGGGGGGCGCTCCCCGTTGTCAACACTTGCCGTGTTCNTTCACGCNCTGCCCCACATC
CAACCCCAACGG Clone Rv334
:::::::::::::Rv334T7.seq:::::::::::::
GTTCTTGGGCCCATGCGGAGGTATCGCCGTTTCCACCACGCGGTCGGGGTGGCGTTGCATTAGCTCACCGATGGTGCGCTTGTGCAGGCCGCCGGGATACCC
CGAGTGCCGGTAAACCATCTTGTGCTGC Clone Rv335
:::::::::::::Rv335SP6.seq:::::::::::::
CAATACTCAAGCTTGGCGTGCCGTTCCAACCCGAATTGGCTTTCGGCGCCATCGGTGAGGACGGCGTGCGGGTGCTCAACNACNACGTCGTCCGCGGGACAC
ACCTCGATGCTGCCGCCATGGACGCGGTCGAACGCAAGCAGCTGATCGAGCTACAACGCCGCGCGGAACGCTTCCGCCGCGGGCGTGACCGCATCCCGTTGA
CCGGGCGGATC :::::::::::::Rv335T7.seq:::::::::::::
CNTCATGATGATCATCACCCGAAGTGTGGTAGCCGCAGTGGTTATCGTGGGTACCGTCGTGCTTTCCATGGGCGCCTCTTTCGGGCTTTCCGTATTGGTCTG
GCAGGACATTCTGGGTATCGAGTTGTACTGGATGGTGTTGGCGATGTCGGTGATCCTGCTCCTGGCGGTGGGATCCGACTACAATCTGCTGCTGATTTCCCG
GTTGAAAGAGGAAATTGGGGCCGGATTGAACACCGGAATTATCCGTGCCATGGCTGGTACCGGGGGAGTGGTGACGGCTGCCGGCATGGTGTTCGCCGTTAC
CATGTCGTTGTTTGTGTTCAGCGATTTGCGAATTATTGGTCAGATCGGTACCAC Clone Rv336
:::::::::::::Rv336SP6.seq:::::::::::::
ATACTCAAGCTTTTACGGTGATCGCNCATCACCTGGTTCATGAACTGGAAGCAGCGCAGCGCTTCCTTTTCGGCCGCAACATGAGCCAGCCTCTCGTCGGCG
GTCGGGTGCAGGTGCTCGGGCAGCTCGGCCGCNACAGCCGCCTGACCCTGAAACCAGCTTCCATATCCCGCGANNAACGACGCCAGTCCGCTACGTNACCCC
TCCGCGACTGTCCATGGACAACAGCGCGTTCTCCACCGACCGGGCCCGGGTGTGGGGTNTT :::::::::::::Rv336T7.seq:::::::::::::
GCTGGTAGAGTCGCTGACCGGTGCAGGTTTCGACAATGTGGTGCCGGTTCGGCGGCTACGTGCCATCGAGACACTGGCGCAGGCTATCGCACCCGTTATCGG
CTACGAGCAAATCGCGGTATGCGTTCTTGAGCATGAGTCGGCGACCGTCGTCATGGTCGACACCCACGACGGAAAGACGCAGATCGCCGTCAAGCATGTGTG
CCGCGGATTATCAGGACTGACCTCCTGGCTGACCGGCATGTTTGGTCGCGATGCCTGGCG Clone Rv337
:::::::::::::Rv337SP6.seq:::::::::::::
GCTTTCCGCCGATACCCGCCATGTCNCGCACATCCAGGACTTCTGGGGGGATCCGCTGACAGCGGCGGGATCCCAAAGTGCGGATGATCGGGCCGCCTACGT
CGTGGTGTACCTCGTCGGTAACAACGAAACCGAAGCGTATGACTCGGTCCACGCGGTGCGGCACATGGTGGACACCACACCGCCACCGCACGGGGTGAAGGC
CTATGTCACCGGTCCGGCANCACTCAATGCCGACCAGGCCGAGGCCGGANACAAAANTATCGCTAAGGTCACCGCGATCACNAGCATGGTGATCGCAGCAAT
GTTGCTAGTGATCTATCGCTCCGTAATTA :::::::::::::Rv337T7.seq:::::::::::::
CTTCCAACCCGAATTGGCTTTCGGCGCCATCGGTGAGGACGGCGTGCGGGTGCTCAACGACGACGTCGTCCGCGGGACACACCTCGATGCTGCCGCCATGGA
CGCGGTCGAACGCAAGCAGCTGATCGAGCTACAACGCCGCGCGGAACGCTTCCGCCGCGGGCGTGACCGCATCCCGTTGACCGGGCGGATCGCGGTGATCGT
CGATGACGGCATCGCCACCGGAGCGACGGCCAAGGCGGCGTGCCANGTCGCCCGGGCGCACGGTGCGGACAAGGTGGTGCTGGCGGTCCCGATCGGCCCA TABLE 3-continued End sequences of the polynucleotide inserts cloned in the named recombinant BAC vectors contained in the I-1945 *M. tuberculosis* H37Rv genomic DNA library.

Clone Rv338
:::::::::::::Rv338SP6.seq:::::::::::::
TACTCAAGCTTCGCGAGATCCGGATGGCACTCACGCTGGACAAGACCTTCACAAAATCTGAAATCCTGACCCGATACTTGAACCTGGTCTCGTTCGGCAATA
ACTCGTTCGGCGTGCAGGACGCGGCGCAAACGTNCTTCGGCATCAACGCGTCCGANCTGAATTGGCAGCAAGCGGCGCTGCTGGCCGGCATGGTGCAATCNA
CCAGCACGCTCAACCCGTA :::::::::::::Rv338T7.seq:::::::::::::
CCCACGACTTTCTCCTCGATCAGTTGGATTTGTACGAAGAGGCAACGAAAGCAGTGATCCTCGGGATGGTCGACGCCTACATCGACCCGCCGTTCACGCCGC
ACAGCCTGCTAGATGCGCTGGGCGAGCAGGTCCCACAGTTCGCCGCTAAGGCACGGCGTCTGTTCCCGTCCGGATCGCCATTCGGCCTCGGCGTCCTGCTCC
CATTCGATCAATAGGGCTGGCAGCTCCGTCGGCAGGGGCCTACGCCTCACCCCGTCACG Clone Rv339
:::::::::::::Rv339SP6.seq:::::::::::::
CTCAAGCTTATGCGCGCCGGCCGAGGTCTGCTCACGGCAACCCCTGAAGTTTAGGGGACNACCTACTCAGCGCAAAATTTCGCTAATGTGAGTCCGCCCCAC
CAGGGGNANATCAACCCATGTCGATCATGATCTACCCGGATACCGGATTGGCGGTAGCGCCCACGATCGTCNAAATNTCCGCCTGAATCATCGGATAGCTGA
TCCGGCGTCAACGCGTTTTGANTTCACCGCGCAACAGCCGCCAGGCCGGCCCGCANCGANCCGATCTCNTCGGGCCGCATGGGCCCCAATCTTNTCG :::::::::::::Rv339T7.seq:::::::::::::
GTGTGTGGTGGAACCCATCTGAGCAGTGTGCCAAACCGGGGCAGACAGCTCCCAATTGACGTGAGCCCGCTCACTTGCTGGGTAAGCGTC Clone Rv33
:::::::::::::Rv33SP6.seq:::::::::::::
CTTTACACTTCCTGCATCCGGCTCGTATGTTGTGTGGAATTGTGAGCGGATAACAATTTCACACAGGAAACAGCTATGACCATGATTACGCCAAGCTATTTA
GGTGACACTATAGAATACTCAAGCTTGGGCGTGACGGCCACCGGGGCCACTCCGCACCATCTGTACCCGACCAAGATCTAC :::::::::::::Rv33T7.seq:::::::::::::
CAGGCATGCAAGCTTTAGCTGCCCGAATGCGTCACCCCGATGCGCCCAGATCGGGGCTTCGCAGATAAAGCACGAACAGGCGGGCAAAACGTCNATCTCGGA
GCCGGAAGGGCAATCAGCCGACCGTCGACGAACGACACCGGCGAGACCACTTAGGCAGTGACGGCCGGCCCGAACATTACGCGCTCGTTGATTAGGCGTTCG
GTCTCGTCCGCGGTCATGCCGAGCAGCTTGCGGCAGATCTGAACGCTGTCCTGTCCGGGCAGCGGCGCCGGGCGTTGGGGTGCCTGCCCGAATGTGACGAAA
CGGAGCCGGACCCGTCTCGGCGGGCCGCGGACGGCGATCCGC Clone Rv340
:::::::::::::Rv340SP6.seq:::::::::::::
CNCAAGCTTGCGGATGTTACCCCTGACAGCCTGAACTATGTCNAAACACACGGCACCGGAACGGTGTTGGGGGACCCCATCGANTTCGAGTCGCTGGCGGCC
ACTTATGGCCTGGGTAAAGGCCAGGGCNANAGCCCGTGCGCATTGGGGTCGGTCAAAACCAACATCGGCCACCTGGAGGCGGCCGCCGGTGTGGCTGGATNC
ATCAAGGCGGTGCTGGCGGTGCAACGTGGGCACATTCCCCGCAACTTGCACTTCACCCGGTGGAACCCGGCCATCNACGCGTCGGCNACGCGGCTGTTCGTG
CCNACCNAAAACCCCCCGTGGCCGGCGGC :::::::::::::Rv340T7.seq:::::::::::::
GGAACCGGTAACCAGATCAGCTCGTCGACCTCACTGCCGGGGGTGAATTCCCCACCGGTGCTGCGCGCTGCCCAGTAGTGCACCTTCTTGACGCCTCGAAAA
GGGGAGTCGGTCGGGTAGGTCACCGTCAGGAGCCGCCTACCCAGGTTGGCGCNATAGCCGGTCTCCTCGAGTATCTCCCGCACCGCCCCCACCGGTGCGGTC
TCACCCANATCCACTTTGCCCTTGGGCAGCGACCAGTCGTCGTANCNGGGGCGGTGAATGACAACGATCTCGACCGGCCCTTCCN Clone Rv341
:::::::::::::Rv341SP6.seq:::::::::::::
TACTCAAGCTTCAGAACAGGCCTGTTGTGGGCNCACCCGGCTCGCCGAGTTCTGCACGCACCGCCTCAAGTGCGGCCCGCACCGCCGGCATCTCCCGGTCAC
GCAGGGCCGCGGCCCGCGCCGCAGCGACGGCGTGTTCGCGCAGTTCGCCGTCAATGATGCTGACCTGATCGGCCACCCGGGCGTTCTCGGCGTCGTCGCGTT
CACTAATCGCGGTGCTCAGCAGCGTCTCGACAGCCACCACCCGAGTGGCGACCAGCTGC :::::::::::::Rv341T7.seq:::::::::::::
TAATGTCTTGCCAACGTCACCACAATCGCGATGAATTCAATCATGCCGCCCAGGGCGGCCAACCCAATGGTGGCCGCGAGCGGCAGCTCGATCGCAGCGCGG
AGGTTGCCGGCCGCCAGTTGATTCACGAACAGGGTGAGGTCATAGGCGGGCAGGATAGTGACGAAGGCAAGACCTATATCTGCCGTCGGAAGAAGAATCGAG
TAGCCGGTCGACACAACGGAAGCGAAAGTGTCCGCGATGTTGATGAGCGTCGCCGGTTGTGGCGGCGGTGGCGGC Clone Rv343
:::::::::::::Rv343SP6.seq:::::::::::::
TACTCAAGCTTTCGTCAGTTCATCGCGCCAGCAGACCAACAAGAGCATCGGGACATACGGAGTCAACTACCCGGCCAACGGTGATTTCTTGGCCGCCGCTGA
CGGCGCGAACGACGCCAGCGACCACATTCAGCANATGGCCAGCGCGTGCCGGGCCACGAGGTTGGTGCTCGGCGGCTACTCCCAGGGTGCGGCCGTGATCGA
CATCGTCACCGCCGCACCACTGCCCGGCCTCGGGTTCACGCAGCCGTTGCCGCCCGCAGCGGANNATCACATCGCCGCGATCGCCCTGTTC :::::::::::::Rv343T7.seq:::::::::::::
CCACCCGTGTAATTTGGGATGGGCNAAAAGGCNAAGCACCGCGTGGCCACGAACGCCGGGAGGGACAATCTCGGGCGGCTAGGGCTTCTCGCGGGAAGGCCC
GAACGTACGGCGTTTCAACACGTCGCGTCGCCCTCCGACCGCGAACATTCGGGGATGGCAGCAACCTGGTAGCACCCTGGCCGGGCGATGATCTGCAGCGTC
GCCGCGGGTAGTCGCCGCCCGGGCGGCTACAGTCTGAAACGCGATGACCATCGATGTGTGGATGCAGCATCCGACG Clone Rv344
:::::::::::::Rv344SP6.seq:::::::::::::
TCAAGCTTTAGCTGCCCGAATCCGTCANCCCGATGCNCCCAGATCGGGGCTTCGCANATAAAGCACNAACAGGCGGGCAAAACGTCNATCTCGGAGCCGGAA
GGGCAATCANCCGACCGTCNACAAACGACACCGGCGANACCACTTAGGCAGTGACGGCCGGCCCGAACATTACNCGCTCGTTGATTAGGCGTTCGGTCTCGT
CCGCGGTCATGCCGAGCAGCTTGCGGCANATCTGAACGCTGTCCTGTCCGGGCAGCGGCGCCGGGCGTTGGGGTGCCTGCGGAATGTGACNAAACGGAGCCG
GACCCNTCTCGGCG :::::::::::::Rv344T7.seq:::::::::::::
CCGGGGCCACTCCGCACAATCNGTACCNNACCAANATCTACACCATCGAATACGACGGCGTCGCCGANTTTCCGCGGTACCCGCTCAACTTTGTGTCGACCC
TCAACGCCATTGCCGGCACCTACTACGTGCACTCCAACTACTTCATCCTGACGCCGGAACAAATNGACGCNTCGGTTCCGCTGACCAATACGGTCGGTCCC TABLE 3-continued End sequences of the polynucleotide inserts cloned in the named recombinant BAC vectors contained in the I-1945 *M. tuberculosis* H37Rv genomic DNA library.

Clone Rv346
:::::::::::::Rv346SP6.seq:::::::::::::
NCTGGCCTTTGGTCCACACTAANACAATACTCAAGCTTCCGGCCGCAGAGCCGCCAACTCACGATATCGTTAACCGATATCCCGAGCCGATAGCTGGCGGGC
TCGGGTGGTGGCCAGCGGCGCTGCGACNAAAGGTGTGACCGTCATGAAACAGACACCACCGGCGGCCGTCGGCCGTCGTCACCTGCTCGANATCTCAGCATC
CGCAGCCGGTGTGATCGCGCTTTCGGCGTGTNGTGGGTCNCCGCCCGAGCCCGGCAAAGGCCGGCCCGACACAACCCCGGAAC :::::::::::::Rv346T7.seq:::::::::::::
CATCTGCCCACCACACGGACCGCGGTGCGGACGCGGCTGACGCGCCTGGTGGTCAGCATCGTGGCCGGTCTGCTGTTGTATGCCAGCTTCCCGCCGCGCAAC
TGCTGGTGGGCGGCGGTGGTTGCGCTCGCATTGCTGGCCTGGGTGCTGACCCACCGCGCGACGACACCGGTGGGTGGGCTGGGCTACGGCCTGCTATTCGGC
CTGGTGTTCTACGTCTCGTTGTTGCCGTGGATCGGCGAGCTGGTGGGCCCCGGGCCCTGGTTGGCACT Clone Rv347
:::::::::::::Rv347SP6.seq:::::::::::::
GACAATACTCAAGCTTGACTGGCCACCCACCGGCATGACCACCGACAGGCCCGACTGGTCGTACCACTCGAACGCCGGGGTGTTGATGTCCCAGCCGCTGAA
NTCGTCCTGCGCGCGCAGGCCGTCNAACAGGTACAGGGCGGGCGAATTGGCACCACCACTTTGGAATTGGACCTTGATGTCACGGCCCATCGACGGCGACGG
CACCTGCAGGTACTCCACCGGCAAGCCCGGCCGGGAAAATGCCCCCGCGGTCNCCGTGCCACCGACGGCGCCGANCAAACCCGACACTAGGGCCGCGCCNAC
GGCCCCGACCACNANTCNACGCGACATACCCGTGACGGCGCCACNAACCCTGTCAACA :::::::::::::Rv347T7.seq:::::::::::::
CCTCCAACTCGGCGGGGAAGCGACNCCAGCCTACCGAGCTTGGAGTCCANGACGCCAGCGGCGGCGTCGGTCTGCGTCGTGGTGCCGCCGGGGTGGCGTTGG
CTGGCAACGATCTCCACCCAGCCGGTCGGGTTACCCACGATCTCGGCATANACGCGGGCCGAGGCCGGTGCGATACCGTATTGCGTCAATTGGACGCGGTT
GTGCATTCGGCTAGCTCGGTTGCCACACCCGTCAGGGGTTCGACGTTGGCGGGTTCGGCGGGCCCCANCACCGCTGTCACCATGCCCGCCAAGCCGACCTGC
GGCGCCACCAACTGCAGCACCANCATGTCGCCGTCGCGCGCCGCGATCACATGG Clone Rv348
:::::::::::::Rv348SP6.seq:::::::::::::
CTCAAGCTTTTTGAGCGTCGCGCGGGGCANCTTCGCCGGCAATTCTACTANCGAGAANTCTGGCCCGATACGGATCTGACCGAANTCGCTGCGGTGCANCCC
ACCCTCATTGGCGATGGCGCCGACNATGGCGCCTGGACCGATCTTGTGCCGCTTGCCGACGGCGACGCGGTAGGTGGTCAAGTCCGGTCTACGCTTGGGCCT
TTGCGGACGGTCCCGACGCTGGTCGCGGTTGCGCCGCNAAAGCGGCGGGTCGGGTGCCATCAGGAATGCCTCNCCGCCGCGGCACTGCACGGCCACTGCCGC
GGCGA :::::::::::::Rv348T7.seq:::::::::::::
CNCCAGCTTGATTGGTCTGGTTGCATTGGCCAGCTGCGCGAGCCTGGCTCACTTCAACTACGACGACCGCAAACAATTGCCGCCTTCGGATCCGAGTTCGGT
TGGGTACGCGGCAATGGAGCACCATTTCTCGGTGAATCAGACTATTCCTGAGTACTTGATCATCCACTCTGCACACGACCTGCGAACCCCGCGCGGCCTTGC
CGACCTGGAGCAGCTGGCGCAACGTGTGAGCCAGATCCCAGGCGTTGCCATGGTTCGCGGTGTGACCCGGCCAAACGGGGAAAC Clone Rv349
:::::::::::::Rv349SP6.seq:::::::::::::
CAATACTCAAGCTTGACTGGGCCCGCACCTTCGGCGCCACCCACACCGTCAACGCCCGCGAAGTCNACGTCGTCCAGGCCATCGGCGGCCTCACGGATGGAT
TCGGCGCGGACGTGGTGATCGACGCCGTCGGCCGACCGGAAACCTACCAGCAGGCCTTCTACGCCCGCGATCTCGCCGGAACCGTTGTGCTGGTGGGTGTTC
CNACGCCCGACATGCGCCTGGACATGCCGCTGGTCNACTTCTTCTCTCACGG :::::::::::::Rv349T7.seq:::::::::::::
TCGACGGTTTGGCGGCCTTAAATGCACTGAGGTCGTCAATTGACCCCACAGCGGAAATGCCGACTATTCGCAGGCCTCCTTCGCCTTGGCTGCCGGAGAGGG
GCTCCGCGGGAACCGCATGCAGGTATATGACCTCGGTTTCTCGGGTGCTACCGCGTGCCTTGTNTANGATNANCTCGGCGTTGGAATTGTCCAGCCGGCCCA
ATTCATCGAGCGCANATTCGTACACNTGGCCGGCGGCGACATACGCTTCACCGTGGATCTGCTCCACACGGACCGCCCTGTCGGGATCCTGCTCACGGGTAA
CGGAACTTACGTGGCACTCGG Clone Rv34
:::::::::::::Rv34SP6.seq:::::::::::::
GACCACGCCAGGCTAATCACGTGACGCTACCGAATACCCTNCCTAGTGGTGCAGGCTCCCGCTGGAAATGGCCCTGTACCAACTCGCGCACCGGTGCCAG :::::::::::::Rv34T7.seq:::::::::::::
CGGCACCCGACCCCTTTGAGCCGTCCGCCGTGGCCGCGGTGGAACTGGCCGACGAGGGACTGATCGTGCTGGGCAAATTGGTCGATGGCACGCTGGCCGCCG
ATCTGAAGGTCN Clone Rv350
:::::::::::::Rv350SP6.seq:::::::::::::
CTCAAGCTTGCCGTTACCCCGACTTCCGGAGGGACACCATGAGCACCGCCAGCCGAGCACGAGGCCAAACTCCGCCGACGCAGGCCGGTTGGACTTGTCGTG
CTGGACAAGGGGTTTAGCCGCCGAAGCAGTGACGTACATCGGCGAAAAGCAGTTCGCCTGTCGACCGACGGNGCNNACCGTGAGGCTAGGGAAGCGAGGAGC
ACATGGCCGCCGACCCGCAATGTACACGCTGCAAGCAAACCATCGAACCCGGATGGCTATNCNTCACCGCCCATCGCCGCGGT :::::::::::::Rv350T7.seq:::::::::::::
CATGTCGCGCACATCCAGGACTTCTGGGGGATCCGCTGACAGCGGCGGGATCCCAAAGTGCGGATGATCGGGCCGCCTACGTCGTGGTGTACCTCGTCGGT
AACAACGAAACCGAAGCGTATGACTCGGTCCACGCGGTGCGGCACATGGTGGACACCACACCGCCACCGCACGGGGTGAAGGCCTATGTCACCGGTCCGGCA
GCACTCAATGCCGACCAGGCCGAGGCCGGAGACAAAAGTATCGCTAAGGTCACCGCGATCACGAGCATGGTGATCGCAGCAATG Clone Rv351
:::::::::::::Rv351SP6.seq:::::::::::::
ATACTCAAGCTTCGGTACGGTGGCGGGCCGTGCTGCTGGCCGCGGTCGCGGCGTGCGCGGCCTGCGGTCTCGTTTACNAGCTCGCGCTGCTGACACTGGCGG
CNAGCCTGAACGGCGGCGGGATCGTGGCCACCTCCCTGATCGTCGCGGGCTACATAGCCGCGCTGGGAGCAGGCGCCTTGCTGATCAAGCCGCTACTTGCAC
ACGCGGCCATCGCGTTCATCGCCGTGGAGGCGGTGCTGGGCATCATCGGCG :::::::::::::Rv351T7.seq:::::::::::::
TGTCAAGTCCTTTCAGATCTCNTTTTTATGACATGACTGGAGATCTGTCTAGATTGCAGCTCCTGTGAGCGTGGGTACCGGATTCAAGCCGGTCGGTCACGC
CGCGGTGGTACCGGCTTTGCGGCAGTGCTCGGCCTCGAGTTCGGCGATCGCGCGCGAAGTGCGTTCGCGCAGCAAGATCGCGGCCGTAATGCCGGCGATGAC
CGCGATGACCAGAGCGATCCAGGAGAACCGTTCCAACCAGTGCTGGGCGGCCATCCCGGCGAAGTAGACCAGTGCAGTGGTGCC TABLE 3-continued End sequences of the polynucleotide inserts cloned in the named recombinant BAC vectors contained in the I-1945 *M. tuberculosis* H37Rv genomic DNA library.

Clone Rv352
:::::::::::::Rv352SP6.seq:::::::::::::
CAATACTCAAGCTTCAAAACAGGCCTGTTGTGGGCGCACCCGGCTCGCCGAGTTCTGCACGCACCGCCTCAANTGCGGCCCGCACCGCCGGCATCTCCCGGT
CACGCAGGGCCGCGGCCCGCGCCGCANCGACGGNGTGTTCGCGCAGTTCGCCGTCAATGATGCTGACCTGATCGGCCACCCGGGCGTTCTCGGCGTCGTCNC
GTTCACTAATCGCGGTGCTC :::::::::::::Rv352T7.seq:::::::::::::
TACGCTGGCGCTGGAGGGAGCCANNTACAACATCCACGCCAATGCTCTTGCCCCGATCGCGGCGACCAGGATGACCCAGGACATCCTGCCGCCCGAAGTACT
GGAAAAGCTCACACCCGAGTTCGTCGCACCGGTGGTGGCCTACCTGTGCACCGAGGAGTGTGCCGACAACGCATCGGTGTACGTCGTCGGTGGTGGCAAGGT
GCAGCGAGTTGCGCTGTTTGGCAACGACGGCGCCAACTTCGACAAACCGCCGTCGGTACAAGATGTTGCGGCGCGGTGGGCCGAGATCACCGATCTGTCCGG
TGCGAAAATTGCTG Clone Rv353
:::::::::::::Rv353SP6.seq:::::::::::::
GCTTTTCCCGTCCGTCNNCGCTCAACCGCGTGAGGCCGAAGCGGNTGGTTACGACTCCCTGTTTGTGATGGACCACTTCTACCAACTGCCCATGTTGGGGAC
NCCCGACCAGCCGATGCTGGAGGCCTACACGGCCCTTGGTGCGCTGGCCACGGCGACCGANCGGCTGCNNNTGGGCGCGTTGGTGACCGGCAATACCTACCG
CAGCCCGACCCTGCTGGCAAANATCATCACCACGCTCGACGTGGTTAGCGCCGGTCGAGCGATCCTCGGCATTGGAGCCGGTTGGTTTGANCTGGAACA :::::::::::::Rv353T7.seq:::::::::::::
CNGCTTTTTAATGGCCTTGACNTGGGCGNGCCGGCCACCGGGGCCACTCCGCACAATCTGTACCCGACCAAGATCTACACCATCGAATACGACGGCGTCGCC
GACTTTCCGCGGTACCCGCTCAACTTTGTGTCGACCCTCAACGCCATTGCCGGCACCTACTACGTGCACTCCAACTACTTCATCCTGACGCCGGAACAAATT
GACGCAGCGGTTCCGCTGACCAATACGGTCGGTCCCACGATGACCCAGTACTACATCATTCGCACGGAGAACCTGCCGCTGCTAGAGCCACTGCGATCGGTG
CCGATCGTGGGGAACCCACTGGCGAACCTGGTTCAACCAAACTTGAAGGTGATTGTTAACCTGGGCTACGGCGACCCGGCCTATG Clone Rv354
:::::::::::::Rv354SP6.seq:::::::::::::
CTCAAGCTTGCCGGGAGGGTGCATGGCCGACTCGGATTTACCCACCANGGGGCGCCAACGCGGTGTCCGCGCCGTCNAGCTGAACGTTGCTGCCCGCCTGGA
GAACCTGGCGCTGCTGCGCACCCTGGTCGGCGCCATCGGCACCTTCGAGGACCTGGATTTCGACGCCGTGGCCGACCTGAGGTTGGCGGTGGACGAGGTGTG
CACCCGGTTGATTCGCTCGGCCTTGCCGGATGCCACCCTGCGCCTGGTGGTCGATCCGCGAAAANACGAANTTGTGGTGGAGGCTTCTGCTGCCTGCGACAC
CCACNACGTGGTGGCACCGGGCAGCTTTAGCTGGCAT :::::::::::::Rv354T7.seq:::::::::::::
CCGACGCCGTCGTGGCCACCAACACCGCGACCAGCACCGTGACCCGGACCGGGGTGCCGCGCGAACCGGTCTTGGCCAATTGCCGCGGCACCAAGCCGTCGC
GCGCCATGGCGAACAGCACGCGGCATTGCCCGAGCATCAACACCATCACCACCGTGGTAAGCCCGGCCAGCGCGCCGACGGAGATGATGCCGCTGGCCCAGT
ACACCCCGTTGGCCTGGAACGCGGTGGCCAGATTTGCCGGCCCGCGGCCCGGTACGGTCCGCAGTTGGGTGTATGGAACCATGCCCGACAGCACCACCG Clone Rv355
:::::::::::::Rv355SP6.seq:::::::::::::
TTNACTGGCCTTTGGTCCACACTAGACAATACTCAAGCTTCCAGGACATCGTCATCGCGACCAAAACCGCGAGCTAGGTCGGCATCCGGGAAGCATCGCGAC
ACCGTGGCGCCGAGCGCCGCTGCCGGCAGGCCGATTAGGCGGGCAAATTAGCCCGCCGCGGCTCCCGGCTCCGANTACGGCGCCCCGAATGGCGTCACCGGC
TGGTAACCACGCTTGCGCGCCTGGGCGGCGGCCTGCCGGATCAGGTGGTAAATGCCGACA :::::::::::::Rv355T7.seq:::::::::::::
NGACGTCTTCCATCCGCGCGTCGTTTTGGCGGGTTGGCCACAGCAGCCCGCCGGTGACGGCGACGATGCTGGGCTGGTTGCGGCCCTGCGCCACCGCGGCTT
GCATGCTGGTTGGCTGTCTTGGGACGATCCCGAAATAGTCCACGCGGATCTGGTGATTTTGCGGGCTACCCGCGATTACCCCGCGCGGCTCGACGAGTTTTT
GGCCTGGACTACCCGCGTGGCCAATCTGCTGAACTCGCGGCCGGTGGTGGCCTGGAATGTCGAGCGCCGTTACCTA Clone Rv356
:::::::::::::Rv356SP6.seq:::::::::::::
CTTCCTCCTGAGTACCNCCCGTNTACTTTGGGATGGGTAAAAAGGCGAATCNCCGTTTGGTCACGAACGCCGGGAGGGACAATCTCGGGCGGCTGGGGCCTC
TCGCGGGAANGCCCGAATGTACGGTGTCTCGACACTTCCCNTCCCCCTCCG :::::::::::::Rv356T7.seq:::::::::::::
GAGCATCGGGACNTACGGAGTCAACTACCCGGCCAACGGTGATTTCTTGGCCGCCGCTGACGGCGCGAACGACGCCNGCGACCACATTCAGCAGATGGCCAG
CGCGTGCCGGGCCACGAGGTTGGTGCTCGGCGGCTACTCCCAGGGTGCGGCCNTGATCNACATCGTCACCGCCGCACCACTGCCCGGCCTCGGGTTCACGCA
GCCGTTGCCGCCCNCAGCGGACGATCACNTCGCCGCGATCGCC Clone Rv357
:::::::::::::Rv357SP6.seq:::::::::::::
TACTCATGANCATCCTTTAATCANNGCTTTGCGTTTTTTTATTAAATCTTGCAATTTACTGCAAAGCAACAACAAAATCGCAAAGTCATCAAAAAACCGCAA
AGTTGTTTAAAATAAGAGCANCACTACAAAAGGAGATAAGAAGAGCACATACCTCAGTCACTTATTATCACTAGCGCTCGCCGCAGCCGTGTAACCGAGCAT
AGCGAGCGAACTGGCGAGGAAGCAAAGAAGAACTGTTCTGTCAGATAGCTCTTACGCNCA Clone Rv358
:::::::::::::Rv358SP6.seq:::::::::::::
CTCAAGCTTCAGGTCAATGTGCNCCAAGCCCTGACGCTGGCCGACCAGGCCACCGCCGCCGGANACNCTGCCAAGGCCACCGAATACAACAACGCCGCCGAG
GCGTTCGCANCCCAGCTGGTGACCGCCGAGCANANCGTCAAAAACCTCAAGACGCTGCATGACCAGGCGCTTANCNCCGCANCTCAGGCCAAGAAGGCCGTC
NAACGAAATGCGATGGTGCTGCACCANAAGATCGCCGAGCGAACCAAGCTGCTCAGCCNG :::::::::::::Rv358T7.seq:::::::::::::
CATGGTGGCACTGTAGCGACGTGCTGCAATCAAGGTCATGCCCGACTCTGGTCAGCTCGGANCCGCTGACACCCCGCTAAGGCTGCTCAGCTCGGTGCATTA
CCTCACCGACGGCGAACTCCCCCAGCTTTACGACTATCCGGATGACGGCACCTGGTTGCGGGCGAACTTCATCATCAGCTTGGACGGCGGCGCTACCGTCGA
TGGCACCAGCGGGGCGATGGCCGGGCCCGGCGACCGATTCGTCTTCAACCTGTTGCGTGAACTTGCCGACGTCATCGTGGTCGGCGTGGGCACCGTGCGCAT
TGAGGGCTACTCCGGCGTCCGGATGGGTGTCGTCCAGCGCCAGCAC TABLE 3-continued End sequences of the polynucleotide inserts cloned in the named recombinant BAC vectors contained in the I-1945 *M. tuberculosis* H37Rv genomic DNA library.

Clone Rv359
::::::::::::Rv359SP6.seq::::::::::::
TACTCAAGCTTGCGGGTGATCGCCTTGGTCAACGGCACCGTGATCGGATCGGGGTCNACCGCACAAATGGACTGGAGCTTCGGCGAANTCATCGCCTATGCC
TCGCGGGGGGTGACGCTGACCCCGGGTGACNTGTTCGGCTCGGGCACGGTGCCCACCTGCACGCTCGTCTATCACCTCNGGCCACCGGAATCATTCCCGGGC
TGG ::::::::::::Rv359T7.seq::::::::::::
GTTGGNGCCTCGTCGGCGAACAGTTCTCGCACGATTTCCGGATTAGCGGGACTGGTCACCAGTTGGGTATGCGGGAAGGCGCTGACGTTCGCCGCGATTAGC
TGTTTGATGGACGCGGTGGTGATGTTCTGATCACGGAACTGGCTGTAATAGCCCAGGGTCGCCACGCTTTCATCCGGGCCCGGACCCGGCGCACCGAGCGTG
TCGCGCAGGTATGCGACGTGATTTTCGCTGAAGTCCCCGTACCCGGAGAACT Clone Rv35
::::::::::::Rv35SP6.seq::::::::::::
TGCTTCCGGCTCGTATGTTGTGTGGAATTGTGANCGGATAACAATTTCACACAGGAAACAGCTATGACCATGATTACGCCAAGCTATTTAGGTGACACTATA
GAATACTCAAGCTCCAGGTCAATGTGCGCCAAGCCCTGACGCTGGCCGACCAGGCCACCGCCGCCGGAGACGCTGCCTTTGTCACCGAATACAACAACGCCG
CCGAGGCGTTCGCAGCCCAGCTGGTGACCGCCGAGCAGAGCGTCGAAGACCTCAAGACGCTGCATGACCAGGCGCTTAGCGCCGCAGCTCAGGCCAAGAATG
CCGTCGAACGAAATGCGATGGTGCTGCGGCATAAGATCGCCGAGCGAACCAAGCTGCTCAGCCAGCTCGAGCAGGCGAAGATGCACGAGCA ::::::::::::Rv35T7.seq::::::::::::
CAGGCATGCAAGCTTCGGAGGCAGACCCGTGCATGGTGGCACTGTAGCGACGTGCTGCAATCAAGGTCATGCCCGACTCTGGTCAGCTCGGAGCCGCTGACA
CCCCGCTAAGGCTGCTCAGCTCGGTGCATTACCTCACCGACGGCGAACTCCCCCAGCTTTACGACTATCCGGATGACGGCACCTGGTTGCGGGCGAACTTCA
TCAGCAGCTTGGACGGCGGCGCTACCGTCGATGGCACCAGCGGGGCGATGGCCGGGCCCGGCGACCGATTCGTCTTCAACCTGTTGCGTGAACTTGCCGACG
TCATCGTGGTCGGCGTGGGCACCGTGCGCATTGAAGGCTACTCCGGCGTCCGGATGGGTGTCGTCCATCGCCA Clone Rv360
::::::::::::Rv360SP6.seq::::::::::::
TACTCAAGCTTGGGGTGGCGCTGTCGGTCGGTGTGCTTGGCGGCGTCGGTATCAACACCGCCCACGAAATGGGGCACAAGAAGGATTCGCTGGAGCGGTGGC
TGTCCAAAATCACCCTCGCCCANACCTGCTACGGGCACTTCTACATCGAGCACAACCGTGGCCATCACGTCCGGGTGTCCACACCGGAGGACCCGGCGTCGG
CGCGGTTCGGCNAAACGTTGTGGGANTTCCTGCCCCGCANTGTTATCGGCGGCTTGCGCT ::::::::::::Rv360T7.seq::::::::::::
GGCCATCGCCACCGCNCCGCGGCGAACGCTCAAAGGCACCTACTGGCACCAAGGCCCCACACGTCACCCTGTGACCTCCTGCGCCGACCCCGCCCGAGGTCC
TGGCCGTTACCACCGAACGGGCGAGCCGGGAGTCTGGTACGCATCGAACAAAGAGCAAGGTGCATGGGCGGAGTTGTTCCGCCACTTCGTCGATGACGGGGT
CGATCCATTCGAGGTCCGTCGCCGCGTCGGTCGAGTGGCGGTCACACTCCANGTACTCGACCTCACAGACGAGAGGACTCGATCCCATCTAGGTGTGGACGA
AACAGATCTTCTGTCCGACGACTACACCACCACCCAGGCCATCGC Clone Rv361
::::::::::::Rv361SP6.seq::::::::::::
GCTTGCGGGTGATCGCCTTGGTCAACGGCACCGTGATCGGATCGGGGTCNACCGCNCAGATGGACTGGANCTTCGGCGAANTCNTCGCCTATGCCTCGCGGG
GGGTGACCCTGACCCCGGGTGACNTGTTCGGCTCGGGCACGGTGCCCACCTGCACGCTCGTCAAGCACCTCNGGCCACCGGAATCATTCCCGGGCTGGCTGC
ACNACGGCGACNTGGTCNCCCTCCAGGTCGAAGGGCTGGGCNAAACAANGCAGACCGTCCGGACAANCGGCACTCCTTTTCCGTTGGCTCTTCGGCCGAATC
CGGACGCCNAACCCGACCGGCG ::::::::::::Rv361T7.seq::::::::::::
GTTCTCGCACGATTTCCGGATTAGCGGGACTGGTCACCAGTTGGGTATGCGGGAAGGCGCTGACGTTCGCCGCGATTAGCTGTTTGATGGACGCGGTGGTGA
TGTNCTGATCACGGAACTGGCTGTAATANCCCAGGGTCGCCNCGCTTTCATCCGGGCCCGGACCCGGCGCACCGAGCGTGTCGCGCAGGTATGCGACGTGAT
TTTCGCTGAAGTCCCCGTACCCGGAGAACTCGAACACGCTGAGGCGCTCGTCACCGTCGTNNCGGCGACCAAGCGCGGCGAGCAACTGCGCAAAATCGTTAA
GANAGGTCGAATCGTTGAAATTCGGCACCACCTGCACC Clone Rv363
::::::::::::Rv363SP6.seq::::::::::::
CACAAGACAATACTCAAGCTTCAGGTCAATGTGCNCCAAGCCCTGACGCTGGCCGACCAGGCCACCGCCGCCGGANACGCTGCCAAGGCCACCGAATACAAC
AACGCCGCCGAGGCGTTCGCAGCCCAGCTGGTGACCGCCGAGCANANCGTCNAAAACCTCAAGACGCTGCATGACCAGGCGCTTANCGCCNCAGCTCAGGCC
AAGAAGGCCGTCGAACGAAATGCGATGGTGCTGCAGCANAANATCGCCGANCGAACCAAGCTGCTCAGCCAGCTCGAGCAG ::::::::::::Rv363T7.seq::::::::::::
CCACCCGTGCATGGTGGCACTGTAGCGACGTGCTGCAATCAAGGTCATGCCCGACTCTGGTCAGCTCGGAGCCGCTGACACCCCGCTAAGGCTGCTCAGCTC
GGTGCATTACCTCACCGACGGCGAACTCCCCCAGCTTTACGACTATCCGGATGACGGCACCTGGTTGCGGGCGAACTTCATCAGCAGCTTGGACGGCGGCGC
TACCGTCGATGGCACCAGCGGGGCGATGGCCGGGCCCGGCGACCGATTCGTCTTCAACCTGTTGCGTGAACTTGCC Clone Rv364
::::::::::::Rv364SP6.seq::::::::::::
GCTTTCCGCCGATACCCNCCATGTCCCGCACATCCAGGACTTCTGGGGGGATCCGCTGACAGCGGCGGGATCCCAAAGTGCGGATGATCGGGCCGCCTACGT
CGTGGTGTACCTCGNCGGTAACAACGAAACCGAANCGTATGACTCNGTCCACGCGGTG ::::::::::::Rv364T7.seq::::::::::::
CAACCCGANTTGGCTTTCGGCGCCNTCGGTGAGGACGGCGTGCGGGTGCTCAACGACGACGTCGTCCGCGGGACACACCTCGATGCTGCCGCCATGGACGCG
GTCGAACGCAAGCAGCTGATCGATCTACNACGCCGNGNGGAACGCTTCNGCCGCGGGCGTGACCGCNTCCCGTT Clone Rv365
::::::::::::Rv365SP6.seq::::::::::::
GGGATGGGCAAAAAGGCGAAGCACCGCGTGGCCACGAACGCCGGGAGGGACAATCTCGGGCGGCTAGGGCTTCTCGCGGGAAGGCCCGAACGTACGGCGTTT
CAACACGTCGCGTCGCCCTCCGACCGCGAACATTCGGGGATGGCAGCAACCTGGTAGCACCCTGGCCGGGCGATGATCTGCCAGCGTCCCCGCGGGTAGTCG
CCGCCCGGGCGG TABLE 3-continued End sequences of the polynucleotide inserts cloned in the named recombinant BAC vectors contained in the I-1945 *M. tuberculosis* H37Rv genomic DNA library.

:::::::::::::Rv365T7.seq:::::::::::::
CAGCAGACCAACAAGAGCATCGGGACATACGGAGTCAACTACCCGGCCAACGGTGATTTCTTGGCCGCCGCTGACGGCGCGAACGACGCCAGCGACCACATT
CAGCAGATGGCCAGCGCGTGCCGGGCCACGAGGTTGGTGCTCGGCGGCTACTCCCACGGTT Clone Rv366
:::::::::::::Rv366SP6.seq:::::::::::::
CTCAAGCTTGACTGGCCACCCACCGGCATGACCACCGACAGGCCCGACTGGTCGTACCACTCGAACGCCGGGGTGTTTGA :::::::::::::Rv366T7.seq:::::::::::::
TTGGTGCCCGGAATGGCGAGTCCCATTTANTCGCTGATTTGTTTGAACAGCGACGAAACCGGTGTTGAAAATGTCGCCTGGGTCGGGGATTCCCTCTCCAAG
CAAGAGTAACTGGCCCCAAATAAAGTTACTCGTCGTCTTGCAAAGACCGCTACCCGATGCCATTTATGTGTTTCCTTACGCTCNNNNTTCCGGTGCGCCATC
ATTATCTGCACCTTTGCACTGCACATTGAGCTTAGCAGCGCTCG Clone Rv367
:::::::::::::Rv367T7.seq:::::::::::::
GAATTNGCTTTCGGCGCCATCGGCCCAGGACCGCGTGCGGGTGCTCAACGACGACGTCGTCCGCGGGACACACCTCGATGCTGCCGCCATGGACGCGGTCGA
ACGCAAGCAGCTGATCGAGCTACAACGCCGCGCGGAACGCTTCCGCCGCGGGCGTGACCGCATCCCGTTGACCGGGCGGATCGCNGTGATCGTCGATGACGG
CATCGCCACCGGAGCGACGGCCAAGGCGGCGTGCCAGGTCGCCCGGGCGCACGGTGCGGACAAGGTGGTGCTGGCGGTCCCGATCGGCCCAGACGACATCGT
GGCGAGATTCGCCGGGTACGCCGATGAAGTGGTGT Clone Rv368
:::::::::::::Rv368SP6.seq:::::::::::::
TAAAGCTTTCGTCAGTTCATNGNGCCCCCGGACCAACAAAAGCATCGGGACATACGGAGTCAACTACCCGGCCAACGGTGATTTCTTGGCCGCCGCTGACGG
CGCNAACGACGCCAGCGACCACATTCAGCAGATGGCCAGCGCGTGCCGGGCCACGAGGTTGGTGCTCGGCGGCTACTCCCAGGGTGCGGCCGTGATCNACAT
CGTCACCGCCGCACCACTGCCCGGCCTCGGGTTCACGCAGCCGTTGCCGCCCGCAGCGGACGATCACNTCGCCGCGATCGCCCTGTTCGGGAATCCCTCGGG
CCGCGCTGGCGGGCTGATGAGCGCCCTGACCCCTCAATTCGGGTCCAANACCATCNACCTCTGCAACAACGGCGACCCGATTTGTTCGGACGGCAACCGGTG
GCGANCGCACCT :::::::::::::Rv368T7.seq:::::::::::::
CCGGGAGGGACCATCNCGGGCGGCTNCGGCTTCTCTCCGGAAGGTTCTANNGTNNNGCGTTTCNACNCTTCCCGTCGCCCTGCGACCGCCGAACATTCGGGG
TATGGNNGCANCCTGTNAGCATCCNGGCCGGGC Clone Rv369
:::::::::::::Rv369SP6.seq:::::::::::::
CTCAAGCTTCCGCATCAGATCGCTATAGAACCGGTGCGCGTCCCCACCGAGTGGCTGGTCGCCTTCCAGCACGATCGTTACCGCGTTATCGGAATCAAACTC
NCCGAACACCTGACCAACGCGCTTGATCGCCTGAATCGATGCGGCGTCGCTGGGGCTCATCGATACCGAGTGTGCTTTTCCGACCACTTCCAGTTGCGGTAC
GGCGAGATTGACAAAGGCGGTGAAGCCCAGCCAGAGCAGGACGATCACCNCCGCAAACCGGCGGATTTGCCCG :::::::::::::Rv369T7.seq:::::::::::::
GCTTGGCAGCCTGCGGCTGGGCGCCCTNGAGCTCTTCGATCTGGATCTCCGGACTCGAGATGCTCACTTGCCCGGCCGTGGACGTACCCATTGCGGCCGGGA
CCCCAGCGCCCCAGGTGACCAGCGAGTTGGGCTGCACGCTGACCGGCCCGTCGGGGTCGACGCCGGTAACGGTCAGCAGCTCCGANGTCCNNCTGATCCCGA
CCGCAGCTGCCAATGCGCGGCTGGCAGCCGACGTGGATGTGCCGGGGCCTAGATCGCGGGGCAGCAGCGAGACCGCGTCACCGACGGTCATCACCTTGCCGA
GTTTNGGCCTGCCGCAN Clone Rv36
:::::::::::::Rv36SP6.seq:::::::::::::
GCTTCCGGCTCGTATGTTGTGTGGAATTGTGAGCGGATAACAATTNCACACAGGAAACAGCTATGACCATGATTACGCCAAGCTATCTAGGTGACACTATAG
AATACTCAAGCTTGAGCCATCGGGCTATCAGCTGGTTGATGTCCCG :::::::::::::Rv36T7.seq:::::::::::::
CAGGCATGCAAGCTTGTCGTCTATCACATCCGACCACCAACCGCCCGACGGCTCGGCAGAACGCCTCCGCATATGGGTCGACGACCAGCGGGTCGGACTTCT
GGGCTGCCAGCGCTCGCGCCGTCGCGACAAACAGCGCGGTCGAACCGACACTCCTTGTGATGTCCCACCTATCACCTTCGGTACGCACCCAATCGACCCTAC
GCGGCTAGCTCAGCCCCGATCTTCCAGAGCTCCGCCCG Clone Rv370
:::::::::::::Rv370SP6.seq:::::::::::::
GCTTTTTGAGCGTCGCGCGGGGCGGCTTCCCCGGCAATTCTACTAGCGAGAAGTCTGGCCCGATACGGATCTGACCGAAGTCGCTGCGGTGCAGCCCACCCT
CATTGGCGATGGCGCCGACNATGGCGCCTGGACCGATCTTGTGCCGCTTGCCGACGGCGACGCGGTAGGTGGTCAATTCCGGTCTACGCTTGGGCCTTTGCG
GACGGTCCCGACGCTGGTCGCGGTTG :::::::::::::Rv370T7.seq:::::::::::::
CGANCCTGTTCGACGGCTACCTGAATCACCCCGATNCCACCGCCGCGGCGTTCGACGCCGACAGCTGGTACCGCACCGGCGACGTCGCGGTGGTCGACGGCA
GTGGGATGCACCGCATCGTGGGACGCGAGTCGGTCGACTTGATCAAGTCGGGTGGATACCGGGTCGGCGCCGGTGAAATTGAAACGGTGCTGCTCGGGCATC
CGGACGTGGCGGAGGCGGCAGTCGTCGGGGT Clone Rv371
:::::::::::::Rv371SP6.seq:::::::::::::
NAAGCTTTGTCACACCAAGTGTTTCNACCAGNCGCTCCATCCGGCGAAGTGGATACTCCCAGCAGGTAGCAGGTCGCCACCACGCTGGTCAGTGCGCGTTCA
GCTCGCTTGCGGCGCTGCAGCAGCCAGTCCGGGAAATAGCTGCCCTGGCG :::::::::::::Rv371T7.seq:::::::::::::
CGCTGGNCGCCGGCGCTGGGCTGCGGTAACCAATTACCACAACACTTTTCGGTAGCCGAACAGCGGCGCGTACCAGCGAAATGGCACAGCCACCGCAGTCGC
CGACATCCCGCGAAGATGTGGCAGATTTTCGTGCGGTCGAGCCGGCGAAGGCCTAGCGTCATTGTTGCCTGGCAAGGTTGCTGGGCCCGG TABLE 3-continued End sequences of the polynucleotide inserts cloned in the named recombinant BAC vectors contained in the I-1945 *M. tuberculosis* H37Rv genomic DNA library.

Clone Rv373
:::::::::::::Rv373SP6.seq:::::::::::::
CTCAAGCTTCTTCTGCCCCTTGCCGTTNCGGATNACATCCCGCAGCGACTCGGCTTCGGCGTCGATGTCGAAGTTCTCGATCAGCTTCTGGATCGACTCCGC
GCCCATGGCACCGGTGAAGTACTCGCCGTAGCGGTCGACNAGTTCGCGGTAGAGGTTTTCGTCNACNATCAGCTGCTTGGGCGCCANCTTGGTGAAAGTGCT
CCAAATGTCCTCCAACCGGTCCAGCTCACGCTGCGCGCGGTCACGGATCTGGCGCATCTCGCGCTCGCCGCCGTCGCGAACTTGCGCCGCGCATCGGCCTTG
GGGCCC :::::::::::::Rv373T7.seq:::::::::::::
GTTCACACCTACCTACTATGCCNCAATTCNCCGACACGGGTGGCATCAACACGGGCGATAAGGTGGAAATCGCTGGGGTGAACGTCGGGCTGGTGCGCTCGC
TGGCAATCCGCGGCAACCGCGTGTTGATCGGATTCTCGTTGCCCGGCAAGACAATCGGGATGCAAAGCCGGGCAGCAATTCNCNCCNACACCATTCTTGGCC
GTAAGAACCTGGAGATCGAACCCCGCGGTTCGGAGCCGTTGAAACCCAACGGTTTCCTGCCGTTGGCGCANACCACTACGCCATACCAAATC Clone Rv374
:::::::::::::Rv374SP6.seq:::::::::::::
CTCAAGCTTTACGCCGACGCCGGCCTACACAACACCAAGGAAACGATTGCCTACTGCCGAATCGGGGAACGGTCCTCGCACACCTGGTTCGTGTTGCGGGAA
TTACTCGGACACCAAAACGTCAAGAACTACGACGGCAGTTGGACAGAATACGGCTCCCTGGTGGGCGCCCCGATCGAGTTGGGAAGCTGATATGTGCTCTGG
ACCC :::::::::::::Rv374T7.seq:::::::::::::
TCCCNCATGGGATAACGGGTTTAGATTTCNACAACGGCACCGTGTTTCTCAACAAGCCGGTCATCAGCTGGGCCGGCGACAACGGTATCTACTTCACCCGCT
TTCGCCCGTACAAGAAAAACCACTAGGCCACCATCGAGTCCAAGAACAACCACCTGGTCCGCAAGTACGCGTTCTACTACCGCTATGACACCGCCGAGGAAC
GCGCCGTGCTCAACCGGATGTGGAAGCTGGTCAACGACCGCCTCAACTACCTCACCCCGACCATCAAACCGATC Clone Rv375
:::::::::::::Rv375SP6.seq:::::::::::::
CTCAAGCTTGGGTGTTGCCGATCACCGGAAGCCNCATGATCAGCCACGTTTCGCGCCGCCCGGCATACGGCGGCGTACCGATCTCCGCGTCATACACCCGCG
GGTAATCGCCGACGGTGCCGGTTCGCGAGCCGAAGGTGACAACGCTGATTGAATCNAGTTCCANGTCCAGCGGGT :::::::::::::Rv375T7.seq:::::::::::::
TNAACAGCTCGCGGCAGCCCACGACCTGCTGCGTCGGATTGCCGGCGGCGAGATCAATTCCAGGCAGCTCCCGGACAATGCGGCTCTGCTGGCCCGCAACGA
ANGACTCGAGGTCACCCCGGTGCCCGGGGTCGTGGTGCACCTGCCGATCGCACAGGTTGGCCCACAACCGGCCGCTTGATGNNNNGTCGGCAAGCCCGGCAG
TNGCCAAACCCAGCGTGATCANGCTCGGCTCGCGAGTTCGGCGAANAAGTGGCTCGCCTGATCACCTACCATCGGCCANGATCTGCGTGTCA Clone Rv376
:::::::::::::Rv376SP6.seq:::::::::::::
GCCACCCGGCTTGGCGTCGACTCCCGTTCNGCACATCATACGGTCCCCGGTACTGTCCAACTGCGCCGGTGCGCTAGCCAAACGTCACGACTCTCAGTGATC
CCAGTTCGTGATCCGGCCGGTGGCGCCGCTGCGGCGGGGGCTNATNTACTTCGGACTNATTATCTCATCCAAAGGACACCGGGCCGGTGGCTGGAATCCCAT
GGTGCGATCGGCCACACAN :::::::::::::Rv376T7.seq:::::::::::::
CCGACCTGGTATCTTCCGATAGCGCGCGTTGATATCCGGTCTGATCTCCTGCCCTTAACGCCGGATCTCAGCAGGTCCCCATGCAAAGATCCGAGGTGTCCC
NGATCTAGGGGTCCTCGTCCTCCAGATGATGGAGCAAGTCGGCCC Clone Rv377
:::::::::::::Rv377SP6.seq:::::::::::::
CTCAAGCTTCGGCTCAGGCGGCGCTGCCGGTAACGTCGCTGACCGGTGCAGGTTTCGACAATGTGGTGCCGGTTCGGCGGCTACGTGCCATCAAGACACTGG
CGCAGGCTATCGCACCCGTTATCGGCTACAAACAAATCGCGGTATGC :::::::::::::Rv377T7.seq:::::::::::::
CATCACCTGNTTCATGAACTGGAAGCACCGCAGCGCTTCCTTTTCGGCCGCAACATGAGCCAGCCTCTCGTCGGCGGTCGGGTGCAGGTGCTCGGGCAGCTC
GGCCGCGACAGCCGCCTGACCCTGAAACCAGCTTCCATATCCCGCGACGAACGACGCCAGTCCGCTACGTAACCCCTCCGCGACTGTCCATGGACAACAGCG
CGTTCTCCACCGACCGGGCCCGGGTGTGGGGTGT Clone Rv378
:::::::::::::Rv378SP6.seq:::::::::::::
AGCTTAGCTTCCCGCCCCGGCAATAGGGCTCCAGCTCATCCGGTGTGACCAGATAGGGGCCCAGGGTGATACCGCTGTCTTTGCCCTTGGCCTGTCCGATGC
GCAGCTGGCCCTCCAGCATCTGCAGGTCCCGTGCGGACCAGTCGTTGAAAATGGTATAGCCGATGATCGACCG :::::::::::::Rv378T7.seq:::::::::::::
CCNGAACAGAAGCGGCGGTTCCTACCGCGGTGTGCGGCCGGCGCGATATCGGCCTTTTTACTAACCGAACCCGATGTGGGCTCCGATCCGGCGCGCATGGCA
TCGACGGCGACGCCGATCGATGACCGCCAGGCTTACCACCTT Clone Rv379
:::::::::::::Rv379SP6.seq:::::::::::::
CTCAAGCTTGCGCGACTCGACAAGCATTCTTGACAGTTGTTTTGGCTCGGCATGGTTAGCCAAGGTTCTGCGGTCCCACCAGATCATCTTGGTCCGGTAGCG
CTCGTCCGGGTATGCTGCCGCCGGGATTCTCGCTGCTATTACTCCCCCCGAAGAACGCCACCGGTCCAGCGC :::::::::::::Rv379T7.seq:::::::::::::
GCNAGGCGGTATAGCTTCCCGTCGTACCGGCGACCGCCAGCCGAGAAGCTCGTTTTCCCAGTGTTGCTGGGGATTCTCACGCTGCTGCTGAGTGCGTGCCAG
ACCGCTTCCGCTTCGGGTTACAACGAGCCGCGGGGCTACGATCGTGCGACGCTGAAGTTGGTGTTCTCCATGGACTTGGGGATGT Clone Rv37
:::::::::::::Rv37SP6.seq:::::::::::::
GTGTGGAACCGTGAGCGGATAACAATTTCACACAGGAAACAGCTNTGACCTTGATTACGCCAAGCTATTTAGGTGAGGCTATATTAATACTCAAGATTGCGG
TCGAGCACATCGGCCCAAGAACCGCCGAAGGCACGGCGGAACGCCTGCGGCACATGGGGCGACGACCAGCGGGTCGGACTTCTGGGCTGTCCAGCCGGATCG
CGCCGTCGCGA TABLE 3-continued End sequences of the polynucleotide inserts cloned in the named recombinant BAC vectors contained in the I-1945 *M. tuberculosis* H37Rv genomic DNA library.

:::::::::::::Rv37T7.seq:::::::::::::
CACTGTCAGTACATATGCGCCGCTCCTCCTCATCGCTGCGCTCGGCATCGTCGCCGGCGGTCATGGCGTCACCCTACCCAAGCCGAACGCGAAACGAGAACG
TGTTCCATTATTAGGGTGTGAGCACCAATACCAGATTGCTCACCAGGAACTCACGCAGCACCGGGACGGATGTCAGCCACCACGCCCATCTGGGGTGGTAGC
GGGGAAATACGGCTAACGCGGCTCCGGTGCCGGCAGCCCAGCGCAGACCCTCGGCGGCGGACACGGCAAACAACGACGACCCATAGTTGTTCTTTGCCGGAT
GGCCGTGTTTGCGGACATATCGGGCGGCGGCGCGGGCGCCGCCGAGGTAGTGGCTGAGGCCCATCTCGTGCCCGCCGAATGGCCCCAGCCAAACCGTGTA Clone Rv381
:::::::::::::Rv381SP6.seq:::::::::::::
CTCAAGCTTTTACGGTGATCGCGCATCACCTGGTTCATGAACTGGAAGCAGCGCAGCGCTTCCTTTTCGGCCGCAACATGAGCCANCCTCTCGTCGGCGGTC
GGGTGCAGGTGCTCGGGCAGCTCGGCCGCGACAGCCGCCTGACCCTGAAACCAGCTTCCATATCCCGCGACNAACGAC :::::::::::::Rv381T7.seq:::::::::::::
CTCAGAAGCCGCTAGCTGGTAGAGTCGCTGACCGGTGCACGTGGCGNCAATGTGCGCTGCCGGTTCGCG Clone Rv382
:::::::::::::Rv382SP6.seq:::::::::::::
CTCAAGCTTGCGCTCATCAAGCGCGAACAGCAGGGCGGTCGGCTGGTCGCCATGACGGGTGACGGGACCAATGACGCACCCGCGCTCGCGCAAGCCGATGTC
GGGGTGGCNATNAATACCGGCACCCAGGCGGCCCGGGAAGCCGGCAACATGGTCNATCTCCACTCC :::::::::::::Rv382T7.seq:::::::::::::
ACTTCTATTTCGACTGGTGTGCTGTGGCGCGATCCGACTGCCGGCGTGGTCAAGGCCGGCCAGTTGTGGGATNCCACAGGCAC Clone Rv383
:::::::::::::Rv383SP6.seq:::::::::::::
GCTTGTCGTATTCCGTGGCACTGTCAGACATATGCGCCGCTCCTCCTCATCGCTGCGCTCGGCATCGTCGCCGGCGGTCATGGCGTCACCCTACCCAAGCCG
AACGCGAAACGAGAACGTGTTCCATTATTAGGGTGTGAGCACCAATACCAGATTGCTCACCAGGAACTCAC :::::::::::::Rv383T7.seq:::::::::::::
CGATATTCGTCGGCCGCGTTGTCTCGACTGGGTCGCGT Clone Rv384
:::::::::::::Rv384SP6.seq:::::::::::::
GACCTCGGCCACCAAGCCGGACGCGACCGTCGAGGTGGCGATCCGGCTTGGCGTCGACCCGCGTAAGGCAGACCACATGGTCCGCGGCACGGCCANCCTGCC
ACACGGCACTGGTAAGACTGCCCGCGTCGCGGCN :::::::::::::Rv384T7.seq:::::::::::::
CCGGAAGTCTAGGGGACGACCTACTCAGCGCAAAATGTCGCTAATGTGAGTCCGCCCCACCAGGGCAGATCAACCCATGTCGATGATGACCTACCCGGATAC
CGGATTGGCGGT Clone Rv385
:::::::::::::Rv385SP6.seq:::::::::::::
AGCTTCAGTTCCTCCACGACGCGTTCCCAAATGAATTTCCCGATCCCACAATCTCGGTTCAGATACAGGTCGCCATACCCCTTACTTCGGNAACGCTGGGCG
GATTGGCCCTGCCGCTG :::::::::::::Rv385T7.seq:::::::::::::
CCGCCTACGGGTCGAACATGCATCCCGAGACCGATGCTCGAGCGCGCACCCCACTCGCCGATGGCCGGAACCGGCTGGTTACCCGGGTGGCGGCTGACC Clone Rv386
:::::::::::::Rv386SP6.seq:::::::::::::
GCGGCTGGTTACGACTCCCTGTTTGTGATGGACCACTTCTACCAACTGCCCATGTTGGGGACGCCCGACCAGCCGATGCTGGAGGCCTACACGGCCCTTGGT
GCGCTGGCCACGGCGACCGAGCGGCTGCAACTGGGCGCNTTGGTNACCGGCAATACCTACCGCAGCCCGACCCTGCTGGCAAAGATCATCACCACGCTCGAC
GTGGTTAGCGCCGGTCGAGCGATCCTCGGCATTGGAGCCGGTTGGTTTGAGCTGGAACACCGCCAGCTCGGCTTCGAGTTCGGCACTTTCAGTGACCGGTTC
AN :::::::::::::Rv386T7.seq:::::::::::::
GCCTTTCCGCACAATCTGTACCCCAGGACCNTCTAAAAAATCGAATACGACGGCGTCGCCGACTTTCCGCGGTACCCGCTCAACTTTGTGTCGACCCTCAAC
GCCATTGCCGGCACCTACTACGTGCACTCCAACTACTTCATCCTGACGCCGGAACAAATTGACGCAGCGGTTCCGCTGACCANTNNTGTCGGTCCCACGATG
ACCCAGTACTACATCATTCGCACGGAGAACCTGCCGCTGCTAGAGCCACTGCGATCGGTGCCGATCGTGGGGAACCCACTGGCGAACCTGGTTCAACCAAAC
TTGAAGGTGATTGTTAACCTGG Clone Rv387
:::::::::::::Rv387T7.seq:::::::::::::
GCAGACCAACAAGATGCATCGGGATCATACGCCGTCAACTACCCGGCCAACGGTGATTTCTTGGCCGCCGCCCAC Clone Rv388
:::::::::::::Rv388SP6.seq:::::::::::::
CTCAAGCTTGCCAAAGAGACCTCGTCCACCAAGCNGGACGCGACCGTCNAGGTGGCGATCCGGCTTGGCGTCCACCCGCGTAAGGCANACCANATGGTTCGC
GGCACGGTCAACCTGCCACACGGCACTGGTAANACTGCCCGCGTCGCGGTATTCGCGGTTGGTGAAAAGGCGATGCTGCCGTTGCCGCGGGGGGCGGATGTT
GTCGGGAGTGACAATCTGATCGANAGGATTCAGGGCGGCTGGCTGGAATTCGATGCCGCGATCGCGACACCGGATCAGATGGCCAAAGTCGGTCNCATCGCT
CGGGTGCTGGGTC :::::::::::::Rv388T7.seq:::::::::::::
CCACGGCGTGGATCAAGGTACCGGCCGGGATGTTGCGCAATGGCAGGTTGTTGCCCGGCTTGATGTCGGCGTTAGCGCCGGATTCCACCACATCCCCTTGCG
AAAGTCCGTTGGGTGCAATGATGTAGCGCTTCTCCCCATCGAGATAGTGGAGCAACGCAATCCGTGCGGTACGGTTCGGGTCNTACTCGATGTGCGCGACCT
TGGCGTTGACACCATCTTTGTCATTGCGGCGAAAGTCGATCATCCGGTAAGCGCGCTTATGACCGCCGCCTTTGTGCCGGGTGGTAATCCGGCCATGCGCGT
TGCGTC TABLE 3-continued End sequences of the polynucleotide inserts cloned in the named recombinant BAC vectors contained in the I-1945 *M. tuberculosis* H37Rv genomic DNA library.

Clone Rv389
:::::::::::::Rv389SP6.seq:::::::::::::
GGCGGCTGCGTCGGCGAGATGATCGCCCGGTGCCACCCCGATCCGTGCCTCGGTCAGCGCCAACGTGCTTTCCGGTCCGGCGACCACCATGTCGCATGCGCC
CGAC :::::::::::::Rv389T7.seq:::::::::::::
GCAATCGCCTTGGCGGTCGCCGGGTTGTCACCGGTGATCATCNCGGNGCGGATGCTCATNCGGCGCATTTCGTCNAATCGTTCCCGTATGCCCACCTTGACG
ATGTCCTTCATATGGACCACGCCGATGGCCCNCGCGCTNCTG Clone Rv38
:::::::::::::Rv38SP6.seq:::::::::::::
CCGGCTCGTATGTTGTGTGGAATTGTGAGCGGATAACAATTTCACACAGGAAACAGCTATGACCATGATTACGCCAAGCTATTTAGGTGACACTATAGAATA
CTCAAGCTTCCACATCGGTATGCCAAAGCATTGCGCCGCTATCGATTTCGCGCTGGCATCGCCAAGGTGGACTTCTTGCTCAGCGACGAGATCCCGTGGTCG
GATCCGCGGCTGCGGCGGGCTGCGACCCTGCATCTCGGCGGCACCCGTGACCAGATGGCGCGCGCCGAGGCAGACGTCGCGGCGGGACGCCACGCCGACTGG
CCGATGGTGCTGGCCGCGTGTCCGCACGTCGCCGACCCCGGCCGCATCGACGAAACCGGCCGCCGTCCGTTCTGGACCTATGCCCACGTGCCGTCGGGGTCC
ACGCTCGACGCGACCGAGACCGT :::::::::::::Rv38T7.seq:::::::::::::
CGCGTCCACCGCAGCGTGAGATTGGTGGCGCCATTCGTCGTGGTGTAGCTGCTGTTGGCGGCGTCGCCGTATTGTGCGGGCCAGCCTTGTGCGGGGGCCGCT
TCTACCCACGAGTCGGCACTTCCGCAACCGCCCAGCTCGACCGCGATTACGGCGGCCGCAACGGCCGCCGGAAGGCGTCTCGCAAGCGCCTTATCCTTTCGC
AGGTTCCCAGATCCTTCCGCTACGTGGGTCGCTCATCGGCGGGCCCGGCCGAATGAGTACAGGTGAGGGTAACCGCTACAAATGAAGTTGGTCAGTGCTGGC
CAACTGTGTAATGGTTGCCCGGCTCGGGTCACCACGTACATTCTGGCAAGGCGGGCGAGATTCGGTTCCTCGCGTCCTTGGCCGGTGGCGGTTCCCGGTTGT
CCGTGGGCGTGTCGTGTACGTGGTGTAAGTGTCGTGAACTCCTCAGTTTGGGCT Clone Rv390
:::::::::::::Rv390SP6.seq:::::::::::::
CTCAAGCTTGCGCTGGATCTGGCGGCTGAGCCTGTTCTTGGGCAACATGCCGAGGGATCGCCTTTTCCACCACGCGGTCGGGGTGGCGTTGCATTAGCTCAC
CGATGGTGCGCTTGTGCAGGCCGCCGGGATACCCCGAGTGCCGGTAAACCATCTTGTGCTGCAGTTTGTCGCCGCTGATGGCGACCTTGTCGGCGTTGATCA
CNATGACNAAGTCACCGCCATCGACATTGGGGGCGAACGTCGGCTTGTGCTTGCCGCGCAGCAGGTTGGCCGCCGCGACGGCAAGGCGGCCAANCACCACGT
C :::::::::::::Rv390T7.seq:::::::::::::
TTTGGGATGGGCAAAAAGGCGAAGCNCCGCGTGGCCACGAACGCCGGGAGGGACAATCTCGGGCGGCTAGGGCTTCTCGCGGGAAGGCCCGAACGTACGGCG
TTTCAACACGTCGCGTCGCCCTCCGACCGCGAACATTCGGGGATGGCAGCAACCTGGTAGCACCCTGGCCGGGCGATGATCTGCAGCGTCGCCGCGGGTAGT
CGCCGCCCGGGCGGCTACAGTCTGAAACGCGATGACCATCGATGTGTGGATGCAGCATCCGACGCAACGGTTCCTACACGGCGATATGTTCGCCTCGCTGCG
CCGGTGGACCGGTGGGTCTATCCCGGA Clone Rv391
:::::::::::::Rv391SP6.seq:::::::::::::
CTCAAGCTTCGTCATAAGACCATGGTGCGCTTTCTTTCACCCGTCCANAGTCGGGGGCATCCGCACCGGCTCGCATCGCATCATCCTCCCACGACGGGCCGC
TCATCAGCTTGGGCCATTTCAATGTACTTGATACCCCGCGCTGCGGGTAGGCCACTGCNACAATTCAAACACGGTGTCACACGGTGAATANTGTCNANATGG
GCTCTGATCAACCGTCNCAAACCCGGTTTC :::::::::::::Rv391T7.seq:::::::::::::
GAATTCTGCGTGCACCGCTATGGGTTGCAGCAGCGGCTGGCGCCGCACACCCCACTGGCCCGGGTGTTTTCGCCCCGAACCCGGATCATGGTGAGCGAAAAG
GAGATTCGCCTGTTCGATGCTGGGATTCGCCACCGCGAGGCCATCGACCGATTACTCGCCACCGGGGTGCGAGAGGTGCCGCAGTCCCGCTCCGTCGACGTC
TCCGACGATTCATCCGGCTTCCGCCGTCGGGTGGCGGTAGCCGTCGATGAAATCGCTGCCGGCCGCTACCACAAGGTGATTCTGTCCCGTTGTGTCGAAGTG
CCTTTCGCGATCGACTTTCCGTTGACCTACCGGCTGGGGCGTCTGCACAACACCCCGGTGAGGTCGTTTTTGTTGCAGTTGGGCGGAATCCGTGCTCTGGGT
TACAGCCCCGAACTCGTCNCGGCGGTGCGCGC Clone Rv392
:::::::::::::Rv392SP6.seq:::::::::::::
GCAGTTGGGAATCGCTCTGCAGCAAACCANTATTCTGCGCGACGTTCGAGAGGACTNTTTGAATGGACGGATCTACCTGCCGCGCGACGAGCTGGACCGATT
AGGCGTACNCCTCCGCCTGGACGACTCCGGGGCACTCGATGACCCCGACGGACGGCTCGCGGCACTGCTGCGGTTCANTGCCNACCGCGCCGCANACTGGTA
TTCGCTGGGACTGCGGCTGATTCCACACCTCGACCGCCGCAGCGCTGCCTGCTGTGCGGCCATGTCTGGCATCTACCGCCGTCNGCTCGCCTTGATCAGACC
ATCGCCGGCGGTCGTCTACCATCGGCGAATCTCTCTGTTCGGGACTGAANAANGCCCAAGTGGCGGCGGCAGCACTGGNCTCTTCGGTAACCTGCNGACCGC
CCATTGGACCGCTACCG :::::::::::::Rv392T7.seq:::::::::::::
TTGATCTGGACGTCTGAGACGGTGATCGGNCCGAACCTGAATTGTCCGGTAATGCCCAGCGCAGAAAGCANGGTGGTGGCCGGGGCGGTGAANCCGGCGTCG
GCGGCACCGTCGAAGTCGATGTGGATTGCCGGAATGGGGATGTCCGGCACGGCGAAGCCGTAGTTCGCTTGTCCCGTGAGGCCCANGTGGATGGGGGGAAGG
ATCGTGGTGTCCGGGATGATAATGGGGCCGATGCCGCCGGTTGAAGTCCAGTGGATCGGGAATTCGGGAATCGTGATGCCGACGTTCAGGCCGAACAGGCCC
TCCAAGTTGCCTCGCCACNAGATGCCGTTGCTGAAGTTGCCCGACATGAGGGCGCCGGTGTCCACATTGCCCGAATTGGCGACGCCGGTGTTGGC Clone Rv393
:::::::::::::Rv393SP6.seq:::::::::::::
CACGTAGGCGCCGTCCATAAATNACTCCGCCGCGCTTCGCACATCCTCGTANCGATCCTTGGCGAGCAGGTCAACCGGGCGCTGCCCGTCNAGGAGCCGGTT
TTTGGCGTGCAGCCACTGGCCGACACCTCGGGGGGTAAGCGAATCCGAGAGCAGGAGGACNAGGTCACGAANCTGCGCCAGCCGGTCGTACCGCTCAGGGCG
GATGTCGCCGGTCCGCCACCCGCGTACCGCCCGATCGGACACCTGTATGACCGCGGCGACNTCGACCTGGGTGACGCCGAAGGGTTTCAGGGCATCNACNAT
CTCGCTGGCCTCGACCGCCCGGTCCAGGGTGACCGCCATCGTGGTTCCTCCGCAACTTCCGGTTCTACTACCGTAAACGCTACCG :::::::::::::Rv393T7.seq:::::::::::::
CGGGGAACGGTCCTCGCACACCTGGTTCGTGTTGCGGGAATTACTCGGACANCAAAACGTCAAGAACTACGACGGCAGTNGGACAGAANACGGCTCCCTGGT
GGGCGCCCCGATCGAGTTGGGAAGCTGATATGTGCTCTGGACCCAAGCAAGGACTGACATTGCCGGCCAGCGTCGACCTGGAAAAAGAAACGGTGATCACCG
GCCGCGTAGTGGACGGTGACGGCCAGGCCGTGGGCGGCGCGTTTCGTGCGGCTGCTGGGACNCCTCCGACGAGTTCACCGCCGGGAGGTCGTCGCGTCGGCC
ACCGGGCGAATTTCCGGTTCTTCGCCGCGCCCCGGGATCCTGGGACCGCNGGCGCGCGCTGTT TABLE 3-continued End sequences of the polynucleotide inserts cloned in the named recombinant BAC vectors contained in the I-1945 *M. tuberculosis* H37Rv genomic DNA library.

Clone Rv396
:::::::::::::Rv396SP6.seq:::::::::::::
CTCAAGCTTTGTCCGACAAGCGTTCCCGGGCGGTCAGCAAGCGAACGTCGGTTGGCCCACTGCGGGTCGATATTGCCGCCAGGGA :::::::::::::Rv396T7.seq:::::::::::::
CGTCAGCACGGCGACGTCGCGNTACGCCGAGCAGTTACACAATCGCTCTGCAGCAAACCAATATTCTGCGCGACGTTCGAGAGGACTTCTTGATTGGACTG Clone Rv39
:::::::::::::Rv39SP6.seq:::::::::::::
CTGCATCCGGCTCGTATGTTGTGTGGAATTGTGAGCGGATAACAATTTCACACAGGAAACAGCTATGACCATGATTACGCCAAGCTATTTAGGTGACACTAT
AGAATACTCAAGCTTCGCGCAGCGGCGGGTTGACCCGGTTCACGCCGTCATAGCTGGCCAATCTGGCATCGTCGATCANCATGTGGTGGGGGGTGACCTCGG
CGGTGATCGAAATACCCTGGTCCTTATCCCATTTCAGGATTTCGACGGTGCCCGCGGCCGACGCGTGACAGATGTGCACCCGGGCGCCGGCGTCACGGGCCA
GCAAGGCGTCGCGGGCGACGATCGATTCCTCGGCGGCCCGCGGCCATCCCGCCAGGCCCAGCCGCGCCGCCATGGGTCCCTCGTGCGCGACGGCGCCGACCG
TCAGCCGGGGCTCCTCGGCGTGCTGGGCGATCAGCACGCCCAAACCGGTG :::::::::::::Rv39T7.seq:::::::::::::
CCGACGCGCACTACGTGCTGGTGTCCACCCGCGACCCGCACCGGCACGAGCTACGCAGCTACCGCATCGTCGATGGCGCTGTCACCGAGGAACCTGTCAATG
TCGTCGAGCAGTACTGAACCGTTCCGAGAAAGGCCAGCATGAACGTCACCGTATCCATTCCGACCATCCTGCGGCCCCACACCGGCGGCCAGAAGAGTGTCT
CGGCCAGCGGCGATACCTTGGGTGCCGTCATCAGCGACCTGGAGGCCAGCTATTCGGGCATTTCCGAGCGCCTGATGGACCCGTCTTCCCCAGGTAAGTTGC
ACCGCTTCGTGAACATCTACGTCAACGACGAAGACGTGCGGTTCTCCGGCGGCTTGGCCACCGCGATCGCTGACGGTGACTCGGTCACCATCCTCCCCGCCG
TGGCCGGTGGGTGAGCGGACACATGACACGATACGACTCACTGTTGCATGCCTTG Clone Rv3
:::::::::::::Rv3SP6.seq:::::::::::::
TGCTTCCGGCTCGTATGTTGTGTGGAATTGTGAGCGGATAACAATTTCACACAGGAAACAGCTATGACCATGATTACGCCAAGCTATTTAGGTGACACTATA
GAATACTCAAGCTTGCCGGGAGGGTGCATGGCCGACTCGGATTTACCCACCAAGGGGCGCCAACGCGGTGTCCGCGCCGTCGAGCTGAACGTTGCTGCCCGC
CTGGAGAACCTGGCGCTGCTGCGCACCCTGGTCGGCGCCATCGGCACCTTCGAGGACCTGGATTTCGACGCCGTGGCCGACCTGAGGTTGGCGGTGGACGAN
GTGTGCACCCGGTTGATTCGCTCGGCCTTGCCGGATGCCACCCTGCGCCTGGTGGTCGATCCGCGAAAAGACGAAGTTGTGGTGGAGGCTTCTGCTGCCTGC
GACACCCACGACGTGGTGGCACGGGCAGCTTTAGCTGGCATTCCT :::::::::::::Rv3T7.seq:::::::::::::
GGAAACACCGNCGCCGTCGTGGCCACCAACACCGCGACCAGCACCGTGACCCGGACCGGGGTGCCGCGCGAACCGGTCTTGGCCAATTGCCGCGGCACCAAG
CCGTCGCGCGCCATGGCGAACAGCACGCGGCATTGCCCGAGCATCAACACCATCACCACCGTGGTAAGCCCGGCCAGCGCGCCGACGGAGATGATGCCGCTG
GCCCAGTACACCCCGTTGGCCTGGAACGCGGTGGCCAGATTTGCCGGCCCGCGGCCCGGTACGGTCCGCAGTTGGGTGTATGGAACCATGCCCGACAGCACC
ACCGATACCGCGACGTAGAGAAGGGTCACGACCCCCAGCGACGCGAGAATCCCTCGAGGGACGTCTCGTTGAGGACGCTTGGTCTCCTCGGCCATGGTGGCC
ACGATGTCAAACCCGATAAACGCGAAGAACACGATCGATGCCCGGCCAGCACGCCGTA Clone Rv40
:::::::::::::Rv40SP6.seq:::::::::::::
CCTGCTTCCGGCTCGTATGTTGTGTGGAATTGTGAGCGGATAACAATTTCACACAGGAAACAGCTATGACCATGATTACGCCAAGCTATTTAGGTGACACTA
TAGAATACTCAAGCTTGTCCTCGGGCGTGGCCTCGGCCAAGAAATCGTCGACGCCGGCCTCCTGTGCAATCGCCTTGGCGGTCGCCGGGTTGTCACCGGTGA
TCATCACGGTGCGGATGCTCATTCGGCGCATTTCGTCGAAGCGTTCCCGTATGCCCACCTTGACGATGTCCTTCAGATGGACGACGCCGATGGCCCGCGCGC
TGCTGTTATCGGTCCATTCCGCAACGACTAGGGGTGTCCCCCCGCCGGAGCTGATGCCGTCGACAATGGCACCCACCTCCTCAGTGGGGTGGCCACCGTGAT
CGCAAAACCACTTCATCACCGCAGCCGCGGCACCTTGCGGATCCGAACGGATGCGCTC :::::::::::::Rv40T7.seq:::::::::::::
TTCGTTCGATGGCGCCGCCCCGGCTACGGTTTGACCTGTGGGTGTCGAATTGGGGTCAAATTCCGAGGTCGGCGCGCTAAGAGTGGTCATCCTGCACCGCCC
GGGGGCCGAACTGCGCCGGCTCACACCGCGCAACACCGACCAGCTGCTGTTCGACGGCCTGCCCTGGGTATCCCGCGCGCATGACGAGCACGACGAATTCGC
CGAGCTGCTGGCTTCCCGCGGTGCGGAAGTGCTGTTGCTGTCGGACCTGTTGACTGAGGCACTACATCACAGCGGGGCCGCCCGCATGCAGGGGATCGCCGC
TGCCGTCGACGCACCGCGGCTGGGACTGCCGCTGGCGCAAGAACTTTCGGCCTACCTGCGTATCTCGACCCAAGCANGTTGGCGCATGTGCTGACGCCGGCA
TGACTTCAACGAACTCCCNTCCGACACGCCGAACGAAGTGTCGTTGGTGTTGCGTATGC Clone Rv412
:::::::::::::Rv412SP6.seq:::::::::::::
GCGGCGAGTGTGGTGGGTGCCGAACACGAATCCAACGACGCACTGGCGGAGAGATACCACTTGCTGTACTGGAAGCACGTGCTGATGATCTCCCGTGGAATG
TGCCTCGCCGCCGTCTATCGAAAACAGTGAGCATGCTGCG :::::::::::::Rv412T7.seq:::::::::::::
CAACCGCGCTCGGCGCGTCTGGGCCTTCCGCCGGCTCCGCCGACAATTCTATCTCTGGATCAGCGGGGCTCTCCGGGCCGGCCTCCGCGAACTCAACAGGCC
GCGCCTTCCGGCCGAAACATTCCCTAGCCATATATGATCGCACCTCGATACACGATCTGGCGGCAACACCGCAAAGCGTCCGACGGGCCCAACCTCCGCAAT
TCAGGTATCCGGG Clone Rv413
:::::::::::::Rv413SP6.seq:::::::::::::
GAAGGTCGGCGAAGGTGTGGCTGGNTGCCGATCACGAATCCAATGATGCAGTGGTCGGAAGATATTAGCCACTTGCTGTTCTGGAGACAGGTGCTGATGATC
TCCCGTGGAATGTCCCTCGACTCCGTCTATCGAAATCTGTGAACA :::::::::::::Rv413T7.seq:::::::::::::
TCCTGCGCTCTGGGCCATTCTCGGGTCTGCCGACAATTCTATCTCTGGATCTGTGGGGCTCTCTTGGCCGGCCTCNGCGATCTCTTCANGGCGCGCCTTCCG
GCCGAAACATTCCCTATCCATATATGATCGCACCTCTATACACCGTTTGGCGGCAACACCGCAAAGTGTCTGTCG Clone Rv414
:::::::::::::Rv414SP6.seq:::::::::::::
AGCTTTACGCTGGCGTATCAGCGTTGGGGCCGCTGCCATTTCGGTCGCCCAACGCGTTGCCAGCTCCCTGCGCTGTCAGGGCTTGCGCGCCAAACTGGCCAC
CGCAACAAACTTGGCTGAGCTTGATC TABLE 3-continued End sequences of the polynucleotide inserts cloned in the named recombinant BAC vectors contained in the I-1945 *M. tuberculosis* H37Rv genomic DNA library.

:::::::::::::Rv414T7.seq:::::::::::::
CTCTATCTGGCGTCACATTCGCAATCTTTAGATTGCAGATATCGATAAAATCACCCGCGCGACAAGACCGCCATGTCATCCTTTCGATGTTATTTCGCCGGC
CTGGGGAAAGCGCAACGACGTTGCCTACACGTTCCGCCGT Clone Rv415
:::::::::::::Rv415SP6.seq:::::::::::::
AGCTTTNCCTTGCATCTGCACCCCGATCCACGTCAGCCACGTCGGCGTTCTCCACCAAGAAGTTGCGGGCATTCTCCTTGCCCTGGCCGAGCTGCTCGCCCT
CGTAGGTGAACCAGGCACCCGACTTGCGGATGAGGCCCTGATCCACACCCATGTCGATCAGCGAGCCCTCCCTGCTGATTCCCTTGCCGTAGAGGATGTCGA
ACTCGGCCTGCTTGAAGGGGGGCGAACAGTTGTGCACGACAACCCCTTCGGCGACGAGGGTGTGCAGTTCCTCGACCTCGAGGTCGAACGTTCGTGCCCGCC
GCGTTGGCAGCACTTCTCGGATCACGGAATAGCGGANTTCTTCCGCCAGCATGTCGTGCAGGAATTTGTCATCCAGGGCATCCGCGAGCGCCTGCACGCG :::::::::::::Rv415T7.seq:::::::::::::
ACTGTCNAGGGAATGCTTCGCAGCATCTACCTGCAGTCGCTTGTGCATAAGCGGACGGCCCNACCTGTTCGTGTTCCGGGACACCAGACGCGGGAGCACCGG
CAGTACGGCGAAAGGTTTGAGCGGAAGGAGTTGCGCAAATCGGGGCGCCCCAACACCCGTCCGCAAGACGCGGTCAACGACCTGTTTCAGGCGATCAGGGTC
ACCGACTCACCTGCACTGAGAACAAGCGATCTGCTGATCTGCCAGAAGATGGACATGAATGTCCACGGCAAGCCTGATGGCCTGCCGCTCTTCCGGGAATGT
TTGGC Clone Rv416
:::::::::::::Rv416SP6.seq:::::::::::::
TGAATTATGATCCCGACACAACTGCATCANTTTAGCCGCGTCGNGATGCTATCCGCCGACGGTTTGGANCNGGTCCGTGTCGTTCGTGTTGATCTCACCCGA
AGTTGTGTCCGCCGCCGCCGGGGATCTAGCGAACGTGGGATCGACAATCAGCGCCGCCAACAAGGCGGCAGCGGCTGCGACCACGCAGGTGCTGGCCGCGGG
CGCCGATNAGGTGTCAGCGCGCATCGCGGCGCTGTTTGGTATGTACGGCCTGNAATATCCGGCGATCAGTGCGCAAGTTGCCGCGTATCACCANCAGTCCGT
GCAG :::::::::::::Rv416T7.seq:::::::::::::
AACGGGGACCNCAAGAAACCATTCAANAACGAGGGGTCGTCACCAACGTCGAAACCGACGGTTGCCAGCCGGCCCACGATATTGCGTGCTCGAGGGTCCGCT
GTACCCTCACCGAACGTGAGTCCCACACCGCGGAGGCGGGCGACTCTGGCGTCGTTAGCAGCCGAGCTCAAGGTGTCCCGCACCACTGTCTCGAATGCTTTT
AACCGACCGGATCAGCTCTCCGCCGATCTACGTGAACGAGTGCTTGCCACGGCCAAGCGACTGGGCTATGCCGGACCGGATCCGGTGGCGCGATCGTTGCGG
ACCCGCAAAGCCGGTGCGGT Clone Rv417
:::::::::::::Rv417SP6.seq:::::::::::::
AGCTTTGGAGCCNCNCCGANCCNCCGGTACGCCCCGCCACCGCCGTACCCGGCACCCGACCCCTTTGAGCCGTTCGCCGTGGCCGCGGTGGANCTGGCCGAC
GAGGGACTGATCGTGCTGGGCAAAGTGGTCGATGGCACGCTGGCCGCCGATCTGAAGGTCGGCATGGAGATGGAGCTGACGACCATGCCGCTGTTCGCCGAC
NACGACGGTGTGCAGCGCATCGTCTACGCGTGGCGGATCCCATCGCGCGCCGGCGACNATGCANAGCGCANCGATGCTGAGGAGCGGCGCCGATGAGGATGA
GCGCGCCGGAACCCGTTTACNTCCTGGGTGCCGGTATGCACCCGTGGGGGAAATGGGGTAATGACTTC :::::::::::::Rv417T7.seq:::::::::::::
TTCTCNCATCGTTCGTACTNNGATGGGACGCTGCTGCCCGAGGCGATCCTGGCCAACCGGCTCTCGCCGGCGCTGACCTTCGGCGGGGCGAACCTGAACTTC
TTTCCGATGGGCGCTTGGGCCAAACGTACCGGGGCTATCTTCATTCGGCGTCAGACGAAAGATATTCCCGTCTACCGCTTCGTATTACGTGCTTACGCCGCG
CAGCTGGTGCAAAACCATGTCAACCTCACCTGGTCGATCGAAGGGGGTCGGACCAGAACGGGCAAGCTACGGCCACCGGTGTTCGGGATCCTGCGTTACATC
ACCGATGCGGTCGACGAAATCGACGGTCCCGAAGTGTATTTGGTGCCGACCTCGATCGTGTACGAACAGCTGCACGAAGTGGAAGCCATGACCACCGAAGCC
TATGGCGCCGTGAA Clone Rv418
:::::::::::::Rv418SP6.seq:::::::::::::
TTCTTCCGGGTACCGCTGATCGGCGGCACCATCACGCACCCGGTGCAGGGCGAGGCGGCCGCCGGTGTGGTGTTGCTACGGCCGGCCAGCCCGGGTACCGGT
GTGATCGCCGGTGGTGCGGCCCGCGCGGTGCTGGAATGTGCGGGGGTGCACGACATCTTGGCCAAGTCGCTGGGCAGTGACAACGCGATCAATGTGGTGCAC
GCCACCGTGGCCGCGCTCAAGCTGCTGCACCGTCCGGAGGAGGTGGCGGCGCGCCGCGGTTTGCCAATAGAAGACGTCCCCCCGGCCGGGATGCTG :::::::::::::Rv418T7.seq:::::::::::::
GTCGAAAGTGACCATCTCTACCTTGAGTGCCATACCGCCCGACCCTATGCCTCGGATAGCTCGGCGGAAAGAAACGCTTGCAGTGCCGCCGAATAGGCGGCT
ACGTCGTGAGCGCCCATCAACTCTCGCGCGGAGTGCATCGCCAGCTGGGCGGCGCCGACGTCGACCGTGGGGATTCCGGTGCGCGCCCGCGGCCAACGGCCCG
ATCGTCGACCCGCACGGCAGATCGGCGCGATGTTCGTAACGCTGCATAGGCACTCCCGCGCGCTGGCAGGCCAGTTGCGAAACGCCCCCGCCGGGTGCCTTC
CGTCGGTTGGCTTTACCGCAAATTTGGGGTTGCCCCT Clone Rv419
:::::::::::::Rv419SP6.seq:::::::::::::
AAAGCCACGGAAACGATTGCCTACTGCCGAATCGGGGAACGGTCCTCGCACACCTGGTTCGTGTTGCGGGAATTACTCGGACACCAAAACGTCAAGAACTAC
GACGGCAGTTGGACAGAATACGGCTCCCTGGTGGGCGCCCCGATCGAGTTGGGAAACTGATATGTGCTCTGGACCCAAGCAAGGACTGACATTGCCGGCCAG
CGTCTACCTGGAAAAA :::::::::::::Rv419T7.seq:::::::::::::
TTTCGCCACCGCNAGGTCGTGCGCGTTCCAGAAAAGCGTGGTTTCGCCGGGCGCGAGGATTCGACGGTCCAACTGACCAGCCGGTCCCGCCACCCGTTAGGC
AGGATCGCGGTGTCTATATGTTCGCCCTCGGCATAAACGCCATTGCTGCGGTGAAAATCGGACATCTCGCCGATTGCCACGTCTACATGATCCGCTTTGTCC
CGCGCCGGGTCGTTGACAAACGCGATGTCNGCCTCCTGGGAAGCGGTGGC Clone Rv41
:::::::::::::Rv41SP6.seq:::::::::::::
TCGCCAAGTGGATTCGTGCTCACCNACGAGATCCGTGGTCGGATCCGCNGCTGCGGCGGGCTGCGACCCTGCATCTCGGCGGCACCCGTGACCAAATGGCGC
GCGCCGAAGCAGACGTCTCGGCGGGACGCCACGCCGACTGGCCGATGGTGCTGGCCCGCGTGTCCGCNCGTCNCCGACCCCGGCCGCATCNACCAAACCGGCC
GCCGTCCGTTCTGGACCTATCCCACGTGCCNTCGGGGTCCACGCTCGACGCGACCGANAACGTAACCAGCGTCCTCGANCGGTTCGCCCCCGGCTTCCGTGA
CATCGTGGTGGCGGCCGCGCCGT TABLE 3-continued End sequences of the polynucleotide inserts cloned in the named recombinant BAC vectors contained in the I-1945 *M. tuberculosis* H37Rv genomic DNA library.

:::::::::::::Rv41T7.seq:::::::::::::
GTACCGTCACCATGATCGCCCCCATCGGCATCGGTGAGCTGATAGATCCCAGCCGGTTTCGCCAACCCCGGAGCGATCTTGGCGCGCTGCTNGTNGTCNCTG
ANACNTAGCCACCAACAGAGCCCGGTGTGCGACAAGANGACTGATCGGATCTCTCCGGACACNTCGAGGGGGTCNTCAGGAGNCCGGGCGCCACCCCGAGGT
AAGCCTCCGCCCAGCCTCACACCGCGACCGGGTATCNCAAGTCGCGCAATAANCCCACCACCTCCTCGGACCCCACGTTGTATGCGGCTGGGT Clone Rv42
:::::::::::::Rv42SP6.seq:::::::::::::
ATACTCAAGCTTAGACCTCACTGATGTGGCGGGACGCGGGAGATAACCGCGGTTCGAGCCGTTCAACAGTGGTGGTTCCCACACCAGTTGTTTGCCTTTGCG
AAGTAAAGCGATTCGATTTGCTCGAAAAGAGGGCTGGCTGCTCGTGAGGGACATCCATGGCCGATACCTCAGCGATCTCAACGGTCAAGCGACTGCATGTTT
GGCGCAAGGTATCGCTAAGCATAGGTTCGTGACGGATTTGACAGCAAGAGCTTTCCAAAGATTGCTGTCCACATANTGATTCGCATCTCTACACCTCTTCGC
CGGTGCTGTCAAGAGCCATTCGAATCAGTTATCTCGCTCGTGCTTGGAANAAATTTTCCCAGCCTGCGTTGGACAAACCGCGTCGCCAAAGCGGT :::::::::::::Rv42T7.seq:::::::::::::
AGCTTCCCGAGAAACAGTGCATTCCCTAAGCAGCCCGTTGTCACGCCGATGAGTGAAGAGTGCACGCAATCGCCGGAATCCGGCAAAGCCCTGCACAAGCGA
AATCAACCCGGAGGCTGACAAGGCAACGTCGGTGATCCGTACCGCCTGGTTGGACAAACGGCAGAAGGCGGCCTCGTCCGGTCCATCTACGCCGAGCACACT
GGTGATAGCGCGCATCGGCATCGGTGCGGCCACGGTGGAGACGACGTCCGCGGGCGTCTGGGTCAGTAACCCGCCGACCAGTTCTCGGGCAAGCTGGTCGAC
CATCGGGCGCCACGTCTCCAACGCGCCACGCGCCATACCTGGTGCCAGTTGCTTGCGCATCCGGGTGTGCGCCGGCGGATCGGACGTCGCAGAAACGCAGCC
ACCCCGTGAGAAGTGACCCACGGCGCTGGACACGTGTCTGGTTAC Clone Rv43
:::::::::::::Rv43SP6.seq:::::::::::::
CGGCCGGGATGTGCGCAATGGCAGGTTGTCGCCCGGCTTGATGTCGGCGTTAGCGCCGGATTCCACCACATCCCCTTGCGAAAGTCCGTTGGGTGCAATGAT
GTANCGCTTCTCCCCATCGAGATAGTGGAGCAACGCAATCCGTGCGGTACGGTTCGGGTCGTACTCGATGTGCGCGACCTTGGCGTTGACACCATCTTTGTC
ATGGCGGCGAAAGTCGATCATCCGGTAAGCGCGCTTATGACCGCCGCCTTTGTGCCNGGTGGTAATCCGGCCATGCGCGTTGCGTCCACCGCGACCGTGCAG
CGGGCGCACCAGCGACNTCTCCGGGGTTGACCGGGTGATCTCGGCGAAATCAGATACGCTGGCGCCGCGACGACCAGGCGTCGTGGGCTTGTACTTGCGAAT
TGCCATGGTCTAATCAGGTCTTTCTCTCACCTCTCGTCGCCGGGCTAGGGCGCATTGCCTGCTCCT :::::::::::::Rv43T7.seq:::::::::::::
TAGCGGTGTAACCAACTCCCGGGTCACCACCCGCAAACCTCTTGCGGCAACAGCACCGTCGACGCGTCAACCGGGCTGCCCGGAATCCTGTGGATGGGCATC
GAGTGCATGGTCACGACGTCCCCGACGCGGCCGGTGGCAACGACAAGTGGCCCGGATGCACCACAAATGACGGCCGCACACCGGTGGGGACGGCCAGCACGA
GAGCCGTGTCGCCGAAGTCGACGCTAATGCCGTAGGCATTGGCCGTCACAACAGGCGACGCCCCGCGTACCACCGAGTCCACGGNGGTTGGGCGGTCTCCTC
GGCCAACCAGGCGTGAACCCGGCGGATCCGAATGCAGCAAGACCCGTGGGC Clone Rv44
:::::::::::::Rv44-2ndSP6.seq:::::::::::::
CCATTGGTCGGTGTGCGCATACCANTACNACGCGCCGGGCACCTGACGCGGCGGCCGCAACCATTCGGTGGCCATCGCCATCGTCTGCCACCCGGTCAACGG
ACGCACCTTCTCCTGGCCGACCTAGTGCGCCCACCCGCCGCCGTTGCGTCCCATCGATCCGGTCAACATGAGCAGCGCCAACACCGAGCGGTACATGACATC
TGCTGTGGAACCAGTGACANATTCCGCCGCCCATGATGATCNTCGACCGTCCTCCGGATTCGGTC :::::::::::::Rv44-2ndT7.seq:::::::::::::
GCCGGCCTGGTCAAAGGGGCGTCCGAAGGANCCGGGCTGGGTAACAAGTTCCTGGCTCATATCCGCGAATGCGACGCCATTTGTCAGGTGGTGCGGGTGTTC
GTCGACGACNACGTGACTCATGTCACCGGACGGGTCGATCCCCAGTCCGACATTGAGGTCGTCGAGACCGAGCTGATCCTGGCAGATCTGCAAACCCTGGAG
CGGGCCACGGGCCGGCTGGAGAANGAAGCNCGCACCAACAAGGCGCGCAAGCCGGTCTACGACCCGGC Clone Rv45
:::::::::::::Rv45SP6.seq:::::::::::::
GATCCACTGACCACGATGACATATCGAAATGCTCGACGATTCCGATGGCGATCAAGGCCACGATGCCCTGGCCGTTGGGCGGTATCTGGTGGATGGTGTACC
CGCGGTAGGTTCCCGTGATCGTGTCGACCCAGTCCACGCGATGGGCGGCGAGGTCGTCGGCACGCATCACCCCGCCGTNTGCCGCCGAGTGCGCCTCGAGTT
TGGCGGCCAGCTCTCCCCGGTAGAACTCTCACCGTTGGTCGCCGCGATCTTCTCTANCGTCGCCGCGTGGTCAGGAAAGGTAAACAGCTCACCGGGTTTCGG
CGCTCGTCCGCCGGGCATGAACGCATCTGCGAATCCGGGCTGGGATGCGAACAACGGACCTGTGCCG :::::::::::::Rv45T7.seq:::::::::::::
TCTACTGCCGAATCGGGGAACGGTCCTCGCCCACCNGGTTCGTGTTGCCGGAATTACTCAGGACACCGAAACGTCGAGAACTACGAGCGGAGTTGGACANAA
TACCGCTCCCNGGTGGGCGCCCCCATCGANTTGGGAAGCNGAAATGTGCTCTGGACCCCACCCAAGAATGACATTGCCGGCCGCCCTCCAACTGGAAATAGA
AACNGTGATCACCCGCCGCGTTCTTGGAAGGAATGGCATGCCCTGGGCCGGGCGTTCCTTCCGCTGCCGGACTCCTCCCACCAATTCACCGCCGAAGGCGTC
CCGTCTGC Clone Rv46
:::::::::::::Rv46SP6.seq:::::::::::::
ATACTCAAGCTTCTGTCACCGAAATCCCGCATGGGATAACGGGTTTAGATTTCGACAACGGGACCGTGTTTCTCAACAAGCCGGTCATCAGCTGGGCCGGCG
ACAACGGTATCTACTTCACCCGCTTTCGCCCGT :::::::::::::Rv46T7.seq:::::::::::::
CTGGCTCAAGCGCTCGGCGCGCAGGTGAACTCGGACCGGCTCGACGTCGCCGAACGCGAGGCGGTGCTGGCCCACGCCGACGCCGTCGTCGCACATATCGGC
ACCGTGCACAAGTCTACAACAACGCCGGCATCGCGTACAACGGCAACGTCGACAAGTCGGAGTTCAAGGACATCGAGCGCATCATCGACGTCGACTTCTGGG
GCGTCCTCCACGGGCCC Clone Rv47
:::::::::::::Rv47SP6.seq:::::::::::::
CCGCCCTCCGCATTATGGGTCAAGAACCATCGGGTCGGACTTCTGGGCTTCCAACGCTCGCGCCGTCCCN :::::::::::::Rv47T7.seq:::::::::::::
CCGTGGCACTGTCAGACATATGCGCCGCTCCTCCTCATCGCTGCGCTCGGCATCGTCGCCGGCGGTCATGGCGTCACCCTACCCAAGCCGAACGCGAAACGA
GAACGTGTTCCATTATTAGGGTGTGAGCACCAATACCAGATTGCTCACCAGGAACTCACGCAGCACCGGGACGGATGTCGGCCACCACGCCCATCTGGGGTG
GTAGCGGGGAAATACCGCTAACGCGGCTCCGGTGCCG TABLE 3-continued End sequences of the polynucleotide inserts cloned in the named recombinant BAC vectors contained in the I-1945 *M. tuberculosis* H37Rv genomic DNA library.

Clone Rv48
:::::::::::::Rv48SP6.seq:::::::::::::
TACTCAAGCTTGTCCAAATATCGAAGCGTCGGGTCGCGAGGCTCGGTCGGCAGCTCCAGCAAAACCCGCTCCACCCCTAGATGCCGGTATCCCTCAAGGTCT
TTATCCGCCGCTTCACCCCACTGGCACACGGTCACCGGCACGTCGCCCCCGGCCATGGCGCGCAACCGCTGAAGCGGACCCGACAGCCGCTGCGGTGATGGA
CTGATCGCGATCCACCCGGCATTGAGCCGGGCTATCCGCGGGAAGTTCGCCGGTCCCCCGCCCACATACAGCGGAGGATAGGGCTTTGTCACCGGCTTCGGC
CAGCAGTAGATCGGATCGAAGTCCACATATGTCCCATGGAATTCCGCCTGCTCCTGCGTTCAGATCTCGATTATCGCGCGCAACCGCTCATCGATCACACGT
CCGCGCACCGCAGGGTCCACACCATGGTTGGCGACTTCTTCGCGCAACCAGCCACACCCACGCCGAAACGAAACCGTCCCTGCG :::::::::::::Rv48T7.seq:::::::::::::
CAGGCATGCAAGCTTGGCCAACTCCTCATCGGACTTGAAGGTGCCGTCCTCGTTGGCGGCCCTGCTCCACGGCACGTTGATGGCACCAGGAATGTGTCCGGG
CCGCTGGCTTTGTTCCTGCGGCAGGTGCGCGGGGGCCAGGATCTTGCCGGAGAACTCGTCGGGAGAGCGCACGTCGATGAGGTTCTTGACGTTGATGGCCGC
CAGGACCTCGTCGCGGAATGCCCGAATCGTGTTATCCGGCGGGGANGCGGTGTAGGAAGTCACCGGCCGGCTGACCGGGTCGCTGGACAGCGGGCGTCCGTC
GAGCTCC Clone Rv49
:::::::::::::Rv49SP6.seq:::::::::::::
ATACTCAAGCTTCAAAACAGGCCTGTTGTGGGCGCACCCGGCTCGCCGAGTTCTGCACGCACCGCCTCAAGTGCGGCCCGCACCGCCGGCATCTCCCGGTCA
CGCAGGGCCGCGGCCCGCGCCGCAGCGACGGCGTGTTCGCGCAGTTCGCCGTCAATGATGCTGACCTGATCGGCCACCCGGGCGGTCTCGGCGTCGTCCCGT
TCACTAATCGCGGTGCTCAGCAGCGTCTCGACAGCCACCACCCGAGTGGAGACCAGATGCNCCACCACGGACCGCAGCGATGCCAGTCACCTCACCCGTCC :::::::::::::Rv49T7.seq:::::::::::::
CAGGCATGCAAGCTTTGCAGTTGCTGAGTAATGTCGGCCAACGTCACCACAATCGCGATGAATTCAATCATGCCGCCCAGGGCGGCCAACCCAATGGTGGCC
GCGAGCGGCAGCTCGATCGCAGCGCGGAGGTTGCCGGCCGCCAGTTGATTCACGAACAGGGTGAGGTCATAGGCGGGCAGGATAGTGACGAAGGCAAGACCT
AGATCTGCCGTCGGAAGAAGAATCGAGTATCCGGTCGACACAACGGAAGCGAAAGTGTCCGCGATGTTGATGAGCGTCGCCGGTTGTGGCGGCGGTGGCGGC
GGTAGCACCGTCCGCACATACCGCGGGAACGCGGGCATCCGAATTTGGGGCAGGGTGTTCAAGGCGGCTGGCAACTCACCATGAATCT Clone Rv4
:::::::::::::Rv4SP6.seq:::::::::::::
CCGGCTCGTATGTTGTGTGGAATTGTGACCGGATAACAATTTCACACAGGAAACAGCTATGACCATGATTACGCCAAGCTATTTAGGTGACACTATAGAATA
CTCAAGCTTGGCCGCAGGGCCGAGTCGATTGGTCGCGGTCGCCTCGACAGTTAGCTTATGCAATGCTAACTTCGGGGCAAAGTTCAGGCGGATCGGCCGATG
GCGGGCGTAGGTGAAGGAGACAGCGGAGGCGTGGAGCGTGATGACATTGGCATGGTGGCCGCTTCCCCCGTCGCGTCTCGGGTAAATGGCAAGGTAGACGCT
GACGTCGTCGGTCGATTTGCCACCTGCTGCCGTGCCCTGGGCATCGCGGTTTACCAGCGTAAACGTCCGCCGGACCTGGCTGCCGCCCGGTCTGGTTTCGCC
GCGCTGACCCGCGTCGCCCATGACAGTGCGACCCTGNACCGGGCTGGCC :::::::::::::Rv4T7.seq:::::::::::::
GTGTGCTGTCAATTCAGAGCTGAGCCTGATGCACTCAACTTACTGAGCATGCTAACGCTGGTCGTGCGGGTCTTGTTCCCGCGTGTCGGCAGGGCACAGGCT
CGGGGCGTAGCTGGGAGAGGCCCCGGTCAAGCCCGGAGAGCAGTGCTCAGTCCGCCAGCTTGACCGACTTTCGATGAGAACGCGCTTCTCGCCGTATTGAAC
TGGCGTGCTGACGGTCGCTGAGCAGCGCTCGCCGAGTGCGGCCGCTGATTCTTTCATCGAGCCAGGAGGCGCATTCGTGTTCGGCCGCCTGCGGGTCGGCCC
CATCGTCGACGCGATCCGTCACCCACTCCTCGATCAGGTCTGCCTCATCGAACGGGCCAACGGTGCTGTCGGAGTAAGTGTGCGTGGGCACGCGAGCCGGGT
GCTGTGGTACACCCACCGTTGCATGAACAA Clone Rv50
:::::::::::::Rv50SP6.seq:::::::::::::
ATACTCAAGCTTCACCAGGCGCCGGCGGGCCGCGGCGCCAAGCCAGGCAGCCGCGCTCGGCGCGTCGGGGCCTTCCGCCGGCTCGGCCGACAGTTCGATCTC
TGGATCGGCGGGGCTCTCCGGGCCGGCCTCGGCGACCTCAGCGGGCCGCGCCTTCCGGCCGAACCATTCCCTAGCCATAGATAACCGCACCTCAATGCACGG
TTTGGCGGCAACCCGG :::::::::::::Rv50T7.seq:::::::::::::
AGCTTCCGTCACGACCCGCCCTCGCCGGTGCCGGCGCCATCGGTCATCGGATCTCATGACGACGTCACGTAGGCCCGCTAGCCGCGAGCGGGCGCGGTCAAC
TGGCGAGGCGGCGGCGACGTGACTGAGCTGGCCGAGCTGGACCGGTTCACCGCGGAACTACCGTTCTCGCTCGACGACTTTCAGCAGCGGGCTTGCAGCGCG
CTGGAACGCGGCCACGGTGTTGCTGGTGTGCGCGCCGACCGGCGCTGGCAAGACGGTGGTCG Clone Rv51
:::::::::::::Rv51SP6.seq:::::::::::::
ATACTCAAGCTTGCCGGGACCGCGGAACAGAACCGGCGGTTCCTACCGCGGTGTGCGGCCGGCGCGATATCGGCCTCCCGACTAACCGAACCCGATGTGGGC
TCC :::::::::::::Rv51T7.seq:::::::::::::
ACGTTGGCTCTGCCGGAACGTATTTCCAGCGGCACGCATTCGGCGTGGGTGCCGGGCGCCGAGTTGCGTCGCTGGGATCACGCAGCAGTCGCCGGCGGCTGC
CGTCGGGCTATGAATTGCACCGAGCCGGAAAATCCNCAC Clone Rv52
:::::::::::::Rv52SP6.seq:::::::::::::
ATACTCAAGCTTGTCGTATTCCGTGGCACTGTCAGACATATGCGCCGCTCCTCCTCATCGCTGCGCTCGGCATCGTCGCCGGCGGTCATGGCGTCACCCTAC
CCAAGCCGAACGCGAAACGAGAACGTGTTCCATTATTAGGGTGTGAGCACCAATACCAGATTGCTCACCAGGAACTCACGCAGCACCGGGACGGATGTCAGC
CACCACCCCCATCTGGGGTGGTAGCGGGGA :::::::::::::Rv52T7.seq
CGTTGGTAGCCCGATATGCATAGTGTATCTTACTGAACATGATTTCCATTATGGAGCCCGGGGTGCCGGCAGCGCGAACGGTGCGCCGTCAGACGCGGGCGG
CACTGACCAGGGTGTTGCGGGCGAACATCGGCCCGGCTTCGGATTCCGGTCCGGGTACCGGGCGACCCACCGCTTCGAGGTA Clone Rv53
:::::::::::::Rv53SP6.seq:::::::::::::
ATACTCAAGCTTGGCCAACTCCTCATCGGACTTGAAGGTGCCGTCCTCGTTGGCGGCCCTGCTCCACGGCACGTTGATGGCACCAGGAATGTGTCCGGGCCG
CTGGCTTTGTTCCTGCGGCAGGTGCGCGGGGGCCATGATCTTGCCGGAAAACTCGTCGGGAGAGCGCACGTCGATGAGGTTCTTGACGTTGATGGCCGCCAG
GACCTCGTCGCGGAATGCCCGAATCGTGTTATCCGGCGGGGAGGCGGTGTATGAGGTCACCGGCCGGCTGACCGGGTCGCTGGACAGCGGGCGTCCGTCCAG
CTCCCACTTCTTGCGGGCGCCGTCCAACNACTTGACTTCTCCTGG TABLE 3-continued End sequences of the polynucleotide inserts cloned in the named recombinant BAC vectors contained in the I-1945 *M. tuberculosis* H37Rv genomic DNA library.

:::::::::::::Rv53T7.seq:::::::::::::
ATATCTTAAGCGTCGGGTCCCGAGGCTCGGTCGGCAGCTCCAGCAAAACCCGCTCCACCCCTAGATGCCGGTATCCCTCAAGGTCTTTAGCCGCCGCTTCAC
CCCACTGGCACACGGTCACCGGCACGTCGCCCCCGGCCATGGCGCGCAACCGCTGAAGCGGACCCGACAGCCGCTGCGGTGATGGACTGATCGCGATCCACC
CGGCATTGAGCCGGGCTATCCGCGGGAAGTTCGCCGGTCCCCCGCCCACATACAGCGGAGGATAGGGCTTTGTCACCGGCTTCGGCCAGCAGTAGATCGGAT
CGAAGTCCACATATGTCCCATGGAATTCCGCCTGCTCCTGCGTCCAGATCTCGATTATCGCGCGCAACCGCTCATCGATCACACGTCCGCGCACCGCAGGGT
CCACACCATGGTTGGCGACTTCTTCGCGCA Clone Rv54
:::::::::::::Rv54SP6.seq:::::::::::::
ATACTCAAGCTTGTCGCGGTAAACCCGCAGCAGGGCGGTGGGTGCGGTGTCAAAAACAACCACACTTCTTTGCGGTTCGGTGATCTCGACACCGGCCGCGAG
CCGACCACCATGCGCGCGTAAATCGGCGATCAGCGCGTCGGCTATCGCCTGGGTGCCGCCCACCGGAATCGGCCAGCCGACCGAATGGGCCAGCGTTGCCAG
CATCAGTCCGGCGCCGGCCGACACCAGTGACGGCAACGGTGAAATCGCGTGGGCGGCAACGCCGGTGAACAACGCGCGGGCATCCTCGCCCGCCAGCGACCG
CCAGGCAGGGGTGCCCTGGGCCAGCATCCGCAGCCCGAGACGCAGGACCGAGCCCAGTGCAGTAGGCAAAGACCGCTTGTCGGAGACATGAACTCCACGACC
GT :::::::::::::Rv54T7.seq:::::::::::::
AGCTTATTGAACCGCGGGTCGCAGGCAAAGTGGACCTCATAACGACTCGGGTCCAGCGACCGCGCCAACACGAACGGCCGGACGACGTGGGCCAGGGTCGCG
GCCTCCCCTACAAACAGGATCCGTTGCCTGCGAGCGACAGGCTCCGGTGCGGCGTTGGGCGCCGTGCTCGTCCCAGCGTCCGGTCCCGGGTCGCCGGCGACG
CTTGTTTCCTCCATACTCGCCCCCTAATCTCGAGGCAGCCCGTACCCGCAGGCAACCTCCCAAAAATGCAATCCCCCAAAATGCAATGCGTCGAGCTATTTC
TCACACCGACCGCTAGTTGCGGATCAGAAATCCGTTGGGCGCGGAAGTCCAGCCGAATTTGTTCTCCCGCTCCGCATCATGCTTGTAATCGTTTGGAAATTC
ATCCTCATATGCCTCGATCGCTTCATAGGGTCCAGGCCAAACCGGGCA Clone Rv55
:::::::::::::Rv55SP6.seq:::::::::::::
CTTCCGGCTCGTATGTTGTGTGGAATTGTGAGCGGATAACAATTTCACACAGGAAACAGCTATGACCATGATTACGCCAAGCTATTTAGGTGACACTATAGA
ATACTCAAGCTTGGCCACCTCGCGGTGTGTGGTGGAACCCATCTGAGCAGTGTGCCAAACCGGGGCAGACAGCTCCCAATTGACGTGAGCCCGCTCACTTGC
TGGGTAAGCGTCG :::::::::::::Rv55T7.seq:::::::::::::
TAGCGCCCCCTCCCGGGCGGAGCTCCACGGCGTGGATCAAGGTACCGGCCGGGATGTTGCGCAATGGCAGGTTGTTGCCCGGCTTGATGTCGGCGTTAGCGC
CGGATTCCACCACATCCCCTTGCGAAAGTCCGTTGGGTGCAATGATGTAGCGCTTCTCCCCATCGAGATAGTGGAGCAACGCAATCCGTGCGGTACGGTTCG
GGTCGTACTCGATGTGCGCGACCTTGGCGTTGACACCATCTTTGTCATTGCGGCGAAAGTCGATCATCCGGTAAGCGCGCTTATGACCGCCGCCTTTGTGCC
GGGTGGTAATCCGGCCATGCGCGTTGCGTCCACCGCGACCGTGCAGCGGGCGCACCAGCGACTTCTCCGGGGTTGACCGGGTGATCTCGGCGAAATCAGATA
CGCTGGCGCCGCGACGACCAAGCGTCGTGGGCTTGTTCTTGCGAATTGCATGTCTAATCAGGTCTTTCTC Clone Rv56
:::::::::::::Rv56SP6.seq:::::::::::::
TGAAACTATATAATACTCAAGCTTGCCAAAGAAGACCTCGTCGACCAAGCAGGACGCGACCGTCGAGGTGGCGATCCGGCTTGGCGTCGACCCGCGTAAGGC
AAACCAGATGGTTCGCGGCACGGTCAACCTGCCACACGGCACTGGTAAGACTGCCCGCGTCGCGGTATTCGCGGTTGGTGAAAAGGCCGATGCTGCCGTTGC
CGCGGGGGCGGATGTTGTCGGGAGTGACGATCTGATCGAAAGGATTCAGGGCGGCTGGCTGGAATTCGATGCCGCGATCGCGACACCGGATCAGATGGCCAA
AGTCGGTCGCATCGCTCGGGTGCTGGGTCCGCGCGGCCTGATGCCCAACCCGAAAACCGGCACCGTCACCGCCGACGTCGCCAAGGCCGTCGCGGACATCAA
GGGCGGCAAGATCAACTTCCGGGTTGACAAGCAGGCCAACCTGCACTTCTC :::::::::::::Rv56T7.seq:::::::::::::
GCTGAGCTCCACGGCGTGGATCAAGGTACCGGCCGGGATGTTGCGCAATGGCAGGTTGTTGCCCGGCTTGATGTCGGCGTTAGCGCCGGATTCCACCACATC
CCCTTGCGAAAGTCCGTTGGGTGCAATGATGTAGCGCTTCTCCCCATCGAGATAGTGGAGCAACGCAATCCGTGCGGTACGGTTCGGGTCGTACTCGATGTG
CGCGACCTTGGCGTTGACACCATCTTTGTCATTGCGGCGAAAGTCGATCATCCGGTAAGCGCGCTTATGACCGCCGCCTTTGTGCCGGGTGGTAATCCGGCC
ATGCGCGTTGCGTCCACCGCGACCGTGCAGCGGGCGCACCAGCGACTTCTCCGGGGTTGACCGGGTGATCTCGGCGAAATCAGATACGCTGGCGCCGCGACG
ACCAGGCGTCGTGGGCTTGTACTTGCGAATTGCCATGTCTAATCAGGTCTTTCTCT Clone Rv57
:::::::::::::Rv57SP6.seq:::::::::::::
ATACTCAAGCTTGTTGGTGACCTCGCCGGCGAACAGTTCTCGCACGATTTCCGGATTAGCGGGACTGGTCACCAGTTGGGTATGCGGGAAGGCGCTGACGTT
CGCCGCGATTAGCTGTTTGATGGACGCGGCGGTGATGTCCTGATCACGGAACTGGCTGTAATAGCCCAGGGTCGCCACGCTTCCATCCGGGCCCGGACCCGG
C :::::::::::::Rv57T7.seq:::::::::::::
GATGATCGCCGGTGCCACCCCGATCCGTGCCTCGGTCAGCGCGAACGTGCTTTCCGGTCCGGCGACCACCATGTCGCACGCACCGACCAGGCCGAACCCGCC
GGCCCGCACATGCCCGTTGATGGCGCCGACCACCGGCAGCGGCGACTCGACGATGGCGCGCAACAGCGCCGTCATTTCCCGCGCCCGCGCCACCGCCATCCG
GTACGGATCACCACCACCTCCGCCGGCCTCGCTGAGGTCC Clone Rv58
:::::::::::::Rv58SP6.seq:::::::::::::
ATACTCAAGCTTGCCGCAATCGAAACCAACCTGTTTGTGCCGCAAGAAATTACGCCGTGGCCCGGCGCCGATCAAGAAACGCCCCGGCGCGCGGCGGTGTCG
TCGTATGGCATGACGGGCACCAATGTGCACGCCATTGTCGAGCAGGCACCGGTGCCAGCCCCCGAATCCGGTGCACCAGGCGACACCCCGGCCACACCCGGT
ATCGACGGCGCGCTGCTGTTCGCGCTGTCGGCCAGCTCGCAGGACGCGCTGCGGCAAACCGCCGCGCGGCTGGCCGATTGGGTCT :::::::::::::Rv58T7.seq:::::::::::::
TTGGCGGGTTGGCCACANCANCCCGCCGGTGACGGCGACGATGCTGGGCTGGTTGCGGCCCTGCGCCACCGCGGCTTGCATGCTGGTTGGCTGTCTTGGGAC
GATCCCGAAATAGTCCACGCGGATCTGGTGATTTTGCGGGCTACCCGCGATTACCCCGCGCGGCTCGACGAGTTTTTGGCCTGGACTACCCGCGTGGCCAAT
CTGCTGAACTCGCGGCCGGTGGTGGCCTGGAATGTCCANCGCCGTTCACCTACGTGACCTTGATGGGATCCGGGGGNT Clone Rv59
:::::::::::::Rv59SP6.seq:::::::::::::
NCGTGGACACCGGTGTCGANCGCCACCAGCCGCATGTCTGCANGTCNATTCCGTCCTCGGCAACATCTTGAATGCCGAGCAGCGCCTGGGCGTGATCGGCAA
CCGGGGATGACCGCTCGCCGATCCGCTCGACAATCCCGGCGGCACGTGACATGCCGGCGGACGGCTCGACGAGCTGGAACTTCAGCGACGACGATCCGGAAT TABLE 3-continued End sequences of the polynucleotide inserts cloned in the named recombinant BAC vectors contained in the I-1945 *M. tuberculosis* H37Rv genomic DNA library.

TGATCACCAGCACGGTGCTACTCATGGACCCCTGCGCCTGAATCCCGTGATGGCCACGGTGTTGACTATTCGTCGACAGTGCACCCGAGATAGTCTTCACGG
CTGCGT

::::::::::::Rv59T7.seq::::::::::::
CATGTATTGCCGTGCTCACGGCGCCACGCTCGATGGTTTCTCGAAGTCTCCGGGCTGGTGTACAGCTTCTCGTTGATCTCGTTCGCCACGCCGTCCTCTTCC
CGCCGACGACCCGATCTCGATCTCCANAATGATCTTGGCGGCCGCCGCCGCCTTGAGCAGCTCCTGGGCGATGGCCAGGTTCTCATCGATGGGCACTGCCGA
CCGTCCCACATGTGCGACGGAACAAAGATGTCACCTTGCTCACGCGTGCGCNAGATCNCANAAGGGCCGGACATACTGTCNACTTGTCCTTGGGCAGTGGTC
CGTGTCAGCCCACGTGACGGGTACTTGGCGCGATAACGTGGTG Clone Rv5
::::::::::::Rv5SP6.seq::::::::::::
GCCACCACGACCCGGCCGTAACTCTGCTCACGGAAATGCGGCCAGGCCGCGCGTAGCACGTGGTATCCGCCATAAAGGTGCACCTTAAGCACGGCGTCCCAA
TTCTCGAACGACATCTTGTGGAAGGTGCCGTCGCGCAAGATCCCGGCGTTGCTCACCACACCGTGCACGGCGCCGAATTCGTCAAGCGCGGTCTTGATGATG
TTCGCTGCGCCGTCCTCGGTGGCGACGCTGTCCTTAGTTGGCGACCGCCCGGCCCCCCTTGTCGCGAATCTCGGCGACGACCTCATCGGCCATCGCCGAACG
GCGCCCGTGCCCGTCGCGGGCGCCACCGAGGTCGTTGACCACGA ::::::::::::Rv5T7.seq::::::::::::
CAGGCATGCAACCTTTGTCCACACGGCGTCTACTCCGTGCAAGGTCCGACCGCTTCCACGTCCCGCCGTGACGGTGCTCCATCTCCCTCAGCAACGCGTGAA
GTGGTCCGATCCCGCGGCTTCAGG Clone Rv60
::::::::::::Rv60SP6.seq::::::::::::
GTTGAGACGCAACCAGCGCACAACGACGATTTGGCGTAGCGGCGGACGTCTGCTCGATTCGATCACGTCGCGCTCGCATCGAGCATGGCCCGCGACGCTACA
CGATCGCCGTCGTCGATGACACGACCGAGCCGTACGCCGGCCGTAAGCCGCGCCAGGATTCGGCGAAAAACGTCTACGTGGCGGGTGTACTGGGTGTCGAAT
GATTCGTGGGGTGCGTATGCGTCCTGCAATCGTCGACATAGATCCGTCGCCGCATCGCGTCGACAACTCCGGGTGAGTGGAATACACTTGCCGATCACGCGA
CGTGCGCGGATCGATGCCGACCGAAATACGACCACATGGCTCTTGTTGCNCAGTGTTGGCGGCATCAAATACCCTCAGTGCCGTCCGAC ::::::::::::Rv60T7.seq::::::::::::
TTNCCGCCTTNACGCCTACTCCNAGACGATGCTCGACGCGTGTGAGCACACGGCGCTGCTGTAGACGGCACGGCGCAGCTGGATCGCGCTTGGTGCACCCAA
GCCTCTACGCGCGTCGCTGCGTCGTCATCGGGTACCGAACATATTCCGGTCGTTGCGCAGAGTGTGCATGTGCGGCTCTTGTGAACGAACATAGCAAAGCGT
ATATGTCTGTGGCGGCTCTGCAGATATCGCGATAATACGTATATACATAAGGTGGCGCGCGATCTATCGGTATATCCGTTATGGCGGACGTGCGTGAGCGTG
AGTCGCGGCGCATCGCGCACTTCGCGATCGCGTGACTGGTCCTCGCGACTGCGCGCATGCGTAGC Clone Rv61
::::::::::::Rv61SP6.seq::::::::::::
GGTGATGACGCACTTGCTTCGAATGAGTCATTGACTACTCCCGTGGTTGTCCTGCGATGGTGGAGTGCCGCGCAGCCTTGCCCGANGTCGCGATCGCGTCGC
GGGCTTCGGGGAGCAGACTGACCTGCAGATGGAAGTCGTGCCACATGCCCGCGAACGGCGAGCTCGATGCTTGTTTTCGAAGNGCGCANGCGGTTTCGATCT
TGTCCGCGTCAACGCAGATCGGATCTCGCCGCGGTCTGCATGACGATGGGCGCAGGCCCGCTCATGTCCCGTAGACGGGGAGATACGGGCAGCCGCGGATCG
AGACCTACGTAGCGCGGCGCCCATCGTGCCATCGACGAAGAATGACGGATCGCGCAGCGCCGTCGCGTCGCTTCGATGTCACGCGAGATCGCCACGGCAGAT
CAGCGATGCGCGGGC ::::::::::::Rv61T7.seq::::::::::::
CGGTACGCCGGCAACAAACGCCTTGTGACGAGCGCGTCCGAGCGGTCATCGGCCTCCACCGTCATGCACAGCTCCTTCTCCAGGTCTACGCCGACGTCGCGG
TCCACATTGGTGAGCTTGGCGAATGCCTCGGCAACCTCGTCGAAATGCGCCTCCGCGTCCGCATCGAAGGTCGCCATGTCAAAGATCAACTCGACGTAGTAG
CTAGTTACCGCATCAGGTCAGTGTTTGCTGGCCTCGGAGTCCGGCCGAACAATGGCCATTTCCCGCGACTCTAGAATCCAGTCATCGTCTCGGTGACGACGC
CTTGCCGATCACATAGCTCGACCGGATCGGAGAGAATCTGGTCTCGT Clone Rv62
::::::::::::Rv62SP6.seq::::::::::::
ATACTCAAGCTTAAGCGCAGCAGTACCGGCGGTGCCTGGGCATCCCAGCAAAACGGGGAGCTCAACGAACGATTCCTGAACGAAGGGTCGTCCACCAACCTC
CAAACCGAACGGTTGCCAGCCCCGGC ::::::::::::Rv62T7.seq::::::::::::
GCAAGTCCGCTCAATGTGGTTGTGATCACANGACTACGTCGCCTCAATCAGCTCAAACGTCACCCCGTGGCGTGCTGCGCAGCATGAAGGTCGGCGCCCGCA
CGATGTGGGCGAAGCAACAGGTAATAACTGGTCGGCATGGGTCAACCCTCATTGGGCCGTTGCGGATCGGGTGCACGCCCGGAGTGCCGGTCGAACTCAACA
CCGCCTTCACCGATCTTTTCGTCGAAAATGGCGGTCGTGTCGGGGTATACGTCCGCGATCCCACGAGGCGGAATCCGCTGAGCCGCACTGA Clone Rv63
::::::::::::Rv63SP6.seq::::::::::::
ATACTCAAGCTTCGCGCCCTCAAGCGGCTGAAGGTGGTTCCGGCGTNCCAACNGTCGGGCAACTCGCCGATGGGCATGGTGCTCGACNCCGTCCCGGTGATC
CCGCCGGAGCTGCGCCCGATGGTGCAGCTCGACGGCGGCCGGTTCGCCNCGTCCGACTTGAACGACCTGTACCGCAGGGTGATCAACCGCNACNNCNNGCTG
AAAAGGCTGATCGATCTGGGTGCGCCGGAAATCATCGTCAACAACNAGAANCGGATGCTGCNGGAATCCGTGGACGCGCTGTTCGACAATGGCCGCCGCGGC
CGGCCCGTCACCGGGCCGGGCAACCGTCCGCTCAAGTCGCTTTCCGATCTGCTCA ::::::::::::Rv63T7.seq::::::::::::
TGCGCATGGCAGTTGTTGCCGGCTTGAGTCGCGTTAGCGCGGATTCCACCACATCCCTTGCGAAGTCGTGGGTGCAATGATGTAGCGCTTCTCCCATCGAGA
TAGTGGAGCAACGCAATCCGTGCGTACGTTGGGTCGTACTCGAGTGCGCANCTTGGCGTTGACACCATCTTTGTCATTGCGGCGAAGTCGATCATCCGGTAA
GCGCGCTTATCGACGCCGCCTCTGTGCCGGGTGGTAATCCGGCCATGCGCTTGCGTCCACCGCGACGTGCAGCGGGCGCACACCGACTTCTCCGGGTGACGG
GTGATCTCGGCGAATCAGAACCTGGCGCGCGACACAGCGTCGTGGCTGTACTTGC Clone Rv64
::::::::::::Rv64SP6.seq::::::::::::
TGGGTGATCAGATACTGGCTAGTTGGTCGGGTGGGGTGATCGAAGATCGCGGTGGCCGGCAGCGTTACTGCGGTGACGCTGTTAAGCGGTTACGTACTCCAC
GGCACTCAANGAATTANATCCCGAATCGGCAAACCCTGGCCAGCGTCGAGTCCGCAGCGCCGTCGCGGGGGGGACCGCTGCGGCATGCTCACATACCACCTC
GATCGCTGCGGGAGTTGCTCGTCGGCCGACCGACCGGCCAGCCGGGCGGCAAACCGGAGGACCCAAGATTCAGCACCACCATCGCTAGCCCGATCTGGCCGC
GCGTGG TABLE 3-continued End sequences of the polynucleotide inserts cloned in the named recombinant BAC vectors contained in the I-1945 *M. tuberculosis* H37Rv genomic DNA library.

::::::::::::Rv64T7.seq::::::::::::
TCGTAGCGGTTGCGACCANTCCGCGGACAGCTCCGCCACGCGACGGGTCGGGATCACCGCGGTCAAACCACCGAGCGGCGAGGATCTCTGGCCGTCGACGTG
ACCGCGCACGGCCGCGGTGATGGCCAGTCCCGACCGCCGTTCCACTTGGCGTACGCGCTGGATGTGTTGTGCCGCAACGGAATCCCACCTCAATTATGACCT
CGTTGTGGGCGAGCGCGGTATCGTACGCCCGACCAGGAATCGTCGATGCTATCTCACGTCACCGAAGGCCTCTCCCAGCACACCGCATCCAGAACGTGCACA
CNGTCGACATGTCTCGGCGGATCCGCCTGCAGAACGAACGCCANGTGCGCTGTGCGACACGGGTCGCGATCACCGCTCGCACGCGGAGATCGGCACACGCGC
AGCGCATCGATCATAATCTCTCGATGCGGTCTCCACCACCGAACAG Clone Rv65
::::::::::::Rv65SP6.seq::::::::::::
ATACTCAAGCTTCGCTGAGGTGGTGGGGCACGATCACGTCACCGCACCGCTGTCGGTGGCGCTGGATGCCGGCCGGATCAACCACGCGTACCTGTTCTCTGG
GCCGCGTGGCTGCGGAAAGACGTCGTCAGCGCGTATCCTGGCNCGGTCGTTGAACTGTGCGCAGGGCCCTACCGCCAACCCGTGCGGGGTCTGCGAATCCTG
CGTTTCGTTGGCGCCCAACGCCCCCGGCAGCATCGACGTGGTAGAGCTGGATGCCGCCAGCCACGGCGGCGTGGACGACACCCGCGAGCTGCGGGACCGCGC
GTTCTATGCGCCGGTCCACTCACGGTACCGGGTATTTATCGTCGACGAGGCGCACATGGT ::::::::::::Rv65T7.seq::::::::::::
GCACTCACGCTGGTACAAGACCTTCACAAAATCTGAAATCCTGACCCGATACTTGAACCTGGTCTCGTTCGGCAATAACTCGTTCGGCGTGCAGGACGCGGC
GCAAACGTACTTCGGCATCAACGCGTCCGACCTGAATTGGCAGCAAGCGGCGCTGCTGGCCGGCATGGTGCAATCGACCAGCACGCTCAACCCGTACACCAA
CCCCGACGGCGCGCTGGCCCGGCGGAACGTGGTCCTCGACACCATGATCGAGAACCTTCCCGGGGAGGCGGAGGCGTTGCGTGCCGCCAAGGCCGATCCGCT
GGGGGTACTGCCGCAGCCCAATGAGTTGCCGCGCGGCTGCATCGCGGCCGGCGACCG Clone Rv66
::::::::::::Rv66SP6.seq::::::::::::
ATACTCAAGCTTGTATAAAAAGATCGGTGAGCGCATCGATTCGCTCCGCCGGGTTTGCCGCTGCGGCGGCGGAGCTGCCGTGACCGTCTATTTGGGTGATCA
GATACTGGGCTAGTTCGGTCGGGGTGGGGTGATCGAAGATCGCGGTGGCCGGCAGCGTTACTGCGGTGACGGCTGTTAAGCGGTTACGTACCTCCACGGCAC
TCAAGGAATTAAATCCCGAATCGGCAAACGCCTGGCCAGCGTCGAATCCGGCAGCGCCGTCGCGCCCCAGCACCGCTGCGGCATGCTCACATACCACCTCCA
TCGCTGCGGCGAATTGCTCGTCGGCCGACCGACCGGCCAGCCGGGCGGCAAACCCGGAAGA ::::::::::::Rv66T7.seq::::::::::::
CCTCATCATATGCCGATAGAGCTCTACATATTCAGGAGATCACCATGGCTCGTGCGGTCGGGATCGACTCGGGACCACCAACTCCGTCGTCTCGGTTCTGGA
ANGTGGCGACCNGGTCGTCGTCGCCAACTCCGGAGGGCTCCAGGACCACCCGTCAATTGTCGCGTTCGCCCGCAACGGTGAGGTGCTGGTCNGCCAGCCCGC
CAAGAACAGGCAGTGACCAACGTCGATCGCACCGTGCGCTCGGTCAAGCGACCATGGGCAGCGACTGGTCCATAGAGATTGACGCAAGAAATACACGCCCGG
AGATCTCGCCGCATTCTGATGAACTGAACGCGACCCGAGGCTACTCGGTGANGACATNACGACGCGTTATCACACCCCGCCTNCTTCAATGACCCCACGTCN
GGCACCAAGGACCCGGCAATCGCGGCTCACTTGCGCGATNGTCNACAACCAACGCGNCGCCTGGCTACGGGCTCAACAAGGCANAAGACACAATCCGCTCTC
GATTGGTG Clone Rv67
::::::::::::Rv67SP6.seq::::::::::::
ATACTCAAGCTTATCGAGGCGGCGCATACCGAAGCGTGGGAAATCCAGACCGAATACCGCGACGTGCTGGACACTTTGGCCGGCGAGCTGCTGGAAAAGGAG
ACCCTGCACCGACCCGAGCTGGAAAGCATCTTCGCTGACGTCGAAAAGCGGCCGCGGCTCACCATGTTCGACAACTTCGGTGGCCGGATCCCGTCGGACAAA
CCGCCCATCAAGACACCCGGCGAGCTCGCGATCGAACGCGGCGAACCTTGGCCCCAGCCGGTCCCCGAGCCGGCGTTCAAGGCGGCGATTGCGCATGCTACC
CAAGCCGCTGAGGCCGCCCGGTCCGACCCGGCCAAACCGGGCACGGCGCCAACGGTTCGCCCGCCGGCACCACCGGTCCGGTGACCGCAGTACGGTCCCCCC
AGCCTGACTACCGTGCCCCGGCGGGCT ::::::::::::Rv7T7.seq::::::::::::
TGGCCGGGCTGGTAGCCCGCGTATGGCAAGGTTCCGCTCAATGTGGTTGTGATGCAGCAGGACTACGTTCGCCTCAATCAGCTCAAACGTCACCCCCGTGGC
GTGCTGCGCAGCATGAAGGTCGGCGCCCGCACGATGTGGGCGAAGGCAACAGGTAAGAACCTGGTCGGCATGGGTCGAGCCCTCATTGGGCCGTTGCGGATC
GGGTTGCAGCGCGCCGGAGTGCCGGTCGAACTCAACACCGCCTTCACCGATCTTTTCGTCGAAAATGGCGTCGTGTCCGGGGTATACGTCCGCGATTCCCAC
GAGGCGGAATCCGCTGAGCCGCAGCTGATCCGGGCTCGCCGCGGCGTGATCCTGGCCTGTGGTGGTTTCGAGCATAACGAGCAGATGCGAAT Clone Rv68
::::::::::::Rv68SP6.seq::::::::::::
GTCCAGTCAAGCATCGGTCCTCTCCGACTACGCCAAGANTGGCGACGTGTCAGTGCANACAGCGGANATGGTGGCGCCTATGCGTCGACGCTCACAAACNGC
GGTGANCGCGTTCTGGTCGTGCACCATCGAGCCGTGCCAGCCCGGCCGCGTGCCGTCAGCCGCATCCACTGGATGCCTTCTCGGNGTTTCAATCANGTACAN
GCGACGTTCGCCACCATCGTGCCGGGGCACGGTTAGCGAGAAACCGCCGACTTCACCGATTGCCTCGGTGATGCCGTCGAACAGATCGGGCCTATTGTCGAC
AGCCAGTGTGATNCGTATTTGCCGCCGTGCTCCTCGTCGCAACGATGCGAACACAGATCCGTGGNGGACGATAGCGGCTGACAANGTGGGGGCAACACAATC
ACATGCCACATTTCTTCATTTCACGCCCACAACCCAGACTTCGTCTCGATGNGCCG ::::::::::::Rv68T7.seq::::::::::::
CACGCGGTCTGGCCCGATCCGAAGATCCCTTTGCCGGCGTGGCGGCTCTGCTCGGCGGTGTTGTACACTTCTCGAACACCTCGGCACCGACACCACCACCGT
NGCTTGAACACCGCCAACATCGGCAGCAGATCTTGATGGTCCTGGTGAATCCCACGGTGACTTTGGAGTGGAAGGCGCCATACTGATCGCCGCGCCAGCACA
TGAGCTAGCGGCAGGAAAACCAGCAGCCGCTCACCTTGCGCAGCAGCGTCNGGTGATATGCCTGGCGCCCTTAATCTCGTGAACCAGTTGGATTGGGTCAAC
TGGCAGCCTTGGGTCTCCGGTGGTGCCGANGTGTANATAAGCTCCCGGGTCCGTCAACGTANTGCGCAGGCGGCGGTTACTCGGCGGGTCAACGAGCCCCGC
TCGTGAGCNATCAGCCTTTGGACCGAACGGGATTCATACTCCGCAGGCGGCCCTCCGAAATCGGCACATGTCCTTTGATCGTTCGCAACAN Clone Rv69
::::::::::::Rv69T7D3.seq::::::::::::
GGCCATGTCACATCGGTGGTACAGGTAAACCGCGCCGTGTGCGCGGTCTCGGAGATCAGAACGTGGTCGCAGTTGAACCGCGGGCTTTCAGCCAGTCGCGAT
AATCGGCGGAAGTCGGCGCCTGCCGCCCCAACTAGCGCGACTCGCCACCTAGCACACCGATGGCGAAGGCCATGTNTCCGGCCACGCCGCCGCGGTGCATCA
CCAAGTCATCGACTAGGAAGCTAAGCGACANCTTGTGCAGGTGTTCGGGCAGTAGCTGCTCGGAAAATCGGCTGGAAACCGCATCAAATGGTCGGTCCAATC
GAACCGGTTACCCGATCGTCACAAAAATCTCCGTCCT Clone Rv6
::::::::::::Rv6SP6.seq::::::::::::
GGGTCTACAACCACCGGGTCTGACTTCTGGGCTTCCACCGCTCGCGCCGTCGCGACAAACAGCGCGGTCGAACCGACACTCGTTGTGATGTCCCAGCTATCA
CCTCCGGTAGGCACCCAATCGACCCTACCCGGCTATCTCACCCCCGATCTCCAGGCTCCGCCGATCCATGCGCATCCCGGTCCGGATCCC TABLE 3-continued End sequences of the polynucleotide inserts cloned in the named recombinant BAC vectors contained in the I-1945 *M. tuberculosis* H37Rv genomic DNA library.

::::::::::::Rv6T7.seq::::::::::::
CAGGCATGCAAGCTTGTCGTATTCCGTGGCACTGTCAGACATATGCGCCGCTCCTCCTCATCGCTGCGCTCGGCATCGTCGCCGGCGGTCATGGCGTCACCC
TACCCAAGCCGAACGCGAAACGAGAACGTGTTCCATTATTAGGGTGTGAGCACCAATACCAGATTGCTCACCAGGAACTCACGCAGCACCGGGACGGATGTC
AGCCACCACGCCCATCTGGGGTGGTAGCGGGGAAATACGGCTAACGCGGCTCCGGTGCCGGCAGCCCAGCGCAGACCCTCGGCGGCGGACACGGCTAACAAC
GACGACCCATAGTTGTTCTTTGCCGGATGGCCGTGTTTGCTGACATATCGGGCGCGGCGCCGGCGCCGCC Clone Rv70
::::::::::::Rv70SP6D2.seq::::::::::::
NCTACGCTGCTGAATGTTGTGCGCCGGAGGANCTCAAGACCCACGCGGTTGTACGCGGACNTGCGACATGTTCAACCGCCGGA ::::::::::::Rv70T7D3.seq::::::::::::
CTAACCAACAAGCCATGGTGGTTGGCGCCGTCGAGAGGTCGGCGGTCGCCACAACGGGAAGATCGCCTTGAGCGTCGCTCGACCGCCGCCTCGAGTTGGGTC
ATAACGAAGTACTGATGCCGATCATGTCGACGTGTCCGTCGCATCAGCGTGCAGCGGCGACCCCTCGACGAGCCTCGGTGCCGCCGCGGCCAGGGCACCAGC
TGTTTTAGCGCATTGTGCTCCGCCGGTAATAAAGGANGTCGGTCGCCTCCGCTGCTGTGGTTGCGGAATAACATCTTCCCTTCCTGCAACAGGATGAGAATG
GTTTTAATTGCTC Clone Rv71
::::::::::::Rv71SP6.seq::::::::::::
CTAAGCTTTCGGGTCCGCCGCCACTAGTACCGCGTTGCCGGCCCCGCCGACCTAGAATGTTCCGCCCATTGCCGTTTCCTCCCGCCGCCGGGTT ::::::::::::Rv71T7.seq::::::::::::
TCTGGTGCCGGGTGTGCCGACGGGTCCGTCCGCCTCTGCTTCGATGATTCTGTGATGCGACCGGCAACGTCCTCGTTGTTCGGTGTCTATGTGGTCCGTCTC
TCCTTGTTCCGCATACGATT Clone Rv72
::::::::::::Rv72SP6D2.seq::::::::::::
GCGATCGNTNACCACAAGGGCGCAACCGTTCGCGCGTCGACTGAACGTGCTGCCGCCTGGAGAACTGGCGCTGCTGCCACCTGGTCGGCGCATCGGCACTTC
GAGGACTGGATTTCGACGCGTGGCCCGACCTGANGTNGGCGGTGGACNNGTGTGCACCCGGTTGATTCCTCGGCCTTGCCGGGATGCCACCTGCGCCTGGTG
GTCGAT ::::::::::::Rv72T7D3.seq::::::::::::
CGTGACCGGACGGGGTGCCGCGCGAACCGGTCTTGGCCAATTGCCGGGGACTGGGGCTGGAGTATAAAGCGGGCCTGTTGCCGGAAGATAAAGTCAAAGCGG
TGACCGAGCTGAATCAACATGCGCCGCTGGCGATGGTCGGTGACGGTATTAACGACCGCCAGCGATGAAAGCTGCCGCCATCGGGATTGCAATGGGTAGCGG
CACAGACTGGCGCTGGAAACCGCCGACGCACATTAACCATAACCACCTGCGCGGCTGGTGCAAATGATTGAACTGGCACGNCCACTCACGCCAATATCCGCC
AGAACATCACTATTGCGCTGGG Clone Rv73
::::::::::::Rv73SP6.seq::::::::::::
ATACTCAAGCTTCTTACCCANAGCATGAACCCCGCCGTCCAATGCCGCCACCGTGGTGCTGTCGGCCGGCCGGGTGCGGGCACAATCGCCGAGTTCGGCGAA
CAGATCCTCGAAGGTCTTCACGGCCAGCGATTGTTGCACGTGTCAGCCAGCCAAGTCACGGTGGTTTGACGCCACACGTTCGCCACCGCCGCGCCGCGCATT
AGGGCATCCTAATATAGGTTAGGCTACCCTANTTATTCCTGTGGTCNAAGGAGGCAGCCGAACGTGACCTTCCCGATGTGGTTCGCAGTTCCGCCGGAAGTG
CCGTCAGCATGGCTGTCCACCGGCATGGGCCCCGGTCCGCTGCTGGCCGCGGCCAGGGCGTGGCACGCGCTGGCCGCGCAATACACCGAAATTGCAACGGAA
CTCGCAAGCGTGCTCGCTGCGGTGCAGGCAACTCGTGGCAGGGGCCCAGCGCCGACGGTTCGTCNTCCCCATCAACCGTTCCGTATTGGCTAACCACCTGCA
CGGTGGCACCGCACAACGCCGCCACAAACGCGCCCCGGTATAC ::::::::::::Rv73T7.seq::::::::::::
GGCCGAACTTAATCGGTTGTTGGCGGCTGCCGAGTTGGGTCACTCGGGGGGTGTGCACTGGCACATGGTGGGCCGGATTCAACGCAACAAAGCCGGGTCGCT
GGCTCGCTGGGCGCACACCGCTCACTCGGTGGACAGCTCGCGGTTGGTGACCGCGCTGGATCGGGCGGTTGTTGCGGCGCTGGCCGAACACCGTCGTGGCGA
GCGGCTGCGGGTTTACGTCCAGGTCAGCCTCGACGGTGACGGATCCCGGGGCGGCGTCGACAGCACGACGCCCGGCGCCGTAGACCGGATTTGCGCGCAGGT
GCAGGAGTCAGAGGGCCTCGAACTGGTCGGGTTGATGGGCATTCCGCCGCTGGATTGGGACCCGACGAAGCCTTTGACCGGCTGCAATCGGAGCACAACCGG
GTGCGTGCGATGTTCCCGCACGCGATCGGTCTGTCGCGGGCATGTCCAACAACTTGAAATCCCGTCAACATGGTCGAC Clone Rv74
::::::::::::Rv74SP6.seq::::::::::::
GCTTCCCCTGATACTCGACCAGCCCCACTCGGGCCAATACGTGAATGTCCTAGCATTTTTCACCCGTTCACGGGCTAGTCGAGTAGTAGACGATTGATTAGC
CTGAACGTACCTCCGACGGCCAGCTGACGAACGGGTTTGACGGA ::::::::::::Rv74T7D3.seq::::::::::::
TCAGCTGTCTGTAGAAGGGCTGGCGATACTGTGCACTGTCTGATATCGCNNCGTNGTGGGACTATNCAGNCCATNANGATGCGGTTCNGNNNNTGCAGAGNA
TCCTGGNACACATNCGGTTCACGTTAATCANCATCGCGANTTNCTNCGTNTTCGATTANTTCTGCTAACGNNTCTNNNAGTGCCTGCGGGTCGACTCTAGAG Clone Rv75
::::::::::::Rv75SP6D2.seq::::::::::::
NCTCTGCCGGGCNAGAGCGCAGAGTCGGACGGCTTCGTCGATCGTGAAGCGACCNTGCGATGANCAGATATCGNTNACACTGCTCANAAACTTCGGATCATC
GNTGATACACAGGCCAACGGGTAGCGGTTGTCCAACCGCTTCGTCAACGANATGGGATCGTGACGANCCTACGCTCGCAGGATATGTCGCNGACCNGNTCTA
GANAN ::::::::::::Rv75T7D3.seq::::::::::::
CACTTCATGCTCGTGCGTTGGCNTCGATTTGCNCGAGNGGTTAGCTCCTCGAGTGNGTGACGTATCACTCCGGCNGACTANCCGTATCNGCGTCCCGCACCG
GTCAACTGGTCTAGCCACACCGGGGAGAATNCNCGACCGGNGCTATCGACCNATCACGGCTTGTCGNNAAGATAGNCAGCC Clone Rv76
::::::::::::Rv76SP6.seq::::::::::::
ATACTCAAGCTTGCCAACCGCCACCCTGCATCCGGGGGGCGAGCACTGCTCCGCCGACCAGTACGAACCAACCTGCGGTGCCCAGGCCATTGACAATGTGCT
GGTCGGCGCCCGCGAGTTCTAGCACAGCAACGCCGCGGCCACCACAGGGGCG TABLE 3-continued End sequences of the polynucleotide inserts cloned in the named recombinant
BAC vectors contained in the I-1945 M. tuberculosis H37Rv genomic DNA library.

::::::::::::::Rv76T7.seq::::::::::::::
CGGTCGGTGTGCTTGGCGGCGTCGGTATCAACACCGCCCACGAAATGGGGCACAAGAAGGATTCGCTGGAGCGGTGGCTGTCCAAGATCACCCTCGCCCAGA
CCTGCTACGGGCACTTCTACATCGAGCACAACCGTGGCCATCACGTCCGGGTGTCCACACCGGAAGACCCGGCGTCGGCGCGGTTCGGCAAAACTTTGTGGG
ATTTCCCGCCCCCCC Clone Rv77
::::::::::::::Rv77SP6.seq::::::::::::::
AATACTCAAGCTTCGCGGAGGTGGTGGGGCAGGAGCACGTCACCGCGCCGCTGTCGGTGGCGCTGGATGCCGGCCGGATCAACCACGCGTACCTGTTCTCTG
GGCCGCGTGGCTGCGGAAAGACGTCGTCAGCGCGTATCCTGGCGCGGTCGTTGAACTGTGCGCAGGGCCCTACCGCCAACCCGTGCGGGGTCTGCGAATCCT
GCGTTTCGTTGGCGCCCAACGCCCCCGGCAGCATCGACGTGGTAGAGCTGGATGCCGCCAGCCACGGCGGCGTGGAGCAACCCCGCGAGCTGCGGGACCGCC
C ::::::::::::::Rv77T7.seq::::::::::::::
GATGGCACTCACGCTGGACAAGACCTTCACAAAATCTGAAATCCTGACCCGATACTTGAACCTGGTCTCGTTCGGCAATAACTCGTTCGGCGTGCAGGACGC
GGCGCAAACGTACTTCGGCATCAACGCGTCCGACCTGAAATTGGCAGCAAACCGGCGCTGCTGGGCCGGGCATGGTGCAATCCGAACAAGCACGCTCAACCC
GTACACCAACCCCGAAGGGCCGCTGGCCCGGCGGAACCTTGTCCTCCA Clone Rv78
::::::::::::::Rv78SP6.seq::::::::::::::
AACAGCTATGACCATGATTACGCCAAGCTATTTAGGTGACACTATAGAATACTCAAGCTTCTGGGCGTCGTGGTGCCCGGCCTGCCGGTGCAGGAACTGGAT
TTTACTGCCATCTCTCGCGACCCTGAGGTGGTCCAGGCTTACAACACCGACCCACTCGTGCACCACGGACGGGTTCCGGCCGGGATTGGCCGCGCGCTGCTG
CANGTGGGCGAGACCATGCCGCGGCGANCACCGGCATTGACCGCGCCGCTGCTAGTGCTGCACGGCACCGATGACCGGCTGATCCCCATCGAAGGCAGCCGT
CGCCTGGTCNAATGTNTNGGATCNGCCGACGTGCANCTGAANGANTATCCCCGGCTGTNCCACNAGGTGTTCAACGAACCGGANCGCAACCAAGTG ::::::::::::::Rv78T7.seq::::::::::::::
CAAGGCATACGCCAAGACCCAAGGGATCGCAGTCACCTCCGTCAACGGCCTGGTCGCCGGCCACGGGTCCGTGCAGGAGACGTGGCTGGCCATGCAAAGCGC
CGCCGCCTTATCAGGAACGCCCCGGCTTGTCGGCTTTTCCTGCATCGACACATTTCCGGAGGTGTTGTGGTTGGCGCANCGCGCGAGACAGGCCTGGGATGG
CGTGCGCATCGTCATCGGGAATGCGATGGCAACACTGAACTACGAGCGCATCCTGCGCCAGCATGACTGTTTCGACTACGTCGTCGTTGGCGACGGGGANGT
AGCGTTCACCAAGCTGGCCTTGGCCCTGGCGAATGACCTGCGGTTGACGACTCCCGGGACTAACCCGCCGTANTGAGCAAGGACAGATTCTGCGCACACCCT
CCTCGCTGGTCGACCTTGACA Clone Rv79
::::::::::::::Rv79SP6.seq::::::::::::::
AACAGCTATGACCATGATTACGCCAAGCTATTTAGGTGACACTATAGAATACTCAAGCTTGCCGGTGATCTGGGTGGCCAACTCGGCGGGCACCATCTCCAT
CACGACNGCAAACGCTCCGGCTTCGGCGACAGCGATCGCGTCTGCGATNGTTTGTTCGGCGGCGTCTCCGCGGCCCTGCACCCGGAAGCCGCCCAAGGTGTT
GACNCTTTGCGGGGTGAAGCCGATGTGTGCCATCACCGGGATNCCCGCCGCGGTCAGACANGCGATTTGCTCGGCCACCCGCTCACCGCCCTCGANCTTGAC
NGCATGTGCGCCGCCGTCCTTGAAGAAACCGGTGGCGGNGGCAACCC ::::::::::::::Rv79T7.seq::::::::::::::
CGTTGAGATCCAGCTGCGCACTGTGCAGCGCCTCGGTGGTCTGCTCGGCCTGCCGGGATAACTCGTTGAGCTTGGCCAGCGCGTCGTCGGCCGGATCAGCCA
GCACATTCGCGGCCAGGACGCCGGAGGAGACGGTGAAGCTCGCAAAGAAACCTATGGCGGACCGCATGATTACACGCGCGATCAACCACCTCTGGTCGAGCC
TCAAAATTTGCTTCCTTAAACGGGCCATCGACGGATGACGTCGAGCTGGTTTAGGTCTCAAACAGGTTACGAAACGATCTCGGAATTGTCCAAAAGGGGAAG
TTAAGAAAATGGATAGATTTCTACCATTTCGCTGTGGACGATCGTACTTCTGCTATAGGGCTCCAGGGGCATCGACACGCAACGACCTTACGCGACACCGGA
TCCGCGCTGGCGGCGGAACGGCACCANGCGCAACCGAAGGGCCAATCCGACATCGG Clone Rv7
::::::::::::::Rv7SP6.seq::::::::::::::
ATACTCAAGCTTATCTAGGCGCCAGCTTGATTGGTCTGGTTGCATTGGCCAGCTGCGCGAGCCTGGCTCACTTCAACTACAACAACCGCAAACAATTGCCGC
CTTCGGATCCGAGTTCGGTTGGGTACGCGGCAATGGANCACCATTTCTCGGTGAATCAGACTATTCCTGAGTACTTGATCATCCACTCTGCACACGACCTGC
GAACCCCGCGCGGCCTTGCCGACCTGGAGCAGCTGGCGCAACGTGTGAGCCANATCCCAGGCGTTGCCATGGTTCGCGGTGTGACCCGGCCAAACGGGGAAA
CCCTTGAACAGGCCCGGGCGACATACCAAGCCGGCCAAGTTGGCAACCGGCTGGGCGGCGCGTCGCGAATGATCGATGAGCGCACCGGCGACCTGAATCGGC
TGGCATCGGGTGCCAACCTGTTGGCCGACAATCTCGGTGACTTCGCGGTCAAGTCAGCCGGGCCGTTGCGGGTGTCCGCAGCCTTGTCCAGCCCCTCGCTTA
CTCCA ::::::::::::::Rv7T7.seq::::::::::::::
CAGGCATGCAAGCTTTTTGAGCGTCGCGCGGGGCAGCTTCGCCGGCAATTCTACTAGCGAGAAGTCTGGCCCGATACGGATCTGACCGAAGTCGCTGCGGTG
CAGCCCACCCTCATTGGCGATGGCGCCGACGATGGCGCCTGGACCGATCTTGTGCCGCTTGCCGACGGCGACGCGGTAGGTGGTCAAGTCCGGTCTACGCTT
GGGCCTTTGCGGACGGTCCCGACGCTGGTCGCGGTTGCGCCGCGAAAGCGGCGGGTCGGGTGCCATCAGGAATGCCTCACCGCCGCGGCACTGCACGGCCAG
TGCCCGCGGCGATTCAGCCATCGGGACATCATGCTCGCTTCATACTCCTCGACCAGTCGGCGGAACAGCTCGATTCCCGGAACGCCCACGCATGGTG Clone Rv80
::::::::::::::Rv80SP6.seq::::::::::::::
AACAGCTATGACCATGATTACGCCAAGCTATTTAGGTGACACTATAGAATACTCAAGCTTGTAGAAAAAGATCGGTGAGCGCATCGATTCGCTCCGCCGGGT
TTGCCGCTGCGGCGGCGGAGCTGCCGTGACCGTCTATTTGGGTGATCAGATACTGGGCTAGTTCGGTCGGGGTGGGGTGATCGAAGATCGCGGTGGCCGGCA
GCGTTACTGCGGTGACAGCTGTTAAGCGGTTACGTATCTCCACGGCACTCAAGGAATTAAATCCCGAATCGGCAAACGCCTGGCCAGCGTCNAGTCCGGCAG
CGCCGTCNCGCCCCAGCACCGCTGCGGCATGCTCACATACCACCTCGATCGCTGCGGCGANTTGCTCGTCNGCCGACCGACCGGCCANCCGGGCGGCAAACC
CNGAAGACCCAAGAATTCATCACCACCATCGCTAGC ::::::::::::::Rv80T7.seq::::::::::::::
CCTTCTTGACACCCACCTCGCCATCGACCTTGAGCACTCCGTCGTAGTTGGTGAACATGTGACCGGCGATCGGGCGGGTGAACGCGTACTGGGTGTCGGTGT
CGACGTTCATCTTCACCACGCCGTAGCGCAGCGCCTCCTCGATCTCCGACTTAAGCGAACCCGAGCCGCCGTGGAACACGAAATCNAACGGCTTGGCGTCNG
CCGGCAGTCCGAGCTTGGCCGCCGCCACCTGTTGCCCTTGCGCAAGGATGTCNGGGCGAANCTTGACGTTGCCGGGCTTGTANACGCCATGCACGTTGCCGA
ACGTCNCGGCCAGCANGTATTTGCCGTGCTCACCGGCGCCCANCGCCTCGATGGTTTTCTCGAAGTCCTCCGGGCTGGTGTACAGCTTCTCGTTGATCTCGT
TCGCCACGCCGTCCTCTTCGCCGCCGACG TABLE 3-continued End sequences of the polynucleotide inserts cloned in the named recombinant BAC vectors contained in the I-1945 *M. tuberculosis* H37Rv genomic DNA library.

Clone Rv81
:::::::::::::Rv81SP6.seq:::::::::::::
AACAGCTATGACCATGATTACGCCAAGCTATTTAGGTGACACTATAGAATACTCAAGCTTGGAAAGGAGATCCCCGGGAACCTGGTGGCAACCCCGCCATTG
GGGTTGTTGGGATTGCCGATCAGCGTGAANGAAAGCTCGTCTGGAGACAGCGGGTCGGCCGAAGCCGCAAGATTGGCCATCACTAGTGACGANATCGTGGCG
CTCTGCGAGTANCCNAAGACAGTGACGTTGTTNCCGGCGGCAATTTGCTGCCGAATCGCACTTTCGAGAATGACNGCACCCTGCGCCACCGANGAATCNAAA
GTGAGGTTCTTGATCACGACCACCGGGTNGAGCCCTTGGGGCGTGAAGANCGCCTGCGCNATAACACCCGGGACGCTGCCACTCATGTNCAGCGCGTTCGCG
ANCTCNACATATCT :::::::::::::Rv81T7.seq:::::::::::::
TCCTGGTGATCGANGGCCGCGGTTCCGGCCGAAAATCCGGTTCGGGTTCGGGTCGCGGTTCCAACTTGANCGCGGTCCGCAGCTGATTCACCGTGGCAACGC
CGGCCAACTGCGCATAATGCGCATCCGAACCCTCACCCGCCCGCCCCGCGATCACCCCAACCTGATCCAACGACAACCGCCCCTCCCGCATACCCCGGGCGC
AGCGCGGAAACTCCGGCAACCGCCGCGCCACCGTGGCGATCGTGTGGGCGTTGCCTGACGAACANCCCATCTTCCAGGCCACCAACCCCGCCACCGACCGCG
CCCCCGTCACACCCCACAACCCGTCGCGATCCAGCTCAGCCACGATCTCCACAATGCGCCCATCAATCGCATTGCGCTGAACGGGCAACTCCGCCAACTCCT
CCAA Clone Rv82
:::::::::::::Rv82SP6.seq:::::::::::::
AACAGCTATGACCATGATTACGCCAAGCTATTTAGGTGACACTATAGAATACTCAAGATCTGGTACCCATCCGTGATACATTGAGGCTGTTCCCTGGGGGTC
GTTACCTTCCACGAGCAAAACACGTAGCCCCTTCAGAGCCAGATCCTGAGCAAGATGAACAGAAACTGAGGTTTGTAAACGCCACCTTTTATGGGCAGCAAC
CCCGATCACCGGTGGAAATACGTCTTCAGCACGTCGCAATCGCGTACCAAACACATCACGCATATGATTAATTTGTTCAATTGTATAACCAACACGTTGCTC
AACCCGTCCTCGAATTTCCATATCCGGGTGCGGTAGTCGCCCTGCTTTCTCGGCATCTCTGATAGCCTGAGAAGAAACCCCAACTAAATCCGCTGCTTCACC
TATTCTCCAGCGCCGGGTTATTTTCCTCGCTTCCGGGCTGTCATCATTAAACTGTGCAA Clone Rv83
:::::::::::::Rv83SP6.seq:::::::::::::
AACAGCTATGACCATGATTACGCCAAGCTATTTAGGTGACACTATAGAATACTCAAGCTTANCGCCACCTCCCGGGCGGAACTCCACGGCGTGGATNAAGGT
ACCGGCCGGGATGTTGCGCAATGGCAGGTTGTTGCCCGGCTTGANGTCCGCGTTAGCGCCGGATTCCACCACATCCCCTTGCGAAANTCCGTTGGGTNCNAT
GATGTNNCGCTTCTCCCCNTCNANATAATGGANCAACGCNATCCGTGCGGTACGGTTCGGGTCNTACTCCATGTNCGCGACCTTGGCGTTGANACCATCTTT
GTCATTGCGGCGAAAGTCNATCATCCGGTNAGCNCGCNTATGANCGCCGCCTTTGTGCCGGGTGGTAATCCGGCCATGCGCNTTGCGTCCACCGCGAACGTG
CAACGGGGGCNCCAACGANTTCTCCNGGGTTGAACCGGTNATCT :::::::::::::Rv83T7.seq:::::::::::::
TGTGTGTCGGTGGTAACCCATCTGAGCAGTGTGCCAAACCGGGGCAGCCAGCTCCCAATTGACGTGAGCCCGCTCACTTGCTGGGTAAGCGTCG Clone Rv84
:::::::::::::Rv84SP6.seq:::::::::::::
AACAGCTATGACCATGATTACGCCAAGCTATTTAGGTGACACTATANAATACTCAAGCTTGCGGGTNATNGCCTTGGTCAACGGCACCGTGATCGGATCNGG
GTCTACCGCACACATNGACTGGAGCTTCGGCGAANTCATCGCCTATGCCTCGCGGGGGGTGACGCTGANCCCNGGTGACNTGTTCNGCTCNGGCACGGTGCC
CACCTGCACGCTCNTCNAACACCTCANGCCACCGGAATCATTCCCNGGCTGGCTGCACGANAGCGANNTTGTCNCCCTCCAAGTCTAAAGGCTGGGCGANAN
AAGCANAACGTCCCGACNAACGGCACTCCTTTTCCNTTTGCTCTTC :::::::::::::Rv84T7.seq:::::::::::::
GAAATCATTGATGGTTTGAGTCACCAGGCCGATCAAGCCTTCGCCGAGCCAAATTCCAATCAAGAGGCCCAAGCCCGTACCAATCAGCCCGGCAACGAGGGA
TTCCGTCATTATCAGCCAAAATAACTGCTCTCGGGTTACACCCAAACAGCGCAATATGGCGAAAAACGGTCGCCGTTGCACGACATTAAATGTCACGGTATT
GTAGATTAAAAAGATACCCACCAACAANGCAATCAAACTGAGAGCGGTTAAATTGACCGTAAAAGCGTCCGTCATCTGTTTGACNGTGTCCCGTTGGGTATC
CGACGTTTCCATACGCACACCGGCCGGCAGTCTTTGTTGGATGCGTNTTGCAATGGCCTCATCTTTGATGATCAAATCGATGTNGCTCAGTCTTCCGGGCAT
ATGGAACAACTCTTGGGCCGTGGAAATATCAGCAATGATA Clone Rv85
:::::::::::::Rv85SP6.seq:::::::::::::
CTTTCGCCCAGGCCGGCGCGGATGTCCTCATCGCTTCACGAACATCATCCGAGCTTGACGCTGTCGCCGAACAGATCCGCGCTGCCGGCCGCCGCGCCCACA
CCGTTGCCGCCGATCTGGCCCATCCCGAGGTGACCGCGCAGCTGGCTGGTCAGGCCGTCGGAGCTTTCGGGAAGCTCGACATCGTCGTCAACAACGTTGGCG
GCACCATGCCCAACACGCTGCTAAGCACCTCGACCAANGACCTCGCGGACGCCTTCGCCTTCAACGTGGGCACCGCCCACGCGCTGACCGTCGCGGCGGTGC
CGTTGATGCTGGAACACTCCGGCGGCGGCAGCGTGATCAACATCAGCTCCACCATGGGCCGGCTGGCGGCGCGGGGTTTC :::::::::::::Rv85T7.seq:::::::::::::
TGTGGGCTCCGATCCGGCGCGCATGGCATCGACGGCGACGCCGATCGATGACGGCCAGGCTTACGAGCTTGAGGGTGTGAAGTTGTGGACCACCAACGGTGT
GGTAGCGGACCTGCTAGTGGTTATGGCGCGGGTACCGCGCAGTGAAGGGCNCCGAGGGGGAATCANCGCCTTTGTCGTCGAGGCTGATTCGCCCGGGATCAC
CGTGGAGCGGCGCAACAAGTTCATGGGACTGCGTGGCATCGAAAACGGCGTGACCCGGCTTCNTCGCGTCAGGGTGCCCAAAGACAACTTGATCGCANGGAA
GCGACGGTCTGAAGATCGCGCTGACCACACTCAACGCCGGACGGCTGTCCCTACCGGCGATCCAACCGGAGT Clone Rv86
:::::::::::::Rv86SP6.seq:::::::::::::
GAGCTGGCCGAGCTGGACCGGTTCACCGCGGAACTACCGTTCTCGCTCGACGACTTTCAGCAGCGGGCTTGCAGCGCGCTGGAACGCGGCCACGGTGTGCTG
GTGTGCGCGCCGACCGGCGCTGGCAAGACAGTGGTCGGCGAGTTCGCCGTGCACCTGGCGCTGGCGGCCGGCAGTAAATGTTTCTACACCACGCCGCTGAAA
GCCCTGAGCAACCAAAAGCACACCGATCTCACAGCACGCTACGGCCGTGACCAGATCTGGCTGCTGACCGGTGACCTGTCNGTCAACGGCAACCGCCGGTGG
TGGTGATGACCACCGAAATGCTGCGCAACATGCTCTAC :::::::::::::Rv86T7.seq:::::::::::::
GATCTCTGGATCGGCGGGGCTCTCCGGGCCGGCCTCGGCGACCTCAGCGGGCCGCGCCTTCCGGCCGAACCATTCCCTAGCCATAGATGACCGCACCTCGAT
GCACGTTTGGCGGCAACGCGGCAAGGCGTCNGTCGGGCCCAGCCGCGGCAATGCGGGTACCCGGGAGCGCGGGTCNGTANACCANCGCTGGACTGCGTCGCG
CGGTGCGTCNACNTCAAAGTCCCCGGCGTCCCATATCGCGTATGACGCGGGCGCGCCCGGCACCANGGGTGCCGATCCGGCCGTCTCGAACACCACCGGCCC
GCCAGCCGCCGCGGGTCCGGCAGCNAACCCGCCCGCGCCGATACCCGCTGCCCGCGTGCGTGATTGACCGCCGCGCGCACGCTGGCCANGGATCAAAGCCCG
TG TABLE 3-continued End sequences of the polynucleotide inserts cloned in the named recombinant BAC vectors contained in the I-1945 *M. tuberculosis* H37Rv genomic DNA library.

Clone Rv87
::::::::::::Rv87SP6.seq::::::::::::
GGACGCGTAGCCCGCCAGGCCGGTCAGGGTGCCCTTCCAGTCCACGCCGCTGTGGTCGGCGAACCGCTTATCTTCAATCGAGACGATCGCCAGCTTCATCGT
GTTGGCGATCTTGTCCGAGGGCACCTCGAACCGGCGCTGCGAGTNCAGCCACGCGATCGTGTTGCCCTTCGCGTCGACCATCGTCGATACCGCAGGCACTTG
CCCCTCGAGCAGCTGGGCCGAGCCGTTGGCAACGACCTCAGANGCACGATTGGACATCAGCCCTAGCCCGCCTGCGAACGGGAACGTCAGCGCAGTGGCGAC
GACACTGGCCAACAGACAGCACCCAGCCAGCTTCAGAACGGTGATCGCGGCCGGGAAGCGCTCGGGCATGCGTNCTACAGTAGCGACCTCCTGTCACTCCAC
GTGCCGCTCGGTCCAATAGAATCTTTCCGCGGGCGGGTGAATCTCTGCNGGATCGGGGCNGGCGC ::::::::::::Rv87T7.seq::::::::::::
GCTCGTTGCCGGCGGCGATCTCGTCGAGCTCGTCTTCCATCGCCGCGGTGAAGTCGTAGTCGACGAGCCGACCGAAATGCTGCTCGAGCAGACCGGTTACCG
CGAACGCCACCCATGACGGCACCAGTGCACTGCCCTTCTTGTGCACGTNGCCGCGATCCTGGATGGTCTTGATGATCGACGANTAGGTCGACGGGCGGCCGA
TGCCCAGCTCCTCGAGCGCTTTGACCAGCGACGCCTCNGTGTNNCGGGCCGGCGGGTTGGTGGCATGGCCGTCTGGGGTCAACTCGACNATGTCCAACCGTT
GACCCGGGGTCAGATGGGGCAGTCGCCGCTCGGCATCGTCAGCCTCGCCGC Clone Rv88
::::::::::::Rv88SP6.seq::::::::::::
GTCTTTCGATGGCTGCTTCTTCGGCGCTGACGCTGGCGATCTATCACCCCCAGCAGTTCGTCTACGCGGGAGCGATGTCGGGCCTGTTGGACCCCTCCCAGG
CGATGGGTCCCACCCTGATCGGCCTGGCGATGGGTGACGCTGGCGGCTACAAGGCCTCCGACATGTGGGGCCCGAAGGAGGACCCGGCGTGGCAGCGCAACG
ACCCGCTGTTGAACGTCNGGAANCTGATCGCCAACNACACCCNCGTCTGGGTGTACTGCGGCAACNGCAAGCCGTCGGATCTGGGTGGCAACAACCTGCCGG
CCAAGTTCCTCGAGGGCTTCGTGCGGACCATCAACATCAAGTTCCAAGACGCCTACAACGCCNGTGGCGGCCACAACCGCGTGTTCGACTTCCCGG ::::::::::::Rv88T7.seq::::::::::::
GCCAGGTCGAGGTCCCATGCGCGTGGGCCATTGATGCTGATCGCCAGGACGTCAAANATTTGGTCCGGCGTCAGCTGGGCGAAAAACGTGGGCCCCAGGACT
TGCCCGGAGCTGCCCGGGTTCCCGTCGCGCAGCTCGGCGGCCCCGGTCAGAAANAAATTGCGCCAGGTCGCACACTCCGCGCCGTANGCCAGCTGCTCCAGG
GTGTCGGCATAGAGCCCGCGGGCCGCAGCGTGCTCGCTGTCGGCGAACACCGCATGGTCGAGAAGCGTTGCCGCCCAACGGAAATCACCTGCGTCNAANGCT
TCGCGGGCCAACTCCAGCACTCGGTCGATG Clone Rv89
::::::::::::Rv89SP6.seq::::::::::::
NAAACGTTCCGGCTTNGGTGCCGGGCGCTTATTTGCGTCTCTGGGATCACNCTCAGTCGCCGGCGGCTGCCGTTGGGCTATNANTTGCACCGANCCGGAAAA
TCCGCACNANAACTGCNAGTAGCGGCCTGCAGAANTGCATCCTCGGCGAANCNGACTACCGGTGGACANCNACAAGCGCCGCCGAACAACGCACTGGCCCGA
GGGATNGGCGTCTATCGGCCCCGCCCGTCGAACTNGGAACAGACNGTGCGGTTCTACCGTGATCTGGTGGGAATGCTCNACCANACCTTCCCNANNGCTACG
GAACNACGGCGCGATATTCNGCCNTCCCANCTCGAGCCTGACNCTNGATATCGTCGANNCTCACCATCNCGATCNGCTGTGCCGGTNTTGCTCGGACTN ::::::::::::Rv89T7.seq::::::::::::
CGAACGACGAACNCCNCAAGCCATGGTGGTTGGCGCCGTCAAAAGGTCCGCGGTCGCCACTACTGGAAAATCGCCTTGAGCGTCNCTCGACCNCCGCCTCGA
GTTGGGTCNTAACGAAATACCTGATGCCGATCANGTCNACGTCTCCGTCGCNNCAACGTGCAGCGGCGACCCACTCTACNANGTCTCGGTNCCGCCNCGGCC
AGNGCACCACCAGTGACNAATCCNTGCGCCNTCGGGCCNAGCANTCCCGGTGCNACCGNGGTGGGTCCGGCGATGGTNGGGTGTNCTCNNTACNGGAACGCC
AGCGCNATCANCATCGGCANACTCNCGTCGATGTGCCGCGGCGCAACCATCCCCCACAATGATCNGGTGCGTCTGATCAGGCN Clone Rv8
::::::::::::Rv8SP6D.seq::::::::::::
TTAGGCGTGACGGCCACCGGGGCCACTCCGCACAATCTGTACCCGACCAAGATCTACACCATCGAATACGACGGCGTCGCCGACTTTCCGCGGTACCCGCTC
AACTTTGTGTCGACCCTCAACGCCATTGCCGGC ::::::::::::Rv8T7D4.seq::::::::::::
CGTCACCCCGATGCGCCCAGATCGGGGCTTCGCAGATAAAGCACGAACTGGCGGGCAAAACGTCGATCTCGGAGCCGGAAGGGCAATCAGCCGACCGTCGAC
GAACGACACCGGCGAGACCACTTAGGCAGTGACGGCCT Clone Rv90
::::::::::::Rv90SP6.seq::::::::::::
CTTTTCNCGATGTCTCATGATNCCNANGGAGAACNNTGCNANCNCNGCCGCTGACNTNGCNCACCGCTNTGGCNGNGGTGACATTGGTGGTGGTTGCGGGCT
GCNACGCCCGACTCGANGCCGANCCATNTNTTGCGGCCGACCGCNTNTCGTCTCNACCGCANNCCCNATCTCNGCCGCNCCCGGTGGANCTACNGCTNCTTC
GCCATCTCTCGCCNATGGCTCCNGCGNNTCGCNCAACGTNTGGTTTGGTNANCTGCCTACCTGGTCNT ::::::::::::Rv90T7.seq::::::::::::
GCTGCGCCAGTCGTTCGGTGCGGTCATGCCGTTGGACCNACCATCGGAGTTAGTTGCCGAACCGCGGACCACCGCAAGCACCCGGTCCTGGTCGCGCACCGC
GTCGGCCAACCGCTTGAGCACCACCACGCCGCAGCCCTCGCCGCGCACGAATCCATCCGCGTTGGCGTCNAANCTGTNGCATCGGTCGGTCGGTGACAGCGC
CGACCACTTGGACAGCGCGATGGCGGTGAACGGTNANTAGGTGACCTGCCNCCNCGCCCGCCAATGCCCACCTCCGCTTCACNCATGCGAATGGTCTGACAC
GCCNAGTGAATTGCCACCAGCGACAACAAAAATCGGTATCTNCNGCGACGGCGGACACGCNATCCCNACTGATACTCGATCCGCCCCACCGCTTGNANCTCC
GGGTTCCNGTGCTCATGTACCNTCATGTCGGTCTGCGCNCGATATTGACGATCGTGTTTCCCACGANNANAGANCCTCATCACGCCGGTTCGAGTGCCG Clone Rv91
::::::::::::Rv91SP6.seq::::::::::::
CTGTGTGCGGNCGGCGCGATATCGGCCTTTTTACTAACCGAACCCGATGTGGGCTCCGATCCGGCGCGCATGGCATCTACNGCGACGCCGATCGATGACGGC
CAGGCTTACGAGCTTGAGGGTGTGAANTTGTGGACCNCCAACGGTGTGGTAGCGGACCTGCTANTGGTTATGGCGCGGGTACCGCGCAGTGAANGGCACCGA
GGGGGAATCANCGCCTTTGTCGTCTANGCTGATTCTCCCGGGATCACCNTGGAGCGCNCCNCNANTTCATGGGACTGCGTGGCATCCAANACGGCGTGACCG
GCTTCATCCNTCNGGGTGCCCAAAGACAACTTGATCNGCNNGGAAGCGACGTCTGAANATCGCGCTGATCNCACTCAACGCCGGACGCTGTCCTACCGGCGA
TCGCACCGGANTTGCCAANCCGCGCTNANNATNCGCGNGAATGNCCGTCCACNANTGCATGG ::::::::::::Rv91T7.seq::::::::::::
TGGGGTGCCGGGCGCCGAGTTGCGTCCCTGGGATCACGCAGAGTCGCCGGCGGCTGCCGTTGGGCTATGAATTGCACCGAGCCGGAAAATCCGCANCAAAAC
TGCGAGTAGCGGCCTGCAGAAGTGCANCCTCGGCGAAACGGAGTACGGTGGACAACGAAAAGCGCCGCCGAACNACGCACTGGCCCGAGGGATTGGCGTCAA
TCGGCCCCGCCCGTCGAACTTGGAAGANACANTGCGGTTCTACCGTGATCTGGTGGGAATGCTCCAACNNACCTTCNCCGAAAGCTACGGAAGCNACGGCGC
GATNTTCGGCCTTCCCAGCTCGACCTGACGCTGGAAATCG TABLE 3-continued End sequences of the polynucleotide inserts cloned in the named recombinant BAC vectors contained in the I-1945 *M. tuberculosis* H37Rv genomic DNA library.

Clone Rv92
:::::::::::::Rv92SP6.seq:::::::::::::
NGGCNGGGAAGTTAATGCCCTACTGGTTCNATGCTCNCACNTCNCCNGTGACNNCCTGCNCCGACCCGCCGAGGTCCTGNCCGTNACCACCGANCNGGCGAT
CCGGGACTCTNGTACGCATCCAACANNGANCAACGTGCACGGGCGGAGTNGTNCCGCCACTTCGNCNATGACGGGGTCGATCCNTTCGACGTCCGTCGCCGC
GTCGGTCGAGTGGCGGTCACNCTCCNNGTACTCGACCNCACNGACGAGAGGACTCGANCCCATCTACGTGTGGACGAAACANATCTTCTGTCCNACGACTAC
ACCACCACCCAGGCCATCGCCGNCGCCCGCGANGCCCCTTCGACGCCNTACTGGTCCNGNGGNGGCGCTCTCCGGTTGTCTNNCNCNTGNCGTGTTCCTTCA
CNCACTGCCCNACATCGANCCCGAGCNATNCNANGTCCGTCAATC :::::::::::::Rv92T7.seq:::::::::::::
GGACACTGTTCGCGTGCCCCTCGTCAAAGCCGGAGTGGTCGTGCTGCGCCGGACCCGACCCGACCTTCAGCGGGGGTTCACAGCTCCGTGGGTGCCGTTACT
TCCGATCGCCGCAGTGTGCGCGTGCCTGTGGCTGATGCTGAACCTCACCGCGTTGACTTGGATCCGGTTCGGGATCTGGCTGGTGGCCGGAACCGCGATTTA
TGTCNGCTACGGGCGCCGGCACTCGGCGCATGGCCTTCGGCAAGCNCNANANAACGCGACCCGGAGGTGTTGAACTAGCTTCGCCGCGTATTTACAAATTGC
NTTATATGTCTACACATAAGACGCAAACTGCTCTATTGTCAANTCCCANCGTGGTGTGGCNCATGAAGATGTTTGG Clone Rv94
:::::::::::::Rv94SP6.seq:::::::::::::
TCCTTCTCGGTATCGGTTTGGGCTGTCACCANCAGTTGGTAGTTCTTCACGTNCTGTTGTTCGAGCGTCNAGCCGTCGCGCGTGTCNANGTCNCCGGACGCG
TATCCCGCCAGGCCGGTCANGGTGCCCTTCCANTCCACGCCGCTGTGGTCGGCGAACGCTNATCTTCAATCGAGACCATCGCCAGCTTCATCNTGTTGGCGA
TCTTGTCNNACGGCACCTCNAACCGGCGCTNCTAGTACNCCACNCNATCNTGTTNCCTTCNCGTCNACATCCTCGATNCCNCNTGCACTTTCCCTCGANCNC
CTGGGCCGAGCCGTTGGCANTNACCTCNGAGCCCCATTGGACATCANCCCANCCCGCCTGCGAACGGGAACGTCAGCNCNCTGGCGACAACCTGGCCAACAN :::::::::::::Rv94T7.seq:::::::::::::
CACNCCGTGATCGCNAGCCCCNGTAGAAATNGTTGAGCCAGTTGGTGCGGCGCTCGTTGCCGGCGGTNATCTCGTCGAGCTCNTCTTCCATCGCCGCGGTGA
AGTCGTACTCGACNAGCCGACCNAAATGCTGCTCNAGCAGACCGGTTACCNNNAACNCCNCCTCNTGACNGCACCAGTGCNCTGCCCTTCTTGTGCACGTAC
CCGCNATCCTGGATGGTCTTGATGATCNACTANTNTGTCGACGGGCGGCCGATGCCCATCTCCTCNAGCGCTTTGACCAGCGACNCCTCGGTGTATCGGGCC
GGCGGGTTNGTGGCATGGCCGTCTGGGGTCANCTCNACNATNTTCANCCGTTGACCCGGGGTCACA Clone Rv95
:::::::::::::Rv95SP6.seq:::::::::::::
TGGCCTTCTTGNCANGGGCNNACATNNGCTATNGCGAGCGTGTAACCGATCATCNTCCNGGCGACTGTGGCCTGANCGGCAAGGGTNGCCTNATTCNTCCTC
CTGNGGCATGGTTNCCACACGGAATGNCGGTAAGTCTGGTCGGCAACCTGGCCCGCTGCGGGTTGGGTTCGGATTCGCTCGGCTANTAAGGTGCTCGCCTGG
TGTNACNACTAATCNCNATATACNCTTANCGGGAGTNGNCGTCCCGATCCTNGCCCTGCCGCNGGCGATCNCGTTCGCANCACCGCCACCGGAACTCNCAAN
GTGCGCTCATCGGGCTCTACGCGCCATCTTCCCCGGATTCTTCGCGGCNGNGTNCCGNGGGACCCCGGACTGTGACNGGCCCAACGGCTCATCATCG :::::::::::::Rv95T7.seq:::::::::::::
CCGGATAGCGGTGTCTGAACTTCGCCCGTTCCCTCCANCGCATTGAGCTTCAGCCCGACCGGCAGGTNNGGAGTCGGCATGCGGTCCTTCGCCCCGACCCCG
CTGGCTAAATANCCACCCCCGAGCGCGGTCACGGTCTTTGCACCGGGACGACGCATACCGGCAGCGCGAACATCNCCGCGGGCTGCAGCNTGAACGTCCAAT
ACCANTCNAACAGTGTCCGCGCGTNAAAACCCGANCCGGCGGTCGCTTCNGTAATCAACGGCTCCTGCGCAACCAGCTGCAAGTCGCCGGTGCCACCGGCGT
TGACGATCTTGATGTCTGCGANCTCGCGCACCAGCTCGACGGCCCGGGCA Clone Rv96
:::::::::::::Rv96SP6.seq:::::::::::::
CCTCCCGACCACATACAGGCAAAGTAATGGCATTACCGCGAGCCATTACTCCTACGCGCGCAATTAACGAATCCACCATCGGGGCAGCTGGTGTCGATAACG
AAGTATCTTCAACCGGTTGAGTATTGAGCGTATGTTTTGGAATAACAGGCGCACGCTTCATTATCTAATCTCCCAGCGTGGTTTAATCAGACGATCGAAAAT
TTCATTGCAGACAGGTTCCCAAATAGAAAGAGCATTTCTCCAGGCACCAGTTGAAGAGCGTTGATCAATGGCCTGTTCAAAAACAGTTCTCATCCGGATCTG
ACCTTTACCAACTTCATCCGTTTCACGTACAACATTTTTTAGAACCATGCTTCCCCAGGCATCCCGAATTTGCTCCTCCATCCACGGGGACTGAGAGCCATT
ACTATTGCTGTATTTGGTAAGCAAAATACGT Clone Rv9
:::::::::::::Rv9SP6.seq:::::::::::::
CTTCACNTCCGTACGGCTCGGGTACGCTTCGGTCNCATTGTGCGAGTGATAGATGACGACCGGGACCTCGTCGGCATCTTCCATAGCCCGCCACACCTTCAG
TTGCTCACCGGAATCCAACCGGTANAAGGTCGGCGANCGCTCNGCATTGGTCATCGGGATATGCCGCTCGGGACGGTCANAGCCCTCGGGTCCGGCCAGCAC
TCCGCAGGCTTCGTCGGGGTGGTCGCGACGCGCATGGGCCACCATCGCATTCACCAGGTCTGCGCGAATCACCAGCACGTANACGGTTCCTTTCCTAAGCAA
CACCGAANTTTCAGGACCCGAATGCTCCGGGAAACATGTCACGGTAGGTCGGTATTCCGGCTACCGGCTGANCATTGAGCACGCCGGCCAGCACCGCACGAA
CCAGGCAATCAGCCGCCGCCGCACCCGACCGCGG :::::::::::::Rv9T7.seq:::::::::::::
CAGGCATGCAAGCTTGATGCCGCCGAAACCGAGCGTGAGCACGCCGCCAGCCACCACGCGCGGGTCGGGCGCCGGGCCCGGGCCGCCAGGCTGCTCCGCTCG
GTGATGGCACGCCACCGCGACACCACCCGGCTGCGCTACGTCGAGCCATACCGGGCGGAGCTACATCGGCTCGGCCGCCCAGTGTTCGGGCCCTCTTTCGAG
GTCGAGGTCGATACCGATTTGCGCATCCGCAGCCGCACCCTGGACGACAGAACCGTGCCCTACGAATTGCTTGTCGGGCGGGGCCAAAGAACAGCTTGGCAT
CCTGGCGCGATTGGCCGGCGCGGCGCTGGTCGCCAAGGAAGACCCGTTCCGGTGCTGAT

TABLE 4

End sequences of the polynucleotide inserts cloned in the named recombinant BAC vectors contained in the I-XXXX *M. bovis* strain Pasteur genomic DNA library.

RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character << - >> denotes an uncertain base residue.

TABLE 4-continued

End sequences of the polynucleotide inserts cloned in the named recombinant BAC vectors contained in the I-XXXX *M. bovis* strain Pasteur genomic DNA library.

Clone X0001
:::::::::::::::X0001SP6.seq:::::::::::::
AAG-
TCGGGTTTCCACACGCGCGGTTTGACCCTAGTCATATGTAATCATGTGTACCATGTGCGGGCGCTTTTCGACGGC
CGCGAACCACCGGA-ATTTCCTGTGATTTCACTGCATGCGTACCATCTGGCACAATTGAGCA-TTGTCT-TCGCGG
TGGTCGG-CGGGTTGCGTGCCGCCTGCTGCGA-ATGCACCA-TAAGCCCGAACCCACCGGCTTGGTGACCACCGC
ACGCTGCGTGTGTGGGGGGTAACCACTCCGCGACCCCAAGGATGGTCATTTCCAATGAACCGGCTGGACTTCGTCC
A-A :::::::::::::X0001T7.seq:::::::::::::
GTCGCGGTTCGATCGACCCGATCTTCACCTCGTAACCTCGATGCTTAGCAGGATCCAGCTTGACCGCGTTTGGCT
CTACCCACTCTTTGAGTGGCGCCGTCGCCTGTGCCCCATCGGTGTTCATGACGAACGCTTCGAAAGACTTCCTCT
TGTGAGCCGGAATGTCTGCGTAAAGAAGTTCCATGTCCGGGAAGTAGACCCGGTCGCCCTCCACGTGGTACTCC
TTCGAGGTCCGCTTCTCGCCGGATCCGATAAACACCGGCCCCAGGCACCGCAGCGTGAGTTCGAACGGCTTCAG
GTAGGTGTTCATGCGGCGGACTCCGGGAGTGCGAGAAATAGCGGTCGCGCGTAGCTGTAGACCGGATGGTTTCC
GCCCAGGCTGACGTCGAAGATGCCTCCTTGGAAGGGGCGCGA Clone X0002
:::::::::::::X0002SP6.seq:::::::::::::
AACTCAAGTTTTTACGGTGATCGCGCATCACCTGGTTCATGAACTGGAAGCAGCGCAGCGCTTCCTTTTCGGCCG
CAACATGAGCCAGCCTCTCGTCGGCGGTCGGGTGCAGGTGCTCGGGCAGCTCGGCCGCGACAGCCGCCTGACC
CTGAAACCAGCTTCCATATCCCGCGAC-
AACGACGCCAGTCCGCTACGTAACCCCTCCGCGACTGTCCATGGACAACAGCGCGTTCTCCACCGACCGGGCCC
GGGTGT :::::::::::::X0002T7.seq:::::::::::::
GTGCAGGTTTCGACAATGTGGTGCCGGTTCGGCGGCTACGTGCCATCGAGACACTGGCGCA-GCTATCGCACCC
GTTATCGGCTGCGAGCAAATCGCGGTATGCGTTCTTGAGCATGAGTCGGCGACCGTCGTCATGGTCGACACCCA
CGACGGAAAGACGCAGATCGCCGTCAAGCATGTGTGCCGCGGATTATCAGGACTGACCTCCTGGCTGACCGGCA
TGTTTGGTCGCGATGCCTGGCGCCCGGCCGGCGTGGTCGTGGTCGGCTCGGATAGCGAGGTCAGCGAATTCTCG
TGGCAGCTCGAAAGGGTCCTGCCGGTGCCGGT Clone X0003
:::::::::::::X0003SP6.seq:::::::::::::
TTCGAGTCATGCGCCCGCCTCGACCACGAA-ATGCACGTCG-GGTTCGATCGACCCGATCTTCACCTCGTAACCTC
GATGCTTAGCAGGATCCAGCTTGACCGCGTTTGGCTCTACCCACTCTTTGAGTGGCGCCGTCGCCTGTGCCCCAT
CGGTGTTCATGACGAACGCTTCGAAAGACTTCCTCTTGTGAGCCGGAATGTCTGCGTAAAGAAGTTCCATGTCC
GGGAAGTAGACCCGGTCGCCCTCCACGTGGTACTCCTTCGAGGTCCGCTTCTC :::::::::::::X0003T7.seq:::::::::::::
GTCATGTGTACCATTTGCGGGCGCTTTTCGACGGCCGCGAAACACCGGAGATTTCCTGTGATTTCACTGCATGCG
TACCGTCTGGCACAATTGAGCAGTTGTCTGTCGCGGTGGTCGGCCGGGTTGCGTGCCGCCTGCTGCGAGATGCA
CCAATAAGCCCGAACCCACCGGCTTGGTGACCACCGCACGCTGCGTGTGGGGGGTAACCACGCCGCGACCCCA
AGGATGGTCATTTCCAATGAACCGGCTGGACTTC-TCAACAA Clone X0004
:::::::::::::X0004T7.seq:::::::::::::
AACAGCGCGGTTGAACTGATAGGTGCGGCCCGGCTCGAGCAGGCCGGGCCATTTGTTCGATGCGGTTACCGAAA
GATCTCTTCGGTGACCTGCCCGCCGCCGGCCAGCTCGGCCCAGTGCCCGGCGTTGGCCGCCGCGGCGACGATCT
TGGCGTCCACGGTGGTCGGGG Clone X0006
:::::::::::::X0006T7.seq:::::::::::::
GCATCTGGGCTGGCGGTGGTTCGCCGCTCCGAAGCCGTCGAACACCATCGCCAGCGCGGCTTCCACATCAACGA
CCATTTCGGCCAGCTTGCGGCGCATCAGCGGCTTGTCGATGAGCGCCCCACCGAATGCCCGCCGCTGCCCGGCG
TA-CACAGCGATTCGACCAGCGCGCGGCGCGCGTTGCCGAGGGCGAACGAAGCGGTGCCCAACCGCAATCTGTT
GGTCAGCTCCATCATGCGGGTGAGTCCCTTGCCG Clone X0007
:::::::::::::X0007SP6.seq:::::::::::::
ATCGGTTTCCAGCAACAGCCGATCGACGGCTTCGCCCA-GGCCGCTCCCGGGCGACCCGACCATTGCTGTCGCC
GCGTAACGCCATCACGGATGACGCGCAGTTCGTCGCTGTCTAGCTCCACCATCGCCTGCACACCGGCGGCCAG-
ACCCATTGGCCGTCGCACTCGTA-
AGCAGGTAATCCTCGTCGACGGACTCGGTAACCACCGCCGCCAGCTCCGCTGCCAGGTCGGCGGGGTTGACACC
GGCGGGCATCGGGATGGACGACGACGCGGTGCTGCTGACGGCGCCTGTC :::::::::::::X0007T7.seq:::::::::::::
AGCGGTTTCCCA-GCGGGATGTGCTGTGAGCGCCGCACCACCAGCGCCGACGCTAAGGATGGAACGCACGGCAT
CTTCTGACGCGTAACCGCGTTGTGATCGCGAGCTGAGGAGACGGTATGGGGGAGGGTTCTCGGAGGCCATCTGG
GATGTTGATGTCTGTCGATCTTGAGCCGGTGCAACTCGTCGGCCCGGACGGTACGCCGACGGCCGAACGCCGCT
ACCACCGTGACCTTCCTGAGGAAACGCTGCGTTGGCTCTACGAGATGATGGTGGTCACCCGCGAGCTGGATACC
GAATTCGTCAATCTGCACG TABLE 4-continued End sequences of the polynucleotide inserts cloned in the named recombinant BAC vectors contained in the I-XXXX *M. bovis* strain Pasteur genomic DNA library.

Clone X0008
::::::::::::::X0008SP6.seq::::::::::::::
CAAGCTTCCACAGGTAGGGATCGAGGAACAGCGCGTTGAACTGATAGGTGCGGCCCGGCTCGAGCAGGCCGGC
CATTTGTTCGATGCGGTTACCGAAAATCTCTTCGGTGACCTGCCCGCCGCCGGCCAGCTCGGCCCAGTGCCCGG
CGTTGGCCGCCGCGGCAACGATCTTGGCGTCCACGGTGGTCGGGGTCATGCCCGCGAGCAGGATCGGCGAGCG
GCCGGTCAGCCGGGTGAACTTCGTCGAAAGCTTGACCCTGCCGTCGGGGAGGCGAACCACGGTCGGTGCGTAN
CTCCACCAAGCCCGGGCAACCTCGGGGGTGGCGCC ::::::::::::::X0008T7.seq::::::::::::::
TGGACCTCATGACAACGCGGCGGCGATTACCCCCGCTACCGCCAGCAGCATGACGGCGGTAGCGAACACCGCC
GGATGCAGCGCAGGTGCGTCGATGTGCTCACGGAATCGCCCCGGCACCGCGATCTCGAGGATCACCAGTGCCAC
CCCCTGCAGCGCGACACCGACGATTCCGTACACCGCCACGCCGATCAGGCCCTGGGCCAGCTGGCGTATATGGC
GGCGATGGTGACGATGGCCAGCGCCACATACATTGTGGCGGCCAGAACCACGGCGTTGGGGCGGCGGTCGATG
AACACTAGGCGACGCAGATCGCCCGGGGTCAACAGGTTGACCATCAGAAAGCCTGCGA Clone X0009
::::::::::::::X0009SP6.seq::::::::::::::
TTTGGTGCGGCCGGCAATCAACTTC-
GCTC-CAGCGGTTTCCCAGGCGGGATGTGCTGTGAGCGCCGCACCACCAGCGCCGACGCTAAGGATGGAACGCA
CGGCATCTTCTGACGCGTAACCGCGTTGTGATCGCGAGCTGAGGAGACGGTATGGGGGAGGGTTCTCGGAGGC
CATCTGGGATGTTGATGTCTGTCGATCTTGAGCCGGTGCAACTCGTCGGCCCGGACGGTACGCCGACGGCCGAA
CGCCGCTACCACCGTGACCTTCCTGAGGAAACGCTGCGTTGGCTCTACGATATGATGGTGGTCACCCG ::::::::::::::X0009T7.seq::::::::::::::
CGCCCAGGGCCGCTCCCGGGCGACCCGACCATTGCTGTCGCCGCGTAACGCCATCACGGATGACGCGCAGTTCG
TCGCTGTCTAGCTCCACCATCGCCTGCACACCGGCGGCCAGGACCCATTGGCCGTCGCACTCGTAGAGCAGGTA
ATCCTCGTCGACGGACTCGGTAACCACCGCCGCCAGCTCCGCTGCCAGGTCGGCGGGGTTGACACCGGCGGGC
ATCGGGATGGACGACGACGCGGTGCTGACGGCGCCTGTCGCGACGCTGAGCTCGGACACAGCTAGTAAATGTA
GCCTAACCTACTTAATGGGTCGCAGCCCCCCGGGGTCGTCGCATGTCCAACGTTGCTCGACTGGAAGAAAATGC
TCGTCGGGGAGCAAATGGCACC Clone X0010
::::::::::::::X0010SP6.seq::::::::::::::
AATACTCAATCTTGATCGGTTTCCAGCAACAGCCGATCGACGGCTTCGCCCAGGGCCGCTCCCGGGCGACCCGA
CCATTGCTGTCGCCGCGTAACGCCATCACGGATGACGCGCAGTTCGTCGCTGTCTAGCTCCACCATCGCCTGCA
CACCGGCGGCCAGGACCCATTGGCCGTCGCACTCGTAGAGCAGGTAATCCTCGTCGACGGACTCGGTAACCACC
GCCGCCAGCTCCGCTGCCAGGTCGGCGGGGTTGACACCGGCGGGCATCGGGATGGACGACGACGCGGTGCTGA
CGGCGCCTGTCGCGACTCTGAGCTCGG ::::::::::::::X0010T7.seq::::::::::::::
GGATGTGCTGTGAGCGCCGCACCACCAGCGCCGACGCTAAGGATGGAACGCACGGCATCTTCTGACGCGTAACC
GCGTTGTGATCGCGAGCTGAGGAGACGGTATGGGGGAGGGTTCTCGGAGGCCATCTGGGATGTTGATGTCTGTC
GATCTTGAGCCGGTGCAACTCGTCGGCCCGGACGGTACGCCGACGGCCGAACGCCGCTACCACCGTGACCTTCC
TGAGGAAACGCTGCGTTGGCTCTACGAGATGATGGTGGTCACCCGCGAGCTGGATACCGAATTCGTCAATCTGC
AGCGCCAGGGGGAAGCTGGCGTTGTACACGCCCTGTCGCGGGCAGGAAGCCGCGCAGGTGGGTGCGGCGGCTT
GCCTACGCAAAACCGACTGGTTGTTCCCC Clone X0012
::::::::::::::X0012SP6.seq::::::::::::::
ATCACGACAACAGCGACGGTGTGTCGGATCAGCGGCCCCCGTTGCCGGGCAATGTTGAGGCGTTTCTGCGTCTG
GTTGAGGCCGGCTGGGAC-
CCGAGGTGGCTCGTCGGCCACATGGGCAGCACACCACCGTGGTGATGCATCTAGACGTGCAGGACCGTGCCGCT
GGCCTGCA ::::::::::::::X0012T7.seq::::::::::::::
GCGGCTACGTGCCATCGAGACACTGGCGCAGGCTATCGCACCCGTTATCGGCTGCGAGCAAATCGCGGTATGCG
TTCTTGAGCATGAGTCGGCGACCGTCGTCATGGTCGACACCCACGACGGAAAGACGCAGATCGCCGTCAAGCAT
GTGTGCCGCGGATTATCAGGACTGACCTCCTGGCTGACCGGCATGTTTGGTCGCGATGCCTG Clone X00013
::::::::::::::X0013T7.seq::::::::::::::
TACAAGCGGCACCTCGCCGGTGAACTGACCGTTCGCACGCTGCGCACCGCCGCCGGGCGCGTGCTCGGCGCGC
CGGCGGCCCCCGAGGCCTGAGAGGGGAACCAACCATGCAGGTGAACATGACGGTAAACGGCGAGCCCGTCACC
GCCGAGGTCGAACCCCGGATGCTGCTGGTCCATTTTCTCCGTGATCAGCTGCGGCTCACCGGAACTCACTGGGG
CTGTGATACCAGCAACTGCGGGACATGCGTGGTGGAGGTCGACGGCGTGCCGGTGAAATCCTGCACGATGCTCG
CCGTGATGGCCTCCGGGC Clone X0014
::::::::::::::X0014T7.seq::::::::::::::
AGCGGCTGGTTACGACTCCCTGTTTGTGATGGACCACTTCTACCAACTGCCCATGTTGGGGACGCCCG-
CC-TCCGATGCTGGAAGCCTACACTGCCCTTGGTGCGCTGGCC-C-GCGACCGAGCGGCTGCAACTGGGCGC-
TTGGTGACC-GCAATACCTACCGCACCCC-ACCCTGCTGG-CAAA-
ATCATCACCACGCTCGACTTGGTTAGCGCCGGTCGA-CGATCCTCGGCATTGGAACCGGTTGGTTT- TABLE 4-continued End sequences of the polynucleotide inserts cloned in the named recombinant BAC vectors contained in the I-XXXX *M. bovis* strain Pasteur genomic DNA library.

Clone X0015
:::::::::::::X0015SP6.seq:::::::::::::
ACGCGCGCCGATCATATCTGCTATGGATGTACAATTCAGCTCTTGCTGTTATACCAGTATATGGTGTACTATTTG
ATCTATGCTGACGTGTGAGATGCGGGAATCGGCCCTGGCTCGACTCGGCCGGGCTCTGGCTGATCCGACGCGGT
GCCGGATTCTGGTGGCGTTGCTGGATGGCGTTTGCTATCCCGGCCAGCTAGCTGCGCACCTCGGGTTGACCCGA
TCGAATGTGTCCAACCATCTGTCGTGTTTGCGGGGCTGCGGGCTGGTA-
TCCCAACCTATGAGGGCCGGCAGGTTCGGTAT :::::::::::::X0015T7.seq:::::::::::::
CCGCGCTGCTGCTGACGTCGGTCGAACGTGCGACACGTCTGCGAATACCGGCCGAACGCTGGGTTTATCCACAG
GCTGGCACCGACGCCCACGACACACCGGCCGTCGCCGACCGCCACCGACTGCATCGGTCGACGGCCATTCGGAT
CGCCGGTGCCCGGGCGCTGGAACTGGCTGGGCTGGGGCTCGATGACATCGAATACGTCGACCTGTATTCGTGCT
TTCCCTCCGCTGTCCAAGTCGCCGCAATCGAACTCGGCCTGGACACCGACGATCCTGCCCGCCCGCTGACCGTC
ACCGGGGGCCTGACCTTCGCCGGCGGGCCGTGGAGCAATTACGTCACGCACTCCAT Clone X0016
:::::::::::::X0016SP6.seq:::::::::::::
CAGGCGTGCAATGACCTGCACTGCGCCGGA-A-TCCCTAACCCACTAAACCGGGGCCGCTCACAAGCCGTGCAGC
TCGGTCAGCGTCAGGTGCGCGACCAGGAA-
TAATGAGCAGACCCGTGCCGTCAACGATGGTGGCGATCATCGGCCCCGAAACGATGGCCGGGTC-
ATGCGCAACTTCTTCAGCAGCGGCGGAAGGACGGCA-CCACCAGCGAC-ACCACACCACGAT :::::::::::::X0016T7.seq:::::::::::::
GCGAA-CACTTCGTCAACTTCCAGGGCTGCCCGCACCAAGTATTTCGACGAGTATTTCCGTCGGGCCGCCGCCGC
CGGCGCGCGGCAGGTGGTCATCCTGGCGGCGGGGCTGGACTCGCGCGCGTACCGGCTGCCTTGGCCCGACGGG
ACCACGGTTTTTGAGCTGGACCGCCCGCAGGTCCTTGATTTCAAGCGCGAGGTGCTCGCCAGCCACGGTGCCCA
ACCGCGCGCCCTGCGCCGCGAGATCGCCGTCGACCTGCGTGACGATTGGCCACAAGCCTTGCGGGACAGTGGTT
TCGATGCGGCTGCACCGTCGGCATGGATTGCCGAAGGGCT Clone X0017
:::::::::::::X0017SP6.seq:::::::::::::
TTGGGC-TTGCCC-CAATA-GGCCCCAATCAAAAGCCGAGCAGGTGGAACCTA-CGCATTCGCCTC-TCGT-TGTGC
ACCCGAGCCATCGCACGCGCGGGAATTCCCGGAT-TC-CCGTATTCTCCGGCGGCCGGGCTAACCCATCCCA-GCC
GAACGGTTGGCTC-TGCCGTGGGTCCCGTGTTGGCCGATCGGGGCGTCACCGGGGGTGCTCGGGTGCGG-
TGACCATGGC-AACTGCCCC-ATGGGCCGACCCTGGTGCAGATAAACCTG :::::::::::::X0017T7.seq:::::::::::::
TGGTGGAGGTCCCCACCAA-ACCCGGCCGTAACTCTGCTCACGGAAATGCGG-CAGGCCGCGCGTAGCACGTGGT
ATCCGCCATAAAGGTGCACCTTAAGCACGGCGTCCCAATTCTCGAACGACATCTTGTGGAAGGTGCCGTCGCGC
AAGATCCCGGCGTTGCTCACCACACCGTGCACGGCGCCGAATTCGTCAAGCGCGGTCTTGATGATGTTCGCTGC
GCCGTCCTCGGTGGCGACGCTGTCGGTA-TTGGCGACCGCCCGGCCCCCCTTGTCGCGAAATCTCGGCGACGAC
CTCATCGGCCATCGCCGAACCGGGCGCCCG Clone X0018
:::::::::::::X0018SP6.seq:::::::::::::
GCCGGCCAAACTGGCCGGCGGGGTTGCTGTC-TCAAGGTGGGTTCCGCCACCAA-ACC-
CACTCAAGGATCGCAAGGAAAGC-
TCAAGGATGCGGTCGCGGCCGCCAAGGCCGCGGTCAAGGAGGGCATCGTCCCTGGTGGGGGA-CCTCCCTCATC
CACCAGGCCCGCAAGGCGCTGACCGAACTGC-TGCGTC-C-GACCGGTGACAA-GTCCTCGGTGTCCACGTGT-CTC
CGAAGCCCTTGCCGCTCCGTTGTTCTGGATC-CC-CCAAC-CTGGCTTGGACGGCTC-
GTGGTGGTCAACAAGGTCAGCGAGCTACCCGCCGGGCATGGGCTGAACGTGA Clone X0018
:::::::::::::X0018T7.seq:::::::::::::
CGAACCT-
AATTGTCCTGTAATGCCCAGCTCACCAA-GCATGGCTGGTGGCCGGGGCGGTGAAGCCGGCGTCTGCGGCACCG
TCCAACTC-ATGTGGAT-GCCGGAATGGGGATGTCCGG-ACGGCGAATCCGTA-
TTCGCTTGTCCCGTGAGGCCCAGGTGGATGGGGGGAAGGATC-TGGTGTCCGGGATGAT-
ATGGGGCCGATGCCGCCGGTTGAAGTCCACTGGATCGGGAATTCGGGAATCGTGAT-
CCGACGTTCAGGCCGAAC Clone X0019
:::::::::::::X0019SP6.seq:::::::::::::
CTAACGGAATGAAAGCCCTGGTGGCCGT-TCGGCGGTGGCCGTCGTCGCACTGCTCGGTGTATCTTCCGCCCAAG
CTGATCCCGAGGCGGATCCCGGCGCAGGTGAGGCCAACTATGGTGGCCCCCCAAGTTCCCCACGTCTTGTCGAT
CACACCGAATGGGCGCA-
TGGGGAATTCTGCCCAGCCTCCGGGTCTACCCGTCCCAAGTTGGGCGTACA-CCTCCCGCCGCCTCGGGATGGCC
GCTGCCGACCCGGCCTGGGCC-AGGTTCTCGCGCTGTCACCGGAAGCCGACATGCCGGC :::::::::::::X0019T7.seq:::::::::::::
CCGCGGGACAC-CCTC-ATGCTGCCGCCATGGACGCGGTCGAACGCAAGCAGCTGATCGAGCTACAACGCCGCG
CGGAACGCTTCCGCCGCGGGCGTGACCGCATCCCGTTGACCGGGCGGATCGCGGTGATCGTCGATGACGGCATC
GCCACCGGAGCGACGGCCAAGGCGGCGTGCCAGGTCGCCCGGGCGCACGGTGCGGACAAGGTGGTGCTGGCG
GTCCCGATCGGCCCA-ACGACATCGTGGCGAAGATTCGCCGGGTACGCCGATGATGTGGTGTGTTTGGCGACGC
CGGCGTTGT TABLE 4-continued End sequences of the polynucleotide inserts cloned in the named recombinant BAC vectors contained in the I-XXXX *M. bovis* strain Pasteur genomic DNA library.

```
Clone X0020
::::::::::::::X0020T7.seq::::::::::::::
CTCTGGGACCGGCCACGGTGCC-CCGGCGTTCCCGGACGTGCTGCGCCAGGTGTCCGGCGGCCGCGTGCATGGT
GTTCCCGGATCGGCCGCTGGCCAGAGCCCACCGGTGAATCTGGCGCCTGGCCGACCACCGTGCGCCGTAGGCTT
GCGATCGTGCAGCGCTGGCGTGGCCAGGACGAGATCCCGACGGATTGGGGCAGATGCGTGCTCACCATCGGGG
TATTTGACGGCGTGCACCGCGGGCACGCCGAACTGATCGCGCACGCGGTCAAAGGCGGC

Clone X0021
::::::::::::::X0021SP6.seq::::::::::::::
AATACTCAAGCTTTCGTCAGTTCATTGCGCCAGCAGACCAACAA-AGCATCGGGACATACGGA-TCAACTACCCG
GCCAACGGTGATTTCTTGGCCGCCGCTGACGGCGCGAACGACGCCAGCGACCAC-TTCAGCAAATGGCCA-CGCG
TGCCGGGCCACGAGGTTGGTGCTCGGCGGCTACTCCCAGGGTGCGGCCGTGATC-ACATC-TCACCGCCGCACCA
CTGCCCGGCCTCGGGTTCACGCAGCCGTTGCCGCCCGCAGCGGAC-
ATCACATCGCCGCGATCGCCCTGTTCGGGAATCCCTC-GGCCGCGCTGGCGGGCTGATTAAC

::::::::::::::X0021T7.seq::::::::::::::
TGCCGCGGATTTGGCTGGCTGCCCAATATTCAGAATCGGGCCTTTCTTTTTGCGCGACAATAAGGTCACAGTAAA
CCCTCGTTTTGTGAGATGCGGGGCGGGCCGGGCGAA-TCGACCTCGAGTGAATGGATCTCGAGTGAATGGACAG
GGCATCGCCTACGAGTCGCATCCCCATCCAACAGACCGGTGCTCTTGCATCGGACCCTGAAGGTCCCGCACGGA
GGGTGTGGTTGCCGGCGCGGGGTCACGGTGCGGTAGCGACGTAGTGTTTGAACGAATTTCTTGATGCTCCAACC
TGTTTGGTGTTCAATCCAGTTCT

Clone X0175
.....X0175SP6.....
AA-CTTGCGCGCTCGGCCGGGTC-AGCATCCAGCTGCTCGGCAAGGAGGCCAGCTAC-C-TCGCTGCGTATGCCCA
GCGGTGAGATCCGCCGGGTC-ACGTCCGCTGCCGCGCGACCGTCGGCGAAGTGGGCAATGCCGAGCAGGCAAAC
ATCAACTGGGGCAAGGCCGGTCGGATGCGGTGGAAGGGCAAGCGCCCGTCGGTCCGGGGCGTGGTGAT-AACC
CGGTC-ACCACCCGCACGGCGGTGGTGAGGGTAAAACCTCCGGCGGCCGTCACCCGGTTAGCCCGTGGGGCAA

.....X0175T7.....
A-TCGAAAGTGACCATCTCTACCTTGAGTGCCATACCGCCCGACCCTATGCCTCGGATAGCTCGGCGGAAAGAAA
CGCTTGCAGTGCCGCCGAATAGGCGGCTACGTCGTGAGCGCCCATCAACTCTCGCGCGGAGTGCATCGCCAGCT
GGGCGGCGCCGACGTCGACCGTGGGGATTCCGGTGCGCGCCGCGGCCAACGGCCCGATCGTCGACCCGCACGG
CAGATCGGCGCGATGTTCGTAACGCTGCATAGGCACTCCCGCGCGCTGGCAGGCCAGTGCGAACGCCGCCGCG
GTGCGTCCG
```

References

Altschul, S. F., W. Gish, W. Miller, E. W. Myers, and D. J. Lipman. 1990. Basic local alignment search tool. J. Mol. Biol. 215:403-10.

Balasubramanian, V., M. S. Pavelka, Jr., S. S. Bardarov, J. Martin, T. R. Weisbrod, R. A. McAdam, B. R. Bloom, and W. R. Jacobs, Jr. 1996. Allelic exchange in *Mycobacterium tuberculosis* with long linear recombination substrates. J. Bacteriol. 178:273-279.

Barany F., 1991, Proc. Natl. Acad. Sci. USA. 88:189-193.

Bensimon, A., A. Simon, A. Chiffaudel, V. Croquette, F. Heslot, and D. Bensimon. 1994. Alignment and sensitive detection of DNA by a moving interface. Science. 265: 2096-2098.

Bergh, S., and S. T. Cole. 1994. MycDB: an integrated mycobacterial database. Mol. Microbiol. 12:517-534.

Birnboim, H. C. and J. Doly. 1979. A rapid alkaline extraction procedure for screening recombinant plasmid DNA. Nucleic Acids Res. 7:1513-1523.

Burg J. L. et al., 1996, Mol. and Cell. Probes, 10:257-271.

Cai, L., J. F. Taylor, R. A. Wing, D. S. Gallagher, S. S. Woo, and S. K. Davis. 1995. Construction and characterization of a bovine bacterial artificial chromosome library. Genomics. 29:413-425.

Canard, B., and S. T. Cole. 1989. Genome organization of the anaerobic pathogen *Clostridium perfringens*. Proc. Natl. Acad. Sci. USA 86:6676-6680.

Chu B. C. F. et al., 1986, Nucleic Acids Res., 14:5591-5603.

Chuang S. et al., 1993. Global regulation of gene expression in *Escherichia coli*. J. Bact., 175(7): 2026-2036.

Chuang, S., D. L. Daniels, and F. R. Blattner. 1993. Global regulation of gene expression in *Escherichia coli*. J. Bacteriol. 175:2026-2036.

Cole, S. T., R Brosch, K. Eiglmeier, T. Garnier, S. V. Gordon, C. Churcher, D. Harris, K. Badcock, D. Basham, D. Brown, T. Chillingworth, R. Connor, R Davies, K. Devlin, T. Feltwell, S. Holroyd, S. Gentdes, K. Jagels, J. McLean, S. Moule, L. Murphy, K. Oliver, J. Osborne, J. Parkhill, M. Quail, M-A. Rajandream, J. Rogers, S. Rutter, K. Seeger, J. Skelton, R. Squares, S. Squares, J. Sulston, K. Taylor, S. Whitehead and B. G. Barrell. 1997. Genome Sequence of *Mycobacterium tuberculosis* H37Rv. Microbial Comparative Genomics, 2:174.

Collins, D. M., and D. M. Stephens. 1991. Identification of an insertion sequence, IS1081, in *Mycobacterium bovis*. FEMS Microbiol. Lett. 67:11-15.

Cousins D. et al., 1998, 36(1): 168-170.

De Wit D. et al., 1990, J. Clin. Microbiol., 28: 2437-2441.

Dear, S., and R. A. Staden. 1991. Sequence assembly and editing program for the efficient management of large projects. Nucleic Acids Res. 19:3907-3911.

Duck P. et al., 1990, Biotechniques, 9:142-147.

Guateli J. C. et al., 1990, Proc. Natl. Acad. Sci. USA, 87:1874-1878.

Kievitis T. et al., 1991, J. Virol. Methods, 35:273-286.

Kim, U. J., B. W. Birren, T. Slepak, V. Mancino, C. Boysen, H. L. Kang, M. I. Simon, and H. Shizuya. 1996. Construction and characterization of a human bacterial artificial chromosome library. Genomics. 34:213-218.

Kwoh D. Y. et al., 1989, Proc. Natl. Acad. Sci. USA, 86:1173-1177.

Landegren U. et al., 1988, Science, 241:1077-1080.

Liu, Y. G., and R. F. Whittier. 1995. Thermal asymmetric interlaced PCR: automatable amplification and sequencing of insert end fragments from P1 and YAC clones for chromosome waling. Genomics. 25:674-681.

Lizardi P. M. et al., 1988, Bio/technology, 6:1197-1202.

Matthews J. A. et al., 1988, Anal. Biochem., 169:1-25.

Michalet, X., R. Ekong, F. Fougerousse, S. Rousseaux, C. Schurra, N. Hornigold, M. Vanslegtenhorst, J. Wolfe, S. Povey, J. S. Beckmann, and A. Bensimon. 1997. Dynamic molecular combing—stretching the whole human genome for high-resolution studies. Science. 277:1518-1523.

Misumi D. J., D. L. Nagle, S. H. McGrail, B. J. Dussault, Jr., J. S. Smutko, H. Chen, O. Charlat, G. M. Duyk, C. Ebeling, L. Baldini G. A. Carlson, and K. J. Moore. 1997. The physical and genetic map surrounding the Lyst gene on mouse chromosome. Genomics. 40:147-150.

Pavelka, M. S., Jr., and W. R. Jacobs, Jr. 1996. Biosynthesis of diaminopimelate, the precursor of lysine and a component of peptidoglycan, is essential function of Mycobacterium smegmatis. J. Bacteriol. 178:6496-6507.

Philipp, W. J., S. Nair, G. Guglielmi, M. Lagranderie, B. Gicquel, and S. T. Cole. 1996a. Physical mapping of *Mycobacterium bovis* BCG pasteur reveals differences from the genome map of *Mycobacterium tuberculosis* H37Rv and from *M. bovis*. Microbiology. 142:3135-3145.

Philipp, W. J., S. Poulet, K. Eiglmeier, L. Pascopella, V. Balasubramanian, B. Heym, S. Bergh, B. R. Bloom, W. R. Jacobs, Jr., and S. T. Cole. 1996b. An integrated map of the genome of the tubercle *bacillus, Mycobacterium tuberculosis* H37Rv, and comparison with *Mycobacterium leprae*. Proc. Natl. Acad. Sci. USA. 93:3132-3137.

Poulet S. et al., 1995, Arch. Microbiol., 163: 87-95.

Ross B C, 1992, J. Clin. Microbiol., 30: 942-946.

Sambrook, J., E. F. Fritsch, and T. Maniatis. 1989. Molecular cloning: a laboratory, manual 2nd ed. Cold Spring Harbor Laboratory, NY: Cold Spring Harbor. N.Y.

Sanchez-Pescador R, 1988, J. Clin. Microbiol., 26(10):1934-1938.

Segev D., 1992, in <<Non-radioactive Labeling and Detection of Biomolecules>>. Kessler C. Springer Verlag, Berlin, New-York, 197-205.

Sheng, Y., V. Mancino, and B. Birren. 1995. Transformation of *Escherichia coli* with large DNA molecules by electroporation. Nucleic Acids Res. 23:1990-1996.

Shinnick T. M. et al., 1987, J. Bact., 169(3): 108-1088.

Shizuya, H., B. Birren, U. J. Kim, V. Mancino, T. Slepak, Y. Tachiiri, and M. Simon. 1992. Cloning and stable maintenance of 300-kilobase-pair fragments of human DNA in *Escherichia coli* using an F-factor-based vector. Proc. Natl. Acad. Sci. USA. 89:8794-8797.

Spargo C. A. et al., 1996, Mol. and Cell. Probes, 10:247-256

Stone B. B. et al., 1996, Mol. and Cell. Probes, 10:359-370.

Trieselman B. A. et al., 1992. Transcriptionally active regions in the genome of the archaebacterium *Haloferax volcanii*. J. Bact., 174: 30-34.

Trieselmann, B. A., and R. L. Charlebois. 1992. Transcriptionally active regions in the genome of the archaebacterium *Haloferax volcanii*. J. Bacteriol. 174:30-34.

Urdea M. S. et al., 1991, Nucleic Acids Symp. Ser., 24:197-200.

Urdea M. S., 1988, Nucleic Acids Research, 11: 4937-4957.

Van Soolingen D., 1993, J. Clin. Microbiol., 31: 1987-1995.

Willets, N., and R. Skurray. 1987. Structure and function of the F-factor and mechanism of conjugation. In *Escherichia coli* and *Salmonella Typhimurium*: Cellular and Molecular Biology (F. C. Neidhardt, Ed) Vol. 2 pp 1110-1133, Am. Soc. Microbiol., Washington, D.C.

Woo, S. S., J. Jiang, B. S. Gill, A. H. Paterson, and R. A. Wing. 1994. Construction and characterization of a bacterial artificial chromosome library of *Sorghum bicolor. Nucleic Acids Res* 22:4922-4931.

Zimmer, R., and A. M. V. Gibbins. 1997. Construction and characterization of a large-fragment chicken bacterial artificial chromosome library. Genomics. 42:217-226.

What is claimed is:

1. A method of detecting the presence of antibodies of *Mycobacterium tuberculosis* in a biological sample comprising: (a) contacting the biological sample with a composition comprising the product of expression of at least one open reading frame (ORF) contained in the polynucleotide set forth in SEQ ID NO: 1, wherein the ORF comprises nucleotides 8077-9042 of SEQ ID NO: 1; and (b) detecting whether an immunological complex is formed between the expression product and antibodies contained in the biological sample, wherein the presence of a complex indicates the presence of antibodies to *Mycobacterium tuberculosis* antigens in the biological sample.

2. A method of detecting the presence of antibodies to *Mycobacterium tuberculosis* antigens in a biological sample comprising:

(a) contacting the biological sample with a composition comprising the polypeptide set forth in SEQ ID NO: 732; and (b) detecting whether an immunological complex is formed between the polypeptide and antibodies contained in the biological sample, wherein the presence of a complex indicates the presence of antibodies to *Mycobacterium tuberculosis* antigens in the biological sample.

3. A method of detecting the presence of antibodies of *Mycobacterium tuberculosis* in a biological sample comprising:

(a) contacting the biological sample with a composition comprising the product of expression of at least one open reading frame (ORF) contained in the polynucleotide set forth in SEQ ID NO: 1, wherein the ORF comprises nucleotides 2082-3878 (ORF 3), or 11516-12634 (ORF 11) of SEQ ID NO: 1; and (b) detecting whether an immunological complex is formed between the expression product and antibodies contained in the biological sample, wherein the presence of a complex indicates the presence of antibodies to *Mycobacterium tuberculosis* antigens in the biological sample.

* * * * *